United States Patent
Chahwan et al.

(10) Patent No.: US 11,306,306 B1
(45) Date of Patent: Apr. 19, 2022

(54) SELECTIVE DEGRADATION OF PROTEINS

(71) Applicant: SyntheX, Inc., San Francisco, CA (US)

(72) Inventors: Charly Chahwan, San Francisco, CA (US); Maria Soloveychik, San Francisco, CA (US)

(73) Assignee: SYNTHEX, INC., San Francisco, CA (US)

( * ) Notice: Subject to any disclaimer, the term of this patent is extended or adjusted under 35 U.S.C. 154(b) by 0 days.

(21) Appl. No.: 17/317,798

(22) Filed: May 11, 2021

Related U.S. Application Data

(63) Continuation of application No. PCT/US2020/033089, filed on May 15, 2020.

(60) Provisional application No. 62/848,509, filed on May 15, 2019, provisional application No. 62/854,273, filed on May 29, 2019.

(51) Int. Cl.
| | |
|---|---|
| *C12N 15/65* | (2006.01) |
| *C12N 15/81* | (2006.01) |
| *C12N 15/10* | (2006.01) |
| *C12N 15/62* | (2006.01) |
| *C12N 9/50* | (2006.01) |
| *C12N 9/10* | (2006.01) |
| *C07K 14/395* | (2006.01) |
| *G01N 33/50* | (2006.01) |

(52) U.S. Cl.
CPC ........ *C12N 15/1055* (2013.01); *C07K 14/395* (2013.01); *C12N 9/104* (2013.01); *C12N 9/63* (2013.01); *C12N 15/1086* (2013.01); *C12N 15/625* (2013.01); *C12N 15/65* (2013.01); *C12N 15/81* (2013.01); *C12Y 203/02* (2013.01); *C12Y 304/21026* (2013.01); *G01N 33/502* (2013.01); *C07K 2319/50* (2013.01); *C07K 2319/80* (2013.01); *C07K 2319/95* (2013.01); *G01N 2333/9108* (2013.01); *G01N 2500/10* (2013.01)

(58) Field of Classification Search
None
See application file for complete search history.

(56) References Cited

U.S. PATENT DOCUMENTS

| | | |
|---|---|---|
| 10,188,691 B2 | 1/2019 | Chahwan et al. |
| 2004/0265791 A1 | 12/2004 | Tetsu et al. |
| 2006/0223089 A1 | 10/2006 | Vidal et al. |
| 2008/0261819 A1 | 10/2008 | Lorens et al. |
| 2009/0130676 A1 | 5/2009 | Brent et al. |
| 2017/0368132 A1 | 12/2017 | Chahwan et al. |
| 2019/0216879 A1 | 7/2019 | Chahwan et al. |
| 2020/0347462 A1 | 11/2020 | Soloveychik et al. |
| 2020/0361991 A1 | 11/2020 | Chahwan et al. |

FOREIGN PATENT DOCUMENTS

| | | |
|---|---|---|
| WO | WO-2017205852 A2 | 11/2017 |
| WO | WO-2019099678 A1 | 5/2019 |
| WO | WO-2019104244 A1 | 5/2019 |
| WO | WO-2020229818 A1 | 11/2020 |
| WO | WO-2020232343 A1 | 11/2020 |

OTHER PUBLICATIONS

Li et al. Inactivation of SAG/RBX2 E3 ubiquitin ligase suppresses KrasG12D-driven lung tumorigenesis. Feb. 2014. The Journal of Clinical Investigation. Vol. 124, No. 2, p835-846. (Year: 2014).*
Meinhardt et al. Rheostats and Toggle Switches for Modulating Protein Function. Dec. 30, 2013. PLOS One. Vol. 8, Issue 12, e83502, pp. 1-11. (Year: 2013).*
Miller et al. Computational predictors fail to identify amino acid substitution effects at rheostat positions. Jan. 30, 2017. Scientific Reports. Vol. 7, No. 41329, pp. 1-13. (Year: 2017).*
Chekan et al. Characterization of the macrocyclase involved in the biosynthesis of RiPP cyclic peptides in plants. PNAS 114(25):6551-6556 (Jun. 20, 2017).
Chinen et al. Chapter 3: Multidrug Sensitive Yeast Strains, Useful Tools for Chemical Genetics. IntechOpen, pp. 29-51, Dec. 20, 2017. Retrieved Jun. 3, 2021 from URL: https://www.intechopen.com/books/the-yeast-role-in-medical-applications/multidrug-sensitive-yeast-strains-useful-tools-for-chemical-genetics. From The Yeast Role in Medical Applications, Abdulkhair, ed., first published Jan. 2018.
Co-pending U.S. Appl. No. 17/171,841, inventors CHAHWAN; Charly et al., filed on Feb. 9, 2021.
PCT/US2020/033089 International Search Report and Written Opinion dated Aug. 3, 2020.
Varshavsky, 1996, The N-end rule: Functions, mysteries, uses. Proc. Nat. Acad. Sci. USA, 93:12142-12149.
PCT/US2018/061292 Written Opinion dated Feb. 5, 2019.

* cited by examiner

*Primary Examiner* — Channing S Mahatan
(74) *Attorney, Agent, or Firm* — Wilson Sonsini Goodrich & Rosati

(57) ABSTRACT

The present disclosure provides methods to identify peptides and small molecule moieties that are able to functionally bridge an interaction between a target protein and an E3 ubiquitin ligase to mediate the degradation of the target protein. Some moieties can degrade specific target variants, but not others. The moieties create a neosubstrate for an E3 ligase of interest. The methods described enable generation of compounds able to selectively degrade specific targets within cells with implications for drug development for pathological conditions. The disclosure also describes the generation of modified peptides using post-translational modification enzymes, such as N-methyltransferases, prolyloligopeptidases, lactamases, hydroxylases, and dehydratases, along with methods of using the same.

24 Claims, 12 Drawing Sheets
Specification includes a Sequence Listing.

W603

| | | | |
|---|---|---|---|
| G.vacc_Pcyt | 590 | DMLRFHKFTLGYLWTGDYGCSDKEEEFK | 617 SEQ ID NO:129 |
| G.fusi_Pop | 608 | DMLKFPKFTFGALLRSEYGDPEDPEAFD | 635 SEQ ID NO:130 |
| L.raph_Pop | 610 | DMLKFPKFTFGALWCSEYGDPDDPEAFD | 637 SEQ ID NO:131 |
| L.novz_Pop | 607 | DMLRFPKFTFGALWRSEYGDPEDPEDFD | 634 SEQ ID NO:132 |
| L.late_Pop | 608 | DMLRFPKFTFGALWRSEYGDPEDPEDFD | 635 SEQ ID NO:133 |
| L.edod_Pop | 608 | DMLRFPKFTFGALWRSEYGDPEDPEDFD | 635 SEQ ID NO:134 |
| D.bisp_Pop | 610 | DMLRFPKFTFGALWCSEYGDPEDPEAFD | 637 SEQ ID NO:135 |
| O.olea_Pop | 608 | DMLRFPKFTFGASWRSEYGDPEDPEDFD | 635 SEQ ID NO:136 |
| G.marg_PopB | 606 | DLLKFHKFTGGQAWISEYGNPSIREEFD | 633 SEQ ID NO:137 |
| A.bisp_PopB | 606 | DLLKFNKFTGGMAWTSEYGNPFIKEDFD | 633 SEQ ID NO:138 |
| G.marg_PopA | 610 | DLLKFHKFTIGKAWTSDTGNPDDPNDFD | 637 SEQ ID NO:139 |
| A.bisp_PopA | 634 | DLLKFPKFTIGKAWISDYGDPEDPRDFD | 661 SEQ ID NO:140 |

CTCAGTTTCCCAAGTTCACGTTTGGTGCTTTGTTGCGTTCGGAATATGGCGATGTAT SEQ ID NO:141
GAGTCAAAGGGTTCAAGTGCAAACCACGAAACAACGCAAGCCTTATACCGCTACATA 615    620    625
P  K  F  T  F  G  A  L  W  R  S  E  Y  G  D                SEQ ID NO:142

FIG. 5A

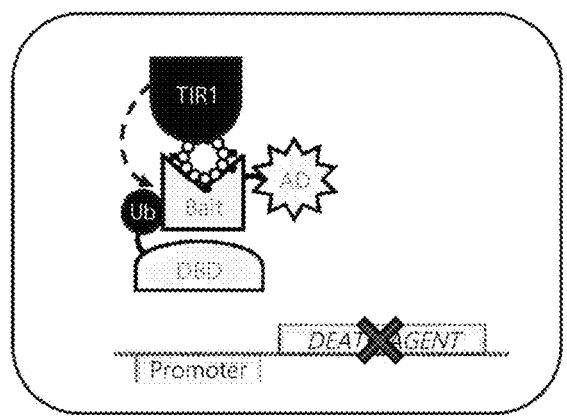
FIG. 10A
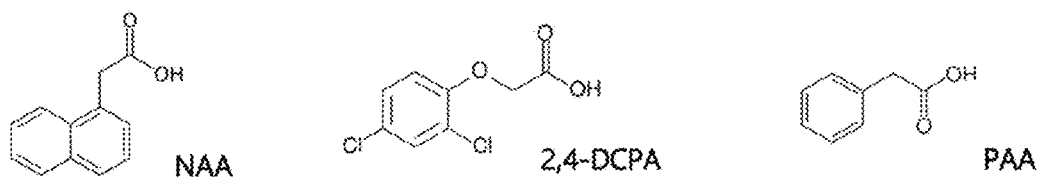
FIG. 10B
FIG. 10C

Coronatine

SELECTIVE DEGRADATION OF PROTEINS

CROSS-REFERENCE

This application is a continuation application of International Application No. PCT/US20/33089, filed on May 15, 2020, which claims the benefit of U.S. Provisional Application No. 62/848,509, filed on May 15, 2019 and U.S. Provisional Application No. 62/854,273, filed on May 29, 2019, which are incorporated herein by reference in their entirety.

SEQUENCE LISTING

The instant application contains a Sequence Listing which has been submitted electronically in ASCII format and is hereby incorporated by reference in its entirety. Said ASCII copy created on May 11, 2021, is named 50607_710_301_SL.txt and is 576,624 bytes in size.

BACKGROUND

Degrading proteins in a precise manner can be a key for controlling cellular functions. Many pathological conditions are characterized by aberrant functions of cellular pathways, either due to precocious protein expression or the expression of malfunctional variants. Thus, compounds that can specifically and precisely degrade the accumulation of such proteins or the malfunctioning faulty variants could be beneficial to treating various ailments. New technologies are being developed to discover and develop novel molecules to mediate protein degradation.

However, limited options exist to screen for molecules that accomplish functional degradation in an efficient manner. Accordingly, there is a need for development of methods and compositions that accomplish selective target protein degradation in precise and selective ways. The methods in this invention describe a screening platform that enables the creation of neosubstrates for specific E3 ligases by using compound libraries that are able to bridge an interaction between said E3 ligase and a target protein, leading to its degradation. The technology is amenable to various drug moieties, as well as DNA encoded libraries of peptides and macrocycles, which will mostly likely be close drug candidates due to their bivalent nature. The platform describes a selection approach, where only molecules that are able to yield functional target degradation are present.

Macrocyclic peptide natural products have been identified and isolated from a wide variety of species including bacteria, fungi, plants, algae, molluscs, and mammals. They are a recognized source of diverse biologically active molecules. Some cyclic peptides from marine sources have been approved by the Food and Drug Administration (FDA) such as ziconotide, a cyclic peptide isolated from the toxin of the cone snail species *Conus magus*. Ziconotide is an analgesic drug used for severe and chronic pain that works by selective blocking of N-type calcium channels which control neurotransmission at many synapses. Macrocyclic peptide compounds have also shown considerable promise in a wide range of other therapeutic areas and have yielded several clinically approved therapeutics for cancer, immunomodulation (e.g. cyclosporin A), and fungal infections (e.g. echinocandins).

The utility and fields of application of these compounds are often limited by the low yields of their extraction from their natural sources, challenges in their organic synthesis, and the inability to source large numbers of variants to optimize activity. For this reason, biotechnological or semi-synthetic approaches beginning with natural starting materials are often utilized for drug manufacture. A particularly exciting group of macrocyclic peptides are the multiply backbone N-methylated cyclic peptides (cyclic peptides that are N-methylated at multiple locations on the peptide backbone). These compounds have interesting pharmacological properties, e.g. increased bioavailability due to increased permeability through intestinal epithelial membranes, and increased half-life in vivo due to increased stability towards proteases. The prototypical representative of this family of peptides is the immunomodulator Cyclosporin A. Cyclosporin A is an 11-mer cyclic peptide that was originally isolated from the ascomycete *Tolypocladium inflatum*, which synthesizes Cyclosporin A via a highly complex non-ribosomal peptide synthetase (NRPS) specifically referred to as cyclosporin synthase. The backbone methylation of cyclosporin occurs during the elongation of the peptide via built-in methyltransferase domains within cyclosporin synthase. Many teams over the past couple of decades have attempted to re-engineer or evolve the NRPS machinery in order to produce altered versions or diversified derivatives of their natural product (e.g. different amino acids, different size cycle, different N-methylation patterns, etc.), but these efforts have proven to be disappointingly unfruitful and challenging.

The currently established methods for producing these types of multiply N-methylated cyclic peptides involve the fermentation of large cultures of the corresponding microorganisms that naturally produce these compounds followed by elaborate fractionation and purification methods. A few alternatives have been established for a handful of compounds that either rely on a total chemical synthesis or a mixed enzymological and semi-synthetic hybrid strategy.

Ribosomally synthesized and post-translationally modified peptides (RiPPs) are a diverse class of natural products of ribosomal origin consisting of more than 22 subclasses that are produced by a variety of organisms, including bacteria, eukaryotes, and archaea. RiPPs are typically produced as an all-L pro-protein that is encoded on a gene that is transcribed by the regular RNA Polymerase II machinery (in eukaryotes) and then translated by the ribosome. The active macrocycle is encoded within a cassette that is flanked by N- and C-terminal signal recognition motifs. After its translation, the all-L pro-protein is processed by a set of modifying enzymes that introduce several modifications (e.g. side chain acylation, isomerization of some or all positions from L- to D-amino acids, side chain hydroxylation, backbone N-methylation, end-to-end cyclization, disulfide bridge formation, tryptathionine bridge formation, and many others) that liberate the cassette peptide out of the pro-protein and then convert it into the final natural product. The N- and C-terminal signal recognition motifs act as docking sites for the processing enzymes and guide the order and kinetics of catalysis.

One of the recurrent features about RiPP processing enzymes is that many of them are virtually completely agnostic to the sequence of the encoded active peptide within the cassette, thereby affording a high tolerability of substitutions in the cassette. Studies on the Amatoxin/Phallatoxin/MSDin family of poisonous mushroom RiPPs confirm the notion of the promiscuity of the corresponding prolyloligopeptidase/macrocyclase, PopB, towards a variety of naturally occurring active peptide cassette sequence variants as well as towards many synthetically derived variants. Such findings present the possibility for a straightforward strategy to generate widely diversified derivatives of a RiPP-based natural product by simply altering the DNA of the cassette coding sequence within the pro-protein encoding gene.

SUMMARY

Disclosed herein are methods for identifying one or more molecules that elicit degradation of a first test protein in a host cell. The method may comprise expressing in the host cell (i) an E3 ubiquitin ligase or a functional fragment thereof; (ii) a first fusion protein comprising a first DNA-binding moiety, the first test protein, and a first gene-activating moiety. The host cell may comprise a promoter sequence for controlling expression of a death agent wherein the first DNA-binding moiety specifically binds to the promoter sequence. The molecule may be delivered to the host cell. In the absence of the molecule, expression of the death agent may be activated. In the presence of the molecule, the first test protein may be degraded by the E3 ubiquitin ligase.

In some embodiments, the method further comprises expressing a second fusion protein comprising a second DNA-binding moiety, a second test protein, and a second gene-activating moiety in the host cell, wherein the host cell further may comprise one or more positive selection reporters driven by one or more promoters with a sequence specific for the second DNA-binding moiety.

In some embodiments, the method further comprises a plurality of positive selection reporters which are disposed within the host cell, wherein each positive selection reporter of the plurality of positive selection reporters is operably linked to a promoter sequence specific for the second DNA-binding moiety. In some embodiments, the positive selection reporter(s) are encoded in a plasmid disposed within the host cell.

In some embodiments, the molecule may be part of a library of molecules. In some embodiments, the molecule from the library may be delivered exogenously. In some embodiments, the molecule may be produced within the cell. In some embodiments, the molecule may be produced within the cell from a DNA encoded library.

In some embodiments, methods for identifying a molecule that selectively mediates the degradation of a specific test protein in a host cell while preserving a second test protein are described. The methods may comprise: expressing in the host cell a first fusion protein comprising the test protein with an activation domain and a DNA-binding moiety; a second test protein with an activation domain and a DNA-binding moiety; expressing in the host cell a third protein comprising an E3 ligase along with the required ubiquitination machinery components; and delivering a molecule from a library to the host cell, wherein a sequence of a gene for expressing a negative selection death agent is disposed within the host cell and operably linked to a promoter DNA sequence specific for the DNA binding moiety of the first fusion protein, wherein a positive selection reporter is disposed within the host and operably linked to a promoter DNA sequence specific for the DNA binding moiety of the second fusion protein and wherein, in the absence of the molecule, the expression of the first test protein causes the gene activating moiety to activate expression of the death agent, while the expression of the second test protein causes the gene activating moiety to activate the expression of the positive selection reporter.

In some embodiments, the molecule from the library is delivered exogenously. In some embodiments, the molecule is produced within the cell. In some embodiments, the molecule is produced within the cell from a DNA encoded library. In some embodiments, the host cell comprises more than one sequence for expressing a positive control reporter that is activated by a promoter DNA sequence specific for a DNA binding moiety. In some embodiments, the host cell comprises more than one sequence for expressing a death agent that is activated by a promoter DNA sequence specific for a DNA binding moiety. In some embodiments, the host cell comprises an integrated DNA encoding the first fusion protein, an integrated DNA encoding the second fusion protein, an integrated DNA encoding the third fusion protein; a plasmid DNA encoding the death agent; and a plasmid DNA encoding a positive selection reporter.

In some embodiments, the first test protein is a variation of KRAS. In some embodiments, the second test protein is KRAS. In some embodiments, the first test protein is androgen receptor splice variants ARV (ARV3, ARV7, or ARV9). In some embodiments, the second test protein is wild-type androgen receptor. In some embodiments, the first test protein is a variation of IDH. In some embodiments, the second test protein is wild-type IDH. In some embodiments, the first test protein is Myc. In some embodiments, the first test protein is CCNE. In some embodiments, the first test protein is Estrogen Receptor (ER). In some embodiments, the first test protein is IKZF1 or IKZF2. In some embodiments, the first test protein is PD-1 or PDL-1. In some embodiments, the first test protein is CTLA-4. In some embodiments, the first test protein is Tau. In some embodiments the first test protein is Act1/CIKS (Connection to IκB Kinase and Stress-activated protein kinases). In some embodiments the first test protein is an Ets Transcription factor variant (ETV1, ETV2, ETV3, ETV4, or ETV5). In some embodiments, the DNA binding moiety is derived from LexA, cI, Gli-1, YY1, Glucocorticoid receptor, TetR, or Ume6. In some embodiments, the gene activating moiety is derived from VP16, GAL4, NF-κB, B42, BP64, VP64, or p65.

In some embodiments, the death agent is an overexpressed product of genetic element selected from DNA or RNA. In some embodiments, the genetic element is a Growth Inhibitory (GIN) sequence such as GIN11. In some embodiments, the death agent is a ribosomally encoded xenobiotic agent, a ribosomally encoded poison, a ribosomally encoded endogenous or exogenous gene that results in severe growth defects upon mild overexpression, a ribosomally encoded recombinase that excises an essential gene for viability, a limiting factor involved in the synthesis of a toxic secondary metabolite, or any combination thereof. In some embodiments, the death agent is Cholera toxin, SpvB toxin, CARDS toxin, SpyA Toxin, HopUl, Chelt toxin, Certhrax toxin, EFV toxin, ExoT, CdtB, Diphtheria toxin, ExoU/VipB, HopPtoE, HopPtoF, HopPtoG, VopF, YopJ, AvrPtoB, SdbA, SidG, VpdA, Lpg0969, Lpg1978, YopE, SptP, SopE2, SopB/SigD, SipA, YpkA, YopM, Amatoxin, Phallacidin, Killer toxin KP1, Killer toxin KP6, Killer Toxin K1, Killer Toxin K28 (KHR), Killer Toxin K28 (KHS), Anthrax lethal factor endopeptidase, Shiga Toxin, Saporin Toxin, Ricin Toxin, or any combination thereof.

In some embodiments, the host cell is a fungus or bacteria. In some embodiments, the fungus is *Aspergillus*. In some embodiments, the fungus is *Pichia pastoris*. In some embodiments, the fungus is *Komagataella phaffii*. In some embodiments, the fungus is *Ustilago maydis*. In some embodiments, the fungus is *Saccharomyces cerevisiae*.

In some embodiments, the molecule is small molecule. In some embodiments, the small molecule is peptidomimetic. In some embodiments, the molecule is peptide or protein. In some embodiments, the peptide or protein is derived from naturally occurring protein product. In certain embodiments, the peptide or protein is synthesized protein product. In some embodiments, the peptide or protein is product of recombinant genes. In some embodiments, the molecule is a peptide or protein expressed from test DNA molecule inserted into the host cell, wherein the test DNA molecule comprises DNA sequences that encodes polypeptides, forming the library. In some embodiments, the library comprises polypeptides 60 or fewer amino acids in length. In some embodiments, the DNA sequence encodes a 3'UTR of mRNA. In some embodiments, the 3'UTR is the 3'UTR of sORF1. In some embodiments, the polypeptides comprise a common N-terminal sequence of Methionine-Valine-Asparagine. In some embodiments, the polypeptides in the library are processed into cyclic or bicyclic peptides in the host cell.

Disclosed herein, in certain embodiments, is a plasmid vector. In some embodiments, the plasmid vector comprises a DNA sequence encoding a first polypeptide inserted in frame with Gal4-DNA binding domain ("DBD") and VP16 activation domain (AD), a DNA sequence encoding a second polypeptide inserted in frame with Ume6-DNA binding domain ("DBD") and VP16 activation domain (AD), and a DNA sequence encoding a third polypeptide. In certain embodiments, a host cell comprises the plasmid vectors.

Disclosed herein, in certain embodiments, is a library of plasmid vectors, each plasmid vector comprising: a DNA sequence encoding a different peptide sequence operably linked to a first switchable promoter; a DNA sequence encoding a death agent under control of a second switchable promoter; and a DNA sequence encoding a positive selection reporter under control of a third switchable promoter. In some embodiments, the different peptide sequence encodes a common N-terminal stabilization sequence. In some embodiments, the DNA sequence encodes a mRNA sequence comprising a 3'UTR. In some embodiments, the different peptide sequence is 60 amino acids or fewer in length. In some embodiments, the different peptide sequences are random. In some embodiments, the different peptide sequences are pre-enriched for binding to a target. In some embodiments is a library of host cells, each comprises a library of the plasmid vectors.

Disclosed herein, in certain embodiments, is a library of plasmid vectors, each plasmid vector comprising: a DNA sequence encoding a peptide N-methyltransferase operably linked to a first switchable promoter; a prolyloligopeptidase operably linked to a second switchable promoter; In some embodiments, the different peptide sequence is 18 amino acids or fewer in length. In some embodiments, the different peptide sequences are random. In some embodiments, the different peptide sequences are pre-enriched for binding to a target. In some embodiments is a library of host cells, each comprises a library of the plasmid vectors.

Described herein is a host cell configured to accelerate the degradation of a specific protein. The host cell may express an E3 ubiquitin ligase or a functional fragment thereof; a first fusion protein comprising a first test protein, a first DNA-binding moiety, and a first gene-activating moiety; a death agent, wherein the expression of the death agent is under control of a promoter DNA sequence specific for the first DNA-binding moiety; and a polypeptide of 60 or fewer amino acids, wherein the polypeptide modulates an interaction between the first fusion protein and the E3 ubiquitin ligase in a manner that leads to accelerated degradation of the first fusion protein.

In some embodiments, the host cell further comprises a second fusion protein comprising a second DNA-binding moiety, a second test protein, and a second gene-activation moiety; and a positive selection reporter, wherein the expression of the positive reporter is under control of a second promoter DNA sequence specific for the second DNA-binding moiety.

In some embodiments, the polypeptide encodes an N-terminal sequence for peptide stabilization. In some embodiments, the polypeptide is a macrocycle. In some embodiments, the polypeptide is an N-methylated macrocycle. In some embodiments, the polypeptide is an encoded product of an mRNA, wherein the mRNA comprises a 3'UTR. In some embodiments, the mRNA is an encoded product of a DNA molecule, wherein the DNA molecule is delivered into the host cell exogenously. In some embodiments, synthetic compound libraries can be tested.

In some embodiments, the host cell is a eukaryote or a prokaryote. In some embodiments, the host cell is animal, plant, a fungus, or bacteria. In some embodiments, the host cell is a haploid yeast cell. In some embodiments, the host cell is a diploid yeast cell. In some embodiments, the diploid yeast cell is produced by mating a first host cell comprising DNA sequences encoding the first chimeric gene, the second chimeric gene, and the third chimeric gene, to a second host cell comprising DNA sequences encoding the death agent, positive selection reporter, and the mRNA comprising a nucleotide sequence encoding a polypeptide. In some embodiments, the fungus is *Aspergillus*. In some embodiments, the fungus is *Pichia pastoris*. In some embodiments, the fungus is *Komagataella phaffii*. In some embodiments, the fungus is *Ustilago maydis*.

Disclosed herein are kits for accelerated degradation of selective target proteins. A kit may comprise a first plasmid vector encoding a first fusion protein comprising a first test protein that may be inserted in frame between a first DNA-binding moiety and an activating domain; a second fusion protein that may be inserted in frame between a second DNA-binding moiety and a second activating domain; and the library of plasmid vectors mentioned above.

In some embodiments, the kit further comprises a second plasmid vector configured for expressing an E3 ligase within a host cell. In some embodiments, the first vector may encode an E3 ubiquitin ligase.

Disclosed herein are methods for identifying one or more molecules that elicit degradation of a first test protein. The methods may comprise expressing in a plurality of host cells: (i) an E3 ubiquitin ligase or a functional fragment thereof; and (ii) a first fusion protein comprising a first DNA-binding moiety, the first test protein, and a first gene-activating moiety. The plurality of host cells may each comprise a promoter sequence for controlling expression of a death agent and the first DNA-binding moiety may specifically bind to the promoter sequence such that expression of the death agent is activated in the absence of a molecule that recruits the E3 ubiquitin ligase to the first fusion protein in a manner that results in ubiquitination and premature degradation of the first fusion protein. The method may comprise delivering a different molecule to each of the plurality of host cells and identifying a molecule that elicits degradation of the first test protein based on survival of a cell into which the molecule was delivered.

Disclosed herein, in certain embodiments, is a method for identifying a molecule that selectively facilitates an interaction between a first test protein and a second test protein leading to its degradation, comprising: expressing in the host cell a first fusion protein comprising the first test protein and a DNA-binding moiety and a gene activating moiety; expressing in the host cell a second fusion protein comprising the second test protein a DNA-binding moiety and a gene activating moiety; expressing in the host cell a third protein comprising an E3 ubiquitin ligase; and delivering a molecule from a library to the host cell such that the molecule forms a bridging interaction between the first test protein and the E3 ubiquitin ligase, leading to its selective degradation; wherein a sequence of a gene for expressing a death agent is disposed within the host cell and operably linked a promoter DNA sequence specific for the DNA binding moiety of the first fusion protein; wherein a positive selection reporter is disposed within the host cell and operably linked to a promoter DNA sequence specific for the DNA binding moiety of the second fusion protein. The first test protein may form a functional transcription factor that activates expression of the death agent; and the second test protein may form a functional transcription factor that activates expression of a positive selection reporter.

In some embodiments, the host cell comprises more than one sequence for expressing a death agent that is activated by the promoter DNA sequence specific for a DNA binding moiety. In some embodiments, the host cell comprises more than one sequence for expressing a positive control reporter that is activated by a promoter DNA sequence specific for a DNA binding moiety.

In some embodiments, the host cell comprises an integrated DNA encoding the first fusion protein, an integrated DNA encoding the second fusion protein, an integrated DNA encoding the third fusion protein; a plasmid DNA encoding the death agent; and a plasmid DNA encoding a positive selection reporter.

In some embodiments, the DNA binding moiety is derived from LexA, cI, Gli-1, YY1, Glucocorticoid receptor, TetR, or Ume6. In some embodiments, the gene activating moiety is derived from VP16, Gal4, NF-κB, B42, BP64, VP64, or p65. In some embodiments, the death agent is a genetic element wherein overexpression of genetic material results in growth inhibition of the host cell. In some embodiments, the death agent is an overexpressed product of DNA. In some embodiments, the death agent is an overexpressed product of RNA. In some embodiments, the sequence of the gene for expressing the death agent is a Growth Inhibitory (GIN) sequence such as GIN11. In some embodiments, the death agent is a ribosomally encoded xenobiotic agent, a ribosomally-encoded poison, a ribosomally-encoded endogenous or exogenous gene that results in severe growth defects upon mild overexpression, a ribosomally-encoded recombinase that excises an essential gene for viability, a limiting factor involved in the synthesis of a toxic secondary metabolite, or any combination thereof. In some embodiments, the death agent is Cholera toxin, SpvB toxin, CARDS toxin, SpyA Toxin, HopUl, Chelt toxin, Certhrax toxin, EFV toxin, ExoT, CdtB, Diphtheria toxin, ExoU/VipB, HopPtoE, HopPtoF, HopPtoG, VopF, YopJ, AvrPtoB, SdbA, SidG, VpdA, Lpg0969, Lpg1978, YopE, SptP, SopE2, SopB/SigD, SipA, YpkA, YopM, Amatoxin, Phallacidin, Killer toxin KP1, Killer toxin KP6, Killer Toxin K1, Killer Toxin K28 (KHR), Killer Toxin K28 (KHS), Anthrax lethal factor endopeptidase, Shiga Toxin, Saporin Toxin, Ricin Toxin, or any combination thereof.

In some embodiments, the first test protein is a variation of KRAS. In some embodiments, the second test protein is KRAS. In some embodiments, the first test protein is androgen receptor splice variants ARV (ARV3, ARV7, or ARV9). In some embodiments, the second test protein is wild-type androgen receptor. In some embodiments, the first test protein is a variation of IDH. In some embodiments, the second test protein is wild-type IDH. In some embodiments, the first test protein is Myc. In some embodiments, the first test protein is CCNE. In some embodiments, the first test protein is Estrogen Receptor (ER). In some embodiments, the first test protein is IKZF1 or IKZF2. In some embodiments, the first test protein is PD-1 or PDL-1. In some embodiments, the first test protein is CTLA-4. In some embodiments, the first test protein is Tau. In some embodiments the first test protein is Act1/CIKS (Connection to IκB Kinase and Stress-activated protein kinases). In some embodiments the first test protein is an Ets Transcription factor variant (ETV1, ETV2, ETV3, ETV4, or ETV5).

In some embodiments, the molecule is small molecule. In some embodiments, the small molecule is peptidomimetic. In some embodiments, the molecule is peptide or protein. In some embodiments, the peptide or protein is derived from naturally occurring protein product. In some embodiments, the peptide or protein is synthesized protein product. In some embodiments, the peptide or protein is product of recombinant genes. In some embodiments, the peptide or protein is expressed product of test DNA molecule inserted into the host cell, wherein the test DNA molecule comprises of DNA sequences that encodes polypeptides, forming the library. In some embodiments, the library comprises of sixty or fewer amino acids.

In some embodiments, the peptide or protein is a product of post-translational modification. In some embodiments, the post-translational modification includes cleavage. In some embodiments, the post-translational modification includes cyclization. In some embodiments, the post-translational modification includes bi-cyclization. In some embodiments, the cyclization comprises reacting with prolyl endopeptidase. In some cases, the prolyl endopeptidase may be one selected from SEQ ID NOs: 42-58 or functional fragments thereof. In some cases, the prolyl endopeptidase may be one with at least 80%, 85%, 90%, 92%, 95%, 97% or 99% sequence identity to one of SEQ ID NOs: 42-58.

In some embodiments, the cyclization comprises reacting with beta-lactamase. In some cases, the lactamase may be one selected from SEQ ID NOs: 119-120 or functional fragments thereof. In some cases, the lactamase may be one with at least 80%, 85%, 90%, 92%, 95%, 97% or 99% sequence identity to one of SEQ ID NOs: 119-120.

In some embodiments, the bicyclization comprises reacting with hydroxylase and dehydratase. In some cases, the hydroxylase may comprise SEQ ID NO: 123 or functional fragments thereof. In some cases, the hydroxylase may be one with at least 80%, 85%, 90%, 92%, 95%, 97% or 99% sequence identity to SEQ ID NO: 123. In some cases, the dehydratase may be one selected from SEQ ID NOs: 124-127 or functional fragments thereof. In some cases, the dehydratase may be one with at least 80%, 85%, 90%, 92%, 95%, 97% or 99% sequence identity to one of SEQ ID NOs: 124-127.

In some embodiments, the bicyclization is formed by a tryptathionine bridge. In some embodiments, the post-translational modification includes methylation. In some embodiments, the methylation comprises reacting with N-methyltransferase. In some cases, the N-methyltransferase is one selected from SEQ ID NOs: 61-116 or functional fragments thereof. In some cases, the N-methyltransferase may be one with at least 80%, 85%, 90%, 92%, 95%, 97% or 99% sequence identity to one of SEQ ID NOs: 61-116. In some embodiments, the post-translational modification includes halogenation. In some embodiments, the post-translational modification includes glycosylation. In some embodiments, the post-translational modification includes acylation. In some embodiments, the post-translational modification includes phosphorylation. In some embodiments, the post-translational modification includes acetylation.

In some embodiments, the test DNA molecule comprises of gene sequence expressing modifying enzyme. In some embodiments, the test DNA molecule comprises of a gene sequence expressing N-terminal sequence of methionine-valine-asparagine. In some embodiments, the test DNA molecule comprises of a gene sequence encoding a 3'UTR. In some embodiments, the 3'UTR is 3'UTR of sORF1.

In some embodiments, the host cell is a eukaryote or a prokaryote. In some embodiments, the host cell is animal, plant, a fungus, or bacteria. In some embodiments, the fungus is *Aspergillus*. In some embodiments, the fungus is *Pichia pastoris*. In some embodiments, the fungus is *Komagataella phaffii*. In some embodiments, the fungus is *Ustilago maydis*.

Disclosed herein are compositions and methods comprising genes and peptides associated with cyclic and backbone-methylated macrocyclic peptides and macrocyclic peptide production in a cell. In particular, the present invention relates to using genes and proteins from *Gymnopus* species encoding peptides specifically relating to gymnopeptides in addition to proteins involved with processing of such types of cyclic peptides. In a preferred embodiment, the present invention also relates to methods for making small peptides and small cyclic peptides including peptides like gymnopeptides through heterologous expression in a eukaryotic, prokaryotic, or cell free system.

The methods further describe the uses of the enzymes heterologously to produce libraries of macrocycles, with possible N-terminal methylation events, inside a host cell to enable screening for functional molecules. In some instances, the functional molecules can modulate the interaction of two proteins, either to disrupt or bridge a protein-protein interaction. Also described is selection of modified macrocycles that are able to bridge an interaction between an E3 ubiquitin ligase and a protein, leading to functional degradation of the protein.

In some embodiments, described herein are methods of producing cyclic peptides. The method for producing cyclic peptides may comprise recombinantly expressing a prolyloligopeptidase; and contacting the prolyloligopeptidase with a linear peptide such that the linear peptide is converted to a cyclic peptide; wherein the active site of prolyloligopeptidase does not have a tryptophan residue at a position corresponding to amino acid position 603 of SEQ ID NO: 55, and/or an asparagine residue at a position corresponding to amino acid 563 of SEQ ID NO: 55.

In some embodiments, the prolyloligopeptidase has a leucine at amino acid position 603 corresponding to amino acid position 603 of SEQ ID NO: 55, and/or a serine residue at amino acid position 563 corresponding to amino acid position 563 of SEQ ID NO:55. In some embodiments, the prolyoligopeptidase comprises a sequence corresponding to any one of SEQ ID NOs: 42-58. In some embodiments, the prolyoligopeptidase is one with at least 80%, 85%, 90%, 92%, 95%, 97% or 99% sequence identity to one of SEQ ID NOs: 42-58.

In some embodiments, contacting the prolyloligopeptidase with the linear peptide occurs within a cell. In some embodiments, contacting the prolyloligopeptidase with the linear peptide does not occur within a cell. In some embodiments, the linear peptide is recombinantly expressed. In some embodiments, the cyclic peptide comprises 18 or more amino acids.

In some embodiments, described herein are methods of identifying a cyclic peptide which disrupts an interaction between a first test protein and a second test protein. The method may comprise: (a) expressing in the host cell: (i) a first fusion protein comprising a first DNA-binding moiety, the first test protein, and a first gene-activating moiety; and (ii) a second test protein; and (b) delivering the peptide to the host cell; wherein, in the absence of the cyclic peptide, expression of a death agent is activated.

In some embodiments, described herein are methods of identifying a cyclic peptide which bridges an interaction between a first test protein and a second test protein. The method may comprising: (a) expressing in the host cell: (i) a first fusion protein comprising a first DNA-binding moiety, the first test protein, and a first gene-activating moiety; and (ii) a second test protein; and (b) delivering the peptide to the host cell; wherein, in the absence of the cyclic peptide, expression of a death agent is activated.

In some embodiments, described herein are methods of methylating a peptide. The method may comprise: recombinantly expressing an N-methyl transferase; and contacting the N-methyltransferase with a peptide such that a plurality of nitrogens in the backbone of the peptide are methylated; wherein N-methyl transferase comprises the sequence of one of SEQ ID NOs: 61-116.

In some embodiments, the contacted peptide is a cyclic peptide. In some embodiments, the peptide or cyclic peptide comprises 18 or more amino acids. In some embodiments, contacting the N-methyltransferase with the peptide occurs within a cell. In some embodiments, contacting the N-methyltransferase with the peptide does not occur within a cell. In some embodiments, the peptide is recombinantly expressed.

In some embodiments, described herein are methods for identifying a cyclic peptide that disrupts an interaction between a first test protein and a second test protein. The method may comprise: (a) expressing in the host cell: (i) a first fusion protein comprising a first DNA-binding moiety, the first test protein, and a first gene-activating moiety; and (ii) a second test protein; and (b) delivering the peptide to the host cell; wherein, in the absence of the cyclic peptide, expression of a death agent is activated.

In some embodiments, described herein are methods for identifying a cyclic peptide that bridges an interaction between a first test protein and a second test protein. The method may comprise: (a) expressing in the host cell: (i) a first fusion protein comprising a first DNA-binding moiety, the first test protein, and a first gene-activating moiety; and (ii) a second test protein; and (b) delivering the peptide to the host cell; wherein, in the absence of the cyclic peptide, expression of a death agent is activated.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 5A illustrates the conservation of the tryptophan residue present in the active site of relative prolyloliogopeptidases incapable of macrocyclizing larger peptides. The sequence read illustrates the loss of the tryptophan residue in the active site of a prolyloligopeptidase isolated from *Gymnopus fusipes* capable of macrocyclizing larger peptides. FIG. 5A discloses SEQ ID NOS 129-142, respectively, in order of appearance.

FIG. 5C discloses SEQ ID NOS 143-156, respectively, in order of appearance.

FIGS. 10A-C illustrate a positive readout assay for degradation of a target protein using high throughput screening of bridging agents such as NAA, PAA, and 2,4-DCPA.

DETAILED DESCRIPTION

Figure 1:
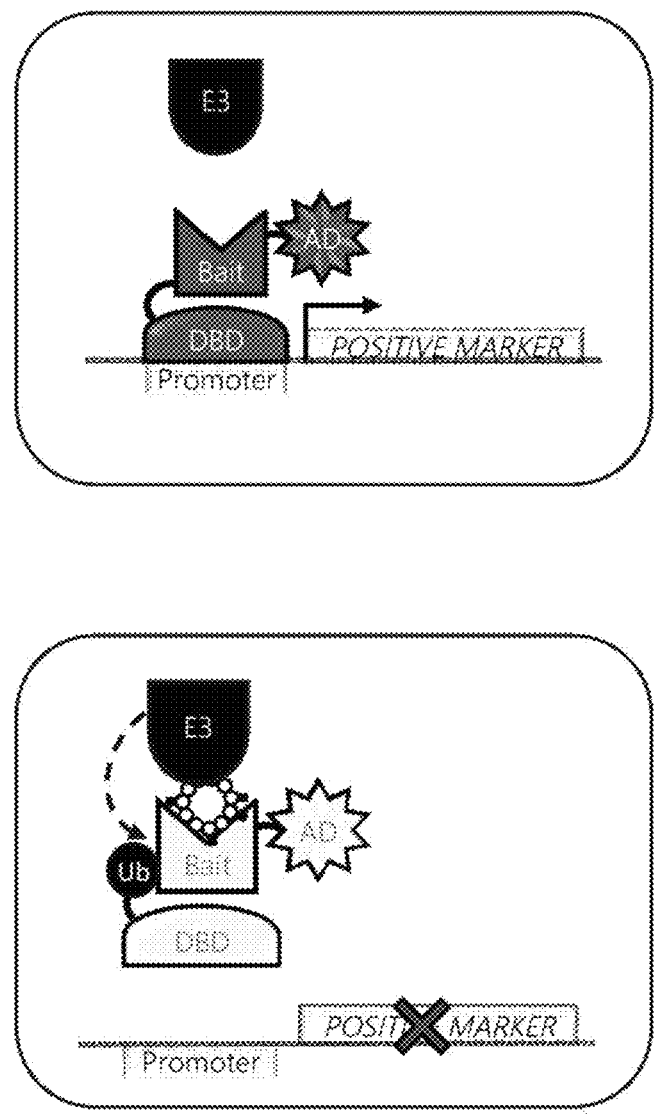
FIG. 1 illustrates a platform to identify a compound that specifically mediates a protein (Bait) interaction with an E3 ubiquitin ligase leading to its degradation and thus causing a loss of expression of a positive marker required for cell growth.

The present disclosure provides a system that can use a unified eukaryotic or prokaryotic one-hybrid system in which a bait expression plasmid is used in both organismal contexts. Additionally, an extensive series of leucine zipper fusion proteins of known affinities can be generated to compare the efficiency of interaction detection using such systems. The yeast system can produce a quantitative readout over a dynamic range. In addition, modified expression vectors disclosed herein can be used for expression of a protein of interest in both eukaryotes and prokaryotes.

The present disclosure also provides a system for delivering molecules across the cell membrane. The cell membrane presents a major challenge in drug discovery, especially for biologics such as peptides, proteins, and nucleic acids. One potential strategy to subvert the membrane barrier and deliver biologics into cells is to attach them to "cell penetrating peptides" (CPPs). Despite three decades of investigation, the fundamental basis for CPP activity remains elusive. CPPs that enter cells via endocytosis generally exit from endocytic vesicles in order to reach the cytosol. Unfortunately, the endosomal membrane has proven to be a significant barrier towards cytoplasmic delivery of these CPPs such that often a negligible fraction of the peptides escapes into the cell interior. What are thus needed are new scaffolds and structures that impart peptides with highly proficient intrinsic cell penetrating ability to various cell types. Several naturally occurring polyketides and peptides exhibit remarkable cell permeability (e.g. cyclosporine and amanitins). These peptides are characterized by specific modifications (e.g., N-methylation of the backbone and cyclization or bicyclization) that can play a crucial role in their cell membrane permeability. The compositions and methods disclosed herein describe methods and approaches that enable the general utilization of similar modifications to generate compositions that may be of high therapeutic value and that may be capable of degrading proteins with high selectivity.

Definitions

As used herein, "reporter gene" refers to a gene whose expression can be assayed. Such genes include, for example, LacZ, β-glucuronidase (GUS), amino acid biosynthetic genes, the yeast LEU2, HIS3, LYS2, or URA3 genes, nucleic acid biosynthetic genes, the mammalian chloramphenicol transacetylase (CAT) gene, the green fluorescent protein (GFP) or any surface antigen gene for which specific antibodies are available. Reporter genes can result in both positive and negative selection.

An "allele" refers to a DNA sequence of a gene which includes a naturally occurring, or pathogenic variant of a gene. Expression of differing alleles may lead to different protein variants.

A "promoter" is a DNA sequence located proximal to the start of transcription at the 5' end of an operably linked transcribed sequence. The promoter can contain one or more regulatory elements or modules, which interact in modulating transcription of the operably linked gene. Promoters can be switchable or constitutive. Switchable promoters allow for reversible induction or repression of operably linked target genes upon administration of an agent. Examples of switchable promoters include but are not limited to the LexA operator and the alcohol dehydrogenase I (alcA) gene promoter. Examples of constitutive promoters include the human beta-actin gene promoter.

"Operably linked" describes two macromolecular elements arranged such that modulating the activity of the first element induces an effect on the second element. In this manner, modulation of the activity of a promoter element can be used to alter or regulate the expression of an operably-linked coding sequence. For example, the transcription of a coding sequence that is operably-linked to a promoter element can be induced by factors that activate the promoter's activity; transcription of a coding sequence that is operably-linked to a promoter element can be inhibited by factors that repress the promoter's activity. Thus, a promoter region is operably-linked to the coding sequence of a protein if transcription of such coding sequence activity is influenced by the activity of the promoter.

"In frame" as used herein throughout, refers to the proper positioning of a desired sequence of nucleotides within a DNA fragment or coding sequence operably linked to a promoter sequence, thereby permitting transcription and/or translation.

"Fusion construct" refers to recombinant genes that encode fusion proteins.

A "fusion protein" is a hybrid protein, i.e., a protein that has been constructed to contain domains from at least two different proteins. Fusion proteins described herein can be a hybrid proteins that possess both (1) a transcriptional regulatory domain from a transcriptional regulatory protein or a DNA binding domain from a DNA binding protein and (2) a heterologous protein to be assayed for interaction status. The protein that is the source of the transcriptional regulatory domain may different from the protein that is the source of the DNA binding domain. In other words, the two domains may be heterologous to each other.

A transcriptional regulatory domain of a bait fusion protein can either activate or repress transcription of target genes, depending on the biological activity of the domain. Bait proteins of the disclosure may also be part of a fusion protein where a protein of interest is operably linked to a DNA binding moiety and a transcriptional activation domain.

"Bridging interaction" refers to an interaction between a first protein and a second that occurs only when one or both of the first protein and the second protein interact with a molecule, such as a peptide or small molecule from a library. In some cases, the bridging interaction between the first protein and the second protein is direct, while in other cases the bridging interaction between the first protein and the second protein is indirect. In some cases, the interaction leads to an activity of one protein being exerted on a second protein, such as ubiquitination and subsequent degradation.

"Expression" is the process by which the information encoded within a gene is revealed. If the gene encodes a protein, then expression involves both transcription of the DNA into mRNA, the processing of mRNA (if necessary) into a mature mRNA product, and translation of the mature mRNA into protein.

As used herein, a "cloning vehicle" is any entity that is capable of delivering a nucleic acid sequence into a host cell for cloning purposes. Examples of cloning vehicles include plasmids or phage genomes. A plasmid that can replicate autonomously in the host cell is especially desired. Alternatively, a nucleic acid molecule that can insert (integrate) into the host cell's chromosomal DNA is useful, especially a molecule that inserts into the host cell's chromosomal DNA in a stable manner, that is, a manner that allows such molecule to be inherited by daughter cells.

Cloning vehicles are often characterized by one or a small number of endonuclease recognition sites at which such DNA sequences may be cut in a determinable fashion without loss of an essential biological function of the vehicle, and into which DNA may be spliced in order to bring about its replication and cloning.

The cloning vehicle can further contain a marker suitable for use in the identification of cells transformed with the cloning vehicle. For example, a marker gene can be a gene that confers resistance to a specific antibiotic on a host cell.

The word "vector" can be used interchangeably with "cloning vehicle."

As used herein, an "expression vehicle" is a vehicle or vector similar to the cloning vehicle that is especially designed to provide an environment that allows the expression of the cloned gene after transformation into the host. One manner of providing such an environment is to include transcriptional and translational regulatory sequences on such expression vehicles, such transcriptional and translational regulatory sequences being capable of being operably linked to the cloned gene. Another manner of providing such an environment is to provide a cloning site or sites on such vehicle, wherein a desired cloned gene and a desired expression regulatory element can be cloned.

In an expression vehicle, the gene to be cloned is usually operably-linked to certain control sequences such as promoter sequences. Expression control sequences will vary depending on whether the vector is designed to express the operably-linked gene in a prokaryotic or eukaryotic host and can additionally contain transcriptional elements such as enhancer elements, termination sequences, tissue-specificity elements, or translational initiation and termination sites.

A "host" refers to any organism that is the recipient of a cloning or expression vehicle. The host may be a bacterial cell, a yeast cell or a cultured animal cell such as a mammalian or insect cell. The yeast host may be *Saccharomyces cerevisiae*.

A "host cell" as described herein can be a bacterial, fungal, or mammalian cell or from an insect or plant. Examples of bacterial host cells are *E. coli* and *B. subtilis*. Examples of fungal cells are *S. cerevisiae* and *S. pombe*. Non-limiting examples of mammalian cells are immortalized mammalian cell lines, such as HEK293, A549, HeLa, or CHO cells, or isolated patient primary tissue cells that have been genetically immortalized (such as by transfection with hTERT). Non-limiting example of the plant is *Nicotiana tabacum* or *Physcomitrella patens*. A non-limiting example of insect cell is a sf9 (*Spodoptera frugiperda*) cell.

A "DNA-binding domain (DBD)," or a "DNA-binding moiety" is a moiety that is capable of directing specific polypeptide binding to a particular DNA sequence (i.e., a "protein binding site"). These proteins can be homodimers or monomers that bind DNA in a sequence specific manner. Exemplary DNA-binding domains of the disclosure include LexA, cI, glucocorticoid receptor binding domains, and the Ume6 domain.

A "gene activating moiety" or "activation domain" ("AD") is a moiety that is capable of inducing (albeit in many instances weakly inducing) the expression of a gene to whose control region it is bound (one example is an activation domain from a transcription factor). As used herein, "weakly" is meant below the level of activation effected by GAL4 activation region II and is preferably at or below the level of activation effected by the B42 activation domain. Levels of activation can be measured using any downstream reporter gene system and comparing, in parallel assays, the level of expression stimulated by the GAL4 region II-polypeptide with the level of expression stimulated by the polypeptide to be tested.

The term "sequence identity" as used herein in the context of amino acid sequences is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

Screening for Functional Degraders of a Target Protein

Selective protein degradation is a unique approach to drug discovery. The ability to selectively degrade an aberrant protein or its isoform poses a controlled approach to selectively target certain pathologies such as cancer. Compounds that accomplish selective degradation through bridging to E3 ubiquitin ligases are catalytic in nature, and are not required in stoichiometric levels, making them lucrative drug compounds. Screening for compounds that selectively bridge a protein of interest to an E3 ubiquitin ligase doesn't always guarantee a functional degradation of the target protein in question. Screening for compounds that are able to functionally degrade a target protein by forming a transient tertiary complex between itself, the target, and an E3 ligase is difficult to perform. Current screens rely on identifying compounds specific to the target and chemically linking them to anther moiety that binds to a specific E3 ligase, creating large molecules that are limited to targets with known small molecule binders.

Methods and systems of the disclosure can involve the intracellular selection of peptide based selective degraders. Stated differently, various systems described herein can be used to screen for molecules that selectively lead to the degradation of a target protein by creating a functional interaction between the target protein and an E3 ubiquitin ligase or directly to the proteasome. A model organism, for example *Saccharomyces cerevisiae*, can be employed, for the coexpression of a target of interest with a specific E3 ubiquitin ligase and a test DNA molecule comprising a DNA sequence that encodes a randomized peptide library. This can allow for the selection of unbiased peptides that lead to a functional degradation of the target of interest using selection mechanisms (e.g., stringent viability readout selection mechanisms). The method can involve a permutation of a yeast one-hybrid system that can rely on the degradation of a transcription factor that requires an interaction between the test protein fused to a DNA binding domain (DBD) and transcription activation domain (AD) by the proteasome or through a specific E3 ubiquitin ligase via a peptide-mediated interaction (see FIGS. 1 and 2).

Methods and systems of the disclosure can use the reconstitution of a transcription factor mediated by a test protein fused to an AD, for example, VP16, NF-κB AD, VP64AD, BP64 AD, B42 acidic activation domain (B42AD), or p65 transactivation domain (p65AD) and a DBD, for example, LexA, cI, Gli-1, YY1, glucocorticoid receptor binding domain, or Ume6 domain. Similarly, the test protein can comprise an AD and bind to DNA through another binding partner.

Methods and system of the disclosure can also use two different proteins, or two variants of one protein, fused to different DBDs and ADs. The system can identify compounds that bridge one of the proteins to an E3 ligase leading to its degradation, while preserving an active version of the other test protein. For example, degrading one component in a complex without affecting the rest of the complex integrity (see FIG. 3). This system can also be used to identify selective inhibitors that degrade a specific isoform without affecting another variant (see FIG. 4).

Expression of the protein of interest can direct RNA polymerase to a specific genomic site and allow for the expression of a genetic element. The genetic element can be, for example, a gene that encodes a protein that enables an organism to grow on selection media. The selection media can be specific to, for example, ADE2, URA3, TRP1, KANR, or NATR, and will lack the essential component (Ade, Ura, Trp) or include a drug (G418, NAT). Markers that can detect when a protein is no longer present (for example when the protein is degraded by an external composition) can be referred to as counter-selection markers, such as the URA3 gene, and can be poor or leaky (easily masked by the selection of mutants that escape the selection). This leakiness of the selection marker can lead to a high false positive rate.

Methods and systems of the disclosure can combine a strong negative selection marker with the intracellular stabilization of the production of short peptides or macrocycles to screen for mediators of bridging interactions between a target protein and an E3 ubiquitin ligase. An inducible one-hybrid approach can be employed, which can drive the expression of any one or combination of several cytotoxic reporters (death agents) as well as positive selection markers. A method of the disclosure involving induced expression of a combination of cytotoxic reporters in a one-hybrid system can allow for a multiplicative effect in lowering the false-positive rate of the one-hybrid assay, as all of the cytotoxic reporters must simultaneously be "leaky" to allow for an induced cell to survive.

Disclosed herein, in certain embodiments, is a method for identifying a molecule that can selectively bridge an interaction between a first test protein and an E3 ubiquitin ligase to mediate functional degradation of the test protein in a host cell. A second test protein may be used as a positive control, such as, while the molecule mediates degradation of the first test protein, it may not affect expression of the second test protein. The method may comprise expressing in the host cell a first fusion protein comprising the first test protein and a DNA-binding moiety and a gene activating moiety; an E3 ubiquitin ligase or a fragment thereof or in some cases, the E3 ubiquitin ligase and its associated machinery; and delivering a molecule from a library to the host cell. The host cell may comprise a promoter sequence for controlling expression of a death agent. The promoter may be specific to the DNA-binding moiety in the first fusion protein such that in the absence of the molecule, expression of the death agent is activated. When the molecule is present, the first test protein may be degraded by the E3 ubiquitin ligase.

FIG. 1 shows an example of the method to identify a compound that bridges a protein-protein interaction between a target bait protein and an E3 ubiquitin ligase, wherein the bridging between the two proteins leads to a functional ubiquitination of the target bait protein and its subsequent degradation. DBD refers to a specific DNA-binding domain. AD refers to an activation domain. E3 refers to an E3 ubiquitin ligase of interest. The broken arrow indicates functional ubiquitination of the bait protein leading to its degradation and prevention of its activation of the death agent. The circle refers to a peptide, macrocycle or a small molecule. These could be from a library. In this example, survival of the cells can be assayed with or without a bridging agent. The top panel illustrates a base case where the bait is driving the expression of a positive marker required for cell growth. The panel below shows the case where a bridging agent is able to functionally bridge the bait protein to a specific E3 ligase of interest. In this case, the bait becomes degraded and cells cannot grow, as they cannot express the positive marker required for growth.

Figure 2:
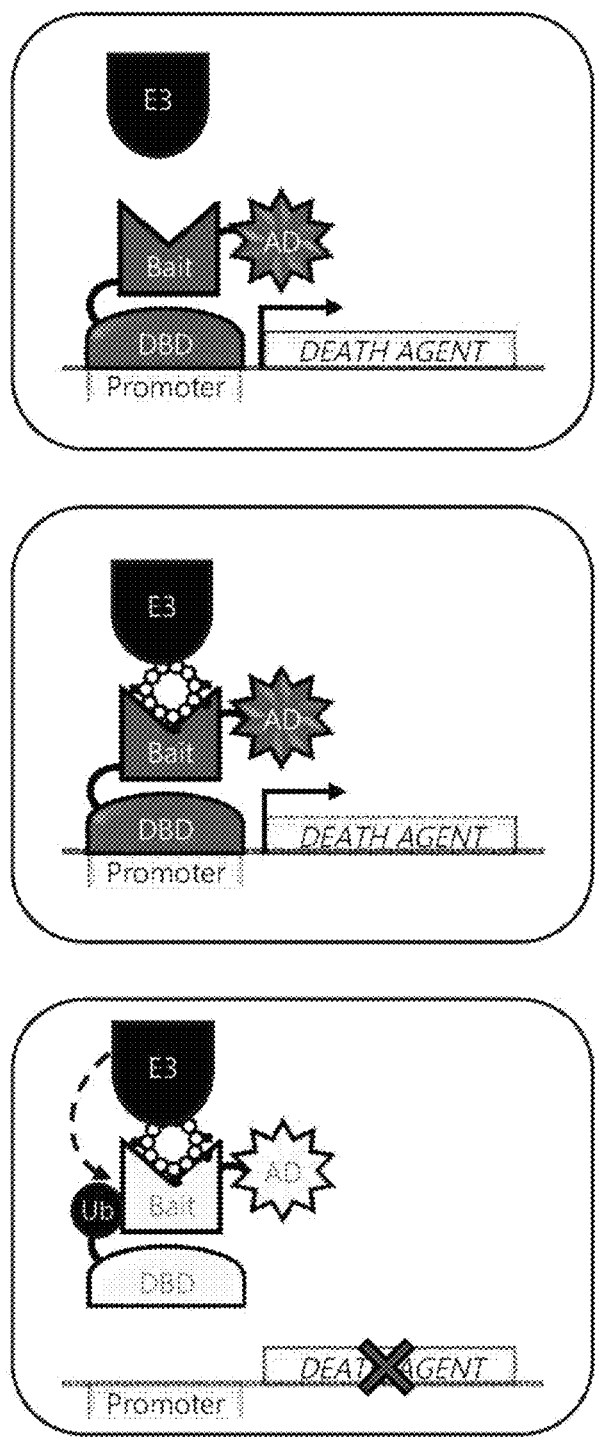
FIG. 2 illustrates a platform to identify a compound that mediates a protein interaction with an E3 ubiquitin ligase leading to its degradation.

FIG. 2 Shows an example wherein the target bait is operationally linked to a negative selection marker that prevents growth in the presence of the target. Three scenarios are shown; the top panel illustrates a base case where the bait is driving the expression of a death agent, leading to cell death. The following panel illustrates a case where a compound is able to bridge an interaction between a bait protein and an E3 ligase but does not lead to functional ubiquitination and subsequent degradation, leading to the expression of the death agent, and cell death. The bottom panel shows a case where a compound is able to bridge between the bait protein and an E3 ligase that leads to its degradation and the loss of transcription of the death agent, leading to cell survival. In some embodiments, a peptide library may be replaced with an exogenous library that includes compounds other than peptides like small molecules. In some embodiments, the small molecules are peptidomimetics.

Figure 3:
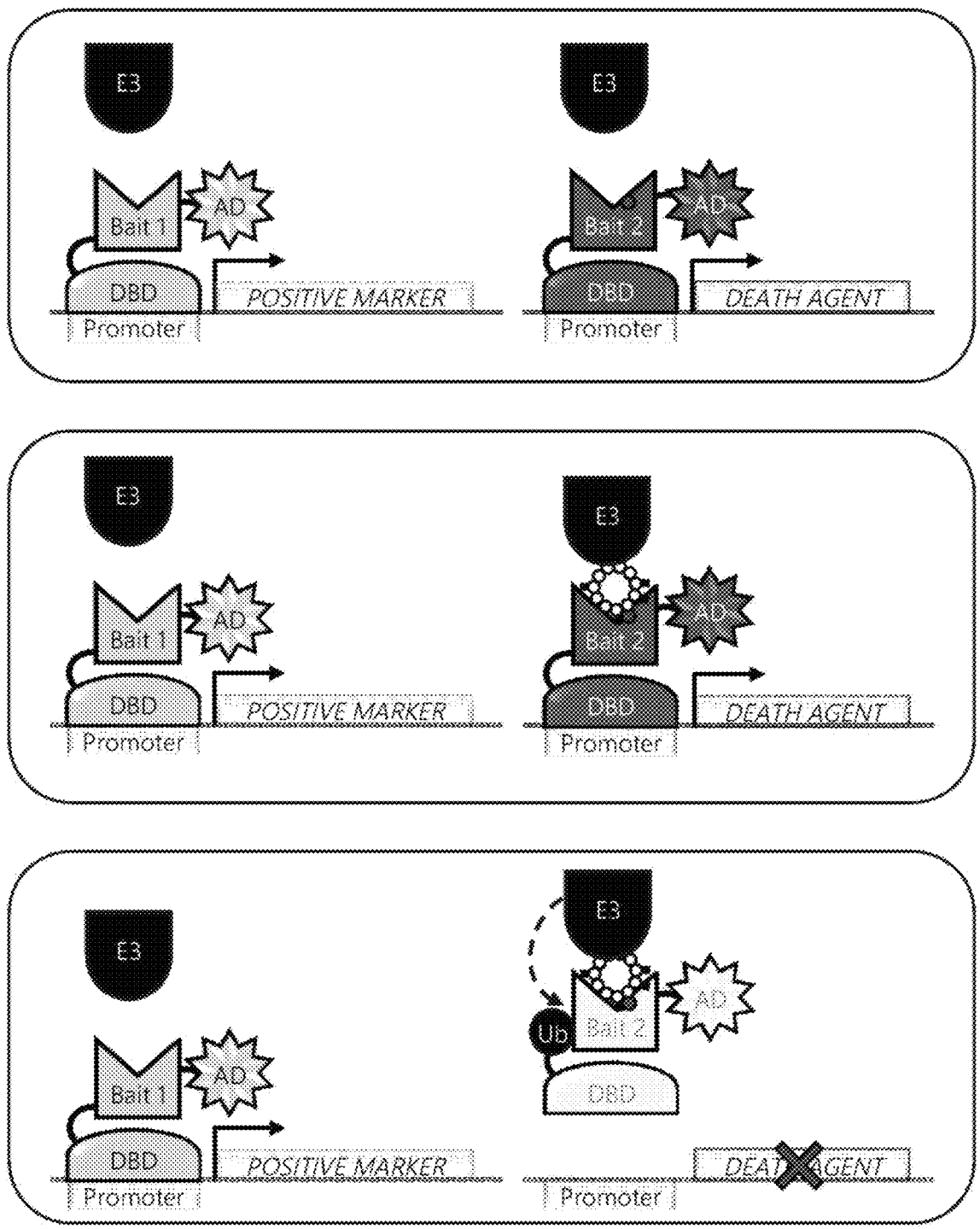
FIG. 3 illustrates a platform to identify a compound that specifically mediates a protein (Bait 2) interaction with an E3 ubiquitin ligase leading to its degradation, while maintaining the active expression of another protein (Bait 1).
Figure 4:
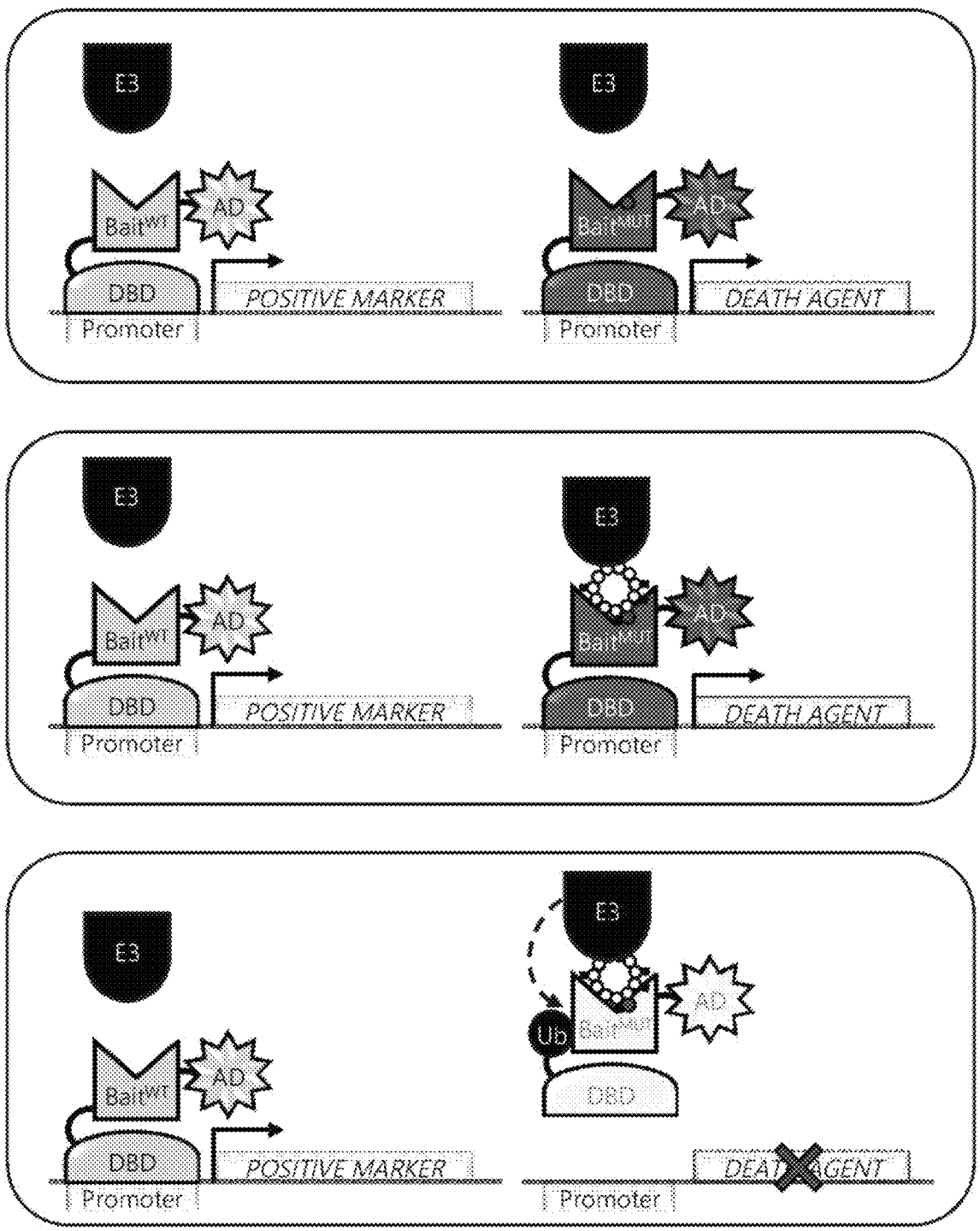
FIG. 4 illustrates a platform to identify a compound that specifically mediates a protein (Bait$^{MUT}$) interaction with an E3 ubiquitin ligase leading to its degradation, while maintaining the active expression of another protein (Bait$^{WT}$).

FIGS. 3 and 4 show a platform to identify a compound that degrades a bait target protein in a variant-specific manner. FIG. 3 describes an analogous assay in which Bait 1 and Bait 2 are related (but different) proteins (e.g., protein variants). FIG. 4 describes an analogous assay in which $Bait^{WT}$ refers to a WT allele of a protein and $Bait^{MUT}$ refers to a pathological allele that is targeted for degradation. As in FIG. 2, DBD refers to a promoter-specific DNA-binding domain. AD refers to an activation domain. E3 refers to an E3 ubiquitin ligase of interest. The broken arrow indicates functional ubiquitination of the bait protein leading to its degradation and prevention of its activation of the death agent. The circle refers to a peptide, macrocycle or a small molecule. Three scenarios are shown; the top panel illustrates a base case where each bait is driving the expression of either a positive marker or a death agent, leading to cell death. The following panel illustrates a case where a compound is able to bridge an interaction between a bait protein and an E3 ligase but does not lead to functional ubiquitination and subsequent degradation, leading to cell death. The bottom panel shows a case where a compound is able to bridge between the bait protein and an E3 ligase that leads to its degradation and the loss of transcription of the death agent, leading to cell survival. In all cases, selection against degradation of the non-specific protein is avoided by requiring its functional presence to drive a positive selection marker. Selective peptide-mediated degradation is assayed by survival due to (1) the absence of expression of the death agent and (2) and expression of the positive selection reporter (which provides evidence of selectivity).

In some embodiments, a screen to identify a peptide or small molecule that can mediate the degradation of a target protein may involve testing the peptide or small molecule against a population of host cells in which different cells in the population express different E3 ligases. The host cells can then be transformed with or otherwise subjected to a candidate peptide/small molecule from a library. In such cases, each of the host cells may comprise the same target protein and/or death agent. Surviving cells may be sequenced to identify the E3 ligase that successfully interacts with the peptide/small molecule. In another example, each well of an assay may comprise a plurality of different host cells in which different host cell express different E3 ligases. A peptide/small molecule from a library may then be transformed or otherwise introduced into each well for the identification of a peptide/small molecule that successfully interacts with the target protein and leads to cell survival.

Examples of targets for degradation are oncogenic proteins such as K-Ras oncogenic alleles, Cyclin D family, Cyclin E family, c-MYC, EGFR, HER2, PDGFR, VEGF and beta-catenin, or oncogenic variants such as IDH1 (R132H, R132S, R132C, R132G, and R132L) or IDH2 (R140Q, R172K).

Examples of E3 ubiquitin ligases that can be used on the system can be chosen from a list including, but not limited to multisubunit E3 ligases of the Culin families (CRL1, CRL2, CRL3, CRL4, CRL5, and CRL7) and single subunit E3 ligases of the RING, RING-Between-RING (RBR), and HECT families consisting of, but not limited to Cereblon, Skp2, MDM2, FBXW7, DCAF1, DCAF15, VHL, AFF4, AMFR, ANAPC11, ANKIB1, AREL1, ARIH1, ARIH2, BARD1, BFAR, BIRC2, BIRC3, BIRC7, BIRC8, BMI1, BRAP, BRCA1, CBL, CBLB, CBLC, CBLL1, CCDC36, CCNB1IP1, CGRRF1, CHFR, CNOT4, CUL9, CYHR1, DCST1, DTX1, DTX2, DTX3, DTX3L, DTX4, DZIP3, E4F1, FANCL, G2E3, HACE1, HECTD1, HECTD2, HECTD3, HECTD4, HECW1, HECW2, HERC1, HERC2, HERC3, HERC4, HERC5, HERC6, HLTF, HUWE1, IRF2BP1, IRF2BP2, IRF2BPL, Itch, KCMF1, KMT2C, KMT2D, LNX1, LNX2, LONRF1, LONRF2, LONRF3, LRSAM1, LTN1, MAEA, MAP3K1, MARCH1, MARCH10, MARCH11, MARCH2, MARCH3, MARCH4, MARCH5, MARCH6, MARCH7, MARCH8, MARCH9, Mdm2, MDM4, MECOM, MEX3A, MEX3B, MEX3C, MEX3D, MGRN1, MIB1, MIB2, MID1, MID2, MKRN1, MKRN2, MKRN3, MKRN4P, MNAT1, MSL2, MUL1, MYCBP2, MYLIP, NEDD4, NEDD4L, NEURL1, NEURL1B, NEURL3, NFX1, NFXL1, NHLRC1, NOSIP, NSMCE1, PARK2, PCGF1, PCGF2, PCGF3, PCGF5, PCGF6, PDZRN3, PDZRN4, PELI1, PELI2, PELI3, PEX10, PEX12, PEX2, PHF7, PHRF1, PJA1, PJA2, PLAG1, PLAGL1, PML, PPIL2, PRPF19, RAD18, RAG1, RAPSN, RBBP6, RBCK1, RBX1, RC3H1, RC3H2, RCHY1, RFFL, RFPL1, RFPL2, RFPL3, RFPL4A, RFPL4AL1, RFPL4B, RFWD2, RFWD3, RING1, RLF, RLIM, RMND5A, RMND5B, RNF10, RNF103, RNF11, RNF111, RNF112, RNF113A, RNF113B, RNF114, RNF115, RNF121, RNF122, RNF123, RNF125, RNF126, RNF128, RNF13, RNF130, RNF133, RNF135, RNF138, RNF139, RNF14, RNF141, RNF144A, RNF144B, RNF145, RNF146, RNF148, RNF149, RNF150, RNF151, RNF152, RNF157, RNF165, RNF166, RNF167, RNF168, RNF169, RNF17, RNF170, RNF175, RNF180, RNF181, RNF182, RNF183, RNF185, RNF186, RNF187, RNF19A, RNF19B, RNF2, RNF20, RNF207, RNF208, RNF212, RNF212B, RNF213, RNF214, RNF215, RNF216, RNF217, RNF219, RNF220, RNF222, RNF223, RNF224, RNF225, RNF24, RNF25, RNF26, RNF31, RNF32, RNF34, RNF38, RNF39, RNF4, RNF40, RNF41, RNF43, RNF44, RNF5, RNF6, RNF7, RNF8, RNFT1, RNFT2, RSPRY1, SCAF11, SH3RF1, SH3RF2, SH3RF3, SHPRH, SIAH1, SIAH2, SIAH3, SMURF1, SMURF2, STUB1, SYVN1, TMEM129, Topors, TRAF2, TRAF3, TRAF4, TRAF5, TRAF6, TRAF7, TRAIP, TRIM10, TRIM11, TRIM13, TRIM15, TRIM17, TRIM2, TRIM21, TRIM22, TRIM23, TRIM24, TRIM25, TRIM26, TRIM27, TRIM28, TRIM3, TRIM31, TRIM32, TRIM33, TRIM34, TRIM35, TRIM36, TRIM37, TRIM38, TRIM39, TRIM4, TRIM40, TRIM41, TRIM42, TRIM43, TRIM43B, TRIM45, TRIM46, TRIM47, TRIM48, TRIM49, TRIM49B, TRIM49C, TRIM49D1, TRIM5, TRIM50, TRIM51, TRIM52, TRIM54, TRIM55, TRIM56, TRIM58, TRIM59, TRIM6, TRIM60, TRIM61, TRIM62, TRIM63, TRIM64, TRIM64B, TRIM64C, TRIM65, TRIM67, TRIM68, TRIM69, TRIM7, TRIM71, TRIM72, TRIM73, TRIM74, TRIM75P, TRIM77, TRIM8, TRIM9, TRIML1, TRIML2, TRIP12, TTC3, UBE3A, UBE3B, UBE3C, UBE3D, UBE4A, UBE4B, UBOX5, UBR1, UBR2, UBR3, UBR4, UBR5, UBR7, UHRF1, UHRF2, UNK, UNKL, VPS11, VPS18, VPS41, VPS8, WDR59, WDSUB1, WWP1, WWP2, XIAP, ZBTB12, ZFP91, ZFPL1, ZNF280A, ZNF341, ZNF511, ZNF521, ZNF598, ZNF645, ZNRF1, ZNRF2, ZNRF3, ZNRF4, Zswim2, and ZXDC.

Expression of Proteins in the Host Cells

One or more plasmid constructs may be used to express different proteins in the host cell. The number of plasmids used may depend on the host cell, presence of integrated constructs in the host cell amongst other conditions.

In some cases, a method of identifying a molecule that elicits degradation of a first test protein may use proteins such as: an E3 ubiquitin ligase, a molecule from a library of molecules and a first fusion protein comprising a first test protein, a first DNA-binding moiety and a gene-activating domain. The method may also use a promoter driving the expression of a death agent, such as the promoter sequence is specific for the first DNA-binding moiety. In addition to this scheme, in some cases, the method may also utilize a second fusion protein comprising a second DNA-binding domain and a gene-activating moiety along with a promoter driving the expression of a positive or negative marker such as the promoter sequence is specific for the second DNA-binding moiety.

The proteins and nucleic acid sequences mentioned above may be provided to the host cell in the form of plasmids. In some cases, the nucleic acid sequences of the proteins and nucleic acids comprising the promoter and death agents/positive and negative markers may be integrated into the host cell. In some cases, the molecule from a library of molecules is a small molecule/compound and does not need to be encoded on a plasmid.

For instance, in one example, the first fusion protein may be provided in a plasmid (Plasmid 1), the E3 ubiquitin ligase may be provided in a separate plasmid (Plasmid 2) and the DNA encoded molecule from a library may be provided in a separate plasmid (Plasmid 3). All three plasmids may be transfected into a plurality of host cells. In cases where a second fusion protein is also being used, the second fusion protein may be provided in plasmid 1 or in a separate plasmid (Plasmid 4). The expression constructs of the plasmids may also be combined in one or two plasmids to reduce the number of plasmids to be transfected. Additionally, the constructs comprising the promoters driving the death agent or the positive/negative selection markers may also be provided in the plasmids or otherwise, they may be integrated into the host cell.

In another instance, the first fusion protein may be genetically integrated into the host cell whereas Plasmids 2 and 3 comprising the E3 ubiquitin ligase and the molecule from the library of molecules are transfected into the host cell. In this example, the second fusion protein may also be integrated into the host cell or in some cases, be provided as a plasmid.

In yet another instance, the first fusion protein and the E3 ubiquitin ligase are both integrated into the host cell and the molecule from the library of molecules is transfected in the form of a plasmid into the host cell. The second fusion protein, as mentioned above, may be integrated into the host cell or it may be provided in a plasmid form. The constructs comprising the promoters driving the death agent or the positive/negative selection markers may also be provided in the plasmids or otherwise, they may be integrated into the host cell.

In another instance, the first fusion protein may be transfected in a plasmid for/integrated into the host cell but an endogenous E3 ubiquitin ligase is used in which case, the integration or transfection of a plasmid containing the E3 ligase may not be needed.

In some cases, the nucleic acid sequences for the fusion protein/proteins, the E3 ubiquitin ligase, the promoter driving the death agent (and promoter driving the positive/negative selection marker, if it is being used) may all be integrated into the host cell. In this case, just a single plasmid comprising the molecule from a library of molecules may be transfected into the host cell.

In some embodiments, the host cell or cells disclosed herein comprises a plasmid vector. The plasmid can contain, for example, two restriction sites that enable the integration of two proteins that constitute the bait and E3 ligase of interest. The bait protein of interest can involve an oncogene (such as Cyclin E family, Cyclin D family, c-MYC, EGFR, HER2, K-Ras, PDGFR, Raf kinase, and VEGF). The bait protein of interest can involve an effector of an inflammatory response (such as IL-17RA, IL-17RB, IL-17RC, IL17-RD, IL17-RE, Act1 (CIKS), and IL-23R).

A plasmid can be configured to express two proteins that constitute the bait and E3 ligase of interest and an additional factor, for example, a variant of one of the bait protein. The variants for targeting can be KRAS (G12D, G12V, G12C, G12S, G13D, Q61K, or Q61L, etc.) and the control variant is WT KRAS. The additional factor can also be another protein bound to the bait protein, or another target of the E3 ligase.

In some embodiments, the host cell disclosed herein comprise a plasmid wherein a DNA sequence encoding a first polypeptide is inserted in frame with Gal4-DBD and in frame with VP64-AD, and a DNA sequence encoding for a second polypeptide comprising of an E3 ubiquitin ligase.

In some embodiments, the first test protein is a variant of KRAS, the E3 ubiquitin ligase is VHL.

A plasmid can encode for the fusion of an activation domain or another gene activating moiety and a DBD to each protein driven by either a strong promoter and terminator (such as ADH1), or by an inducible promoter (such as GAO. Other exemplary activation domains include those of VP16 and B42AD. In some embodiments, the DNA binding moiety is derived from LexA, TetR, Lad, Gli-1, YY1, glucocorticoid receptor, or Ume6 domain and the gene activating moiety is derived from Gal4, B42, or VP64, Gal4, NF-κB AD, Dof1, BP64, B42, or p65. Each protein fusion can be tagged for subsequent biochemical experiments with, for example, a FLAG, HA, MYC, or His tag. The plasmid can also include bacterial selection and propagation markers (i.e. ori and AmpR), and yeast replication and selection markers (i.e. TRP1 and CEN or 2 um). The plasmid may contain multiple bait proteins fused to different DBDs and ADs. The plasmid can also be integrated into the genome at a specified locus.

Disclosed herein, in certain embodiments, is a library of plasmid vectors, each plasmid vector comprising: a DNA sequence encoding a different peptide sequence operably linked to a first switchable promoter; a DNA sequence encoding a death agent under control of a second switchable promoter; and a DNA sequence encoding a positive selection reporter under control of a third switchable promoter.

Expression of Selection Markers

Positive Selection Markers

An efficient expression of a test protein can direct a RNA polymerase to a specific genomic site, and allow expression of a protein that enables an organism to grow on selection media. The selection media can be specific to, for example, ADE2, URA3, TRP1, KAN$^R$, or NAT$^R$, and can lack the essential component (Ade, Ura, Trp) or can include a drug (G418, NAT). A plasmid can encode for one or more positive selection markers that enable an organism to grow on selection media.

Negative Selection Markers

An inducible one-hybrid approach can be employed, which can drive the expression of any one or combination of several cytotoxic reporters (death agents) as well as positive selection markers. A method of the disclosure involving induced expression of a combination of cytotoxic reporters in a one-hybrid system can allow for a multiplicative effect in lowering the false-positive rate of the one-hybrid assay, as all of the cytotoxic reporters must simultaneously be "leaky" to allow for an induced cell to survive. The cytotoxic reporters can be comprised or contain domains of various polypeptides, for example as shown in Table 1.

TABLE 1

Amino acid sequences of exemplary toxins

| | | |
|---|---|---|
| Cholera toxin (CtxA) | SEQ ID NO.: 1 | MVKIIFVFFIFLSSFSYANDDKLYRADSRPPDEIKQSGGLMPRGQSEYFDRGTQMNIN LYDHARGTQTGFVRHDDGYVSTSISLRSAHLVGQTILSGHSTYYIYVIATAPNMFNV NDVLGAYSPHPDEQEVSALGGIPYSQIYGWYRVHFGVLDEQLHRNRGYRDRYYSNL DIAPAADGYGLAGFPPEHRAWREEPWIHHAPPGCGNAPRSSMSNTCDEKTQSLGVK FLDEYQSKVKRQIFSGYQSDIDTHNRIKDEL |
| SpvB toxin (Salmonella enterica) | SEQ ID NO.: 2 | MLILNGFSSATLALITPPFLPKGGKALSQSGPDGLASITLPLPISAERGFAPALALHYSS GGGNGPFGVGWSCATMSIARRTSHGVPQYNDSDEFLGPDGEVLVQTLSTGDAPNPV TCFAYGDVSFPQSYTVTRYQPRTESSFYRLEYWVGNSNGDDFWLLHDSNGILHLLG KTAAARLSDPQAASHTAQWLVEESVTPAGEHIYYSYLAENGDNVDLNGNEAGRDR SAMRYLSKVQYGNATPAADLYLWTSATPAVQWLFTLVFDYGERGVDPQVPPAFTA QNSWLARQDPFSLYNYGFEIRLHRLCRQVLMFHHFPDELGEADTLVSRLLLEYDENP ILTQLCAARTLAYEGDGYRRAPVNNMMPPPPPPPPMMGGNSSRPKSKWAIVEESK QIQALRYYSAQGYSVINKYLRGDDYPETQAKETLLSRDYLSTNEPSDEEFKNAMSV YINDIAEGLSSLPETDHRVVYRGLKLDKPALSDVLKEYTTIGNIIDKAFMSTSPDKA WINDTILNIYLEKGHKGRILGDVAHFKGEAEMLFPPNTKLKIESIVNCGSQDFASQLS KLRLSDDATADTNRIKRIINMRVLNS |
| CARDS toxin (Mycoplasma pneumoniae) | SEQ ID NO.: 3 | MSENLYFQGHMPNPVREVYRVDLRSPEEIFEHGESTLGDVRNFFEHILSTNFGRSYFI STSETPTAAIRFEGSWLREYVPEHPRRAYLYEIRADQHFYNARATGENLLDLMRQRQ VVEDSGDREMAQMGIRALRTSFAYQREWFTDGPIAAANVRSAWLVDAVPVEPGHA HHPAGRVVETTRINEPEMHNPHYQELQTQANDQPWLPTPGIATPVHLSIPQAASVAD VSEGTSASLSFACPDWSPPSSNGENPLDKCIAEKIDNYNLQSLPQYASSVKELEDTPV YLRGIKTQKTFMLQADPQNNNVELVEVNPKQKSSFPQTIFFWDVYQRICLKDLTGA QISLSLTAFTTQYAGQLKVHLSVSAVNAVNQKWKMTPQDIAITQFRVSSELLGQTEN GLEWNTKSGGSQHDLYVCPLKNPPSDLEELQIIVDECTTHAQFVTMRAASTFFVDVQ LGWYWRGYYYTPQLSGWSYQMKTPDGQIFYDLKTSKIFFVQDQNQNVFFLHNKLNK QTGYSWDWVEWLKHDMNEDKDENFKWYESRDDLTIPSVEGLNFRHIRCYADNQQ LKVIISGSRWGGWYSTYDKVESNVEDKILVKDGFDRF |
| SpyA Toxin (Streptococcus pyogenes) | SEQ ID NO.: 4 | MLKKRYQLAMILLLSCFSLVWQTEGLVELFVCEHYERAVCEGTPAYFTFSDQKGAE TLIKKRWGKGLVYPRAEQEAMAAYTCQQAGPINTSLDKAKGKLSQLTPELRDQVA QLDAATHRLVIPWNIVVYRYVYETFLRDIGVSHADLTSYYRNHQFNPHILCKIKLGT RYTKHSFMSTTALKNGAMTHRPVEVRICVKKGAKAAFVEPYSAVPSEVELLFPRGC QLEVVGAYVSQDHKKLHIEAYFKGSL |
| HopU1 (Pseudomonas syringae) | SEQ ID NO.: 5 | MNINRQLPVSGSERLLTPDVGVSRQACSERHYSTGQDRHDFYRFAARLHVDAQCFG LSIDDLMDKFSDKHFRAEHPEYRDVYPEECSAIYMETAQDYSSHLVRGEIGTPLYRE VNNYLRLQHENSGREAEIDNHDEKLSPHIKMLSSALNRLMDVAAFRGTVYRGIRGD LDTIARLYHLFDTGGRYVEPAFMSTTRIKDSAQVFEPGTPNNIAFQISLKRGADISGSS QAPSEEEIMLPMMSEFVIEHASALSEGKHLFVLSQI |
| Chelt toxin | SEQ ID NO.: 6 | MKTIISLIFINIFPLFVSAHNGNFYRADSRSPNEIKDLGGLYPRGYYDFFERGTPMSISL YDHARGAPSGNTRYDDGEVSTTTDIDSAHEIGQNILSGYTEYYIYLIAPAPNLLDVNA VLGRYSPHPQENEYSALGGIPWTQVIGWYVVNNGVLDRNIHRNRQFRADLFNNLSP ALPSESYQFAGFEPEHPAWRQEPWINFAPPGCGRNVRLTKHINQQDCSNSQEELVYK KLQDLRTQFKVDKKLKLVNKTSSNNIIFPNHDFIREWVDLDGNGDLSYCGFTVDSD GSRKRIVCAHNNGNFTYSSINISLSDYGWPKGQRFIDANGDGLVDYCRVQYVWTHL YCSLSLPGQYFSLDKDAGYLDAGYNNSRAWAKVIGTNKYSFCRLTSNGYICTDIDSY STAFKDDDQGWADSRYWMDIDGNGGDDYCRLVYNWTHLRCNLQGKDGLWKRVE SKYLDGGYPSLRFKIKMTSNKDNYCRIVRNHRVMECAYVSDNGEFHNYSLNMPFSL YNKNDIQFIDIDGDNRDDICRYNSAPNTMECYLNQDKSFSQNKLVLYLSAKPISSLGS GSSKIIRTFNSEKNSSAYCYNAGYGTLRCDEFVIY |
| Certhrax toxin | SEQ ID NO.: 7 | MKEIIRNLVRLDVRSDVDENSKKTQELVEKLPHEVLELYKNVGGEIYITDKRLTQHE ELSDSSHKDMFIVSSEGKSFPLREHFVFAKGGKEPSLIIHAEDYASHLSSVEVYYELG KAIIRDTFPLNQKELGNPKFINAINEVNQQKEGKGVNAKADEDGRDLLFGKELKKNL EHGQLVDLDLISGNLSEFQHVFAKSFALYYEPHYKEALKSYAPALFNYMLELDQMR FKEISDDVKEKNKNVLDFKWYTRKAESWGVQTFKNWKENLTISEKDIITGYTGSKY DPINEYLRKYDGEIIPNIGGDLDKKSKKALEKIENQIKNLDAALQKSKITENLIVYRRV SELQFGKKYEDYNLRQNGIINEEKVMELESNFKGQTFIQHNYMSTSLVQDPHQSYSN DRYPILLEITIPEGVHGAYIADMSEYPGQYEMLINRGYTEKYDKESIVKPTREEDKGK EYLKVNLSIYLGNLNREK |

TABLE 1-continued

Amino acid sequences of exemplary toxins

| | | |
|---|---|---|
| EFV toxin | SEQ ID NO.: 8 | MSQLNKWQKELQALQKANYQETDNQLFNVYRQSLIDIKKRLKVYTENAESLSFSTR<br>LEVERLFSVADEINAILQLNSPKVEKTIKGYSAKQAEQGYYGLWYTLEQSQNIALSM<br>PLINHDYIMNLVNAPVAGKRLSKRLYKYRDELAQNVTNNIITGLFEGKSYAEIARWI<br>NEETEASYKQALRIARTEAGRTQSVTTQKGYEEAKELGINIKKKWLATIDKHTRRTH<br>QELDGKEVDVDEEFTIRGHSAKGPRMFGVASEDVNCRCTTIEVVDGISPELRKDNES<br>KEMSEFKSYDEWYADRIRQNESKPKPNFTELDFFGQSDLQDDSDKWVAGLKPEQV<br>NAMKDYTSDAFAKMNKILRNEKYNPREKPYLVNIIQNLDDAISKFKLKHDIITYRGV<br>SANEYDAILNGNVEKEEKSTSINKKVAEDFLNFTSANKDGRVVKFLIPKGTQGAYIG<br>TNSSMKKESEFLLNRNLKYTVEIVDNILEVTILG |
| ExoT | SEQ ID NO.: 9 | MBIQSSQQNPSFVAELSQAVAGRLGQVEARQVATPREAQQLAQRQEAPKGEGLLSR<br>LGAALARPFVAIIEWLGKLLGSRAHAATQAPLSRQDAPPAASLSAAEIKQMMLQKA<br>LPLTLGGLGKASELATLTAERLAKDHTRLASGDGALRSLATALVGIRDGSLIEASRT<br>QAARLLEQSVGGIALQQWGTAGGAASQHVLSASPEQLREIAVQLHAVMDKVALLR<br>HAVESEVKGEPVDKALADGLVEHFGLEAEQYLGEHPDGPYSDAEVMALGLYTNGE<br>YQHLNRSLRQGRELDAGQALIDRGMSAAFEKSGPAEQVVKTFRGTQGRDAFEAVK<br>EGQVGHDAGYLSTSRDPSVARSFAGLGTITTLFGRSGIDVSEISIEGDEQEILYDKGTD<br>MRVLLSAKDGQGVTRRVLEEATLGERSGHSEGLLDALDLATGTDRSGKPQEQDLRL<br>RMRGLDLA |
| CdtB | SEQ ID NO.: 10 | MKKIICLELSFNLAFANLENFNVGTWNLQGSSAATESKWSVSVRQLVSGANPLDILM<br>IQEAGTLPRTATPTGRHVQQGGTPIDEYEWNLGTLSRPDRVFIYYSRVDVGANRVNL<br>AIVSRMQAEEVIVLPPPTTVSRPIIGIRNGNDAFFNIHALANGGTDVGAIITAVDAHFA<br>NMPQVNWMIAGDFNRDPSTITSTVDRELANRIRVVFPTSATQASGGTLDYAITGNSN<br>RQQTYTPPLLAAILMLASLRSHIVSDHFPVNERKF |
| Diptheria toxin | SEQ ID NO.: 11 | MSRKLFASILIGALLGIGAPPSAHAGADDVVDSSKSFVMENFSSYHGTKPGYVDSIQ<br>KGIQKPKSGTQGNYDDDWKGFYSTDNKYDAAGYSVDNENPLSGKAGGVVKVTYP<br>GLTKVLALKVDNAETIKKELGLSLTEPLMEQVGTEEFIKRFGDGASRVVLSLPFAEG<br>SSSVEYINNWEQAKALSVELEINFETRGKRGQDAMYEYMAQACAGNRVRRSVGSS<br>LSCINLDWDVIRDKTKTKIESLKEHGPIKNKMSESPNKTVSEEKAKQYLEEFHQTALE<br>HPELSELKTVTGTNPVFAGANYAAWAVNVAQVIDSETADNLEKTTAALSILPGIGSV<br>MGIADGAVHHNTEEIVAQSIALSSLMVAQAIPLVGELVDIGFAAYNFVESIINLFQVV<br>HNSYNRPAYSPGHKTQPFLHDGYAVSWNTVEDSIIRTGFQGESGHDIKITAENTPLPI<br>AGVLLPTIPGKLDVNKSKTHISVNGRKIRMRCRAIDGDVTFCRPKSPVYVGNGVHAN<br>LHVAFHRSSSEKIHSNEISSDSIGVLGYQKTVDHTKVNSKLSLFFEIKS |
| ExoU/VipB | SEQ ID NO.: 12 | MKLAEIMTKSRKLKRNLLEISKTEAGQYSVSAPEHKGLVLSGGGAKGISYLGMIQAL<br>QERGKIKNLTHVSGASAGAMTASILAVGMDIKDIKKLIEGLDITKLLDNSGVGFRAR<br>GDRERNILDVIYMMQMKKHLESVQQPIPPEQQMNYGILKQKIALYEDKLSRAGIVIN<br>NVDDIINLTKSVKDLEKLDKALNSIPTELKGAKGEQLENPRLTLGDLGRLRELLPEEN<br>KHLIKNLSVVVTNQTKHELERYSEDTTPQQSIAQVVQWSGAHPVLFVPGRNAKGEY<br>IADGGILDNMPEIEGLDREEVLCVKAEAGTAFEDRVNKAKQSAMEAISWFKARMDS<br>LVEATIGGKWLHATSSVLNREKVYYNIDNMIYINTGEVTTNTSPTPEQRARAVKNG<br>YDQTMQLLDSHKQTFDHPLMAILYIGHDKLKDALIDEKSEKEIFEASAHAQAILHLQ<br>EQIVKEMNDGDYSSVQNYLDQIEDILTVDAKMDDIQKEKAFALCIKQVNFLSEGKLE<br>TYLNKVEAEAKAAAEPSWATKILNLLWAPIEWVVSLFKGPAQDFKVEVQPEPVKVS<br>TSENQETVSNQKDINPAVEYRKHAEVRREHTDPSPSLQEKERVGLSTTFGGH |
| HopPtoE | SEQ ID NO.: 13 | MNRVSGSSSATWQAVNDLVEQVSERTTLSTTGYQTAMGRLNKPEKSDADALMTM<br>RRAQQYTDSAKRTYISETLMNLADLQQRKIYRTNSGNLRGAIEMTPTQLTDCVQKC<br>REEGFSNCDIQALEIGLHLRHKLGISDFTIYSNRKLSHNYVVIHPSNAFPKGAIVDSWT<br>GQGVVELDEKTRLKEKHREENYAVNAMHEWIERYGQAHVID |
| HopPtoF | SEQ ID NO.: 14 | MGNICGTSGSRHVYSPSHTQRITSAPSTSTHVGGDTLTSITIQLSHSQREQFLNMHDP<br>MRVMGLDHDTELFRTTDSRYIKNDKLAGNPQSMASILMHEELRPNRFASHTGAQPH<br>EARAYVPKRIKATDLGVPSLNVMTGSLARDGIRAYDHMSDNQVSVKMRLGDFLER<br>GGKVYADASSVADDGETSQALIVTLPKGQKVPVERV |
| HopPtoG | SEQ ID NO.: 15 | MQIKNSHLYASRMVQNTENASPKMEVTNAIAKNNEPAALSATQTAKTHEGDSKG<br>QSSNNSKLPFRAMRYAAYLAGSAYLYDKTANNFFLSTTSLHDGKGGFTSDARLNDA<br>QDKARKRYQNNHSSTLENKNSLLSPLRLCGENQFLTMIDYRAATKIYLSDLVDTEQ<br>AHTSILKNIMCLKGELTNEEAIKKLNPEKTPKDYDLTNSEAYISKNKYSLTGVKNEET<br>GSTGYTSRSITKPFVEKGLKHFIKATHGEKALTPKQCMETLDNLLRKSITLNSDSQFA<br>AGQALLVFRQVYAGEDAWGDAERVILKSHYNRGTVLQDEADKIELSRPFSEQDLAK<br>NMFKRNTSIAGPVLYHAYIYIQEKIFKLPPDKIEDLKHKSMADLKNLPLTHVKLSNSG<br>VGI,EDASGLGDSFTALNATSCVNHARIMSGEPPLSKDDVVILIGCLNAVYDNSSIR<br>HSLREIARGCFVGAGFTVQDGDDFYKQICKNASKQFYNG |
| VopF | SEQ ID NO.: 16 | MFKISVSQQANVMSTSDTAQRSSLKISIKSICNKSLSKKLHTLAEKCRRFSQELKEHT<br>ASKKQIVEQATTTVRESSLTKSDSELGSSRSLLTSDVLSSSSSHEDLTAVNLEDNDSV<br>FVTIESSSELIVKQDGSIPPAPPLPGNIPPAPPLPSAGNIPTAPGLPKQKATTESVAQTSD<br>NRSKLMEEIRQGVKLRATPKSSSTEKSASDPHSKLMKELINHGAKLKKVSTSDIPVPP<br>PLPAAFASKPTDGRSALLSEIAGFSKDRLRKAGSSETLNVSQPTVAESSIPEAYDLLLS<br>DEMFNLSPKLSETELNTLADSLADYLFKAADIDWMQVIAEQTKGSTQATSLKSQLE |

TABLE 1-continued

Amino acid sequences of exemplary toxins

```
                        QAPEYVKAFCDEILKFPDCYKSADVASPESPKAGPSSVIDVALKRLQAGRNRLFSTID
                        AKGTNELKKGEAILESAINAARSVMTAEQKSALLSSNVKSATEKVESELPCMEGFAE
                        QNGKAAFNALRLAFYSSIQSGDTAQQDIARFMKENLATGFSGYSYLGLTSRVAQLE
                        AQLAALTTK

YopJ        SEQ ID      MIGPISQINISGGLSEKETSSLISNEELKNIITQLETDISDGSWFHKNYSRMDVEVMPAL
            NO.: 17     VIQANNKYPEMNLNLVTSPLDLSIEIKNVIENGVRSSRFIINMGEGGIHFSVIDYKHIN
                        GKTSLILFEPANENSMGPAMLAIRTKTAIERYQLPDCHFSMVEMDIQRSSSECGIFSFA
                        LAKKLYIERDSLLKIHEDNIKGILSDGENPLPHDKLDPYLPVTFYKHTQGKKRLNEYL
                        NTNPQGVGTVVNKKNETIVNRFDNNKSIVDGKELSVSVHKKRIAEYKTLLKV

AvrPtoB     SEQ ID      MAGINGAGPSGAYFVGHTDPEPASGGAHGSSSGASSSNSPRLPAPPDAPASQARDRR
            NO.: 18     EMLLRARPLSRQTREWVAQGMPPTAEAGVPIRPQESAEAAAPQARAEEERHTPEADA
                        AASHVRTEGGRTPQALAGTSPRHTGAVPHANRIVQQLVDAGADLAGINTMIDNAM
                        RRHAIALPSRTVQSILIEHFPHLLAGELISGSELATAFRAALRREVRQQEASAPPRTAA
                        RSSVRTPERSTVPPTSTESSSGSNQRTLLGRFAGLMTPNQRRPSSASNASASQRPVDR
                        SPPRVNQVPTGANRVVMRNHGNNEADAALQGLAQQGVDMEDLRAALERHILHRR
                        PIPMDIAYALQGVGIAPSIDTGESLMENPLMNLSVALHRALGPRPARAQAPRPAVPV
                        APATVSRRPDSARATRLQVIPAREDYENNVAYGVRLLSLNPGAGVRETVAAFVNNR
                        YERQAVVADIRAALNLSKQFNKLRTVSKADAASNKPGFKDLADHPDDATQCLFGEE
                        LSLTSSVQQVIGLAGKATDMSESYSREANKDLVFMDMKKLAQFLAGKPEHPMTRET
                        LNAENIAKYAFRIVP

SdbA        SEQ ID      MHKKYNYYSLEKEKKTFWQHILDILKAPERLPGWVVSFFLARNITHVALNPNNIPQQ
            NO.: 19     RLIHLTKTSNRPEDDIVVINFKKRPPHKWENDTLIKIANTIAALPFVTPRLRTRLHYDN
                        ENDINHVNKLLAEIDALVQGKSKQKYCKGRAFDWSKIHLKGLEFLDPKMRGYVYE
                        QLHEKYGYVSYTTKRKPNIEFFTLKTPDGSELDSVQVTGEDEEKKPMGERKFIITCIA
                        RDQNFINWIKDLNYTAKNLGATAISFNYRGVDYSRGLVWTENNLVDDILAQVQRLI
                        SLGADPKNICLDGMCIGGAVATIAAAKLHEGMKVKLNNERSFTSLSSLVFGFIVPE
                        LQTANWWSPLTYGRFLLAGVVYALLTPLIWLAGWPVDVTKAWNRIPAQDKMYSV
                        VRDKDNGLYDGVIHDHFCSIASLVDSQINSILYKLSTDQPLTEEEKQILCDDQFSHHF
                        KPSQSVLKNPKYKGPHFISRQDLVAELGHREEYTNHDYFLDRLREKFQLDRATRPV
                        ALAEDGEKDIDGISSQLSNNKERPLIIASSGGTGHISATHGHNDLQSKTDNVVITQHH
                        AELYKNKPFSITSVLIRIGVWFTSLPILEDILKGVMRFIGYPVLPSSSIFWDQMSKIQQS
                        ETKKENGIETGRTRPYVDMLLDIYPEGYEYTAFNNATHLTSSIEDIQTMISFKGHVEE
                        DNRNIVYQNILQRLMHAAKQNTPYTRLISTQALSLGAICDAVKYYNTVFLPVYNAE
                        RGTSYQPIAIDQYMTDLPSLGCIHFMNNLEELTSEQRQLMEIHAVNMSEPFKEAHFG
                        KEQGFKAVHNIDPRNNPMIRNAFKDPSLTKYLDKTQSFDLHENVYKKEKQNALPVL
                        NGKEKITIKPHAKIASIMIGSLAANASADYAKYLLNQGYEHIFLFGGLNDSIAARIDQI
                        INSYPAPTRDEIRKKIILLGNQSDVEMAPIMTRSNCVVIRGGGLSVMEQMAMPIMDD
                        KIVLLHEIEDNEEGPLTSGLSWEDGNSDKLIEYLSEKGAYAKKTSPGLCSGHLHEAEK
                        SFEKKYHGQLKSTETKKKVDLTIPQQETYSLKKEWDRKTGYTESGHILSHQHRFFNT
                        IPEVREPFCSKEDLHHNELSSQSLVSVSAG

SidG        SEQ ID      MSRSKDEVLEANDSLFGITVQTWGTNDRPSNGMMNFADQQFFGGDVGHASINMKL
            NO.: 20     PVTDKTKQWIEKYCYSQTYDQFKKVKGNEDKTYEEYLKTAKRLIPVELKTQVTRKA
                        QYDSNGNLVTTHEKAYEQIYFDIDWSWWPGRLQNTEDDMVWEREGKHFEYDEKW
                        KEYLQPEQRVHRGKLGSRKMDYAPTSIIIIQRDIPTSELEKITRDHKEITIEEKLNVVK
                        LLQSKIDEMPHTKMSPSMELMFKNLGINVEKLLDETKDNGVDPTNLEAMREYLTNR
                        LTERKLELETELSEAKKEVDSTQVKNKVEDVYYDFEYKLNQVRKKMEEVNSQLEK
                        MDSLLHKLEGNTSGPIPYTAEIDELMSVLPFLKEELELENGTLSPKSIENLIDHIDELK
                        NELASKQEKKNERNLNLIKKYEELCEQYKDDEEGLEEALWEEGIDVEEVNSAKKDIS
                        KPAPEIQKLTDLQEQLRN+56IKESGVKLSSELEETLNSSVKMWKTKIDSPCQVISESSVK
                        ALVSKINSTRPELVKEKEQLPEQEESLSKEAKKAQEELIKIQEFSQFYSENSSAYMVIG
                        LPPHHQVSLPLAVNGKRGLHPEAMLKKMHELVAGPEKKEFNLHTNNCSLTSIEVLS
                        AGAQHDPLLHSIMGTRALGFFGTPQQVLENAKLTSKTINEGKKSNIFTPLVTASPLDR
                        ALGYAMSIYMDPEASKAKQNAGLALGVLVGLAKTPGHIGSLLNPKQGFNDILNTLN
                        LVYSRNSTGLKVGLTLMALPAMIVLAPLAAIQKGVEVIAETIAKPFKLIANLFKQKPE
                        STDEITVSVGSKKVAEKEGSYSNTALAGLVNSKIKSKIDENTITVEFQKSPQKMIEEIE
                        SQLKENPGKVVVLSEKAHNAVLKFVSKSDDEALKQKFYDCCNQSVARSQKFAPKT
                        RDEIDELVEEVTSTDKTELTTSPRQEPSMSSTIDEEENIDSEHQIETGTESTMRI

VpdA        SEQ ID      MKTKQEVSQQDKLKDSKSSTPLQTKETWFISDALNITFDPYDFSISVTEQAMPYRIV
            NO.: 21     FSGGGSRILAHIGALDELTRHGLKFTEFSGSSAGAMVAAFAYLGYNCSEIKQIISWFN
                        EDKLLDSPLIFNFNNIKQIFNKGGLSSAKLMRQAANYVILKKVMDIISDEKFKTRFAK
                        FQNFLEENIYRCPENITFQTLARIKEICPECELGEKLFITGTNLSTQKHEVFSIDTTPSM
                        ALADAIIISANLPIAFERICYQGNVYSDGGISNNLPAHCFSEKGHKTTFLKHKDDVDFS
                        VLALQFDNGLEENALYSQNPIPKWSWLSNTFYSLITGHPNVTENWYEDLQILRRHAH
                        QSILIKTPTIALTNLTISQDTKKALVESGRTAAKTYLELHEFYTDDYGNIRHNECLHE
                        KFQKPEELLDYCVLHSHFELLKKIKQAISCSQYLEKGYKHYLCELCDNLLPPQLKCP
                        NEGSGTEQPEIKLEKDTIICEKNNNSGLTFSMTFFGVSPLVKTLNQDSPELKIKLFTG
                        LYPILIQNWQNLCPVSGISGILNSIRMSFVEISSTDTCIKTLIDKLNEIEIGHFLIFVFKAA
                        LKNYDKHDFILLLKNLKHLHHSIELIRNKPFHSDDRFYGQWSFEGHDPKRILEFIKSD
                        DISGLMTILEDKKALPNNKPN

Lpg0969     SEQ ID      MVSLEHIQKLISECRKLGKDGLDNGTNGLIPELEIDVVPPSAFLGVGNNPAIFVNSKT
            NO.: 22     YKLMRTTHEKWVENKTIVFKSYLLSQPAIKIIGAIVHETGHAFNVAAKIPNTEANCI
                        FEIEVLMRLFQVKSPLLLGCTELDMQSYFKSRLTDYNKCVKDCQCLAEMVEFITHQF
```

TABLE 1-continued

Amino acid sequences of exemplary toxins

```
                    KLDEVSISEKENQIPLLSISNKWPGLFAKKQIAPDMDKLLTSPVTITPEVKILFYQLVK
                    EHFHSPETEIKLDI

Lpg1978    SEQ ID   MYKIYSYLGWRIDMKTENLPQAGQEAQIDKKIHFIWVGHEVIPQKNIQVVSEWAEKN
           NO.: 23  PGYETHWVDKKIAPAKELDLFILDMKSKGITVKDINEEGVCRDSIRHELDQESPNYG
                    MVSDMLRLNILAAEGGIYLDSDILCSAPFPDEIYAPFGFLLSPWSQGANNTLCNDIILC
                    SKGNQIIQQLADAIEQSYIARDSFEFTHEYASMKETKGERIAKTLGVTGPGFLFHQLK
                    KMGILNDKSEMEAIHWELQDQRYLIDGSVKEPDYFYVPQNNTNDASWVPSIKRPGIE
                    NMSFQERLENAVQLIAFDIQKTGLFNLDHYANELKVKQNSWCIAAETSPELKPDSYL
                    LIRPRDKTGEWTLYYVDEDKKLNPVTLPVIKGAIKLSEVSDPLRKFHTLLSQVSDPV
                    NPTAHELKQIGRALIELKPRQDEWHCKNKWSGAEEIAQELWQRITSNETLRAQIKQC
                    FTQFESLKPRVAELGLTRASGAGTEVEAHESTVKEQEIISQNTVGEEGTKEKNSVQL
                    ASENSSDEKIKTAHDLIDEIIQDVIQLDGKLGLLGGNTRQLEDGRVINIPNGAAMIFDD
                    YKKYKQGELTAESALESMIKIAKLSNQLNRHTFFNQRQPETGQFYKKVAAIDLQTTI
                    AAEYDNNHGLRI

YopE       SEQ ID   MKISSFISTSLPLPTSVSGSSSVGEMSGRSVSQQTSDQYANNLAGRTESPQGSSLASRII
           NO.: 24  ERLSSVAHSVIGFIQRMFSEGSHKPVVTPAPTPAQMPSPTSFSDSIKQLAAETLPKYM
                    QQLNSLDAEMLQKNHDQFATGSGPLRGSITQCQGLMQFCGGELQAEASAILNTPVC
                    GIPFSQWGTIGGAASAYVASGVDLTQAANEIKGLAQQMQKLLSLM

SptP       SEQ ID   MLKYEERKLNNLTLSSFSKVGVSNDARLYIAKENTDKAYVAPEKFSSKVLTWLGK
           NO.: 25  MPLFKNTEVVQKHTENIRVQDQKILQTFLHALTEKYGETAVNDALLMSRINMNKPL
                    TQRLAVQITECVKAADEGFINLIKSKDNVGVRNAALVIKGGDTKVAEKNNDVGAES
                    KQPLLDIALKGLKRTLPQLEQMDGNSLRENFQEMASGNGPLRSLMTNLQNLNKIPE
                    AKQLNDYVTTLTNIQVGVARFSQWGTCGGEVERWVDKASTHELTQAVKKIHVIAK
                    ELKNVTAELEKIEAGAPMPQTMSGPTLGLARFAVSSIPINQQTQVKLSDGMPVPVNT
                    LTFDGKPVALAGSYPKNTPDALEAHMKMLLEKECSCLVVLTSEDQMQAKQLPPYF
                    RGSYTFGEVHTNSQKVSSASQGEAIDQYNMQLSCGEKRYTIPVLHVKNWPDHQPLP
                    STDQLEYLADRVKNSNQNGAPGRSSSDKHLPMIHCLGGVGRTGTMAAALVLKDNP
                    HSNLEQVRADFRDSRNNRMLEDASQFVQLKAMQQLLMTTAS

SopE2      SEQ ID   MTNITLSTQHYRIHRSDVEPVKEKTTEKDIFAKSITAVRNSFISLSTSLSDRFSLHQQT
           NO.: 26  DIPTTHPHRGNASEGRAVLTSKTVKDFMLQKLNSLDIKGNASKDPAYARQTCEAILS
                    AVYSNNKDQCCKLLISKGVSITPFLKEIGEAAQNAGLPGEIKNGVFTPGGAGANPFV
                    VPLIASASIKYPHMFINHNQQVSFKAYAEKIVMKEVTPLFNKGTMPTPQQFQLTIENI
                    ANKYLQNAS

SopB/SigD  SEQ ID   MQIQSFYHSASLKTQEAFKSLQKTLYNGMQILSGQGKAPAKAPDARPEIIVLREPGA
           NO.: 27  TWGNYLQHQKASNHSLHNLYNLQRDLLTVAATVLGKQDPVLTSMANQMELAKVK
                    ADRPATKQEEAAAKALKKNLIELIAARTQQQDGLPAKEAHRFAAVAFRDAQVKQL
                    NNQPWQTIKNTLTHNGHHYTNTQLPAAEMKIGAKDIFPSAYEGKGVCSWDTKNIHH
                    ANNLWMSTVSVHEDGKDKTLFCGIRHGVLSPYHEKDPLLRHVGAENKAKEVLTAA
                    LFSKPELLNKALAGEAVSLKLVSVGLLTASNIFGKEGTMVEDQMRAWQSLTQPGK
                    MIHLKIRNKDGDLQTVKIKPDVAAFNVGVNELALKLGFGLKASDSYNAEALHQLLG
                    NDLRPEARPGGWVGEWLAQYPDNYEVVNTLARQIKDIWKNNQHHKDGGEPYKLA
                    QRLAMLAHEIDAVPAWNCKSGKDRTGMMDSEIKREIISLHQTHMLSAPGSLPDSGG
                    QKIFQKVLLNSGNLEIQKQNTGGAGNKVMKNLSPEVLNLSYQKRVGDENIWQSVK
                    GISSLITS

SipA       SEQ ID   MVTSVRTQPPVIMPGMQTEIKTQATNLAANLSAVRESATTTLSGEIKGPQLEDFPALI
           NO.: 28  KQASLDALFKCGKDAEALKEVFTNSNNVAGKKAIMEFAGLFRSALNATSDSPEAKT
                    LLMKVGAEYTAQIIKDGLKEKSAFGPWLPETKKAEAKLENLEKQLLDIIKNNTGGEL
                    SKLSTNLVMQEVMPYIASCIEHNFGCTLDPLTRSNLTHLVDKAAAKAVEALDMCHQ
                    KLTQEQGTSVGREARHLEMQTLIPLLLRNVFAQIPADKLPDPKIPEPAAGPVPDGGK
                    KAEPTGINININIDSSNHSVDNSKHINNSRSHVDNSQRHIDNSNHDNSRKTIDNSRTFI
                    DNSQRNGESHHSTNSSNVSHSHSRVDSTTHQTETAHSASTGAIDHGIAGKIDVTAHA
                    TAEAVTNASSESKDGKVVTSEKGTTGETTSFDEVDGVTSKSIIGKPVQATVHGVDDN
                    KQQSQTAEIVNVKPLASQLAGVENVKTDTLQSDTTVITGNKAGTTDNDNSQTDKTG
                    PFSGLKFKQNSFLSTVPSVTNMIISMHFDARETFLGVIRKALEPDTSTPFPVRRAFDGL
                    RAEILPNDTIKSAALKAQCSDIDKHPELKAKMETLKEVITHHPQKEKLAEIALQFARE
                    AGLTRLKGETDYVLSNVLDGLIGDSWRAGPAYESYLNKPGVDRVITTVDGLHMQR

YpkA       SEQ ID   MKSVKIMGTMPPSISLAKAHERISQHWQNPVGELNIGGKRYRIIDNQVLRLNPHSGF
           NO.: 29  SLFREGVGKIFSGKMFNFSIARNLTDTLHAAQKTTSQELRSDIPNALSNLFGAKPQTE
                    LPLGWKGEPLSGAPDLEGMRVAETDKFAEGESHISIIETKDKQRLVAKIERSIAEGHL
                    FAELEAYKHIYKTAGKHPNLANVHGMAVVPYGNRKEEALLMDEVDGWRCSDTLR
                    TLADSWKQGKINSEAYWGTIKFIAHRLLDVTNHLAKAGVVHNDIKPGNVVFDRASG
                    EPVVIDLGLHSRSGEQPKGFTESFKAPELGVGNLGASEKSDVFLVVSTLLHCIEGFEK
                    NPEIKPNQGLRFITSEPAHVMDENGYPIHRPGIAGVETAYTRFITDILGVSADSRPDSN
                    EARLHEFLSDGTIDEESAKQILKDTLTGEMSPLSTDVRRITPKKLRELSDLLRTHLSSA
                    ATKQLDMGGVLSDLDTMLVALDKAEREGGVDKDQLKSFNSLILKTYRVIEDYVKG
                    REGDTKNSSTEVSPYHRSNFMLSIVEPSLQRIQKHLDQTHSFSDIGSLVRAHKHLETL
                    LEVLVTLSQQGQPVSSETYGFLNRLAEAKITLSQQLNTLQQQQESAKAQLSILINRSG
                    SWADVARQSLQRFDSTRPVVKFGTEQYTAIHRQMMAAHAAITLQEVSEFTDDMRN
                    FTVDSIPLLIQLGRSSLMDEHLVEQREKLRELTTIAERLNRLEREWM
```

TABLE 1-continued

Amino acid sequences of exemplary toxins

| | | |
|---|---|---|
| YopM | SEQ ID NO.: 30 | MFINPRNVSNTFLQEPLRHSSNLTEMPVEAENVKSKTEYYNAWSEWERNAPPGNGE QREMAVSRLRDCLDRQAHELELNNLGLSSLPELPPHLESLVASCNSLTELPLPQSLK SLQVENNNLKALPDLPPSLKKLHVRENDLTDLPELPQSLESLRVDNNNLKALSDLPP SLEYLTASSNKLEELPELQNLPFLAAIYADNNLLETLPDLPPSLKKLHVRENDLTDLP ELPQSLESLQVDNNNLKALSDLPPSLEYLTASSNKLEELPELQNLPFLAAIYADNNLL ETLPDLPPHLEILVASYNSLTELPELPQSLKSLRVDNNNLKALSDLPPSLEYLTASSNK LEELPELQNLPFLAAIYADNNLLETLPDLPPSLKKLHVRENDLTDLPELPQSLTFLDVS DNNISGLSELPPNLYYLDASSNEIRSLCDLPPSLVDLNVKSNQLSELPALPPHLERLIA SFNYLAEVPELPQNLKQLHVEQNALREFPDIPESLEELEMDSERVVDPYEFAHETTD KLEDDVFE |
| Amatoxin | SEQ ID NO.: 31 | MSDINATRLPIWGIGCNPCVGDDVTTLLTRGEALC |
| Phallacidin | SEQ ID NO.: 32 | MSDINATRLPAWLVDCPCVGDDVNRLLTRGESLC |
| Killer toxin KP1 | SEQ ID NO.: 33 | MIKPERSILTILIGILCLLAYVLANGEPHDGDNEWSSYCSDQGFRRSDDGLVTTPDVG QESIGKNSINGSELVDYLQCLKVRLNGQKQVVSNDGWLLLLVQEPSVNVTQKAMSE CNYNVSSGHKAGSYIQVTNTPADYKVISRRGSYEGDQLPEDVKPYFGVQKTSDYRPI SKRINPNLTLRQLAYNPAALNMCSLWCNSCISRSCPYYIAELTVHVNNIHHGTVWLH HFCRNASPQGGNLYSTLTISHKDTAYYVGTGWWKVRSTAATTNDVAGDWYPASW NQYWCGPHY |
| Killer toxin KP6 | SEQ ID NO.: 34 | MLIFSVLMYLGLLLAGASALPNGLSPRNNAFCAGFGLSCKWECWCTAHGTGNELR YATAAGCGDHLSKSYYDARAGHCLFSDDLRNQFYSHCSSLNNNMSCRSLSKRTIQD SATDTVDLGAELHRDDPPPTASDIGKRGKRPRPVMCQCVDTTNGGVRLDAVTRAA CSIDSFIDGYYTEKDGFCRAKYSWDLFTSGQFYQACLRYSHAGTNCQPDPQYE |
| Killer Toxin K1 | SEQ ID NO.: 35 | MTKPTQVLVRSVSILFFITLLIILVVALNDVAGPAETAPVSLLPREAPWYDKIWEVKD WLLQRATDGNWGKSITWGSEVASDAGVVIEGINVCKNCVGERKDDISTDCGKQTLA LLVSIFVAVTSGHHLIWGGNRPVSQSDPNGATVARRDISTVADGDIPLDFSALNDILN EHGISILPANASQYVKRSDTAEHTTSFVVTNNYTSLHTDLIHHGNGTYTTFTTPHIPA VAKRYVYPMCEHGIKASYCMALNDAMVSANGNLYGLAEKLFSEDEGQWETNYYK LYWSTGQWIMSMKFIEESIDNANNDFEGCDTGH |
| Killer Toxin K28(KHR) | SEQ ID NO.: 36 | MGHLAILFSHAVLNIATAVASSDSIYLKGHRVGQDIDSLYRVYDNGTMYPVTFNEW LNDLTGMNDLATNNATILKRDSSDVSCVTETCQYVDYHVDDEGVITIDISTYRIPVE WDSGSAGNASYGVSKRDTKYETECKKKICGINVSGFCNAYDFAVHAFDEGGSVYNP VSGITDRIKEATKRDKTECLGYELDHVRIDPAVDWSISISTWKQGSANCDTQASADS LKCAAQKALESEHNHQKTAFCIHLDNGGSFNLDIRLISELSFSKYNPWALPCPKYKG SNSWQVVSDCFQ |
| Killer Toxin K28 (KHS) | SEQ ID NO.: 37 | MPRFAIIFALLIAYSLFLSTLFTGSIPDRANTVTSNAPCQVVIWDWIRTRRICNCCSRLC YSLLGRSNLSRTAKRGVCTIAGAVLATAAVIVAAVLVGKSSGSATKRGLTKTISVLN HTIPFTDHILNGQTLSNGTGSNEVTIGFSGYAVHATIKRASTTDIISWVIPESMEPTLAR VASYVSSSSINLAAVPDTGGNASALSFQNAVQEFATSWVSMTYDQSYGDLRNVAN DEGGEEILILMRKRSYRISFQVIETGSTALLLRTRRVSQLITMTYLVTVQARVGIQIG DIFQHYGGIDNYVMTSISVLRTLEDKAFHENKLLIVREPPNKSNQDANQSYRLRPFSA NDLIQNLKSVDIGFLAFCSFEDKYAHYPEIEVIMKITIFISKGNLWSHYVIQARYVRKR VMKVRGQMPGGLLTNMESLLNIVSTPNLNISEFHIQTHSMSQSKPMYFQKQCYSSQ NNIIYIYNSIHITCGAVYVIVHDVRTPSVFVLIELRNCKPLKNSWCETTKTSPRDTKIK KNEYNETVCRRAGALLDGRVRTIRFLMMRTHWSRVKGVSCNTANRLSRFCNHVVS YYPSQNATHILLPTSLRAESLEQQYTTRPLSSSNNRFCCLKSIFINNCKKACESPSLVS CNLQQTAELLMVYYLYICEACYVSRNHDLLSKQCMSTVRAVYVARMRLPKFRSTFP CMPRLCWLVNGVVVV |
| Anthrax lethal factor endopeptidase | SEQ ID NO.: 38 | MHVKEKEKNKDENKRKDEERNKTQEEHLKEEVIKHIVKIEVKGEEAVKKEAAEKLL EKVPSDVLEMYKAIGGKIYIVDGDITKHISLEALSEDKKKIKDIYGKDALLHEHYVY AKEGYEPLVLVIQSSEDYVENTEKALNVYYEIGKILSRDILSKINQPYQKFLDVLNTIK NASDSDGQDLLFTNQLKEHPTDFSVEFLEQNSNEVQEVFAKAFAYYIEPQHRDVLQL YAPEAFNYMDKFNEQEINLSLEELKDQRMLSRYEKWEKIKQHYQHWSDSLSEEGRG LLKKLQIPIEPKKDDIIHSLSQEEKELLKRIQIDSSDFLSTEEKEFLKKLQIDIRDSLSEEE KELLNRIQVDSSNPLSEKEKEFLKKLKLDIQPYDINQRLQDTGGLIDSPSINLDVRKQ YKRDIQNIDALLHQSIGSTLYNKIYLYENMNINNLTATLGADLVDSTDNTKINRGIFN EFKKNFKYSISSNYMIVDINERPALDNERLKWRIQLSPDTRAGYLENGKLILQRNIGL EIKDVQIIKQSEKEYIRIDAKVVPKSKIDTKIQEAQLNINQEWNKALGLPKYTKLITFN VHNRYASNIVESAYLILNEWKNNIQSDLIKKVTNYLVDGNGRFVFTDITLPNIAEQYT HQDEIYEQVHSKGLYVPESRSILLHGPSKGVELRNDSEGFIHEFGHAVDDYAGYLLD KNQSDLVTNSKKFIDIFKEEGSNLTSYGRTNEAEFFAEAFRLMHSTDHAERLKVQKN APKTFQFINDQIKFIINS |
| Shiga Toxin | SEQ ID NO.: 39 | MKCILLKWVLCLLLGFSSVSYSREFTIDFSTQQSYVSSLNSIRTEISTPLEHISQGTTSV SVINHTPPGSYFAVDIRGLDVYQARFDHLRLIIEQNNLYVAGFVNTATNTFYRFSDFA HISVPGVTTVSMTTDSSYTTLQRVAALERSGMQISRHSLVSSYLALMEFSGNTMTRD ASRAVLRFVTVTAEALRFRQIQREFRQALSETAPVYTMTPGDVDLTLNWGRISNVLP EYRGEDGVRVGRISFNNISAILGTVAVILNCHHQGARSVRAVNEESQPECQITGDRPV IKINNTLWESNTAAAFLNRKSQSLYTTGE |

TABLE 1-continued

Amino acid sequences of exemplary toxins

| | | |
|---|---|---|
| Saporin Toxin | SEQ ID NO.: 40 | MKSWIMLVVTWLIILQTTVTAVIIYELNLQGTTKAQYSTFLKQLRDDIKDPNLHYGG TNLPVIKRPVGPPKFLRVNLKASTGTVSLAVQRSNLYVAAYLAKNNNKQFRAYYFK GFQITTNQLNNLFPEATGVSNQQELGYGESYPQIQNAAGVTRQQAGLGIKKLAESMT KVNGVARVEKDEALFLLIVVQMVGEAARFKYIENLVLNNFDTAKEVEPVPDRVIILE NNWGLLSRAAKTANNGVFQTPLVLTSYAVPGVEWRVTTVAEVEIGIFLNVDNNGLP SIIYNNIISGAFGDTY |
| Ricin Toxin | SEQ ID NO.: 41 | MYAVATWLCFGSTSGWSFTLEDNNIFPKQYPIINFTTAGATVQSYTNFIRAVRGRLT TGADVRHDIPVLPNRVGLPINQRFILVELSNHAELSVTLALDVTNAYVVGYRAGNSA YFFHPDNQEDAEAITHLFTDVQNRYTFAFGGNYDRLEQLAGNLRENIELGNGPLEEA ISALYYYSTGGTQLPTLARSFIICIQMISEAARFQYIEGEMRTRIRYNRRSAPDPSVITL ENSWGRLSTAIQESNQGAFASPIQLQRRNGSKFSVYDVSILIPHALMVYRCAPPPSSQ FSLLIRPVVPNFNADVCMDPEPIVRIVGRNGLCVDVRDGRFHNGNAIQLWPCKSNTD ANQLWTLKRDNTIRSNGKCLTTYGYSPGVYVMIYDCNTAATDATRWQIWDNGTIIN PRSSLVLAATSGNSGTTLTVQTNIYAVSQGWLPTNNTQPFVTTIVGLYGLCLQANSG QVWIEDCSSEKAEQQWALYADGSIRPQQNRDNCLTSDSNIRETVVKILSCGPASSGQ RWMFKNDGTILNLYSGLVLDVRRSDPSLKQIILYPLHGDPNQIWLPLF |

In some embodiments, the death agent is an overexpressed product of genetic element selected from DNA or RNA. In some embodiments, the genetic element is a Growth Inhibitory (GIN) sequence such as GIN11.

In some embodiments, the death agent is a ribosomally encoded xenobiotic agent, a ribosomally encoded poison, a ribosomally encoded endogenous or exogenous gene that results in severe growth defects upon mild overexpression, a ribosomally encoded recombinase that excises an essential gene for viability, a limiting factor involved in the synthesis of a toxic secondary metabolite, or any combination thereof. In some embodiments, the ribosomally encoded death agent is Cholera toxin, SpvB toxin, CARDS toxin, SpyA Toxin, HopU1, Chelt toxin, Certhrax toxin, EFV toxin, ExoT, CdtB, Diphtheria toxin, ExoU/VipB, HopPtoE, HopPtoF, HopPtoG, VopF, YopJ, AvrPtoB, SdbA, SidG, VpdA, Lpg0969, Lpg1978, YopE, SptP, SopE2, SopB/SigD, SipA, YpkA, YopM, Amatoxin, Phallacidin, Killer toxin KP1, Killer toxin KP6, Killer Toxin K1, Killer Toxin K28 (KHR), Killer Toxin K28 (KHS), Anthrax lethal factor endopeptidase, Shiga Toxin, Saporin Toxin, Ricin Toxin, or any combination thereof. The cytotoxic reporter or death agent may be a protein with a sequence selected from SEQ ID Nos: 1-41. The cytotoxic reporter may be a variant of a naturally found cytotoxic reporters. Such a variant can have at least 70%, 75%, 80%, 85%, 90%, 95%, 96%, 97%, 98%, or 99% sequence identity to SEQ ID NOs: 1-41.

Along with one or more positive selection markers, a plasmid can also include one or more negative selection markers under control of a different DNA binding sequence to enable binary selection. The plasmid can encode for one or more of negative selection markers in Table 1 driven by a promoter which depends on the DBD present in the bait protein integration plasmid—DNA Binding Sequence (DBS), for example, the LexAop sequence (DBS) which can become bound by LexA (DBD). In some embodiments, to ensure repression of the 'death agents,' the plasmid can include a silencing construct such as a TetR'-Tup11 fusion driven by a strong promoter (such as ADH1) to bind the DBD and silence transcription in the presence of doxycycline. The plasmid can comprise bacterial selection and propagation markers (i.e. ori and AmpR), and yeast replication and selection markers (i.e. LEU2 and CEN or 2-micron) as well.

Disclosed herein, in certain embodiments, is a library of plasmid vectors, each plasmid vector comprising a DNA sequence encoding a different peptide sequence operably linked to a first switchable promoter; a DNA sequence encoding a death agent under control of a second switchable promoter; and a DNA sequence encoding a positive selection reporter under control of a third switchable promoter. Plasmids comprising a promoter driving different E3 ubiquitin ligases may also be included in the library of vectors.

Addition or Expression of Modulators

A molecule from a library that can selectively bridge a bait protein of interest and a specific E3 ubiquitin ligase leading to the bait protein degradation can be screened by use of positive and/or negative selection markers in a host cell.

In some embodiments, the molecule is small molecule. In some embodiments, the small molecule is peptidomimetic. The host cell can be made to become permeabilized to small molecules, for example by deletion of drug efflux pump encoding genes such as PDR5. Genes encoding for transcription factors such as PDR1 and PDR3 that induce expression of efflux pumps including but not restricted to the 12 genes described by 12geneΔ0HSR (Chinen, 2011). The host cell could be further permeabilized to small molecules by interference with the synthesis and deposition of ergosterol in the plasma membrane such as by the deletion of ERG2, ERGS, and/or ERG6 or driving their expression under a regulatable promoter.

In other embodiments, the molecule is a peptide, macrocycle or protein. In some embodiments, the peptide or protein is derived from naturally occurring protein product. In another embodiment, the peptide or protein is a synthesized protein product. In other embodiments, the peptide or protein is a product of recombinant genes.

In some embodiments, the molecule is introduced to the host cell exogenously. In other embodiments, the molecule is the expression product of test DNA inserted into the host cell, wherein the test DNA comprises of DNA sequences that encodes a polypeptide. DNA encoded libraries can be formed by delivery of a plurality of test DNA molecules into host cells. In some embodiments, the peptide sequences of the polypeptides in the library are random. In some embodiments, the different peptide sequences are pre-enriched for binding to a target.

To screen for peptides that selectively facilitate the degradation of a protein of interest, peptides from a randomized peptide library can be applied to or expressed internally from the host cell. A plasmid can be further used to express a randomized peptide library (such as a randomized NNK 60-mer sequences). The plasmid can include a restriction site for integration of a randomized peptide library driven by a strong promoter (such as the ADH1 promoter) or an inducible promoter (such as the GAL1 promoter).

In some embodiments, the randomized peptide library is about 60-mer. In some embodiments, the randomized peptide library is from about 5-mer to 20-mer. In some embodiments, the randomized peptide library is less than 15-mer.

The library can also initiate with a fixed sequence of, for example, Methionine-Valine-Asparagine (MVN) for N-terminal stabilization and/or another combination of high-half-life N-end residues (see, for e.g., Varshaysky. Proc. Natl. Acad. Sci. USA. 93:12142-12149 (1996)) to maximize the half-life of the peptide, and terminate with the 3'UTR of a short protein (such as sORF1). The peptide can also be tagged with a protein tag such as Myc. In some embodiments, N-terminal residues of the peptide comprise Met, Gly, Ala, Ser, Thr, Val, or Pro or any combination thereof to minimize proteolysis.

The plurality of different short peptide sequences can be randomly generated by any method (e.g. NNK or NNN nucleotide randomization). The plurality of different short peptide sequences can also be preselected, either by previous experiments selecting for binding to a target, or from existing data sets in the scientific literature that have reported rationally-designed peptide libraries.

In some embodiments, the library comprises polypeptides about 60 amino acids or fewer in length. In another embodiment, the library comprises polypeptides about 30 or fewer amino acids in length. In another embodiment, the library comprises polypeptides about 20 or fewer amino acids in length.

Modification of Facilitating Peptides

The peptide that leads to the selective degradation of the target can also be a product of post-translational modifications. The post-translational modification can include any one or combination of cleavage, cyclization, bi-cyclization, methylation, halogenation, glycosylation, acylation, phosphorylation, and acetylation. In some embodiments, the methylation comprises reacting with an N-methyltransferase. In some embodiments, the post-translational modification is done by naturally occurring enzymes. In some embodiments, the post-translational modification is done by synthetic enzymes. In some embodiments, the synthetic enzymes are chimeric.

The peptide can be ribosomally synthesized and post-translationally modified peptide (RiPP) whereby the core peptide is flanked by prepropeptide sequence comprising a leader peptide and recognition sequences which signal for the recruitment of maturation, cleavage, and/or modifying enzymes such as excision or cyclization enzymes including, for example, lanthipeptides maturation enzymes from *Lactococcus lactis* (LanB, LanC, LanM, LanP) patellamide biosynthesis factors from cyanobacteria (PatD, PatG), butelase 1 from *Clitoria ternatea*, and POPB from *Galerina marginata, Lentinula edodes, Omphalotacae olearis, Dendrothele bispora*, or *Amanita bisporigera*, or other species. In some embodiments, the cyclization or bicyclization enzymes are synthetic chimeras.

In one example, the variable peptide library region is embedded within the primary sequence of a modifying enzyme (e.g., the homolog of the omphalotin N-methyltransferase enzyme from *Dendrothele bispora, Marasmius fiardii, Lentinula edodes, Fomitiporia mediterranea, Omphalotus olearius* or other) and contains random residues, some of which may be post-translationally decorated by additional modifications like hydroxylation, halogenation, glycosylation, acylation, phosphorylation, methylation, acetylation. This diversified variable region is excised and modified to form N-to-C cyclized, optionally backbone N-methylated macrocycles by the action of a prolyl endopeptidase belonging to the PopB family and N-methyltransferases belonging to the omphalotin methyltransferase family. An exemplary list of prolyl endopeptidases is shown in Table 2. The prolyl endopeptidases may be a protein with a sequence selected from SEQ ID NOs: 42-58. The prolyl endopeptidases may be encoded by a nucleotide sequence selected from SEQ ID NOs: 59 or 60. The prolyl endopeptidase may be a variant of a naturally found prolyl endopeptidases. Such a variant can have at least 70%, 75%, 80%, 85%, 90%, 95%, 96%, 97%, 98%, or 99% sequence identity to SEQ ID NOs: 42-58. An exemplary list of N-methyltransferases is shown in Table 3. The methyltransferase may be a protein with a sequence selected from SEQ ID Nos: 61-116. The methyltransferases may be encoded by a nucleotide sequence selected from SEQ ID Nos: 117 or 118. The prolyl endopeptidase may be a variant of a naturally found methyltransferases. Such a variant can have at least 70%, 75%, 80%, 85%, 90%, 95%, 96%, 97%, 98%, or 99% sequence identity to SEQ ID NOs: 61-116.

TABLE 2

Amino acid and nucleotide sequences of prolyl endopeptidase type cyclizing enzymes

| | | |
|---|---|---|
| *Galerina marginata* CBS 339.88 | SEQ ID NO.: 42 KDR68475.1 hypothetical protein GALMADRAFT_78538 | MSSVTWAPGNYPSTRRSDHVDTYQSASKGEVPVPDPYQWLEESTDEVDK WTTAQADLAQSYLDQNADIQKLAEKFRASRNYAKFSAPTLLDDGHWYWF YNRGLQSQSVLYRSKEPALPDFSKGDDNVGDVFFDPNVLAADGSAGMVLC KFSPDGKFFAYAVSHLGGDYSTIYVRSTSSPLSQASVAQGVDGRLSDEVKW FKFSTIIWTKDSKGFLYQRYPARERHEGTRSDRNAMMCYHKVGTTQEEDII VYQDNEHPEWIYGADTSEDGKYLYLYQFKDTSKKNLLWVAELDEDGVKS GIHWRKVVNEYAADYNIITNHGSLVYIKTNLNAPQYKVITIDLSKDEPEIRD FIPEEKDAKLAQVNCANEEYFVAIYKRNVKDEIYLYSKAGVQLTRLAPDFV GAASIANRQKQTHFFLTLSGFNTPGTIARYDFTAPETQRFSILRTTKVNELDP DDFESTQVWYESKDGTKIPMFIVRHKSTKFDGTAAAIQYGYGGFATSADPF FSPIILTFLQTYGAIFAVPSIRGGGEFGEEWHKGGRRETKVNTFDDFIAAAQF LVKNKYAAPGKVAINGASNGGLLVMGSIVRAPEGTFGAAVPEGGVADLLK FHKFTGGQAWISEYGNPSIPEEFDYIYPLSPVHNVRTDKVMPATLITVNIGD GRVVPMHSFKFIATLQHNVPQNPHPLLIKIDKSWLGHGMGKPTDKNVKDA ADKWGFIARALGLELKTVE |
| *Amanita bisporigera* | SEQ ID NO.: 43 ADN19205.1 prolyl oligopeptidase | MPPTPWAPHSYPPTRRSDHVDVYQSASRGEVPVPDPYQWLEENSNEVDEW TTAQTAFTQGYLDKNADRQKLEEKFRASKDYVKFSAPTLLDSGHWYWFY NSGVQSQAVLYRSKKPVLPDFQRGTRKVGEVYFDPNVLSADGTAIMGTCR FSPSGEYFAYAVSHLGVDYFTIYVRPTSSSLSQAPEAEGGDGRLSDGVKWC |

TABLE 2 -continued

Amino acid and nucleotide sequences of prolyl endopeptidase type cyclizing enzymes

| | | |
|---|---|---|
| | | KFTTITWTKDSKGFLYQRYPARESLVAKDRDKDAMVCYHRVGTTQLEDII<br>VQQDKENPDWTYGTDASEDGKYIYLVVYKDASKQNLLWVAEFDKDGVK<br>PEIPWRKVINEFGADYHVITNHGSLIYVKTNVNAPQYKVVTIDLSTGEPEIR<br>DFIPEQKDAKLTQVKCVNKGYFVAIYKRNVKDEIYLYSKAGDQLSRLASDF<br>IGVASITNREKQPHSFLTFSGFNTPGTISRYDFTAPDTQRLSILRTTKLNGLN<br>ADDFESTQVWYKSKDGTKVPMFIVRHKSTKFDGTAPAIQNGYGGFAITAD<br>PFFSPIMLTFMQTYGAILAVPNIRGGGEFGGEWHKAGRRETKGNTFDDFIA<br>AAQFLVKNKYAAPGKVAITGASNGGFLVCGSVVRAPEGTFGAAVSEGGVA<br>DLLKFNKFTGGMAWTSEYGNPFIKEDFDFVQALSPVHNVPKDRVLPATLL<br>MTNAGDDRVVPMHSLKFVANLQYNVPQNPHPLLIRVDKSWLGHGFGKTT<br>DKHTKDAADKWSFVAQSLGLEWKTVD |
| Hypsizygus<br>marmoreus] | SEQ ID NO.: 44<br>KYQ30898.1<br>Prolyl<br>endopeptidase | MAISPTPWTPNTYPPTRRSSHVDIYKSATRGEVRVADPYQWLEENTEETDK<br>WTTAQEEFTRSYLDKNTDRQRLEDAFRTSTDYAKFSSPTLYEDGRWYWFY<br>NSGLQPQPLIYRSKGKTLPDFSQDDNVVGEVFFDPNLLSDDGTAALSIYDFS<br>DCGKYFAYGISFSGSDFSTIYVRSTESPLAKKNSGSTDDDRLSDEIKHVKFS<br>AVTWTKDSKGFFYQRYPAHENAKEGIETGGDVDAMIYYHVIGTSQSEDILV<br>HSDKSNPEWMWSIDITEDGKYLILYTMKDSSRKNLMWIAELSKNEIGPNIQ<br>WNKIIDVFDAEYHLITNDGPILYVKTNADAPQYKLVTMDISGDKDISRDLIP<br>EDKNANLVQVDCVNRDTFAVIYKRNVKDEIYLYSKTGIQLSRLASDFVGA<br>ASISSREKQPHFFVTMTGFSTPGTVARYDFGAPEEQRWSIYRSVKVNGLNP<br>DDFESKQVWYESKDGTKIPMFIVRHKATKFDGTAPAIQYGYGGFSISINPFF<br>SPTILTFLQTYGAVLAVPNIRGGAEFGEDWHKAGTREKKGNVFDDFVAAT<br>QYLVKNKYAGEGKVAINGGSNGGLLVGACINRAPEGTFGAAVAEVGVMD<br>LLKFSKFTIGKAWTSDYGDPDDPKDFDFICPLSPLHNIPTDRVLPPTMLLTA<br>DHDDRVVPMHSFKHAATLQYTLPHNPHPLVIRIDKKAGHGAGKSTEKRIKE<br>SADKWGFVAQSLGLVWQEPA |
| Conocybe<br>apala | SEQ ID NO.: 45<br>ACQ65797.1<br>prolyl<br>oligopeptidase | MPPSTPNEYPPTRRSDDVLTYRSEKNGEVVVPDPYQWLEHNTEETDKWTT<br>AQAAFTRAHLDKNPKRNALEEAFTAANDYAKFSAPQLHDDGRWYWYYN<br>TGLQAQTCLWRTRDDTIPDFSKQLDEDVGEIFFDPNALSKDGTAALSTYRF<br>SRDGKYFAYAIAQSGSDFNTIYVRPTDSPLTKRDESGRDPSRLADEVKFVKF<br>SGITWAPNSEGFFYQRYPHIDGATLEEGGIATRRDLHAMVYYHRVGTPQSE<br>DILIHRDPANPEWMFGVNVTDNGEYIELYISKDSSRKNMLWVANFAMNKI<br>GEQFQWRKVINDFAAEYDVITNHGPVYYFRTDDGAPKHKILSINIDTNERK<br>LLVPESEDAALFSTVCVNKNYMALIYKRNVKDEVHLYTLEGKPVRRLAED<br>FVGACTISGKEKQPWFFVTMSGFTSPSTVGRYNFQIPEEENRWSIFRAAKIK<br>NLNPNDFEASQVWYKSKDGTNVPMFIVRHKSTQFDGTAPALQYGYGGFSI<br>SIDPFFSASILTFLKVYGAILVVPSIRGGNEFGEEWHRGGMKQNKVNCFDDF<br>IAATNHLVEHKYAAPGKVAINGGSNGGLLVAACINRAPEGTFGAAIAEVGV<br>HDMLKFHKFTIGKAWTSDYGNPDDPHDFDYIYPISPVHNVPTDKILPPTLLL<br>TADHDDRVVPMHTFKLAATLQHTLPHNPPLLLRVDKKAGHGAGKPLQL<br>KIREQADKWGFVAQSFQLVWRDGV |
| Amanita<br>bisporigera | SEQ ID NO.: 46<br>GenBank<br>HQ225841.1<br>POPB | MPPTPWAPHSYPPTRRSDHVDVYQSASRGEVPVPDPYQWLEENSNEVDEW<br>TTAQTAFTQGYLDKNADRQKLEEKFRASKDYVKFSAPTLLDSGHWYWFY<br>NSGVQSQAVLYRSKKPVLPDFQRGTRKVGEVYFDPNVLSADGTAIMGTCR<br>FSPSGEYFAYAVSHLGVDYFTIYVRPTSSSLSQAPEAEGGDGRLSDGVKWC<br>KFTTITWTKDSKGFLYQRYPARESLVAKDRDKDAMVCYHRVGTTQLEDII<br>QQDKENPDWTYGTDASEDGKYIYLVVYKDASKQNLLWVAEFDKDGVKPE<br>IPWRKVINEFGADYHVITNHGSLIYVKTNVNAPQYKVVTIDLSTGEPEIRDFI<br>PEQKDAKLTQVKCVNKGYFVAIYKRNVKDEIYLYSKAGDQLSRLASDFIGV<br>ASITNREKQPHSFLTFSGFNTPGTISRYDFTAPDTQRLSILRTTKLNGLNADD<br>FESTQVWYKSKDGTKVPMFIVRHKSTKFDGTAPAIQNGYGGFAITADPFFSP<br>IMLTFMQTYGAILAVPNIRGGGEFGGEWHKAGRRETKGNTFDDFIAAAQFL<br>VKNKYAAPGKVAITGASNGGFLVCGSVVRAPEGTFGAAVSEGGVADLLKF<br>NKFTGGMAWTSEYGNPFIKEDFDFVQALSPVHNVPKDRVLPATLLMTNAG<br>DDRVVPMHSLKFVANLQYNVPQNPHPLLIRVDKSWLGHGFGKTTDKHTK<br>DAADKWSFVAQSLGLEWKTVD |
| Lentinula<br>edodes | SEQ ID NO.: 47<br>GenBank<br>GAW09065.1<br>The DOE Joint<br>Genome<br>Institute (JGI)<br>011197;<br>LENED_011197) | MFSATQESPTMSVPQWDPYPPVSRDETSAITYQSKLCGSVTVRDPYSALEV<br>PFDDSEETKAFVHAQRKFARTYLDEIPDRETWLQTLKESWNYRRFTVPKRE<br>SDGYTYFEYNDGLQSQMSLRRVKVSEEDTILTESGPGGELFFDPNLLSLDG<br>NAALTGSMMSPCGKYWAYGVSEHGSDWMTTYVRKTSSPHMPSQEKGKD<br>PGRMDDVIRYSRFFIVYWSSDSKGFFYSRYPPEDDEGKGNTPAQNCMVYY<br>HRLGEKQEKDTLVYEDPEHPFWLWALQLSPSGRYALLTASRDASHTQLAK<br>IADIGTSDIQNGIQWLTIHDQWQARFVIIGDDDSTIYFMTNLEAKNYLVATL<br>DIRHSEAGVKTLVAENPDALLISASILSTDKLVLVYLHNARHEIHVDLNTG<br>KPIRQIFDNLIGQFSLSGRRDDNDMFVFHSGFTSPGTIYRFRLNEDSNKGTLF<br>RAVQVPGLNLSDFTTESVFYPSKDGTPIHMFITRLKDTPVDGTAPVYIYGYG<br>GFALAMLPTFSVSTLLFCKIYRAMYVVPNIRGGSEFGESWHREGMLDKKQ<br>NVFDDFNAATKWLVANKYANKYNVAIRGGSNGGVLTTACANQAPELYRC<br>VITIGGIIDMLRFPKFTFGALWRSEYGDPEDPEDFDFIYKYSPYHNIPSGDVV<br>LPAMLFFTAAYDDRVSPLHSFKHVAALQYNFPNGPNPVLMRIDLNTGHFA<br>GKSTQKMLEETADEYRCDLLCCNLQL |

TABLE 2 -continued

Amino acid and nucleotide sequences of prolyl endopeptidase type cyclizing enzymes

| | | |
|---|---|---|
| *Omphalotacae olearis* | SEQ ID NO.: 48<br>The DOE Joint Genome Institute (JGI) 2090;<br>OMPOL1_2090 | MSFPGWGPYPPVERDETSAITYSSKLHGSVTVRDPYSQLEVPFEDSEETKAF<br>VHSQRKFARTYLDENPDREAWLETLKKSWNYRRFSALKPESDGHYYFEYN<br>DGLQSQLSLYRVRMGEEDTVLTESGPGGELFFNPNLLSLDGNAALTGFVMS<br>PCGNYWAYGVSEHGSDWMSIYVRKTSSPHLPSQERGKDPGRMNDKIRHV<br>RFFIVSWTSDSKGFFYSRYPPEDDEGKGNAPAMNCMVYYHRIGEDQESDV<br>LVHEDPEHPFWISSVQLTPSGRYILFAASRDASHTQLVKIADLHENDIGTNM<br>KWKNLHDPWEARFTIVGDEGSKIYFMTNLKAKNYKVATFDANHPDEGLT<br>TLIAEDPNAFLVSASIHAQDKLLLVYLRNASHEIHIRDLTTGKPLGRIFEDLL<br>GQFMVSGRRQDNDIFVLFSSFLSPGTVYRYTFGEEKGHSSLFRAISIPGLNLD<br>DFMTESVFYPSKDGTSVHMFITRPKDVLLDGTSPVLQYGYGGFSLAMLPTF<br>SLSTLLFCKIYRAIYAIPNIRGGSEYGESWHREGMLDKKQNVFDDFNAATE<br>WLIANKYASKDRIAIRGGSNGGVLTTACANQAPGLYRCVITIEGIIDMLRFP<br>KFTFGASWRSEYGDPEDPEDFDFIFKYSPYHNIPPPGDTIMPAMLFFTAAYD<br>DRVSPLHTFKHVAALQHNFPKGPNPCLMRIDLNSGHFAGKSTQEMLEETA<br>DEYRLKVQ |
| *Gymnopus fusipes* | SEQ ID NO.: 49 | MSMSLLGVYPPVKRDEASAITYQSKLHGSVIVHDPYSALEIPSNDSLETKAF<br>VLSQGKESRAYLDEIPTRKNWLKILKSNWSYRRFSALKRESDNHFYFEYND<br>GLQPQSSIYRVKVGEEDSILTESGPGGELFFDPNLLSLDGVAALTGAAMSPS<br>GKYWAYGVSEHGNNSMTIYVRKTSSPHQPSQEKGTDPGRMNDVLQHIRM<br>LFVSWTRDSKGFFYQRYPPEKNEGNGNAPGQNCKIYYHYIGTEQDSDILIH<br>EDPDHPDWFSYVQLSPSGQYVLLLINRDSSLNYLAKIADLSVNDIGTHIQW<br>KNLHDSWNHFTMIGNDYSVIYFKTNLDAQNYKVATIDFLQPEMGFTTLVK<br>ENPNSVLVEAKIFREDKLVLLYQQNASHQIHIYDLKSGAWLQQIFKNLTGFI<br>TTVPNGRAEDEMFFLYNDFITPGTIYQYKFDDESDKGLVFRAIQIDGLNLDD<br>FVTESKFYPSKDGTSVHMFITRPKDVLIDGTAAVYMYGYGGFSISVLPTFSIS<br>TLLFCKIYRAMYVVPNIRGGSEFGESWHREGMLDKKQNGHDDFHAAAEW<br>LIANKYAKKDCVAIRGGSSGGILTTACANQAPELYRCVITIEGIIDMLKFPKF<br>TFGALLRSEYGDPEDPEAFDYIYKYSPYHNIPLGDVVMPPMLFFNAGYDDR<br>VPPLHTFKHVAALQHRFPKGPNPILMRMDLSSGHYAGKSVQKMIEETADE<br>YSFIGKSMGLTMQVRAK |
| *Lentinula novae-zelandiae* | SEQ ID NO.: 50 | MSVPQWVSYPPVSRDATSAITYQSKLRGSVTVRDPYSALEVPFDDSEETKA<br>FVHAQRKFARTYLDEIPDR<br>ETWLQTLKESWNYRRFTVPKRESDGYTYFEYNDGLQSQMSLRRVKVSEED<br>TILTESGPGGELFFDPNLLSLDGNAALTGSMMSPCGKYWAYGVSEHGSDW<br>MTTYVRKTSSPHMPSQEKGKDPGRMDDVVRYSRFFIVYWSSDSKGFFYSR<br>YPPEDDEGKGNAPAQNCMVYYHRLGERQEKDTLVYEDPEHPFWLWALQL<br>SPSGRYALLTASRDASHTQLAKIADIGTSDIQNGIQWLTIHDQWQARFVIIG<br>DDDSTIYFMTNLEAKNYLVATLDIRHSEAGVKTLVAENPDALLISASILSTD<br>KLVLVYLHNARHEIHVHDLNTGKPIRQIFDNLIGQFSLSGRRDDNDMFIFHS<br>GFTSPGTIYRFRLNEDSNKGTLFRAIQVPGLNLDFTTESVFYPSKDGTPIHM<br>FITRLKDTPVDGTAPVYIYGYGGFALAMLPTFSVSTLLFCKIYRAMYVVPNI<br>RGGSEFGESWHREGMLDKKQNVFDDFNAATKWLVANKYANKYNVAIRG<br>GSNGGVLTTACANQAPELYRCVITIGGIIDMLRFPKFTFGALWRSEYGDPED<br>PEDFDFIYKYSPYHNIPSGDVVLPAMLFFTAAYDDRVSPLHSFKHVAALQY<br>YFPNGPNPVLMRIDLNTGHFAGKSTQKMLEETADEYSFIGKSMGLVMCVQ<br>NEHASKQWSCVVT |
| *Lentinula raphanica* | SEQ ID NO.: 51 | MSIPRWGPYPPVRRDETSAITYQSKLHGSVTVPDPYSALEVPYNDDEESEIK<br>TFVSEQRKFARTYLDENPDRERWLQVLKESWNYERFTVPKRESDGHTYFE<br>YNDGLQSQMTLRRVKTGQEDTILTESGPGGELFFDPNMISLDGNAALTGSM<br>MSPCGKYWAYGVSEHGSDWMTIYVRETSSPHQPSQEKGKDTGRMDDVVH<br>SSRFFIVYWTSDSKGFFYSRYPPEDDEGKGNSPAKNCMVYYHRLGEKQED<br>DALIYEDPEHPFWLWAVQLSPSGRFALLTASRDASHTQMAKIADLSSGDVR<br>NGVNWLTIHDKWEARFLIIGDDDSKIYFLTNLEAVNYKVVTLDTRCPEAGT<br>NTLVPENPDALLISASIVSADKLALVYLQNAKHDIYIHDLSTGKPTRRLFED<br>LIGQFALSGRREDNDMFVFYSGFTSPGTIYRYKFDEEDNNGTLFRAMRVPG<br>LDLDKFTTESVFYPSKDGTKVHMFITRLKNTLVDGTAPVYMYGYGGFALA<br>MLPTFSVSTLLFCKTYRAMYVVPNIRGGSEFGESWHREGMLDKKQNVFDD<br>FNAAAEWLIANKYAKSNCVAIRGGSNGGVLTTACTNQAPELFRCVVTIGGI<br>IDMLRFPKFTFGALWCSEYGDPDDPEAFDYIYKYSPYHNIPSGKVVIPAMIF<br>FTAAYDDRVSPLHTFKHVAALQYNFPTGPNPIMMRIDLNTGHYAGKSTQK<br>MLEETADEYSFIGRSMELTMHTQNHWSCVTS |
| *Lentinula lateritia* | SEQ ID NO.: 52 | MSVPQWVPYPPVSRDDTSAITYQSKLRGSVTVRDPYSALEVPFDDSEETKA<br>FVHAQRKFARMYLDEIPDR<br>ETWLQTLKESWNYRRFTVPKRESDGYTYFEYNDGLQSQMSLRRVKVSEED<br>TILTESGPGGELFFDPNLLSLDGNAALTGSMMSPCGKYWAYGVSEHGSDW<br>MTTYVRKTSSPHMPSQEKGKDPGRMDDVIRYSRFFIVYWSSDSKGFFYSRY<br>PPEDDEGKGNTPAQNCMVYYHRLGEKQEKDTLVYEDPEHPFWLWALQLS<br>PSGRYALLTASRDASHTQLAKIADIGTSDIQNGIQWLTIHDQWQARFVIIGD<br>DDSTIYFMTNLEAKNYLVATLDIRHSEAGVKTLVAENPDALLISASILSTDK<br>LVLVYLHNARHEIHVHDLNTGKPIRQIFDNLIGQFSLSGRRDDNDMFVFHS<br>GFTSPGTIYRFRLNEDSNKGTLFRAIQVPGLNLDFTTESVFYPSKDGTPIHM<br>FITRLKDTPVDGTAPVYIYGYGGFALAMLPTFSVSTLLFCKIYRAMYVVPNI<br>RGGSEFGESWHREGMLDKKQNVFDDFNAATKWLVANKYANKYNVAIRG<br>GSNGGVLTTACANQAPELYRCVITIGGIIDMLRFPKFTFGALWRSEYGDPED |

TABLE 2 -continued

Amino acid and nucleotide sequences of prolyl endopeptidase type cyclizing enzymes

| | | |
|---|---|---|
| | | PEDFDFIYKYSPYHNIPSGDVVLPAMLFFTAAYDDRVSPLHSFKHVAALQY<br>YFPNGPNPVLMRIDLNTGHFAGKSTQKMLEETADEYSFIGKSMGLVMCVQ<br>NEHASKQWSCVVT |
| Dendrothele<br>bispora | SEQ ID NO.: 53 | MSVPQWGPYLPVDRDETSAITYRTKLHGSVTVPDPYSGLEAPLDESAKTKA<br>FVHSQRKFARTYLDENPDK<br>EVWLETLKQSWNYKRFTVPRHESDDHIYFEYNDGLQSQLSLHRVKVGDED<br>TILTESGPGGELFFDPNMISLDGNASLTGFIMSPCGKYWAYGVSEHGSDWM<br>TIYVRETSSPHVPSQERGKDPGRMDDEVRHSRFFIVSWTGDSKGFFYSKYPP<br>EENEGKGNAPAKNCIVYYHRLGEKQENDTLVHKDSGHPFWLWSLQTTPSG<br>RYALLAASRDASHTQLAKIADIHDNDIGASMKWINLHDSWEARFSIIGDDD<br>SKIYFMTNLQAPNYKVAIFDACHPSPDADLTTLVAEDPNALLIAASIHAKDK<br>LALVYLRDARHEIHVHDLVTGRLLRRILGDLVGQFMVTGRRADNDMFIFY<br>SGFTSPGTVYRYKFDDERDTCSLFRAIRIPGLDLDKFVTESVFYPSKDGTSIH<br>MFITRPKDVLLDGTAPVLQYGYGGFALAMLPTFSVSTLLFCKIYRAMYVVP<br>NIRGGSEYGESWHRAGMLGNKQNVFDDLNAATEWLVANKYANKDRVAI<br>RGGSNGGVLTTACANQAPGLYRCVITIGGIIDMLRFPKFTFGALWCSEYGD<br>PEDPEAFDFIYKYSPYHNIPSGETVMPAMLFFTAAYDDRVSPLHTFKHVAA<br>LQHSFPHGPNPILMRVDMNSGHYAGKSTQKMLEETADEYSFIGKSMGLTM<br>QVENKSDSNRWSCVVN |
| Dendrothele<br>bispora | SEQ ID NO.: 54 | MPVPGWGSYPPFDRDETSAITYQSKLRGSVTVYDPYSALEVPSNDSEETKA<br>FILEQNKFSRAYLDANPDRQTWLETLKKSWHYRRFTTPTRESDDHFYFLYN<br>DGLLAQSPVYRVKVDDVDSILTESGPGGELFFDPNLLSLDGVATLTGTAMS<br>PCGKYWAYAISEHGNDWMTIYVRKTSSPHHPSQERGKDPGRMDDVIQHCRIFFVSWT<br>DDSKGFFYSKWPPDENQGNGNAPGVDCKIYYHRIAVFLSEDPEHPGWFWN<br>VEVSPSGQYALLLGTRDASLNQLVKLADLHTSDIETGIQWTTLHDSWQARF<br>SIIGNDNSLIYFRTNLEAENHRVAAFNVHHPQAGFTTLVPGSLDSVLLDAKL<br>YGINKLVLVYQHLAKHEIYLHDIETGRRLRQIFTDLAGKMTISGRRADHEMFVLYSD<br>FISPGTLYRQLLNRYKFDKDTDKGLLFRTIKVDALNLDDFVTESEFYPSKDG<br>TLVHMFITHPKDVFTDGTAPVLMYGYGGFGAPMFPNFSISNLLFCNIYRGIG<br>GSEFGESWHREGMLEKKQNVFDDFRAAAEWLVTNKYARKGGVAIRGGSN<br>GGIMTTACSNQAPELYGCVITIAGLQDMLRYTKFTFGDLLRSEYGNPENPEDFDYIY<br>KYSPYHNIPLKEVTMPPMLFLQSDYDDRVSPLHTYKHVAALQHRFPKGPNP<br>IILRIDLDSGHYAGKSTMRLIEETADEYRWDLDSSSSSCYYI |
| Gypsophila<br>vaccaria | SEQ ID NO.: 55 | MATSGFSKPLHYPPVRRDETVVDDYFGVKVADPYRWLEDPNSEETKEFVD<br>NQEKLANSVLEECELIDKFKQKIIDFVNFPRCGVPFFRRANKYFHFYNSGLQA<br>QNVFQMQDDLDGKPEVLYDPNLREGGRSGLSLYSVSEDAKYFAFGIHSGL<br>TEWVTIKILKTEDRSYLPDTLEWVKFSPAIWTHDNKGFFYCPYPPLKEGEDHMTRSAV<br>NQEARYHFLGTDQSEDILLWRDLENPAHHLKCQITDDGKYFLLYILDGCDD<br>ANKVYCLDLTKLPNGLESFRGREDSAPFMKLIDSFDASYTAIANDGSVFTF<br>QTNKDAPRKKLVRVDLNNPSVWTDLVPESKKDLLESAHAVNENQLILRYL<br>SDVKHVLEIRDLESGALQHRLPIDIGSVDGITARRRDSVVFFKFTSILTPGIVYQCDL<br>KNDPTQLKIFRESVVPDFDRSEFEVKQVFVPSKDGTKIPIFIAARKGISLDGS<br>HPCEMHGYGGFGINMMPTFSASRIVFLKHLGGVFCLANIRGGGEYGEEWH<br>KAGFRDKKQNVFDDFISAAEYLISSGYTKARRVAIEGGSNGGLLVAACINQ<br>RPDLFGCAEANCGVMDMLRFHKFTLGYLWTGDYGCSDKEEEFKWLIKYSPIHNVRR<br>PWEQPGNEETQYPATMILTADHDDRVVPLHSFKLLATMQHVLCTSLEDSP<br>QKNPIIARIQRKAAHYGRATMTQIAEVADRYGFMAKALEAPWID |
| Fragment of<br>Gymnopus<br>fusipes<br>prolyloligo-<br>peptidase | SEQ ID NO.: 56 | MSMSLLGVYPPVKRDEASAITYQSKLHGSVIVHDPYSALEIPSNDSLETKAF<br>VLSQGKFSRAYLDEIPTRKNWLKILKSNWSYRRFSALKRESDNHFYFEYND<br>GLQPQSSIYRVKVGEEDSILTESGPGGELFFDPNLLSLDGVAALTGAAMSPS<br>GKYWAYGVSEHGNNSMTIYVRKTSSPHQPSQEKGTDPGRMNDVLQHIRM<br>LFVSWTRDSKGFFYQRYPPEKNEGNGNAPGQNCKIYYHYIGTEQDSDILIH<br>EDPDHPDWFSYVQLSPSGQYVLLLINRDSSLNYLAKIADLSVNDIGTHIQW<br>KNLHDSWNHFTMIGNDYSVIYFKTNLDAQNYKVATIDFLQPEMGFTTLVK<br>ENPNSVLVEAKIFREDKLVLLYQQNASHQIHIYDLKSGAWLQQIFKNLTGFI<br>TTVPNGRAEDEMFFLYNDFITPGTIYQYKFDDESDKGLVFRAIQIDGLNLDD<br>FVTESKFYPSKDGTSVHMFITRPKDVLIDGTAAVYMYGYGGFSISVLPTFSIS<br>TLLFCKIYRAMYVVPNIRGGSEFGESWHREGMLDKKQNGHDDFHAAAEW<br>LIANKYAKKDCVAIRGGSSGGILTTACANQAPELYRCVITIEGIIDMLKFPKF<br>TFGALLRSEYGDPEDPEAFDYIYKYSPYHNIPLGDVVMPPMLFFNAGYDDR<br>VPPLHTFKHVAALQHRFPKGPNPILMRMDLSSGHYAGKSVQKMIEETADE<br>YSFIGKSMGLTMQVRAKPSNNRWSCVVT |
| Lentinula<br>edodes | SEQ ID NO.: 57 | MSVPQWDPYPPVSRDETSAITYQSKLCGSVTVRDPYSALEVPFDDSEETKA<br>FVHAQRKFARTYLDEIPDR<br>ETWLQTLKESWNYRRFTVPKRESDGYTYFEYNDGLQSQMSLRRVKVSEED<br>TILTESGPGGELFFDPNLLSLDGNAALTGSMMSPCGKYWAYGVSEHGSDW<br>MTTYVRKTSSPHMPSQEKGKDPGRMDDVIRYSRFFIVYWSSDSKGFFYSRY<br>PPEDDEGKGNTPAQNCMVYYHRLGEKQEKDTLVYEDPEHPFWLWALQLS<br>PSGRYALLTASRDASHTQLAKIADIGTSDIQNGIQWLTIHDQWQARFVIIGD<br>DDSTIYFMTNLEAKNYLVATLDIRHSEAGVKTLVAENPDALLISASILSTDK<br>LVLVYLHNARHEIHVHDLNTGKPIRQIFDNLIGQFSLSGRRDDNDMFVFHS<br>GFTSPGTIYRFRLNEDSNKGTLFRAVQVPGLNLSDFTTESVFYPSKDGTPIH<br>MFITRLKDTPVDGTAPVYIYGYGGFALAMLPTFSVSTLLFCKIYRAMYVVP |

TABLE 2 -continued

Amino acid and nucleotide sequences of prolyl endopeptidase type cyclizing enzymes

|  |  |  |
|---|---|---|
|  |  | NIRGGSEFGESWHREGMLDKKQNVFDDFNAATKWLVANKYANKYNVAIR GGSNGGVLTTACANQAPELYRCVITIGGIIDMLRFPKFTGALWRSEYGDPE DPEDFDFIYKYSPYHNIPSGDVVLPAMLFFTAAYDDRVSPLHSFKHVAALQ YNFPNGPNPVLMRIDLNTGHFAGKSTQKMLEETADEYSFIGKSMGLVMCA QNEHASKQWSCVVT |
| Omphalotus olearis | SEQ ID NO.: 58 | MSFPGWGPYPPVERDETSAITYSSKLHGSVTVRDPYSQLEVPFEDSEETKAF VHSQRKFARTYLDENPDR EAWLETLKKSWNYRRFSALKPESDGHYYFEYNDGLQSQLSLYRVRMGEE DTVLTESGPGGELFFNPNLLSLDGNAALTGFVMSPCGNYWAYGVSEHGSD WMSIYVRKTSSPHLPSQERGKDPGRMNDKIRHVRFFIVSWTSDSKGFFYSR YPPEDDEGKGNAPAMNCMVYYHRIGEDQESDVLVHEDPEHPFWISSVQLT PSGRYILFAASRDASHTQLVKIADLHENDIGTNMKWKNLHDPWEARFTIVG DEGSKIYFMTNLKAKNYKVATFDANHPDEGLTTLIAEDPNAFLVSASIHAQ DKLLLVYLRNASHEIHIRDLTTGKPLGRIFEDLLGQFMVSGRRQDNDIFVLF SSFLSPGTVYRYTFGEEKGHSSLFRAISIPGLNLDDFMTESVFYPSKDGTSVH MFITRPKDVLLDGTSPVLQYGYGGFSLAMLPTFSLSTLLFCKIYRAIYAIPNI RGGSEYGESWHREGMLDKKQNVFDDFNAATEWLIANKYASKDRIAIRGGS NGGVLTTACANQAPGLYRCVITIEGIIDMLRFPKFTFGASWRSEYGDPEDPE DFDFIFKYSPYHNIPPPGDTIMPAMLFFTAAYDDRVSPLHTFKHVAALQHNF PKGPNPCLMRIDLNSGHFAGKSTQEMLEETADEYSFIGKSMGLTMQTQGSV DSSRWSCVTV |
| Oligoprolyl-peptidase enzyme DNA sequence from Gymnopus fusipes | SEQ ID NO.: 59 | ```
   1 aagcacacca ctgataatta tgcttcagat agagtgaagc ctagtgagag acaaaatctt
  61 tcagactgct cttaaaaggc tgaatttcag aacaaccgaa acgttgatcg atcggctgaa
 121 atggtaaccg atcaccattt cggtagtact gaagtggttg aactgtctta aaatgcttca
 181 cccagaccga agtataatta tcagcggtgt gagagacatt acaggattga caggacttta
 241 tttttgaaagt aggcttttc gattccgcct aataaatcat acaaggccca tgctgaattt
 301 gaccaatcac ataacagtgc gttgtattga aatttgacga tcctatctac ttggtgtcga
 361 gctgccggtg tccaaatgaa cgaggttgtc agaatactgc cgatttcaat gcttatggaa
 421 cgcactgtac aaggaagctg gcaatagaaa ccatgccgtc aatcctagtt caatggtatc
 481 tttcacagtt cctgttgcat atgccagtt ttattaattt ctgtcactca tgaccaataa
 541 ccgtgtcttg tatgaagata acgtggcaaa atctctatat ccttataaga aacaaacccc
 601 ttcgtccgct acgtgtcttt gaaacccaca ctatgccat gtcacttta ggtgtatatc
 661 ctcctgttaa acgggacgaa gcctcagcca ttacctacca aagcaaactt cacggttctg
 721 tcattgtgca tgatccatac agcgcgcttg aaataccttc taatgatagt ttggagacaa
 781 aggtttgcga cacaatcctg ccatgtaaaa aatcgagaca ttcagtattt caggcatttg
 841 tcctctcaca aggtaaattt tcacgggctt acttggatga aattccgaca aggtaagaga
 901 attttcaaac aatgaacaac ttaaatctat ttcatatcag gaaaaattgg ttgaaaatat
 961 taaagagtaa ctggagttac cggcggtttt ctgccttgaa gcgtgaaagt gacaaccatt
1021 tctatttcga atataatgat ggccttcaac cccagtcatc catttatcgg gtgaaggttg
1081 gtgaagagga ttccatcctt actgaatctg gacctggggg tgaattgttt tttgatccca
1141 atttgctttc attggatggg gttgctgcac ttactggtgc tgcgatgagt ccttctggga
1201 agtactgggc atatgttgta tctgaacatg ttgatctttt tccactcaag ctatactaat
1261 tattgaccta ataaatattg aacagggaaa caattcaatg acaatttatg ttcgaaaaac
1321 ttcatcacca catcaaccat ctcaagaaaa gggaacagat cccggacgga tgaatgatgt
1381 tctccaaacc attcgcatgc tctttgtgtc ctggacaaga gatagcaaag gtttgaatac
1441 acagagagtg cttaagctgg aatattcat catttatcc ttcaaaggtt tcttctacca
1501 aagatatcca ccagaaaaa atgaaggaaa tgggaatgca ccagggcaga attgcaaggt
1561 gaaactatct gacatcattg agtgcatgtg ccctctgaag catgttgtag atatatatc
1621 actacattgg gacagaacag gatagtgaca tccttattca gtaaggatag tgcatttctt
1681 gaagccaggc caaactcaaa tcatccttca gtgaggaccc tgatcatccg gactggttct
1741 catatgtaca gctctcccca aggtaaaatg gtctcacact gcaaagattc ctgattaata
1801 tcataccatg tagtggtcaa tatgtcctgc tactcataaa tgtatgtact tgaatttcta
1861 ctatccattg tactctgatt gtggattaaa cagcgtgatt caagtttaaa ttacctcgcc
1921 aagattgctg atttatctgt caatgatatt gggacccata tccaatggaa gaatttgcat
1981 gattcttgga accatttcac aatgttaaga gcttcatgag tttcttcata tactatgaac
2041 tgatctattt caattacata ctcaactgat aggattggga atgactactc tgtcatctat
2101 ttcaaaacaa atctggatgc acagaactac aaagttgcaa caatcgactt tcttcaacca
2161 gagatgggct tcacaactct ggtcaaggaa atcccaatt cagtccttgt ggaggccaaa
2221 atattcagag aagacaagct tgtgcttttg taccagcaga atgctagcca tcaaatacac
2281 atttatgatc tcaagagtgg cgcatggctt caacaaatct tcaagaatct aactggattc
2341 ataactacag ttccaaatgg gcgcgctgaa gatgagatgt tttttctcta caatgacttt
2401 attacacctg ggacaatata tcagtcagtg tttaccatat atcggtggtc catcattttc
2461 agctgacaga cacggaaaca gataaaattt gatgatgaaa gtgacaaggg cttggtgttc
2521 cgtgccatcc aaatcgatgg actcaaccta gatgatttcg tgacagaatc agtaagtaaa
2581 tataactata tcaactttg gggcactccg taactgaggt gttcagaagt tttacccatc
2641 caaggatgga acttcgtaat ttctctcgtt aactttgata cgtcaacttc tggttgacaa
2701 aaaaacatag ggttcacatg ttcatccatc gcccgaagga tgtactcatc gacggaactg
2761 ccgcagtcta tatgtatggc tatgtggct tctcaatctc agtgcttccg acgttctcca
2821 tctcaaccct gctatttgc aaaatttacc gggcaatgta tgtcgtgcct aacatacggt
2881 aagggtattt tggacaact tgaagtcca tttacttacc tggctgccaa tttagcggag
2941 gtcggagtt tggagaatca tggcaccggg aggtgagtc atgtcaagtt gcacacaatg
3001 tacaagcttt actcaaccat gtctttcagg gaatgttgga caaaaacag aatgacatg
3061 atgacttcca tgcagctgct gaatggctca tcgcaaataa gtacgccaaa aaggattgtg
3121 ttgccattcg cggggggtcc agcggaggtg cggagtccaa gaactgcttt tgtagccaga
3181 ttgaactttt tcagggtgat tttgactacc gcatgtgcaa atcaagcacc cgaactctac
3241 cgctgtgtaa ttaccattga aggcataatt gacatgctca aagtttgtag tttgtgaatc
``` |

TABLE 2 -continued

Amino acid and nucleotide sequences of prolyl endopeptidase type cyclizing enzymes

|  |  |  |
|---|---|---|
|  | 3301 | acctttacat caaaatctca ctcatttgta tgccctcagt ttcccaagtt cacgtttggt |
|  | 3361 | gctttgttgc gttcggaata tggcgatgta tgtattcaat ttatcatttc tgaattgaat |
|  | 3421 | gagtctgaca gacctactta gcccgaggac ccagaagctt ttgactacat ctacaagtta |
|  | 3481 | gcttttctcat cctccacag tcatccgctc agacctaacc atgtagatac tcgccttatc |
|  | 3541 | ataacattcc gttgggtgat gtagtcatgc caccgatgct attcttcaat gcgggatatg |
|  | 3601 | atgaccgcgt tcctcctcta cacagtaagc caagtgtttg attccttcaa gaccaagcta |
|  | 3661 | accccctaac aagccttcaa gcatgttgct gcactacaac atagattttcc taaaggcccg |
|  | 3721 | aatccaattc tcatgcgcat ggacctaagt tcagggcatt atgctggcaa ggtttgtatt |
|  | 3781 | tcactctcca agacatgctc tttgcaaaat ttattcttgt agagtgtaca aaagatgatt |
|  | 3841 | gaggaaactg cagatgaata caggtgtggt caatgggtct tattacatgc atcattttct |
|  | 3901 | aactgatttg ggtctactag cttcattggg aagtctatgg ggcttactat gcaagtcaga |
|  | 3961 | aaaccat ctaataaccg ttggtcctgt gtagtgactt ga |

| Oligoprolyl-peptidase enzyme cDNA sequence from *Gymnopus fusipes* sequence. Underlined are positions where SNPs are present, as well as their potential codons | SEQ ID NO.: 60 | 1 atgtccatgt cacttttagg tgtatatcct cctgttaaac gggacgaagc ctcagccatt |
|---|---|---|
|  |  | 61 acctaccaaa gcaaacttca cggttctgtc attgtgcatg atccatacag cgcgcttgaa |
|  |  | 121 ataccttcta atgatagttt ggagacaaag gcatttgtcc tctcacaagg taaattttca |
|  |  | 181 cgggcttact tggatgaaat tccgacaagg aaaaattggt tgaaaatatt aaagagtaac |
|  |  | 241 tggagttacc ggcggtttc tgccttgaag cgtgaaagtg acaaccattt ctatttcgaa |
|  |  | 301 tataatgatg gccttcaacc ccagtcatcc atttatcggg tgaaggttgg tgaagaggat |
|  |  | 361 tccatcctta ctgaatctgg acctgggggt gaattgtttt ttgatcccaa tttgctttca |
|  |  | 421 ttggatgggg ttgctgcact tactggtgct gcgatgagtc cttctgggaa gtactgggca |
|  |  | 481 tatggtgtat ctgaacatgg aaacaattca atgacaattt atgttcgaaa acttcatca |
|  |  | 541 ccacatcaac catctcaaga aaagggaaca gatcccggac ggatgaatga tgttctccaa |
|  |  | 601 cacattcgca tgctctttgt gtcctggaca agatagca aaggtttctt ctaccaaaga |
|  |  | 661 tatccaccag agaaaaatga aggaaatggg aatgcaccag ggcagaattg caagatatat |
|  |  | 721 tatcactaca ttgggacaga acaggatagt gacatcctta tcatgagga ccctgatcat |
|  |  | 781 ccggactggt tctcatatgt acagctctcc ccaagtggtc aatatgtcct gctactcata |
|  |  | 841 aatcgtgatt caagttt(a/t)aa ttacctcgcc aagattgctg atttatctgt caatgatatt |
|  |  | 901 gggacccata tccaatggaa gaatttgcat ggattcttgga accatttcac aatgattggg |
|  |  | 961 aatgactact ctgtcatcta tttcaaaaca aatctggatg cacagaactca caaagttgca |
|  |  | 1021 acaatcgact ttcttcaacc agagatgggc ttcacaactc tggtcaagga aatcccaat |
|  |  | 1081 tcagtccttg tggaggccaa atattcaga gaagacaag ttgtgcttt gtaccagcag |
|  |  | 1141 aatgctagca tcaaataca catttatgat ctcaagagtg gcg(c/a)atggct tcaacaaatc |
|  |  | 1201 ttcaagaatc taactggatt cataactaca gttccaaatg ggcgcgctga agatgagatg |
|  |  | 1261 ttttttctct acaatgactt tattacacct gggacaatat atcaatataaa atttgatgat |
|  |  | 1321 gaaagtgaca agggcttggt gttccgtgcc atccaaatcg atggactcaa cctagatgat |
|  |  | 1381 ttcgtgacga aatcaaagtt ttacccatcc aaggatggaa cttcggttca catgttcatc |
|  |  | 1441 acccgcccga aggatgtact catcgacgga actgccgcag tctatatgta tggctatggt |
|  |  | 1501 ggcttctcaa tctcagtgct tccgacgttc tccatctcaa ccctgctatt ttgcaaaatt |
|  |  | 1561 taccgggcaa tgtatgtcgt gcctaacata cgcggaggtt cggagtttgg agaatcatggp |
|  |  | 1621 caccgggagg gaatgttgga caaaaaacag aatggacatg atgacttcca tgcagctgct |
|  |  | 1681 gaatggctca tcgcaaataa gtacgccaaa aaggattgtg ttgccattcg cggggggtcc |
|  |  | 1741 agcggaggga ttttgactac cgcatgtgca aatcaagcac ccgaactcta ccgctgtgta |
|  |  | 1801 attaccattg aaggcataat tgactgctc aaatttccca agttcacgtt tggtgctttg |
|  |  | 1861 ttgcgttcgg aatatggcga tcccgaggac ccagaagctt ttgactacat ctacaaatac |
|  |  | 1921 tcgccttatc ataacattcc gttgggtgat gtagtcatgc caccgatgct attcttcaat |
|  |  | 1981 gcgggatatg atgaccgcgt tcctcctcta cacaccttca agcatgttgc tgcactacaa |
|  |  | 2041 catagatttc ctaaaggccc gaatccaatt ctcatgcgca tggacctaag ttcagggcat |
|  |  | 2101 tatgctggca agagtgtaca aaagatgatt gaggaaactg cagatgaata cagcttcatt |
|  |  | 2161 gggaagtcta tggggcttac tatgcaagtc agagcaaaac catctaataa ccgttggtc |
|  |  | 2221 tgtgtagtga cttga |

TABLE 3

Exemplary amino acid and nucleotide sequences of N-methyltransferases

| *Anomoporia bombycina* | SEQ ID NO.: 61<br>The DOE Joint Genome Institute (JGI) 1346513 | MSSPAVETKVPASPDVTAEVIPAPPSSHRPLPFGLRPGKLVIVGSGIGSIGQFTL<br>SAVAHIEQADRVFFVVADPATEAFIYSKNKNSVDLYKFYDDKKPRMDTYIQ<br>MAEVMLRELRKGYSVVGVIYGHPGVFVTPSHRAISIARDEGYSAKMLPGVS<br>AEDNLFADIGIDPSRPGCLTYEATDLLLRNRTLVPSSHLVLFQVGCIGLSDFRF<br>KGFDNINFDVLLDRLEQVYGPDHAVIHYMAAVLPQSTTTIDRYTIKELRDPVI<br>KKRITAISTFYLPPKALSPLHEESAAKLGLMKAGYKILDGAQAPYPPFPWAGP<br>NVVPIGIAYGRRELAAVAKLDSHVPPANYKPLRASNAMKSTMIKLATDPKAF<br>AQYSRNPALLANSTPGLTTPERKALQTGSQGLVRSVMKTSPEDVAKQFVQA<br>ELRDPTLAKQYSQECYDQTGNTDGIAVISAWLKSKGYDTTPTAINDAWADM<br>QANSLDVYQSTYNTMVDGKSGPAITIKSGVVYIGNTVVKKFAFSKSVLTWSS<br>TDGNPSSATLSFVVLTDDDGQPLPANSYIGPQFTGFYWTSGAKPAAANTLGR<br>NGAFPSGGGGSGGGGGSSSQGADISTWVDSYQTYVVTTAGSWKDEDILKI<br>DDDTAHTITYGPLKIVKYSLSNDTVSWSATDGNPFNAVIFFKVNKPKANPT<br>AGNQFVGKKWLPSDPAPAAVNWTGLIGSTADPKGTAAANATASMWKSIGI<br>NLGVAVSAMVLGTAVIKAIGAAWDKGSAAWKAAKAAADKAKKDAEAAE<br>KDSAVDDEKFADEEPPDLEELPIPDADPLVDTDVDVTDVDTDVDTDVDTDVD<br>VTDVDVTDVDVTDVDVTDVDVTDVDVVDVLDVVVI |

TABLE 3-continued

Exemplary amino acid and nucleotide sequences of N-methyltransferases

| | | |
|---|---|---|
| *Armillaria gallica* | SEQ ID NO.: 62<br>The DOE Joint Genome Institute (JGI) 1000654 | MPANKGTLTIAGSGIASIGHITLETLSYIQGADKVYYVITDPATEAFIQDKSEG<br>DCFDLTVYYDKNKIRYETYVQMCEVMLRDVRADYNVVGVFYGHPGVFVSP<br>SHRAIAIARDEGYRARMLPGVSAEDYMFSDLGFDPAVPGCMTQEATAMLNH<br>NKKLDPSIHNIIWQVGAVGIDTMVFDNRKFHLLVDRLEEDFGPDHRVVNYIG<br>AVLPQSTTVMDEFTIGDLRKEDVVKQFTTVSTFYVPPRTRAPVDQEAMQKF<br>GPSDAPLAHTVRHLYPPSKWAGTQTSVVPAYGPCERAAVDRIADYTPPPDH<br>MILRASPAIRQFMTDLALNPGLRDRYKADPVAVLDATPDLSTQEKFALSFDK<br>PGPVYTVMRATPAAIASGQEPTFDDIAGATESASPPLFVIT |
| *Armillaria gallica* | SEQ ID NO.: 63<br>The DOE Joint Genome Institute (JGI) 622643 | MPANKKGTLTIAGSGIASIGHITLETLSYIQEADKVYYAITDPATEAFIQDKSE<br>GDCFDLTVYYDKNKIRYETYVQMCEVMLRDVRADYNVVGVFYGHPGVFV<br>SPSHRAIAIARDEGYRARMLPGVSAEDYMFSDLGFDPAVPGCMTQEATAML<br>NHNKKLDPSIHNIIWQVGAVGIDTMVFDNRKFHLLVDRLEEDFGPDHRVVN<br>YIGAVLPQSTTVMDEFTIGDLRKEDVVKQFTTVSTFYVPPRTRAPVDQEAMQ<br>KFGPSDAPLVYPPSKWAGTQTFVVPAYGPCERAAVDRIADYTPPPDHMILRA<br>SPAIRQFMTDLALNPGLRDRYKADPVAVLDATPDLSTQEKFALSFDKPGPVY<br>IVMRATPAAIASGQEPTFDDIAGATESASPPLFIIVQVPA |
| *Arthrobotrys oligospora* | SEQ ID NO.: 64<br>The DOE Joint Genome Institute (JGI) 4309 | MSEGGKLILVGTGVRSLCQLTLEAIDEIERADVIYYAVRDATTEGFIKKRNKE<br>AIDLYQYFINDEEIPEADIYIQIAEVMLAATRKGRRVVGAFFGHPGLFMSPNR<br>RALAIAQAEGYTAKILPGVSVDDCLLADLGVDPSFIGCLTCEARDFMIHDHL<br>GLTSRHVIMYEVGYLGFYGDDSKTDYFEYFVNRLEEIYGNEHSLVNYTAAIS<br>PLMQPVINTLTIGDLRKPEVRKQITSASTLYPPPKEILKLNKFGCDLLDQGITN<br>KEQFQHAIFPGQPLYQLIGKALPHEAYSEHAQQVIAGLHRRKISPRYPLYRAS<br>AAMQSTMEDIYLKNEVRKEYLISPTSFTLRVVPGLKEMEKIALASGNYSQID<br>GAMKSGDLDQLTTGAIEIGNYKVILYSGYAIGYERATFAIADFTNFSFFNIY |
| *Armillaria ostoyae* | SEQ ID NO.: 65<br>The DOE Joint Genome Institute (JGI) 252778 | MPANKKGTLTIAGSGIASIGHITLETLSYIQEADKVYYAITDPATEAFIHDKSK<br>GDCFDLSVYYDKNKNRYETYVQMCEVMLRDVRADYNVLGVFYGHPGVFV<br>SPSHRAIAIARDEGYRARMLPGVSAEDYMFSDLGFDPAVPGCMTQEATAMLI<br>HNKKLDPLIHNIIWQVGSVGVDTMVFDNRKFHLLVDRLEEDFGLDHKVVHY<br>IGAVLPQSTTVMDEFTIGDLRKEDVVKQFTTMSTFYVPPRTPAPVDQEAMQK<br>FRSLDAPLARTVHLYPPSKWAGTQTSVVPAYGPYERAAVDRIADYTPPPDH<br>MILRASPAIRQFMMDLALNPGLRDRYKADPVAVLDATPDLSTQEKFALSFD<br>KPGPVYTVMRATPAAIASGQEPTFDGIAGAAKPASFPGVAPLIIISV |
| *Apodospora peruviana* | SEQ ID NO.: 66<br>The DOE Joint Genome Institute (JGI) 642771 | MAAEHATPSPVETHFGRTVPAMGRRPGKLVMVGSGIKSISHMTLETVSHIEQ<br>ADKVFYCVADPGTELFVKSKAKWSFDLYTLYDNDKNRYITYVQMAELCLQ<br>AARDGFFSVGVFYGHPGVFVSPSHRAIGIAKREGIEAYMLPGISAEDCLFADL<br>GVDPSFTGCQTYEATDLLLRDRPISPYSHLIVWQVGVVGDTGFNFGGFTQTK<br>FQVLVDRLEEVYGSDHRLIHYFASTLSHGPAHIEPLRISDLRKPEVEKRMNGI<br>STFYVPQIGKSAHNPKTAERLGLRVDSKTPDRSFGHLIGPAISYNTLETRAVQ<br>ALKTHKPSPSYRKNRLPTSTLPVLTALATSPKAVAHFKRNTTQFLDAFPDMA<br>THVKKVLQTGSPGLLRLLSLNSSADVAAKFVQAEFRDSTLASKYAAVLREN<br>NGDPDGETNIIKFLQDQGYDTTPEDVSTAYLSAISVDLNTYAGYYASTFTNG<br>GVGPNILIQNGAVTVDDTVIKNPVYAQSLLQWSIKDGNAFNAKLTFRILTDD<br>DGKPLAPGAYIGPQFYGTYWKSEEPSTPNIQGKTGTAPIKPVNPVTPVTPTPL<br>DTFTGNFVAYKADATTGKWSEDGTFVVSDPAGSTVPTAVYKGKTLNNYQY<br>SGNETLTWSSTDGNDSNGSISFFINKTATSTNPTLGAQATGRVWAPAEAMPA<br>KVNFFMSLGQSANPSTQSVPSQSASEWKSVGINVGVGLATMLLGTAIIEAIK<br>WRIKLKANPTDPEINQGVKDSSEKVSQSSEQQEAVQKSSVESDASGSADVQP<br>SDIPVPDAPVTTTTDTTTTDTTTTDTTTTDTTTTDTTTTDTTTTDTTTTDTTT<br>TTDVTTDVTTDVDVVVDVDVIVIL |
| *Bjerkandera adusta* | SEQ ID NO.: 67<br>The DOE Joint Genome Institute (JGI) 128644 | MSTTTSNNAGSLTIAGSGIASVAHITLETLSHIREADKVFYIVCDPATEAFIHD<br>NAKAEAVDLTVYYDTNKARYDSYVQMAEVMLQDVRGGKDVLGIFYGHPG<br>VFVSPSHRALAIARSEGYKAKMLPGVSAEDYLFADLEFDPSVHGCATFEATE<br>LLLREKPLNTTMHNIIWQVGAVGVDDMVFTNSKLHVLVDRLEKDFGPEHQV<br>VHYIGAVLPGSRTVMDTFTVADLCKDDVVKQFNPSSTLYIPPRSLAANSSDIA<br>ASLGAKPDHPLVDPTLFPPLRWTKSTSPEAPAYGPLEQAAVAELANHKVPSQ<br>HKVLAASPAMRTLVAELNVALRKKLAADPKAFAGGREGLTEVEKLAVGTG<br>NVGTMGAVMRALPGGEQSTDMVTSPASIEQQSRREAFFLIVLIVSTRILH |
| *Cercospora beticola* | SEQ ID NO.: 68<br>GenBank XP_023455951.1 | MPSQTSIWNHIDELTRHDVFPSTEAGKGELVVVGTGIASIRQMTVEALDYIQR<br>ADKVFYATLDAVTETFIKHHAPSAEDLYQYYDTEKNRVTTYVQMAEVILSS<br>VRKGKLTVAVFYGHPGVFVTPSHRAIYIARHEGYKAQMLPGVSAEDCLYAD<br>LGIDPASSGCSMYEASFLLNEPNRLDSRHHLIIWQVGCVGKEAMIFDNKEIYK<br>LADYLEAEYGPDHPVIAYLAAIQPFHDSKMDKMTVQDLRDQDKVQNIPITA<br>GTTLYVPPKKLPANPPAYKDMAIGYQLALTSAFRISHPDLDVVETYQEEKS<br>WCEELASWSPPKSYNANAAPPVLRRIAVKLALLHHRLHGNVALSDVANAIT<br>TAEPSLTDEEANLLRQFVGHLDFMKKERPPQSVTTSIINNTIVPPIVTQLNIIR<br>KDGSIMKGVKKPSLYVY |
| *Ceratobasidium sp.* (anastomosis group I, AG-I) | SEQ ID NO.: 69<br>The DOE Joint Genome | MASITTGRDTTKSGSLIIAGSGISSVAHLTLETVSHLKNADNVFYLVGDPVTE<br>AFIQENNSTTNLVAHYATSKHRYQTYVEMAEVMLREVRAGHSVFGIFYGH<br>PGVLTTPAHRALTLARQEGYEARMLPGVSSVDYMFADLELEPGQHGCMIHE<br>ATDLLARDRRLDPSVHNILQPSRVGSATLEKEASKFQLLVDRLVRDFGPDH<br>KIVHYSGAVLPQSSSAMVVFVIENLRNEQLANQIRSTSILYIPPRDIVPVHPDA |

TABLE 3-continued

Exemplary amino acid and nucleotide sequences of N-methyltransferases

| | | |
|---|---|---|
| | Institute (JGI)486605 | AAALKLPDMLGLLSTSVQWVGPRFIETADYGPVERKFVDQLERQVIPEGQQS LRASTAMRKFMINLALDPNGLKEYKESPSAVAAGVPGLTDRERSALAIASEG PIFVVMSRTDDEEPTEEQLMEADRNGARIVDSCTMCTLGGGRNS |
| Ceratobasidium sp. (anastomosis group I, AG-I) | SEQ ID NO.: 70 The DOE Joint Genome Institute (JGI)594340 | MTTPSDTNKKGTLTIAGSGIASIRHITLETLSYIKESDKIYYLVADPATEAFIIE NANGSCVSLYGLYGIDKIRYDTYVQMSEVLLRDVRAGFDVLGIFYGHPGVF VSPTQRAMSIALEEGFQARMLPGVSAEDYLFADLRVDPCMFGCAAYEATEL LYRKRRLNPTMQNIIWQVGKRFTIIKLTSPDTQNSKFGLLVDHLEEDYGPDH KVVHYIGAVLPQATTVIQPYTISELRKPEVASQIRACSTFYIPPRDEILPDASMS ERLGLDAPISHLLGGRYPRPAWSVSGFKTAPAYGPREKHLVAELNVRGIPEP DMVLFASQPMRKFMADLALKPRLRDSYRSNPQVIVDAVKGLTSLENMALK LNRVTAITRVMSVNPTALILGIEPTETDLAIDPYMDNGDPKIVVSG |
| Cerrena unicolor | SEQ ID NO.: 71 The DOE Joint Genome Institute (JGI) 312586 | MATQKSGSLTIAGSGIASIGHITLETLSYIEQADKVYYAVADPATEAFIQDKS KVECFDLTVYYDKDKIRFETYIQMSEVMLRDVRAGHSVLGIFYGHPGVFVCP SHRAIAIALSEGYKARMLPGISAEDYMFSDIGFDPALPGCTTQEATHLLLHNK KLDPSMHNIIWQVGGVGADTMNFDNRQFHQLVDCLERDFGSSHKVVHYIG AVMPQSTTIMDEFSIADLRKEEVVKQFTTWSTFYIPPRDAAPVDEGIMQSLGL SSNDMQYTMYPPSSTMRLGIRSPNLDVYGRAGRAAIEKLDHHTPAARHQVL RASPAIRKFMEDLALKSDLRDRYKADPHTVLDAIPGLTSQEKIALGEGKPGP VYKVMRATGRETADGQEHVPHDLTTTDEPGAPVLLLLLLQTT |
| Cerrena unicolor | SEQ ID NO.: 72 The DOE Joint Genome Institute (JGI) 361677 | MATTKTGSLTIAGSGIASVAHITLEVLSYLQEADKIYYAIVDPVTEAFIQDKSK GRCFDLRVYYDKDKMRSETYVQMSEVMLRDVRSGYNVLAIFYGHPGVFVC PTHRAISIARSEGYTAKMLPGVSAEDYMFSDIGFDPAVPGCMTQEATSLLIYN KQLDPSVHNIIWQVGSVGVDNMVFDNKQFHLLVDHLERDFGSIHKVIHYVG AIMPQSATVMDEYTISDLRKEDVVKKFTTTSTLYIPPREIAIMQALEF SGNGDRYMALSQLRGVHARNSGLCAYGPAEQAAVDKLDHHTPPDDYEVLR ASPAIRRFTEDLALKPDLRSRYKEDPLSVLDAIPGLTSQEKFALSFDKPGPVY KVMRATPAAIAAGQEHSLDEIAGSADSESPGALATTIVVIVHI |
| Cladosporium fulvum | SEQ ID NO.: 73 The DOE Joint Genome Institute (JGI) 186945 | MPSQSIWSHIAELTRGGPVPKDVPHKGELVVVGTGIASLRQLTVEALDYIQR ADVVFYATLDAVTEAFIKQHAKAAENLYQYYDTEKNRNATYTQMAETILAS VRKGNMTVAVFYGHPGVFVTPSHRAIYIARQEGYKAKMLPGVSAEDCLYA DLDIDPASSGCSMYEASELLLEPDRLDSRHHLIIWQVGCVGKEAMVFDNKEL YKLADYLEAEYGPKHPAIAYLAAIQPFNDSKMDHMTVEDLRDPEKVRSIPIN AGTTLYVPPKKLPANPQAYKDIEIGYKLGLTSAFRISHPELDVAETYSEIEKG WCEELVSWTPPKSYIPNAATPALRRIAIKLALLHHRLHGSMSLEDIANAATA AEPSLTTDESDLLKQSVGFLDSMFNKERPPQSVTTSIVRSVVPPIVTQLNIIRK DGTVMMGDGKPSIYVF |
| Chalara longipes | SEQ ID NO.: 74 The DOE Joint Genome Institute (JGI) 462219 | MATSSSFQQLPRGSLTIVGSGERSIIQFTTEALMHIEAAEKLYYCVLDAATRG FIKAKNSNSVDLYECYSNTKPRYETYIQMTEAMLRSVRDGLKATVVLYGHP GVFIHPSHRAIAIARSEGYDAWMLLGISVEDYLFADLLIDPSNPGTQTVEATEI LLKERPLLTSSHVIIYQVGCIGNFTFNFSGIKNDKFDALVDRLIQEYGPDHPLV NYQAAISPLSEASIGRHIVSDLRKAEVQESVTGASTFYIPPKTVLQVTPQGAK LVSESDELPTYLSKDVPVFPPFPFNQSLAPIAPAYSSAERKAIEELDNHITPLEY RKYNASSAMQKTVESISFSLDTIKKFRESPSAFASSIEELEPHEIDALSTGSGER IDAAMQGNAAVNPNAAWLITFAIIFGK |
| Coprinopsis marcescibilis | SEQ ID NO.: 75 The DOE Joint Genome Institute (JGI) 670214 | MDATANPKAGQLTIVGSGIASINHMTLQAVACIETADVVCYVVADGATEAFI RKKNENCIDLYPLYSETKERTDTYIQMAEFMLNHVRAGKNVVGVFYGHPGV FVCPTHRAIYIARNEGYRAVMLPGLSAEDCLYADLGIDPSTVGCITYEATDM LVYNRPLNSSSHLVLYQVGIVGKADFKFAYDPKENHHFGKLIDRLELEYGPD HTVVHYIAPIFPTEEPVMERFTIGQLKLKENSDKIATISTFYLPPKAPSAKVSL NREFLRSLNIADSRDPMTPFPWNPTAAPYGEREKKVILELESHVPPPGYRPLK KNSGLAQALEKLSLDTRALAAWKTDRKAYADSVSGLTDDERDALASGKHA QLSGALKEGGVPMNHAQLTFFFIISNL |
| Coprinellus micaceus | SEQ ID NO.: 76 The DOE Joint Genome Institute (JGI) 1707844 | MIGASLAKKGQLTIVGSGIASISHLTLQAVSAIENADIVCYVVADGATEAFIR KKNPNSLDLYHLYGEDKQRTDTYIQMAEFMLIRVRQGQNVVGVFYGHPGV FVCPTHRALYIARSEGYKARMLPGLSAEDCLFADLGIDPSSVGCVTYEATDL LVFKRPINPASHLVLYQVGIVGKSNFKFDYTSDENIHFTKLLDRLEEAYGPEH SVTHYIAPLFPTEDPIAEEYTIAQLRLPEIRDKIHTISTFYVPPKTSESLIYDEVL LASLGVTHKPSVPYPWNPEATPYGPREKKAIELLAEHEPPKGYRPLKERSGL LAVLEKLCLEPLEMKKYNEDRQAYADGLKGLTENEKEALVKGDHRTLAGA LKVGDTPTNPAALVFTFIITRLD |
| Cystostereum murrayi | SEQ ID NO.: 77 The DOE Joint Genome Institute (JGI) 1185527 | MPAPRKGTLTIAGSGIASIGHITLETLSHIQGADKIHYAVTDPATEAFILEKSK DSSSCFDLGIYYDKNKMRYETYVQMCEVMLRDVRGGHNVLGIFYGHPGVF VSPTHRAIALARDEGYTAKMLPGISAEDYMFSDLGFDPAFPGCMTQEATILL VRGRKLDPSVHNIIWQVGGVGVDTMVFDNANFYILVDRLEEDLGPDHKVV HYIGAVLPQSTAVIDEFTVAGLRKEEVVKQITTVSTFYLPPRTLLHADQDMV QKLGLSDSLGKRAVHVYPRTKWINAESPSPPAYGPFERAAVDRLADHTIPSN HLFLRGSQALRQLMTDLALQPTLRARYVADPTSVLDDVTGMSAEETFALTL RHPAPVFKVMRATGEAIANGVPTLGEIAESANSSIAGSSCALIGFFVVVLEI |

TABLE 3-continued

Exemplary amino acid and nucleotide sequences of N-methyltransferases

| | | |
|---|---|---|
| *Coprinellus pellucidus* | SEQ ID NO.: 78<br>The DOE Joint Genome Institute (JGI) 554111 | MPSTTRGSLTLAGAGVTSIGHLTLQTVSAIENADIVCYILNDPVTEAFIIKKNP<br>NVYDLYQLYDDGKPRIETYHQMVEVLMSKVRSGQDVVGLFTGHPGVVNTP<br>AAQAFKIARQEGYTARMLPGITTNDALLADVVADPALGGAMAYEATDFLN<br>NNRVLHPEMNVFIQQVGVVGNKHFNFMEMRSSLLDKLIDRLEETYGGEKEII<br>HYIAPMLPIDKPVMQKMTVSDLKKPEYKAKIVPSSTFYITPNEQLSSVLDSTE<br>GKKKLHREAMSALANHTHGKNYAPMKENLALTEALERLALEPKSLEAYRSDP<br>QSYVNENGRGLTEEERKALVTGRGIRELLSDGPVAAHRIAPLALV |
| *Dendrothele bispora* | SEQ ID NO.: 79<br>The DOE Joint Genome Institute (JGI) 758933 | MPVRIPSPQKEAGSLTIVGTGIESIGQITLQAISHIETASKVFYCVVDPATEAFI<br>RTKNKNCFDLYPYYDNGKHRMDTYIQMAEVMLKEVRNGLDVVGVFYGHP<br>GVFVSPSHRALAIAESEGYKARMLPGVSAEDCLFADLRIDPSHPGCMTYEAS<br>DFLIRERPVNIHSHLVLWQVGCVGVADFNSGGFKNTKFDVLVDRLEQEYGA<br>DHPVVHYMASILPYEDPVTDKFTVSQFRDPQIAKRICGISTFYIPPKETKDSNV<br>EAMHRLQLLPSGKGVLKETGRYPSNKWAPSGSFHDVDPYGPRELAAVTKLK<br>SHTIPEHYQPLATSKAMTDVMTKLALDPRVLSEYKASRQDFVHSVPGLTPNE<br>KNALVKGEIAAIRCGMKNIPISEKQWELRDGLVTKFIVVPIWVSIDDTTGNLE |
| *Dendrothele bispora* | SEQ ID NO.: 80<br>The DOE Joint Genome Institute (JGI) 765759 | MESSTQTKPGSLIVVGTGIESIGQMTLQALSYIEAASKVFYCVIDPATEAFILT<br>KNKNCVDLYQYYDNGKSRMDTYTQMAELMLKEVRNGLDVVGVFYGHPG<br>VFVNPSHRALAIARSEGYQARMLPGVSAEDCLFADLCIDPSNPGCLTYEASD<br>FLIRERPVNVHSHLILFQVGCVGIADFNFSGFDNSKFTILVDRLEQEYGPDHT<br>VVHYIAAMMPHQDPVTDKFTIGQLREPEIAKRVGGVSTFYIPPKARKDINTDI<br>IRLLEFLPAGKVPDKHTQIYPPNQWEPDVPTLPPYGQNEQAAITRLEAHAPPE<br>EYQPLATSKAMTDVMTKLALDPKALAEYKADHRAFAQSVPDLTPQERAAL<br>ELGDSWAIRCAMKNMPSSLLEAASQSVEEASMNGFPWVIVTGIVGVIGSVVS<br>SA |
| *Fomitiporia mediterranea* | SEQ ID NO.: 81<br>The DOE Joint Genome Institute (JGI) 25792 | MATSTETTEKKGSLTIAGTGIASIKHITLETLSYIKEAEKVYYLVADPATEAFI<br>QDNASGTCFNLHVFYDTNKHRYDSYVQMAEVMLLDVRAGHSVLGIFYGHP<br>GVFVSPSHRAIAIAREEGFKAHMLPGISAEDYMFADIGFDPATHGCVSYEATE<br>LLVRDKPLLPSSHNIIWQVGAIGANAMVFDNGKFNILVDRLEQVFGPDHKVV<br>HYIGAVLPQSTSTIEAYTISDLRKGDVVEKFSTTSTLYVPPSVEARLSGIMVRE<br>LGLEDSGFHTKSSQSRTLWAGPVTSSAPAYGPQERIVIAQIDKDVIPDSHQILQ<br>ASDAMKKTMANLALNPKLSEEYYASPSTVVEKVTGLSEQEKKALILCSAGAI<br>HMVMAATQTNIAQGHQWSAEELEAAGTPHPALALLVVIICLI |
| *Fomitiporia mediterranea* | SEQ ID NO.: 82<br>The DOE Joint Genome Institute (JGI) 30904 | MAATTETMKKGSLTIAGSGIASIKHMTLETVSHIKEAEKVYYIVTDPATEAYI<br>KDNAVGACFDLRVFYDTNKPRYESYVQMSEVMLRDVRVGHSVLGIFYGHP<br>GVFVSPSHRAIAIAKEEGFQARMLPGISAEDYLFADIGFDPAAHGCMSYEATE<br>LLVRNKPLNTSTHNIIWQVGALGAEAMVFDNAKFSLLVDRLEQDYGSDHKV<br>VHYIGAILPQADPTVEAYIVADLRKEDVVKQFNAISTLYIPPRVAGKELDDM<br>AKKLGIADSAAYLKNHYPQAPYTGPEFATDPAYGPREKAVIDQIDNHAAPEG<br>HTVLHASDALKKLNTDLALSPKFLEEYKENPMPILEAMDGLTNEEKAALMQ<br>NPLGATHELMWATPDEIANGRALPVVNFMAYGGYGGYYGGGCRPCPCCVV<br>TDRWSSGGSNKCNMVNNLNV |
| *Fomitiporia mediterranea* | SEQ ID NO.: 83<br>The DOE Joint Genome Institute (JGI) 162487 | MAATTETTKKGSLTIAGSGIASIKHMTLETVSHIKEVEKVYYIVSDPATEAYI<br>KDNAVGTCFDLRVFYDTNKPRYESDVQMSEVMLRDVRAGHSVLGIFYGHP<br>GVFVSPSHRAIAIAKEEGFQARMLPGISAEDYLFADIGFDPAVHGCMSYEATE<br>LLVRNKPLNTSTYNIIWQVGALGAEAMVFDNAKFSLLVDRLERDYGSDHKV<br>VHYIGAILPQADSTIEAHTVSDLRKEDIVKQFNAISTLYIPPRVAGKFLDDMV<br>EKLGIADPATFLKNHYTQPPYSGPEFATDPAYGPREKAVIDQIDNHAAPEGH<br>TVLHATDALKKLNTDLALSPKFLKEYKENPMPILEAMDGLTDEEQAALMQN<br>PLGATHELMWATPDEIANGRVLPVVNFCFLGGNRRGYRRGYQAVNYGGSY<br>NTYIINNF |
| *Fomitiporia mediterranea* | SEQ ID NO.: 84<br>The DOE Joint Genome Institute (JGI) 117392 | MATSTETAQKKGSLTIAGTGIASIKHITLETLSYIKEAEKVYYLVADPATEAFI<br>HDNASGTCFNLHVFYDTNKLRYDSYVQMAEVMLRDVRAGNSVLGLFYGHP<br>GVFVSPSHRAIAVAREEGFKAQTLPGISAEDYMFADIGFDPASHGCVSYEAT<br>DLLARDKPLLPSSHNIIWQVGAIGANAMVFDNGKFNVLVDRLERDFGPNHK<br>VVHYIGAVLPQSTSKVEQYTVADLRKDYVVKTFTTTSTLYVPPCVDAGISNI<br>MARELGLEDSTGLRTRGNQPLPLKTGPAISLASVYGSHERTTIAQIDKGVTPD<br>TLQILQASDAMKKLMADLALKPKLLEKYRGNPSVVIDEVTGLAPQEKAALT<br>LCSAGAIYMVMAASQIDIAKGRQWSTEELKTAADVSAPVILVLSQYNTVH |
| *Gyromitra esculenta* | SEQ ID NO.: 85<br>The DOE Joint Genome Institute (JGI) 514041 | MSVQPQSSAKKGGLVVVGSGIRSVSQLTLEAVMHIEKADTVLYCVCDPSTE<br>GFIKRKNKNAIDIYGYYSDLKERPDAFVQMAEVILREVRKGINVVAVFYGHP<br>GIFVHPSRRALAIAKKEGYAARMLPGISAEDCLFADLLVNPSFPGAQLVEASD<br>IVYRARPLATSCHVVIFQAACFGHWKYNFTAPENGKFPDHLVNRLQKDYGPD<br>HPIVSYMAAVSPLEDPVINRHTISDLYKADVVKKEITPNCTLYIPPKDLLPISPA<br>GELIILGHQAGPDETPKEPPLPIHHYLAPEEETYGPQETSAVAALEKGAISADY<br>RPYCASPAMQKVTESLSLDPEVLKTYRESPQAFAESIPGLEAREVKALASGSP<br>VKIHDSMWVEGKSEVRW |
| *Gymnopilus junonius* | SEQ ID NO.: 86<br>The DOE Joint | MATPIATTTNTPTKAGSLTIAGSGIASVGHITLETLAYIKESHKVFYLVCDPVT<br>EAFIQENGKGPCINLSIYYDSQKSRYDSYLQMCEVMLRDVRNGLDVLGVFY<br>GHPGVFVSPSHRAIALAREEGFNAKMLAGVSAEDCLFADLEFDPASFGCMTC<br>EASELLIRNRPLNPYIHNVIWQVGSVGVTDMTFNNNKFPILIDRLEKDFGPNH |

TABLE 3-continued

Exemplary amino acid and nucleotide sequences of N-methyltransferases

| | | |
|---|---|---|
| | Genome Institute (JGI) 1778734 | TVIHYVGRVIPQSVSKIETFTIADLRKEEVMNHFDAISTLYVPPRDISPVDPTM AEKLGPSGTRVEPIEAFRPSLKWSAQNDKRSYAYNPYESDVVAQLDNYVTP EGHRILQGSPAMKKFLITLATSPQLLQAYRENPSAIVDTVEGLNEQEKYGLKL GSEGAVYALMSRPTGDIAREKELTNDEIANNHGAPYAFVSAVIIAAIICAL |
| *Gymnopus fusipes* | SEQ ID NO.: 87 | MQSSTQKQAGSLTIVGSGIESISQITLQSLSHIEAASKVFYCVVDPATEAYLLA KNKNCVDLYQYYDNGKPRMDTYIQMAEVMLREVRNGLDIVGVFYGHPGV FVNPSQRAIAIAKSEGYQARMLPGISAEDCLFADLGIDPCNPGCVSYEASDFLI RERPVNVSSHFILWQVGCIGVADFTFVKFNNSKFGVLLDRLEHEYGADHTV VHYIAAVLPYENPVIDKLTISQLRDTEVAKRVSGISTFYIPPKELKDPSMDIMR RLELLAADQVPDKQWHFYPTNQWAPSAPNVVPYGPIEQAAIVQLGSHTIPEQ FQPIATSKAMTDILTKLALDPKMLTEYKADRRAFAQSALELTVNERDALEM GTFWALRCAMKKMPSSFMDEVDANNLPVVAVVGVAVGAVAVTVVVSLND LTDSVN |
| *Hydnomerulius pinastri* | SEQ ID NO.: 88 The DOE Joint Genome Institute (JGI) 28991 | MPVPTTTNKNGSLTIAGSGIASIRHMTLETLSAIKSADKVYYTVCDPATEAFI QDNATGSCSDLTVYYDKEKSRYDTYVQMCEVMLREVRAGHNVLGVFYGH PGVFVSPSHRAIAIARAEGYKAEMLAGVSAEDYMFADLGFDPAAHGCVTYE ATEMLLRKKQLNPATHNIIWQVGGVGVSNMIFDNARFHLLVDRLEDTFGPD HQVVHYIGAVLPLSVKTMETYTIADLRKEDVVAQFNPTSTLYIPPRDVSPND PEVAQQLSSFEAVVRSKYPPPGWTTSEPSSALAYGPRERDAIAQLDSHVAPD SHKVLRASSAIRRLMADLALSPELLATYRKDPQAVVAATEGLTVQEKAALS LNKAGAIYGVMKATPYDIANNRSLSVADMGAINEPAALTTMINIHVTHV |
| *Lentinula edodes* | SEQ ID NO.: 89 The DOE Joint Genome Institute (JGI) 1040599 | METPTLNKSGSLTIVGTGIESIGQMTLQTLSYIEAADKVFYCVIDPATEAFILT KNKDCVDLYQYYDNGKSRMDTYTQMSEVMLREVRKGLDVVGVFYGHPGV FVNPSLRALAIAKSEGFKARMLPGVSAEDCLYADLCIDPSNPGCLTYEASDFL IRERPTNIYSHFILFQVGCVGIADFNFTGFENSKFGILVDRLEKEYGAEHPVVH YIAAMLPHEDPVTDQWTIGQLREPEFYKRVGGVSTFYIPPKERKEINVDIIREL KFLPEGKVPDTRTQIYPPNQWEPEPVPTVPAYGSNEHAAIAQLDTHTPPEQYQ PLATSKAMTDVMTKLALDPKALAEYKADHRAFAQSVPDLTANERTALEIGD SWAFRCAMKEMPISLLDNAKQSMEEASEQGFPWIIVVGVVGVVGSVVSSA |
| *Lentinula lateritia* | SEQ ID NO.: 90 The DOE Joint Genome Institute (JGI) 755966 | METPTLNKSGSLTIVGTGIESIGQMTLQTLSYIEAADKVFYCVIDPATEAFILT KNKDCVDLYQYYDNGKSRMDTYTQMSEVMLREVRKGLEVVGVFYGHPGV FVNPSLRALAIAKSEGYKARMLPGVSAEDCLYADLCIDPSNPGCLTYEASDF LIRERPTNIYSHFILFQVGCVGIADFNFTGFENSKFGILVDRLEKEYGADHPVV HYIAAMLPHEDPVTDQWTIGQLREPEFYKRVGGVSTFYIPPKERKEINVDIIR ELKFLPEGKVPDTRTQIYPPNQWEPEPVPTVPAYGSNEHAAIAQLDAHSAPEQ YQPLATSKAMTDVMTKLALDPKALAEYKADHRAFAQSVPDLTANERTALEI GDSWAFRCAMKEMPVSLLDNAKQSMEEASEQGFPWIIVVGVVGVVGSVVS SA |
| *Lentinula raphanica* | SEQ ID NO.: 91 The DOE Joint Genome Institute (JGI) 642948 | MESSTQTKTGSLIIVGTGIESIGQMTLQTLSYIEAADRVFYCVIDPATEAFILTK NKNCVDLYQYYDNGKTRMDTYTQMSEVMLREVRKGLKVVGVFYGHPGVF VNPSLRALAIAKSEGFKARMLPGVSAEDCLYADLCIDPSNPGCLTYEASDFLI RERPANIYSHFILFQVGCVGIADFSFTGFDNSKFGVLVDRLEKEYGGDHPVV HYIAAMLPHEEPVTDKFTIAQLREPEVYKRVGGVSTFYIPPKERKEINADIIHQ LKFLPEGKVPDKRTQIFPPNQWEPEVPTLPAYGPNDYATIALIDSHTPPEQYQ PLATSKAMTDVMIKLALDPQALEEYKADHRAFAQSIPDLTTHERIALEMGDS WAFRCAMKDMPQSLLERAQQNMEESAQHGFPWIIVVGVVGVVGSVVSSA |
| *Mycosphaerella eumusae* | SEQ ID NO.: 92 GenBank KXT02930.1 | MASSSVWSYIDHLTQEDDISSSCGDAGDKKGELVVVGTGIASLRQMTVEAL DYIQRADMVFYVVLDAMTECFIQTHAKKHHDLYQYYDKNKPRNASYVQM AELMVQSVRDGNLTVAVYYGHPGVFVFPTHRAIHIAREEGYKAKMLPGVSA EDCLYADLGIDPGTTGCSMFEATYLLNEPDRLDPRNHVIIWQPGCVGKSTMV FDNSEIHELADYLEKTYGPEYPIIAYLAAVRPFNDPQIDKLMVKDLRDLEKLK AIPFNAATTLYIPPKTLPVVPQDMEDPIELQLARNSAFRMSHPEMNLVDNYT KQDKQWVEDLKHFVPPNDYKRMTASTAMRRAAIKLALLHHRLHGVLPREL IADRALSKSGLTPNEAESLRVMIDNLDLFLREGVERPPAVNGVSVIVFALLIIR NEDQRVNLHGGKMGWKRSVVVN |
| *Marasmius fiardii* | SEQ ID NO.: 93 The DOE Joint Genome Institute (JGI) 958901 | MTFNDKKGSLTIAGSGIASIRHITLETLSHIERADKVYYLVADPATEAFIQDKS KGDYVDLAIYYDKDKNRYESYVQMSEVILNDVRAGYNVLGVFYGHPGVFV SPSHRTVAIARDEGYRVNMLPGVSAQDYMFSDIGFDPAIPGCTIQEASTILFL DKRLDPTVHNIIGQVGCVGVGTMAFDNRQFHLLVDHLEKDFGPEHKVVHYI GAVLPQSATVKDEFKIADLRKDDVVKQISTISTFYIPPRQVTPVPKEVAEKLG FHPLPTLPISTRIYPFLGSKASSSSTSFYEPFERNAVDRLQNHLPPLDYNTLRAS PAVRQFMTDLALRPDVLNLYQADPMVLVDEIPGLTPSEKSALRSGDPGPVYE LMRSNFTREKSTQMGAIVFVSI |

TABLE 3-continued

Exemplary amino acid and nucleotide sequences of N-methyltransferases

| | | |
|---|---|---|
| *Mycena rosella* | SEQ ID NO.: 94<br>The DOE Joint Genome Institute (JGI) 934645 | MALKKPGSLTIAGSGIASIGHITLETLALIKEADKIFYAVTDPATECYIQENSR<br>GDHFDLTTFYDTNKKRYESYVQMSEVMLRDVVRAGRNVLGIFYGHPGVFVA<br>PSHRAIAIAREEGFQAKMLPGISAEDYMFADLGFDPSTYGCMTQEATELLVR<br>NKKLDPSIHNIIWQVGSVGVDTMVFDNGKFHLLVERLEKDFGLDHKIQHYIG<br>AILPQSVTVKDTFAIRDLRKEEVLKQFTTTSTFYVPPRTPAPIDPKAVQALGLP<br>ATVTKGAQDWTGFQSVSPAYGPDEMRAVAALDSFVPSQEKAVVHASRAMQ<br>SLMVDLALRPALLEQYKADPVAFANTRNGLTAQEKFALGLKKPGPIFVVMR<br>QLPSAIASGQEPSQEEIARADDATAFIIIYIVQG |
| *Mycena rosella* | SEQ ID NO.: 95<br>The DOE Joint Genome Institute (JGI) 1200894 | MALNKPGSLTIAGSGIASIGHITLETLALIKEADKIFYAVTDPATECYIQENSR<br>GDHFDLTTFYDTNKKRYESYVQMSEVMLREVRAGRNVLGIFYGHPGVFVAP<br>SHRAIAIAREEGFQAKMLPGISAEDYMFADLGFDPSTQGCMTQEATELLVRN<br>KKLDPSVHNIIWQVGSVGVDTMVFDNGKFHLLVERLEKDFGLDHKIQHYIG<br>AILPQSVTVKDAFAIRDLRKEEVLKQFTTTSTFYIPPRAPAPIDAKVLQALGLP<br>PPAQATKDRTGYGPLEKQAVAALDSFIPSQEKQVVHASPAMQSLMADLALR<br>PALFEQYKADPVGFANTRNLNGLTAQEKFALGFNKSGPIFAVMRHLPSAIAS<br>GQERSQEEIAHAADDKELLALVVVIVQ |
| *Omphalotus olearius* | SEQ ID NO.: 96<br>The DOE Joint Genome Institute (JGI) 2087 | METSTQTKAGSLTIVGTGIESIGQMTLQALSYIEAAAKVFYCVIDPATEAFILT<br>KNKNCVDLYQYYDNGKSRLNTYTQMSELMVREVRKGLDVVGVFYGHPGV<br>FVNPSHRALAIAKSEGYRARMLPGVSAEDCLFADLCIDPSNPGCLTYEASDFL<br>IRDRPVSIHSHLVLFQVGCVGIADFNFTGFDNNKFGVLVDRLEQEYGAEHPV<br>VHYIAAMMPHQDPVTDKYTVAQLREPEIAKRVGGVSTFYIPPKARKASNLDI<br>IRRLELLPAGQVPDKKARIYPANQWEPDVPEVEPYRPSDQAAIAQLADHAPP<br>EQYQPLATSKAMSDVMTKLALDPKALADYKADHRAFAQSVPDLTPQERAA<br>LELGDSWAIRCAMKNMPSSLLDAARESGEEASQNGFPWVIVVGVIGVIGSV<br>MSTE |
| *Phlebiopsis gigantea* | SEQ ID NO.: 97<br>The DOE Joint Genome Institute (JGI) 54959 | MSSASSDSNTGSLTIAGSGIASVRHMTLETLAHVQEADIVFYVVADPVTEAYI<br>KKNARGPCKDLEVLFDKDKVRYDTYVQMAETMLNAVREGQKVLGIFYGHP<br>GVFVSPSRRALSIARKEGYAKMLPGISSEDYMFADLEFDPAVHGCCAYEAT<br>QLLLREVSLDTAMSNIIWQVGGVGVSKIDFENSKVKLLVDRLEKDFGPDHH<br>VVHYIGAVLPQSATVQDVLKISDLRKEEIVAQFNSCSTLYVPPLTHANKFSGN<br>MVKQLFGQDVTEVSSALCPTPKWAAGSHLGDVVEYGPREKAAVDALVEHT<br>VPADYRVLGGSLAFQQFMIDLALRPAIQANYKENPRALVDATKGLTTVEQA<br>ALLLRQPGAVFGVMKLRASEVANEQGHPVAPASLDHVAFTAPSPASLDHVA<br>FSAPNPASLDHVAFIAPTPASLDHVAFSAPTPASLDHVSFGTPTSASLDHVAF<br>EAPVPASLDHVAFAAPVPASLDHVAFAAPTPASLDHVAFAAPTPASLDHVAF<br>AVPVPASLDHIAFSVPTPASLDHVAFAVPVPDHVAGIPCM |
| *Phlebiopsis gigantea* | SEQ ID NO.: 98<br>The DOE Joint Genome Institute (JGI) 80884 | MSHDATTTKRGSLTIAGSGIASVAHITLETVAYLAEADSVFYIVADPVTEAFI<br>HKNAKVPCQDLHVFYDKDKSRYDTYVQMAETMLNSVRAGEKVLGIFYGHP<br>GVFVSPSRRALAIAREEGYEAKMLPGVSAEDYMFADLEFDPATHGCCAYEA<br>THILLKNIPLDTSINNIIWQVGGVGVTKIDFENSKFKFLVDRLEKDFGLDHKV<br>VHYIGAVLPQSATVKEVYTISDLRKPEVATQFNACSTLYVPPRKGAADPFPA<br>HVVEQLLGTTTSKVVDALYPVAQWDLGNNLPAVPAYGPYEQKVVAAMGD<br>HTTPDDYRALAGSPAMQQFMAELALRPTLQAKYRASPQAVVDATPGLTDLE<br>RAALLLNAAGPVLAVMKPRAGEVMTVDKLKESVTPSAAYLFIFIVIAAAAHI<br>LV |
| *Pseudocercos pora musae* | SEQ ID NO.: 99<br>GenBank KXS93410.1 | MASTVWSYFDQLTRDDDFGSCEDACSKQGELVVVGTGIASLRQMTVEALD<br>YIQRADMVFYVVLDAMTEAFIQTHAKKHHDLYQYYDKNKPRSASYIQMAE<br>LMVQSVRDGNLTVAVYYGHPGVFVFPTHRAIHIAREEGFKAKMLPGVSAED<br>CLYADLGIDPGSTGCSMFEATYLLNEPDRLDPRNHVIIWQPGCVGKSAMVFD<br>NSEIHELADYLEKTYGAEYPVIAYLAAVRPFNDPQIDKLMVKDLRDLEKLRA<br>IPFNAATTLYIPPKTLPAVPQDIANPIEVQLARNSAFRLSHPEMNLVDMYTKQ<br>DKQWCDDLKHFVPPNDYKPMTATPAMRRLAIKLALLHHRLHGALPTELIAS<br>KALSKSELSSSEAESLRLMIKNLDLFLREGVERPPAVNGVSVIVFALLIIRSED<br>QRVGFDGKMEWKRSVVVN |
| *Porodaedalea chrysoloma* | SEQ ID NO.: 100<br>The DOE Joint Genome Institute (JGI) 797528 | MPVSTTTTKNGTLVIAGSGIASIAHITLETLSHIKESDRVYYIVGDPATEAFIQD<br>NASGTCFDLTIFYDTNKVRYDSYVQMCEVMLRDVRAGHTVLGVEYGHPGV<br>FVSPSHRAIAIARDEGYKARMLPGVSAEDYLFADLGEDPATHGCTSYEATDL<br>LVRNKPLNASTHNIIWQVGGVGVGTMVFDNAKFHLLVDRLEKDFGPSHTVV<br>HYIGAVLPQSITTMDKLTIADLRKDAVVKQFNPTSTFYIPPRDISLDPLDTMAK<br>KLGMDDASARPVSLYPPSRWTGTKFTTAPAYGPREKDVIAKIDTYAAPKDH<br>KILHASRSMKKLMTDLALNPKLLEKYRANTKAVVEATEGLSAQEKAALNM<br>DLAGPVHAVMKATPSDITDGREMSVDAVASATEPSAALILLLV |
| *Rhizopogon vinicolor* | SEQ ID NO.: 101<br>The DOE Joint Genome Institute (JGI) 805340 | MITSNSSNGSNSTKCGTLTIAGSGIASVAHITLETLSYIKESEKIFYLVCDPVTE<br>AYIQDNTTADCFDLSVFYGKNKGRHDSYIQMCEVMLKAVRAGHDVLGVFY<br>GHPGVFVSPSHRAIAVARQEGYKAKMLPGISAEDYMFADLEFDPSLSGCKTC<br>EATEILLRDKPLDPSIQNIIWQVGGVDMEFEKSKFQLLVDRLEKDFGPGH<br>KVVHYIGAVLPQSTTTMDTFTIADLRKEDVAKQFGTISTLYVPPRDEGHVNP<br>SMAEAFGTPAGPARLNDSVKWVGPKLSIVSANGPHQRDVIAQIDTHIAPEGH<br>KKLHASAAMKKFMTDLALRPKFLDEYKLNPVAVVESAQGLSNLEQFGLKF<br>ARGGPVDALMKATESDIASGRQLTEEEIAKGNGPPGAAATVLLLGALIITLSL<br>NFS |

TABLE 3-continued

Exemplary amino acid and nucleotide sequences of N-methyltransferases

| Rhizopogon vinicolor | SEQ ID NO.: 102 The DOE Joint Genome Institute (JGI) 749423 | MSTKRGTLTIAGSGIASVGHITLGTLSYIKESDKIFYLVCDPVTEAFIYDNSTA DCFDLSVFYDKTKGRYDSYIQMCEVMLKAVRAGHDVLGVFYGHPGVFVSP SHRAIAVARQEGYKAKMLPGISAEDYMFADLEFDPSVSGCKTCEATEILLRD KPLDPTIQNIIWQVGSVGVVDMEFSKSKFQLLVDRLEKDFGPDHKVVHYIGA VLPQSTTTMDTFTIADLRKEDVAKQFGTISTLYIPPRDEGHVNLSMAKVFGGP GASVKLNDSIKWAGPKLNIVSANDPHERDVIAQVDTHVAPEGHKKLRVSAA MKKFMTDLALKPKFLEEYKLDPVAVVESAEGLSNLERFGLKFARSGPADAL MKATESDIASGRQLTEEEIAQGTGPVGLQTALALLVLLGLGVAIVTRPDD |
|---|---|---|
| Rhizopogon vinicolor | SEQ ID NO.: 103 The DOE Joint Genome Institute (JGI) 700323 | MTTSNSSNGTKRGTLTIAGSGIASVGHITLGTLSYIKESDKIFYLVCDPVTEAFI HDNSTADCFDLSVFYDKNKGRYDSYIQMCEVMLKDVRAGHHVLGVFYGHP GVFVSPSHRAIAVARQEGYNAKMLPGISAEDYMFADLEFDPSLYGCKTCEAT EILLRDKPLDPSIHNIIWQVGSVGVVDMEFSKSKFHLLVDRLEKDFGLEHKV VHYIGAVLPQSATTMDTFTIADLRKEDVAKQFGTISTLYIPPRDERPFNPRMA EAFGSPAAPAMPISSVKWAGPKLNIPPVYGPHERDVIAQIDTHVAPEGHKKL HTSAAMKKFMTDLAMKPKLLEEYKRDPVAVVEAAEALSDLEKFGLKFARV GPADVLMKATESDIASGRQLTEEEIAKANGPQGLGTIILVWHTVHGIA |
| Rhizopogon vinicolor | SEQ ID NO.: 104 The DOE Joint Genome Institute (JGI) 769711 | MTTDIKRGTLTIAGSGIACIAHITLETLSYIKESDKLFYLVCDPVTEAFIQDNAT GGCFDLSVFYDKNKSRYDSYIQMCEVMLKAVRVGYDVLGVFYGHPGVFVS PSHRAIAVAREEGYKARMLPGISAEDYLFADLEFDPSLHGCNTYEATELLLR GKPLDPLIHNIIWQVGSVGVIDMEFEKSKFHLLVDRLENDFGPDHKVVHYIG AVLPQSTTTMDTFTISDLRKEDVAKQFGTISTLYVPLRDEALVNPIMAEAFGR TAAPVTMNSSVKWAGPKLNIVSAYGPHERSVIAQIDTHVAPEGHKKLHTSTA MNKFMTDLALKPKFLEEYKLDPAAVVESAEGLSNMEKFGLKVAKAGAAHI LMKATESDIASGRQLTEDEIARADGPEGLAVVVIVLVATVALLALLV |
| Rhizopogon vinicolor | SEQ ID NO.: 105 The DOE Joint Genome Institute (JGI) 854502 | MTTGTERGTLTIAGSGIACVAHITLETLSYIKESDKLFYLVCDPVTEAFIQDNA TGDCFDLSVFYDKNKSRYDSYIQMCEVMLKAVRAGHHVLGVFYGHPGVLV SPSYRAIAVAREEGYKARMLPGISAEDYLFADLEFDPCFPSGCNTYEATELLL RDRSLDPSIHNIIWQVGSVGVTDMEFEKSKLNLLVDRLENDFGPDHKVVHYI GAVLPQSTTTMDTFAVSDLHKEDVAKQFGTISTLYIPPRDEAPVSSNMMEVL NRPPVPNMPPPSVMWVAPKLNISSAYTPHERDVIAQIDTHVAPEGYKKLHTS AAMKKFMTDLALKPKFVEEYMLDPVAVIESAEGLSDVEKFALKVAKGGAA NILMKATESEIASGRHLTEDEISNAVGPLGLSATVVLVVAEAVVIMAMAVLV |
| Rhizopogon vinicolor | SEQ ID NO.: 106 The DOE Joint Genome Institute (JGI) 710394 | MTTGTERGTLTIAGSGIACVAHITLQMLSYIKESDKLFYLVCDPVTEAFIQDN ATGDCFDLSVFYDKNKSRHDSYIQMCEIMLRAVRADHHVLGVFYGHPGIFV SPSYRAMAVAREEGYKAKMLPGISTEDYLFADLEFDPCLPGCNTYEATELLL RDRSLDPSIHNIIWQVGSVGVIDIQFEKSKFHLLVDRLEDFGPDHKVVHYIG AVLPQSTTTMDTFTISDLRKEDVAKQFGTISTLYIPPRDKPLAHPGMAEAIGS LTAPAKLYSPVKWAGPKLNIVSPYSPYERDVIARIDTHVAPEGHKKLYTSAA MKKFMTDLALKPKLLEEYMLDPVAVVESADGLSDVEKFGLKLAKDGVANI LMMATESDIASGRHLAEDEIAKAKGPLGLLTVVLVIVGSSLVVHRLT |
| Rhizopogon vinicolor | SEQ ID NO.: 107 The DOE Joint Genome Institute (JGI) 777202 | MTTSNSSDGTKRGTLTIAGSGIASVGHITLGTLSYIKESDKIFYLVCDPVTEAFI HDNSTADCFDLSVFYDKNKGRYDSYIQMCEVMLKAVRAGHDVLGVFYGHP GVFVSPSHRAIAVARQEGYKAKMLPGISAEDYMFADLEFDPSLYGCKTCEAT EILLRDKPLDPTIQNIIWQVGSVGVVDMEFSKSKFHLLVDRLEKDFGPDHKV VHYIGAVLPQSATIMDTFTIADLRKEDVAKQFGTISTLYIPPRDERPVHSGMA EAFGSPAAVKPNTSIKWAGPKLNIVSACGPHEPDVIAQIDTHVAPEGYKKL HASVSMKKFMTDLALKPKFLEEYKLDPVAVVEAAEGLSDLEKFGLKFARDG PADTLMKATESDIASGRQLTEEEVANGNGPLGLQTVVVVWLTTKIVSPEL |
| Rhizopogon vinicolor | SEQ ID NO.: 108 The DOE Joint Genome Institute (JGI) 777713 | MTTDTKRGTLTIAGSGIASIAHITLETLSYIKESDKLFYLVCDPVTEAFIQDNA TGDFFDLSVFYDKNKSRYDSYIQMCEIMLRAVRAGHSVLGIFYGHPGVFVSP SHRAIAVAREEGYKARMLPGVSAEDYMFADLEFDPSQSTCNTYEATELLLR DRPLDPAIQNIIWQVGSVGVVDMEFEKSKFHLLVDRLEQDFGPDHKVVHYIG AVLPQSTTTMDIFTISDLRKENVAKQFGTISTLYIPPRDEGPVSSSMTQAFDFK AGAMVYSPVKWAGPKLNIVSALSPYERDVISQIDTHVAPEGYKILHTSAAMN KFMTDLSLKPKFLEEYKLYPEAVVESAEGLSNLEKFGLKFGSDGAVYILMKA TESDIASGRQLTEDEIAKHKSVGFPTVLVILPTVIVVLIGRE |
| Sanghuangporus baumii | SEQ ID NO.: 109 GenBank OCB86575.1 | MAGSQKGTLTIAGSGIASIGHITLETLSYIQEADKIHYAVADPATEAFILDKSK DSSHCFDLTVYYDTNKMRYETYVQMCEVMLRDVRGGYNVLGIFYGHPGVF VSPSHRAIAIARDEGYIAKMLPGVSAEDYMFSDIGFDPAVPGCMSQEATGLL VCKKKLDPSIHNIIWQVGSVGVDTMNREFHILVDRLEEDFGLDHKVVHYIGA VLPQSTTVMDEFTIADLRKEEVVKQITTTSTFYLPPRSMAHIDQDMLQKLRLS LSPVEHVMHVYPRSKWASAESPNPPAYGPIEREAVSHLTNHTIPNDHQFLRG SRPLRQLMVDLALQPGLRNRYKADPASVLDAIPGMSAEEKFALTLNHAAPIF KVMRASRADGEAPTLDEIAGTVNPSLACPAIVVCFVGIMVIVIAL |
| Serendipita vermifera ssp. bescii | SEQ ID NO.: 110 The DOE Joint Genome | MASSTHPKRGSLTIAGTGIATLAHMTLETVSHIKEADKVYYIVTDPVTQAFIE ENAKGPTFDLSVYYADKYRTSYVQMAEVMLNAVREGCNVLGLFYGHP GIFVSPSHRALAIAREEGYEARMLPGVSAEDYMFADLGLDPALPGCVCYEAT NFLIRNKPLNPATHNILWQVGAVGITAMDFENSKFSLLVDRLERDLGPNHKV VHYGAVLPQSATIMETYTIAELRKPEVIKRISTTSSTFYIPPRDSEAIDYDMV |

TABLE 3-continued

Exemplary amino acid and nucleotide sequences of N-methyltransferases

| | | |
|---|---|---|
| | Institute (JGI) 781716 | ARLGIPPEKYRKIPSYPPNQWAGPNYTSTPAYGPEEKAAVSQLANHVVPNSY KTLHASPAMKKVMIDLATDRSLYKKYEANRDAFVDAVKGLTELEKVALKM GTDGSVYKVMSATQADIELGKEPSIEELEEGRGRLLLVVITAAVVV |
| Thanatephorus cucumeris | SEQ ID NO.: 111 The DOE Joint Genome Institute (JGI) 718597 | MATFTEDNHPKRGSLIIAGSGIASVAHFTLETVSHLKNADKVFYLVNDPVTE AFIQENNPDTFDLVTFYSETKPRYHSYVEMAEIMLKEVRAGHKVLGIFYGHP GVFVHPSRRALFIARQENYEARMLPGISSEDYMFADLELDPAEFGCMTCEAT ELIARNRPLNTSVHNIIWQAGIVGVSTLEYQESKFQLLVDRLERDFGPEHKVV HYVGAIRMTPQAQSAMVVYSIQELRNPAVANFINSGSTLYVPPRLRDVPRVD PDSATALGLPPVTTGFLSASPTWVGSRFVTPSSYGDLENNIVAQMNENRSRS RITEPSPAMKGLMIKLAQELKLQEEYKKDPAKVAADTPDLKEIERRALSYGL DNTIRAVMSHRGSSSGPTEEQLKEISWEGSTIKHVTASSIAQ |
| Trypethelium eluteriae | SEQ ID NO.: 112 The DOE Joint Genome Institute (JGI) 416528 | MAPSTSDRSKLPVAGYRPGRLVMVGSGIKSIAHLTLEAIGHIEQADKVFFVV ADMTTAAFIHSRNANAVDMYNLYDIGKPRYHTYVQMAERMLREVRNGFY VVGVFYGHPGIFVNPSHRAIAIARQEGHQAFMLPGISAEACLFADVGIDPSTS GCQTIEATDLLLRNRPINTGSHLIIFQVGIVGDSGFHPQGFKNTKLHVLLEKLT EVYGSGHRLVHYIAPSMATVEPTIDFLTLGALKKSRNARRVTGISTFYIPPKH DVQPSPSAAKKLGLKVQQGAKSRNFGRLTMPEDPYGPRERVAIDELDKHKD PAWYKRVRASQPMFDLLYRLGSDPRAAAKFKANPDKFLIPYDSDLTQTERA ALLTRRSFPVRQALQPSADDVANQVVQRLFRDPSFATQWASTLKKNKSDPN GEQNIIAWLKQQGYDTTPEAVDSAYLQALNVDLDIYDSAYATSFSGGSTGPL IVILNGKVTVAGVEIKNPIYSQSILSWGTTDGNEYNAQLFLRVLTNDDGKPLP QNAYVGPQLYGYYWSPNSVKPTKPNINGKVGQPSPSNGSDPVQPTPLSKFA ATYNTYIAGATGKYAADSQLVVANPEPNTTVTYKGIVIKKWTYANESLSWL ATDGNAQNVAIRFFINTSSTSSDPTLGPQFLGTTWAQGQNPPSKSNFFGQIGQ SADPDTTANILTKANTWIQFGLNLVNGIAAMLICHALMSLFKARNAEAANPS PENQQAEQQAEQDANDAINEQEAIQDNAADQGGNEEVDPNDLDPDEAGEP NANADADADADADADADADADADADADAEADADAEADADADAEA DADAEADADAEADADADIDIDIDADVVDIIL |
| Trichophaea hybrida | SEQ ID NO.: 113 The DOE Joint Genome Institute (JGI) 914024 | MTQGSLFIVGSGIRSIAQLTLEAIMHIENADKVFYVVCDPVTEGFIKEKNPNA VDLYEYYSNTKLRNETYIQMAEIMLREVRSGLRVVGVFYGHPGNFVSPTRR ALAIARDEGYVAKMLPGISADDCLFADLLIDPCYPGLQTVEATDVLVRNRPL QTTSHVVIYQVGVICKSGFDFYSIENDKFDHFVTRLQEDYGPNHPVVNYVAA VSPLAEPTIQRHTISELFKDSVKASISGVSTFYIPPKELLPLTAAGEKLILDLNT DKAAVQVKTYPPLPYCPLSTGQQAYGAYEKSVIEKIKNHTTPAGYKPYQTSR AMHKALERLYLDPETVKKYRRDPEGFAAEFEGLKENEAEALRSGNPDSCAS LGAAVLHAVAVWIAC |
| Talaromyces islandicus | SEQ ID NO.: 114 GenBank CRG85870.1 | MSTSEHHRPASHGFRPGKLVIVGSGIRSISQFTLEAVAHIEHADKVFYCVADP GTDAFIERHNKNAVDLYNLYGDGKPRHQTYTQMAEVILQEVRKGFSVVGVF YGHPGVFVNPAHRAVSIAASEGYEATMLPGVSAEDCLYADLLIDPSRPGCQT LEATDVLLRKRPIAKDCHVIIFQVGAVGDLGFNFKGFKNTKFEILVQHLLEVY GPDHSVVHYIASQLTFAAPIRDRYAIQDLVKPEVAKRITGISTFYLPPKDLLQP DEVAAKSLGLVSRPTTTASFGPYAPDQPYGPRELAAIKALKAHKDPANYNK TRASPALYQALESLALNPKDVLKFRSSREKFIARIDGLTKPEQKALRFASTGLI RQVLKSSAKDIATKFVQDEFRNPTLATQYAQILKENRNKTDGIDKITEWLKA QGYDTTPEAIGEAYKQELSRNLDSYDGKYTTNVDGKPGPQLLLQKGTVLVD GVKIPNWSYSSSQLSWTVEDGNPSSAMLHFQLLTNDTGKPLPPGSYIGPQFY GLYWRKGSSKPTGNNTVGKVGEVPPPDPITPVKPTPISAWLDTYQTYLKSSS GTWDKAGELAITGDETNPTVTYKGKQIQKYSYQNETISWSSADGNPNNALS FYFNKNPTQKNPAPGNQFSGKYWESGQAPPTAANLFGQIGSSSSPGTAANDA MTAAQWKTIGINLGVGILTFVLGDFTLKAINALIKWVRNPTKENRDALDQA NDDAGEAEAQQEAVEAEGADLNPGGDIVDAGDVPAQAAEAAEAAEAAEV AEVAEVAEAAEAEAEAEAAEVAEVAEVAEVAEVAEVVDVVEVII |
| Wilcoxina mikolae | SEQ ID NO.: 115 The DOE Joint Genome Institute (JGI) 650847 | MPQGSLTIVGSGIRSIAQLTLEALMHIENADKVFYVVCDPATEGFIKQKNPNA VDLYEYYSNTKLRNETYIQMAEIMLREVRSGLRVVGVFYGHPGNFVSPTRR ALAIAQDEGYVAKMLPGISADDCLFADLLIDPCYPGLQTVEATDVLVRDRPL QITSHVVIYQVGVICKSGFDFTSIENDKFDHFVNRLQQDYGPSHPVINYVAAV SPLAEPTIQRYTISDLFKDSVKACISGVSTFYLPPKELLPITDVGEKLILDLGTD KAALQVKTYPPLPYCPLSTGQQPYGPYEKAVIERIKDHTTPADYRPYNTSQA MYKALERLYLDPEAVKKYRRDPEGFAAAFEGLKENEAQALKSGNPDSSASL GHVRHPV |
| Lentinula novae- zelandiae | SEQ ID NO.: 116 | METPTLNNSGSLTIVGTGIESIGQMTLQTLSYIEAADKVFYCVIDPATEAFILT KNKDCVDLYQYYDNGKSRMDTYTQMSEVMLREVRKGLDVVGVFYGHPGV FVNPSLRALAIAKSEGYKARMLPGVSAEDCLYADLCIDPSNPGCLTYEASDF LIRERPTNIYSHFILFQVGCVGIADFNFTGFENSKFGILVDRLEKEYGADHPVV HYIAAMLPHEEPVTDQWTIGQLREPEFYKRVGGVSTFYIPPKERKEINVDIIRE LKFLPEGKVPDTRTQIYPPNQWEPEVPTVPAYGSNEHAAIAQLDAHSAPEQY QPLATSKAMTDVMTKLALDPKALAEYKADHRAFAQSVPDLTANERTALEIG DSWAFRCAMKEMPVSLLDNAKQSMEEASEQGFPWIIVVGVVGVVGSVVSSA |

TABLE 3-continued

Exemplary amino acid and nucleotide sequences of N-methyltransferases

| | | | | | | |
|---|---|---|---|---|---|---|
| Partial methyltransferase enzyme DNA sequence Gymnopus fusipes | SEQ ID NO.: 117 | 1 gactgcgtcg | acttgtatca | gtattacgac | aatggcaaat | ccagaatggc tacttacacc |
| | | 61 caaatgtcag | aggtaagctc | cgtacacttc | aacagttgcc | aggacccgat gctgacatat |
| | | 121 gcgtagctca | tggtcaggga | agtccgcaag | ggcctcgatg | tcgtgggcgt cttctatgga |
| | | 181 cacccgggag | tgttcgtgaa | cccttctcac | cgagctctgg | ctatcgccag gagtgagggc |
| | | 241 taccgagcga | ggatgctccc | aggcgtgtct | gcggaagatt | gcctcttcgc cgacttgtgc |
| | | 301 attgatcctt | cgaacccggg | ttgcttgacc | tacgaagcat | cggatttcct gatcagggat |
| | | 361 cgtccggtca | gcatccacag | tcacttggtc | ctgttccaag | tcggttgtgt tggtattgca |
| | | 421 gacttcacat | ttgtaagatt | caatgtaagc | attcagtatt | gcccaagatt ttgtgtctaa |
| | | 481 aatgttacct | ggttcagaat | tcaaaatttg | gggtacttct | cgaccggctc gagcacgaat |
| | | 541 atggcgctga | tcatacagtt | gtgcactata | tcgcagccat | gctgccttac gagaatccag |
| | | 601 tgattgacaa | actcaccatc | agccagctcc | gtgacaccga | gatcgcgaag cgcgtgagtg |
| | | 661 gtatatcgac | cttctatatc | cctccaaagg | agctaaagga | cccgagcatg gatatcatgc |
| | | 721 gccgcctaga | acttttggct | gttgaccaag | ttccagataa | gcaatggcac ttctacccaa |
| | | 781 caaaccagtg | ggcaccatct | gcacccaacg | tagttcctta | tggaccaaga gaacaagccg |
| | | 841 ccattgtcca | gttgggcagt | cacaccattc | cagagcaatt | tcagcctatt gctacttcca |
| | | 901 aagctatgac | tgacatcttg | acaaagctgg | ctttggaccc | caagatgctc actgagtaca |
| | | 961 aggctgaccg | tcgtgccttt | gctcaatctg | cgctggagtt | gacagtcaat gagagagat |
| Partial methyltransferase enzyme cDNA sequence Gymnopus fusipes | SEQ ID NO.: 118 | 1 gactgcgtcg | acttgtatca | gtattacgac | aatggcaaat | ccagaatggc tacttacacc |
| | | 61 caaatgtcag | agctcatggt | cagggaagtc | cgcaagggcc | tcgatgtcgt gggcgtcttc |
| | | 121 tatggacacc | cgggagtgtt | cgtgaaccct | tctcaccgag | ctctggctat cgccaggagt |
| | | 181 gagggctacc | gagcgaggat | gctcccaggc | gtgtctgcgg | aagattgcct cttcgccgac |
| | | 241 ttgtgcattg | atccttcgaa | cccgggttgc | ttgacctacg | aagcatcgga tttcctgatc |
| | | 301 agggatcgtc | cggtcagcat | ccacagtcac | ttggtcctgt | tccaagtcgg ttgtgttggt |
| | | 361 attgcagact | tcacatttgt | aagattcaat | aattcaaaat | ttggggtact tctcgaccgg |
| | | 421 ctcgagcacg | aatatggcgc | tgatcataca | gttgtgcact | atatcgcagc catgctgcct |
| | | 481 tacgagaatc | cagtgattga | caaactcacc | atcagccagc | tccgtgacac cgagatccgg |
| | | 541 aagcgcgtga | gtggtatatc | gaccttctat | atccctccaa | aggagctaaa ggacccgagc |
| | | 601 atggatatca | tgcgccgcct | agaacttttg | gctgttgacc | aagttccaga taagcaatgg |
| | | 661 cacttctacc | caacaaacca | gtgggcacca | tctgcaccca | acgtagttcc ttatggacca |
| | | 721 agaacaag | ccgccattgt | ccagttgggc | agtcacacca | ttccagagca atttcagcct |
| | | 781 attgctactt | ccaaagctat | gactgacatc | ttgacaaagc | tggctttgga ccccaagatg |
| | | 841 ctcactgagt | acaaggctga | ccgtcgtgcc | tttgctcaat | ctgcgctgga gttgacagtc |
| | | 901 aatgagagag | at | | | |

Gymnopeptide A (GymA) and Gymnopeptide B (GymB) are two related multiply N-methylated cyclic octadecapeptides that were isolated from the spindleshank mushroom *Gymnopus fusipes* (*G. fusipes*) (also known as *Collybia fusipes*). GymA and GymB differ at one position (serine for GymA vs. threonine for GymB). Several aggressive adherent cancer cell lines (e.g. HeLa, A431, T47D, MCF7, MDA-MB-231) exhibit hypersensitivity to both GymA and GymB, with IC50 values in the low nanomolar range.

It was surprising to discover that rather than utilizing an NRPS to synthesize these peptide macrocycles, the genome of *G. fusipes* encodes for one gene containing a nucleic acid sequence that encodes the 18 amino acids of GymB. The 18-amino acids sequence lies at the C-terminus of an open reading frame that encodes for a putative S-Adenosylmethionine (SAM) dependent methyltransferase. Hereinafter, the gene encoding for the methyltransferase followed by the GymB peptide sequence cassette is referred to as the gymnopeptide precursor gene, GymMAB.

The GymMAB gene is present in a cluster that also includes another open reading frame encoding a prolyl-oligopeptidase (GymP), which cleaves and cyclizes the methylated gymnopeptide cassettes. These enzymes bear weak resemblance to the *G. marginata* and *Amanita* species prolyl-oligopeptidase PopB proteins and the *O. olearis* omphalotin-producing enzymes, and form a distinct family of RiPPs/RiPP-processing-enzymes with unique structural and functional features that allow them to accommodate the relatively large-sized 18-mer macrocycle.

Furthermore, careful examination of several *Gymnopus* species that are closely related to *G. fusipes*, such *Gymnopus earle, Gymnopus dryophilus, Gymnopus ocior, Gymnopus acervatus, Gymnopus luxurians, Gymnopus androsaceus* (also known as *Marasmius androsaceus* or *Setulipes andro-*

*saceus*) *Micromphale foetidum, Micromphale perforans, Marasmius fiardii. Rhodocollybia maculata*, and *Rhodocollybia butyracea* failed to detect any genes that encode for orthologs or other related genes to the aforementioned enzymes identified in *G. fusipes*. On the other hand, the biosynthetic gene cluster of enzymes involved in the production of the omphalotins are present in a wide group of closely related species such as *Omphalotous olivascens* as well as *Lentinula* species, including *Lentinula edodes, Lentinula aciculospora, Lentinula raphanica, Lentinula novaezelandiae, Lentinula boryana*, and *Lentinula lateritia*. Thus, the identified genetic cluster appears to be horizontally transferred.

Enzymes such as the methyltransferase and prolyloligopeptidase isolated from species such as *G. fusipes* can be used to generate methylated macrocycles. The methylated macrocycles may be screened using the methods described herein. The enzymes can be integrated into host cells and used to generate DNA-encoded libraries of RiPPs. The enzymes can also be used to manufacture specific macrocycles of interest at scale in heterologous prokaryotic or eukaryotic expression systems. Uses of the enzymes in heterologous expression systems may include, but are not limited to, reverse Y2H systems as described in PCT/US2018/061292 (published as WO 2019/099678) and U.S. application Ser. No. 15/683,586 (published as US20170368132A1), which are hereby incorporated by reference in their entireties (and in particular with respect to the reverse hybrid and related yeast systems disclosed therein).

The macrocycles generated using the methods described herein may be used as drugs. Such drugs may be used for the treatment of various diseases or conditions. The macrocycles generated using the methods described herein may be used to modulate protein-protein interaction between a first and second protein. The macrocycles generated using the methods described herein may be used to disrupt protein-protein interaction between a first and second protein.

Disclosed herein, in certain embodiments, is a method of detection or degradation of a target protein that is mediated by a molecule that links a first target or test protein to a second target protein in a host cell, comprising: expressing in the host cell a first fusion protein comprising the first test protein, a second protein; delivering a first molecule to the host cell; modifying the first molecule while in the host cell via a modifying enzyme, such as a prolyloligopeptidase and/or a methyltransferase; and allowing the first molecule to bridge the interaction between the first test protein and the second protein, wherein the first molecule is a product of an encoded DNA sequence, wherein the first molecule comprises a randomized polypeptide library and one or more modifying enzymes, wherein the one or more modifying enzymes modify the randomized polypeptide library.

The prolyloligopeptidases described herein may be ones that are able to macrocyclize relatively large peptides. The prolyloligopeptidases described herein may be ones that are able to macrocyclize peptides comprising at least 5 amino acids, at least 7 amino acids, at least 10 amino acids, at least 15 amino acids, at least 18 amino acids, at least 20 amino acids or at least 25 amino acids. The prolyloligopeptidases described herein may be ones that are able to macrocyclize peptides comprising at most 7 amino acids, at most 10 amino acids, at most 15 amino acids, at most 18 amino acids, at most 20 amino acids or at most 25 amino acids.

Figure 5B:
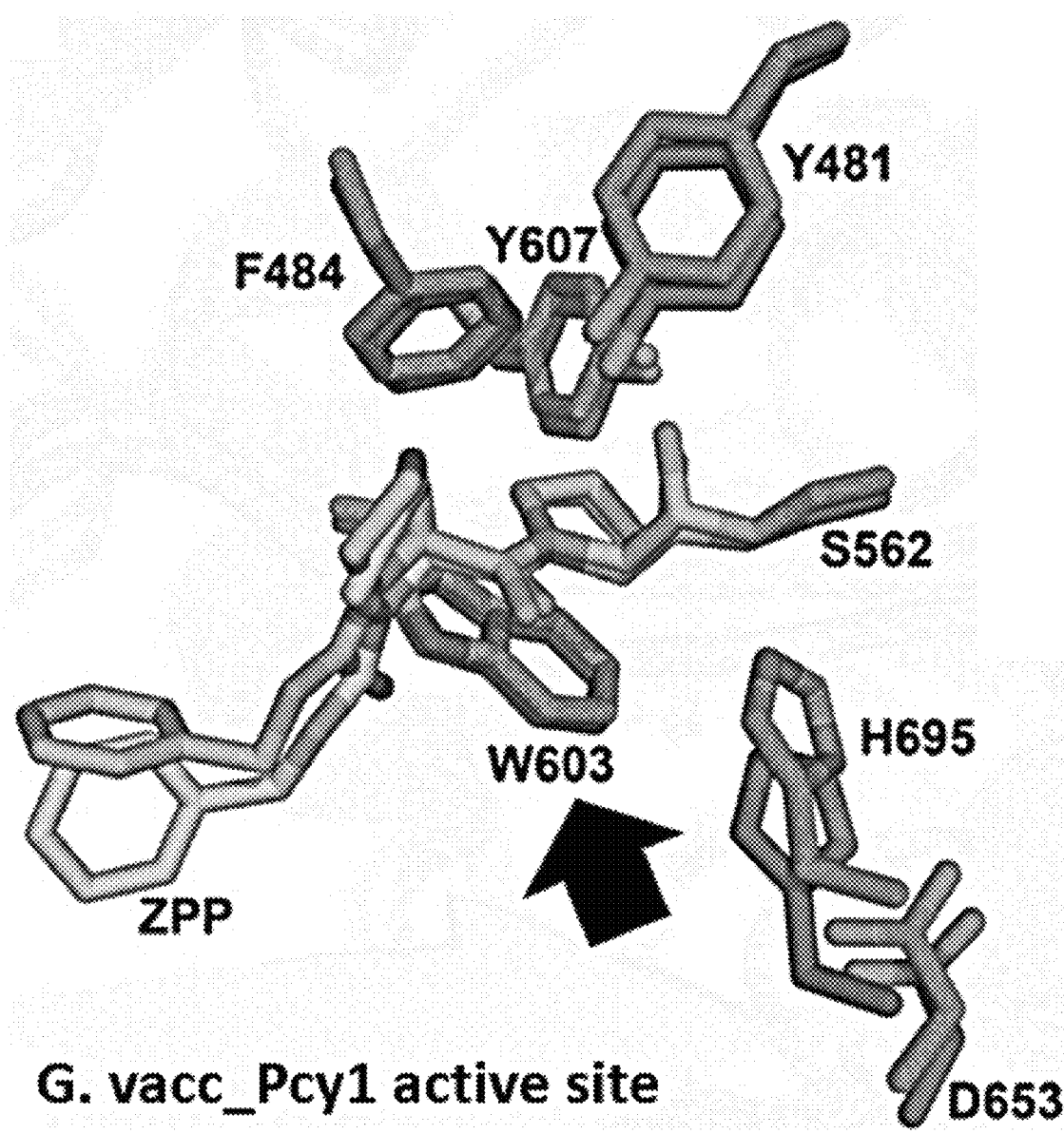
FIG. 5B shows the structure of a plant prolyloligopeptidase homolog with an arrow directed towards the tryptophan residue in the active site of the enzyme at position 603.
Figure 5C:
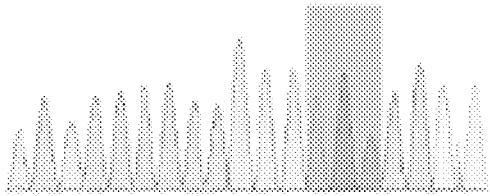
FIG. 5C illustrates the conservation of the asparagine residue present in the active site of relative prolyloliogopeptidases incapable of macrocyclizing larger peptides. The sequence read illustrates the loss of the asparagine residue in the active site of a prolyloligopeptidase isolated from *Gymnopus fusipes* capable of macrocyclizing larger peptides.
Figure 5D:
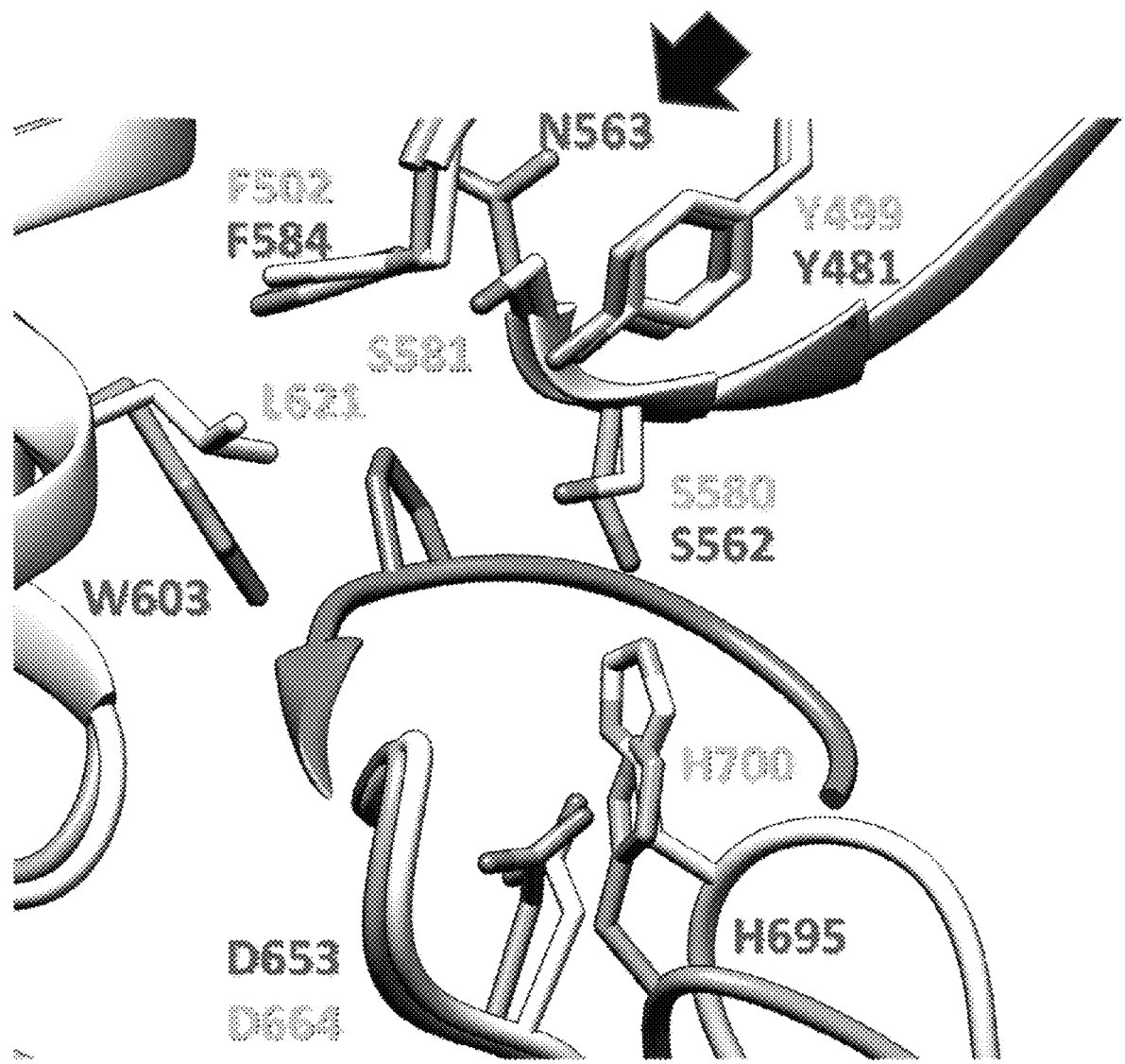
FIG. 5D shows the structure of a plant prolyloligopeptidase homolog with an arrow directed towards the asparagine residue in the active site of the enzyme at position 563.

The tryptophan at position 603 appears to be highly conserved in relative prolyloligopeptidases that are not capable of relatively large macrocyclizing peptides. Similarly, the asparagine at position 563, adjacent to the active site serine at position 562, is also conserved in these same prolyloligopeptidases. "Position 603" and "Position 563", as used herein, refer to the position of the active-site tryptophan and the position of the asparagine adjacent to the active-site serine in the prolyloligopeptidase of SEQ ID NO: 55, respectively, along with corresponding amino acid in other prolyloligopeptidases. In other words, position 603 or position 563 of a prolyloligopeptidase that differs from SEQ ID NO: 55 may not necessarily be the 603rd or 563rd amino acid in that protein, but rather is the position that aligns with position 603 or 563 of SEQ ID NO: 55 when the prolyloligopeptidase is aligned with it, regardless of the distance of that amino acid from the N-terminus of the protein. Without being bound by theory, the mutation of these highly conserved tryptophan and asparagine residues to other amino acids, such as leucine and serine, respectively, may be key to enable its structural flexibility to accommodate peptides such as the larger 18-mer gymnopeptides. Additionally, the substitution of tryptophan at position 603 with another residue such as leucine may play an important role in expanding the cleavage site recognition specificity of the oligopeptidase from being directed towards small secondary amine residues such as proline or sarcosine (N-methyl-glycine) to enable cleavage at secondary amine sites with bulkier side chains such as N-methyl-valine, N-methyl-isoleucine, or N-methyl-leucine. Consistent with this premise, while the N-terminal cut site of the Gymnopeptides AB precursor protein is at a proline residue, the C-terminal cut site is at a methyl-valine residue. Prolyloligopeptidases belong to the family of serine proteases. The mechanism of action of serine peptidases involves an acyl enzyme intermediate. Both the formation and the decomposition of the acyl enzyme proceed through the formation of a negatively charged tetrahedral intermediate that is stabilized by the oxyanion binding site providing two hydrogen bonds to the oxyanion. In prolyloligopeptidases one of the hydrogen bonds is formed between the oxyanion and the main chain amide group of asparagine 563, which is directly adjacent to the catalytic serine, serine 562. The second hydrogen bond is among this type of serine peptidases and is provided by the hydroxyl group of tyrosine 481 (position 481 of SEQ ID NO:55). In the chymotrypsin-type members of the serine protease family of enzymes the hydrogen bonds are contributed by the main chain amide groups of the catalytic serine residue and that of a glycine residue that is at a −2 position from the catalytic serine. The substitution of the highly conserved asparagine at position 563 with serine renders the serine 563 residue and the glycine 561 residue (position 561 of SEQ ID NO:55) positioned identically to the active site serine and glycine hydrogen bond donors of chymotrypsin-type proteases. This substitution may play an important role to enable the enzyme to toggle between using two different active-site serines for each of the two cleavage events, for example serine 562 could be the active site residue involved in the N-terminal proline-directed cut with the two hydrogen bonds to the oxyanion contributed by the main chain amide of the serine residue at position 563 and the hydroxyl group of the tyrosine at position 481, while serine 563 is the active site residue involved in the second N-methyl-valine directed cut with the two hydrogen bonds to the oxyanion contributed by the main chain amides of serine at position 563 and glycine at position 561, or vice versa. The combination of this novel wider catalytic pocket due the substitution of tryptophan 603 with leucine and a toggle-switchable active site serine due to the substitution of asparagine 563 with serine render this new oligopeptidase particularly suited at recognizing a wide variety of secondary amine residues with bulky side chains at the cleavage site and incorporate larger sizes of macrocycles than any of the previously characterized members of the family. Shown in FIG. 5A is an alignment of various related enzyme species around this residue. Also shown is the sequence read from the *Gymnopus fusipes* enzyme. FIG. 5B shows the protein structure of a plant Pop homolog, highlighting the position of W603 within the active site (adapted from world wide web address: pnas.org/cgi/doi/10.1073/pnas.1620499114). The arrow in the figure below points to the tryptophan residue. Shown in FIG. 5C is an alignment of various related enzyme species around a Serine residue. Also shown is the sequence read from the *Gymnopus fusipes* enzyme. FIG. 5D shows the protein structure of a plant Pop homolog, highlighting the position of N563 within the active site (adapted from world wide web address: pnas.org/cgi/doi/10.1073/pnas.1620499114). The arrow in the figure below points to the asparagine residue.

In some cases, the tryptophan residue in the active site of a prolyloligopeptidase, which corresponds to the conserved tryptophan at position 603 of SEQ ID NO: 55, may be replaced with a different amino acid residue. For instance, in some cases the tryptophan residue in the active site of a prolyloligopeptidase may be replaced with a leucine residue. In some cases, the prolyloligopeptidases used herein do not comprise a tryptophan residue at the 603 position in the active site of the enzyme, wherein the position 603 corresponds to the active site of SEQ ID NO: 55.

In some cases, the asparagine residue in the active site of a prolyloligopeptidase, which corresponds to the conserved asparagine at position 563 of SEQ ID NO: 55, may be replaced with a different amino acid residue. For instance, in some cases the asparagine residue in the active site of a prolyloligopeptidase may be replaced with a serine residue. In some cases, the prolyloligopeptidases used herein do not comprise a asparagine residue at the 563 position in the active site of the enzyme, wherein the position 563 corresponds to the active site of SEQ ID NO: 55.

In other embodiments, the cyclization comprises reacting with beta-lactamase. A variable region is excised and end-to-end cyclized by the actions of an N-methyltransferase and a beta-lactamase family member. Table 4 shows an exemplary list of lactamase and amino acid sequences of the processed cyclic peptides. The lactamase may be a protein with a sequence selected from SEQ ID NOs: 119-120. The lactamase may be a variant (e.g., a non-natural variant) of a naturally occurring lactamase. Such a variant can have at least 70%, 75%, 80%, 85%, 90%, 95%, 96%, 97%, 98%, or 99% sequence identity to SEQ ID NOs: 119-120. In some embodiments, some of the sidechains of the randomized residues are subsequently isomerized from the L- to D-configuration or decorated with additional modifications like hydroxylation, halogenation, glycosylation, acylation, phosphorylation, methylation, and acetylation.

TABLE 4

Amino acid sequences of the N-methyltransferase and beta-lactamase processed cyclic peptides

| Organism | Identifier | Sequence |
|---|---|---|
| Rhizophogun vinicolor | SEQ ID NO.: 119 GenBank OAX32863.1 hypothetical protein beta-lactamase (transpeptidase) | MAKVFGLVLGFLSQTFTYPSQVWFSPVGANNGQVITPELSNSIQETLDVWNI TGLSVAIIPKSGEPEYHSWGDRTEDGESVTQDTLFHMASVSKAFCVSALGIL MDDFEHGRNVTPLPPALTEFNWHTSIQDLLPGEWQLMDEWASRKANMKDI LSHVSGLPRHDFAFGPYESPKEAVSRLRYLRPAFELREQWSYNNQMFMVAG HIVETYSGKTYTSFVEDRIFTPLGMSSSTFSPAKAAKTGKFTQGWTSSGRLLP ELFPEDMVMLMAGAGGVISSAVDMSKWVALWLNKGVYDNVTVIPSSVYG NASQSYAVSISTPVDSEHSIQGYGLGWFQNSYLGHNVVYHSGSIPGLSMLVS FLPDDDVGFVVFANGGDKAAPVMNISNSIIDAALHLRSGPAPPIMPEKKAVT SPSEDIVNLELPLEEFSGTYTDPGYGTFTFCSPSSSSSYCQQVMTDFTAVDSVH PSAPSPLQLLAAWPRMGSSHIRAVHQSGNKFLLLCTALFPEGYGRDSTPFETA EIGTPGATAEFVVEDGKVVGFGLFGLVDQVTERERTQTTVKDRAEVWFDKV |
| Rhizophogun vinicolor | SEQ ID NO.: 120 GenBank OAX34183.1 hypothetical protein beta-lactamase (transpeptidase) | MIMAKVFGLVLGFLSQTFTYPSQIRLSPVGVNNGQVITPELSNSIQETLDVWN ITGLSVAIIPKSGEPEYHSWGDRTEDGESVTQDTLFHMASVSKAFCVSALGIL MDDFEHGRNVTPLPPALTEFNWHTSIQDLLPGEWQLMDEWASRKANVKDIL SHVSGLPSHHFAFGPYESPKEVVSRLRYLRPAFELREQWSYNNQMFTVAGHI VETYSGKTYTSFVEDRIFTPLGMFSSTFSPAKAVKTGKFTQGWTSSGRLLPEF FQEDMIMPMAGPGGVISSAVDMSKWVALWLNKGVHDNVTIIPSSVYGNAS QSYAVSISTPVDSEHSILGYGLGWFRNSYLGHDVVYHSGSIPGLSTLVSFLPD DDVGFVVFANGDNKAAPVMNISNRIIDAALHLRSGPAPPIMPEKKAVTSPSE DIVNLELPLEEFSGTYTDPGYGTFTFCSPSSSSPYCQQVIANFTTVDSVRPSAP SSLQLLAAWPRVGSSHIRTVHQSGNKFMLLPTALFPEGYGRDSTPFETAEIGT RGAPVEFVVEDGRVVGFGLFGLVGQVTERERTQTTVKDRAGVWFDKV |
| Rhizophogun vinicolor | SEQ ID NO.: 121 GenBank OAX32862.1 hypothetical N-methyltransferase | MSTKRGTLTIAGSGIASVGHITLGTLSYIKESDKIFYLVCDPVTEAFIYDNSTA DCFDLSVFYDKTKGRYDSYIQMCEVMLKAVRAGHDVLGVFYGHPGVFVSP SHRAIAVARQEGYKAKMLPGISAEDYMFADLEFDPSVSGCKTCEATEILLRD KPLDPTIQNIIWQVGSVGVVDMEFSKSKFQLLVDRLEKDFGPDHKVVHYIGA VLPQSTTTMDTFTIADLRKEDVAKQFGTISTLYIPPRDEGHVNLSMAKVFGGP GASVKLNDSIKWAGPKLNIVSANDPHERDVIAQVDTHVAPEGHKKLRVSAA MKKFMTDLALKPKFLEEYKLDPVAVVESAEGLSNLERFGLKFARSGPADAL MKATESDIASGRQLTEEEIAQGTGPVGLQTALALLVLLGLGVAIVTRPDD |
| Rhizophogun vinicolor | SEQ ID NO.: 122 GenBank OAX34185.1 hypothetical protein FAD/NAD(P)-dependent oxidoreductase, D-aminoacid dehydrogenase | MTSDNLQPEVISANWLKSLEAASSTGDTASFVSHFLPDGWFRDMLCFTWNF RTLSGQEKIHGFISEVVDGQSRLSYSHLHDFKLDDHSVNAPSPFKLPGPPDIEG VQGAFTFSITKPAAYGRGFFRLTQDVHGNWKALTLFTNMQDLVGHEESSAD EYDPHEKANPTVVIVIKVGGGQSGLICAARLGKLGIRALVIDKNARVGDIWR QRYAEALPSFAVLSRQETQVPEPYAAYSQISKLLPYPSNFPKYLPKGKLANFL ESYAINQELCIWLSSTVSPSPVYDSFSARWTVEVEHENRKVILHPKHLVLATG HGRPRIPTWNGMDDFQGTLYHSDFHRDAEKFRGKCVVVIGAGNASGDICED FVAQGAAEVTIVQRSATCVVSSATADAFVFKLPFSDKTPIEELDFRHNSMPLA FVLQLMKSGGTQHMKAHDKEHHEGLRKAGFNLTWEPSPGSGEVGLLGFVF ERAGSGTMIDTGFGKLIVEGTVKVKQGGQNISHFDKEGITFKDGSKLPADVIV AATGNELTMDAIRAVLGDTIAEQLPPKVWGLDAEGELNQMYRPSGHPGLW FAVGSLGMTRFCSKHLGLQILAQEVGIA |

In some embodiments, the cyclization comprises reacting with a prolyl endopeptidase, an N-methyltransferase, and a hydroxylase. In some embodiments, the bicyclization comprises further modification of the indicated anchored residues on the cyclized peptide, forming an internal tryptathionine bridge. The first step may involve hydroxylation of the 2-position of the indole ring of the tryptophan residue by a hydroxylase belonging to the cytochrome P450 family of oxygenases. An example of such hydroxylase is shown in TABLE 5. The hydroxylase may be a protein with a sequence selected from SEQ ID NO: 123. The hydroxylase may be a variant (e.g., a non-natural variant) of a naturally found hydroxylase. Such a variant can have at least 70%, 75%, 80%, 85%, 90%, 95%, 96%, 97%, 98%, or 99% sequence identity to SEQ ID NO: 123.

TABLE 5

| | | |
|---|---|---|
| Amino acid sequences of a hydroxylase | | |
| Galerina marginata CBS 339.88 | SEQ ID NO.: 123 KDR84981.1 hypothetical protein GALMADRAFT_260690 | MGKMAYHTVLDDIALYLLGSAALVIFYRSFFYPYFLSGRRLAPGPTKGELSK ELKQFNNEINVHFLRHMVKEYGPIFRLVGAPMIPGPGLVVCTPTAQQRILVSN SINYGQPRLAFFRWVTGGLFTLPEREHRGMRKILDPVFSFRNLISTTGVYYNT VQSLITIFRSKIDGENGAKDGDVILVYEWLARLAIDNVSEAILGFKLDTLHDP NNELITTLDELSRIPTAAFELLVRVPGFLRLVTFDSVRHSTLWQRRVPGRLGV FFTFMRCLSTIRKNALAIKATILQEDSANRDLNVISVLQHMQSSDETANADIA GNIIMLWMSGRATIATRISWLLWLLAKDQQCQQQLRDEIAPLFSRDPRPDYR SLDKLQWLDSVIMESIRLFLFGPNIRVALNDDYIDGVFVPKGTVVVIPLDLFT RGDIWGEDPDQFKPARWLDSTKRYKISPPFLSFLTGPHRCIAKGMAIMQTKIV IASLIANFEFKPAYEGQHVEGNPSIIGHGMPLHVKPIRPS |

Step 2 may involve the formation of a tryptathionine bridge between the 2'-hydroxyl position on tryptophan and the thiol group from the cysteine residue. This condensation reaction is catalyzed by a novel family of dehydratases. Examples of the dehydratases are shown in TABLE 6. The dehydratases may be a protein with a sequence selected from SEQ ID NOs: 124-127. The dehydratases may be a variant (e.g., a non-natural variant) of a naturally found dehydratases. Such a variant can have at least 70%, 75%, 80%, 85%, 90%, 95%, 96%, 97%, 98%, or 99% sequence identity to SEQ ID NOs: 124-127.

TABLE 6

| | | |
|---|---|---|
| Amino acid sequences of dehydratases | | |
| Galerina marginata CBS 339.88 | SEQ ID NO.: 124 KDR80488.1 hypothetical protein GALMADRAFT_136963 | MPYVPDPKYFEHREQSSGATLYYCLVCRDGRERQPHHIKTHEASQAHRTAL SVFDSQAESSSQQTHGNPTQPGYFDPVIDDAVRALLVSGSGDPHQPLYPAGH PNVYGEPNFTDSRRRTSPVTGIDWDQFEAQEDTHAVPSAQDQLRADICQATL DWLNDDISDDDEREPSEVDSVDSDAESDREPIPDDQPRKRARTNRDNPISED WYPWQDKITCTLDILMHLPRSVFSRKQLDLFLWLLRVNNVDDVPTGKSMK MLNKILQGMCGIETIAYEGKLGHNYHVNNIAQILAQELCNPKVGPHIYFYPE DSGDNLAEARQAARWLHELRPEETTPMIHLPSGDYYIYEPAMLSNRSFCIPFR WFTRNGKFHARAWSLETGVVDNTLGWIVHKENEVEISEDDLLKDFTRFSSD CEAYNVPHPSRILGVSCADSGNLLPWNHTNPVLGNRWRQLAKGHRTLCLPL WMYCDDTSGNTSKKWNEHNSFLFTLAGLPREHTAKEYNIHFLCTSNLAPPL EMMDGVVSQIEAAQQNGIWAWDCVRKEPVLIFPTILALLGDNPMHSEFACHI GLRGKFFCRTCWVKGSDAQDDANIVTPGLHETPENSPAPSPAPSPAPSPAPSP APSPALSMAPQSQPPTPSEPSMQVPAPPSTAAPTKARGKKKETMSAMLNRIT AFIKPGRLRNKSETQKTLQNFKEQAQTIGAKTKLKTARTETGIKDTVQEFFFE KLFSSYKNKRGPQAKQEALDQAVNQLPSDITSPVWRLKGLDPHQDTPVEILH VVLLGFIKYFWRDLVQNQINDDQKQTLIQRLNSFDVTGLGITQLGGETLVNY AGSLTGRDFRAVAQVAPFVIYDMVPADVFDAWLALSKLVPLVWQPYIENV AQYLTTLEHEIHVFLLRTARWTTGWFNKSKFHIILHLPSHIRRFGPAILFATEA FESFNAVIRAKSVHSNRQAPSRDIALAFAQGNRIRHLLSGGHFLSADTHMVV DPDQPQLGQYERLARGRWRSVGPGPGHLVSAEPILPSYLGIPPQSTTSSAGLC KRTKTPPQTFLQTLTGLKLPNVSRPGARELWQTCSEVYLLNDDKCLIGHHVI VQRQSEQASFVSPPFIARIGEILQKVGSANHAHDKPDGILVQTLKSSEVADKF QMPRLVPQNEWSFVPLADILCTVNAQHDCDRNGCTASGFRYVYQERIQTND QRPVVEHVNQPEDFILNTAQMRDALHLQKFRIRSRSLDEQTIIHESVARTINQ RKAQDNSSSGTGGAGVSGRGRGRGRGGGVEGPSTSRGRGGGIEGRGASS SSGNGRGRGRGARSAQSVPF |
| Galerina marginata CBS 339.88 | SEQ ID NO.: 125 KDR74877.1 hypothetical protein GALMADRAFT_99137 | MPRKKPAPECFETDEASKMIRCLICKENDTVQQGTWIKHGSASQHIETNAHK LAVARREQLLQVQQEEERRLQEIYGGNTIPLSGNAQLYPTYPRANMYGNQD AVDTDMDNQNSPPQAYMLCDADIPDLGIKPIERPDPSQERERLRQQVEQLLL QAEHEDEFGSPDDPDDLTSTNIAQAFADLDLEEMLDEEEVFDYFNQVSPEHD YYPYPNKTTMLLDILDNLPRLRMSSNQLRLILWLLKQTGVSNVPSFSGFRNM QTHLRNMCGTTPKQHVSSLGNIFYSNNIGESVMRDFANPEVAKHLHLYPEET EGPISEVWQAERWKEFAPSELTPMFSQGHRQFFIDEVAQLQDGQYVIPRNWV MRKGKLTSDCHIVTVNPVRFSKLHGSLVLVLKQCFQSGWTLLSETQIFHADD FQFNYFDVVSRIRGPISWSEGTEVPAMPNNLRELAGDDDLVVIMVPLWCDD |

TABLE 6-continued

Amino acid sequences of dehydratases

|  |  |  |
|---|---|---|
|  |  | VSGNKSKQYNKHINVYMANSNIPGRLLQQEYFVRFVSTSPNATSPEQFSALK<br>DQINETQKKPIQCYNAHTNKKTRAILRVPGLPADNPQQSEESCHMGGNANC<br>KCRKCHVGGPHEKKESNEGYHEHYLTGIKRSAEETRLELEKQIKLAMYGVE<br>KPINETQTNTGTKDKVAQHWIDILLAKSRELKSANPSRSVEEIAQELQTWFDE<br>QPGDKINPLLSIAGLDPTQDTPVEILHTILLGIVKYAWHHLHSNWTEAEQNLF<br>TVRLQSTDIDGLSVPPIRVAYMMQYRNGLIGKHFKTLMQTLPFHVHGTVSD<br>AQFKLVKAIGELGSVLWVHEIGDMEKYLSDLEILIGNVLDAFAEIDPSTAMY<br>ARFIYEPMPVPSKIIVKLKLHMLPHLIEDIKRFGPAIRNSTEVFECFNAIFRLCSI<br>LSNHQAASRDIALKFASMDRLKHMLSGGYWLSEVEEGKFEWIRAGENVRNI<br>LQSEPTIQRHLGWAPSAKFQSGRKRTPPTSWENTKASQFMDSEETAAIGFPNP<br>RLLSWRKGVTTTAQSGDRCSTGSWVVARNHKVCYILASHYCSIAKNDQGES<br>CIGRIHEIIGPDEKSASSTGIITLECFQLGKEHHPDFGLPTLQRPQADLPKYILK<br>AWQDPLFIFSAHHDCHTASCQATALQPQLQERQLTSRMNKLIAHNDSDHFII<br>NLYGLHNAILLREFLPRELTAPQPLHQDRKAFHYEVAAKLRVQQAEKRAKT<br>NARRKATRAANKAKQVERQKQNPDHEQESEQEMDERPNSENGSDIELGGD<br>DDIEVETRRKRRRN |
| Hypsizygus marmoreus | SEQ ID NO.: 126<br>KYQ37095.1<br>hypothetical protein<br>Hypma_08924 | MGRRAEELPAYVELSEDGTLVRCNLCLMHNRLDYSKEWIQRKGWRSHKGS<br>GIHDRSEAKQRVLDDAAMDLQEPASAEVEVVTFNDILIINAPKTPTGNMQSE<br>EQAMWDHFDAGSFTLEAGEDPNHSSQRLYQDLARKADAYGAWDGTEALPE<br>YRDLDDVSQFLDEDEEEDLLSEILRGLGLEEEHEDSSDRNPAEELNSPWYPY<br>GSKLMFLLDTIDNLPRLRISGAMMRVFLWLLREVGVRQVPSFDKLRKIQRKL<br>REGSGVPTVHWMSPKGNAYSFNDPAVIVANDWASPITRPHLRRYPVIPKDG<br>VITEVYHAEKWHREINRHFLTPMYDDGFRHYFIDELAQLKDGRYAVPVRWL<br>EDVDGRIVADAWRVELEDDNRATIIDTATVRIHSQELALNFEEIIESNLMPEW<br>SDTTTEAGHPSRMPNPDRALAEGDPIYTSFIDIFGDDVSGNRSKSWNKHWNM<br>YISHRNLPRKLLHQQYHTHFVSTSTFASIPEQFVGVKEAIESTHSKPVKVRDA<br>DTGKQIRLKIYCNCGPGDNPSQSETSGHIGGNGNYPCRKCHTGGTQKSKETD<br>EGFYKMFTAGEARSSKETLAEVKSQVEAACTGVAKTVADAQSDTGVKDAY<br>TQYWIDAIIEKARAMQKENPGMPTTTIQATLIKWVYDHEEAIYNSFLTLDGF<br>DASRDTPVEILHTILLGIVKYLWHRSHTSWNAAQKKIYSTRLQGTNTQGLSIH<br>HIRANYIMQYANSLIGRQLKTLAQVNVFHVYDLVDPLRFLFTKATGELCALL<br>WFTEIRDLEEYLSDVDIAAANVLDIAAVIDPSKIVSKIKYHLLSHLREDIIRFGP<br>LVGVATEVFECFNAVFRYCSILSNHLAPSRDIAYKLAAQETMKHFLSGGWW<br>HVKDSVDLQGNPKWVQPGPSVRTFMASNPVLHTLCGWTRNNDSTPGTVKS<br>EPRKRGPDKQTLLPLVRLAWLETQGSRALNNTSPNNETQWQRCKYVIAETQ<br>DQCNVGSWVFARSPLLENIPIPGRIVEILQDTSASPSAFVVIDVFQVSATRDEV<br>FGMPVLLRRFNECCLHVIPASSVIFDFNAQHDCRYAKCEATGEQPLIQERVPS<br>GVTENFVVHKAIDRYLINIHALHNAHLIRATLPRDLTAPIPYAPNREAHHSAI<br>AAELRSAQDTKRAKTAAKTAANAAAKKAEAALKDTTSGPAAKRRRVDDEG<br>SGEEDNRDVDMVSV |
| Galerina marginata CBS 339.88 | SEQ ID NO.: 127<br>KDR73903.1<br>hypothetical protein<br>GALMADRAFT_141673 | MAKGRKLNNPLPDFIEISNDGLQVRCTLCLAARQHNGSGWIKRGSVSNHLK<br>SDNHTNSLEAHEMKKSAEKAEGRSVQEEIAMEEGMDFVILSSKIQPEITAPAR<br>APRRSNEEQEMWDRYTLGGEVFDAGVDHTLVEAAEERKRLEREATDFDLWH<br>GADFLPEEDPNDGELLLDELEQDDILSELLRNAHLNAPDAADVLTEEPRAAA<br>DPRICDAWSPYESKMMFLLDTLDNLPRLRISNSLMNVFLWILREGGARDVPS<br>LYHLRQVQTTLRKSTGVPTTQHKSPKGNVYSMNDPRTLVAMDWANPVICD<br>HIRRYPVIPRNGVISEVYHAQKWRKDVDPHTLSPMYDAGNCHYYIDEVARL<br>KNGTFIIPVRWLEDEDEDRNVCADAYVVQFDDQFIASVVDGETIIVQASDLQNN<br>FLDLKDMGLLPTWGNQTIESGHPARMPNPDRALAEGDPLYTSWIDVFGDDV<br>SGNRSKNWNKHWNIYISHRNLPRKLLQQEFHTHFVSTSPVASVTEQFHGIKQ<br>VIELTHKSPVKVRHGTSGAQIRFKINVCGPGDNPAQSEVCGHIGVNGNKLC<br>RKCHTGGTHEVKESDEGFNSLFEPGDARSAQEIVADVESQVQLACLGIAQHV<br>QNQQTKNGIKDAYTQYWIDYLINRARTLRKEQPRRTTADIQSELLVWVQEH<br>KDEIYNPFLKLDGFDAAVDTPVEILHTILLGIVKYLWHGSHTSWTAIQKQTYS<br>VRLQSTDTSGLSIHAIRANYIMQYANSLIGRQFKTIAQVNVFHVYDLVDTTQF<br>LLTKAVGELTALLWIPEIANMEEYLLDVEAAAANVLDLFALIDPSKMTNKLK<br>LHLLVHLKADILRFGPLVGVATETFECFNAIFRFCSIYSNHLAPSRDIAFQLAS<br>QEVLKYRLTGGWWPASDGEWKRPGPSVRNFIHDHPTLQALLGWTKEEKLV<br>NGSFRLEPLKRDASQKIESRKHLPWLQTQGAKAVNSSEDNDSKWTACRFAV<br>ANSGDKCSVGSWVFATSPFNSNQSVTGRIVEVLAESEGKRAVVVLDIFEVCS<br>TRHKIFGMPMLARRHEEPVYAVIASTNIEFLYNVQHDCPLAKCTASGKQPLI<br>QERVESGLFKTYIEHKPIERFVINTHAFHNAHRLRAVLQRSLVVPIPLYPPEIR<br>KTKHAEFAHNLQATQKVKLEARAAQKAKEIITPADKTDSTIPKKRTRSEMET<br>ETDDTAIATQADVFFNAQGCP |

Step 3 describes S-oxygenation of the tryptathionine thiol by a flavin-monooxygenase enzyme that converts it to a sulfinyl form. Examples of such monooxygenase are shown in TABLE 7. Step 4 describes potential future modification steps such as hydroxylation of side chains on the peptide such as the hydroxylation of position 6 on the indole ring of the tryptathionine-forming tryptophan residue by a P450 family monooxygenase. The monooxygenase may be a protein with a sequence selected from SEQ ID NO: 128. The monooxygenase may be a variant (e.g., a non-natural variant) of a naturally found monooxygenase. Such a variant can have at least 70%, 75%, 80%, 85%, 90%, 95%, 96%, 97%, 98%, or 99% sequence identity to SEQ ID NO: 128.

TABLE 7

Amino acid sequences of monoxygenases

| | | |
|---|---|---|
| Galerina marginata CBS 339.88 | SEQ ID NO.: 128 KDR68385.1 hypothetical protein GALMADRAFT_104945 | MVQIKRLLLGFLSSPSQTPLESNHGPVPSKSIAVVGAGSAGLAMLRTLVELEA FSRNNWEVVLYEERESVGGIWLPDNNDVFPPEIPKTPLYPLLRTNTPVPSMTY PGFPFPPSTPLYPRHDHVEAYHLRYARRHNLLDFIKFDTMVEKAFWNGTPEE GYWNLTLSSKEGRMRYKTFDHLVVATGNNHIPHIPVWKGQEDWLASPANH SRKIIHSVYYRGPEAFSNQTVLIVGNGGSGRDAATQILGYASQTFMSIRRSYG PVDDGVIVKPDISHFTEAGVVFVDGTILDPDVILLGTGYEMQKPLLSEGGELS FDPTAKDNSSVRGTLVTNGHYIFPLHRHIFSLSPRYPPNALAFIGLLSFIASCPS DIAQSLFAAHAILDPSILPPRHLLLEELASYEDKARRQGLDPYLKGPIMLNNTS NDYQDELVEYLKQKNAIPDDGKKFVEEWRREILAYHYLQRGWSRIEKLGM GPAWTEGVKTEAQWFDLMTRVNEWQKNWETENGIAFRVDLDLTG |

The sequence which flanks the encoded random peptide library can be modified by using N-term and C-term flanks from the MSDIN family genes (toxin preproprotein sequences) identified in the genomes of *Amanita bisporigera* and *Amanita phalloides*.

The enzymes can additionally be targeted to a specific cellular compartment to increase peptide synthesis efficiency and increase yield for peptide production purposes.

Disclosed herein, in certain embodiments, is a method of detecting degradation of a target protein that is mediated by a molecule that links a target or test protein to an E3 ubiquitin ligase in a host cell, comprising: expressing in the host cell a first fusion protein comprising the first test protein, an E3 ubiquitin ligase; delivering a first molecule to the host cell; modifying the first molecule while in the host cell via a modifying enzyme; and allowing the first molecule to bridge the interaction between the first test protein and the E3 ubiquitin ligase, wherein the first molecule is a product of an encoded DNA sequence, wherein the first molecule comprises a randomized polypeptide library and one or more modifying enzymes, wherein the one or more modifying enzymes modify the randomized polypeptide library.

Host Cells

In some embodiments, the host cell is a eukaryote or a prokaryote. In some embodiments, the host cell is from animal, plant, a fungus, or bacteria. In some embodiments, the fungus is *Aspergillus* or *Pichia pastoris*. In some embodiments, the host cell is a haploid yeast cell. In other embodiments, the host cell is a diploid yeast cell. In some embodiments, the diploid yeast cell is produced by mating a first host cell comprising DNA sequences encoding the first chimeric gene, the second chimeric gene, and the third chimeric gene, to a second host cell comprising DNA sequences encoding the death agent, positive selection reporter, and the mRNA comprising a nucleotide sequence encoding a polypeptide. In some embodiments, the plant is *Nicotiana tabacum* or *Physcomitrella patens*. In some embodiments, the host cell is a sf9 (*Spodoptera frugiperda*) insect cell.

Disclosed herein, in certain embodiments, is a host cell configured to express a first fusion protein comprising a first test protein, a first DNA-binding moiety and a first gene activating moiety; an E3 ubiquitin ligase; a death agent, wherein the expression of the death agent is under control of a promoter DNA sequence specific for the DNA-binding moiety and a polypeptide of 60 or fewer amino acids, wherein the polypeptide modulates an interaction between the first test protein and the E3 ubiquitin ligase to lead to the first test protein's accelerated degradation.

In some embodiments, the host cell may also comprise a second fusion protein, comprising a second DNA-binding moiety, a second test protein, and a second gene-activation moiety; and a positive selection reporter, wherein the expression of the positive reporter is under control of a second promoter DNA sequence specific for the second DNA-binding moiety.

The host cell may have a mutant background enabling uptake of small molecules. In some cases, the host cell has a mutant background enabling increased transformation efficiency.

Disclosed herein, in certain embodiments, is a host cell comprising a plasmid vector wherein a DNA sequence encoding a first polypeptide is inserted in frame with Gal4-DBD and VP64-AD, and a second polypeptide is inserted in frame with LexA-DBD and VP64-AD, and wherein a DNA sequence encodes an E3 ubiquitin ligase.

Disclosed herein, in certain embodiments, is a kit comprising of the described plasmids; and transfectable host cells compatible with the plasmids, or any combination thereof. In some embodiments, the provided host cells are already transfected with components of the plasmids. In some embodiments, the kit includes selectable agents for use with host cells transfected with the plasmids. In some embodiments a library of variants of either plasmid are provided, wherein more than a single pair of bait proteins or E3 ubiquitin ligases are provided. Such a library can be used to, for example, screen for agents with selective protein targeting. In some embodiments a library of variants of the polypeptide plasmid are provided, wherein a plurality of different short test polypeptide sequences for screening are provided. The plurality of different short peptide sequences can be randomly generated by any method (e.g. NNK or NNN nucleotide randomization). The plurality of different short peptide sequences can also be preselected, either by previous experiments selecting for binding to a target, or from existing data sets in the scientific literature that have reported rationally-designed peptide libraries.

The host cell can additionally be made to be permeable to small molecules, for example by deletion of drug efflux pump encoding genes such as PDR5. Genes encoding for transcription factors such as PDR1 and PDR3 that induce expression of efflux pumps including but not restricted to the 12 genes described by 12geneΔ0HSR (Chinen, 2011). The host cell could be further permeabilized to small molecules by interference with the synthesis and deposition of ergosterol in the plasma membrane such as by the deletion of ERG2, ERGS, and/or ERG6 or driving their expression under a regulatable promoter.

The host cell can additionally carry mutations to enable more efficient transformation with vectors and/or more efficient uptake small molecules.

The mentioned plasmids can be used in various permutations. In some embodiments, integration of the plasmids into the genome of the host cell is followed by transformation of a library with randomly encoded peptides using, for example, NNK or NNN codons.

In some embodiments, to perform a screen to identify a peptide that can mediate the degradation of a target protein, the host cell is propagated in selection media to ensure the presence of the required plasmids and expression of a non-target protein (e.g. on media lacking the positive selection marker for yeast, or in media containing antibiotic for human or bacterial cells). This host cell can then be transformed with the peptide library plasmid, and immediately transferred to selection media to ensure all components are present (i.e. on media lacking both plasmid selection markers for yeast, or antibiotics for bacterial or mammalian cells), and are inducing expression of any inducible component such as the target protein which activates expression of the death agent (e.g. with Gal, doxycycline, etc).

In other embodiments, the plasmids are used as a 'plug and play platform' utilizing the yeast mating type system, where the one or more (or two or more) plasmids (or the genetic elements therein) are introduced into the same cell by cell fusion or cell fusion followed by meiosis instead of transfection. This cell fusion involves two different yeast host cells bearing different genetic elements. In this embodiment, yeast host cell 1 is one of MATa or MATalpha and includes an integration of the target protein and E3 ubiquitin ligase plasmid. In this embodiment, yeast host cell 1 strain can be propagated on positive selection media to ensure the proteins are present. In this embodiment, the yeast host cell 2 can be the opposite mating type. This strain carries (or has integrated) the randomized peptide library and 'death agent' (e.g. cytotoxic reporter) plasmid. Yeast host cell 2 can be generated via large batch high efficiency transformation protocols which ensure a highly diversified library variation within the cell culture. Aliquots of this library batch can then be frozen to maintain consistency. In this embodiment, the strains are mated in batch to result in a diploid strain that carries all the markers, the target protein, E3 ligase, positive selection, 'death agents' and peptide. This batch culture then can be propagated on solid medium that enables selection of all the system components (i.e. media lacking both positive selection markers) and inducing expression of any inducible component (i.e. with Gal).

Surviving colonies from limiting dilution experiments performed on host cells bearing both the target protein and E3 ligase and library/cytotoxic constructs (either introduced to the cell by transfection or mating) can constitute colonies with a specific target protein has been degraded by a peptide and no longer triggers the death cascade triggered by the encoded 'death agents' (e.g. cytotoxic reporters) while maintaining the expression of a bait variant protein driving a positive selection marker. The peptide sequence can be obtained by DNA sequencing the peptide-encoding region of the plasmid in each surviving colony.

To ensure that survival is due to the degradation of the target rather than stochastic chance or faulty gene expression, an inducible promoter can be used to inactivate the production of either the E3 ligase or the peptide and confirm specificity. In some embodiments, cell survival is observed only on media with galactose wherein all the components are expressed; and no survival is observed on media without galactose when expression of the peptide is lost.

The plasmids can also be isolated and re-transformed into a fresh host cell to confirm specificity. Biochemical fractionation of the viable host cells which contain the target, E3 ligase, peptide, positive selection and 'death agent' followed by pull-down experiments can confirm an interaction between the peptide sequence and either target protein or E3 ligase using encoded tags that are part of the fusion constructs (e.g. Myc-tag, HA-tag, His-tag). This is also helpful to perform SAR to determine the binding interface.

The peptides to be used in the screening assay can be derived from a complex library that involves post-translational modifying enzymes. The modified peptides can be analyzed by methods such as mass spectrometry, in addition being sequenced to ID the primary sequence. The peptides can also be tested for inherent membrane permeability by reapplying them onto the host cells exogenously (from a lysate) and observing for reporter inactivation or activation.

Once enough surviving host cell colonies are sequenced, highly conserved sequence patterns can emerge and can be readily identified using a multiple-sequence alignment. Any such pattern can be used to 'anchor' residues within the library peptide insert sequence and permute the variable residues to generate diversity and achieve tighter binding. In some embodiments, this can also be done using an algorithm developed for pattern recognition and library design. Upon convergence, the disrupting peptide pattern, as identified through sequencing, can be used to define a peptide disruptor sequence. Convergence is defined by the lack of retrieval of any new sequences in the last iteration relative to the penultimate one.

Figure 6:
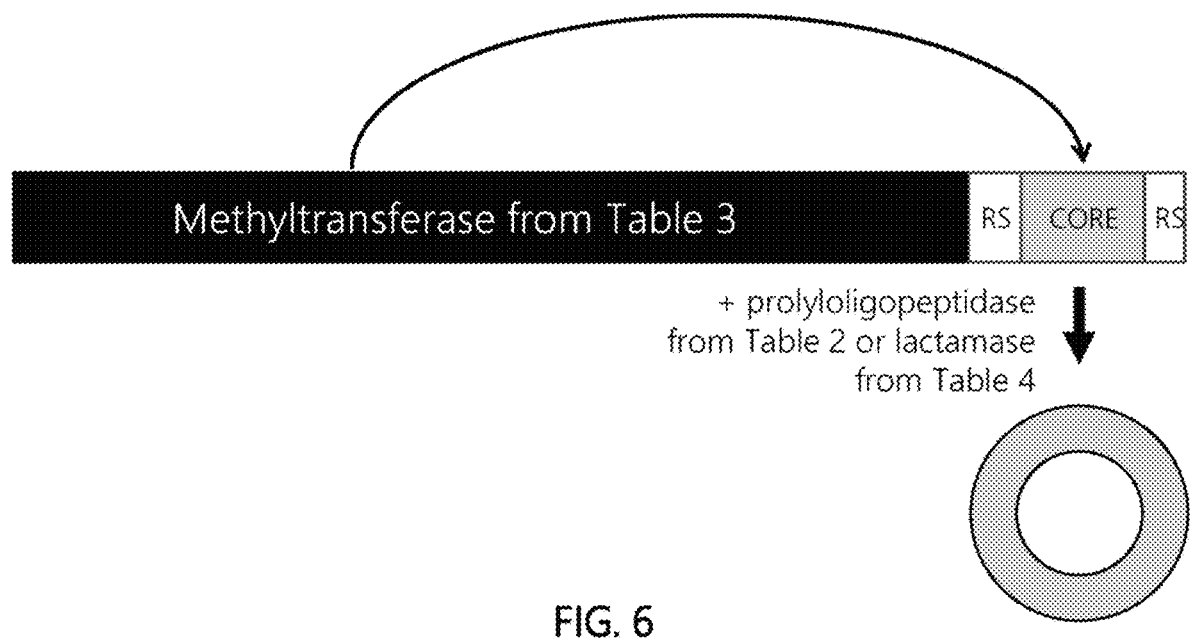
FIG. 6 illustrates a vector platform to generate a library of macrocyclic bridging agents using methyltransferases and prolyloligopeptidases or lactamases.

In some embodiments, a peptide library may be generated and/or used for screening as described herein. The peptides in the generated library may be peptide having drug-like properties. The peptides to be used in the screening assay can be derived from a process that involves enzymes that modify peptides post-translation. For instance, to generate libraries of peptides that have an N-methylated backbone or are macrocyclic in structure, a methyltransferase (such as the ones described in Table 3) may be used to generate the library, along with a prolyloligopeptidase (such as the ones described in Table 2) as shown in FIG. 6. In some instances, the diversified core peptide sequence may initially be flanked by the cognate Recognition Sites (RS) for the corresponding prolyloligopeptidase or lactamase, and subsequently released from the linear product to form a cyclic peptide. Further post translational modifications of the core peptide sequence are possible using enzymes, such as the ones described in Tables 5-7.

Figure 7:
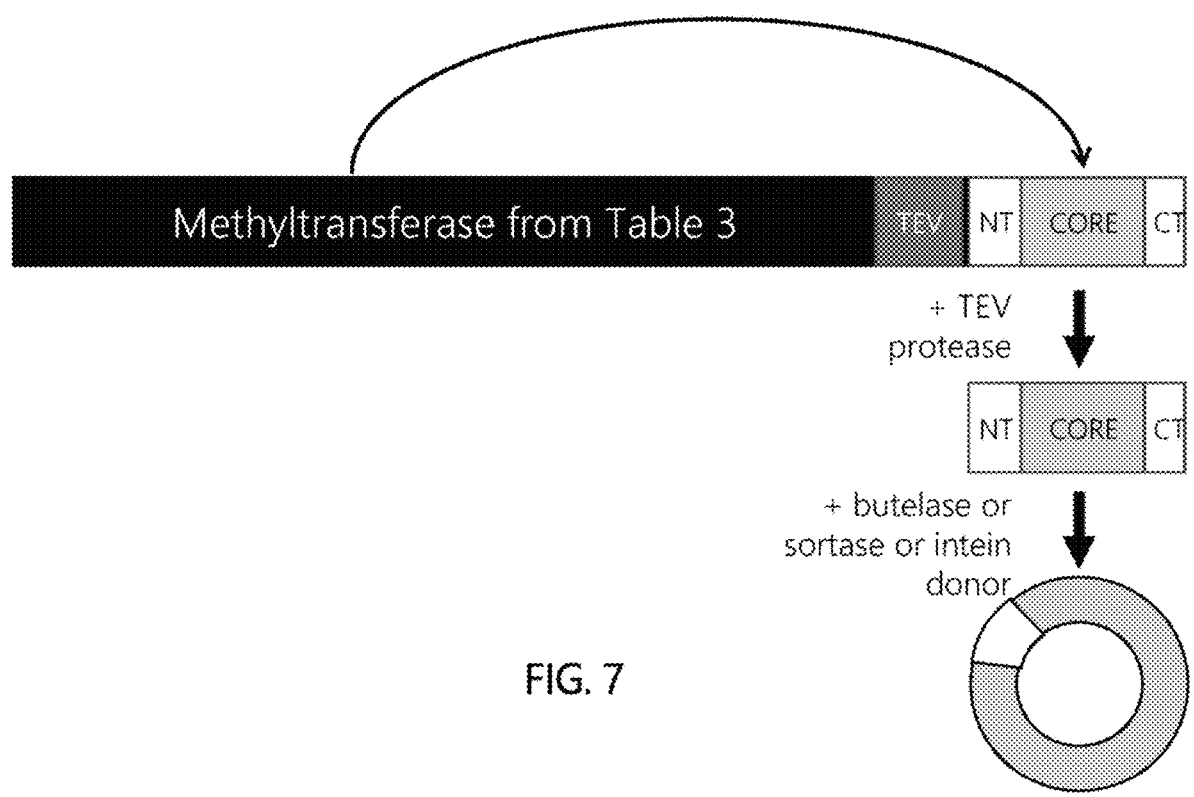
FIG. 7 illustrates a vector platform to generate a library of macrocyclic bridging agents using methyltransferases and processing enzymes.

In an alternative approach, to generate libraries of drug-like N-methylated and/or macrocyclic peptides (e.g., for use in a system designed to identify "bridging" peptides or peptides that inhibit a protein-protein interaction), a methyltransferase (such as the ones described in Table 3) may be used, where a protease cleavage site (such as TEV protease) is inserted upstream of the diversified core peptide sequence as shown in FIG. 7. After methylation of the core sequence, protease induction may release the core peptide flanked by recognition sites (N-Term or C-Term sites) for further processing enzymes such as butelase, or sortase that enable cyclization. Alternatively, intein donor sites can be included to induce cyclization. In some cases, the cyclization process may introduce a minimal 'scar' sequence within the final macrocycle. Further post translational modifications of the core peptide sequence are possible using the enzymes described in Tables 5-7.

EXAMPLES

Example 1: Method for Identifying a Molecule that Leads to Selective Protein Degradation This is an example of a system that uses two variants of one protein, fused to different DBDs to identify facilitator for a specific variant degradation. An integration plasmid is used to integrate into *Saccharomyces cerevisiae* proteins that constitute the proteins of interest and an E3 ligase. The plasmid encodes for the fusion of an AD (VP64) and DBD (Gal4) with KRas (G12D), and another fusion construct of AD (VP64) and DBD (LexA) with KRas, and the E3 ubiquitin ligase Cereblon (CRL4-CRBN). The protein fusion sequences are tagged with either FLAG, MYC or HA. The plasmid further includes yeast replication and selection markers (TRP1 and CEN). The plasmid also has sites for integration into the genome at a specified locus.

The *Saccharomyces cerevisiae* is co-transformed with a selection and library plasmid for the expression of a randomized peptide library, NNK 20-mer sequences. The selection plasmid is driven by a strong promoter, ADH1. The selection and library plasmid also comprises a sequence that encodes a HIS tag.

The selection and library plasmid additionally comprises a LexAop sequence, which induces 'death agents' (cytotoxic reporter expression) when bound by a functional transcriptional factor that is formed by Gal4—KRas (G12D)—VP64 fusion protein. The selection and library plasmid also contains a positive selection marker, ADE2 which is under control of LexA—KRas—VP64 fusion protein and leading to expression of the positive selection marker when the fusion protein is expressed. The plasmid further includes yeast replication and selection markers (TRP1 and CEN).

The screen is performed by mating the strains in a batch to result in a diploid strain, which carries all the markers, the target protein, the E3 ligase, the positive selection, the death agents, and the peptide. This batch culture is then propagated on solid medium, which enable selection of all the system components (media lacking two nutritional components) and induce expression of any inducible component with Gal.

Surviving colonies constitute cells with degraded KRas (G12D), that can no longer trigger the death cascade induced by the encoded death agents, the degradation of which has been facilitated by a peptide bridging to Cereblon. The same cells also express WT KRas that was not targeted and is driving positive selection to enable survival.

The peptide sequence that is able to selectively degrade KRas (G12D) is obtained by DNA sequencing the peptide-encoding region of the selection and library plasmid in each surviving colony.

To confirm specificity, the inducible marker is used to inactivate the production of the E3 ligase and confirm specificity. The plasmid is then isolated and re-transformed into a fresh parental strain to confirm specificity.

Biochemical fractionation of the viable strain that contained the target, E3 ligase, peptide, selection marker, and death agent is followed by pull-down experiments to confirm an interaction between the peptide sequence and either protein using the encoded tags.

An alternative example can be made by switching LexA with Gal4. In another alternative example, fusion proteins in either construct are driven by an inducible promoter, GAL1, instead of ADH1 promoter. In another example, yeast selection marker 2 um is included in the target and E3 ligase integration plasmid and selection and library plasmid, instead of CEN. Similarly, yeast selection marker LEU2 can be used alternatively in another example. In yet another example, the N-terminus of the peptide translated from the selection and library plasmid can alternatively be glycine, alanine, serine, threonine, valine, or proline. In other examples, the genetic reporter in the confirmation plasmid is HIS3 or URA3, in place of ADE2. Either mating types of *Saccharomyces cerevisiae* haploid state can be used as background strain in alternative examples. In other examples, the library of peptides can be expressed from scaffolds that enable post translational modifications. In other examples, background strains also express the enzymes for the cyclization and methylation of peptides like lanthipeptides maturation enzymes from *Lactococcus lactis* (LanB, LanC, LanM, LanP), patellamide biosynthesis factors from cyanobacteria (PatD, PatG), butelase 1 from *Clitoria ternatea*, and GmPOPB from *Galerina marginata* or other species.

Example 2: Negative Readout for Degradation of a Target Protein

Figure 8:
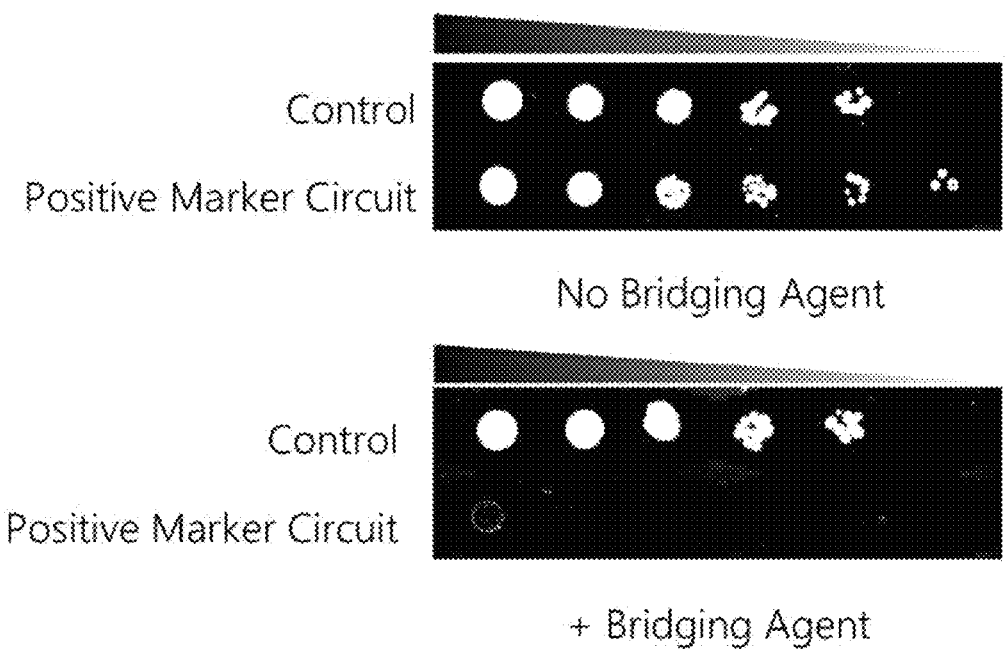
FIG. 8 illustrates a negative readout assay for degradation of a target protein using the mechanism described in FIG. 1.

In this example, the target bait is operationally linked to a positive selection marker that enables growth in the absence of an essential nutrient (schematic as shown in FIG. 1). In this case, cells were plated on a degradation readout media, and survival was assayed with or without a bridging agent. In cases where a bridging agent is able to functionally bridge the bait protein to a specific E3 ligase of interest, the bait becomes degraded and cells cannot grow on degradation readout media, as they cannot express the positive marker required for growth. *Saccharomyces cerevisiae* cells were modified to minimize drug efflux by deletion of drug efflux pumps and transcription factors encoding for their expression as previously described (Chinen, 2011). The E3 ligase used in this example was TIR1. The target was a plant protein (Auxin Responsive Protein—AXR) that is ubiquitinated and degraded in response to Indol Acetic Acid fused to a TetR DBD and an AD. The DBD bound upstream of a positive selection marker, in this case was ADE2. The cells were seeded at OD-1.0 at a 5-fold dilution series with 2 ul spotted onto selection plates without adenine, with or without 25 uM of the bridging agent Naphthalene Acetic Acid (NAA). Plates were incubated at 30° C. and imaged 2 days later. Results are shown in FIG. 8.

Example 3: Positive Readout for Degradation of a Target Protein

Figure 9:
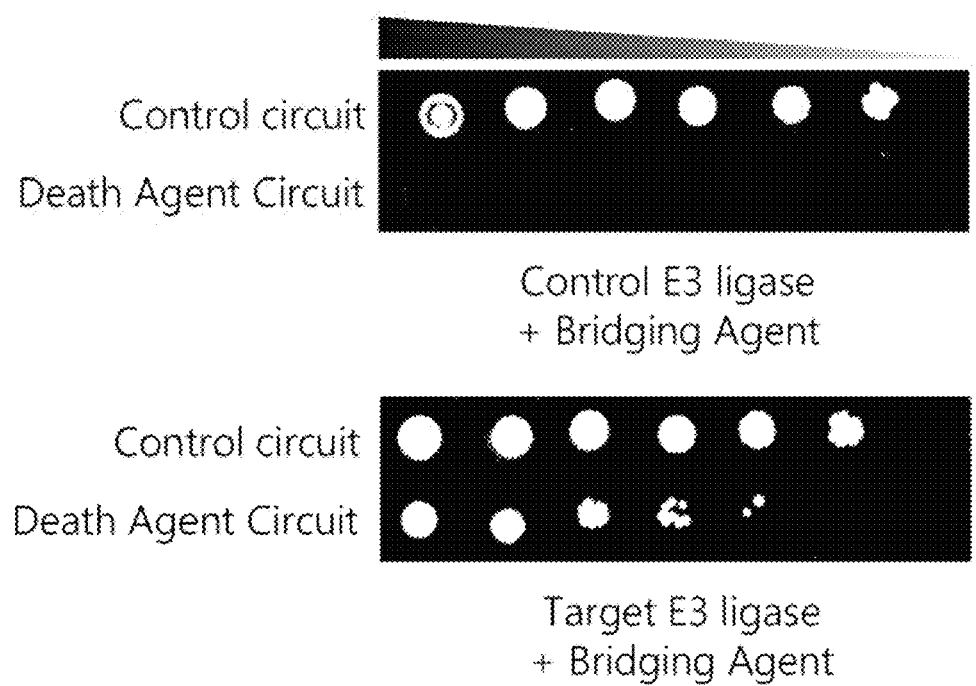
FIG. 9 illustrates a positive readout assay for degradation of a target protein using the mechanism described in FIG. 2.

In this example, the target bait was operationally linked to a 'Death Agent' negative selection marker that prevents cell growth when expressed as also described in FIG. 2. Survival of the cell expressing different E3 ligases was assessed in the presence of an exogenously provided bridging agent. In cases where a bridging agent is able to functionally bridge the bait protein to a specific E3 ligase of interest in a manner that results in ubiquitination of the bait/DBD fusion protein, the bait is degraded and cells grow, as they do not express the 'Death Agent' marker. The cells were modified to minimize drug efflux by deletion of drug efflux pumps and transcription factors encoding for their expression as previously described (Chinen, 2011). The E3 ligase used in this example was TIR1, the control E3 ligase used was CRBN. The target was a plant protein that is ubiquitinated and degraded in response to Indol Acetic Acid fused to a TetR DBD and an AD. Cells also contained a death agent regulated by the DBD-containing fusion protein. The cells were seeded at OD~1.0 at a 5-fold dilution series with 2 ul spotted onto selection plates containing 25 uM of the bridging agent NAA. Plates were incubated at 30° C. and imaged 2 days later. Results are shown in FIG. 9.

In another example, cells expressing a heterologous E3 ligase, in this case TIR1, were assayed for survival to discover bridging agents that can bridge TIR1 to the bait and lead to degradation, thereby enabling cell growth (schematic shown in FIG. 10A). The target was a plant protein (AXR) that is ubiquitinated and degraded in response to Indol Acetic Acid fused to a TetR DBD and an AD. Cells containing the E3 ligases and the death agent were mated to cells containing the target. The mated cells were then aliquoted into a 96 well plate at a starting $OD_{600}$=0.05. In this example, various compounds were used in quadruplicate wells at a concentration of 10 uM, and plated cells starting at $OD_{600}$=0.05 (with the border wells on each side kept as negative controls). Plates were incubated at 30° C. with shaking and continuously monitored for growth using $OD_{600}$ in a Cytation 1 instrument. From the conditions that displayed positive growth, the bridging agents could be identified. The functional bridging agents were NAA (wells C,D/6,7), 2,4-DCPA (wells E,F/8,9), and PAA (wells G,H/8,9) (structures shown in FIG. 10B). The final timepoint shown in FIG. 10C is 48 hrs.

Figure 11A:
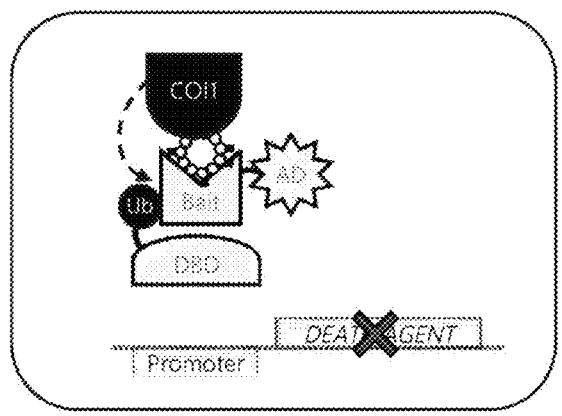
FIGS. 11A-C illustrate a positive readout assay for degradation of a target protein using high throughput screening of bridging agents such as coronatine.
Figure 11B:
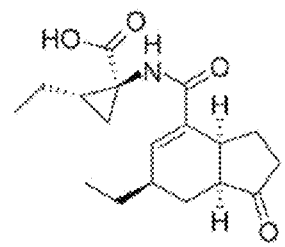
Figure 11C:
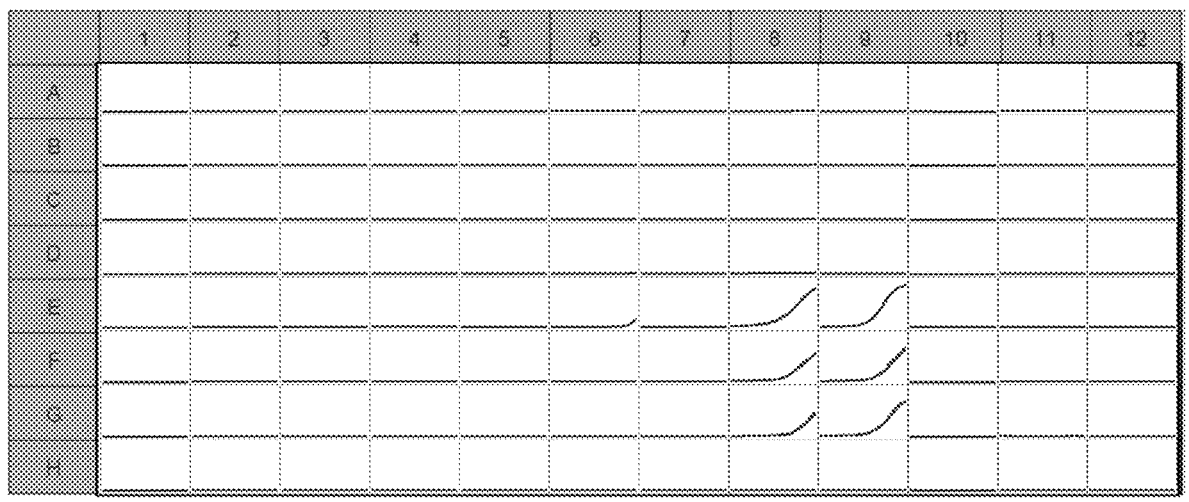

In yet another example, cells expressing a heterologous E3 ligase, in this case COI1b, were assayed for survival to discover bridging agents that can bridge COI1b to the bait and lead to degradation, thereby enabling cell growth (as shown in FIG. 11A). S. cerevisiae cells were modified to minimize drug efflux by deletion of drug efflux pumps and transcription factors encoding for their expression as previously described (Chinen, 2011). The target used was a plant protein (AXR) that is ubiquitinated and degraded in response to Jasmonate-isoleucine fused to a TetR DBD and an AD. Cells containing the E3 ligases and the death agents were mated to cells containing the target. The mated cells were then aliquoted into a 96 well plate at a starting $OD_{600}$=0.05. Various compounds were tested in duplicate wells at a concentration gradient down from 100 uM. The wells that exhibited cell growth contained various concentrations of coronatine (structure shown in FIG. 11B) from 100 uM (wells E8/9), 75 uM (F8/9), to 50 uM (G8/9). Plates were incubated at 30° C. with shaking and continuously monitored for growth using $OD_{600}$ in a Cytation 1 instrument. The final timepoint shown in FIG. 11C is 84 hrs.

SEQUENCE LISTING

```
<160> NUMBER OF SEQ ID NOS: 156

<210> SEQ ID NO 1
<211> LENGTH: 258
<212> TYPE: PRT
<213> ORGANISM: Vibrio cholerae

<400> SEQUENCE: 1

Met Val Lys Ile Ile Phe Val Phe Phe Ile Phe Leu Ser Ser Phe Ser
1               5                   10                  15

Tyr Ala Asn Asp Asp Lys Leu Tyr Arg Ala Asp Ser Arg Pro Pro Asp
            20                  25                  30

Glu Ile Lys Gln Ser Gly Gly Leu Met Pro Arg Gly Gln Ser Glu Tyr
        35                  40                  45

Phe Asp Arg Gly Thr Gln Met Asn Ile Asn Leu Tyr Asp His Ala Arg
    50                  55                  60

Gly Thr Gln Thr Gly Phe Val Arg His Asp Asp Gly Tyr Val Ser Thr
65                  70                  75                  80

Ser Ile Ser Leu Arg Ser Ala His Leu Val Gly Gln Thr Ile Leu Ser
                85                  90                  95

Gly His Ser Thr Tyr Tyr Ile Tyr Val Ile Ala Thr Ala Pro Asn Met
            100                 105                 110

Phe Asn Val Asn Asp Val Leu Gly Ala Tyr Ser Pro His Pro Asp Glu
        115                 120                 125

Gln Glu Val Ser Ala Leu Gly Gly Ile Pro Tyr Ser Gln Ile Tyr Gly
    130                 135                 140

Trp Tyr Arg Val His Phe Gly Val Leu Asp Glu Gln Leu His Arg Asn
145                 150                 155                 160

Arg Gly Tyr Arg Asp Arg Tyr Tyr Ser Asn Leu Asp Ile Ala Pro Ala
                165                 170                 175

Ala Asp Gly Tyr Gly Leu Ala Gly Phe Pro Pro Glu His Arg Ala Trp
            180                 185                 190
```

```
Arg Glu Glu Pro Trp Ile His His Ala Pro Pro Gly Cys Gly Asn Ala
    195                 200                 205

Pro Arg Ser Ser Met Ser Asn Thr Cys Asp Glu Lys Thr Gln Ser Leu
    210                 215                 220

Gly Val Lys Phe Leu Asp Glu Tyr Gln Ser Lys Val Lys Arg Gln Ile
225                 230                 235                 240

Phe Ser Gly Tyr Gln Ser Asp Ile Asp Thr His Asn Arg Ile Lys Asp
                245                 250                 255

Glu Leu

<210> SEQ ID NO 2
<211> LENGTH: 593
<212> TYPE: PRT
<213> ORGANISM: Salmonella enterica

<400> SEQUENCE: 2

Met Leu Ile Leu Asn Gly Phe Ser Ser Ala Thr Leu Ala Leu Ile Thr
1               5                   10                  15

Pro Pro Phe Leu Pro Lys Gly Gly Lys Ala Leu Ser Gln Ser Gly Pro
            20                  25                  30

Asp Gly Leu Ala Ser Ile Thr Leu Pro Leu Pro Ile Ser Ala Glu Arg
        35                  40                  45

Gly Phe Ala Pro Ala Leu Ala Leu His Tyr Ser Ser Gly Gly Gly Asn
    50                  55                  60

Gly Pro Phe Gly Val Gly Trp Ser Cys Ala Thr Met Ser Ile Ala Arg
65                  70                  75                  80

Arg Thr Ser His Gly Val Pro Gln Tyr Asn Asp Ser Asp Glu Phe Leu
                85                  90                  95

Gly Pro Asp Gly Glu Val Leu Val Gln Thr Leu Ser Thr Gly Asp Ala
            100                 105                 110

Pro Asn Pro Val Thr Cys Phe Ala Tyr Gly Asp Val Ser Phe Pro Gln
        115                 120                 125

Ser Tyr Thr Val Thr Arg Tyr Gln Pro Arg Thr Glu Ser Ser Phe Tyr
    130                 135                 140

Arg Leu Glu Tyr Trp Val Gly Asn Ser Asn Gly Asp Asp Phe Trp Leu
145                 150                 155                 160

Leu His Asp Ser Asn Gly Ile Leu His Leu Leu Gly Lys Thr Ala Ala
                165                 170                 175

Ala Arg Leu Ser Asp Pro Gln Ala Ala Ser His Thr Ala Gln Trp Leu
            180                 185                 190

Val Glu Glu Ser Val Thr Pro Ala Gly Glu His Ile Tyr Tyr Ser Tyr
        195                 200                 205

Leu Ala Glu Asn Gly Asp Asn Val Asp Leu Asn Gly Asn Glu Ala Gly
    210                 215                 220

Arg Asp Arg Ser Ala Met Arg Tyr Leu Ser Lys Val Gln Tyr Gly Asn
225                 230                 235                 240

Ala Thr Pro Ala Ala Asp Leu Tyr Leu Trp Thr Ser Ala Thr Pro Ala
                245                 250                 255

Val Gln Trp Leu Phe Thr Leu Val Phe Asp Tyr Gly Glu Arg Gly Val
            260                 265                 270

Asp Pro Gln Val Pro Pro Ala Phe Thr Ala Gln Asn Ser Trp Leu Ala
        275                 280                 285

Arg Gln Asp Pro Phe Ser Leu Tyr Asn Tyr Gly Phe Glu Ile Arg Leu
    290                 295                 300
```

```
His Arg Leu Cys Arg Gln Val Leu Met Phe His His Phe Pro Asp Glu
305                 310                 315                 320

Leu Gly Glu Ala Asp Thr Leu Val Ser Arg Leu Leu Leu Glu Tyr Asp
            325                 330                 335

Glu Asn Pro Ile Leu Thr Gln Leu Cys Ala Ala Arg Thr Leu Ala Tyr
            340                 345                 350

Glu Gly Asp Gly Tyr Arg Arg Ala Pro Val Asn Asn Met Met Pro Pro
        355                 360                 365

Pro Pro Pro Pro Pro Pro Met Met Gly Gly Asn Ser Ser Arg Pro
    370                 375                 380

Lys Ser Lys Trp Ala Ile Val Glu Glu Ser Lys Gln Ile Gln Ala Leu
385                 390                 395                 400

Arg Tyr Tyr Ser Ala Gln Gly Tyr Ser Val Ile Asn Lys Tyr Leu Arg
                405                 410                 415

Gly Asp Asp Tyr Pro Glu Thr Gln Ala Lys Glu Thr Leu Leu Ser Arg
            420                 425                 430

Asp Tyr Leu Ser Thr Asn Glu Pro Ser Asp Glu Phe Lys Asn Ala
        435                 440                 445

Met Ser Val Tyr Ile Asn Asp Ile Ala Glu Gly Leu Ser Ser Leu Pro
450                 455                 460

Glu Thr Asp His Arg Val Val Tyr Arg Gly Leu Lys Leu Asp Lys Pro
465                 470                 475                 480

Ala Leu Ser Asp Val Leu Lys Glu Tyr Thr Thr Ile Gly Asn Ile Ile
                485                 490                 495

Ile Asp Lys Ala Phe Met Ser Thr Ser Pro Lys Ala Trp Ile Asn
            500                 505                 510

Asp Thr Ile Leu Asn Ile Tyr Leu Glu Lys Gly His Lys Gly Arg Ile
            515                 520                 525

Leu Gly Asp Val Ala His Phe Lys Gly Glu Ala Glu Met Leu Phe Pro
            530                 535                 540

Pro Asn Thr Lys Leu Lys Ile Glu Ser Ile Val Asn Cys Gly Ser Gln
545                 550                 555                 560

Asp Phe Ala Ser Gln Leu Ser Lys Leu Arg Leu Ser Asp Asp Ala Thr
                565                 570                 575

Ala Asp Thr Asn Arg Ile Lys Arg Ile Ile Asn Met Arg Val Leu Asn
            580                 585                 590

Ser

<210> SEQ ID NO 3
<211> LENGTH: 601
<212> TYPE: PRT
<213> ORGANISM: Mycoplasma pneumoniae

<400> SEQUENCE: 3

Met Ser Glu Asn Leu Tyr Phe Gln Gly His Met Pro Asn Pro Val Arg
1               5                   10                  15

Phe Val Tyr Arg Val Asp Leu Arg Ser Pro Glu Glu Ile Phe Glu His
            20                  25                  30

Gly Phe Ser Thr Leu Gly Asp Val Arg Asn Phe Phe Glu His Ile Leu
        35                  40                  45

Ser Thr Asn Phe Gly Arg Ser Tyr Phe Ile Ser Thr Ser Glu Thr Pro
    50                  55                  60

Thr Ala Ala Ile Arg Phe Phe Gly Ser Trp Leu Arg Glu Tyr Val Pro
65                  70                  75                  80
```

-continued

```
Glu His Pro Arg Arg Ala Tyr Leu Tyr Glu Ile Arg Ala Asp Gln His
                 85                  90                  95
Phe Tyr Asn Ala Arg Ala Thr Gly Glu Asn Leu Leu Asp Leu Met Arg
            100                 105                 110
Gln Arg Gln Val Val Phe Asp Ser Gly Asp Arg Glu Met Ala Gln Met
        115                 120                 125
Gly Ile Arg Ala Leu Arg Thr Ser Phe Ala Tyr Gln Arg Glu Trp Phe
    130                 135                 140
Thr Asp Gly Pro Ile Ala Ala Asn Val Arg Ser Ala Trp Leu Val
145                 150                 155                 160
Asp Ala Val Pro Val Glu Pro Gly His Ala His Pro Ala Gly Arg
                165                 170                 175
Val Val Glu Thr Thr Arg Ile Asn Glu Pro Glu Met His Asn Pro His
            180                 185                 190
Tyr Gln Glu Leu Gln Thr Gln Ala Asn Asp Gln Pro Trp Leu Pro Thr
        195                 200                 205
Pro Gly Ile Ala Thr Pro Val His Leu Ser Ile Pro Gln Ala Ala Ser
    210                 215                 220
Val Ala Asp Val Ser Glu Gly Thr Ser Ala Ser Leu Ser Phe Ala Cys
225                 230                 235                 240
Pro Asp Trp Ser Pro Pro Ser Ser Asn Gly Glu Asn Pro Leu Asp Lys
                245                 250                 255
Cys Ile Ala Glu Lys Ile Asp Asn Tyr Asn Leu Gln Ser Leu Pro Gln
            260                 265                 270
Tyr Ala Ser Ser Val Lys Glu Leu Glu Asp Thr Pro Val Tyr Leu Arg
        275                 280                 285
Gly Ile Lys Thr Gln Lys Thr Phe Met Leu Gln Ala Asp Pro Gln Asn
    290                 295                 300
Asn Asn Val Phe Leu Val Glu Val Asn Pro Lys Gln Lys Ser Ser Phe
305                 310                 315                 320
Pro Gln Thr Ile Phe Phe Trp Asp Val Tyr Gln Arg Ile Cys Leu Lys
                325                 330                 335
Asp Leu Thr Gly Ala Gln Ile Ser Leu Ser Leu Thr Ala Phe Thr Thr
            340                 345                 350
Gln Tyr Ala Gly Gln Leu Lys Val His Leu Ser Val Ser Ala Val Asn
        355                 360                 365
Ala Val Asn Gln Lys Trp Lys Met Thr Pro Gln Asp Ile Ala Ile Thr
    370                 375                 380
Gln Phe Arg Val Ser Ser Glu Leu Leu Gly Gln Thr Glu Asn Gly Leu
385                 390                 395                 400
Phe Trp Asn Thr Lys Ser Gly Ser Gln His Asp Leu Tyr Val Cys
                405                 410                 415
Pro Leu Lys Asn Pro Pro Ser Asp Leu Glu Glu Leu Gln Ile Ile Val
            420                 425                 430
Asp Glu Cys Thr Thr His Ala Gln Phe Val Thr Met Arg Ala Ala Ser
        435                 440                 445
Thr Phe Phe Val Asp Val Gln Leu Gly Trp Tyr Trp Arg Gly Tyr Tyr
    450                 455                 460
Tyr Thr Pro Gln Leu Ser Gly Trp Ser Tyr Gln Met Lys Thr Pro Asp
465                 470                 475                 480
Gly Gln Ile Phe Tyr Asp Leu Lys Thr Ser Lys Ile Phe Phe Val Gln
                485                 490                 495
Asp Asn Gln Asn Val Phe Phe Leu His Asn Lys Leu Asn Lys Gln Thr
```

```
            500                 505                 510
Gly Tyr Ser Trp Asp Trp Val Glu Trp Leu Lys His Asp Met Asn Glu
        515                 520                 525

Asp Lys Asp Glu Asn Phe Lys Trp Tyr Phe Ser Arg Asp Asp Leu Thr
        530                 535                 540

Ile Pro Ser Val Glu Gly Leu Asn Phe Arg His Ile Arg Cys Tyr Ala
545                 550                 555                 560

Asp Asn Gln Gln Leu Lys Val Ile Ile Ser Gly Ser Arg Trp Gly Gly
        565                 570                 575

Trp Tyr Ser Thr Tyr Asp Lys Val Glu Ser Asn Val Glu Asp Lys Ile
        580                 585                 590

Leu Val Lys Asp Gly Phe Asp Arg Phe
        595                 600

<210> SEQ ID NO 4
<211> LENGTH: 250
<212> TYPE: PRT
<213> ORGANISM: Streptococcus pyogenes

<400> SEQUENCE: 4

Met Leu Lys Lys Arg Tyr Gln Leu Ala Met Ile Leu Leu Leu Ser Cys
1               5                   10                  15

Phe Ser Leu Val Trp Gln Thr Glu Gly Leu Val Glu Leu Phe Val Cys
            20                  25                  30

Glu His Tyr Glu Arg Ala Val Cys Glu Gly Thr Pro Ala Tyr Phe Thr
        35                  40                  45

Phe Ser Asp Gln Lys Gly Ala Glu Thr Leu Ile Lys Lys Arg Trp Gly
    50                  55                  60

Lys Gly Leu Val Tyr Pro Arg Ala Glu Gln Glu Ala Met Ala Ala Tyr
65                  70                  75                  80

Thr Cys Gln Gln Ala Gly Pro Ile Asn Thr Ser Leu Asp Lys Ala Lys
                85                  90                  95

Gly Lys Leu Ser Gln Leu Thr Pro Glu Leu Arg Asp Gln Val Ala Gln
            100                 105                 110

Leu Asp Ala Ala Thr His Arg Leu Val Ile Pro Trp Asn Ile Val Val
        115                 120                 125

Tyr Arg Tyr Val Tyr Glu Thr Phe Leu Arg Asp Ile Gly Val Ser His
    130                 135                 140

Ala Asp Leu Thr Ser Tyr Tyr Arg Asn His Gln Phe Asn Pro His Ile
145                 150                 155                 160

Leu Cys Lys Ile Lys Leu Gly Thr Arg Tyr Thr Lys His Ser Phe Met
                165                 170                 175

Ser Thr Thr Ala Leu Lys Asn Gly Ala Met Thr His Arg Pro Val Glu
            180                 185                 190

Val Arg Ile Cys Val Lys Lys Gly Ala Lys Ala Phe Val Glu Pro
        195                 200                 205

Tyr Ser Ala Val Pro Ser Glu Val Leu Leu Phe Pro Arg Gly Cys
    210                 215                 220

Gln Leu Glu Val Val Gly Ala Tyr Val Ser Gln Asp His Lys Lys Leu
225                 230                 235                 240

His Ile Glu Ala Tyr Phe Lys Gly Ser Leu
                245                 250

<210> SEQ ID NO 5
<211> LENGTH: 264
```

<212> TYPE: PRT
<213> ORGANISM: Pseudomonas syringae

<400> SEQUENCE: 5

```
Met Asn Ile Asn Arg Gln Leu Pro Val Ser Gly Ser Glu Arg Leu Leu
1               5                   10                  15

Thr Pro Asp Val Gly Val Ser Arg Gln Ala Cys Ser Glu Arg His Tyr
            20                  25                  30

Ser Thr Gly Gln Asp Arg His Asp Phe Tyr Arg Phe Ala Ala Arg Leu
        35                  40                  45

His Val Asp Ala Gln Cys Phe Gly Leu Ser Ile Asp Asp Leu Met Asp
    50                  55                  60

Lys Phe Ser Asp Lys His Phe Arg Ala Glu His Pro Glu Tyr Arg Asp
65                  70                  75                  80

Val Tyr Pro Glu Glu Cys Ser Ala Ile Tyr Met His Thr Ala Gln Asp
                85                  90                  95

Tyr Ser Ser His Leu Val Arg Gly Glu Ile Gly Thr Pro Leu Tyr Arg
            100                 105                 110

Glu Val Asn Asn Tyr Leu Arg Leu Gln His Glu Asn Ser Gly Arg Glu
        115                 120                 125

Ala Glu Ile Asp Asn His Asp Glu Lys Leu Ser Pro His Ile Lys Met
    130                 135                 140

Leu Ser Ser Ala Leu Asn Arg Leu Met Asp Val Ala Ala Phe Arg Gly
145                 150                 155                 160

Thr Val Tyr Arg Gly Ile Arg Gly Asp Leu Asp Thr Ile Ala Arg Leu
                165                 170                 175

Tyr His Leu Phe Asp Thr Gly Gly Arg Tyr Val Glu Pro Ala Phe Met
            180                 185                 190

Ser Thr Thr Arg Ile Lys Asp Ser Ala Gln Val Phe Glu Pro Gly Thr
        195                 200                 205

Pro Asn Asn Ile Ala Phe Gln Ile Ser Leu Lys Arg Gly Ala Asp Ile
    210                 215                 220

Ser Gly Ser Ser Gln Ala Pro Ser Glu Glu Glu Ile Met Leu Pro Met
225                 230                 235                 240

Met Ser Glu Phe Val Ile Glu His Ala Ser Ala Leu Ser Glu Gly Lys
                245                 250                 255

His Leu Phe Val Leu Ser Gln Ile
            260
```

<210> SEQ ID NO 6
<211> LENGTH: 601
<212> TYPE: PRT
<213> ORGANISM: Vibrio cholerae

<400> SEQUENCE: 6

```
Met Lys Thr Ile Ile Ser Leu Ile Phe Ile Met Phe Pro Leu Phe Val
1               5                   10                  15

Ser Ala His Asn Gly Asn Phe Tyr Arg Ala Asp Ser Arg Ser Pro Asn
            20                  25                  30

Glu Ile Lys Asp Leu Gly Gly Leu Tyr Pro Arg Gly Tyr Tyr Asp Phe
        35                  40                  45

Phe Glu Arg Gly Thr Pro Met Ser Ile Ser Leu Tyr Asp His Ala Arg
    50                  55                  60

Gly Ala Pro Ser Gly Asn Thr Arg Tyr Asp Asp Gly Phe Val Ser Thr
65                  70                  75                  80
```

```
Thr Thr Asp Ile Asp Ser Ala His Glu Ile Gly Gln Asn Ile Leu Ser
                85                  90                  95

Gly Tyr Thr Glu Tyr Tyr Ile Tyr Leu Ile Ala Pro Ala Pro Asn Leu
            100                 105                 110

Leu Asp Val Asn Ala Val Leu Gly Arg Tyr Ser Pro His Pro Gln Glu
        115                 120                 125

Asn Glu Tyr Ser Ala Leu Gly Gly Ile Pro Trp Thr Gln Val Ile Gly
    130                 135                 140

Trp Tyr Val Val Asn Asn Gly Val Leu Asp Arg Asn Ile His Arg Asn
145                 150                 155                 160

Arg Gln Phe Arg Ala Asp Leu Phe Asn Asn Leu Ser Pro Ala Leu Pro
                165                 170                 175

Ser Glu Ser Tyr Gln Phe Ala Gly Phe Glu Pro Glu His Pro Ala Trp
            180                 185                 190

Arg Gln Glu Pro Trp Ile Asn Phe Ala Pro Pro Gly Cys Gly Arg Asn
        195                 200                 205

Val Arg Leu Thr Lys His Ile Asn Gln Gln Asp Cys Ser Asn Ser Gln
    210                 215                 220

Glu Glu Leu Val Tyr Lys Lys Leu Gln Asp Leu Arg Thr Gln Phe Lys
225                 230                 235                 240

Val Asp Lys Lys Leu Lys Leu Val Asn Lys Thr Ser Ser Asn Asn Ile
                245                 250                 255

Ile Phe Pro Asn His Asp Phe Ile Arg Glu Trp Val Asp Leu Asp Gly
            260                 265                 270

Asn Gly Asp Leu Ser Tyr Cys Gly Phe Thr Val Asp Ser Asp Gly Ser
        275                 280                 285

Arg Lys Arg Ile Val Cys Ala His Asn Asn Gly Asn Phe Thr Tyr Ser
    290                 295                 300

Ser Ile Asn Ile Ser Leu Ser Asp Tyr Gly Trp Pro Lys Gly Gln Arg
305                 310                 315                 320

Phe Ile Asp Ala Asn Gly Asp Gly Leu Val Asp Tyr Cys Arg Val Gln
                325                 330                 335

Tyr Val Trp Thr His Leu Tyr Cys Ser Leu Ser Leu Pro Gly Gln Tyr
            340                 345                 350

Phe Ser Leu Asp Lys Asp Ala Gly Tyr Leu Asp Ala Gly Tyr Asn Asn
        355                 360                 365

Ser Arg Ala Trp Ala Lys Val Ile Gly Thr Asn Lys Tyr Ser Phe Cys
    370                 375                 380

Arg Leu Thr Ser Asn Gly Tyr Ile Cys Thr Asp Ile Asp Ser Tyr Ser
385                 390                 395                 400

Thr Ala Phe Lys Asp Asp Asp Gln Gly Trp Ala Asp Ser Arg Tyr Trp
                405                 410                 415

Met Asp Ile Asp Gly Asn Gly Gly Asp Asp Tyr Cys Arg Leu Val Tyr
            420                 425                 430

Asn Trp Thr His Leu Arg Cys Asn Leu Gln Gly Lys Asp Gly Leu Trp
        435                 440                 445

Lys Arg Val Glu Ser Lys Tyr Leu Asp Gly Tyr Pro Ser Leu Arg
    450                 455                 460

Phe Lys Ile Lys Met Thr Ser Asn Lys Asp Asn Tyr Cys Arg Ile Val
465                 470                 475                 480

Arg Asn His Arg Val Met Glu Cys Ala Tyr Val Ser Asp Asn Gly Glu
                485                 490                 495

Phe His Asn Tyr Ser Leu Asn Met Pro Phe Ser Leu Tyr Asn Lys Asn
```

```
            500                 505                 510

Asp Ile Gln Phe Ile Asp Ile Asp Gly Asp Asn Arg Asp Asp Ile Cys
        515                 520                 525

Arg Tyr Asn Ser Ala Pro Asn Thr Met Glu Cys Tyr Leu Asn Gln Asp
    530                 535                 540

Lys Ser Phe Ser Gln Asn Lys Leu Val Leu Tyr Leu Ser Ala Lys Pro
545                 550                 555                 560

Ile Ser Ser Leu Gly Ser Gly Ser Ser Lys Ile Ile Arg Thr Phe Asn
                565                 570                 575

Ser Glu Lys Asn Ser Ser Ala Tyr Cys Tyr Asn Ala Gly Tyr Gly Thr
            580                 585                 590

Leu Arg Cys Asp Glu Phe Val Ile Tyr
        595                 600

<210> SEQ ID NO 7
<211> LENGTH: 476
<212> TYPE: PRT
<213> ORGANISM: Bacillus cereus

<400> SEQUENCE: 7

Met Lys Glu Ile Ile Arg Asn Leu Val Arg Leu Asp Val Arg Ser Asp
1               5                   10                  15

Val Asp Glu Asn Ser Lys Lys Thr Gln Glu Leu Val Glu Lys Leu Pro
            20                  25                  30

His Glu Val Leu Glu Leu Tyr Lys Asn Val Gly Gly Glu Ile Tyr Ile
        35                  40                  45

Thr Asp Lys Arg Leu Thr Gln His Glu Glu Leu Ser Asp Ser Ser His
    50                  55                  60

Lys Asp Met Phe Ile Val Ser Ser Glu Gly Lys Ser Phe Pro Leu Arg
65                  70                  75                  80

Glu His Phe Val Phe Ala Lys Gly Gly Lys Glu Pro Ser Leu Ile Ile
                85                  90                  95

His Ala Glu Asp Tyr Ala Ser His Leu Ser Ser Val Glu Val Tyr Tyr
            100                 105                 110

Glu Leu Gly Lys Ala Ile Ile Arg Asp Thr Phe Pro Leu Asn Gln Lys
        115                 120                 125

Glu Leu Gly Asn Pro Lys Phe Ile Asn Ala Ile Asn Glu Val Asn Gln
    130                 135                 140

Gln Lys Glu Gly Lys Gly Val Asn Ala Lys Ala Asp Glu Asp Gly Arg
145                 150                 155                 160

Asp Leu Leu Phe Gly Lys Glu Leu Lys Lys Asn Leu Glu His Gly Gln
                165                 170                 175

Leu Val Asp Leu Asp Leu Ile Ser Gly Asn Leu Ser Glu Phe Gln His
            180                 185                 190

Val Phe Ala Lys Ser Phe Ala Leu Tyr Tyr Glu Pro His Tyr Lys Glu
        195                 200                 205

Ala Leu Lys Ser Tyr Ala Pro Ala Leu Phe Asn Tyr Met Leu Glu Leu
    210                 215                 220

Asp Gln Met Arg Phe Lys Glu Ile Ser Asp Asp Val Lys Glu Lys Asn
225                 230                 235                 240

Lys Asn Val Leu Asp Phe Lys Trp Tyr Thr Arg Lys Ala Glu Ser Trp
                245                 250                 255

Gly Val Gln Thr Phe Lys Asn Trp Lys Glu Asn Leu Thr Ile Ser Glu
            260                 265                 270
```

-continued

```
Lys Asp Ile Ile Thr Gly Tyr Thr Gly Ser Lys Tyr Asp Pro Ile Asn
            275                 280                 285

Glu Tyr Leu Arg Lys Tyr Asp Gly Glu Ile Ile Pro Asn Ile Gly Gly
        290                 295                 300

Asp Leu Asp Lys Lys Ser Lys Lys Ala Leu Glu Lys Ile Glu Asn Gln
305                 310                 315                 320

Ile Lys Asn Leu Asp Ala Ala Leu Gln Lys Ser Lys Ile Thr Glu Asn
                325                 330                 335

Leu Ile Val Tyr Arg Arg Val Ser Glu Leu Gln Phe Gly Lys Lys Tyr
            340                 345                 350

Glu Asp Tyr Asn Leu Arg Gln Asn Gly Ile Ile Asn Glu Glu Lys Val
        355                 360                 365

Met Glu Leu Glu Ser Asn Phe Lys Gly Gln Thr Phe Ile Gln His Asn
    370                 375                 380

Tyr Met Ser Thr Ser Leu Val Gln Asp Pro His Gln Ser Tyr Ser Asn
385                 390                 395                 400

Asp Arg Tyr Pro Ile Leu Leu Glu Ile Thr Ile Pro Glu Gly Val His
                405                 410                 415

Gly Ala Tyr Ile Ala Asp Met Ser Glu Tyr Pro Gly Gln Tyr Glu Met
            420                 425                 430

Leu Ile Asn Arg Gly Tyr Thr Phe Lys Tyr Asp Lys Phe Ser Ile Val
        435                 440                 445

Lys Pro Thr Arg Glu Glu Asp Lys Gly Lys Glu Tyr Leu Lys Val Asn
    450                 455                 460

Leu Ser Ile Tyr Leu Gly Asn Leu Asn Arg Glu Lys
465                 470                 475

<210> SEQ ID NO 8
<211> LENGTH: 487
<212> TYPE: PRT
<213> ORGANISM: Enterococcus faecalis
<220> FEATURE:
<223> OTHER INFORMATION: strain V583

<400> SEQUENCE: 8

Met Ser Gln Leu Asn Lys Trp Gln Lys Glu Leu Gln Ala Leu Gln Lys
1               5                   10                  15

Ala Asn Tyr Gln Glu Thr Asp Asn Gln Leu Phe Asn Val Tyr Arg Gln
            20                  25                  30

Ser Leu Ile Asp Ile Lys Lys Arg Leu Lys Val Tyr Thr Glu Asn Ala
        35                  40                  45

Glu Ser Leu Ser Phe Ser Thr Arg Leu Glu Val Glu Arg Leu Phe Ser
    50                  55                  60

Val Ala Asp Glu Ile Asn Ala Ile Leu Gln Leu Asn Ser Pro Lys Val
65                  70                  75                  80

Glu Lys Thr Ile Lys Gly Tyr Ser Ala Lys Gln Ala Glu Gln Gly Tyr
                85                  90                  95

Tyr Gly Leu Trp Tyr Thr Leu Glu Gln Ser Gln Asn Ile Ala Leu Ser
            100                 105                 110

Met Pro Leu Ile Asn His Asp Tyr Ile Met Asn Leu Val Asn Ala Pro
        115                 120                 125

Val Ala Gly Lys Arg Leu Ser Lys Arg Leu Tyr Lys Tyr Arg Asp Glu
    130                 135                 140

Leu Ala Gln Asn Val Thr Asn Asn Ile Ile Thr Gly Leu Phe Glu Gly
145                 150                 155                 160
```

-continued

```
Lys Ser Tyr Ala Glu Ile Ala Arg Trp Ile Asn Glu Glu Thr Glu Ala
                165                 170                 175

Ser Tyr Lys Gln Ala Leu Arg Ile Ala Arg Thr Glu Ala Gly Arg Thr
            180                 185                 190

Gln Ser Val Thr Thr Gln Lys Gly Tyr Glu Glu Ala Lys Glu Leu Gly
        195                 200                 205

Ile Asn Ile Lys Lys Lys Trp Leu Ala Thr Ile Asp Lys His Thr Arg
    210                 215                 220

Arg Thr His Gln Glu Leu Asp Gly Lys Glu Val Asp Val Asp Glu Glu
225                 230                 235                 240

Phe Thr Ile Arg Gly His Ser Ala Lys Gly Pro Arg Met Phe Gly Val
                245                 250                 255

Ala Ser Glu Asp Val Asn Cys Arg Cys Thr Thr Ile Glu Val Val Asp
            260                 265                 270

Gly Ile Ser Pro Glu Leu Arg Lys Asp Asn Glu Ser Lys Glu Met Ser
        275                 280                 285

Glu Phe Lys Ser Tyr Asp Glu Trp Tyr Ala Asp Arg Ile Arg Gln Asn
    290                 295                 300

Glu Ser Lys Pro Lys Pro Asn Phe Thr Glu Leu Asp Phe Phe Gly Gln
305                 310                 315                 320

Ser Asp Leu Gln Asp Asp Ser Asp Lys Trp Val Ala Gly Leu Lys Pro
                325                 330                 335

Glu Gln Val Asn Ala Met Lys Asp Tyr Thr Ser Asp Ala Phe Ala Lys
            340                 345                 350

Met Asn Lys Ile Leu Arg Asn Glu Lys Tyr Asn Pro Arg Glu Lys Pro
        355                 360                 365

Tyr Leu Val Asn Ile Ile Gln Asn Leu Asp Asp Ala Ile Ser Lys Phe
    370                 375                 380

Lys Leu Lys His Asp Ile Ile Thr Tyr Arg Gly Val Ser Ala Asn Glu
385                 390                 395                 400

Tyr Asp Ala Ile Leu Asn Gly Asn Val Phe Lys Glu Phe Lys Ser Thr
                405                 410                 415

Ser Ile Asn Lys Lys Val Ala Glu Asp Phe Leu Asn Phe Thr Ser Ala
            420                 425                 430

Asn Lys Asp Gly Arg Val Val Lys Phe Leu Ile Pro Lys Gly Thr Gln
        435                 440                 445

Gly Ala Tyr Ile Gly Thr Asn Ser Ser Met Lys Lys Glu Ser Glu Phe
    450                 455                 460

Leu Leu Asn Arg Asn Leu Lys Tyr Thr Val Glu Ile Val Asp Asn Ile
465                 470                 475                 480

Leu Glu Val Thr Ile Leu Gly
                485

<210> SEQ ID NO 9
<211> LENGTH: 457
<212> TYPE: PRT
<213> ORGANISM: Pseudomonas aeruginosa

<400> SEQUENCE: 9

Met His Ile Gln Ser Ser Gln Gln Asn Pro Ser Phe Val Ala Glu Leu
1               5                   10                  15

Ser Gln Ala Val Ala Gly Arg Leu Gly Gln Val Glu Ala Arg Gln Val
            20                  25                  30

Ala Thr Pro Arg Glu Ala Gln Gln Leu Ala Gln Arg Gln Glu Ala Pro
        35                  40                  45
```

```
Lys Gly Glu Gly Leu Leu Ser Arg Leu Gly Ala Ala Leu Ala Arg Pro
 50                  55                  60

Phe Val Ala Ile Ile Glu Trp Leu Gly Lys Leu Leu Gly Ser Arg Ala
 65                  70                  75                  80

His Ala Ala Thr Gln Ala Pro Leu Ser Arg Gln Asp Ala Pro Pro Ala
                 85                  90                  95

Ala Ser Leu Ser Ala Ala Glu Ile Lys Gln Met Met Leu Gln Lys Ala
                100                 105                 110

Leu Pro Leu Thr Leu Gly Gly Leu Gly Lys Ala Ser Glu Leu Ala Thr
            115                 120                 125

Leu Thr Ala Glu Arg Leu Ala Lys Asp His Thr Arg Leu Ala Ser Gly
130                 135                 140

Asp Gly Ala Leu Arg Ser Leu Ala Thr Ala Leu Val Gly Ile Arg Asp
145                 150                 155                 160

Gly Ser Leu Ile Glu Ala Ser Arg Thr Gln Ala Ala Arg Leu Leu Glu
                165                 170                 175

Gln Ser Val Gly Gly Ile Ala Leu Gln Gln Trp Gly Thr Ala Gly Gly
            180                 185                 190

Ala Ala Ser Gln His Val Leu Ser Ala Ser Pro Glu Gln Leu Arg Glu
            195                 200                 205

Ile Ala Val Gln Leu His Ala Val Met Asp Lys Val Ala Leu Leu Arg
210                 215                 220

His Ala Val Glu Ser Glu Val Lys Gly Glu Pro Val Asp Lys Ala Leu
225                 230                 235                 240

Ala Asp Gly Leu Val Glu His Phe Gly Leu Glu Ala Glu Gln Tyr Leu
                245                 250                 255

Gly Glu His Pro Asp Gly Pro Tyr Ser Asp Ala Glu Val Met Ala Leu
            260                 265                 270

Gly Leu Tyr Thr Asn Gly Glu Tyr Gln His Leu Asn Arg Ser Leu Arg
        275                 280                 285

Gln Gly Arg Glu Leu Asp Ala Gly Gln Ala Leu Ile Asp Arg Gly Met
290                 295                 300

Ser Ala Ala Phe Glu Lys Ser Gly Pro Ala Glu Gln Val Val Lys Thr
305                 310                 315                 320

Phe Arg Gly Thr Gln Gly Arg Asp Ala Phe Glu Ala Val Lys Glu Gly
                325                 330                 335

Gln Val Gly His Asp Ala Gly Tyr Leu Ser Thr Ser Arg Asp Pro Ser
            340                 345                 350

Val Ala Arg Ser Phe Ala Gly Leu Gly Thr Ile Thr Thr Leu Phe Gly
            355                 360                 365

Arg Ser Gly Ile Asp Val Ser Glu Ile Ser Ile Glu Gly Asp Glu Gln
370                 375                 380

Glu Ile Leu Tyr Asp Lys Gly Thr Asp Met Arg Val Leu Leu Ser Ala
385                 390                 395                 400

Lys Asp Gly Gln Gly Val Thr Arg Arg Val Leu Glu Glu Ala Thr Leu
                405                 410                 415

Gly Glu Arg Ser Gly His Ser Glu Gly Leu Leu Asp Ala Leu Asp Leu
            420                 425                 430

Ala Thr Gly Thr Asp Arg Ser Gly Lys Pro Gln Glu Gln Asp Leu Arg
            435                 440                 445

Leu Arg Met Arg Gly Leu Asp Leu Ala
450                 455
```

-continued

<210> SEQ ID NO 10
<211> LENGTH: 265
<212> TYPE: PRT
<213> ORGANISM: Unknown
<220> FEATURE:
<223> OTHER INFORMATION: Description of Unknown:
CdtB toxin sequence

<400> SEQUENCE: 10

```
Met Lys Lys Ile Ile Cys Leu Phe Leu Ser Phe Asn Leu Ala Phe Ala
1               5                   10                  15

Asn Leu Glu Asn Phe Asn Val Gly Thr Trp Asn Leu Gln Gly Ser Ser
            20                  25                  30

Ala Ala Thr Glu Ser Lys Trp Ser Val Ser Val Arg Gln Leu Val Ser
        35                  40                  45

Gly Ala Asn Pro Leu Asp Ile Leu Met Ile Gln Glu Ala Gly Thr Leu
    50                  55                  60

Pro Arg Thr Ala Thr Pro Thr Gly Arg His Val Gln Gln Gly Gly Thr
65                  70                  75                  80

Pro Ile Asp Glu Tyr Glu Trp Asn Leu Gly Thr Leu Ser Arg Pro Asp
                85                  90                  95

Arg Val Phe Ile Tyr Tyr Ser Arg Val Asp Val Gly Ala Asn Arg Val
            100                 105                 110

Asn Leu Ala Ile Val Ser Arg Met Gln Ala Glu Glu Val Ile Val Leu
        115                 120                 125

Pro Pro Pro Thr Thr Val Ser Arg Pro Ile Ile Gly Ile Arg Asn Gly
    130                 135                 140

Asn Asp Ala Phe Phe Asn Ile His Ala Leu Ala Asn Gly Gly Thr Asp
145                 150                 155                 160

Val Gly Ala Ile Ile Thr Ala Val Asp Ala His Phe Ala Asn Met Pro
                165                 170                 175

Gln Val Asn Trp Met Ile Ala Gly Asp Phe Asn Arg Asp Pro Ser Thr
            180                 185                 190

Ile Thr Ser Thr Val Asp Arg Glu Leu Ala Asn Arg Ile Arg Val Val
        195                 200                 205

Phe Pro Thr Ser Ala Thr Gln Ala Ser Gly Gly Thr Leu Asp Tyr Ala
    210                 215                 220

Ile Thr Gly Asn Ser Asn Arg Gln Gln Thr Tyr Thr Pro Pro Leu Leu
225                 230                 235                 240

Ala Ala Ile Leu Met Leu Ala Ser Leu Arg Ser His Ile Val Ser Asp
                245                 250                 255

His Phe Pro Val Asn Phe Arg Lys Phe
            260                 265
```

<210> SEQ ID NO 11
<211> LENGTH: 560
<212> TYPE: PRT
<213> ORGANISM: Corynebacterium diphtheriae

<400> SEQUENCE: 11

```
Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45
```

```
Lys Pro Gly Tyr Val Asp Ser Ile Gln Lys Gly Ile Gln Lys Pro Lys
        50                  55                  60

Ser Gly Thr Gln Gly Asn Tyr Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
                100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
                260                 265                 270

Glu Glu Phe His Gln Thr Ala Leu Glu His Pro Glu Leu Ser Glu Leu
            275                 280                 285

Lys Thr Val Thr Gly Thr Asn Pro Val Phe Ala Gly Ala Asn Tyr Ala
    290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
        355                 360                 365

Ile Pro Leu Val Gly Glu Leu Val Asp Ile Gly Phe Ala Ala Tyr Asn
    370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Leu His
                405                 410                 415

Asp Gly Tyr Ala Val Ser Trp Asn Thr Val Glu Asp Ser Ile Ile Arg
            420                 425                 430

Thr Gly Phe Gln Gly Glu Ser Gly His Asp Ile Lys Ile Thr Ala Glu
        435                 440                 445

Asn Thr Pro Leu Pro Ile Ala Gly Val Leu Leu Pro Thr Ile Pro Gly
    450                 455                 460

Lys Leu Asp Val Asn Lys Ser Lys Thr His Ile Ser Val Asn Gly Arg
```

```
               465                 470                 475                 480
Lys Ile Arg Met Arg Cys Arg Ala Ile Asp Gly Asp Val Thr Phe Cys
                485                 490                 495

Arg Pro Lys Ser Pro Val Tyr Val Gly Asn Gly Val His Ala Asn Leu
                500                 505                 510

His Val Ala Phe His Arg Ser Ser Glu Lys Ile His Ser Asn Glu
                515                 520                 525

Ile Ser Ser Asp Ser Ile Gly Val Leu Gly Tyr Gln Lys Thr Val Asp
                530                 535                 540

His Thr Lys Val Asn Ser Lys Leu Ser Leu Phe Phe Glu Ile Lys Ser
545                 550                 555                 560

<210> SEQ ID NO 12
<211> LENGTH: 621
<212> TYPE: PRT
<213> ORGANISM: Unknown
<220> FEATURE:
<223> OTHER INFORMATION: Description of Unknown:
      ExoU/VipB toxin sequence

<400> SEQUENCE: 12

Met Lys Leu Ala Glu Ile Met Thr Lys Ser Arg Lys Leu Lys Arg Asn
1               5                   10                  15

Leu Leu Glu Ile Ser Lys Thr Glu Ala Gly Gln Tyr Ser Val Ser Ala
                20                  25                  30

Pro Glu His Lys Gly Leu Val Leu Ser Gly Gly Ala Lys Gly Ile
                35                  40                  45

Ser Tyr Leu Gly Met Ile Gln Ala Leu Gln Glu Arg Gly Lys Ile Lys
        50                  55                  60

Asn Leu Thr His Val Ser Gly Ala Ser Ala Gly Ala Met Thr Ala Ser
65                  70                  75                  80

Ile Leu Ala Val Gly Met Asp Ile Lys Asp Ile Lys Lys Leu Ile Glu
                85                  90                  95

Gly Leu Asp Ile Thr Lys Leu Leu Asp Asn Ser Gly Val Gly Phe Arg
                100                 105                 110

Ala Arg Gly Asp Arg Phe Arg Asn Ile Leu Asp Val Ile Tyr Met Met
                115                 120                 125

Gln Met Lys Lys His Leu Glu Ser Val Gln Gln Pro Ile Pro Pro Glu
                130                 135                 140

Gln Gln Met Asn Tyr Gly Ile Leu Lys Gln Lys Ile Ala Leu Tyr Glu
145                 150                 155                 160

Asp Lys Leu Ser Arg Ala Gly Ile Val Ile Asn Asn Val Asp Asp Ile
                165                 170                 175

Ile Asn Leu Thr Lys Ser Val Lys Asp Leu Glu Lys Leu Asp Lys Ala
                180                 185                 190

Leu Asn Ser Ile Pro Thr Glu Leu Lys Gly Ala Lys Gly Glu Gln Leu
                195                 200                 205

Glu Asn Pro Arg Leu Thr Leu Gly Asp Leu Gly Arg Leu Arg Glu Leu
                210                 215                 220

Leu Pro Glu Glu Asn Lys His Leu Ile Lys Asn Leu Ser Val Val
225                 230                 235                 240

Thr Asn Gln Thr Lys His Glu Leu Glu Arg Tyr Ser Glu Asp Thr Thr
                245                 250                 255

Pro Gln Gln Ser Ile Ala Gln Val Val Gln Trp Ser Gly Ala His Pro
                260                 265                 270
```

-continued

```
Val Leu Phe Val Pro Gly Arg Asn Ala Lys Gly Glu Tyr Ile Ala Asp
            275                 280                 285

Gly Gly Ile Leu Asp Asn Met Pro Glu Ile Glu Gly Leu Asp Arg Glu
        290                 295                 300

Glu Val Leu Cys Val Lys Ala Glu Ala Gly Thr Ala Phe Glu Asp Arg
305                 310                 315                 320

Val Asn Lys Ala Lys Gln Ser Ala Met Glu Ala Ile Ser Trp Phe Lys
                325                 330                 335

Ala Arg Met Asp Ser Leu Val Glu Ala Thr Ile Gly Gly Lys Trp Leu
            340                 345                 350

His Ala Thr Ser Ser Val Leu Asn Arg Glu Lys Val Tyr Tyr Asn Ile
        355                 360                 365

Asp Asn Met Ile Tyr Ile Asn Thr Gly Glu Val Thr Thr Asn Thr
    370                 375                 380

Ser Pro Thr Pro Glu Gln Arg Ala Arg Ala Val Lys Asn Gly Tyr Asp
385                 390                 395                 400

Gln Thr Met Gln Leu Leu Asp Ser His Lys Gln Thr Phe Asp His Pro
                405                 410                 415

Leu Met Ala Ile Leu Tyr Ile Gly His Asp Lys Leu Lys Asp Ala Leu
            420                 425                 430

Ile Asp Glu Lys Ser Glu Lys Glu Ile Phe Glu Ala Ser Ala His Ala
        435                 440                 445

Gln Ala Ile Leu His Leu Gln Glu Gln Ile Val Lys Glu Met Asn Asp
    450                 455                 460

Gly Asp Tyr Ser Ser Val Gln Asn Tyr Leu Asp Gln Ile Glu Asp Ile
465                 470                 475                 480

Leu Thr Val Asp Ala Lys Met Asp Asp Ile Gln Lys Glu Lys Ala Phe
                485                 490                 495

Ala Leu Cys Ile Lys Gln Val Asn Phe Leu Ser Glu Gly Lys Leu Glu
            500                 505                 510

Thr Tyr Leu Asn Lys Val Glu Ala Glu Lys Ala Ala Ala Glu Pro
        515                 520                 525

Ser Trp Ala Thr Lys Ile Leu Asn Leu Leu Trp Ala Pro Ile Glu Trp
    530                 535                 540

Val Val Ser Leu Phe Lys Gly Pro Ala Gln Asp Phe Lys Val Glu Val
545                 550                 555                 560

Gln Pro Glu Pro Val Lys Val Ser Thr Ser Glu Asn Gln Glu Thr Val
                565                 570                 575

Ser Asn Gln Lys Asp Ile Asn Pro Ala Val Glu Tyr Arg Lys Ile Ile
            580                 585                 590

Ala Glu Val Arg Arg Glu His Thr Asp Pro Ser Pro Ser Leu Gln Glu
        595                 600                 605

Lys Glu Arg Val Gly Leu Ser Thr Thr Phe Gly Gly His
    610                 615                 620

<210> SEQ ID NO 13
<211> LENGTH: 211
<212> TYPE: PRT
<213> ORGANISM: Pseudomonas syringae

<400> SEQUENCE: 13

Met Asn Arg Val Ser Gly Ser Ser Ser Ala Thr Trp Gln Ala Val Asn
1               5                   10                  15

Asp Leu Val Glu Gln Val Ser Glu Arg Thr Thr Leu Ser Thr Thr Gly
            20                  25                  30
```

Tyr Gln Thr Ala Met Gly Arg Leu Asn Lys Pro Glu Lys Ser Asp Ala
            35                  40                  45

Asp Ala Leu Met Thr Met Arg Ala Gln Gln Tyr Thr Asp Ser Ala
    50                  55                  60

Lys Arg Thr Tyr Ile Ser Glu Thr Leu Met Asn Leu Ala Asp Leu Gln
65                  70                  75                  80

Gln Arg Lys Ile Tyr Arg Thr Asn Ser Gly Asn Leu Arg Gly Ala Ile
                85                  90                  95

Glu Met Thr Pro Thr Gln Leu Thr Asp Cys Val Gln Lys Cys Arg Glu
            100                 105                 110

Glu Gly Phe Ser Asn Cys Asp Ile Gln Ala Leu Glu Ile Gly Leu His
        115                 120                 125

Leu Arg His Lys Leu Gly Ile Ser Asp Phe Thr Ile Tyr Ser Asn Arg
    130                 135                 140

Lys Leu Ser His Asn Tyr Val Val Ile His Pro Ser Asn Ala Phe Pro
145                 150                 155                 160

Lys Gly Ala Ile Val Asp Ser Trp Thr Gly Gln Gly Val Val Glu Leu
                165                 170                 175

Asp Phe Lys Thr Arg Leu Lys Phe Lys His Arg Glu Glu Asn Tyr Ala
            180                 185                 190

Val Asn Ala Asn Met His Glu Trp Ile Glu Arg Tyr Gly Gln Ala His
        195                 200                 205

Val Ile Asp
    210

<210> SEQ ID NO 14
<211> LENGTH: 204
<212> TYPE: PRT
<213> ORGANISM: Pseudomonas syringae

<400> SEQUENCE: 14

Met Gly Asn Ile Cys Gly Thr Ser Gly Ser Arg His Val Tyr Ser Pro
1               5                   10                  15

Ser His Thr Gln Arg Ile Thr Ser Ala Pro Ser Thr Ser Thr His Val
            20                  25                  30

Gly Gly Asp Thr Leu Thr Ser Ile His Gln Leu Ser His Ser Gln Arg
        35                  40                  45

Glu Gln Phe Leu Asn Met His Asp Pro Met Arg Val Met Gly Leu Asp
    50                  55                  60

His Asp Thr Glu Leu Phe Arg Thr Thr Asp Ser Arg Tyr Ile Lys Asn
65                  70                  75                  80

Asp Lys Leu Ala Gly Asn Pro Gln Ser Met Ala Ser Ile Leu Met His
                85                  90                  95

Glu Glu Leu Arg Pro Asn Arg Phe Ala Ser His Thr Gly Ala Gln Pro
            100                 105                 110

His Glu Ala Arg Ala Tyr Val Pro Lys Arg Ile Lys Ala Thr Asp Leu
        115                 120                 125

Gly Val Pro Ser Leu Asn Val Met Thr Gly Ser Leu Ala Arg Asp Gly
    130                 135                 140

Ile Arg Ala Tyr Asp His Met Ser Asp Asn Gln Val Ser Val Lys Met
145                 150                 155                 160

Arg Leu Gly Asp Phe Leu Glu Arg Gly Gly Lys Val Tyr Ala Asp Ala
                165                 170                 175

Ser Ser Val Ala Asp Asp Gly Glu Thr Ser Gln Ala Leu Ile Val Thr

```
                180              185              190
Leu Pro Lys Gly Gln Lys Val Pro Val Glu Arg Val
            195                 200
```

<210> SEQ ID NO 15
<211> LENGTH: 493
<212> TYPE: PRT
<213> ORGANISM: Pseudomonas syringae

<400> SEQUENCE: 15

```
Met Gln Ile Lys Asn Ser His Leu Tyr Ser Ala Ser Arg Met Val Gln
1               5                   10                  15

Asn Thr Phe Asn Ala Ser Pro Lys Met Glu Val Thr Asn Ala Ile Ala
            20                  25                  30

Lys Asn Asn Glu Pro Ala Ala Leu Ser Ala Thr Gln Thr Ala Lys Thr
            35                  40                  45

His Glu Gly Asp Ser Lys Gly Gln Ser Ser Asn Asn Ser Lys Leu Pro
        50                  55                  60

Phe Arg Ala Met Arg Tyr Ala Ala Tyr Leu Ala Gly Ser Ala Tyr Leu
65                  70                  75                  80

Tyr Asp Lys Thr Ala Asn Asn Phe Phe Leu Ser Thr Thr Ser Leu His
                85                  90                  95

Asp Gly Lys Gly Gly Phe Thr Ser Asp Ala Arg Leu Asn Asp Ala Gln
            100                 105                 110

Asp Lys Ala Arg Lys Arg Tyr Gln Asn Asn His Ser Ser Thr Leu Glu
            115                 120                 125

Asn Lys Asn Ser Leu Leu Ser Pro Leu Arg Leu Cys Gly Glu Asn Gln
        130                 135                 140

Phe Leu Thr Met Ile Asp Tyr Arg Ala Ala Thr Lys Ile Tyr Leu Ser
145                 150                 155                 160

Asp Leu Val Asp Thr Glu Gln Ala His Thr Ser Ile Leu Lys Asn Ile
                165                 170                 175

Met Cys Leu Lys Gly Glu Leu Thr Asn Glu Ala Ile Lys Lys Leu
            180                 185                 190

Asn Pro Glu Lys Thr Pro Lys Asp Tyr Asp Leu Thr Asn Ser Glu Ala
            195                 200                 205

Tyr Ile Ser Lys Asn Lys Tyr Ser Leu Thr Gly Val Lys Asn Glu Glu
        210                 215                 220

Thr Gly Ser Thr Gly Tyr Thr Ser Arg Ser Ile Thr Lys Pro Phe Val
225                 230                 235                 240

Glu Lys Gly Leu Lys His Phe Ile Lys Ala Thr His Gly Glu Lys Ala
                245                 250                 255

Leu Thr Pro Lys Gln Cys Met Glu Thr Leu Asp Asn Leu Leu Arg Lys
            260                 265                 270

Ser Ile Thr Leu Asn Ser Asp Ser Gln Phe Ala Ala Gly Gln Ala Leu
        275                 280                 285

Leu Val Phe Arg Gln Val Tyr Ala Gly Glu Asp Ala Trp Gly Asp Ala
    290                 295                 300

Glu Arg Val Ile Leu Lys Ser His Tyr Asn Arg Gly Thr Val Leu Gln
305                 310                 315                 320

Asp Glu Ala Asp Lys Ile Glu Leu Ser Arg Pro Phe Ser Glu Gln Asp
                325                 330                 335

Leu Ala Lys Asn Met Phe Lys Arg Asn Thr Ser Ile Ala Gly Pro Val
            340                 345                 350
```

```
Leu Tyr His Ala Tyr Ile Tyr Ile Gln Glu Lys Ile Phe Lys Leu Pro
            355                 360                 365

Pro Asp Lys Ile Glu Asp Leu Lys His Lys Ser Met Ala Asp Leu Lys
        370                 375                 380

Asn Leu Pro Leu Thr His Val Lys Leu Ser Asn Ser Gly Val Gly Phe
385                 390                 395                 400

Glu Asp Ala Ser Gly Leu Gly Asp Ser Phe Thr Ala Leu Asn Ala Thr
                405                 410                 415

Ser Cys Val Asn His Ala Arg Ile Met Ser Gly Glu Pro Pro Leu Ser
                420                 425                 430

Lys Asp Asp Val Val Ile Leu Ile Gly Cys Leu Asn Ala Val Tyr Asp
        435                 440                 445

Asn Ser Ser Gly Ile Arg His Ser Leu Arg Glu Ile Ala Arg Gly Cys
450                 455                 460

Phe Val Gly Ala Gly Phe Thr Val Gln Asp Gly Asp Asp Phe Tyr Lys
465                 470                 475                 480

Gln Ile Cys Lys Asn Ala Ser Lys Gln Phe Tyr Asn Gly
                485                 490

<210> SEQ ID NO 16
<211> LENGTH: 530
<212> TYPE: PRT
<213> ORGANISM: Vibrio cholerae

<400> SEQUENCE: 16

Met Phe Lys Ile Ser Val Ser Gln Gln Ala Asn Val Met Ser Thr Ser
1               5                   10                  15

Asp Thr Ala Gln Arg Ser Ser Leu Lys Ile Ser Ile Lys Ser Ile Cys
            20                  25                  30

Asn Lys Ser Leu Ser Lys Lys Leu His Thr Leu Ala Glu Lys Cys Arg
        35                  40                  45

Arg Phe Ser Gln Glu Leu Lys Glu His Thr Ala Ser Lys Lys Gln Ile
    50                  55                  60

Val Glu Gln Ala Thr Thr Thr Val Arg Glu Ser Ser Leu Thr Lys Ser
65                  70                  75                  80

Asp Ser Glu Leu Gly Ser Ser Arg Ser Leu Leu Thr Ser Asp Val Leu
                85                  90                  95

Ser Ser Ser Ser His Glu Asp Leu Thr Ala Val Asn Leu Glu Asp
            100                 105                 110

Asn Asp Ser Val Phe Val Thr Ile Glu Ser Ser Glu Leu Ile Val
        115                 120                 125

Lys Gln Asp Gly Ser Ile Pro Pro Ala Pro Pro Leu Pro Gly Asn Ile
130                 135                 140

Pro Pro Ala Pro Pro Leu Pro Ser Ala Gly Asn Ile Pro Thr Ala Pro
145                 150                 155                 160

Gly Leu Pro Lys Gln Lys Ala Thr Thr Glu Ser Val Ala Gln Thr Ser
                165                 170                 175

Asp Asn Arg Ser Lys Leu Met Glu Glu Ile Arg Gln Gly Val Lys Leu
            180                 185                 190

Arg Ala Thr Pro Lys Ser Ser Thr Glu Lys Ser Ala Ser Asp Pro
        195                 200                 205

His Ser Lys Leu Met Lys Glu Leu Ile Asn His Gly Ala Lys Leu Lys
    210                 215                 220

Lys Val Ser Thr Ser Asp Ile Pro Val Pro Pro Pro Leu Pro Ala Ala
225                 230                 235                 240
```

```
Phe Ala Ser Lys Pro Thr Asp Gly Arg Ser Ala Leu Leu Ser Glu Ile
            245                 250                 255

Ala Gly Phe Ser Lys Asp Arg Leu Arg Lys Ala Gly Ser Ser Glu Thr
        260                 265                 270

Leu Asn Val Ser Gln Pro Thr Val Ala Glu Ser Ser Ile Pro Glu Ala
    275                 280                 285

Tyr Asp Leu Leu Leu Ser Asp Glu Met Phe Asn Leu Ser Pro Lys Leu
290                 295                 300

Ser Glu Thr Glu Leu Asn Thr Leu Ala Asp Ser Leu Ala Asp Tyr Leu
305                 310                 315                 320

Phe Lys Ala Ala Asp Ile Asp Trp Met Gln Val Ile Ala Glu Gln Thr
                325                 330                 335

Lys Gly Ser Thr Gln Ala Thr Ser Leu Lys Ser Gln Leu Glu Gln Ala
            340                 345                 350

Pro Glu Tyr Val Lys Ala Phe Cys Asp Glu Ile Leu Lys Phe Pro Asp
        355                 360                 365

Cys Tyr Lys Ser Ala Asp Val Ala Ser Pro Glu Ser Pro Lys Ala Gly
    370                 375                 380

Pro Ser Ser Val Ile Asp Val Ala Leu Lys Arg Leu Gln Ala Gly Arg
385                 390                 395                 400

Asn Arg Leu Phe Ser Thr Ile Asp Ala Lys Gly Thr Asn Glu Leu Lys
                405                 410                 415

Lys Gly Glu Ala Ile Leu Glu Ser Ala Ile Asn Ala Ala Arg Ser Val
            420                 425                 430

Met Thr Ala Glu Gln Lys Ser Ala Leu Leu Ser Ser Asn Val Lys Ser
                435                 440                 445

Ala Thr Phe Lys Val Phe Ser Glu Leu Pro Cys Met Glu Gly Phe Ala
    450                 455                 460

Glu Gln Asn Gly Lys Ala Ala Phe Asn Ala Leu Arg Leu Ala Phe Tyr
465                 470                 475                 480

Ser Ser Ile Gln Ser Gly Asp Thr Ala Gln Gln Asp Ile Ala Arg Phe
                485                 490                 495

Met Lys Glu Asn Leu Ala Thr Gly Phe Ser Gly Tyr Ser Tyr Leu Gly
            500                 505                 510

Leu Thr Ser Arg Val Ala Gln Leu Glu Ala Gln Leu Ala Ala Leu Thr
                515                 520                 525

Thr Lys
    530

<210> SEQ ID NO 17
<211> LENGTH: 288
<212> TYPE: PRT
<213> ORGANISM: Unknown
<220> FEATURE:
<223> OTHER INFORMATION: Description of Unknown:
      YopJ toxin sequence

<400> SEQUENCE: 17

Met Ile Gly Pro Ile Ser Gln Ile Asn Ile Ser Gly Gly Leu Ser Glu
1               5                   10                  15

Lys Glu Thr Ser Ser Leu Ile Ser Asn Glu Leu Lys Asn Ile Ile
            20                  25                  30

Thr Gln Leu Glu Thr Asp Ile Ser Asp Gly Ser Trp Phe His Lys Asn
        35                  40                  45

Tyr Ser Arg Met Asp Val Glu Val Met Pro Ala Leu Val Ile Gln Ala
```

```
                50                  55                  60
Asn Asn Lys Tyr Pro Glu Met Asn Leu Asn Leu Val Thr Ser Pro Leu
 65                  70                  75                  80

Asp Leu Ser Ile Glu Ile Lys Asn Val Ile Glu Asn Gly Val Arg Ser
                 85                  90                  95

Ser Arg Phe Ile Ile Asn Met Gly Glu Gly Ile His Phe Ser Val
            100                 105                 110

Ile Asp Tyr Lys His Ile Asn Gly Lys Thr Ser Leu Ile Leu Phe Glu
            115                 120                 125

Pro Ala Asn Phe Asn Ser Met Gly Pro Ala Met Leu Ala Ile Arg Thr
130                 135                 140

Lys Thr Ala Ile Glu Arg Tyr Gln Leu Pro Asp Cys His Phe Ser Met
145                 150                 155                 160

Val Glu Met Asp Ile Gln Arg Ser Ser Glu Cys Gly Ile Phe Ser
                165                 170                 175

Phe Ala Leu Ala Lys Lys Leu Tyr Ile Glu Arg Asp Ser Leu Leu Lys
            180                 185                 190

Ile His Glu Asp Asn Ile Lys Gly Ile Leu Ser Asp Gly Glu Asn Pro
            195                 200                 205

Leu Pro His Asp Lys Leu Asp Pro Tyr Leu Pro Val Thr Phe Tyr Lys
    210                 215                 220

His Thr Gln Gly Lys Lys Arg Leu Asn Glu Tyr Leu Asn Thr Asn Pro
225                 230                 235                 240

Gln Gly Val Gly Thr Val Val Asn Lys Lys Asn Glu Thr Ile Val Asn
                245                 250                 255

Arg Phe Asp Asn Asn Lys Ser Ile Val Asp Gly Lys Glu Leu Ser Val
            260                 265                 270

Ser Val His Lys Lys Arg Ile Ala Glu Tyr Lys Thr Leu Leu Lys Val
            275                 280                 285

<210> SEQ ID NO 18
<211> LENGTH: 579
<212> TYPE: PRT
<213> ORGANISM: Pseudomonas sp.

<400> SEQUENCE: 18

Met Ala Gly Ile Asn Gly Ala Gly Pro Ser Gly Ala Tyr Phe Val Gly
 1               5                  10                  15

His Thr Asp Pro Glu Pro Ala Ser Gly Gly Ala His Gly Ser Ser Ser
                 20                  25                  30

Gly Ala Ser Ser Ser Asn Ser Pro Arg Leu Pro Ala Pro Asp Ala
             35                  40                  45

Pro Ala Ser Gln Ala Arg Asp Arg Arg Glu Met Leu Leu Arg Ala Arg
     50                  55                  60

Pro Leu Ser Arg Gln Thr Arg Glu Trp Val Ala Gln Gly Met Pro Pro
65                   70                  75                  80

Thr Ala Glu Ala Gly Val Pro Ile Arg Pro Gln Glu Ser Ala Glu Ala
                85                  90                  95

Ala Ala Pro Gln Ala Arg Ala Glu Glu Arg His Thr Pro Glu Ala Asp
            100                 105                 110

Ala Ala Ala Ser His Val Arg Thr Glu Gly Gly Arg Thr Pro Gln Ala
            115                 120                 125

Leu Ala Gly Thr Ser Pro Arg His Thr Gly Ala Val Pro His Ala Asn
    130                 135                 140
```

```
Arg Ile Val Gln Gln Leu Val Asp Ala Gly Ala Asp Leu Ala Gly Ile
145                 150                 155                 160

Asn Thr Met Ile Asp Asn Ala Met Arg Arg His Ala Ile Ala Leu Pro
                165                 170                 175

Ser Arg Thr Val Gln Ser Ile Leu Ile Glu His Phe Pro His Leu Leu
            180                 185                 190

Ala Gly Glu Leu Ile Ser Gly Ser Glu Leu Ala Thr Ala Phe Arg Ala
        195                 200                 205

Ala Leu Arg Arg Glu Val Arg Gln Gln Glu Ala Ser Ala Pro Pro Arg
    210                 215                 220

Thr Ala Ala Arg Ser Ser Val Arg Thr Pro Glu Arg Ser Thr Val Pro
225                 230                 235                 240

Pro Thr Ser Thr Glu Ser Ser Ser Gly Ser Asn Gln Arg Thr Leu Leu
                245                 250                 255

Gly Arg Phe Ala Gly Leu Met Thr Pro Asn Gln Arg Arg Pro Ser Ser
            260                 265                 270

Ala Ser Asn Ala Ser Ala Ser Gln Arg Pro Val Asp Arg Ser Pro Pro
        275                 280                 285

Arg Val Asn Gln Val Pro Thr Gly Ala Asn Arg Val Val Met Arg Asn
    290                 295                 300

His Gly Asn Asn Glu Ala Asp Ala Ala Leu Gln Gly Leu Ala Gln Gln
305                 310                 315                 320

Gly Val Asp Met Glu Asp Leu Arg Ala Ala Leu Glu Arg His Ile Leu
                325                 330                 335

His Arg Arg Pro Ile Pro Met Asp Ile Ala Tyr Ala Leu Gln Gly Val
            340                 345                 350

Gly Ile Ala Pro Ser Ile Asp Thr Gly Glu Ser Leu Met Glu Asn Pro
        355                 360                 365

Leu Met Asn Leu Ser Val Ala Leu His Arg Ala Leu Gly Pro Arg Pro
    370                 375                 380

Ala Arg Ala Gln Ala Pro Arg Pro Ala Val Pro Val Ala Pro Ala Thr
385                 390                 395                 400

Val Ser Arg Arg Pro Asp Ser Ala Arg Ala Thr Arg Leu Gln Val Ile
                405                 410                 415

Pro Ala Arg Glu Asp Tyr Glu Asn Asn Val Ala Tyr Gly Val Arg Leu
            420                 425                 430

Leu Ser Leu Asn Pro Gly Ala Gly Val Arg Glu Thr Val Ala Ala Phe
        435                 440                 445

Val Asn Asn Arg Tyr Glu Arg Gln Ala Val Val Ala Asp Ile Arg Ala
    450                 455                 460

Ala Leu Asn Leu Ser Lys Gln Phe Asn Lys Leu Arg Thr Val Ser Lys
465                 470                 475                 480

Ala Asp Ala Ala Ser Asn Lys Pro Gly Phe Lys Asp Leu Ala Asp His
                485                 490                 495

Pro Asp Asp Ala Thr Gln Cys Leu Phe Gly Glu Leu Ser Leu Thr
            500                 505                 510

Ser Ser Val Gln Gln Val Ile Gly Leu Ala Gly Lys Ala Thr Asp Met
        515                 520                 525

Ser Glu Ser Tyr Ser Arg Glu Ala Asn Lys Asp Leu Val Phe Met Asp
    530                 535                 540

Met Lys Lys Leu Ala Gln Phe Leu Ala Gly Lys Pro Glu His Pro Met
545                 550                 555                 560

Thr Arg Glu Thr Leu Asn Ala Glu Asn Ile Ala Lys Tyr Ala Phe Arg
```

565                 570                 575

Ile Val Pro

<210> SEQ ID NO 19
<211> LENGTH: 1116
<212> TYPE: PRT
<213> ORGANISM: Unknown
<220> FEATURE:
<223> OTHER INFORMATION: Description of Unknown:
      SdbA toxin sequence

<400> SEQUENCE: 19

Met His Lys Lys Tyr Asn Tyr Tyr Ser Leu Glu Lys Glu Lys Lys Thr
1               5                   10                  15

Phe Trp Gln His Ile Leu Asp Ile Leu Lys Ala Pro Phe Arg Leu Pro
                20                  25                  30

Gly Trp Val Val Ser Phe Phe Leu Ala Arg Asn Ile Thr His Val Ala
            35                  40                  45

Leu Asn Pro Asn Asn Ile Pro Gln Gln Arg Leu Ile His Leu Thr Lys
        50                  55                  60

Thr Ser Asn Arg Pro Glu Asp Ile Val Val Ile Asn Phe Lys Lys
65                  70                  75                  80

Arg Pro Pro His Lys Trp Phe Asn Asp Thr Leu Ile Lys Ile Ala Asn
                85                  90                  95

Thr Ile Ala Ala Leu Pro Phe Val Thr Pro Arg Leu Arg Thr Arg Leu
            100                 105                 110

His Tyr Asp Asn Glu Asn Asp Ile Asn His Val Asn Lys Leu Leu Ala
        115                 120                 125

Glu Ile Asp Ala Leu Val Gln Gly Lys Ser Lys Gln Lys Tyr Cys Lys
    130                 135                 140

Gly Arg Ala Phe Asp Trp Ser Lys Ile His Leu Lys Gly Leu Glu Phe
145                 150                 155                 160

Leu Asp Pro Lys Met Arg Gly Tyr Val Tyr Glu Gln Leu His Glu Lys
                165                 170                 175

Tyr Gly Tyr Val Ser Tyr Thr Thr Lys Arg Lys Pro Asn Ile Glu Phe
            180                 185                 190

Phe Thr Leu Lys Thr Pro Asp Gly Ser Glu Leu Asp Ser Val Gln Val
        195                 200                 205

Thr Gly Glu Asp Glu Lys Lys Pro Met Gly Glu Arg Lys Phe Ile
    210                 215                 220

Ile Thr Cys Ile Ala Arg Asp Gln Asn Phe Ile Asn Trp Ile Lys Asp
225                 230                 235                 240

Leu Asn Tyr Thr Ala Lys Asn Leu Gly Ala Thr Ala Ile Ser Phe Asn
                245                 250                 255

Tyr Arg Gly Val Asp Tyr Ser Arg Gly Leu Val Trp Thr Glu Asn Asn
            260                 265                 270

Leu Val Asp Asp Ile Leu Ala Gln Val Gln Arg Leu Ile Ser Leu Gly
        275                 280                 285

Ala Asp Pro Lys Asn Ile Cys Leu Asp Gly Met Cys Ile Gly Gly Ala
    290                 295                 300

Val Ala Thr Ile Ala Ala Lys Leu His Lys Gly Met Lys Val
305                 310                 315                 320

Lys Leu Asn Asn Glu Arg Ser Phe Thr Ser Leu Ser Ser Leu Val Phe
                325                 330                 335

Gly Phe Ile Val Pro Glu Leu Gln Thr Ala Asn Trp Trp Ser Pro Leu

```
            340             345             350
Thr Tyr Gly Arg Phe Leu Leu Ala Gly Val Val Tyr Ala Leu Leu Thr
        355                 360             365
Pro Leu Ile Trp Leu Ala Gly Trp Pro Val Asp Val Thr Lys Ala Trp
    370                 375             380
Asn Arg Ile Pro Ala Gln Asp Lys Met Tyr Ser Val Val Arg Asp Lys
385                 390              395                 400
Asp Asn Gly Leu Tyr Asp Gly Val Ile His Asp His Phe Cys Ser Ile
                405                 410             415
Ala Ser Leu Val Asp Ser Gln Ile Asn Ser Ile Leu Tyr Lys Leu Ser
            420                 425             430
Thr Asp Gln Pro Leu Thr Glu Glu Lys Gln Ile Leu Cys Asp Asp
        435                 440             445
Gln Phe Ser His His Phe Lys Pro Ser Gln Ser Val Leu Lys Asn Pro
    450                 455             460
Lys Tyr Lys Gly Pro His Phe Ile Ser Arg Gln Asp Leu Val Ala Glu
465                 470              475                 480
Leu Gly His Arg Glu Glu Tyr Thr Asn His Asp Tyr Phe Leu Asp Arg
                485                 490             495
Leu Arg Glu Lys Phe Gln Leu Asp Arg Ala Thr Arg Pro Val Ala Leu
            500                 505             510
Ala Glu Asp Gly Glu Lys Asp Ile Asp Gly Ile Ser Ser Gln Leu Ser
        515                 520             525
Asn Asn Lys Glu Arg Pro Leu Ile Ile Ala Ser Ser Gly Thr Gly
    530                 535             540
His Ile Ser Ala Thr His Gly Ile Ile Asn Asp Leu Gln Ser Lys Thr
545                 550              555                 560
Asp Asn Val Val Ile Thr Gln His His Ala Glu Leu Tyr Lys Asn Lys
                565                 570             575
Pro Phe Ser Ile Thr Ser Val Leu Ile Arg Ile Gly Val Trp Phe Thr
            580                 585             590
Ser Leu Pro Ile Leu Glu Asp Ile Leu Lys Gly Val Met Arg Phe Ile
        595                 600             605
Gly Tyr Pro Val Leu Pro Ser Ser Ile Phe Trp Asp Gln Met Ser
    610                 615             620
Lys Ile Gln Gln Ser Glu Thr Lys Lys Glu Asn Gly Ile Glu Thr Gly
625                 630              635                 640
Arg Thr Arg Pro Tyr Val Asp Met Leu Leu Asp Ile Tyr Pro Glu Gly
                645                 650             655
Tyr Glu Tyr Thr Ala Phe Asn Asn Ala Thr His Leu Thr Ser Ser Ile
            660                 665             670
Glu Asp Ile Gln Thr Met Ile Ser Phe Lys Gly His Val Glu Glu Asp
        675                 680             685
Asn Arg Asn Ile Val Tyr Gln Asn Ile Leu Gln Arg Leu Met His Ala
    690                 695             700
Ala Lys Gln Asn Thr Pro Tyr Thr Arg Leu Ile Ser Thr Gln Ala Leu
705                 710              715                 720
Ser Leu Gly Ala Ile Cys Asp Ala Val Lys Tyr Asn Thr Val Phe
                725                 730             735
Leu Pro Val Tyr Asn Ala Glu Arg Gly Thr Ser Tyr Gln Pro Ile Ala
            740                 745             750
Ile Asp Gln Tyr Met Thr Asp Leu Pro Ser Leu Gly Cys Ile His Phe
        755                 760             765
```

Met Asn Asn Leu Glu Glu Leu Thr Ser Glu Gln Arg Gln Leu Met Glu
770 775 780

Ile His Ala Val Asn Met Ser Glu Pro Phe Lys Glu Ala His Phe Gly
785 790 795 800

Lys Glu Gln Gly Phe Lys Ala Val His Asn Ile Asp Pro Arg Asn Asn
805 810 815

Pro Met Ile Arg Asn Ala Phe Lys Asp Pro Ser Leu Thr Lys Tyr Leu
820 825 830

Asp Lys Thr Gln Ser Phe Asp Leu His Phe Asn Val Tyr Lys Lys Glu
835 840 845

Lys Gln Asn Ala Leu Pro Val Leu Asn Gly Lys Glu Lys Ile Thr Ile
850 855 860

Lys Pro His Ala Lys Ile Ala Ser Ile Met Ile Gly Ser Leu Ala Ala
865 870 875 880

Asn Ala Ser Ala Asp Tyr Ala Lys Tyr Leu Leu Asn Gln Gly Tyr Glu
885 890 895

His Ile Phe Leu Phe Gly Gly Leu Asn Asp Ser Ile Ala Ala Arg Ile
900 905 910

Asp Gln Ile Ile Asn Ser Tyr Pro Ala Pro Thr Arg Asp Glu Ile Arg
915 920 925

Lys Lys Ile Ile Leu Leu Gly Asn Gln Ser Asp Val Glu Met Ala Pro
930 935 940

Ile Met Thr Arg Ser Asn Cys Val Val Ile Arg Gly Gly Gly Leu Ser
945 950 955 960

Val Met Glu Gln Met Ala Met Pro Ile Met Asp Asp Lys Ile Val Leu
965 970 975

Leu His His Glu Asp Asn Glu Glu Gly Pro Leu Thr Ser Gly Leu Ser
980 985 990

Trp Glu Asp Gly Asn Ser Asp Lys Leu Ile Glu Tyr Leu Ser Glu Lys
995 1000 1005

Gly Ala Tyr Ala Lys Lys Thr Ser Pro Gly Leu Cys Ser Gly His
1010 1015 1020

Leu His Glu Ala Glu Lys Ser Phe Glu Lys Lys Tyr His Gly Gln
1025 1030 1035

Leu Lys Ser Thr Glu Thr Lys Lys Lys Val Asp Leu Thr Ile Pro
1040 1045 1050

Gln Gln Glu Thr Tyr Ser Leu Lys Lys Glu Trp Asp Arg Lys Thr
1055 1060 1065

Gly Tyr Thr Glu Ser Gly His Ile Leu Ser His Gln His Arg Phe
1070 1075 1080

Phe Asn Thr Ile Pro Glu Val Arg Glu Pro Phe Cys Ser Lys Glu
1085 1090 1095

Asp Leu His His Asn Glu Leu Ser Ser Gln Ser Leu Val Ser Val
1100 1105 1110

Ser Ala Gly
1115

<210> SEQ ID NO 20
<211> LENGTH: 965
<212> TYPE: PRT
<213> ORGANISM: Legionella pneumophila

<400> SEQUENCE: 20

Met Ser Arg Ser Lys Asp Glu Val Leu Glu Ala Asn Asp Ser Leu Phe

-continued

```
1               5                   10                  15
Gly Ile Thr Val Gln Thr Trp Gly Thr Asn Asp Arg Pro Ser Asn Gly
                20                  25                  30

Met Met Asn Phe Ala Asp Gln Gln Phe Phe Gly Gly Asp Val Gly His
                35                  40                  45

Ala Ser Ile Asn Met Lys Leu Pro Val Thr Asp Lys Thr Lys Gln Trp
    50                  55                  60

Ile Glu Lys Tyr Cys Tyr Ser Gln Thr Tyr Asp Gln Phe Lys Lys Val
65                  70                  75                  80

Lys Gly Asn Glu Asp Lys Thr Tyr Glu Glu Tyr Leu Lys Thr Ala Lys
                85                  90                  95

Arg Leu Ile Pro Val Glu Leu Lys Thr Gln Val Thr Arg Lys Ala Gln
                100                 105                 110

Tyr Asp Ser Asn Gly Asn Leu Val Thr Thr His Glu Lys Ala Tyr Glu
            115                 120                 125

Gln Ile Tyr Phe Asp Ile Asp Trp Ser Trp Pro Gly Arg Leu Gln
            130                 135                 140

Asn Thr Glu Asp Asp Met Val Trp Glu Arg Glu Gly Lys His Phe Glu
145                 150                 155                 160

Tyr Asp Glu Lys Trp Lys Glu Tyr Leu Gln Pro Glu Gln Arg Val His
                165                 170                 175

Arg Gly Lys Leu Gly Ser Arg Lys Met Asp Tyr Ala Pro Thr Ser Ile
                180                 185                 190

Ile His Gln Arg Asp Ile Pro Thr Ser Glu Leu Glu Lys Ile Thr Arg
            195                 200                 205

Asp His Lys Ile His Thr Ile Glu Glu Lys Leu Asn Val Val Lys Leu
        210                 215                 220

Leu Gln Ser Lys Ile Asp Glu Met Pro His Thr Lys Met Ser Pro Ser
225                 230                 235                 240

Met Glu Leu Met Phe Lys Asn Leu Gly Ile Asn Val Glu Lys Leu Leu
                245                 250                 255

Asp Glu Thr Lys Asp Asn Gly Val Asp Pro Thr Asn Leu Glu Ala Met
                260                 265                 270

Arg Glu Tyr Leu Thr Asn Arg Leu Thr Glu Arg Lys Leu Glu Leu Glu
            275                 280                 285

Thr Glu Leu Ser Glu Ala Lys Lys Glu Val Asp Ser Thr Gln Val Lys
        290                 295                 300

Asn Lys Val Glu Asp Val Tyr Tyr Asp Phe Glu Tyr Lys Leu Asn Gln
305                 310                 315                 320

Val Arg Lys Lys Met Glu Val Asn Ser Gln Leu Glu Lys Met Asp
                325                 330                 335

Ser Leu Leu His Lys Leu Glu Gly Asn Thr Ser Gly Pro Ile Pro Tyr
            340                 345                 350

Thr Ala Glu Ile Asp Glu Leu Met Ser Val Leu Pro Phe Leu Lys Glu
        355                 360                 365

Glu Leu Glu Leu Glu Asn Gly Thr Leu Ser Pro Lys Ser Ile Glu Asn
    370                 375                 380

Leu Ile Asp His Ile Asp Glu Leu Lys Asn Glu Leu Ala Ser Lys Gln
385                 390                 395                 400

Glu Lys Lys Asn Glu Arg Asn Leu Asn Leu Ile Lys Lys Tyr Glu Glu
                405                 410                 415

Leu Cys Glu Gln Tyr Lys Asp Asp Glu Glu Gly Leu Glu Glu Ala Leu
            420                 425                 430
```

```
Trp Glu Glu Gly Ile Asp Val Glu Val Asn Ser Ala Lys Lys Asp
            435                 440                 445
Ile Ser Lys Pro Ala Pro Glu Ile Gln Lys Leu Thr Asp Leu Gln Glu
450                 455                 460
Gln Leu Arg Asn His Lys Glu Ser Gly Val Lys Leu Ser Ser Glu Leu
465                 470                 475                 480
Glu Glu Thr Leu Asn Ser Ser Val Lys Met Trp Lys Thr Lys Ile Asp
            485                 490                 495
Ser Pro Cys Gln Val Ile Ser Glu Ser Ser Val Lys Ala Leu Val Ser
            500                 505                 510
Lys Ile Asn Ser Thr Arg Pro Glu Leu Val Lys Glu Lys Gln Leu
            515                 520                 525
Pro Glu Gln Glu Glu Ser Leu Ser Lys Glu Ala Lys Lys Ala Gln Glu
            530                 535                 540
Glu Leu Ile Lys Ile Gln Glu Phe Ser Gln Phe Tyr Ser Glu Asn Ser
545                 550                 555                 560
Ser Ala Tyr Met Val Ile Gly Leu Pro Pro His Gln Val Ser Leu
                565                 570                 575
Pro Leu Ala Val Asn Gly Lys Arg Gly Leu His Pro Glu Ala Met Leu
            580                 585                 590
Lys Lys Met His Glu Leu Val Ala Gly Pro Glu Lys Lys Glu Phe Asn
            595                 600                 605
Leu His Thr Asn Asn Cys Ser Leu Thr Ser Ile Glu Val Leu Ser Ala
            610                 615                 620
Gly Ala Gln His Asp Pro Leu Leu His Ser Ile Met Gly Thr Arg Ala
625                 630                 635                 640
Leu Gly Phe Phe Gly Thr Pro Gln Gln Val Leu Glu Asn Ala Lys Leu
                645                 650                 655
Thr Ser Lys Thr Ile Asn Glu Gly Lys Lys Ser Asn Ile Phe Thr Pro
            660                 665                 670
Leu Val Thr Ala Ser Pro Leu Asp Arg Ala Leu Gly Tyr Ala Met Ser
            675                 680                 685
Ile Tyr Met Asp Pro Glu Ala Ser Lys Ala Lys Gln Asn Ala Gly Leu
            690                 695                 700
Ala Leu Gly Val Leu Val Gly Leu Ala Lys Thr Pro Gly Ile Ile Ile
705                 710                 715                 720
Gly Ser Leu Leu Asn Pro Lys Gln Gly Phe Asn Asp Ile Leu Asn Thr
                725                 730                 735
Leu Asn Leu Val Tyr Ser Arg Asn Ser Thr Gly Leu Lys Val Gly Leu
            740                 745                 750
Thr Leu Met Ala Leu Pro Ala Met Ile Val Leu Ala Pro Leu Ala Ala
            755                 760                 765
Ile Gln Lys Gly Val Glu Val Ile Ala Glu Thr Ile Ala Lys Pro Phe
770                 775                 780
Lys Leu Ile Ala Asn Leu Phe Lys Gln Lys Pro Glu Ser Thr Asp Glu
785                 790                 795                 800
Ile Thr Val Ser Val Gly Ser Lys Lys Val Ala Glu Lys Glu Gly Ser
            805                 810                 815
Tyr Ser Asn Thr Ala Leu Ala Gly Leu Val Asn Ser Lys Ile Lys Ser
            820                 825                 830
Lys Ile Asp Glu Asn Thr Ile Thr Val Glu Phe Gln Lys Ser Pro Gln
            835                 840                 845
```

```
Lys Met Ile Glu Glu Phe Glu Ser Gln Leu Lys Glu Asn Pro Gly Lys
    850                 855                 860

Val Val Val Leu Ser Glu Lys Ala His Asn Ala Val Leu Lys Phe Val
865                 870                 875                 880

Ser Lys Ser Asp Asp Glu Ala Leu Lys Gln Lys Phe Tyr Asp Cys Cys
                885                 890                 895

Asn Gln Ser Val Ala Arg Ser Gln Lys Phe Ala Pro Lys Thr Arg Asp
            900                 905                 910

Glu Ile Asp Glu Leu Val Glu Glu Val Thr Ser Thr Asp Lys Thr Glu
        915                 920                 925

Leu Thr Thr Ser Pro Arg Gln Glu Pro Ser Met Ser Ser Thr Ile Asp
    930                 935                 940

Glu Glu Glu Asn Ile Asp Ser Glu His Gln Ile Glu Thr Gly Thr Glu
945                 950                 955                 960

Ser Thr Met Arg Ile
                965

<210> SEQ ID NO 21
<211> LENGTH: 665
<212> TYPE: PRT
<213> ORGANISM: Legionella pneumophila
<400> SEQUENCE: 21

Met Lys Thr Lys Gln Glu Val Ser Gln Gln Asp Lys Leu Lys Asp Ser
1               5                   10                  15

Lys Ser Ser Thr Pro Leu Gln Thr Lys Glu Thr Trp Phe Ile Ser Asp
            20                  25                  30

Ala Leu Asn Ile Thr Phe Asp Pro Tyr Asp Phe Ser Ile Ser Val Thr
        35                  40                  45

Glu Gln Ala Pro Met Pro Tyr Arg Ile Val Phe Ser Gly Gly Gly Ser
    50                  55                  60

Arg Ile Leu Ala His Ile Gly Ala Leu Asp Glu Leu Thr Arg His Gly
65                  70                  75                  80

Leu Lys Phe Thr Glu Phe Ser Gly Ser Ser Ala Gly Ala Met Val Ala
                85                  90                  95

Ala Phe Ala Tyr Leu Gly Tyr Asn Cys Ser Glu Ile Lys Gln Ile Ile
            100                 105                 110

Ser Trp Phe Asn Glu Asp Lys Leu Leu Asp Ser Pro Leu Ile Phe Asn
        115                 120                 125

Phe Asn Asn Ile Lys Gln Ile Phe Asn Lys Gly Gly Leu Ser Ser Ala
    130                 135                 140

Lys Leu Met Arg Gln Ala Ala Asn Tyr Val Ile Leu Lys Lys Val Met
145                 150                 155                 160

Asp Ile Ile Ser Asp Glu Lys Phe Lys Thr Arg Phe Ala Lys Phe Gln
                165                 170                 175

Asn Phe Leu Glu Glu Asn Ile Tyr Arg Cys Pro Glu Asn Ile Thr Phe
            180                 185                 190

Gln Thr Leu Ala Arg Ile Lys Glu Ile Cys Pro Glu Cys Glu Leu Gly
        195                 200                 205

Glu Lys Leu Phe Ile Thr Gly Thr Asn Leu Ser Thr Gln Lys His Glu
    210                 215                 220

Val Phe Ser Ile Asp Thr Thr Pro Ser Met Ala Leu Ala Asp Ala Ile
225                 230                 235                 240

Ile Ile Ser Ala Asn Leu Pro Ile Ala Phe Glu Arg Ile Cys Tyr Gln
                245                 250                 255
```

```
Gly Asn Val Tyr Ser Asp Gly Ile Ser Asn Asn Leu Pro Ala His
            260                 265                 270

Cys Phe Ser Glu Lys Gly His Lys Thr Thr Phe Leu Lys His Lys Asp
        275                 280                 285

Asp Val Asp Phe Ser Val Leu Ala Leu Gln Phe Asp Asn Gly Leu Glu
    290                 295                 300

Glu Asn Ala Leu Tyr Ser Gln Asn Pro Ile Pro Lys Trp Ser Trp Leu
305                 310                 315                 320

Ser Asn Thr Phe Tyr Ser Leu Ile Thr Gly His Pro Asn Val Thr Glu
                325                 330                 335

Asn Trp Tyr Glu Asp Leu Gln Ile Leu Arg Arg His Ala His Gln Ser
            340                 345                 350

Ile Leu Ile Lys Thr Pro Thr Ile Ala Leu Thr Asn Leu Thr Ile Ser
        355                 360                 365

Gln Asp Thr Lys Lys Ala Leu Val Glu Ser Gly Arg Thr Ala Ala Lys
    370                 375                 380

Thr Tyr Leu Glu Leu His Glu Phe Tyr Thr Asp Asp Tyr Gly Asn Ile
385                 390                 395                 400

Arg His Asn Glu Cys Leu His Glu Lys Phe Gln Lys Pro Glu Glu Leu
                405                 410                 415

Leu Asp Tyr Cys Val Leu His Ser His Phe Glu Leu Leu Lys Lys Ile
            420                 425                 430

Lys Gln Ala Ile Ser Cys Ser Gln Tyr Leu Glu Lys Gly Tyr Lys His
        435                 440                 445

Tyr Leu Cys Glu Leu Cys Asp Asn Leu Leu Pro Pro Gln Leu Lys Cys
    450                 455                 460

Pro Asn Glu Gly Ser Gly Thr Glu Gln Pro Glu Ile Lys Leu Glu Lys
465                 470                 475                 480

Asp Thr Ile Ile Cys Glu Lys Asn Asn Asn Ser Gly Leu Thr Phe Ser
                485                 490                 495

Met Thr Phe Phe Gly Val Pro Ser Pro Leu Val Lys Thr Leu Asn Gln
            500                 505                 510

Asp Ser Pro Glu Leu Lys Ile Lys Leu Phe Thr Gly Leu Tyr Pro Ile
        515                 520                 525

Leu Ile Gln Asn Trp Gln Asn Leu Cys Pro Val Ser Gly Ile Ser Gly
    530                 535                 540

Ile Leu Asn Ser Ile Arg Met Ser Phe Val Glu Ile Ser Ser Thr Asp
545                 550                 555                 560

Thr Cys Ile Lys Thr Leu Ile Asp Lys Leu Asn Glu Ile Glu Ile Gly
                565                 570                 575

His Phe Leu Ile Phe Val Phe Lys Ala Ala Leu Lys Asn Tyr Asp Lys
            580                 585                 590

His Asp Phe Ile Leu Leu Leu Lys Asn Leu Lys His Leu His His Ser
        595                 600                 605

Ile Glu Leu Ile Arg Asn Lys Pro Phe His Ser Asp Asp Arg Phe Tyr
    610                 615                 620

Gly Gln Trp Ser Phe Glu Gly His Asp Pro Lys Arg Ile Leu Glu Phe
625                 630                 635                 640

Ile Lys Ser Asp Asp Ile Ser Gly Leu Met Thr Ile Leu Glu Asp Lys
                645                 650                 655

Lys Ala Leu Pro Asn Asn Lys Pro Asn
            660                 665
```

<210> SEQ ID NO 22
<211> LENGTH: 246
<212> TYPE: PRT
<213> ORGANISM: Legionella pneumophila

<400> SEQUENCE: 22

```
Met Val Ser Leu Glu His Ile Gln Lys Leu Ile Ser Glu Cys Arg Lys
1               5                   10                  15

Leu Gly Lys Asp Gly Leu Asp Asn Gly Thr Asn Gly Leu Ile Pro Glu
            20                  25                  30

Leu Glu Ile Asp Val Val Pro Pro Ser Ala Phe Leu Gly Val Gly Asn
        35                  40                  45

Asn Pro Ala Ile Phe Val Asn Ser Lys Thr Tyr Lys Leu Met Arg Thr
    50                  55                  60

Thr His Glu Lys Trp Val Glu Asn Lys Thr Ile Val Phe Lys Ser Tyr
65                  70                  75                  80

Leu Leu Ser Gln Pro Ala Ile Lys Ile Ile Gly Ala Ile Val His Glu
                85                  90                  95

Thr Gly His Ala Phe Asn Val Ala Ala Lys Ile Pro Asn Thr Glu Ala
            100                 105                 110

Asn Ala Cys Ile Phe Glu Ile Glu Val Leu Met Arg Leu Phe Gln Val
        115                 120                 125

Lys Ser Pro Leu Leu Leu Gly Cys Thr Glu Leu Asp Met Gln Ser Tyr
    130                 135                 140

Phe Lys Ser Arg Leu Thr Asp Tyr Asn Lys Cys Val Lys Asp Cys Gln
145                 150                 155                 160

Cys Leu Ala Glu Met Val Glu Phe Ile Thr His Gln Phe Lys Leu Asp
                165                 170                 175

Glu Val Ser Ile Ser Glu Lys Glu Asn Gln Ile Pro Leu Leu Ser Ile
            180                 185                 190

Ser Asn Lys Trp Pro Gly Leu Phe Ala Lys Lys Gln Ile Ala Pro Asp
        195                 200                 205

Met Asp Lys Leu Leu Thr Ser Pro Val Thr Ile Thr Pro Glu Val Lys
    210                 215                 220

Ile Leu Phe Tyr Gln Leu Val Lys Glu His Phe His Ser Pro Glu Thr
225                 230                 235                 240

Glu Ile Lys Leu Asp Ile
                245
```

<210> SEQ ID NO 23
<211> LENGTH: 644
<212> TYPE: PRT
<213> ORGANISM: Legionella pneumophila

<400> SEQUENCE: 23

```
Met Tyr Lys Ile Tyr Ser Tyr Leu Gly Trp Arg Ile Asp Met Lys Thr
1               5                   10                  15

Glu Asn Leu Pro Gln Ala Gly Gln Glu Ala Gln Ile Asp Lys Lys Ile
            20                  25                  30

His Phe Ile Trp Val Gly His Ile Met Pro Gln Lys Asn Ile Gln Val
        35                  40                  45

Val Ser Glu Trp Ala Glu Lys Asn Pro Gly Tyr Glu Thr Ile Ile Trp
    50                  55                  60

Val Asp Lys Lys Ile Ala Pro Ala Lys Glu Leu Asp Leu Phe Ile Leu
65                  70                  75                  80
```

```
Asp Met Lys Ser Lys Gly Ile Thr Val Lys Asp Ile Asn Glu Glu Gly
                85                  90                  95

Val Cys Arg Asp Ser Ile Arg His Glu Leu Asp Gln Glu Ser Pro Asn
            100                 105                 110

Tyr Gly Met Val Ser Asp Met Leu Arg Leu Asn Ile Leu Ala Ala Glu
        115                 120                 125

Gly Gly Ile Tyr Leu Asp Ser Asp Ile Leu Cys Ser Ala Pro Phe Pro
    130                 135                 140

Asp Glu Ile Tyr Ala Pro Phe Gly Phe Leu Leu Ser Pro Trp Ser Gln
145                 150                 155                 160

Gly Ala Asn Asn Thr Leu Cys Asn Asp Ile Ile Leu Cys Ser Lys Gly
                165                 170                 175

Asn Gln Ile Ile Gln Gln Leu Ala Asp Ala Ile Glu Gln Ser Tyr Ile
            180                 185                 190

Ala Arg Asp Ser Phe Glu Phe Thr His Glu Tyr Ala Ser Met Lys Glu
        195                 200                 205

Thr Lys Gly Glu Arg Ile Ala Lys Thr Leu Gly Val Thr Gly Pro Gly
    210                 215                 220

Phe Leu Phe His Gln Leu Lys Lys Met Gly Ile Leu Asn Asp Lys Ser
225                 230                 235                 240

Glu Met Glu Ala Ile His Trp Glu Leu Gln Asp Gln Arg Tyr Leu Ile
                245                 250                 255

Asp Gly Ser Val Lys Glu Pro Asp Tyr Phe Tyr Val Pro Gln Asn Asn
            260                 265                 270

Thr Asn Asp Ala Ser Trp Val Pro Ser Ile Lys Arg Pro Gly Ile Glu
        275                 280                 285

Asn Met Ser Phe Gln Glu Arg Leu Glu Asn Ala Val Gln Leu Ile Ala
    290                 295                 300

Phe Asp Ile Gln Lys Thr Gly Leu Phe Asn Leu Asp His Tyr Ala Asn
305                 310                 315                 320

Glu Leu Lys Val Lys Gln Asn Ser Trp Cys Ile Ala Ala Glu Thr Ser
                325                 330                 335

Pro Glu Leu Lys Pro Asp Ser Tyr Leu Leu Ile Arg Pro Arg Asp Lys
            340                 345                 350

Thr Gly Glu Trp Thr Leu Tyr Tyr Val Asp Glu Asp Lys Lys Leu Asn
        355                 360                 365

Pro Val Thr Leu Pro Val Ile Lys Gly Ala Ile Lys Leu Ser Glu Val
    370                 375                 380

Ser Asp Pro Leu Arg Lys Phe His Thr Leu Leu Ser Gln Val Ser Asp
385                 390                 395                 400

Pro Val Asn Pro Thr Ala His Glu Leu Lys Gln Ile Gly Arg Ala Leu
                405                 410                 415

Ile Glu Leu Lys Pro Arg Gln Asp Glu Trp His Cys Lys Asn Lys Trp
            420                 425                 430

Ser Gly Ala Glu Glu Ile Ala Gln Glu Leu Trp Gln Arg Ile Thr Ser
        435                 440                 445

Asn Glu Thr Leu Arg Ala Gln Ile Lys Gln Cys Phe Thr Gln Phe Glu
    450                 455                 460

Ser Leu Lys Pro Arg Val Ala Glu Leu Gly Leu Thr Arg Ala Ser Gly
465                 470                 475                 480

Ala Gly Thr Glu Val Glu Ala His Glu Ser Thr Val Lys Glu Gln Glu
                485                 490                 495

Ile Ile Ser Gln Asn Thr Val Gly Glu Glu Gly Thr Lys Glu Lys Asn
```

```
                500                 505                 510
Ser Val Gln Leu Ala Ser Glu Asn Ser Ser Asp Glu Lys Ile Lys Thr
            515                 520                 525

Ala His Asp Leu Ile Asp Glu Ile Ile Gln Asp Val Ile Gln Leu Asp
            530                 535                 540

Gly Lys Leu Gly Leu Gly Gly Asn Thr Arg Gln Leu Glu Asp Gly
545                 550                 555                 560

Arg Val Ile Asn Ile Pro Asn Gly Ala Ala Met Ile Phe Asp Asp Tyr
                565                 570                 575

Lys Lys Tyr Lys Gln Gly Glu Leu Thr Ala Glu Ser Ala Leu Glu Ser
            580                 585                 590

Met Ile Lys Ile Ala Lys Leu Ser Asn Gln Leu Asn Arg His Thr Phe
            595                 600                 605

Phe Asn Gln Arg Gln Pro Glu Thr Gly Gln Phe Tyr Lys Lys Val Ala
            610                 615                 620

Ala Ile Asp Leu Gln Thr Thr Ile Ala Ala Glu Tyr Asp Asn Asn His
625                 630                 635                 640

Gly Leu Arg Ile

<210> SEQ ID NO 24
<211> LENGTH: 219
<212> TYPE: PRT
<213> ORGANISM: Yersinia sp.

<400> SEQUENCE: 24

Met Lys Ile Ser Ser Phe Ile Ser Thr Ser Leu Pro Leu Pro Thr Ser
1               5                   10                  15

Val Ser Gly Ser Ser Val Gly Glu Met Ser Gly Arg Ser Val Ser
            20                  25                  30

Gln Gln Thr Ser Asp Gln Tyr Ala Asn Asn Leu Ala Gly Arg Thr Glu
            35                  40                  45

Ser Pro Gln Gly Ser Ser Leu Ala Ser Arg Ile Ile Glu Arg Leu Ser
        50                  55                  60

Ser Val Ala His Ser Val Ile Gly Phe Ile Gln Arg Met Phe Ser Glu
65                  70                  75                  80

Gly Ser His Lys Pro Val Val Thr Pro Ala Pro Thr Pro Ala Gln Met
                85                  90                  95

Pro Ser Pro Thr Ser Phe Ser Asp Ser Ile Lys Gln Leu Ala Ala Glu
            100                 105                 110

Thr Leu Pro Lys Tyr Met Gln Gln Leu Asn Ser Leu Asp Ala Glu Met
        115                 120                 125

Leu Gln Lys Asn His Asp Gln Phe Ala Thr Gly Ser Gly Pro Leu Arg
    130                 135                 140

Gly Ser Ile Thr Gln Cys Gln Gly Leu Met Gln Phe Cys Gly Gly Glu
145                 150                 155                 160

Leu Gln Ala Glu Ala Ser Ala Ile Leu Asn Thr Pro Val Cys Gly Ile
                165                 170                 175

Pro Phe Ser Gln Trp Gly Thr Ile Gly Gly Ala Ala Ser Ala Tyr Val
            180                 185                 190

Ala Ser Gly Val Asp Leu Thr Gln Ala Ala Asn Glu Ile Lys Gly Leu
        195                 200                 205

Ala Gln Gln Met Gln Lys Leu Leu Ser Leu Met
    210                 215
```

```
<210> SEQ ID NO 25
<211> LENGTH: 543
<212> TYPE: PRT
<213> ORGANISM: Salmonella sp.

<400> SEQUENCE: 25

Met Leu Lys Tyr Glu Glu Arg Lys Leu Asn Asn Leu Thr Leu Ser Ser
1               5                   10                  15

Phe Ser Lys Val Gly Val Ser Asn Asp Ala Arg Leu Tyr Ile Ala Lys
            20                  25                  30

Glu Asn Thr Asp Lys Ala Tyr Val Ala Pro Glu Lys Phe Ser Ser Lys
        35                  40                  45

Val Leu Thr Trp Leu Gly Lys Met Pro Leu Phe Lys Asn Thr Glu Val
    50                  55                  60

Val Gln Lys His Thr Glu Asn Ile Arg Val Gln Asp Gln Lys Ile Leu
65                  70                  75                  80

Gln Thr Phe Leu His Ala Leu Thr Glu Lys Tyr Gly Glu Thr Ala Val
                85                  90                  95

Asn Asp Ala Leu Leu Met Ser Arg Ile Asn Met Asn Lys Pro Leu Thr
            100                 105                 110

Gln Arg Leu Ala Val Gln Ile Thr Glu Cys Val Lys Ala Ala Asp Glu
        115                 120                 125

Gly Phe Ile Asn Leu Ile Lys Ser Lys Asp Asn Val Gly Val Arg Asn
    130                 135                 140

Ala Ala Leu Val Ile Lys Gly Gly Asp Thr Lys Val Ala Glu Lys Asn
145                 150                 155                 160

Asn Asp Val Gly Ala Glu Ser Lys Gln Pro Leu Leu Asp Ile Ala Leu
                165                 170                 175

Lys Gly Leu Lys Arg Thr Leu Pro Gln Leu Glu Gln Met Asp Gly Asn
            180                 185                 190

Ser Leu Arg Glu Asn Phe Gln Glu Met Ala Ser Gly Asn Gly Pro Leu
        195                 200                 205

Arg Ser Leu Met Thr Asn Leu Gln Asn Leu Asn Lys Ile Pro Glu Ala
    210                 215                 220

Lys Gln Leu Asn Asp Tyr Val Thr Thr Leu Thr Asn Ile Gln Val Gly
225                 230                 235                 240

Val Ala Arg Phe Ser Gln Trp Gly Thr Cys Gly Gly Glu Val Glu Arg
                245                 250                 255

Trp Val Asp Lys Ala Ser Thr His Glu Leu Thr Gln Ala Val Lys Lys
            260                 265                 270

Ile His Val Ile Ala Lys Glu Leu Lys Asn Val Thr Ala Glu Leu Glu
        275                 280                 285

Lys Ile Glu Ala Gly Ala Pro Met Pro Gln Thr Met Ser Gly Pro Thr
    290                 295                 300

Leu Gly Leu Ala Arg Phe Ala Val Ser Ser Ile Pro Ile Asn Gln Gln
305                 310                 315                 320

Thr Gln Val Lys Leu Ser Asp Gly Met Pro Val Pro Val Asn Thr Leu
                325                 330                 335

Thr Phe Asp Gly Lys Pro Val Ala Leu Ala Gly Ser Tyr Pro Lys Asn
            340                 345                 350

Thr Pro Asp Ala Leu Glu Ala His Met Lys Met Leu Leu Glu Lys Glu
        355                 360                 365

Cys Ser Cys Leu Val Val Leu Thr Ser Glu Asp Gln Met Gln Ala Lys
    370                 375                 380
```

```
Gln Leu Pro Pro Tyr Phe Arg Gly Ser Tyr Thr Phe Gly Glu Val His
385                 390                 395                 400

Thr Asn Ser Gln Lys Val Ser Ser Ala Ser Gln Gly Glu Ala Ile Asp
            405                 410                 415

Gln Tyr Asn Met Gln Leu Ser Cys Gly Glu Lys Arg Tyr Thr Ile Pro
            420                 425                 430

Val Leu His Val Lys Asn Trp Pro Asp His Gln Pro Leu Pro Ser Thr
            435                 440                 445

Asp Gln Leu Glu Tyr Leu Ala Asp Arg Val Lys Asn Ser Asn Gln Asn
450                 455                 460

Gly Ala Pro Gly Arg Ser Ser Asp Lys His Leu Pro Met Ile His
465                 470                 475                 480

Cys Leu Gly Gly Val Gly Arg Thr Gly Thr Met Ala Ala Ala Leu Val
                485                 490                 495

Leu Lys Asp Asn Pro His Ser Asn Leu Glu Gln Val Arg Ala Asp Phe
                500                 505                 510

Arg Asp Ser Arg Asn Asn Arg Met Leu Glu Asp Ala Ser Gln Phe Val
            515                 520                 525

Gln Leu Lys Ala Met Gln Ala Gln Leu Leu Met Thr Thr Ala Ser
            530                 535                 540

<210> SEQ ID NO 26
<211> LENGTH: 240
<212> TYPE: PRT
<213> ORGANISM: Salmonella typhimurium

<400> SEQUENCE: 26

Met Thr Asn Ile Thr Leu Ser Thr Gln His Tyr Arg Ile His Arg Ser
1               5                   10                  15

Asp Val Glu Pro Val Lys Glu Lys Thr Thr Glu Lys Asp Ile Phe Ala
                20                  25                  30

Lys Ser Ile Thr Ala Val Arg Asn Ser Phe Ile Ser Leu Ser Thr Ser
            35                  40                  45

Leu Ser Asp Arg Phe Ser Leu His Gln Gln Thr Asp Ile Pro Thr Thr
50                  55                  60

His Phe His Arg Gly Asn Ala Ser Glu Gly Arg Ala Val Leu Thr Ser
65                  70                  75                  80

Lys Thr Val Lys Asp Phe Met Leu Gln Lys Leu Asn Ser Leu Asp Ile
                85                  90                  95

Lys Gly Asn Ala Ser Lys Asp Pro Ala Tyr Ala Arg Gln Thr Cys Glu
            100                 105                 110

Ala Ile Leu Ser Ala Val Tyr Ser Asn Asn Lys Asp Gln Cys Cys Lys
            115                 120                 125

Leu Leu Ile Ser Lys Gly Val Ser Ile Thr Pro Phe Leu Lys Glu Ile
130                 135                 140

Gly Glu Ala Ala Gln Asn Ala Gly Leu Pro Gly Glu Ile Lys Asn Gly
145                 150                 155                 160

Val Phe Thr Pro Gly Gly Ala Gly Ala Asn Pro Phe Val Pro Leu
                165                 170                 175

Ile Ala Ser Ala Ser Ile Lys Tyr Pro His Met Phe Ile Asn His Asn
            180                 185                 190

Gln Gln Val Ser Phe Lys Ala Tyr Ala Glu Lys Ile Val Met Lys Glu
            195                 200                 205

Val Thr Pro Leu Phe Asn Lys Gly Thr Met Pro Thr Pro Gln Gln Phe
210                 215                 220
```

Gln Leu Thr Ile Glu Asn Ile Ala Asn Lys Tyr Leu Gln Asn Ala Ser
225                 230                 235                 240

<210> SEQ ID NO 27
<211> LENGTH: 561
<212> TYPE: PRT
<213> ORGANISM: Salmonella typhimurium

<400> SEQUENCE: 27

Met Gln Ile Gln Ser Phe Tyr His Ser Ala Ser Leu Lys Thr Gln Glu
1               5                   10                  15

Ala Phe Lys Ser Leu Gln Lys Thr Leu Tyr Asn Gly Met Gln Ile Leu
            20                  25                  30

Ser Gly Gln Gly Lys Ala Pro Ala Lys Ala Pro Asp Ala Arg Pro Glu
        35                  40                  45

Ile Ile Val Leu Arg Glu Pro Gly Ala Thr Trp Gly Asn Tyr Leu Gln
    50                  55                  60

His Gln Lys Ala Ser Asn His Ser Leu His Asn Leu Tyr Asn Leu Gln
65                  70                  75                  80

Arg Asp Leu Leu Thr Val Ala Ala Thr Val Leu Gly Lys Gln Asp Pro
                85                  90                  95

Val Leu Thr Ser Met Ala Asn Gln Met Glu Leu Ala Lys Val Lys Ala
            100                 105                 110

Asp Arg Pro Ala Thr Lys Gln Glu Glu Ala Ala Ala Lys Ala Leu Lys
        115                 120                 125

Lys Asn Leu Ile Glu Leu Ile Ala Ala Arg Thr Gln Gln Gln Asp Gly
130                 135                 140

Leu Pro Ala Lys Glu Ala His Arg Phe Ala Ala Val Ala Phe Arg Asp
145                 150                 155                 160

Ala Gln Val Lys Gln Leu Asn Asn Gln Pro Trp Gln Thr Ile Lys Asn
                165                 170                 175

Thr Leu Thr His Asn Gly His His Tyr Thr Asn Thr Gln Leu Pro Ala
            180                 185                 190

Ala Glu Met Lys Ile Gly Ala Lys Asp Ile Phe Pro Ser Ala Tyr Glu
        195                 200                 205

Gly Lys Gly Val Cys Ser Trp Asp Thr Lys Asn Ile His His Ala Asn
210                 215                 220

Asn Leu Trp Met Ser Thr Val Ser Val His Glu Asp Gly Lys Asp Lys
225                 230                 235                 240

Thr Leu Phe Cys Gly Ile Arg His Gly Val Leu Ser Pro Tyr His Glu
                245                 250                 255

Lys Asp Pro Leu Leu Arg His Val Gly Ala Glu Asn Lys Ala Lys Glu
            260                 265                 270

Val Leu Thr Ala Ala Leu Phe Ser Lys Pro Glu Leu Leu Asn Lys Ala
        275                 280                 285

Leu Ala Gly Glu Ala Val Ser Leu Lys Leu Val Ser Val Gly Leu Leu
290                 295                 300

Thr Ala Ser Asn Ile Phe Gly Lys Glu Gly Thr Met Val Glu Asp Gln
305                 310                 315                 320

Met Arg Ala Trp Gln Ser Leu Thr Gln Pro Gly Lys Met Ile His Leu
                325                 330                 335

Lys Ile Arg Asn Lys Asp Gly Asp Leu Gln Thr Val Lys Ile Lys Pro
            340                 345                 350

Asp Val Ala Ala Phe Asn Val Gly Val Asn Glu Leu Ala Leu Lys Leu

```
                355                 360                 365
Gly Phe Gly Leu Lys Ala Ser Asp Ser Tyr Asn Ala Glu Ala Leu His
370                 375                 380

Gln Leu Leu Gly Asn Asp Leu Arg Pro Glu Ala Arg Pro Gly Gly Trp
385                 390                 395                 400

Val Gly Glu Trp Leu Ala Gln Tyr Pro Asp Asn Tyr Glu Val Val Asn
                405                 410                 415

Thr Leu Ala Arg Gln Ile Lys Asp Ile Trp Lys Asn Asn Gln His His
                420                 425                 430

Lys Asp Gly Gly Glu Pro Tyr Lys Leu Ala Gln Arg Leu Ala Met Leu
435                 440                 445

Ala His Glu Ile Asp Ala Val Pro Ala Trp Asn Cys Lys Ser Gly Lys
    450                 455                 460

Asp Arg Thr Gly Met Met Asp Ser Glu Ile Lys Arg Glu Ile Ile Ser
465                 470                 475                 480

Leu His Gln Thr His Met Leu Ser Ala Pro Gly Ser Leu Pro Asp Ser
                485                 490                 495

Gly Gly Gln Lys Ile Phe Gln Lys Val Leu Leu Asn Ser Gly Asn Leu
                500                 505                 510

Glu Ile Gln Lys Gln Asn Thr Gly Gly Ala Gly Asn Lys Val Met Lys
            515                 520                 525

Asn Leu Ser Pro Glu Val Leu Asn Leu Ser Tyr Gln Lys Arg Val Gly
530                 535                 540

Asp Glu Asn Ile Trp Gln Ser Val Lys Gly Ile Ser Ser Leu Ile Thr
545                 550                 555                 560

Ser

<210> SEQ ID NO 28
<211> LENGTH: 685
<212> TYPE: PRT
<213> ORGANISM: Salmonella typhimurium

<400> SEQUENCE: 28

Met Val Thr Ser Val Arg Thr Gln Pro Pro Val Ile Met Pro Gly Met
1               5                   10                  15

Gln Thr Glu Ile Lys Thr Gln Ala Thr Asn Leu Ala Ala Asn Leu Ser
                20                  25                  30

Ala Val Arg Glu Ser Ala Thr Thr Leu Ser Gly Glu Ile Lys Gly
                35                  40                  45

Pro Gln Leu Glu Asp Phe Pro Ala Leu Ile Lys Gln Ala Ser Leu Asp
50                  55                  60

Ala Leu Phe Lys Cys Gly Lys Asp Ala Glu Ala Leu Lys Glu Val Phe
65                  70                  75                  80

Thr Asn Ser Asn Asn Val Ala Gly Lys Lys Ala Ile Met Glu Phe Ala
                85                  90                  95

Gly Leu Phe Arg Ser Ala Leu Asn Ala Thr Ser Asp Ser Pro Glu Ala
                100                 105                 110

Lys Thr Leu Leu Met Lys Val Gly Ala Glu Tyr Thr Ala Gln Ile Ile
            115                 120                 125

Lys Asp Gly Leu Lys Glu Lys Ser Ala Phe Gly Pro Trp Leu Pro Glu
            130                 135                 140

Thr Lys Lys Ala Glu Ala Lys Leu Glu Asn Leu Glu Lys Gln Leu Leu
145                 150                 155                 160

Asp Ile Ile Lys Asn Asn Thr Gly Gly Glu Leu Ser Lys Leu Ser Thr
```

165                 170                 175
Asn Leu Val Met Gln Glu Val Met Pro Tyr Ile Ala Ser Cys Ile Glu
                180                 185                 190

His Asn Phe Gly Cys Thr Leu Asp Pro Leu Thr Arg Ser Asn Leu Thr
                195                 200                 205

His Leu Val Asp Lys Ala Ala Lys Ala Val Glu Ala Leu Asp Met
                210                 215                 220

Cys His Gln Lys Leu Thr Gln Glu Gln Gly Thr Ser Val Gly Arg Glu
225                 230                 235                 240

Ala Arg His Leu Glu Met Gln Thr Leu Ile Pro Leu Leu Arg Asn
                245                 250                 255

Val Phe Ala Gln Ile Pro Ala Asp Lys Leu Pro Asp Pro Lys Ile Pro
                260                 265                 270

Glu Pro Ala Ala Gly Pro Val Pro Asp Gly Gly Lys Lys Ala Glu Pro
                275                 280                 285

Thr Gly Ile Asn Ile Asn Ile Asn Ile Asp Ser Ser Asn His Ser Val
                290                 295                 300

Asp Asn Ser Lys His Ile Asn Asn Ser Arg Ser His Val Asp Asn Ser
305                 310                 315                 320

Gln Arg His Ile Asp Asn Ser Asn His Asp Asn Ser Arg Lys Thr Ile
                325                 330                 335

Asp Asn Ser Arg Thr Phe Ile Asp Asn Ser Gln Arg Asn Gly Glu Ser
                340                 345                 350

His His Ser Thr Asn Ser Ser Asn Val Ser His Ser His Ser Arg Val
                355                 360                 365

Asp Ser Thr Thr His Gln Thr Glu Thr Ala His Ser Ala Ser Thr Gly
                370                 375                 380

Ala Ile Asp His Gly Ile Ala Gly Lys Ile Asp Val Thr Ala His Ala
385                 390                 395                 400

Thr Ala Glu Ala Val Thr Asn Ala Ser Ser Glu Ser Lys Asp Gly Lys
                405                 410                 415

Val Val Thr Ser Glu Lys Gly Thr Thr Gly Glu Thr Thr Ser Phe Asp
                420                 425                 430

Glu Val Asp Gly Val Thr Ser Lys Ser Ile Ile Gly Lys Pro Val Gln
                435                 440                 445

Ala Thr Val His Gly Val Asp Asp Asn Lys Gln Gln Ser Gln Thr Ala
                450                 455                 460

Glu Ile Val Asn Val Lys Pro Leu Ala Ser Gln Leu Ala Gly Val Glu
465                 470                 475                 480

Asn Val Lys Thr Asp Thr Leu Gln Ser Asp Thr Val Ile Thr Gly
                485                 490                 495

Asn Lys Ala Gly Thr Thr Asp Asn Asp Asn Ser Gln Thr Asp Lys Thr
                500                 505                 510

Gly Pro Phe Ser Gly Leu Lys Phe Lys Gln Asn Ser Phe Leu Ser Thr
                515                 520                 525

Val Pro Ser Val Thr Asn Met His Ser Met His Phe Asp Ala Arg Glu
                530                 535                 540

Thr Phe Leu Gly Val Ile Arg Lys Ala Leu Glu Pro Asp Thr Ser Thr
545                 550                 555                 560

Pro Phe Pro Val Arg Arg Ala Phe Asp Gly Leu Arg Ala Glu Ile Leu
                565                 570                 575

Pro Asn Asp Thr Ile Lys Ser Ala Ala Leu Lys Ala Gln Cys Ser Asp
                580                 585                 590

```
Ile Asp Lys His Pro Glu Leu Lys Ala Lys Met Glu Thr Leu Lys Glu
            595                 600                 605

Val Ile Thr His His Pro Gln Lys Glu Lys Leu Ala Glu Ile Ala Leu
            610                 615                 620

Gln Phe Ala Arg Glu Ala Gly Leu Thr Arg Leu Lys Gly Glu Thr Asp
625                 630                 635                 640

Tyr Val Leu Ser Asn Val Leu Asp Gly Leu Ile Gly Asp Gly Ser Trp
                645                 650                 655

Arg Ala Gly Pro Ala Tyr Glu Ser Tyr Leu Asn Lys Pro Gly Val Asp
                660                 665                 670

Arg Val Ile Thr Thr Val Asp Gly Leu His Met Gln Arg
                675                 680                 685

<210> SEQ ID NO 29
<211> LENGTH: 732
<212> TYPE: PRT
<213> ORGANISM: Yersinia pseudotuberculosis

<400> SEQUENCE: 29

Met Lys Ser Val Lys Ile Met Gly Thr Met Pro Pro Ser Ile Ser Leu
1               5                   10                  15

Ala Lys Ala His Glu Arg Ile Ser Gln His Trp Gln Asn Pro Val Gly
                20                  25                  30

Glu Leu Asn Ile Gly Gly Lys Arg Tyr Arg Ile Ile Asp Asn Gln Val
            35                  40                  45

Leu Arg Leu Asn Pro His Ser Gly Phe Ser Leu Phe Arg Glu Gly Val
50                  55                  60

Gly Lys Ile Phe Ser Gly Lys Met Phe Asn Phe Ser Ile Ala Arg Asn
65                  70                  75                  80

Leu Thr Asp Thr Leu His Ala Ala Gln Lys Thr Thr Ser Gln Glu Leu
                85                  90                  95

Arg Ser Asp Ile Pro Asn Ala Leu Ser Asn Leu Phe Gly Ala Lys Pro
            100                 105                 110

Gln Thr Glu Leu Pro Leu Gly Trp Lys Gly Glu Pro Leu Ser Gly Ala
            115                 120                 125

Pro Asp Leu Glu Gly Met Arg Val Ala Glu Thr Asp Lys Phe Ala Glu
130                 135                 140

Gly Glu Ser His Ile Ser Ile Glu Thr Lys Asp Lys Gln Arg Leu
145                 150                 155                 160

Val Ala Lys Ile Glu Arg Ser Ile Ala Glu Gly His Leu Phe Ala Glu
                165                 170                 175

Leu Glu Ala Tyr Lys His Ile Tyr Lys Thr Ala Gly Lys His Pro Asn
            180                 185                 190

Leu Ala Asn Val His Gly Met Ala Val Val Pro Tyr Gly Asn Arg Lys
            195                 200                 205

Glu Glu Ala Leu Leu Met Asp Glu Val Asp Gly Trp Arg Cys Ser Asp
210                 215                 220

Thr Leu Arg Thr Leu Ala Asp Ser Trp Lys Gln Gly Lys Ile Asn Ser
225                 230                 235                 240

Glu Ala Tyr Trp Gly Thr Ile Lys Phe Ile Ala His Arg Leu Leu Asp
                245                 250                 255

Val Thr Asn His Leu Ala Lys Ala Gly Val Val His Asn Asp Ile Lys
            260                 265                 270

Pro Gly Asn Val Val Phe Asp Arg Ala Ser Gly Glu Pro Val Val Ile
```

```
              275                 280                 285
Asp Leu Gly Leu His Ser Arg Ser Gly Glu Gln Pro Lys Gly Phe Thr
290                 295                 300
Glu Ser Phe Lys Ala Pro Glu Leu Gly Val Gly Asn Leu Gly Ala Ser
305                 310                 315                 320
Glu Lys Ser Asp Val Phe Leu Val Val Ser Thr Leu Leu His Cys Ile
                325                 330                 335
Glu Gly Phe Glu Lys Asn Pro Glu Ile Lys Pro Asn Gln Gly Leu Arg
                340                 345                 350
Phe Ile Thr Ser Glu Pro Ala His Val Met Asp Glu Asn Gly Tyr Pro
                355                 360                 365
Ile His Arg Pro Gly Ile Ala Gly Val Glu Thr Ala Tyr Thr Arg Phe
    370                 375                 380
Ile Thr Asp Ile Leu Gly Val Ser Ala Asp Ser Arg Pro Asp Ser Asn
385                 390                 395                 400
Glu Ala Arg Leu His Glu Phe Leu Ser Asp Gly Thr Ile Asp Glu Glu
                405                 410                 415
Ser Ala Lys Gln Ile Leu Lys Asp Thr Leu Thr Gly Glu Met Ser Pro
                420                 425                 430
Leu Ser Thr Asp Val Arg Arg Ile Thr Pro Lys Lys Leu Arg Glu Leu
                435                 440                 445
Ser Asp Leu Leu Arg Thr His Leu Ser Ser Ala Ala Thr Lys Gln Leu
450                 455                 460
Asp Met Gly Gly Val Leu Ser Asp Leu Asp Thr Met Leu Val Ala Leu
465                 470                 475                 480
Asp Lys Ala Glu Arg Glu Gly Gly Val Asp Lys Asp Gln Leu Lys Ser
                485                 490                 495
Phe Asn Ser Leu Ile Leu Lys Thr Tyr Arg Val Ile Glu Asp Tyr Val
                500                 505                 510
Lys Gly Arg Glu Gly Asp Thr Lys Asn Ser Ser Thr Glu Val Ser Pro
                515                 520                 525
Tyr His Arg Ser Asn Phe Met Leu Ser Ile Val Glu Pro Ser Leu Gln
                530                 535                 540
Arg Ile Gln Lys His Leu Asp Gln Thr His Ser Phe Ser Asp Ile Gly
545                 550                 555                 560
Ser Leu Val Arg Ala His Lys His Leu Glu Thr Leu Leu Glu Val Leu
                565                 570                 575
Val Thr Leu Ser Gln Gln Gly Gln Pro Val Ser Ser Glu Thr Tyr Gly
                580                 585                 590
Phe Leu Asn Arg Leu Ala Glu Ala Lys Ile Thr Leu Ser Gln Gln Leu
                595                 600                 605
Asn Thr Leu Gln Gln Gln Glu Ser Ala Lys Ala Gln Leu Ser Ile
                610                 615                 620
Leu Ile Asn Arg Ser Gly Ser Trp Ala Asp Val Ala Arg Gln Ser Leu
625                 630                 635                 640
Gln Arg Phe Asp Ser Thr Arg Pro Val Val Lys Phe Gly Thr Glu Gln
                645                 650                 655
Tyr Thr Ala Ile His Arg Gln Met Met Ala Ala His Ala Ala Ile Thr
                660                 665                 670
Leu Gln Glu Val Ser Glu Phe Thr Asp Asp Met Arg Asn Phe Thr Val
                675                 680                 685
Asp Ser Ile Pro Leu Leu Ile Gln Leu Gly Arg Ser Ser Leu Met Asp
690                 695                 700
```

-continued

```
Glu His Leu Val Glu Gln Arg Glu Lys Leu Arg Glu Leu Thr Thr Ile
705                 710                 715                 720

Ala Glu Arg Leu Asn Arg Leu Glu Arg Glu Trp Met
            725                 730

<210> SEQ ID NO 30
<211> LENGTH: 529
<212> TYPE: PRT
<213> ORGANISM: Yersinia sp.

<400> SEQUENCE: 30

Met Phe Ile Asn Pro Arg Asn Val Ser Asn Thr Phe Leu Gln Glu Pro
1               5                   10                  15

Leu Arg His Ser Ser Asn Leu Thr Glu Met Pro Val Glu Ala Glu Asn
                20                  25                  30

Val Lys Ser Lys Thr Glu Tyr Tyr Asn Ala Trp Ser Glu Trp Glu Arg
            35                  40                  45

Asn Ala Pro Pro Gly Asn Gly Glu Gln Arg Glu Met Ala Val Ser Arg
        50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Ser Leu
                85                  90                  95

Val Ala Ser Cys Asn Ser Leu Thr Glu Leu Pro Glu Leu Pro Gln Ser
            100                 105                 110

Leu Lys Ser Leu Gln Val Glu Asn Asn Leu Lys Ala Leu Pro Asp
        115                 120                 125

Leu Pro Pro Ser Leu Lys Lys Leu His Val Arg Glu Asn Asp Leu Thr
130                 135                 140

Asp Leu Pro Glu Leu Pro Gln Ser Leu Glu Ser Leu Arg Val Asp Asn
145                 150                 155                 160

Asn Asn Leu Lys Ala Leu Ser Asp Leu Pro Pro Ser Leu Glu Tyr Leu
                165                 170                 175

Thr Ala Ser Ser Asn Lys Leu Glu Glu Leu Pro Glu Leu Gln Asn Leu
            180                 185                 190

Pro Phe Leu Ala Ala Ile Tyr Ala Asp Asn Asn Leu Leu Glu Thr Leu
        195                 200                 205

Pro Asp Leu Pro Pro Ser Leu Lys Lys Leu His Val Arg Glu Asn Asp
210                 215                 220

Leu Thr Asp Leu Pro Glu Leu Pro Gln Ser Leu Glu Ser Leu Gln Val
225                 230                 235                 240

Asp Asn Asn Asn Leu Lys Ala Leu Ser Asp Leu Pro Pro Ser Leu Glu
                245                 250                 255

Tyr Leu Thr Ala Ser Ser Asn Lys Leu Glu Glu Leu Pro Glu Leu Gln
            260                 265                 270

Asn Leu Pro Phe Leu Ala Ala Ile Tyr Ala Asp Asn Asn Leu Leu Glu
        275                 280                 285

Thr Leu Pro Asp Leu Pro Pro His Leu Glu Ile Leu Val Ala Ser Tyr
290                 295                 300

Asn Ser Leu Thr Glu Leu Pro Glu Leu Pro Gln Ser Leu Lys Ser Leu
305                 310                 315                 320

Arg Val Asp Asn Asn Leu Lys Ala Leu Ser Asp Leu Pro Pro Ser
                325                 330                 335

Leu Glu Tyr Leu Thr Ala Ser Ser Asn Lys Leu Glu Glu Leu Pro Glu
```

-continued

```
            340                 345                 350

Leu Gln Asn Leu Pro Phe Leu Ala Ala Ile Tyr Ala Asp Asn Asn Leu
        355                 360                 365

Leu Glu Thr Leu Pro Asp Leu Pro Pro Ser Leu Lys Lys Leu His Val
    370                 375                 380

Arg Glu Asn Asp Leu Thr Asp Leu Pro Glu Leu Pro Gln Ser Leu Thr
385                 390                 395                 400

Phe Leu Asp Val Ser Asp Asn Asn Ile Ser Gly Leu Ser Glu Leu Pro
                405                 410                 415

Pro Asn Leu Tyr Tyr Leu Asp Ala Ser Ser Asn Glu Ile Arg Ser Leu
            420                 425                 430

Cys Asp Leu Pro Pro Ser Leu Val Asp Leu Asn Val Lys Ser Asn Gln
        435                 440                 445

Leu Ser Glu Leu Pro Ala Leu Pro Pro His Leu Glu Arg Leu Ile Ala
    450                 455                 460

Ser Phe Asn Tyr Leu Ala Glu Val Pro Glu Leu Pro Gln Asn Leu Lys
465                 470                 475                 480

Gln Leu His Val Glu Gln Asn Ala Leu Arg Glu Phe Pro Asp Ile Pro
                485                 490                 495

Glu Ser Leu Glu Glu Leu Glu Met Asp Ser Glu Arg Val Val Asp Pro
            500                 505                 510

Tyr Glu Phe Ala His Glu Thr Thr Asp Lys Leu Glu Asp Asp Val Phe
        515                 520                 525

Glu

<210> SEQ ID NO 31
<211> LENGTH: 35
<212> TYPE: PRT
<213> ORGANISM: Unknown
<220> FEATURE:
<223> OTHER INFORMATION: Description of Unknown:
      Amatoxin sequence

<400> SEQUENCE: 31

Met Ser Asp Ile Asn Ala Thr Arg Leu Pro Ile Trp Gly Ile Gly Cys
1               5                   10                  15

Asn Pro Cys Val Gly Asp Asp Val Thr Thr Leu Leu Thr Arg Gly Glu
            20                  25                  30

Ala Leu Cys
        35

<210> SEQ ID NO 32
<211> LENGTH: 34
<212> TYPE: PRT
<213> ORGANISM: Amanita phalloides

<400> SEQUENCE: 32

Met Ser Asp Ile Asn Ala Thr Arg Leu Pro Ala Trp Leu Val Asp Cys
1               5                   10                  15

Pro Cys Val Gly Asp Asp Val Asn Arg Leu Leu Thr Arg Gly Glu Ser
            20                  25                  30

Leu Cys

<210> SEQ ID NO 33
<211> LENGTH: 291
<212> TYPE: PRT
<213> ORGANISM: Ustilago maydis
```

<400> SEQUENCE: 33

Met Ile Lys Pro Glu Arg Ser Ile Leu Thr Ile Leu Gly Ile Leu
1               5                   10                  15

Cys Leu Leu Ala Tyr Val Leu Ala Asn Gly Glu Pro His Asp Gly Asp
            20                  25                  30

Asn Glu Trp Ser Ser Tyr Cys Ser Asp Gln Gly Phe Arg Arg Ser Asp
            35                  40                  45

Asp Gly Leu Val Thr Thr Pro Asp Val Gly Gln Glu Ser Ile Gly Lys
    50                  55                  60

Asn Ser Ile Asn Gly Ser Glu Leu Val Asp Tyr Leu Gln Cys Leu Lys
65                  70                  75                  80

Val Arg Leu Asn Gly Gln Lys Gln Val Ser Asn Asp Gly Trp Leu
                85                  90                  95

Leu Leu Leu Val Gln Glu Pro Ser Val Asn Val Thr Gln Lys Ala Met
            100                 105                 110

Ser Glu Cys Asn Tyr Asn Val Ser Ser Gly His Lys Ala Gly Ser Tyr
            115                 120                 125

Ile Gln Val Thr Asn Thr Pro Ala Asp Tyr Lys Val Ile Ser Arg Arg
    130                 135                 140

Gly Ser Tyr Glu Gly Asp Gln Leu Pro Glu Asp Val Lys Pro Tyr Phe
145                 150                 155                 160

Gly Val Gln Lys Thr Ser Asp Tyr Arg Pro Ile Ser Lys Arg Ile Asn
                165                 170                 175

Pro Asn Leu Thr Leu Arg Gln Leu Ala Tyr Asn Phe Ala Ala Leu Asn
            180                 185                 190

Met Cys Ser Leu Trp Cys Asn Ser Cys Ile Ser Arg Ser Cys Pro Tyr
            195                 200                 205

Tyr Ile Ala Glu Leu Thr Val His Val Asn Asn Ile His His Gly Thr
    210                 215                 220

Val Trp Leu His His Phe Cys Arg Asn Ala Ser Pro Gln Gly Gly Asn
225                 230                 235                 240

Leu Tyr Ser Thr Leu Thr Ile Ser His Lys Asp Thr Ala Tyr Tyr Val
                245                 250                 255

Gly Thr Gly Trp Trp Lys Val Arg Ser Thr Ala Ala Thr Thr Asn Asp
            260                 265                 270

Val Ala Gly Asp Trp Tyr Pro Ala Ser Trp Asn Gln Tyr Trp Cys Gly
            275                 280                 285

Pro His Tyr
    290

<210> SEQ ID NO 34
<211> LENGTH: 219
<212> TYPE: PRT
<213> ORGANISM: Ustilago maydis

<400> SEQUENCE: 34

Met Leu Ile Phe Ser Val Leu Met Tyr Leu Gly Leu Leu Leu Ala Gly
1               5                   10                  15

Ala Ser Ala Leu Pro Asn Gly Leu Ser Pro Arg Asn Asn Ala Phe Cys
            20                  25                  30

Ala Gly Phe Gly Leu Ser Cys Lys Trp Glu Cys Trp Cys Thr Ala His
            35                  40                  45

Gly Thr Gly Asn Glu Leu Arg Tyr Ala Thr Ala Ala Gly Cys Gly Asp
    50                  55                  60

His Leu Ser Lys Ser Tyr Tyr Asp Ala Arg Ala Gly His Cys Leu Phe
 65                  70                  75                  80

Ser Asp Asp Leu Arg Asn Gln Phe Tyr Ser His Cys Ser Ser Leu Asn
                 85                  90                  95

Asn Asn Met Ser Cys Arg Ser Leu Ser Lys Arg Thr Ile Gln Asp Ser
            100                 105                 110

Ala Thr Asp Thr Val Asp Leu Gly Ala Glu Leu His Arg Asp Asp Pro
        115                 120                 125

Pro Pro Thr Ala Ser Asp Ile Gly Lys Arg Gly Lys Arg Pro Arg Pro
    130                 135                 140

Val Met Cys Gln Cys Val Asp Thr Thr Asn Gly Gly Val Arg Leu Asp
145                 150                 155                 160

Ala Val Thr Arg Ala Ala Cys Ser Ile Asp Ser Phe Ile Asp Gly Tyr
                165                 170                 175

Tyr Thr Glu Lys Asp Gly Phe Cys Arg Ala Lys Tyr Ser Trp Asp Leu
            180                 185                 190

Phe Thr Ser Gly Gln Phe Tyr Gln Ala Cys Leu Arg Tyr Ser His Ala
        195                 200                 205

Gly Thr Asn Cys Gln Pro Asp Pro Gln Tyr Glu
    210                 215

<210> SEQ ID NO 35
<211> LENGTH: 316
<212> TYPE: PRT
<213> ORGANISM: Saccharomyces cerevisiae

<400> SEQUENCE: 35

Met Thr Lys Pro Thr Gln Val Leu Val Arg Ser Val Ser Ile Leu Phe
 1               5                  10                  15

Phe Ile Thr Leu Leu His Leu Val Val Ala Leu Asn Asp Val Ala Gly
                20                  25                  30

Pro Ala Glu Thr Ala Pro Val Ser Leu Leu Pro Arg Glu Ala Pro Trp
            35                  40                  45

Tyr Asp Lys Ile Trp Glu Val Lys Asp Trp Leu Leu Gln Arg Ala Thr
 50                  55                  60

Asp Gly Asn Trp Gly Lys Ser Ile Thr Trp Gly Ser Phe Val Ala Ser
 65                  70                  75                  80

Asp Ala Gly Val Val Ile Phe Gly Ile Asn Val Cys Lys Asn Cys Val
                85                  90                  95

Gly Glu Arg Lys Asp Asp Ile Ser Thr Asp Cys Gly Lys Gln Thr Leu
            100                 105                 110

Ala Leu Leu Val Ser Ile Phe Val Ala Val Thr Ser Gly His His Leu
        115                 120                 125

Ile Trp Gly Gly Asn Arg Pro Val Ser Gln Ser Asp Pro Asn Gly Ala
    130                 135                 140

Thr Val Ala Arg Arg Asp Ile Ser Thr Val Ala Asp Gly Asp Ile Pro
145                 150                 155                 160

Leu Asp Phe Ser Ala Leu Asn Asp Ile Leu Asn Glu His Gly Ile Ser
                165                 170                 175

Ile Leu Pro Ala Asn Ala Ser Gln Tyr Val Lys Arg Ser Asp Thr Ala
            180                 185                 190

Glu His Thr Thr Ser Phe Val Val Thr Asn Asn Tyr Thr Ser Leu His
        195                 200                 205

Thr Asp Leu Ile His His Gly Asn Gly Thr Tyr Thr Thr Phe Thr Thr
    210                 215                 220

```
Pro His Ile Pro Ala Val Ala Lys Arg Tyr Val Tyr Pro Met Cys Glu
225                 230                 235                 240

His Gly Ile Lys Ala Ser Tyr Cys Met Ala Leu Asn Asp Ala Met Val
            245                 250                 255

Ser Ala Asn Gly Asn Leu Tyr Gly Leu Ala Glu Lys Leu Phe Ser Glu
        260                 265                 270

Asp Glu Gly Gln Trp Glu Thr Asn Tyr Tyr Lys Leu Tyr Trp Ser Thr
    275                 280                 285

Gly Gln Trp Ile Met Ser Met Lys Phe Ile Glu Glu Ser Ile Asp Asn
290                 295                 300

Ala Asn Asn Asp Phe Glu Gly Cys Asp Thr Gly His
305                 310                 315

<210> SEQ ID NO 36
<211> LENGTH: 296
<212> TYPE: PRT
<213> ORGANISM: Saccharomyces cerevisiae

<400> SEQUENCE: 36

Met Gly His Leu Ala Ile Leu Phe Ser Ile Ile Ala Val Leu Asn Ile
1               5                   10                  15

Ala Thr Ala Val Ala Ser Ser Asp Ser Ile Tyr Leu Lys Gly His Arg
            20                  25                  30

Val Gly Gln Asp Ile Asp Ser Leu Tyr Arg Val Tyr Asp Asn Gly Thr
        35                  40                  45

Met Tyr Pro Val Thr Phe Asn Glu Trp Leu Asn Asp Leu Thr Gly Met
    50                  55                  60

Asn Asp Leu Ala Thr Asn Asn Ala Thr Ile Leu Lys Arg Asp Ser Ser
65                  70                  75                  80

Asp Val Ser Cys Val Thr Glu Thr Cys Gln Tyr Val Asp Tyr His Val
                85                  90                  95

Asp Asp Glu Gly Val Ile Thr Ile Asp Ile Ser Thr Tyr Arg Ile Pro
            100                 105                 110

Val Glu Trp Asp Ser Gly Ser Ala Gly Asn Ala Ser Tyr Gly Val Ser
        115                 120                 125

Lys Arg Asp Thr Lys Tyr Glu Thr Phe Cys Lys Lys Ile Cys Gly
    130                 135                 140

Ile Asn Val Ser Gly Phe Cys Asn Ala Tyr Asp Phe Ala Val His Ala
145                 150                 155                 160

Phe Asp Phe Gly Gly Ser Val Tyr Asn Pro Val Ser Gly Ile Thr Asp
                165                 170                 175

Arg Ile Lys Glu Ala Thr Lys Arg Asp Lys Thr Glu Cys Leu Gly Tyr
            180                 185                 190

Glu Leu Asp His Val Arg Ile Asp Pro Ala Val Asp Trp Ser Ile Ser
        195                 200                 205

Ile Ser Thr Trp Lys Gln Gly Ser Ala Asn Cys Asp Thr Gln Ala Ser
    210                 215                 220

Ala Asp Ser Leu Lys Cys Ala Ala Gln Lys Ala Leu Glu Ser Glu His
225                 230                 235                 240

Asn His Gln Lys Thr Ala Phe Cys Ile His Leu Asp Asn Gly Gly Ser
                245                 250                 255

Phe Asn Leu Asp Ile Arg Leu Ile Ser Glu Leu Ser Phe Ser Lys Tyr
            260                 265                 270

Asn Pro Trp Ala Leu Pro Cys Pro Lys Tyr Lys Gly Ser Asn Ser Trp
```

```
                275                 280                 285
Gln Val Val Ser Asp Cys Phe Gln
    290                 295

<210> SEQ ID NO 37
<211> LENGTH: 708
<212> TYPE: PRT
<213> ORGANISM: Saccharomyces cerevisiae

<400> SEQUENCE: 37

Met Pro Arg Phe Ala Ile Ile Phe Ala Leu Leu Ile Ala Tyr Ser Leu
1               5                   10                  15

Phe Leu Ser Thr Leu Phe Thr Gly Ser Ile Pro Asp Arg Ala Asn Thr
            20                  25                  30

Val Thr Ser Asn Ala Pro Cys Gln Val Val Ile Trp Asp Trp Ile Arg
        35                  40                  45

Thr Arg Arg Ile Cys Asn Cys Cys Ser Arg Leu Cys Tyr Ser Leu Leu
    50                  55                  60

Gly Arg Ser Asn Leu Ser Arg Thr Ala Lys Arg Gly Val Cys Thr Ile
65                  70                  75                  80

Ala Gly Ala Val Leu Ala Thr Ala Val Ile Val Ala Ala Val Leu
                85                  90                  95

Val Gly Lys Ser Ser Gly Ser Ala Thr Lys Arg Gly Leu Thr Lys Thr
            100                 105                 110

Ile Ser Val Leu Asn His Thr Ile Pro Phe Thr Asp His Ile Leu Asn
        115                 120                 125

Gly Gln Thr Leu Ser Asn Gly Thr Gly Ser Asn Phe Val Thr Ile Gly
    130                 135                 140

Phe Ser Gly Tyr Ala Val His Ala Thr Ile Lys Arg Ala Ser Thr Thr
145                 150                 155                 160

Asp Ile Ile Ser Trp Val Ile Pro Glu Ser Met Glu Pro Thr Leu Ala
                165                 170                 175

Arg Val Ala Ser Tyr Val Ser Ser Ser Ile Asn Leu Ala Ala Val
            180                 185                 190

Pro Asp Thr Gly Gly Asn Ala Ser Ala Leu Ser Phe Gln Asn Ala Val
        195                 200                 205

Gln Glu Phe Ala Thr Ser Trp Val Ser Met Thr Tyr Asp Gln Ser Tyr
    210                 215                 220

Gly Asp Leu Arg Asn Val Ala Asn Asp Glu Gly Gly Glu Ile Leu
225                 230                 235                 240

Ile Leu Met Arg Lys Arg Ser Tyr Arg Ile Ser Phe Gln Val Ile Glu
                245                 250                 255

Thr Gly Ser Thr Ala Leu Leu Leu Arg Thr Arg Arg Val Val Ser Gln
            260                 265                 270

Leu Ile Thr Met Thr Tyr Leu Val Thr Val Gln Ala Arg Val Gly Ile
        275                 280                 285

Gln Ile Gly Asp Ile Phe Gln His Tyr Gly Gly Ile Asp Asn Tyr Val
    290                 295                 300

Met Thr Ser Ile Ser Val Leu Arg Thr Leu Glu Asp Lys Ala Phe His
305                 310                 315                 320

Glu Asn Lys Leu Leu Ile Val Arg Glu Pro Pro Asn Lys Ser Asn Gln
                325                 330                 335

Asp Ala Asn Gln Ser Tyr Arg Leu Arg Pro Phe Ser Ala Asn Asp Leu
            340                 345                 350
```

```
Ile Gln Asn Leu Lys Ser Val Asp Ile Gly Phe Leu Ala Phe Cys Ser
            355                 360                 365

Phe Phe Asp Lys Tyr Ala His Tyr Pro Glu Ile Met Met Lys Ile
370                 375                 380

Thr Ile Phe Ile Ser Lys Gly Asn Leu Trp Ser Ile Ile Tyr Val Ile
385                 390                 395                 400

Gln Ala Arg Tyr Val Arg Lys Arg Val Met Lys Val Arg Gly Gln Met
                405                 410                 415

Pro Gly Gly Leu Leu Thr Asn Met Glu Ser Leu Leu Asn Ile Val Ser
            420                 425                 430

Thr Pro Asn Leu Asn Ile Ser Glu Phe His Ile Gln Thr His Ser Met
            435                 440                 445

Ser Gln Ser Lys Pro Met Tyr Phe Gln Lys Gln Cys Tyr Ser Ser Gln
450                 455                 460

Asn Asn Ile Ile Tyr Ile Tyr Asn Ser Ile His Ile Thr Cys Gly Ala
465                 470                 475                 480

Val Tyr Val Ile Val His Asp Val Arg Thr Pro Ser Val Phe Val Leu
                485                 490                 495

Ile Glu Leu Arg Asn Cys Lys Pro Leu Lys Asn Ser Trp Cys Glu Thr
                500                 505                 510

Thr Lys Thr Ser Pro Arg Asp Thr Lys Ile Lys Lys Asn Glu Tyr Asn
            515                 520                 525

Glu Thr Val Cys Arg Arg Ala Gly Ala Leu Leu Asp Gly Arg Val Arg
            530                 535                 540

Thr Ile Arg Phe Leu Met Met Arg Thr His Trp Ser Arg Val Lys Gly
545                 550                 555                 560

Val Ser Cys Asn Thr Ala Asn Arg Leu Ser Arg Phe Cys Asn His Val
                565                 570                 575

Val Ser Tyr Tyr Pro Ser Gln Asn Ala Thr Ile His Leu Leu Pro Thr
                580                 585                 590

Ser Leu Arg Ala Glu Ser Leu Glu Gln Gln Tyr Thr Thr Arg Pro Leu
            595                 600                 605

Ser Ser Ser Asn Asn Arg Phe Cys Cys Leu Lys Ser Ile Phe Ile Asn
610                 615                 620

Asn Cys Lys Lys Ala Cys Glu Ser Pro Ser Leu Val Ser Cys Asn Leu
625                 630                 635                 640

Gln Gln Thr Ala Glu Leu Leu Met Val Tyr Leu Tyr Ile Cys Glu
                645                 650                 655

Ala Cys Tyr Val Ser Arg Asn His Asp Leu Leu Ser Lys Gln Cys Met
                660                 665                 670

Ser Thr Val Arg Ala Val Tyr Val Ala Arg Met Arg Leu Pro Lys Phe
            675                 680                 685

Arg Ser Thr Phe Pro Cys Met Pro Arg Leu Cys Trp Leu Val Asn Gly
690                 695                 700

Val Val Val Val
705

<210> SEQ ID NO 38
<211> LENGTH: 768
<212> TYPE: PRT
<213> ORGANISM: Bacillus anthracis

<400> SEQUENCE: 38

Met His Val Lys Glu Lys Glu Lys Asn Lys Asp Glu Asn Lys Arg Lys
1               5                   10                  15
```

-continued

```
Asp Glu Glu Arg Asn Lys Thr Gln Glu His Leu Lys Glu Ile Met
             20                  25                  30
Lys His Ile Val Lys Ile Glu Val Lys Gly Glu Ala Val Lys Lys
             35                  40                  45
Glu Ala Glu Lys Leu Leu Glu Lys Val Pro Ser Asp Val Leu Glu
 50                  55                  60
Met Tyr Lys Ala Ile Gly Gly Lys Ile Tyr Ile Val Asp Gly Asp Ile
 65                  70                  75                  80
Thr Lys His Ile Ser Leu Glu Ala Leu Ser Glu Asp Lys Lys Ile
             85                  90                  95
Lys Asp Ile Tyr Gly Lys Asp Ala Leu Leu His Glu His Tyr Val Tyr
                     100                 105                 110
Ala Lys Glu Gly Tyr Glu Pro Val Leu Val Ile Gln Ser Ser Glu Asp
             115                 120                 125
Tyr Val Glu Asn Thr Glu Lys Ala Leu Asn Val Tyr Tyr Glu Ile Gly
             130                 135                 140
Lys Ile Leu Ser Arg Asp Ile Leu Ser Lys Ile Asn Gln Pro Tyr Gln
145                 150                 155                 160
Lys Phe Leu Asp Val Leu Asn Thr Ile Lys Asn Ala Ser Asp Ser Asp
                     165                 170                 175
Gly Gln Asp Leu Leu Phe Thr Asn Gln Leu Lys Glu His Pro Thr Asp
             180                 185                 190
Phe Ser Val Glu Phe Leu Glu Gln Asn Ser Asn Glu Val Gln Glu Val
             195                 200                 205
Phe Ala Lys Ala Phe Ala Tyr Tyr Ile Glu Pro Gln His Arg Asp Val
 210                 215                 220
Leu Gln Leu Tyr Ala Pro Glu Ala Phe Asn Tyr Met Asp Lys Phe Asn
225                 230                 235                 240
Glu Gln Glu Ile Asn Leu Ser Leu Glu Glu Leu Lys Asp Gln Arg Met
             245                 250                 255
Leu Ser Arg Tyr Glu Lys Trp Glu Lys Ile Lys Gln His Tyr Gln His
             260                 265                 270
Trp Ser Asp Ser Leu Ser Glu Glu Gly Arg Gly Leu Leu Lys Lys Leu
             275                 280                 285
Gln Ile Pro Ile Glu Pro Lys Lys Asp Asp Ile Ile His Ser Leu Ser
 290                 295                 300
Gln Glu Glu Lys Glu Leu Leu Lys Arg Ile Gln Ile Asp Ser Ser Asp
305                 310                 315                 320
Phe Leu Ser Thr Glu Lys Glu Phe Leu Lys Lys Leu Gln Ile Asp
             325                 330                 335
Ile Arg Asp Ser Leu Ser Glu Glu Lys Glu Leu Leu Asn Arg Ile
             340                 345                 350
Gln Val Asp Ser Ser Asn Pro Leu Ser Glu Lys Glu Lys Glu Phe Leu
             355                 360                 365
Lys Lys Leu Lys Leu Asp Ile Gln Pro Tyr Asp Ile Asn Gln Arg Leu
 370                 375                 380
Gln Asp Thr Gly Gly Leu Ile Asp Ser Pro Ser Ile Asn Leu Asp Val
385                 390                 395                 400
Arg Lys Gln Tyr Lys Arg Asp Ile Gln Asn Ile Asp Ala Leu Leu His
                     405                 410                 415
Gln Ser Ile Gly Ser Thr Leu Tyr Asn Lys Ile Tyr Leu Tyr Glu Asn
             420                 425                 430
```

```
Met Asn Ile Asn Asn Leu Thr Ala Thr Leu Gly Ala Asp Leu Val Asp
            435                 440                 445

Ser Thr Asp Asn Thr Lys Ile Asn Arg Gly Ile Phe Asn Glu Phe Lys
    450                 455                 460

Lys Asn Phe Lys Tyr Ser Ile Ser Ser Asn Tyr Met Ile Val Asp Ile
465                 470                 475                 480

Asn Glu Arg Pro Ala Leu Asp Asn Glu Arg Leu Lys Trp Arg Ile Gln
                485                 490                 495

Leu Ser Pro Asp Thr Arg Ala Gly Tyr Leu Glu Asn Gly Lys Leu Ile
            500                 505                 510

Leu Gln Arg Asn Ile Gly Leu Glu Ile Lys Asp Val Gln Ile Ile Lys
        515                 520                 525

Gln Ser Glu Lys Glu Tyr Ile Arg Ile Asp Ala Lys Val Val Pro Lys
    530                 535                 540

Ser Lys Ile Asp Thr Lys Ile Gln Glu Ala Gln Leu Asn Ile Asn Gln
545                 550                 555                 560

Glu Trp Asn Lys Ala Leu Gly Leu Pro Lys Tyr Thr Lys Leu Ile Thr
                565                 570                 575

Phe Asn Val His Asn Arg Tyr Ala Ser Asn Ile Val Glu Ser Ala Tyr
            580                 585                 590

Leu Ile Leu Asn Glu Trp Lys Asn Asn Ile Gln Ser Asp Leu Ile Lys
        595                 600                 605

Lys Val Thr Asn Tyr Leu Val Asp Gly Asn Gly Arg Phe Val Phe Thr
    610                 615                 620

Asp Ile Thr Leu Pro Asn Ile Ala Glu Gln Tyr Thr His Gln Asp Glu
625                 630                 635                 640

Ile Tyr Glu Gln Val His Ser Lys Gly Leu Tyr Val Pro Glu Ser Arg
                645                 650                 655

Ser Ile Leu Leu His Gly Pro Ser Lys Gly Val Glu Leu Arg Asn Asp
            660                 665                 670

Ser Glu Gly Phe Ile His Glu Phe Gly His Ala Val Asp Asp Tyr Ala
        675                 680                 685

Gly Tyr Leu Leu Asp Lys Asn Gln Ser Asp Leu Val Thr Asn Ser Lys
    690                 695                 700

Lys Phe Ile Asp Ile Phe Lys Glu Glu Gly Ser Asn Leu Thr Ser Tyr
705                 710                 715                 720

Gly Arg Thr Asn Glu Ala Glu Phe Phe Ala Glu Ala Phe Arg Leu Met
                725                 730                 735

His Ser Thr Asp His Ala Glu Arg Leu Lys Val Gln Lys Asn Ala Pro
            740                 745                 750

Lys Thr Phe Gln Phe Ile Asn Asp Gln Ile Lys Phe Ile Ile Asn Ser
        755                 760                 765

<210> SEQ ID NO 39
<211> LENGTH: 319
<212> TYPE: PRT
<213> ORGANISM: Unknown
<220> FEATURE:
<223> OTHER INFORMATION: Description of Unknown:
      Shiga toxin sequence

<400> SEQUENCE: 39

Met Lys Cys Ile Leu Leu Lys Trp Val Leu Cys Leu Leu Leu Gly Phe
1               5                   10                  15

Ser Ser Val Ser Tyr Ser Arg Glu Phe Thr Ile Asp Phe Ser Thr Gln
                20                  25                  30
```

Gln Ser Tyr Val Ser Ser Leu Asn Ser Ile Arg Thr Glu Ile Ser Thr
                35                  40                  45

Pro Leu Glu His Ile Ser Gln Gly Thr Thr Ser Val Ser Val Ile Asn
 50                  55                  60

His Thr Pro Pro Gly Ser Tyr Phe Ala Val Asp Ile Arg Gly Leu Asp
 65                  70                  75                  80

Val Tyr Gln Ala Arg Phe Asp His Leu Arg Leu Ile Ile Glu Gln Asn
                 85                  90                  95

Asn Leu Tyr Val Ala Gly Phe Val Asn Thr Ala Thr Asn Thr Phe Tyr
                100                 105                 110

Arg Phe Ser Asp Phe Ala His Ile Ser Val Pro Gly Val Thr Thr Val
                115                 120                 125

Ser Met Thr Thr Asp Ser Ser Tyr Thr Thr Leu Gln Arg Val Ala Ala
                130                 135                 140

Leu Glu Arg Ser Gly Met Gln Ile Ser Arg His Ser Leu Val Ser Ser
145                 150                 155                 160

Tyr Leu Ala Leu Met Glu Phe Ser Gly Asn Thr Met Thr Arg Asp Ala
                165                 170                 175

Ser Arg Ala Val Leu Arg Phe Val Thr Val Thr Ala Glu Ala Leu Arg
                180                 185                 190

Phe Arg Gln Ile Gln Arg Glu Phe Arg Gln Ala Leu Ser Glu Thr Ala
                195                 200                 205

Pro Val Tyr Thr Met Thr Pro Gly Asp Val Asp Leu Thr Leu Asn Trp
                210                 215                 220

Gly Arg Ile Ser Asn Val Leu Pro Glu Tyr Arg Gly Glu Asp Gly Val
225                 230                 235                 240

Arg Val Gly Arg Ile Ser Phe Asn Asn Ile Ser Ala Ile Leu Gly Thr
                245                 250                 255

Val Ala Val Ile Leu Asn Cys His His Gln Gly Ala Arg Ser Val Arg
                260                 265                 270

Ala Val Asn Glu Glu Ser Gln Pro Glu Cys Gln Ile Thr Gly Asp Arg
                275                 280                 285

Pro Val Ile Lys Ile Asn Asn Thr Leu Trp Glu Ser Asn Thr Ala Ala
                290                 295                 300

Ala Phe Leu Asn Arg Lys Ser Gln Ser Leu Tyr Thr Thr Gly Glu
305                 310                 315

<210> SEQ ID NO 40
<211> LENGTH: 299
<212> TYPE: PRT
<213> ORGANISM: Saponaria officinalis

<400> SEQUENCE: 40

Met Lys Ser Trp Ile Met Leu Val Val Thr Trp Leu Ile Ile Leu Gln
1                5                  10                  15

Thr Thr Val Thr Ala Val Ile Ile Tyr Glu Leu Asn Leu Gln Gly Thr
                20                  25                  30

Thr Lys Ala Gln Tyr Ser Thr Phe Leu Lys Gln Leu Arg Asp Asp Ile
            35                  40                  45

Lys Asp Pro Asn Leu His Tyr Gly Gly Thr Asn Leu Pro Val Ile Lys
        50                  55                  60

Arg Pro Val Gly Pro Lys Phe Leu Arg Val Asn Leu Lys Ala Ser
65                  70                  75                  80

Thr Gly Thr Val Ser Leu Ala Val Gln Arg Ser Asn Leu Tyr Val Ala

```
            85                  90                  95
Ala Tyr Leu Ala Lys Asn Asn Lys Gln Phe Arg Ala Tyr Tyr Phe
            100                 105                 110

Lys Gly Phe Gln Ile Thr Thr Asn Gln Leu Asn Leu Phe Pro Glu
            115                 120                 125

Ala Thr Gly Val Ser Asn Gln Glu Leu Gly Tyr Gly Glu Ser Tyr
            130                 135                 140

Pro Gln Ile Gln Asn Ala Ala Gly Val Thr Arg Gln Gln Ala Gly Leu
145                 150                 155                 160

Gly Ile Lys Lys Leu Ala Glu Ser Met Thr Lys Val Asn Gly Val Ala
                165                 170                 175

Arg Val Glu Lys Asp Glu Ala Leu Phe Leu Leu Ile Val Val Gln Met
                180                 185                 190

Val Gly Glu Ala Ala Arg Phe Lys Tyr Ile Glu Asn Leu Val Leu Asn
                195                 200                 205

Asn Phe Asp Thr Ala Lys Glu Val Glu Pro Val Pro Asp Arg Val Ile
210                 215                 220

Ile Leu Glu Asn Asn Trp Gly Leu Leu Ser Arg Ala Ala Lys Thr Ala
225                 230                 235                 240

Asn Asn Gly Val Phe Gln Thr Pro Leu Val Leu Thr Ser Tyr Ala Val
                245                 250                 255

Pro Gly Val Glu Trp Arg Val Thr Thr Val Ala Glu Val Glu Ile Gly
                260                 265                 270

Ile Phe Leu Asn Val Asp Asn Asn Gly Leu Pro Ser Ile Ile Tyr Asn
                275                 280                 285

Asn Ile Ile Ser Gly Ala Phe Gly Asp Thr Tyr
                290                 295
```

<210> SEQ ID NO 41
<211> LENGTH: 565
<212> TYPE: PRT
<213> ORGANISM: Saponaria officinalis

<400> SEQUENCE: 41

```
Met Tyr Ala Val Ala Thr Trp Leu Cys Phe Gly Ser Thr Ser Gly Trp
1               5                   10                  15

Ser Phe Thr Leu Glu Asp Asn Asn Ile Phe Pro Lys Gln Tyr Pro Ile
                20                  25                  30

Ile Asn Phe Thr Thr Ala Gly Ala Thr Val Gln Ser Tyr Thr Asn Phe
                35                  40                  45

Ile Arg Ala Val Arg Gly Arg Leu Thr Thr Gly Ala Asp Val Arg His
                50                  55                  60

Asp Ile Pro Val Leu Pro Asn Arg Val Gly Leu Pro Ile Asn Gln Arg
65                  70                  75                  80

Phe Ile Leu Val Glu Leu Ser Asn His Ala Glu Leu Ser Val Thr Leu
                85                  90                  95

Ala Leu Asp Val Thr Asn Ala Tyr Val Val Gly Tyr Arg Ala Gly Asn
                100                 105                 110

Ser Ala Tyr Phe Phe His Pro Asp Asn Gln Glu Asp Ala Glu Ala Ile
                115                 120                 125

Thr His Leu Phe Thr Asp Val Gln Asn Arg Tyr Thr Phe Ala Phe Gly
                130                 135                 140

Gly Asn Tyr Asp Arg Leu Glu Gln Leu Ala Gly Asn Leu Arg Glu Asn
145                 150                 155                 160
```

```
Ile Glu Leu Gly Asn Gly Pro Leu Glu Glu Ala Ile Ser Ala Leu Tyr
                165                 170                 175

Tyr Tyr Ser Thr Gly Gly Thr Gln Leu Pro Thr Leu Ala Arg Ser Phe
            180                 185                 190

Ile Ile Cys Ile Gln Met Ile Ser Glu Ala Ala Arg Phe Gln Tyr Ile
        195                 200                 205

Glu Gly Glu Met Arg Thr Arg Ile Arg Tyr Asn Arg Arg Ser Ala Pro
    210                 215                 220

Asp Pro Ser Val Ile Thr Leu Glu Asn Ser Trp Gly Arg Leu Ser Thr
225                 230                 235                 240

Ala Ile Gln Glu Ser Asn Gln Gly Ala Phe Ala Ser Pro Ile Gln Leu
                245                 250                 255

Gln Arg Arg Asn Gly Ser Lys Phe Ser Val Tyr Asp Val Ser Ile Leu
            260                 265                 270

Ile Pro Ile Ile Ala Leu Met Val Tyr Arg Cys Ala Pro Pro Pro Ser
        275                 280                 285

Ser Gln Phe Ser Leu Leu Ile Arg Pro Val Val Pro Asn Phe Asn Ala
    290                 295                 300

Asp Val Cys Met Asp Pro Glu Pro Ile Val Arg Ile Val Gly Arg Asn
305                 310                 315                 320

Gly Leu Cys Val Asp Val Arg Asp Gly Arg Phe His Asn Gly Asn Ala
                325                 330                 335

Ile Gln Leu Trp Pro Cys Lys Ser Asn Thr Asp Ala Asn Gln Leu Trp
            340                 345                 350

Thr Leu Lys Arg Asp Asn Thr Ile Arg Ser Asn Gly Lys Cys Leu Thr
        355                 360                 365

Thr Tyr Gly Tyr Ser Pro Gly Val Tyr Val Met Ile Tyr Asp Cys Asn
    370                 375                 380

Thr Ala Ala Thr Asp Ala Thr Arg Trp Gln Ile Trp Asp Asn Gly Thr
385                 390                 395                 400

Ile Ile Asn Pro Arg Ser Ser Leu Val Leu Ala Ala Thr Ser Gly Asn
                405                 410                 415

Ser Gly Thr Thr Leu Thr Val Gln Thr Asn Ile Tyr Ala Val Ser Gln
            420                 425                 430

Gly Trp Leu Pro Thr Asn Asn Thr Gln Pro Phe Val Thr Thr Ile Val
        435                 440                 445

Gly Leu Tyr Gly Leu Cys Leu Gln Ala Asn Ser Gly Gln Val Trp Ile
    450                 455                 460

Glu Asp Cys Ser Ser Glu Lys Ala Glu Gln Gln Trp Ala Leu Tyr Ala
465                 470                 475                 480

Asp Gly Ser Ile Arg Pro Gln Gln Asn Arg Asp Asn Cys Leu Thr Ser
                485                 490                 495

Asp Ser Asn Ile Arg Glu Thr Val Val Lys Ile Leu Ser Cys Gly Pro
            500                 505                 510

Ala Ser Ser Gly Gln Arg Trp Met Phe Lys Asn Asp Gly Thr Ile Leu
        515                 520                 525

Asn Leu Tyr Ser Gly Leu Val Leu Asp Val Arg Arg Ser Asp Pro Ser
    530                 535                 540

Leu Lys Gln Ile Ile Leu Tyr Pro Leu His Gly Asp Pro Asn Gln Ile
545                 550                 555                 560

Trp Leu Pro Leu Phe
                565
```

<210> SEQ ID NO 42
<211> LENGTH: 730
<212> TYPE: PRT
<213> ORGANISM: Galerina marginata

<400> SEQUENCE: 42

```
Met Ser Ser Val Thr Trp Ala Pro Gly Asn Tyr Pro Ser Thr Arg Arg
1               5                   10                  15

Ser Asp His Val Asp Thr Tyr Gln Ser Ala Ser Lys Gly Glu Val Pro
            20                  25                  30

Val Pro Asp Pro Tyr Gln Trp Leu Glu Glu Ser Thr Asp Glu Val Asp
        35                  40                  45

Lys Trp Thr Thr Ala Gln Ala Asp Leu Ala Gln Ser Tyr Leu Asp Gln
    50                  55                  60

Asn Ala Asp Ile Gln Lys Leu Ala Glu Lys Phe Arg Ala Ser Arg Asn
65                  70                  75                  80

Tyr Ala Lys Phe Ser Ala Pro Thr Leu Leu Asp Asp Gly His Trp Tyr
                85                  90                  95

Trp Phe Tyr Asn Arg Gly Leu Gln Ser Gln Ser Val Leu Tyr Arg Ser
            100                 105                 110

Lys Glu Pro Ala Leu Pro Asp Phe Ser Lys Gly Asp Asp Asn Val Gly
        115                 120                 125

Asp Val Phe Phe Asp Pro Asn Val Leu Ala Ala Asp Gly Ser Ala Gly
    130                 135                 140

Met Val Leu Cys Lys Phe Ser Pro Asp Gly Lys Phe Phe Ala Tyr Ala
145                 150                 155                 160

Val Ser His Leu Gly Gly Asp Tyr Ser Thr Ile Tyr Val Arg Ser Thr
                165                 170                 175

Ser Ser Pro Leu Ser Gln Ala Ser Val Ala Gln Gly Val Asp Gly Arg
            180                 185                 190

Leu Ser Asp Glu Val Lys Trp Phe Lys Phe Ser Thr Ile Ile Trp Thr
        195                 200                 205

Lys Asp Ser Lys Gly Phe Leu Tyr Gln Arg Tyr Pro Ala Arg Glu Arg
    210                 215                 220

His Glu Gly Thr Arg Ser Asp Arg Asn Ala Met Met Cys Tyr His Lys
225                 230                 235                 240

Val Gly Thr Thr Gln Glu Glu Asp Ile Ile Val Tyr Gln Asp Asn Glu
                245                 250                 255

His Pro Glu Trp Ile Tyr Gly Ala Asp Thr Ser Glu Asp Gly Lys Tyr
            260                 265                 270

Leu Tyr Leu Tyr Gln Phe Lys Asp Thr Ser Lys Lys Asn Leu Leu Trp
        275                 280                 285

Val Ala Glu Leu Asp Glu Asp Gly Val Lys Ser Gly Ile His Trp Arg
    290                 295                 300

Lys Val Val Asn Glu Tyr Ala Ala Asp Tyr Asn Ile Ile Thr Asn His
305                 310                 315                 320

Gly Ser Leu Val Tyr Ile Lys Thr Asn Leu Asn Ala Pro Gln Tyr Lys
                325                 330                 335

Val Ile Thr Ile Asp Leu Ser Lys Asp Glu Pro Glu Ile Arg Asp Phe
            340                 345                 350

Ile Pro Glu Glu Lys Asp Ala Lys Leu Ala Gln Val Asn Cys Ala Asn
        355                 360                 365

Glu Glu Tyr Phe Val Ala Ile Tyr Lys Arg Asn Val Lys Asp Glu Ile
    370                 375                 380
```

```
Tyr Leu Tyr Ser Lys Ala Gly Val Gln Leu Thr Arg Leu Ala Pro Asp
385                 390                 395                 400

Phe Val Gly Ala Ala Ser Ile Ala Asn Arg Gln Lys Gln Thr His Phe
            405                 410                 415

Phe Leu Thr Leu Ser Gly Phe Asn Thr Pro Gly Thr Ile Ala Arg Tyr
        420                 425                 430

Asp Phe Thr Ala Pro Glu Thr Gln Arg Phe Ser Ile Leu Arg Thr Thr
    435                 440                 445

Lys Val Asn Glu Leu Asp Pro Asp Phe Glu Ser Thr Gln Val Trp
450                 455                 460

Tyr Glu Ser Lys Asp Gly Thr Lys Ile Pro Met Phe Ile Val Arg His
465                 470                 475                 480

Lys Ser Thr Lys Phe Asp Gly Thr Ala Ala Ile Gln Tyr Gly Tyr
            485                 490                 495

Gly Gly Phe Ala Thr Ser Ala Asp Pro Phe Phe Ser Pro Ile Ile Leu
            500                 505                 510

Thr Phe Leu Gln Thr Tyr Gly Ala Ile Phe Ala Val Pro Ser Ile Arg
        515                 520                 525

Gly Gly Gly Glu Phe Gly Glu Glu Trp His Lys Gly Arg Arg Glu
530                 535                 540

Thr Lys Val Asn Thr Phe Asp Asp Phe Ile Ala Ala Ala Gln Phe Leu
545                 550                 555                 560

Val Lys Asn Lys Tyr Ala Ala Pro Gly Lys Val Ala Ile Asn Gly Ala
            565                 570                 575

Ser Asn Gly Gly Leu Leu Val Met Gly Ser Ile Val Arg Ala Pro Glu
            580                 585                 590

Gly Thr Phe Gly Ala Ala Val Pro Glu Gly Gly Val Ala Asp Leu Leu
            595                 600                 605

Lys Phe His Lys Phe Thr Gly Gly Gln Ala Trp Ile Ser Glu Tyr Gly
            610                 615                 620

Asn Pro Ser Ile Pro Glu Glu Phe Asp Tyr Ile Tyr Pro Leu Ser Pro
625                 630                 635                 640

Val His Asn Val Arg Thr Asp Lys Val Met Pro Ala Thr Leu Ile Thr
            645                 650                 655

Val Asn Ile Gly Asp Gly Arg Val Val Pro Met His Ser Phe Lys Phe
            660                 665                 670

Ile Ala Thr Leu Gln His Asn Val Pro Gln Asn Pro His Pro Leu Leu
        675                 680                 685

Ile Lys Ile Asp Lys Ser Trp Leu Gly His Gly Met Gly Lys Pro Thr
        690                 695                 700

Asp Lys Asn Val Lys Asp Ala Ala Asp Lys Trp Gly Phe Ile Ala Arg
705                 710                 715                 720

Ala Leu Gly Leu Glu Leu Lys Thr Val Glu
            725                 730

<210> SEQ ID NO 43
<211> LENGTH: 730
<212> TYPE: PRT
<213> ORGANISM: Amanita bisporigera

<400> SEQUENCE: 43

Met Pro Pro Thr Pro Trp Ala Pro His Ser Tyr Pro Pro Thr Arg Arg
1               5                   10                  15

Ser Asp His Val Asp Val Tyr Gln Ser Ala Ser Arg Gly Glu Val Pro
            20                  25                  30
```

```
Val Pro Asp Pro Tyr Gln Trp Leu Glu Glu Asn Ser Asn Glu Val Asp
         35                  40                  45
Glu Trp Thr Thr Ala Gln Thr Ala Phe Thr Gln Gly Tyr Leu Asp Lys
 50                      55                  60
Asn Ala Asp Arg Gln Lys Leu Glu Glu Lys Phe Arg Ala Ser Lys Asp
 65                  70                  75                  80
Tyr Val Lys Phe Ser Ala Pro Thr Leu Leu Asp Ser Gly His Trp Tyr
                 85                  90                  95
Trp Phe Tyr Asn Ser Gly Val Gln Ser Gln Ala Val Leu Tyr Arg Ser
                100                 105                 110
Lys Lys Pro Val Leu Pro Asp Phe Gln Arg Gly Thr Arg Lys Val Gly
                115                 120                 125
Glu Val Tyr Phe Asp Pro Asn Val Leu Ser Ala Asp Gly Thr Ala Ile
130                 135                 140
Met Gly Thr Cys Arg Phe Ser Pro Ser Gly Glu Tyr Phe Ala Tyr Ala
145                 150                 155                 160
Val Ser His Leu Gly Val Asp Tyr Phe Thr Ile Tyr Val Arg Pro Thr
                165                 170                 175
Ser Ser Ser Leu Ser Gln Ala Pro Glu Ala Glu Gly Gly Asp Gly Arg
                180                 185                 190
Leu Ser Asp Gly Val Lys Trp Cys Lys Phe Thr Thr Ile Thr Trp Thr
                195                 200                 205
Lys Asp Ser Lys Gly Phe Leu Tyr Gln Arg Tyr Pro Ala Arg Glu Ser
                210                 215                 220
Leu Val Ala Lys Asp Arg Asp Lys Asp Ala Met Val Cys Tyr His Arg
225                 230                 235                 240
Val Gly Thr Thr Gln Leu Glu Asp Ile Ile Val Gln Gln Asp Lys Glu
                245                 250                 255
Asn Pro Asp Trp Thr Tyr Gly Thr Asp Ala Ser Glu Asp Gly Lys Tyr
                260                 265                 270
Ile Tyr Leu Val Val Tyr Lys Asp Ala Ser Lys Gln Asn Leu Leu Trp
            275                 280                 285
Val Ala Glu Phe Asp Lys Asp Gly Val Lys Pro Glu Ile Pro Trp Arg
        290                 295                 300
Lys Val Ile Asn Glu Phe Gly Ala Asp Tyr His Val Ile Thr Asn His
305                 310                 315                 320
Gly Ser Leu Ile Tyr Val Lys Thr Asn Val Asn Ala Pro Gln Tyr Lys
                325                 330                 335
Val Val Thr Ile Asp Leu Ser Thr Gly Glu Pro Glu Ile Arg Asp Phe
                340                 345                 350
Ile Pro Glu Gln Lys Asp Ala Lys Leu Thr Gln Val Lys Cys Val Asn
                355                 360                 365
Lys Gly Tyr Phe Val Ala Ile Tyr Lys Arg Asn Val Lys Asp Glu Ile
                370                 375                 380
Tyr Leu Tyr Ser Lys Ala Gly Asp Gln Leu Ser Arg Leu Ala Ser Asp
385                 390                 395                 400
Phe Ile Gly Val Ala Ser Ile Thr Asn Arg Glu Lys Gln Pro His Ser
                405                 410                 415
Phe Leu Thr Phe Ser Gly Phe Asn Thr Pro Gly Thr Ile Ser Arg Tyr
                420                 425                 430
Asp Phe Thr Ala Pro Asp Thr Gln Arg Leu Ser Ile Leu Arg Thr Thr
            435                 440                 445
```

-continued

```
Lys Leu Asn Gly Leu Asn Ala Asp Asp Phe Glu Ser Thr Gln Val Trp
    450                 455                 460

Tyr Lys Ser Lys Asp Gly Thr Lys Val Pro Met Phe Ile Val Arg His
465                 470                 475                 480

Lys Ser Thr Lys Phe Asp Gly Thr Ala Pro Ala Ile Gln Asn Gly Tyr
                485                 490                 495

Gly Gly Phe Ala Ile Thr Ala Asp Pro Phe Phe Ser Pro Ile Met Leu
            500                 505                 510

Thr Phe Met Gln Thr Tyr Gly Ala Ile Leu Ala Val Pro Asn Ile Arg
        515                 520                 525

Gly Gly Gly Glu Phe Gly Gly Glu Trp His Lys Ala Gly Arg Arg Glu
    530                 535                 540

Thr Lys Gly Asn Thr Phe Asp Asp Phe Ile Ala Ala Gln Phe Leu
545                 550                 555                 560

Val Lys Asn Lys Tyr Ala Ala Pro Gly Lys Val Ala Ile Thr Gly Ala
                565                 570                 575

Ser Asn Gly Gly Phe Leu Val Cys Gly Ser Val Val Arg Ala Pro Glu
            580                 585                 590

Gly Thr Phe Gly Ala Ala Val Ser Glu Gly Gly Val Ala Asp Leu Leu
        595                 600                 605

Lys Phe Asn Lys Phe Thr Gly Gly Met Ala Trp Thr Ser Glu Tyr Gly
    610                 615                 620

Asn Pro Phe Ile Lys Glu Asp Phe Asp Phe Val Gln Ala Leu Ser Pro
625                 630                 635                 640

Val His Asn Val Pro Lys Asp Arg Val Leu Pro Ala Thr Leu Leu Met
                645                 650                 655

Thr Asn Ala Gly Asp Asp Arg Val Val Pro Met His Ser Leu Lys Phe
            660                 665                 670

Val Ala Asn Leu Gln Tyr Asn Val Pro Gln Asn Pro His Pro Leu Leu
        675                 680                 685

Ile Arg Val Asp Lys Ser Trp Leu Gly His Gly Phe Gly Lys Thr Thr
    690                 695                 700

Asp Lys His Thr Lys Asp Ala Ala Asp Lys Trp Ser Phe Val Ala Gln
705                 710                 715                 720

Ser Leu Gly Leu Glu Trp Lys Thr Val Asp
                725                 730
```

<210> SEQ ID NO 44
<211> LENGTH: 734
<212> TYPE: PRT
<213> ORGANISM: Hypsizygus marmoreus

<400> SEQUENCE: 44

```
Met Ala Ile Ser Pro Thr Pro Trp Thr Pro Asn Thr Tyr Pro Pro Thr
1               5                   10                  15

Arg Arg Ser Ser His Val Asp Ile Tyr Lys Ser Ala Thr Arg Gly Glu
            20                  25                  30

Val Arg Val Ala Asp Pro Tyr Gln Trp Leu Glu Glu Asn Thr Glu Glu
        35                  40                  45

Thr Asp Lys Trp Thr Thr Ala Gln Glu Glu Phe Thr Arg Ser Tyr Leu
    50                  55                  60

Asp Lys Asn Thr Asp Arg Gln Arg Leu Glu Ala Phe Arg Thr Ser
65                  70                  75                  80

Thr Asp Tyr Ala Lys Phe Ser Ser Pro Thr Leu Tyr Glu Asp Gly Arg
                85                  90                  95
```

Trp Tyr Trp Phe Tyr Asn Ser Gly Leu Gln Pro Gln Pro Leu Ile Tyr
                100                 105                 110

Arg Ser Lys Gly Lys Thr Leu Pro Asp Phe Ser Gln Asp Asp Asn Val
            115                 120                 125

Val Gly Glu Val Phe Phe Asp Pro Asn Leu Leu Ser Asp Asp Gly Thr
        130                 135                 140

Ala Ala Leu Ser Ile Tyr Asp Phe Ser Asp Cys Gly Lys Tyr Phe Ala
145                 150                 155                 160

Tyr Gly Ile Ser Phe Ser Gly Ser Asp Phe Ser Thr Ile Tyr Val Arg
                165                 170                 175

Ser Thr Glu Ser Pro Leu Ala Lys Lys Asn Ser Gly Ser Thr Asp Asp
            180                 185                 190

Asp Arg Leu Ser Asp Glu Ile Lys His Val Lys Phe Ser Ala Val Thr
        195                 200                 205

Trp Thr Lys Asp Ser Lys Gly Phe Phe Tyr Gln Arg Tyr Pro Ala His
        210                 215                 220

Glu Asn Ala Lys Glu Gly Ile Glu Thr Gly Gly Asp Val Asp Ala Met
225                 230                 235                 240

Ile Tyr Tyr His Val Ile Gly Thr Ser Gln Ser Glu Asp Ile Leu Val
                245                 250                 255

His Ser Asp Lys Ser Asn Pro Glu Trp Met Trp Ser Ile Asp Ile Thr
            260                 265                 270

Glu Asp Gly Lys Tyr Leu Ile Leu Tyr Thr Met Lys Asp Ser Ser Arg
        275                 280                 285

Lys Asn Leu Met Trp Ile Ala Glu Leu Ser Lys Asn Glu Ile Gly Pro
        290                 295                 300

Asn Ile Gln Trp Asn Lys Ile Ile Asp Val Phe Asp Ala Glu Tyr His
305                 310                 315                 320

Leu Ile Thr Asn Asp Gly Pro Ile Leu Tyr Val Lys Thr Asn Ala Asp
                325                 330                 335

Ala Pro Gln Tyr Lys Leu Val Thr Met Asp Ile Ser Gly Asp Lys Asp
            340                 345                 350

Ile Ser Arg Asp Leu Ile Pro Glu Asp Lys Asn Ala Asn Leu Val Gln
        355                 360                 365

Val Asp Cys Val Asn Arg Asp Thr Phe Ala Val Ile Tyr Lys Arg Asn
        370                 375                 380

Val Lys Asp Glu Ile Tyr Leu Tyr Ser Lys Thr Gly Ile Gln Leu Ser
385                 390                 395                 400

Arg Leu Ala Ser Asp Phe Val Gly Ala Ala Ser Ile Ser Ser Arg Glu
                405                 410                 415

Lys Gln Pro His Phe Phe Val Thr Met Thr Gly Phe Ser Thr Pro Gly
            420                 425                 430

Thr Val Ala Arg Tyr Asp Phe Gly Ala Pro Glu Glu Gln Arg Trp Ser
        435                 440                 445

Ile Tyr Arg Ser Val Lys Val Asn Gly Leu Asn Pro Asp Asp Phe Glu
        450                 455                 460

Ser Lys Gln Val Trp Tyr Glu Ser Lys Asp Gly Thr Lys Ile Pro Met
465                 470                 475                 480

Phe Ile Val Arg His Lys Ala Thr Lys Phe Asp Gly Thr Ala Pro Ala
                485                 490                 495

Ile Gln Tyr Gly Tyr Gly Gly Phe Ser Ile Ser Ile Asn Pro Phe Phe
            500                 505                 510

```
Ser Pro Thr Ile Leu Thr Phe Leu Gln Thr Tyr Gly Ala Val Leu Ala
            515                 520                 525

Val Pro Asn Ile Arg Gly Gly Ala Glu Phe Gly Glu Asp Trp His Lys
530                 535                 540

Ala Gly Thr Arg Glu Lys Lys Gly Asn Val Phe Asp Asp Phe Val Ala
545                 550                 555                 560

Ala Thr Gln Tyr Leu Val Lys Asn Lys Tyr Ala Gly Glu Gly Lys Val
            565                 570                 575

Ala Ile Asn Gly Gly Ser Asn Gly Gly Leu Leu Val Gly Ala Cys Ile
                580                 585                 590

Asn Arg Ala Pro Glu Gly Thr Phe Gly Ala Val Ala Glu Val Gly
            595                 600                 605

Val Met Asp Leu Leu Lys Phe Ser Lys Phe Thr Ile Gly Lys Ala Trp
610                 615                 620

Thr Ser Asp Tyr Gly Asp Pro Asp Pro Lys Asp Phe Asp Phe Ile
625                 630                 635                 640

Cys Pro Leu Ser Pro Leu His Asn Ile Pro Thr Asp Arg Val Leu Pro
            645                 650                 655

Pro Thr Met Leu Leu Thr Ala Asp His Asp Asp Arg Val Val Pro Met
            660                 665                 670

His Ser Phe Lys His Ala Ala Thr Leu Gln Tyr Thr Leu Pro His Asn
            675                 680                 685

Pro His Pro Leu Val Ile Arg Ile Asp Lys Lys Ala Gly His Gly Ala
            690                 695                 700

Gly Lys Ser Thr Glu Lys Arg Ile Lys Glu Ser Ala Asp Lys Trp Gly
705                 710                 715                 720

Phe Val Ala Gln Ser Leu Gly Leu Val Trp Gln Glu Pro Ala
                725                 730

<210> SEQ ID NO 45
<211> LENGTH: 733
<212> TYPE: PRT
<213> ORGANISM: Conocybe apala

<400> SEQUENCE: 45

Met Pro Pro Ser Thr Pro Asn Glu Tyr Pro Pro Thr Arg Arg Ser Asp
1               5                   10                  15

Asp Val Leu Thr Tyr Arg Ser Glu Lys Asn Gly Glu Val Val Val Pro
            20                  25                  30

Asp Pro Tyr Gln Trp Leu Glu His Asn Thr Glu Glu Thr Asp Lys Trp
        35                  40                  45

Thr Thr Ala Gln Ala Ala Phe Thr Arg Ala His Leu Asp Lys Asn Pro
    50                  55                  60

Lys Arg Asn Ala Leu Glu Ala Phe Thr Ala Asn Asp Tyr Ala
65                  70                  75                  80

Lys Phe Ser Ala Pro Gln Leu His Asp Asp Gly Arg Trp Tyr Trp Tyr
                85                  90                  95

Tyr Asn Thr Gly Leu Gln Ala Gln Thr Cys Leu Trp Arg Thr Arg Asp
            100                 105                 110

Asp Thr Ile Pro Asp Phe Ser Lys Gln Leu Asp Glu Asp Val Gly Glu
        115                 120                 125

Ile Phe Phe Asp Pro Asn Ala Leu Ser Lys Asp Gly Thr Ala Ala Leu
    130                 135                 140

Ser Thr Tyr Arg Phe Ser Arg Asp Gly Lys Tyr Phe Ala Tyr Ala Ile
145                 150                 155                 160
```

```
Ala Gln Ser Gly Ser Asp Phe Asn Thr Ile Tyr Val Arg Pro Thr Asp
                165                 170                 175

Ser Pro Leu Thr Lys Arg Asp Glu Ser Gly Arg Asp Pro Ser Arg Leu
            180                 185                 190

Ala Asp Glu Val Lys Phe Val Lys Phe Ser Gly Ile Thr Trp Ala Pro
        195                 200                 205

Asn Ser Glu Gly Phe Phe Tyr Gln Arg Tyr Pro His Ile Asp Gly Ala
    210                 215                 220

Thr Leu Glu Glu Gly Gly Ile Ala Thr Arg Arg Asp Leu His Ala Met
225                 230                 235                 240

Val Tyr Tyr His Arg Val Gly Thr Pro Gln Ser Glu Asp Ile Leu Ile
                245                 250                 255

His Arg Asp Pro Ala Asn Pro Glu Trp Met Phe Gly Val Asn Val Thr
            260                 265                 270

Asp Asn Gly Glu Tyr Ile Glu Leu Tyr Ile Ser Lys Asp Ser Ser Arg
        275                 280                 285

Lys Asn Met Leu Trp Val Ala Asn Phe Ala Met Asn Lys Ile Gly Glu
    290                 295                 300

Gln Phe Gln Trp Arg Lys Val Ile Asn Asp Phe Ala Ala Glu Tyr Asp
305                 310                 315                 320

Val Ile Thr Asn His Gly Pro Val Tyr Tyr Phe Arg Thr Asp Asp Gly
                325                 330                 335

Ala Pro Lys His Lys Ile Leu Ser Ile Asn Ile Asp Thr Asn Glu Arg
            340                 345                 350

Lys Leu Leu Val Pro Glu Ser Glu Asp Ala Ala Leu Phe Ser Thr Val
        355                 360                 365

Cys Val Asn Lys Asn Tyr Met Ala Leu Ile Tyr Lys Arg Asn Val Lys
    370                 375                 380

Asp Glu Val His Leu Tyr Thr Leu Glu Gly Lys Pro Val Arg Arg Leu
385                 390                 395                 400

Ala Glu Asp Phe Val Gly Ala Cys Thr Ile Ser Gly Lys Glu Lys Gln
                405                 410                 415

Pro Trp Phe Phe Val Thr Met Ser Gly Phe Thr Ser Pro Ser Thr Val
            420                 425                 430

Gly Arg Tyr Asn Phe Gln Ile Pro Glu Glu Asn Arg Trp Ser Ile
        435                 440                 445

Phe Arg Ala Ala Lys Ile Lys Asn Leu Asn Pro Asn Asp Phe Glu Ala
    450                 455                 460

Ser Gln Val Trp Tyr Lys Ser Lys Asp Gly Thr Asn Val Pro Met Phe
465                 470                 475                 480

Ile Val Arg His Lys Ser Thr Gln Phe Asp Gly Thr Ala Pro Ala Leu
                485                 490                 495

Gln Tyr Gly Tyr Gly Gly Phe Ser Ile Ser Ile Asp Pro Phe Phe Ser
            500                 505                 510

Ala Ser Ile Leu Thr Phe Leu Lys Val Tyr Gly Ala Ile Leu Val Val
        515                 520                 525

Pro Ser Ile Arg Gly Gly Asn Glu Phe Gly Glu Glu Trp His Arg Gly
    530                 535                 540

Gly Met Lys Gln Asn Lys Val Asn Cys Phe Asp Asp Phe Ile Ala Ala
545                 550                 555                 560

Thr Asn His Leu Val Glu His Lys Tyr Ala Ala Pro Gly Lys Val Ala
                565                 570                 575
```

-continued

```
Ile Asn Gly Gly Ser Asn Gly Leu Leu Val Ala Ala Cys Ile Asn
            580                 585                 590

Arg Ala Pro Glu Gly Thr Phe Gly Ala Ala Ile Ala Glu Val Gly Val
        595                 600                 605

His Asp Met Leu Lys Phe His Lys Phe Thr Ile Gly Lys Ala Trp Thr
610                 615                 620

Ser Asp Tyr Gly Asn Pro Asp Pro His Asp Phe Asp Tyr Ile Tyr
625                 630                 635                 640

Pro Ile Ser Pro Val His Asn Val Pro Thr Asp Lys Ile Leu Pro Pro
                645                 650                 655

Thr Leu Leu Thr Ala Asp His Asp Asp Arg Val Val Pro Met His
            660                 665                 670

Thr Phe Lys Leu Ala Ala Thr Leu Gln His Thr Leu Pro His Asn Pro
        675                 680                 685

His Pro Leu Leu Leu Arg Val Asp Lys Lys Ala Gly His Gly Ala Gly
690                 695                 700

Lys Pro Leu Gln Leu Lys Ile Arg Glu Gln Ala Asp Lys Trp Gly Phe
705                 710                 715                 720

Val Ala Gln Ser Phe Gln Leu Val Trp Arg Asp Gly Val
                725                 730

<210> SEQ ID NO 46
<211> LENGTH: 730
<212> TYPE: PRT
<213> ORGANISM: Amanita bisporigera

<400> SEQUENCE: 46

Met Pro Pro Thr Pro Trp Ala Pro His Ser Tyr Pro Pro Thr Arg Arg
1               5                   10                  15

Ser Asp His Val Asp Val Tyr Gln Ser Ala Ser Arg Gly Glu Val Pro
                20                  25                  30

Val Pro Asp Pro Tyr Gln Trp Leu Glu Glu Asn Ser Asn Glu Val Asp
            35                  40                  45

Glu Trp Thr Thr Ala Gln Thr Ala Phe Thr Gln Gly Tyr Leu Asp Lys
    50                  55                  60

Asn Ala Asp Arg Gln Lys Leu Glu Glu Lys Phe Arg Ala Ser Lys Asp
65                  70                  75                  80

Tyr Val Lys Phe Ser Ala Pro Thr Leu Leu Asp Ser Gly His Trp Tyr
                85                  90                  95

Trp Phe Tyr Asn Ser Gly Val Gln Ser Gln Ala Val Leu Tyr Arg Ser
            100                 105                 110

Lys Lys Pro Val Leu Pro Asp Phe Gln Arg Gly Thr Arg Lys Val Gly
        115                 120                 125

Glu Val Tyr Phe Asp Pro Asn Val Leu Ser Ala Asp Gly Thr Ala Ile
    130                 135                 140

Met Gly Thr Cys Arg Phe Ser Pro Ser Gly Glu Tyr Phe Ala Tyr Ala
145                 150                 155                 160

Val Ser His Leu Gly Val Asp Tyr Phe Thr Ile Tyr Val Arg Pro Thr
                165                 170                 175

Ser Ser Ser Leu Ser Gln Ala Pro Glu Ala Glu Gly Gly Asp Gly Arg
            180                 185                 190

Leu Ser Asp Gly Val Lys Trp Cys Lys Phe Thr Thr Ile Thr Trp Thr
        195                 200                 205

Lys Asp Ser Lys Gly Phe Leu Tyr Gln Arg Tyr Pro Ala Arg Glu Ser
    210                 215                 220
```

```
Leu Val Ala Lys Asp Arg Asp Lys Asp Ala Met Val Cys Tyr His Arg
225                 230                 235                 240

Val Gly Thr Thr Gln Leu Glu Asp Ile Ile Val Gln Gln Asp Lys Glu
            245                 250                 255

Asn Pro Asp Trp Thr Tyr Gly Thr Asp Ala Ser Glu Asp Gly Lys Tyr
            260                 265                 270

Ile Tyr Leu Val Val Tyr Lys Asp Ala Ser Lys Gln Asn Leu Leu Trp
            275                 280                 285

Val Ala Glu Phe Asp Lys Asp Gly Val Lys Pro Glu Ile Pro Trp Arg
            290                 295                 300

Lys Val Ile Asn Glu Phe Gly Ala Asp Tyr His Val Ile Thr Asn His
305                 310                 315                 320

Gly Ser Leu Ile Tyr Val Lys Thr Asn Val Asn Ala Pro Gln Tyr Lys
            325                 330                 335

Val Val Thr Ile Asp Leu Ser Thr Gly Glu Pro Glu Ile Arg Asp Phe
            340                 345                 350

Ile Pro Glu Gln Lys Asp Ala Lys Leu Thr Gln Val Lys Cys Val Asn
            355                 360                 365

Lys Gly Tyr Phe Val Ala Ile Tyr Lys Arg Asn Val Lys Asp Glu Ile
            370                 375                 380

Tyr Leu Tyr Ser Lys Ala Gly Asp Gln Leu Ser Arg Leu Ala Ser Asp
385                 390                 395                 400

Phe Ile Gly Val Ala Ser Ile Thr Asn Arg Glu Lys Gln Pro His Ser
            405                 410                 415

Phe Leu Thr Phe Ser Gly Phe Asn Thr Pro Gly Thr Ile Ser Arg Tyr
            420                 425                 430

Asp Phe Thr Ala Pro Asp Thr Gln Arg Leu Ser Ile Leu Arg Thr Thr
            435                 440                 445

Lys Leu Asn Gly Leu Asn Ala Asp Asp Phe Glu Ser Thr Gln Val Trp
450                 455                 460

Tyr Lys Ser Lys Asp Gly Thr Lys Val Pro Met Phe Ile Val Arg His
465                 470                 475                 480

Lys Ser Thr Lys Phe Asp Gly Thr Ala Pro Ala Ile Gln Asn Gly Tyr
            485                 490                 495

Gly Gly Phe Ala Ile Thr Ala Asp Pro Phe Phe Ser Pro Ile Met Leu
            500                 505                 510

Thr Phe Met Gln Thr Tyr Gly Ala Ile Leu Ala Val Pro Asn Ile Arg
            515                 520                 525

Gly Gly Gly Glu Phe Gly Gly Glu Trp His Lys Ala Gly Arg Arg Glu
            530                 535                 540

Thr Lys Gly Asn Thr Phe Asp Asp Phe Ile Ala Ala Gln Phe Leu
545                 550                 555                 560

Val Lys Asn Lys Tyr Ala Ala Pro Gly Lys Val Ala Ile Thr Gly Ala
            565                 570                 575

Ser Asn Gly Gly Phe Leu Val Cys Gly Ser Val Val Arg Ala Pro Glu
            580                 585                 590

Gly Thr Phe Gly Ala Val Ser Glu Gly Val Ala Asp Leu Leu
            595                 600                 605

Lys Phe Asn Lys Phe Thr Gly Met Ala Trp Thr Ser Glu Tyr Gly
            610                 615                 620

Asn Pro Phe Ile Lys Glu Asp Phe Asp Phe Val Gln Ala Leu Ser Pro
625                 630                 635                 640
```

```
Val His Asn Val Pro Lys Asp Arg Val Leu Pro Ala Thr Leu Leu Met
                    645                 650                 655

Thr Asn Ala Gly Asp Asp Arg Val Val Pro Met His Ser Leu Lys Phe
                660                 665                 670

Val Ala Asn Leu Gln Tyr Asn Val Pro Gln Asn Pro His Pro Leu Leu
                675                 680                 685

Ile Arg Val Asp Lys Ser Trp Leu Gly His Gly Phe Gly Lys Thr Thr
            690                 695                 700

Asp Lys His Thr Lys Asp Ala Ala Lys Trp Ser Phe Val Ala Gln
705                 710                 715                 720

Ser Leu Gly Leu Glu Trp Lys Thr Val Asp
                    725                 730

<210> SEQ ID NO 47
<211> LENGTH: 738
<212> TYPE: PRT
<213> ORGANISM: Lentinula edodes

<400> SEQUENCE: 47

Met Phe Ser Ala Thr Gln Glu Ser Pro Thr Met Ser Val Pro Gln Trp
1               5                   10                  15

Asp Pro Tyr Pro Pro Val Ser Arg Asp Glu Thr Ser Ala Ile Thr Tyr
                20                  25                  30

Gln Ser Lys Leu Cys Gly Ser Val Thr Val Arg Asp Pro Tyr Ser Ala
            35                  40                  45

Leu Glu Val Pro Phe Asp Asp Ser Glu Glu Thr Lys Ala Phe Val His
        50                  55                  60

Ala Gln Arg Lys Phe Ala Arg Thr Tyr Leu Asp Glu Ile Pro Asp Arg
65                  70                  75                  80

Glu Thr Trp Leu Gln Thr Leu Lys Glu Ser Trp Asn Tyr Arg Arg Phe
                85                  90                  95

Thr Val Pro Lys Arg Glu Ser Asp Gly Tyr Thr Tyr Phe Glu Tyr Asn
                100                 105                 110

Asp Gly Leu Gln Ser Gln Met Ser Leu Arg Arg Val Lys Val Ser Glu
            115                 120                 125

Glu Asp Thr Ile Leu Thr Glu Ser Gly Pro Gly Gly Glu Leu Phe Phe
130                 135                 140

Asp Pro Asn Leu Leu Ser Leu Asp Gly Asn Ala Ala Leu Thr Gly Ser
145                 150                 155                 160

Met Met Ser Pro Cys Gly Lys Tyr Trp Ala Tyr Gly Val Ser Glu His
                165                 170                 175

Gly Ser Asp Trp Met Thr Thr Tyr Val Arg Lys Thr Ser Ser Pro His
            180                 185                 190

Met Pro Ser Gln Glu Lys Gly Lys Asp Pro Gly Arg Met Asp Asp Val
        195                 200                 205

Ile Arg Tyr Ser Arg Phe Phe Ile Val Tyr Trp Ser Ser Asp Ser Lys
210                 215                 220

Gly Phe Phe Tyr Ser Arg Tyr Pro Pro Glu Asp Asp Glu Gly Lys Gly
225                 230                 235                 240

Asn Thr Pro Ala Gln Asn Cys Met Val Tyr Tyr His Arg Leu Gly Glu
                245                 250                 255

Lys Gln Glu Lys Asp Thr Leu Val Tyr Glu Asp Pro Glu His Pro Phe
            260                 265                 270

Trp Leu Trp Ala Leu Gln Leu Ser Pro Ser Gly Arg Tyr Ala Leu Leu
        275                 280                 285
```

```
Thr Ala Ser Arg Asp Ala Ser His Thr Gln Leu Ala Lys Ile Ala Asp
    290                 295                 300

Ile Gly Thr Ser Asp Ile Gln Asn Gly Ile Gln Trp Leu Thr Ile His
305                 310                 315                 320

Asp Gln Trp Gln Ala Arg Phe Val Ile Ile Gly Asp Asp Ser Thr
                325                 330                 335

Ile Tyr Phe Met Thr Asn Leu Glu Ala Lys Asn Tyr Leu Val Ala Thr
            340                 345                 350

Leu Asp Ile Arg His Ser Glu Ala Gly Val Lys Thr Leu Val Ala Glu
        355                 360                 365

Asn Pro Asp Ala Leu Leu Ile Ser Ala Ser Ile Leu Ser Thr Asp Lys
    370                 375                 380

Leu Val Leu Val Tyr Leu His Asn Ala Arg His Glu Ile His Val His
385                 390                 395                 400

Asp Leu Asn Thr Gly Lys Pro Ile Arg Gln Ile Phe Asp Asn Leu Ile
                405                 410                 415

Gly Gln Phe Ser Leu Ser Gly Arg Arg Asp Asp Asn Asp Met Phe Val
            420                 425                 430

Phe His Ser Gly Phe Thr Ser Pro Gly Thr Ile Tyr Arg Phe Arg Leu
        435                 440                 445

Asn Glu Asp Ser Asn Lys Gly Thr Leu Phe Arg Ala Val Gln Val Pro
    450                 455                 460

Gly Leu Asn Leu Ser Asp Phe Thr Thr Glu Ser Val Phe Tyr Pro Ser
465                 470                 475                 480

Lys Asp Gly Thr Pro Ile His Met Phe Ile Thr Arg Leu Lys Asp Thr
                485                 490                 495

Pro Val Asp Gly Thr Ala Pro Val Tyr Ile Tyr Gly Tyr Gly Gly Phe
            500                 505                 510

Ala Leu Ala Met Leu Pro Thr Phe Ser Val Ser Thr Leu Leu Phe Cys
        515                 520                 525

Lys Ile Tyr Arg Ala Met Tyr Val Val Pro Asn Ile Arg Gly Gly Ser
    530                 535                 540

Glu Phe Gly Glu Ser Trp His Arg Glu Gly Met Leu Asp Lys Lys Gln
545                 550                 555                 560

Asn Val Phe Asp Asp Phe Asn Ala Ala Thr Lys Trp Leu Val Ala Asn
                565                 570                 575

Lys Tyr Ala Asn Lys Tyr Asn Val Ala Ile Arg Gly Gly Ser Asn Gly
            580                 585                 590

Gly Val Leu Thr Thr Ala Cys Ala Asn Gln Ala Pro Glu Leu Tyr Arg
        595                 600                 605

Cys Val Ile Thr Ile Gly Gly Ile Ile Asp Met Leu Arg Phe Pro Lys
    610                 615                 620

Phe Thr Phe Gly Ala Leu Trp Arg Ser Glu Tyr Gly Asp Pro Glu Asp
625                 630                 635                 640

Pro Glu Asp Phe Asp Phe Ile Tyr Lys Tyr Ser Pro Tyr His Asn Ile
                645                 650                 655

Pro Ser Gly Asp Val Val Leu Pro Ala Met Leu Phe Phe Thr Ala Ala
            660                 665                 670

Tyr Asp Asp Arg Val Ser Pro Leu His Ser Phe Lys His Val Ala Ala
        675                 680                 685

Leu Gln Tyr Asn Phe Pro Asn Gly Pro Asn Pro Val Leu Met Arg Ile
    690                 695                 700
```

-continued

```
Asp Leu Asn Thr Gly His Phe Ala Gly Lys Ser Thr Gln Lys Met Leu
705                 710                 715                 720

Glu Glu Thr Ala Asp Glu Tyr Arg Cys Asp Leu Leu Cys Cys Asn Leu
                725                 730                 735

Gln Leu

<210> SEQ ID NO 48
<211> LENGTH: 723
<212> TYPE: PRT
<213> ORGANISM: Omphalotacae olearis

<400> SEQUENCE: 48

Met Ser Phe Pro Gly Trp Gly Pro Tyr Pro Val Glu Arg Asp Glu
1               5                   10                  15

Thr Ser Ala Ile Thr Tyr Ser Ser Lys Leu His Gly Ser Val Thr Val
                20                  25                  30

Arg Asp Pro Tyr Ser Gln Leu Glu Val Pro Phe Glu Asp Ser Glu Glu
            35                  40                  45

Thr Lys Ala Phe Val His Ser Gln Arg Lys Phe Ala Arg Thr Tyr Leu
    50                  55                  60

Asp Glu Asn Pro Asp Arg Glu Ala Trp Leu Glu Thr Leu Lys Lys Ser
65                  70                  75                  80

Trp Asn Tyr Arg Arg Phe Ser Ala Leu Lys Pro Glu Ser Asp Gly His
                85                  90                  95

Tyr Tyr Phe Glu Tyr Asn Asp Gly Leu Gln Ser Gln Leu Ser Leu Tyr
            100                 105                 110

Arg Val Arg Met Gly Glu Glu Asp Thr Val Leu Thr Glu Ser Gly Pro
        115                 120                 125

Gly Gly Glu Leu Phe Phe Asn Pro Asn Leu Leu Ser Leu Asp Gly Asn
130                 135                 140

Ala Ala Leu Thr Gly Phe Val Met Ser Pro Cys Gly Asn Tyr Trp Ala
145                 150                 155                 160

Tyr Gly Val Ser Glu His Gly Ser Asp Trp Met Ser Ile Tyr Val Arg
                165                 170                 175

Lys Thr Ser Ser Pro His Leu Pro Ser Gln Glu Arg Gly Lys Asp Pro
            180                 185                 190

Gly Arg Met Asn Asp Lys Ile Arg His Val Arg Phe Phe Ile Val Ser
        195                 200                 205

Trp Thr Ser Asp Ser Lys Gly Phe Phe Tyr Ser Arg Tyr Pro Pro Glu
210                 215                 220

Asp Asp Glu Gly Lys Gly Asn Ala Pro Ala Met Asn Cys Met Val Tyr
225                 230                 235                 240

Tyr His Arg Ile Gly Glu Asp Gln Glu Ser Asp Val Leu Val His Glu
                245                 250                 255

Asp Pro Glu His Pro Phe Trp Ile Ser Ser Val Gln Leu Thr Pro Ser
            260                 265                 270

Gly Arg Tyr Ile Leu Phe Ala Ala Ser Arg Asp Ala Ser His Thr Gln
        275                 280                 285

Leu Val Lys Ile Ala Asp Leu His Glu Asn Asp Ile Gly Thr Asn Met
290                 295                 300

Lys Trp Lys Asn Leu His Asp Pro Trp Glu Ala Arg Phe Thr Ile Val
305                 310                 315                 320

Gly Asp Glu Gly Ser Lys Ile Tyr Phe Met Thr Asn Leu Lys Ala Lys
                325                 330                 335
```

```
Asn Tyr Lys Val Ala Thr Phe Asp Ala Asn His Pro Asp Glu Gly Leu
                340                 345                 350

Thr Thr Leu Ile Ala Glu Asp Pro Asn Ala Phe Leu Val Ser Ala Ser
            355                 360                 365

Ile His Ala Gln Asp Lys Leu Leu Val Tyr Leu Arg Asn Ala Ser
        370                 375                 380

His Glu Ile His Ile Arg Asp Leu Thr Thr Gly Lys Pro Leu Gly Arg
385                 390                 395                 400

Ile Phe Glu Asp Leu Leu Gly Gln Phe Met Val Ser Gly Arg Arg Gln
                405                 410                 415

Asp Asn Asp Ile Phe Val Leu Phe Ser Ser Phe Leu Ser Pro Gly Thr
            420                 425                 430

Val Tyr Arg Tyr Thr Phe Gly Glu Glu Lys Gly His Ser Ser Leu Phe
        435                 440                 445

Arg Ala Ile Ser Ile Pro Gly Leu Asn Leu Asp Asp Phe Met Thr Glu
450                 455                 460

Ser Val Phe Tyr Pro Ser Lys Asp Gly Thr Ser Val His Met Phe Ile
465                 470                 475                 480

Thr Arg Pro Lys Asp Val Leu Leu Asp Gly Thr Ser Pro Val Leu Gln
                485                 490                 495

Tyr Gly Tyr Gly Gly Phe Ser Leu Ala Met Leu Pro Thr Phe Ser Leu
            500                 505                 510

Ser Thr Leu Leu Phe Cys Lys Ile Tyr Arg Ala Ile Tyr Ala Ile Pro
        515                 520                 525

Asn Ile Arg Gly Gly Ser Glu Tyr Gly Glu Ser Trp His Arg Glu Gly
530                 535                 540

Met Leu Asp Lys Lys Gln Asn Val Phe Asp Asp Phe Asn Ala Ala Thr
545                 550                 555                 560

Glu Trp Leu Ile Ala Asn Lys Tyr Ala Ser Lys Asp Arg Ile Ala Ile
                565                 570                 575

Arg Gly Gly Ser Asn Gly Gly Val Leu Thr Thr Ala Cys Ala Asn Gln
            580                 585                 590

Ala Pro Gly Leu Tyr Arg Cys Val Ile Thr Ile Glu Gly Ile Ile Asp
        595                 600                 605

Met Leu Arg Phe Pro Lys Phe Thr Phe Gly Ala Ser Trp Arg Ser Glu
610                 615                 620

Tyr Gly Asp Pro Glu Asp Pro Glu Asp Phe Asp Phe Ile Phe Lys Tyr
625                 630                 635                 640

Ser Pro Tyr His Asn Ile Pro Pro Gly Asp Thr Ile Met Pro Ala
                645                 650                 655

Met Leu Phe Phe Thr Ala Ala Tyr Asp Asp Arg Val Ser Pro Leu His
            660                 665                 670

Thr Phe Lys His Val Ala Ala Leu Gln His Asn Phe Pro Lys Gly Pro
        675                 680                 685

Asn Pro Cys Leu Met Arg Ile Asp Leu Asn Ser Gly His Phe Ala Gly
690                 695                 700

Lys Ser Thr Gln Glu Met Leu Glu Glu Thr Ala Asp Glu Tyr Arg Leu
705                 710                 715                 720

Lys Val Gln

<210> SEQ ID NO 49
<211> LENGTH: 733
<212> TYPE: PRT
<213> ORGANISM: Gymnopus fusipes
```

<400> SEQUENCE: 49

```
Met Ser Met Ser Leu Leu Gly Val Tyr Pro Pro Val Lys Arg Asp Glu
1               5                   10                  15

Ala Ser Ala Ile Thr Tyr Gln Ser Lys Leu His Gly Ser Val Ile Val
            20                  25                  30

His Asp Pro Tyr Ser Ala Leu Glu Ile Pro Ser Asn Asp Ser Leu Glu
        35                  40                  45

Thr Lys Ala Phe Val Leu Ser Gln Gly Lys Phe Ser Arg Ala Tyr Leu
50                  55                  60

Asp Glu Ile Pro Thr Arg Lys Asn Trp Leu Lys Ile Leu Lys Ser Asn
65                  70                  75                  80

Trp Ser Tyr Arg Arg Phe Ser Ala Leu Lys Arg Glu Ser Asp Asn His
                85                  90                  95

Phe Tyr Phe Glu Tyr Asn Asp Gly Leu Gln Pro Gln Ser Ser Ile Tyr
            100                 105                 110

Arg Val Lys Val Gly Glu Glu Asp Ser Ile Leu Thr Glu Ser Gly Pro
        115                 120                 125

Gly Gly Glu Leu Phe Phe Asp Pro Asn Leu Leu Ser Leu Asp Gly Val
130                 135                 140

Ala Ala Leu Thr Gly Ala Ala Met Ser Pro Ser Gly Lys Tyr Trp Ala
145                 150                 155                 160

Tyr Gly Val Ser Glu His Gly Asn Asn Ser Met Thr Ile Tyr Val Arg
                165                 170                 175

Lys Thr Ser Ser Pro His Gln Pro Ser Gln Glu Lys Gly Thr Asp Pro
            180                 185                 190

Gly Arg Met Asn Asp Val Leu Gln His Ile Arg Met Leu Phe Val Ser
        195                 200                 205

Trp Thr Arg Asp Ser Lys Gly Phe Phe Tyr Gln Arg Tyr Pro Pro Glu
210                 215                 220

Lys Asn Glu Gly Asn Gly Asn Ala Pro Gly Gln Asn Cys Lys Ile Tyr
225                 230                 235                 240

Tyr His Tyr Ile Gly Thr Glu Gln Asp Ser Asp Ile Leu Ile His Glu
                245                 250                 255

Asp Pro Asp His Pro Asp Trp Phe Ser Tyr Val Gln Leu Ser Pro Ser
            260                 265                 270

Gly Gln Tyr Val Leu Leu Ile Asn Arg Asp Ser Ser Leu Asn Tyr
        275                 280                 285

Leu Ala Lys Ile Ala Asp Leu Ser Val Asn Asp Ile Gly Thr His Ile
290                 295                 300

Gln Trp Lys Asn Leu His Asp Ser Trp Asn His Phe Thr Met Ile Gly
305                 310                 315                 320

Asn Asp Tyr Ser Val Ile Tyr Phe Lys Thr Asn Leu Asp Ala Gln Asn
                325                 330                 335

Tyr Lys Val Ala Thr Ile Asp Phe Leu Gln Pro Glu Met Gly Phe Thr
            340                 345                 350

Thr Leu Val Lys Glu Asn Pro Asn Ser Val Leu Val Glu Ala Lys Ile
        355                 360                 365

Phe Arg Glu Asp Lys Leu Val Leu Leu Tyr Gln Gln Asn Ala Ser His
370                 375                 380

Gln Ile His Ile Tyr Asp Leu Lys Ser Gly Ala Trp Leu Gln Gln Ile
385                 390                 395                 400

Phe Lys Asn Leu Thr Gly Phe Ile Thr Thr Val Pro Asn Gly Arg Ala
```

```
                    405                 410                 415

Glu Asp Glu Met Phe Phe Leu Tyr Asn Asp Phe Ile Thr Pro Gly Thr
                420                 425                 430

Ile Tyr Gln Tyr Lys Phe Asp Asp Glu Ser Asp Lys Gly Leu Val Phe
                435                 440                 445

Arg Ala Ile Gln Ile Asp Gly Leu Asn Leu Asp Asp Phe Val Thr Glu
            450                 455                 460

Ser Lys Phe Tyr Pro Ser Lys Asp Gly Thr Ser Val His Met Phe Ile
465                 470                 475                 480

Thr Arg Pro Lys Asp Val Leu Ile Asp Gly Thr Ala Ala Val Tyr Met
                485                 490                 495

Tyr Gly Tyr Gly Gly Phe Ser Ile Ser Val Leu Pro Thr Phe Ser Ile
                500                 505                 510

Ser Thr Leu Leu Phe Cys Lys Ile Tyr Arg Ala Met Tyr Val Val Pro
            515                 520                 525

Asn Ile Arg Gly Gly Ser Glu Phe Gly Glu Ser Trp His Arg Glu Gly
530                 535                 540

Met Leu Asp Lys Lys Gln Asn Gly His Asp Asp Phe His Ala Ala Ala
545                 550                 555                 560

Glu Trp Leu Ile Ala Asn Lys Tyr Ala Lys Lys Asp Cys Val Ala Ile
                565                 570                 575

Arg Gly Gly Ser Ser Gly Gly Ile Leu Thr Thr Ala Cys Ala Asn Gln
            580                 585                 590

Ala Pro Glu Leu Tyr Arg Cys Val Ile Thr Ile Glu Gly Ile Ile Asp
                595                 600                 605

Met Leu Lys Phe Pro Lys Phe Thr Phe Gly Ala Leu Leu Arg Ser Glu
610                 615                 620

Tyr Gly Asp Pro Glu Asp Pro Glu Ala Phe Asp Tyr Ile Tyr Lys Tyr
625                 630                 635                 640

Ser Pro Tyr His Asn Ile Pro Leu Gly Asp Val Val Met Pro Pro Met
                645                 650                 655

Leu Phe Phe Asn Ala Gly Tyr Asp Asp Arg Val Pro Pro Leu His Thr
            660                 665                 670

Phe Lys His Val Ala Ala Leu Gln His Arg Phe Pro Lys Gly Pro Asn
                675                 680                 685

Pro Ile Leu Met Arg Met Asp Leu Ser Ser Gly His Tyr Ala Gly Lys
            690                 695                 700

Ser Val Gln Lys Met Ile Glu Glu Thr Ala Asp Glu Tyr Ser Phe Ile
705                 710                 715                 720

Gly Lys Ser Met Gly Leu Thr Met Gln Val Arg Ala Lys
                725                 730

<210> SEQ ID NO 50
<211> LENGTH: 744
<212> TYPE: PRT
<213> ORGANISM: Lentinula novae-zelandiae

<400> SEQUENCE: 50

Met Ser Val Pro Gln Trp Val Ser Tyr Pro Pro Val Ser Arg Asp Ala
1               5                   10                  15

Thr Ser Ala Ile Thr Tyr Gln Ser Lys Leu Arg Gly Ser Val Thr Val
                20                  25                  30

Arg Asp Pro Tyr Ser Ala Leu Glu Val Pro Phe Asp Asp Ser Glu Glu
            35                  40                  45
```

```
Thr Lys Ala Phe Val His Ala Gln Arg Lys Phe Ala Arg Thr Tyr Leu
 50                  55                  60

Asp Glu Ile Pro Asp Arg Glu Thr Trp Leu Gln Thr Leu Lys Glu Ser
 65                  70                  75                  80

Trp Asn Tyr Arg Arg Phe Thr Val Pro Lys Arg Glu Ser Asp Gly Tyr
                 85                  90                  95

Thr Tyr Phe Glu Tyr Asn Asp Gly Leu Gln Ser Gln Met Ser Leu Arg
                100                 105                 110

Arg Val Lys Val Ser Glu Glu Asp Thr Ile Leu Thr Glu Ser Gly Pro
                115                 120                 125

Gly Gly Glu Leu Phe Phe Asp Pro Asn Leu Leu Ser Leu Asp Gly Asn
130                 135                 140

Ala Ala Leu Thr Gly Ser Met Met Ser Pro Cys Gly Lys Tyr Trp Ala
145                 150                 155                 160

Tyr Gly Val Ser Glu His Gly Ser Asp Trp Met Thr Thr Tyr Val Arg
                165                 170                 175

Lys Thr Ser Ser Pro His Met Pro Ser Gln Glu Lys Gly Lys Asp Pro
                180                 185                 190

Gly Arg Met Asp Asp Val Val Arg Tyr Ser Arg Phe Phe Ile Val Tyr
                195                 200                 205

Trp Ser Ser Asp Ser Lys Gly Phe Phe Tyr Ser Arg Tyr Pro Pro Glu
210                 215                 220

Asp Asp Glu Gly Lys Gly Asn Ala Pro Ala Gln Asn Cys Met Val Tyr
225                 230                 235                 240

Tyr His Arg Leu Gly Glu Arg Gln Glu Lys Asp Thr Leu Val Tyr Glu
                245                 250                 255

Asp Pro Glu His Pro Phe Trp Leu Trp Ala Leu Gln Leu Ser Pro Ser
                260                 265                 270

Gly Arg Tyr Ala Leu Leu Thr Ala Ser Arg Asp Ala Ser His Thr Gln
                275                 280                 285

Leu Ala Lys Ile Ala Asp Ile Gly Thr Ser Asp Ile Gln Asn Gly Ile
                290                 295                 300

Gln Trp Leu Thr Ile His Asp Gln Trp Gln Ala Arg Phe Val Ile Ile
305                 310                 315                 320

Gly Asp Asp Asp Ser Thr Ile Tyr Phe Met Thr Asn Leu Glu Ala Lys
                325                 330                 335

Asn Tyr Leu Val Ala Thr Leu Asp Ile Arg His Ser Glu Ala Gly Val
                340                 345                 350

Lys Thr Leu Val Ala Glu Asn Pro Asp Ala Leu Leu Ile Ser Ala Ser
                355                 360                 365

Ile Leu Ser Thr Asp Lys Leu Val Leu Val Tyr Leu His Asn Ala Arg
                370                 375                 380

His Glu Ile His Val His Asp Leu Asn Thr Gly Lys Pro Ile Arg Gln
385                 390                 395                 400

Ile Phe Asp Asn Leu Ile Gly Gln Phe Ser Leu Ser Gly Arg Arg Asp
                405                 410                 415

Asp Asn Asp Met Phe Ile Phe His Ser Gly Phe Thr Ser Pro Gly Thr
                420                 425                 430

Ile Tyr Arg Phe Arg Leu Asn Glu Asp Ser Asn Lys Gly Thr Leu Phe
                435                 440                 445

Arg Ala Ile Gln Val Pro Gly Leu Asn Leu Asn Asp Phe Thr Thr Glu
450                 455                 460

Ser Val Phe Tyr Pro Ser Lys Asp Gly Thr Pro Ile His Met Phe Ile
```

```
            465                 470                 475                 480
        Thr Arg Leu Lys Asp Thr Pro Val Asp Gly Thr Ala Pro Val Tyr Ile
                        485                 490                 495

Tyr Gly Tyr Gly Gly Phe Ala Leu Ala Met Leu Pro Thr Phe Ser Val
                        500                 505                 510

Ser Thr Leu Leu Phe Cys Lys Ile Tyr Arg Ala Met Tyr Val Val Pro
                        515                 520                 525

Asn Ile Arg Gly Gly Ser Glu Phe Gly Glu Ser Trp His Arg Glu Gly
                        530                 535                 540

Met Leu Asp Lys Lys Gln Asn Val Phe Asp Asp Phe Asn Ala Ala Thr
        545                 550                 555                 560

Lys Trp Leu Val Ala Asn Lys Tyr Ala Asn Lys Tyr Asn Val Ala Ile
                        565                 570                 575

Arg Gly Gly Ser Asn Gly Gly Val Leu Thr Thr Ala Cys Ala Asn Gln
                        580                 585                 590

Ala Pro Glu Leu Tyr Arg Cys Val Ile Thr Ile Gly Gly Ile Ile Asp
                        595                 600                 605

Met Leu Arg Phe Pro Lys Phe Thr Phe Gly Ala Leu Trp Arg Ser Glu
                610                 615                 620

Tyr Gly Asp Pro Glu Asp Pro Glu Asp Phe Asp Phe Ile Tyr Lys Tyr
        625                 630                 635                 640

Ser Pro Tyr His Asn Ile Pro Ser Gly Asp Val Val Leu Pro Ala Met
                        645                 650                 655

Leu Phe Phe Thr Ala Ala Tyr Asp Asp Arg Val Ser Pro Leu His Ser
                        660                 665                 670

Phe Lys His Val Ala Ala Leu Gln Tyr Tyr Phe Pro Asn Gly Pro Asn
                        675                 680                 685

Pro Val Leu Met Arg Ile Asp Leu Asn Thr Gly His Phe Ala Gly Lys
                        690                 695                 700

Ser Thr Gln Lys Met Leu Glu Glu Thr Ala Asp Glu Tyr Ser Phe Ile
        705                 710                 715                 720

Gly Lys Ser Met Gly Leu Val Met Cys Val Gln Asn Glu His Ala Ser
                        725                 730                 735

Lys Gln Trp Ser Cys Val Val Thr
                        740

<210> SEQ ID NO 51
<211> LENGTH: 741
<212> TYPE: PRT
<213> ORGANISM: Lentinula raphanica

<400> SEQUENCE: 51

Met Ser Ile Pro Arg Trp Gly Pro Tyr Pro Val Arg Arg Asp Glu
        1               5                   10                  15

Thr Ser Ala Ile Thr Tyr Gln Ser Lys Leu His Gly Ser Val Thr Val
                        20                  25                  30

Pro Asp Pro Tyr Ser Ala Leu Glu Val Pro Tyr Asn Asp Asp Glu Glu
                        35                  40                  45

Ser Glu Ile Lys Thr Phe Val Ser Glu Gln Arg Lys Phe Ala Arg Thr
                50                  55                  60

Tyr Leu Asp Glu Asn Pro Asp Arg Glu Arg Trp Leu Gln Val Leu Lys
        65                  70                  75                  80

Glu Ser Trp Asn Tyr Glu Arg Phe Thr Val Pro Lys Arg Glu Ser Asp
                        85                  90                  95
```

```
Gly His Thr Tyr Phe Glu Tyr Asn Asp Gly Leu Gln Ser Gln Met Thr
            100                 105                 110

Leu Arg Arg Val Lys Thr Gly Gln Glu Asp Thr Ile Leu Thr Glu Ser
            115                 120                 125

Gly Pro Gly Gly Glu Leu Phe Phe Asp Pro Asn Met Ile Ser Leu Asp
            130                 135                 140

Gly Asn Ala Ala Leu Thr Gly Ser Met Met Ser Pro Cys Gly Lys Tyr
145                 150                 155                 160

Trp Ala Tyr Gly Val Ser Glu His Gly Ser Asp Trp Met Thr Ile Tyr
                165                 170                 175

Val Arg Glu Thr Ser Ser Pro His Gln Pro Ser Gln Glu Lys Gly Lys
            180                 185                 190

Asp Thr Gly Arg Met Asp Asp Val His Ser Ser Arg Phe Phe Ile
            195                 200                 205

Val Tyr Trp Thr Ser Asp Ser Lys Gly Phe Phe Tyr Ser Arg Tyr Pro
            210                 215                 220

Pro Glu Asp Asp Glu Gly Lys Gly Asn Ser Pro Ala Lys Asn Cys Met
225                 230                 235                 240

Val Tyr Tyr His Arg Leu Gly Glu Lys Gln Glu Asp Ala Leu Ile
                245                 250                 255

Tyr Glu Asp Pro Glu His Pro Phe Trp Leu Trp Ala Val Gln Leu Ser
            260                 265                 270

Pro Ser Gly Arg Phe Ala Leu Leu Thr Ala Ser Arg Asp Ala Ser His
            275                 280                 285

Thr Gln Met Ala Lys Ile Ala Asp Leu Ser Ser Gly Asp Val Arg Asn
            290                 295                 300

Gly Val Asn Trp Leu Thr Ile His Asp Lys Trp Glu Ala Arg Phe Leu
305                 310                 315                 320

Ile Ile Gly Asp Asp Asp Ser Lys Ile Tyr Phe Leu Thr Asn Leu Glu
                325                 330                 335

Ala Val Asn Tyr Lys Val Val Thr Leu Asp Thr Arg Cys Pro Glu Ala
            340                 345                 350

Gly Thr Asn Thr Leu Val Pro Glu Asn Pro Asp Ala Leu Leu Ile Ser
            355                 360                 365

Ala Ser Ile Val Ser Ala Asp Lys Leu Ala Leu Val Tyr Leu Gln Asn
            370                 375                 380

Ala Lys His Asp Ile Tyr Ile His Asp Leu Ser Thr Gly Lys Pro Thr
385                 390                 395                 400

Arg Arg Leu Phe Glu Asp Leu Ile Gly Gln Phe Ala Leu Ser Gly Arg
                405                 410                 415

Arg Glu Asp Asn Asp Met Phe Val Phe Tyr Ser Gly Phe Thr Ser Pro
            420                 425                 430

Gly Thr Ile Tyr Arg Tyr Lys Phe Asp Glu Glu Asp Asn Asn Gly Thr
            435                 440                 445

Leu Phe Arg Ala Met Arg Val Pro Gly Leu Asp Leu Asp Lys Phe Thr
450                 455                 460

Thr Glu Ser Val Phe Tyr Pro Ser Lys Asp Gly Thr Lys Val His Met
465                 470                 475                 480

Phe Ile Thr Arg Leu Lys Asn Thr Leu Val Asp Gly Thr Ala Pro Val
                485                 490                 495

Tyr Met Tyr Gly Tyr Gly Gly Phe Ala Leu Ala Met Leu Pro Thr Phe
            500                 505                 510

Ser Val Ser Thr Leu Leu Phe Cys Lys Thr Tyr Arg Ala Met Tyr Val
```

```
                515                 520                 525
Val Pro Asn Ile Arg Gly Gly Ser Glu Phe Gly Glu Ser Trp His Arg
530                 535                 540

Glu Gly Met Leu Asp Lys Lys Gln Asn Val Phe Asp Asp Phe Asn Ala
545                 550                 555                 560

Ala Ala Glu Trp Leu Ile Ala Asn Lys Tyr Ala Lys Ser Asn Cys Val
                565                 570                 575

Ala Ile Arg Gly Gly Ser Asn Gly Gly Val Leu Thr Thr Ala Cys Thr
            580                 585                 590

Asn Gln Ala Pro Glu Leu Phe Arg Cys Val Val Thr Ile Gly Gly Ile
                595                 600                 605

Ile Asp Met Leu Arg Phe Pro Lys Phe Thr Phe Gly Ala Leu Trp Cys
            610                 615                 620

Ser Glu Tyr Gly Asp Pro Asp Pro Glu Ala Phe Asp Tyr Ile Tyr
625                 630                 635                 640

Lys Tyr Ser Pro Tyr His Asn Ile Pro Ser Gly Lys Val Val Ile Pro
                645                 650                 655

Ala Met Ile Phe Phe Thr Ala Ala Tyr Asp Asp Arg Val Ser Pro Leu
            660                 665                 670

His Thr Phe Lys His Val Ala Ala Leu Gln Tyr Asn Phe Pro Thr Gly
                675                 680                 685

Pro Asn Pro Ile Met Met Arg Ile Asp Leu Asn Thr Gly His Tyr Ala
690                 695                 700

Gly Lys Ser Thr Gln Lys Met Leu Glu Glu Thr Ala Asp Glu Tyr Ser
705                 710                 715                 720

Phe Ile Gly Arg Ser Met Glu Leu Thr Met His Thr Gln Asn His Trp
                725                 730                 735

Ser Cys Val Thr Ser
            740

<210> SEQ ID NO 52
<211> LENGTH: 744
<212> TYPE: PRT
<213> ORGANISM: Lentinula lateritia

<400> SEQUENCE: 52

Met Ser Val Pro Gln Trp Val Pro Tyr Pro Val Ser Arg Asp Asp
1               5                   10                  15

Thr Ser Ala Ile Thr Tyr Gln Ser Lys Leu Arg Gly Ser Val Thr Val
                20                  25                  30

Arg Asp Pro Tyr Ser Ala Leu Glu Val Pro Phe Asp Asp Ser Glu Glu
            35                  40                  45

Thr Lys Ala Phe Val His Ala Gln Arg Lys Phe Ala Arg Met Tyr Leu
        50                  55                  60

Asp Glu Ile Pro Asp Arg Glu Thr Trp Leu Gln Thr Leu Lys Glu Ser
65                  70                  75                  80

Trp Asn Tyr Arg Arg Phe Thr Val Pro Lys Arg Glu Ser Asp Gly Tyr
                85                  90                  95

Thr Tyr Phe Glu Tyr Asn Asp Gly Leu Gln Ser Gln Met Ser Leu Arg
            100                 105                 110

Arg Val Lys Val Ser Glu Glu Asp Thr Ile Leu Thr Glu Ser Gly Pro
        115                 120                 125

Gly Gly Glu Leu Phe Phe Asp Pro Asn Leu Leu Ser Leu Asp Gly Asn
    130                 135                 140
```

```
Ala Ala Leu Thr Gly Ser Met Met Ser Pro Cys Gly Lys Tyr Trp Ala
145                 150                 155                 160

Tyr Gly Val Ser Glu His Gly Ser Asp Trp Met Thr Thr Tyr Val Arg
            165                 170                 175

Lys Thr Ser Ser Pro His Met Pro Ser Gln Glu Lys Gly Lys Asp Pro
        180                 185                 190

Gly Arg Met Asp Asp Val Ile Arg Tyr Ser Arg Phe Phe Ile Val Tyr
    195                 200                 205

Trp Ser Ser Asp Ser Lys Gly Phe Phe Tyr Ser Arg Tyr Pro Pro Glu
    210                 215                 220

Asp Asp Glu Gly Lys Gly Asn Thr Pro Ala Gln Asn Cys Met Val Tyr
225                 230                 235                 240

Tyr His Arg Leu Gly Glu Lys Gln Glu Lys Asp Thr Leu Val Tyr Glu
            245                 250                 255

Asp Pro Glu His Pro Phe Trp Leu Trp Ala Leu Gln Leu Ser Pro Ser
            260                 265                 270

Gly Arg Tyr Ala Leu Leu Thr Ala Ser Arg Asp Ala Ser His Thr Gln
        275                 280                 285

Leu Ala Lys Ile Ala Asp Ile Gly Thr Ser Asp Ile Gln Asn Gly Ile
290                 295                 300

Gln Trp Leu Thr Ile His Asp Gln Trp Gln Ala Arg Phe Val Ile Ile
305                 310                 315                 320

Gly Asp Asp Asp Ser Thr Ile Tyr Phe Met Thr Asn Leu Glu Ala Lys
                325                 330                 335

Asn Tyr Leu Val Ala Thr Leu Asp Ile Arg His Ser Glu Ala Gly Val
            340                 345                 350

Lys Thr Leu Val Ala Glu Asn Pro Asp Ala Leu Leu Ile Ser Ala Ser
        355                 360                 365

Ile Leu Ser Thr Asp Lys Leu Val Leu Val Tyr Leu His Asn Ala Arg
370                 375                 380

His Glu Ile His Val His Asp Leu Asn Thr Gly Lys Pro Ile Arg Gln
385                 390                 395                 400

Ile Phe Asp Asn Leu Ile Gly Gln Phe Ser Leu Ser Gly Arg Arg Asp
            405                 410                 415

Asp Asn Asp Met Phe Val Phe His Ser Gly Phe Thr Ser Pro Gly Thr
            420                 425                 430

Ile Tyr Arg Phe Arg Leu Asn Glu Asp Ser Asn Lys Gly Thr Leu Phe
        435                 440                 445

Arg Ala Ile Gln Val Pro Gly Leu Asn Leu Asn Asp Phe Thr Thr Glu
450                 455                 460

Ser Val Phe Tyr Pro Ser Lys Asp Gly Thr Pro Ile His Met Phe Ile
465                 470                 475                 480

Thr Arg Leu Lys Asp Thr Pro Val Asp Gly Thr Ala Pro Val Tyr Ile
            485                 490                 495

Tyr Gly Tyr Gly Gly Phe Ala Leu Ala Met Leu Pro Thr Phe Ser Val
        500                 505                 510

Ser Thr Leu Leu Phe Cys Lys Ile Tyr Arg Ala Met Tyr Val Val Pro
        515                 520                 525

Asn Ile Arg Gly Gly Ser Glu Phe Gly Glu Ser Trp His Arg Glu Gly
        530                 535                 540

Met Leu Asp Lys Lys Gln Asn Val Phe Asp Asp Phe Asn Ala Ala Thr
545                 550                 555                 560

Lys Trp Leu Val Ala Asn Lys Tyr Ala Asn Lys Tyr Asn Val Ala Ile
```

565                 570                 575
Arg Gly Gly Ser Asn Gly Gly Val Leu Thr Thr Ala Cys Ala Asn Gln
                580                 585                 590

Ala Pro Glu Leu Tyr Arg Cys Val Ile Thr Ile Gly Gly Ile Ile Asp
            595                 600                 605

Met Leu Arg Phe Pro Lys Phe Thr Phe Gly Ala Leu Trp Arg Ser Glu
        610                 615                 620

Tyr Gly Asp Pro Glu Asp Pro Glu Asp Phe Asp Phe Ile Tyr Lys Tyr
625                 630                 635                 640

Ser Pro Tyr His Asn Ile Pro Ser Gly Asp Val Val Leu Pro Ala Met
                645                 650                 655

Leu Phe Phe Thr Ala Ala Tyr Asp Asp Arg Val Ser Pro Leu His Ser
            660                 665                 670

Phe Lys His Val Ala Ala Leu Gln Tyr Tyr Phe Pro Asn Gly Pro Asn
        675                 680                 685

Pro Val Leu Met Arg Ile Asp Leu Asn Thr Gly His Phe Ala Gly Lys
    690                 695                 700

Ser Thr Gln Lys Met Leu Glu Glu Thr Ala Asp Glu Tyr Ser Phe Ile
705                 710                 715                 720

Gly Lys Ser Met Gly Leu Val Met Cys Val Gln Asn Glu His Ala Ser
                725                 730                 735

Lys Gln Trp Ser Cys Val Val Thr
            740

<210> SEQ ID NO 53
<211> LENGTH: 746
<212> TYPE: PRT
<213> ORGANISM: Dendrothele bispora

<400> SEQUENCE: 53

Met Ser Val Pro Gln Trp Gly Pro Tyr Leu Pro Val Asp Arg Asp Glu
1               5                   10                  15

Thr Ser Ala Ile Thr Tyr Arg Thr Lys Leu His Gly Ser Val Thr Val
            20                  25                  30

Pro Asp Pro Tyr Ser Gly Leu Glu Ala Pro Leu Asp Glu Ser Ala Lys
        35                  40                  45

Thr Lys Ala Phe Val His Ser Gln Arg Lys Phe Ala Arg Thr Tyr Leu
    50                  55                  60

Asp Glu Asn Pro Asp Lys Glu Val Trp Leu Glu Thr Leu Lys Gln Ser
65                  70                  75                  80

Trp Asn Tyr Lys Arg Phe Thr Val Pro Arg His Glu Ser Asp Asp His
                85                  90                  95

Ile Tyr Phe Glu Tyr Asn Asp Gly Leu Gln Ser Gln Leu Ser Leu His
            100                 105                 110

Arg Val Lys Val Gly Asp Glu Asp Thr Ile Leu Thr Glu Ser Gly Pro
        115                 120                 125

Gly Gly Glu Leu Phe Phe Asp Pro Asn Met Ile Ser Leu Asp Gly Asn
    130                 135                 140

Ala Ser Leu Thr Gly Phe Ile Met Ser Pro Cys Gly Lys Tyr Trp Ala
145                 150                 155                 160

Tyr Gly Val Ser Glu His Gly Ser Asp Trp Met Thr Ile Tyr Val Arg
                165                 170                 175

Glu Thr Ser Ser Pro His Val Pro Ser Gln Glu Arg Gly Lys Asp Pro
            180                 185                 190

```
Gly Arg Met Asp Asp Glu Val Arg His Ser Arg Phe Phe Ile Val Ser
            195                 200                 205

Trp Thr Gly Asp Ser Lys Gly Phe Phe Tyr Ser Lys Tyr Pro Pro Glu
210                 215                 220

Glu Asn Glu Gly Lys Gly Asn Ala Pro Ala Lys Asn Cys Ile Val Tyr
225                 230                 235                 240

Tyr His Arg Leu Gly Glu Lys Gln Glu Asn Asp Thr Leu Val His Lys
            245                 250                 255

Asp Ser Gly His Pro Phe Trp Leu Trp Ser Leu Gln Thr Thr Pro Ser
            260                 265                 270

Gly Arg Tyr Ala Leu Leu Ala Ala Ser Arg Asp Ala Ser His Thr Gln
            275                 280                 285

Leu Ala Lys Ile Ala Asp Ile His Asp Asn Asp Ile Gly Ala Ser Met
290                 295                 300

Lys Trp Ile Asn Leu His Asp Ser Trp Glu Ala Arg Phe Ser Ile Ile
305                 310                 315                 320

Gly Asp Asp Ser Lys Ile Tyr Phe Met Thr Asn Leu Gln Ala Pro
            325                 330                 335

Asn Tyr Lys Val Ala Ile Phe Asp Ala Cys His Pro Ser Pro Asp Ala
            340                 345                 350

Asp Leu Thr Thr Leu Val Ala Glu Asp Pro Asn Ala Leu Leu Ile Ala
            355                 360                 365

Ala Ser Ile His Ala Lys Asp Lys Leu Ala Leu Val Tyr Leu Arg Asp
            370                 375                 380

Ala Arg His Glu Ile His Val His Asp Leu Val Thr Gly Arg Leu Leu
385                 390                 395                 400

Arg Arg Ile Leu Gly Asp Leu Val Gly Gln Phe Met Val Thr Gly Arg
                405                 410                 415

Arg Ala Asp Asn Asp Met Phe Ile Phe Tyr Ser Gly Phe Thr Ser Pro
                420                 425                 430

Gly Thr Val Tyr Arg Tyr Lys Phe Asp Asp Glu Arg Asp Thr Cys Ser
            435                 440                 445

Leu Phe Arg Ala Ile Arg Ile Pro Gly Leu Asp Leu Asp Lys Phe Val
450                 455                 460

Thr Glu Ser Val Phe Tyr Pro Ser Lys Asp Gly Thr Ser Ile His Met
465                 470                 475                 480

Phe Ile Thr Arg Pro Lys Asp Val Leu Leu Asp Gly Thr Ala Pro Val
                485                 490                 495

Leu Gln Tyr Gly Tyr Gly Gly Phe Ala Leu Ala Met Leu Pro Thr Phe
            500                 505                 510

Ser Val Ser Thr Leu Leu Phe Cys Lys Ile Tyr Arg Ala Met Tyr Val
            515                 520                 525

Val Pro Asn Ile Arg Gly Gly Ser Glu Tyr Gly Glu Ser Trp His Arg
530                 535                 540

Ala Gly Met Leu Gly Asn Lys Gln Asn Val Phe Asp Asp Leu Asn Ala
545                 550                 555                 560

Ala Thr Glu Trp Leu Val Ala Asn Lys Tyr Ala Asn Lys Asp Arg Val
                565                 570                 575

Ala Ile Arg Gly Gly Ser Asn Gly Gly Val Leu Thr Thr Ala Cys Ala
            580                 585                 590

Asn Gln Ala Pro Gly Leu Tyr Arg Cys Val Ile Thr Ile Gly Gly Ile
            595                 600                 605

Ile Asp Met Leu Arg Phe Pro Lys Phe Thr Phe Gly Ala Leu Trp Cys
```

```
                610             615             620
Ser Glu Tyr Gly Asp Pro Glu Asp Pro Glu Ala Phe Asp Phe Ile Tyr
625                 630                 635                 640

Lys Tyr Ser Pro Tyr His Asn Ile Pro Ser Gly Glu Thr Val Met Pro
                645                 650                 655

Ala Met Leu Phe Phe Thr Ala Ala Tyr Asp Asp Arg Val Ser Pro Leu
                660                 665                 670

His Thr Phe Lys His Val Ala Ala Leu Gln His Ser Phe Pro His Gly
                675                 680                 685

Pro Asn Pro Ile Leu Met Arg Val Asp Met Asn Ser Gly His Tyr Ala
            690                 695                 700

Gly Lys Ser Thr Gln Lys Met Leu Glu Glu Thr Ala Asp Glu Tyr Ser
705                 710                 715                 720

Phe Ile Gly Lys Ser Met Gly Leu Thr Met Gln Val Glu Asn Lys Ser
                725                 730                 735

Asp Ser Asn Arg Trp Ser Cys Val Val Asn
                740                 745

<210> SEQ ID NO 54
<211> LENGTH: 723
<212> TYPE: PRT
<213> ORGANISM: Dendrothele bispora

<400> SEQUENCE: 54

Met Pro Val Pro Gly Trp Gly Ser Tyr Pro Pro Phe Asp Arg Asp Glu
1               5                   10                  15

Thr Ser Ala Ile Thr Tyr Gln Ser Lys Leu Arg Gly Ser Val Thr Val
                20                  25                  30

Tyr Asp Pro Tyr Ser Ala Leu Glu Val Pro Ser Asn Asp Ser Glu Glu
            35                  40                  45

Thr Lys Ala Phe Ile Leu Glu Gln Asn Lys Phe Ser Arg Ala Tyr Leu
    50                  55                  60

Asp Ala Asn Pro Asp Arg Gln Thr Trp Leu Glu Thr Leu Lys Lys Ser
65                  70                  75                  80

Trp His Tyr Arg Arg Phe Thr Thr Pro Thr Arg Glu Ser Asp Asp His
                85                  90                  95

Phe Tyr Phe Leu Tyr Asn Asp Gly Leu Leu Ala Gln Ser Pro Val Tyr
            100                 105                 110

Arg Val Lys Val Asp Asp Val Asp Ser Ile Leu Thr Glu Ser Gly Pro
        115                 120                 125

Gly Gly Glu Leu Phe Phe Asp Pro Asn Leu Leu Ser Leu Asp Gly Val
    130                 135                 140

Ala Thr Leu Thr Gly Thr Ala Met Ser Pro Cys Gly Lys Tyr Trp Ala
145                 150                 155                 160

Tyr Ala Ile Ser Glu His Gly Asn Asp Trp Met Thr Ile Tyr Val Arg
                165                 170                 175

Lys Thr Ser Ser Pro His His Pro Ser Gln Glu Arg Gly Lys Asp Pro
            180                 185                 190

Gly Arg Met Asp Asp Val Ile Gln His Cys Arg Ile Phe Val Ser
        195                 200                 205

Trp Thr Asp Asp Ser Lys Gly Phe Phe Tyr Ser Lys Trp Pro Pro Asp
    210                 215                 220

Glu Asn Gln Gly Asn Gly Asn Ala Pro Gly Val Asp Cys Lys Ile Tyr
225                 230                 235                 240
```

```
Tyr His Arg Ile Ala Val Phe Leu Ser Glu Asp Pro Glu His Pro Gly
                245                 250                 255

Trp Phe Trp Asn Val Glu Val Ser Pro Ser Gly Gln Tyr Ala Leu Leu
            260                 265                 270

Leu Gly Thr Arg Asp Ala Ser Leu Asn Gln Leu Val Lys Leu Ala Asp
        275                 280                 285

Leu His Thr Ser Asp Ile Glu Thr Gly Ile Gln Trp Thr Thr Leu His
    290                 295                 300

Asp Ser Trp Gln Ala Arg Phe Ser Ile Ile Gly Asn Asp Asn Ser Leu
305                 310                 315                 320

Ile Tyr Phe Arg Thr Asn Leu Glu Ala Glu Asn His Arg Val Ala Ala
                325                 330                 335

Phe Asn Val His His Pro Gln Ala Gly Phe Thr Thr Leu Val Pro Gly
            340                 345                 350

Ser Leu Asp Ser Val Leu Leu Asp Ala Lys Leu Tyr Gly Ile Asn Lys
        355                 360                 365

Leu Val Leu Val Tyr Gln His Leu Ala Lys His Glu Ile Tyr Leu His
    370                 375                 380

Asp Ile Glu Thr Gly Arg Arg Leu Arg Gln Ile Phe Thr Asp Leu Ala
385                 390                 395                 400

Gly Lys Met Thr Ile Ser Gly Arg Arg Ala Asp His Glu Met Phe Val
                405                 410                 415

Leu Tyr Ser Asp Phe Ile Ser Pro Gly Thr Leu Tyr Arg Gln Leu Leu
            420                 425                 430

Asn Arg Tyr Lys Phe Asp Lys Asp Thr Asp Lys Gly Leu Leu Phe Arg
        435                 440                 445

Thr Ile Lys Val Asp Ala Leu Asn Leu Asp Asp Phe Val Thr Glu Ser
    450                 455                 460

Glu Phe Tyr Pro Ser Lys Asp Gly Thr Leu Val His Met Phe Ile Thr
465                 470                 475                 480

His Pro Lys Asp Val Phe Thr Asp Gly Thr Ala Pro Val Leu Met Tyr
                485                 490                 495

Gly Tyr Gly Gly Phe Gly Ala Pro Met Phe Pro Asn Phe Ser Ile Ser
            500                 505                 510

Asn Leu Leu Phe Cys Asn Ile Tyr Arg Gly Ile Gly Gly Ser Glu Phe
        515                 520                 525

Gly Glu Ser Trp His Arg Glu Gly Met Leu Glu Lys Lys Gln Asn Val
    530                 535                 540

Phe Asp Asp Phe Arg Ala Ala Ala Glu Trp Leu Val Thr Asn Lys Tyr
545                 550                 555                 560

Ala Arg Lys Gly Gly Val Ala Ile Arg Gly Gly Ser Asn Gly Gly Ile
                565                 570                 575

Met Thr Thr Ala Cys Ser Asn Gln Ala Pro Glu Leu Tyr Gly Cys Val
            580                 585                 590

Ile Thr Ile Ala Gly Leu Gln Asp Met Leu Arg Tyr Thr Lys Phe Thr
        595                 600                 605

Phe Gly Asp Leu Leu Arg Ser Glu Tyr Gly Asn Pro Glu Asn Pro Glu
    610                 615                 620

Asp Phe Asp Tyr Ile Tyr Lys Tyr Ser Pro Tyr His Asn Ile Pro Leu
625                 630                 635                 640

Lys Glu Val Thr Met Pro Pro Met Leu Phe Leu Gln Ser Asp Tyr Asp
                645                 650                 655

Asp Arg Val Ser Pro Leu His Thr Tyr Lys His Val Ala Ala Leu Gln
```

```
            660                 665                 670
His Arg Phe Pro Lys Gly Pro Asn Pro Ile Ile Leu Arg Ile Asp Leu
            675                 680                 685

Asp Ser Gly His Tyr Ala Gly Lys Ser Thr Met Arg Leu Ile Glu Glu
            690                 695                 700

Thr Ala Asp Glu Tyr Arg Trp Asp Leu Asp Ser Ser Ser Ser Ser Cys
705                 710                 715                 720

Tyr Tyr Ile

<210> SEQ ID NO 55
<211> LENGTH: 724
<212> TYPE: PRT
<213> ORGANISM: Gypsophila vaccaria

<400> SEQUENCE: 55

Met Ala Thr Ser Gly Phe Ser Lys Pro Leu His Tyr Pro Pro Val Arg
1               5                   10                  15

Arg Asp Glu Thr Val Val Asp Asp Tyr Phe Gly Val Lys Val Ala Asp
                20                  25                  30

Pro Tyr Arg Trp Leu Glu Asp Pro Asn Ser Glu Glu Thr Lys Glu Phe
            35                  40                  45

Val Asp Asn Gln Glu Lys Leu Ala Asn Ser Val Leu Glu Glu Cys Glu
50                  55                  60

Leu Ile Asp Lys Phe Lys Gln Lys Ile Ile Asp Phe Val Asn Phe Pro
65                  70                  75                  80

Arg Cys Gly Val Pro Phe Arg Arg Ala Asn Lys Tyr Phe His Phe Tyr
                85                  90                  95

Asn Ser Gly Leu Gln Ala Gln Asn Val Phe Gln Met Gln Asp Asp Leu
            100                 105                 110

Asp Gly Lys Pro Glu Val Leu Tyr Asp Pro Asn Leu Arg Glu Gly Gly
        115                 120                 125

Arg Ser Gly Leu Ser Leu Tyr Ser Val Ser Glu Asp Ala Lys Tyr Phe
    130                 135                 140

Ala Phe Gly Ile His Ser Gly Leu Thr Glu Trp Val Thr Ile Lys Ile
145                 150                 155                 160

Leu Lys Thr Glu Asp Arg Ser Tyr Leu Pro Asp Thr Leu Glu Trp Val
                165                 170                 175

Lys Phe Ser Pro Ala Ile Trp Thr His Asp Asn Lys Gly Phe Phe Tyr
            180                 185                 190

Cys Pro Tyr Pro Pro Leu Lys Glu Gly Glu Asp His Met Thr Arg Ser
        195                 200                 205

Ala Val Asn Gln Glu Ala Arg Tyr His Phe Leu Gly Thr Asp Gln Ser
    210                 215                 220

Glu Asp Ile Leu Leu Trp Arg Asp Leu Glu Asn Pro Ala His His Leu
225                 230                 235                 240

Lys Cys Gln Ile Thr Asp Asp Gly Lys Tyr Phe Leu Tyr Ile Leu
                245                 250                 255

Asp Gly Cys Asp Asp Ala Asn Lys Val Tyr Cys Leu Asp Leu Thr Lys
            260                 265                 270

Leu Pro Asn Gly Leu Glu Ser Phe Arg Gly Arg Glu Asp Ser Ala Pro
        275                 280                 285

Phe Met Lys Leu Ile Asp Ser Phe Asp Ala Ser Tyr Thr Ala Ile Ala
    290                 295                 300

Asn Asp Gly Ser Val Phe Thr Phe Gln Thr Asn Lys Asp Ala Pro Arg
```

```
        305                 310                 315                 320
Lys Lys Leu Val Arg Val Asp Leu Asn Asn Pro Ser Val Trp Thr Asp
                325                 330                 335

Leu Val Pro Glu Ser Lys Lys Asp Leu Leu Glu Ser Ala His Ala Val
                340                 345                 350

Asn Glu Asn Gln Leu Ile Leu Arg Tyr Leu Ser Asp Val Lys His Val
                355                 360                 365

Leu Glu Ile Arg Asp Leu Glu Ser Gly Ala Leu Gln His Arg Leu Pro
                370                 375                 380

Ile Asp Ile Gly Ser Val Asp Gly Ile Thr Ala Arg Arg Arg Asp Ser
385                 390                 395                 400

Val Val Phe Phe Lys Phe Thr Ser Ile Leu Thr Pro Gly Ile Val Tyr
                405                 410                 415

Gln Cys Asp Leu Lys Asn Asp Pro Thr Gln Leu Lys Ile Phe Arg Glu
                420                 425                 430

Ser Val Val Pro Asp Phe Asp Arg Ser Glu Phe Glu Val Lys Gln Val
                435                 440                 445

Phe Val Pro Ser Lys Asp Gly Thr Lys Ile Pro Ile Phe Ile Ala Ala
                450                 455                 460

Arg Lys Gly Ile Ser Leu Asp Gly Ser His Pro Cys Glu Met His Gly
465                 470                 475                 480

Tyr Gly Gly Phe Gly Ile Asn Met Met Pro Thr Phe Ser Ala Ser Arg
                485                 490                 495

Ile Val Phe Leu Lys His Leu Gly Gly Val Phe Cys Leu Ala Asn Ile
                500                 505                 510

Arg Gly Gly Gly Glu Tyr Gly Glu Glu Trp His Lys Ala Gly Phe Arg
                515                 520                 525

Asp Lys Lys Gln Asn Val Phe Asp Asp Phe Ile Ser Ala Ala Glu Tyr
                530                 535                 540

Leu Ile Ser Ser Gly Tyr Thr Lys Ala Arg Arg Val Ala Ile Glu Gly
545                 550                 555                 560

Gly Ser Asn Gly Gly Leu Leu Val Ala Ala Cys Ile Asn Gln Arg Pro
                565                 570                 575

Asp Leu Phe Gly Cys Ala Glu Ala Asn Cys Gly Val Met Asp Met Leu
                580                 585                 590

Arg Phe His Lys Phe Thr Leu Gly Tyr Leu Trp Thr Gly Asp Tyr Gly
                595                 600                 605

Cys Ser Asp Lys Glu Glu Phe Lys Trp Leu Ile Lys Tyr Ser Pro
                610                 615                 620

Ile His Asn Val Arg Arg Pro Trp Glu Gln Pro Gly Asn Glu Glu Thr
625                 630                 635                 640

Gln Tyr Pro Ala Thr Met Ile Leu Thr Ala Asp His Asp Asp Arg Val
                645                 650                 655

Val Pro Leu His Ser Phe Lys Leu Leu Ala Thr Met Gln His Val Leu
                660                 665                 670

Cys Thr Ser Leu Glu Asp Ser Pro Gln Lys Asn Pro Ile Ile Ala Arg
                675                 680                 685

Ile Gln Arg Lys Ala Ala His Tyr Gly Arg Ala Thr Met Thr Gln Ile
                690                 695                 700

Ala Glu Val Ala Asp Arg Tyr Gly Phe Met Lys Ala Leu Glu Ala
705                 710                 715                 720

Pro Trp Ile Asp
```

```
<210> SEQ ID NO 56
<211> LENGTH: 744
<212> TYPE: PRT
<213> ORGANISM: Gymnopus fusipes

<400> SEQUENCE: 56

Met Ser Met Ser Leu Leu Gly Val Tyr Pro Val Lys Arg Asp Glu
1               5                   10                  15

Ala Ser Ala Ile Thr Tyr Gln Ser Lys Leu His Gly Ser Val Ile Val
            20                  25                  30

His Asp Pro Tyr Ser Ala Leu Glu Ile Pro Ser Asn Asp Ser Leu Glu
        35                  40                  45

Thr Lys Ala Phe Val Leu Ser Gln Gly Lys Phe Ser Arg Ala Tyr Leu
    50                  55                  60

Asp Glu Ile Pro Thr Arg Lys Asn Trp Leu Lys Ile Leu Lys Ser Asn
65                  70                  75                  80

Trp Ser Tyr Arg Arg Phe Ser Ala Leu Lys Arg Glu Ser Asp Asn His
                85                  90                  95

Phe Tyr Phe Glu Tyr Asn Asp Gly Leu Gln Pro Gln Ser Ser Ile Tyr
            100                 105                 110

Arg Val Lys Val Gly Glu Glu Asp Ser Ile Leu Thr Glu Ser Gly Pro
        115                 120                 125

Gly Gly Glu Leu Phe Phe Asp Pro Asn Leu Leu Ser Leu Asp Gly Val
    130                 135                 140

Ala Ala Leu Thr Gly Ala Ala Met Ser Pro Ser Gly Lys Tyr Trp Ala
145                 150                 155                 160

Tyr Gly Val Ser Glu His Gly Asn Asn Ser Met Thr Ile Tyr Val Arg
                165                 170                 175

Lys Thr Ser Ser Pro His Gln Pro Ser Gln Glu Lys Gly Thr Asp Pro
            180                 185                 190

Gly Arg Met Asn Asp Val Leu Gln His Ile Arg Met Leu Phe Val Ser
        195                 200                 205

Trp Thr Arg Asp Ser Lys Gly Phe Phe Tyr Gln Arg Tyr Pro Pro Glu
    210                 215                 220

Lys Asn Glu Gly Asn Gly Asn Ala Pro Gly Gln Asn Cys Lys Ile Tyr
225                 230                 235                 240

Tyr His Tyr Ile Gly Thr Glu Gln Asp Ser Asp Ile Leu Ile His Glu
                245                 250                 255

Asp Pro Asp His Pro Asp Trp Phe Ser Tyr Val Gln Leu Ser Pro Ser
            260                 265                 270

Gly Gln Tyr Val Leu Leu Ile Asn Arg Asp Ser Ser Leu Asn Tyr
        275                 280                 285

Leu Ala Lys Ile Ala Asp Leu Ser Val Asn Asp Ile Gly Thr His Ile
    290                 295                 300

Gln Trp Lys Asn Leu His Asp Ser Trp Asn His Phe Thr Met Ile Gly
305                 310                 315                 320

Asn Asp Tyr Ser Val Ile Tyr Phe Lys Thr Asn Leu Asp Ala Gln Asn
                325                 330                 335

Tyr Lys Val Ala Thr Ile Asp Phe Leu Gln Pro Glu Met Gly Phe Thr
            340                 345                 350

Thr Leu Val Lys Glu Asn Pro Asn Ser Val Leu Val Glu Ala Lys Ile
        355                 360                 365

Phe Arg Glu Asp Lys Leu Val Leu Leu Tyr Gln Gln Asn Ala Ser His
    370                 375                 380
```

Gln Ile His Ile Tyr Asp Leu Lys Ser Gly Ala Trp Leu Gln Ile
385                 390                 395                 400

Phe Lys Asn Leu Thr Gly Phe Ile Thr Thr Val Pro Asn Gly Arg Ala
                405                 410                 415

Glu Asp Glu Met Phe Phe Leu Tyr Asn Asp Phe Ile Thr Pro Gly Thr
            420                 425                 430

Ile Tyr Gln Tyr Lys Phe Asp Asp Glu Ser Asp Lys Gly Leu Val Phe
                435                 440                 445

Arg Ala Ile Gln Ile Asp Gly Leu Asn Leu Asp Phe Val Thr Glu
    450                 455                 460

Ser Lys Phe Tyr Pro Ser Lys Asp Gly Thr Ser Val His Met Phe Ile
465                 470                 475                 480

Thr Arg Pro Lys Asp Val Leu Ile Asp Gly Thr Ala Ala Val Tyr Met
                485                 490                 495

Tyr Gly Tyr Gly Gly Phe Ser Ile Ser Val Leu Pro Thr Phe Ser Ile
                500                 505                 510

Ser Thr Leu Leu Phe Cys Lys Ile Tyr Arg Ala Met Tyr Val Val Pro
            515                 520                 525

Asn Ile Arg Gly Gly Ser Glu Phe Gly Glu Ser Trp His Arg Glu Gly
            530                 535                 540

Met Leu Asp Lys Lys Gln Asn Gly His Asp Asp Phe His Ala Ala Ala
545                 550                 555                 560

Glu Trp Leu Ile Ala Asn Lys Tyr Ala Lys Lys Asp Cys Val Ala Ile
                565                 570                 575

Arg Gly Gly Ser Ser Gly Gly Ile Leu Thr Thr Ala Cys Ala Asn Gln
                580                 585                 590

Ala Pro Glu Leu Tyr Arg Cys Val Ile Thr Ile Glu Gly Ile Ile Asp
                595                 600                 605

Met Leu Lys Phe Pro Lys Phe Thr Phe Gly Ala Leu Leu Arg Ser Glu
                610                 615                 620

Tyr Gly Asp Pro Glu Asp Pro Glu Ala Phe Asp Tyr Ile Tyr Lys Tyr
625                 630                 635                 640

Ser Pro Tyr His Asn Ile Pro Leu Gly Asp Val Val Met Pro Pro Met
                645                 650                 655

Leu Phe Phe Asn Ala Gly Tyr Asp Asp Arg Val Pro Pro Leu His Thr
                660                 665                 670

Phe Lys His Val Ala Ala Leu Gln His Arg Phe Pro Lys Gly Pro Asn
                675                 680                 685

Pro Ile Leu Met Arg Met Asp Leu Ser Ser Gly His Tyr Ala Gly Lys
                690                 695                 700

Ser Val Gln Lys Met Ile Glu Glu Thr Ala Asp Glu Tyr Ser Phe Ile
705                 710                 715                 720

Gly Lys Ser Met Gly Leu Thr Met Gln Val Arg Ala Lys Pro Ser Asn
                725                 730                 735

Asn Arg Trp Ser Cys Val Val Thr
            740

<210> SEQ ID NO 57
<211> LENGTH: 744
<212> TYPE: PRT
<213> ORGANISM: Lentinula edodes

<400> SEQUENCE: 57

Met Ser Val Pro Gln Trp Asp Pro Tyr Pro Pro Val Ser Arg Asp Glu

```
  1               5                  10                 15
Thr Ser Ala Ile Thr Tyr Gln Ser Lys Leu Cys Gly Ser Val Thr Val
                20                 25                 30

Arg Asp Pro Tyr Ser Ala Leu Glu Val Pro Phe Asp Asp Ser Glu Glu
                35                 40                 45

Thr Lys Ala Phe Val His Ala Gln Arg Lys Phe Ala Arg Thr Tyr Leu
    50                 55                 60

Asp Glu Ile Pro Asp Arg Glu Thr Trp Leu Gln Thr Leu Lys Glu Ser
65                 70                 75                 80

Trp Asn Tyr Arg Arg Phe Thr Val Pro Lys Arg Glu Ser Asp Gly Tyr
                85                 90                 95

Thr Tyr Phe Glu Tyr Asn Asp Gly Leu Gln Ser Gln Met Ser Leu Arg
                100                105                110

Arg Val Lys Val Ser Glu Glu Asp Thr Ile Leu Thr Glu Ser Gly Pro
                115                120                125

Gly Gly Glu Leu Phe Phe Asp Pro Asn Leu Leu Ser Leu Asp Gly Asn
                130                135                140

Ala Ala Leu Thr Gly Ser Met Met Ser Pro Cys Gly Lys Tyr Trp Ala
145                150                155                160

Tyr Gly Val Ser Glu His Gly Ser Asp Trp Met Thr Thr Tyr Val Arg
                165                170                175

Lys Thr Ser Ser Pro His Met Pro Ser Gln Glu Lys Gly Lys Asp Pro
                180                185                190

Gly Arg Met Asp Asp Val Ile Arg Tyr Ser Arg Phe Phe Ile Val Tyr
                195                200                205

Trp Ser Ser Asp Ser Lys Gly Phe Phe Tyr Ser Arg Tyr Pro Pro Glu
                210                215                220

Asp Asp Glu Gly Lys Gly Asn Thr Pro Ala Gln Asn Cys Met Val Tyr
225                230                235                240

Tyr His Arg Leu Gly Glu Lys Gln Glu Lys Asp Thr Leu Val Tyr Glu
                245                250                255

Asp Pro Glu His Pro Phe Trp Leu Trp Ala Leu Gln Leu Ser Pro Ser
                260                265                270

Gly Arg Tyr Ala Leu Leu Thr Ala Ser Arg Asp Ala Ser His Thr Gln
                275                280                285

Leu Ala Lys Ile Ala Asp Ile Gly Thr Ser Asp Ile Gln Asn Gly Ile
                290                295                300

Gln Trp Leu Thr Ile His Asp Gln Trp Gln Ala Arg Phe Val Ile Ile
305                310                315                320

Gly Asp Asp Asp Ser Thr Ile Tyr Phe Met Thr Asn Leu Glu Ala Lys
                325                330                335

Asn Tyr Leu Val Ala Thr Leu Asp Ile Arg His Ser Glu Ala Gly Val
                340                345                350

Lys Thr Leu Val Ala Glu Asn Pro Asp Ala Leu Leu Ile Ser Ala Ser
                355                360                365

Ile Leu Ser Thr Asp Lys Leu Val Leu Val Tyr Leu His Asn Ala Arg
                370                375                380

His Glu Ile His Val His Asp Leu Asn Thr Gly Lys Pro Ile Arg Gln
385                390                395                400

Ile Phe Asp Asn Leu Ile Gly Gln Phe Ser Leu Ser Gly Arg Arg Asp
                405                410                415

Asp Asn Asp Met Phe Val Phe His Ser Gly Phe Thr Ser Pro Gly Thr
                420                425                430
```

```
Ile Tyr Arg Phe Arg Leu Asn Glu Asp Ser Asn Lys Gly Thr Leu Phe
        435                 440                 445

Arg Ala Val Gln Val Pro Gly Leu Asn Leu Ser Asp Phe Thr Thr Glu
    450                 455                 460

Ser Val Phe Tyr Pro Ser Lys Asp Gly Thr Pro Ile His Met Phe Ile
465                 470                 475                 480

Thr Arg Leu Lys Asp Thr Pro Val Asp Gly Thr Ala Pro Val Tyr Ile
                485                 490                 495

Tyr Gly Tyr Gly Gly Phe Ala Leu Ala Met Leu Pro Thr Phe Ser Val
                500                 505                 510

Ser Thr Leu Leu Phe Cys Lys Ile Tyr Arg Ala Met Tyr Val Val Pro
            515                 520                 525

Asn Ile Arg Gly Gly Ser Glu Phe Gly Glu Ser Trp His Arg Glu Gly
        530                 535                 540

Met Leu Asp Lys Lys Gln Asn Val Phe Asp Asp Phe Asn Ala Ala Thr
545                 550                 555                 560

Lys Trp Leu Val Ala Asn Lys Tyr Ala Asn Lys Tyr Asn Val Ala Ile
                565                 570                 575

Arg Gly Gly Ser Asn Gly Gly Val Leu Thr Thr Ala Cys Ala Asn Gln
            580                 585                 590

Ala Pro Glu Leu Tyr Arg Cys Val Ile Thr Ile Gly Ile Ile Asp
        595                 600                 605

Met Leu Arg Phe Pro Lys Phe Thr Phe Gly Ala Leu Trp Arg Ser Glu
        610                 615                 620

Tyr Gly Asp Pro Glu Asp Pro Glu Asp Phe Asp Phe Ile Tyr Lys Tyr
625                 630                 635                 640

Ser Pro Tyr His Asn Ile Pro Ser Gly Asp Val Val Leu Pro Ala Met
                645                 650                 655

Leu Phe Phe Thr Ala Ala Tyr Asp Asp Arg Val Ser Pro Leu His Ser
            660                 665                 670

Phe Lys His Val Ala Ala Leu Gln Tyr Asn Phe Pro Asn Gly Pro Asn
        675                 680                 685

Pro Val Leu Met Arg Ile Asp Leu Asn Thr Gly His Phe Ala Gly Lys
        690                 695                 700

Ser Thr Gln Lys Met Leu Glu Glu Thr Ala Asp Glu Tyr Ser Phe Ile
705                 710                 715                 720

Gly Lys Ser Met Gly Leu Val Met Cys Ala Gln Asn Glu His Ala Ser
                725                 730                 735

Lys Gln Trp Ser Cys Val Val Thr
            740

<210> SEQ ID NO 58
<211> LENGTH: 745
<212> TYPE: PRT
<213> ORGANISM: Omphalotus olearis

<400> SEQUENCE: 58

Met Ser Phe Pro Gly Trp Gly Pro Tyr Pro Val Glu Arg Asp Glu
1               5                   10                  15

Thr Ser Ala Ile Thr Tyr Ser Ser Lys Leu His Gly Ser Val Thr Val
                20                  25                  30

Arg Asp Pro Tyr Ser Gln Leu Glu Val Pro Phe Glu Asp Ser Glu Glu
            35                  40                  45

Thr Lys Ala Phe Val His Ser Gln Arg Lys Phe Ala Arg Thr Tyr Leu
```

```
            50                  55                  60
Asp Glu Asn Pro Asp Arg Glu Ala Trp Leu Glu Thr Leu Lys Lys Ser
 65                  70                  75                  80

Trp Asn Tyr Arg Arg Phe Ser Ala Leu Lys Pro Glu Ser Asp Gly His
                     85                  90                  95

Tyr Tyr Phe Glu Tyr Asn Asp Gly Leu Gln Ser Gln Leu Ser Leu Tyr
                100                 105                 110

Arg Val Arg Met Gly Glu Asp Thr Val Leu Thr Glu Ser Gly Pro
            115                 120                 125

Gly Gly Glu Leu Phe Phe Asn Pro Asn Leu Leu Ser Leu Asp Gly Asn
130                 135                 140

Ala Ala Leu Thr Gly Phe Val Met Ser Pro Cys Gly Asn Tyr Trp Ala
145                 150                 155                 160

Tyr Gly Val Ser Glu His Gly Ser Asp Trp Met Ser Ile Tyr Val Arg
                165                 170                 175

Lys Thr Ser Ser Pro His Leu Pro Ser Gln Glu Arg Gly Lys Asp Pro
                180                 185                 190

Gly Arg Met Asn Asp Lys Ile Arg His Val Arg Phe Phe Ile Val Ser
            195                 200                 205

Trp Thr Ser Asp Ser Lys Gly Phe Phe Tyr Ser Arg Tyr Pro Pro Glu
210                 215                 220

Asp Asp Glu Gly Lys Gly Asn Ala Pro Ala Met Asn Cys Met Val Tyr
225                 230                 235                 240

Tyr His Arg Ile Gly Glu Asp Gln Ser Asp Val Leu Val His Glu
                245                 250                 255

Asp Pro Glu His Pro Phe Trp Ile Ser Ser Val Gln Leu Thr Pro Ser
                260                 265                 270

Gly Arg Tyr Ile Leu Phe Ala Ala Ser Arg Asp Ala Ser His Thr Gln
            275                 280                 285

Leu Val Lys Ile Ala Asp Leu His Glu Asn Asp Ile Gly Thr Asn Met
290                 295                 300

Lys Trp Lys Asn Leu His Asp Pro Trp Glu Ala Arg Phe Thr Ile Val
305                 310                 315                 320

Gly Asp Glu Gly Ser Lys Ile Tyr Phe Met Thr Asn Leu Lys Ala Lys
                325                 330                 335

Asn Tyr Lys Val Ala Thr Phe Asp Ala Asn His Pro Asp Glu Gly Leu
                340                 345                 350

Thr Thr Leu Ile Ala Glu Asp Pro Asn Ala Phe Leu Val Ser Ala Ser
            355                 360                 365

Ile His Ala Gln Asp Lys Leu Leu Val Tyr Leu Arg Asn Ala Ser
370                 375                 380

His Glu Ile His Ile Arg Asp Leu Thr Thr Gly Lys Pro Leu Gly Arg
385                 390                 395                 400

Ile Phe Glu Asp Leu Leu Gly Gln Phe Met Val Ser Gly Arg Arg Gln
                405                 410                 415

Asp Asn Asp Ile Phe Val Leu Phe Ser Ser Phe Leu Ser Pro Gly Thr
                420                 425                 430

Val Tyr Arg Tyr Thr Phe Gly Glu Glu Lys Gly His Ser Ser Leu Phe
            435                 440                 445

Arg Ala Ile Ser Ile Pro Gly Leu Asn Leu Asp Asp Phe Met Thr Glu
450                 455                 460

Ser Val Phe Tyr Pro Ser Lys Asp Gly Thr Ser Val His Met Phe Ile
465                 470                 475                 480
```

```
Thr Arg Pro Lys Asp Val Leu Leu Asp Gly Thr Ser Pro Val Leu Gln
            485                 490                 495

Tyr Gly Tyr Gly Gly Phe Ser Leu Ala Met Leu Pro Thr Phe Ser Leu
        500                 505                 510

Ser Thr Leu Leu Phe Cys Lys Ile Tyr Arg Ala Ile Tyr Ala Ile Pro
        515                 520                 525

Asn Ile Arg Gly Gly Ser Glu Tyr Gly Glu Ser Trp His Arg Glu Gly
        530                 535                 540

Met Leu Asp Lys Lys Gln Asn Val Phe Asp Asp Phe Asn Ala Ala Thr
545                 550                 555                 560

Glu Trp Leu Ile Ala Asn Lys Tyr Ala Ser Lys Asp Arg Ile Ala Ile
                565                 570                 575

Arg Gly Gly Ser Asn Gly Gly Val Leu Thr Thr Ala Cys Ala Asn Gln
            580                 585                 590

Ala Pro Gly Leu Tyr Arg Cys Val Ile Thr Ile Glu Gly Ile Ile Asp
            595                 600                 605

Met Leu Arg Phe Pro Lys Phe Thr Phe Gly Ala Ser Trp Arg Ser Glu
610                 615                 620

Tyr Gly Asp Pro Glu Asp Pro Glu Asp Phe Asp Phe Ile Phe Lys Tyr
625                 630                 635                 640

Ser Pro Tyr His Asn Ile Pro Pro Gly Asp Thr Ile Met Pro Ala
                645                 650                 655

Met Leu Phe Phe Thr Ala Ala Tyr Asp Asp Arg Val Ser Pro Leu His
                660                 665                 670

Thr Phe Lys His Val Ala Ala Leu Gln His Asn Phe Pro Lys Gly Pro
            675                 680                 685

Asn Pro Cys Leu Met Arg Ile Asp Leu Asn Ser Gly His Phe Ala Gly
690                 695                 700

Lys Ser Thr Gln Glu Met Leu Glu Glu Thr Ala Asp Glu Tyr Ser Phe
705                 710                 715                 720

Ile Gly Lys Ser Met Gly Leu Thr Met Gln Thr Gln Gly Ser Val Asp
                725                 730                 735

Ser Ser Arg Trp Ser Cys Val Thr Val
            740                 745

<210> SEQ ID NO 59
<211> LENGTH: 3999
<212> TYPE: DNA
<213> ORGANISM: Gymnopus fusipes

<400> SEQUENCE: 59
aagcacacca ctgataatta tgcttcagat agagtgaagc ctagtgagag acaaaatctt      60
tcagactgct cttaaaaggc tgaatttcag aacaaccgaa acgttgatcg atcggctgaa     120
atggtaaccg atcaccattt cggtagtact gaagtggttg aactgtctta aaatgcttca     180
cccagaccga agtataatta tcagcggtgt gagagacatt acaggattga caggacttta     240
ttttgaaagt aggcttttc gattccgcct aataaatcat acaaggccca tgctgaattt      300
gaccaatcac ataacagtgc gttgtattga aatttgacga tcctatctac ttggtgtcga     360
gctgccggtg tccaaatgaa cgaggttgtc agaatactgc cgatttcaat gcttatggaa     420
cgcactgtac aaggaagctg gcaatagaaa ccatgccgtc aatcctagtt caatggtatc     480
tttcacagtt cctgttgcat atgcccagtt ttattaattt ctgtcactca tgaccaataa     540
ccgtgtcttg tatgaagata acgtggcgaa aatctatatt ccttataaga aacaaacccc     600
```

```
ttcgtccgct acgtgtcttt gaaacccaca ctatgtccat gtcacttttta ggtgtatatc    660 ctcctgttaa acgggacgaa gcctcagcca ttacctacca aagcaaactt cacggttctg    720
tcattgtgca tgatccatac agcgcgcttg aaataccttc taatgatagt ttggagacaa    780
aggtttgcga cacaatcctg ccatgtaaaa aatcgagaca ttcagtattt caggcatttg    840
tcctctcaca aggtaaattt tcacgggctt acttggatga aattccgaca aggtaagaga    900
attttcaaac aatgaacaac ttaaatctat ttcatatcag gaaaaattgg ttgaaaatat    960
taaagagtaa ctggagttac cggcggtttt ctgccttgaa gcgtgaaagt gacaaccatt   1020
tctatttcga atataatgat ggccttcaac cccagtcatc catttatcgg gtgaaggttg   1080
gtgaagagga ttccatcctt actgaatctg gacctggggg tgaattgttt tttgatccca   1140
atttgctttc attggatggg gttgctgcac ttactggtgc tgcgatgagt ccttctggga   1200
agtactgggc atatggtgta tctgaacatg ttgatctttt tccactcaag ctatactaat   1260
tattgaccta ataaatattg aacagggaaa caattcaatg acaatttatg ttcgaaaaac   1320
ttcatcacca catcaaccat ctcaagaaaa gggaacagat cccggacgga tgaatgatgt   1380
tctccaacac attcgcatgc tctttgtgtc ctggacaaga gatagcaaag gtttgaatac   1440
acagagagtg cttaagctgg aatatttcat catttatacc ttcaaaggtt tcttctacca   1500
aagatatcca ccagagaaaa atgaaggaaa tgggaatgca ccagggcaga attgcaaggt   1560
gaaactatct gacatcattg agtgcatgtg ccctctgaag catgttgtag atatattatc   1620
actacattgg gacagaacag gatagtgaca tccttattca gtaaggatag tgcatttctt   1680
gaagccaggc caaactcaaa tcatccttca gtgaggaccc tgatcatccg gactggttct   1740
catatgtaca gctctcccca aggtaaaatg gtctcacact gcaaagattc ctgattaata   1800
tcataccatg tagtggtcaa tatgtcctgc tactcataaa tgtatgtact tgaatttcta   1860
ctatccattg tactctgatt gtggattaaa cagcgtgatt caagtttaaa ttacctcgcc   1920
aagattgctg atttatctgt caatgatatt gggacccata tccaatggaa gaatttgcat   1980
gattcttgga accatttcac aatgttaaga gcttcatgag tttcttcata tactatgaac   2040 tgatctatttt caattacata ctcaactgat aggattggga atgactactc tgtcatctat   2100
ttcaaaacaa atctggatgc acagaactac aaagttgcaa caatcgactt tcttcaacca   2160
gagatgggct tcacaactct ggtcaaggaa atcccaatt cagtccttgt ggaggccaaa   2220
atattcagag aagacaagct tgtgcttttg taccagcaga atgctagcca tcaaatacac   2280
atttatgatc tcaagagtgg cgcatggctt caacaaatct tcaagaatct aactggattc   2340
ataactacag ttccaaatgg gcgcgctgaa gatgagatgt tttttctcta caatgacttt   2400
attacacctg gacaatata tcagtcagtg tttaccatat atcggtggtc catcattttc   2460
agctgacaga cacggaacag atataaattt gatgatgaaa gtgacaaggg cttggtgttc   2520
cgtgccatcc aaatcgatgg actcaaccta tgatgatttcg tgacagaatc agtaagtaaa   2580
tataactata ttcaactttg gggcactccg taactgaggt gttcagaagt tttacccatc   2640
caaggatgga acttcgtaat ttctctcgtt aactttgata cgtcaacttc tggttgacaa   2700
aaaaacatag ggttcacatg ttcatcaccc gcccgaagga tgtactcatc gacggaactg   2760
ccgcagtcta tatgtatggc tatggtggct tctcaatctc agtgcttccg acgttctcca   2820
tctcaaccct gctattttgc aaaatttacc gggcaatgta tgtcgtgcct aacatacggt   2880
aagggtattt ttggacaact ttgaagtcca tttacttacc tggctgccaa tttagcggag   2940
```

| | |
|---|---|
| gttcggagtt tggagaatca tggcaccggg aggtgagtct atgtcaatgt gcacacaatt | 3000 |
| tacaagcttt actcaaccat gtctttcagg gaatgttgga caaaaaacag aatggacatg | 3060 |
| atgacttcca tgcagctgct gaatggctca tcgcaaataa gtacgccaaa aaggattgtg | 3120 |
| ttgccattcg cggggggtcc agcggaggtg cggagtccaa gaactgcttt tgtagccaga | 3180 |
| ttgaactttt tcacagggat tttgactacc gcatgtgcaa atcaagcacc cgaactctac | 3240 |
| cgctgtgtaa ttaccattga aggcataatt gacatgctca agtttgtag tttgtgaatc | 3300 |
| acctttacat caaaatctca ctcatttgta tgccctcagt ttcccaagtt cacgtttggt | 3360 |
| gctttgttgc gttcggaata tggcgatgta tgtattcaat ttatcatttc tgaattgaat | 3420 |
| gagtctgaca gacctactta gcccgaggac ccagaagctt ttgactacat ctacaagtta | 3480 |
| gctttctcat ccttccacag tcatccgctc agacctaacc atgtagatac tcgccttatc | 3540 |
| ataacattcc gttgggtgat gtagtcatgc caccgatgct attcttcaat gcgggatatg | 3600 |
| atgaccgcgt tcctcctcta cacagtaagc caagtgtttg attccttcaa gaccaagcta | 3660 |
| accccctaac aagccttcaa gcatgttgct gcactacaac atagatttcc taaaggcccg | 3720 |
| aatccaattc tcatgcgcat ggacctaagt tcagggcatt atgctggcaa ggtttgtatt | 3780 |
| tcactctcca agacatgctc tttgcaaaat ttattcttgt agagtgtaca aaagatgatt | 3840 |
| gaggaaactg cagatgaata caggtgtggt caatgggtct tattcatgc atcattttct | 3900 |
| aactgatttg ggtctactag cttcattggg aagtctatgg ggcttactat gcaagtcaga | 3960 |
| aaaccatcta ataaccgttg gtcctgtgta gtgacttga | 3999 |

<210> SEQ ID NO 60
<211> LENGTH: 2235
<212> TYPE: DNA
<213> ORGANISM: Gymnopus fusipes

<400> SEQUENCE: 60

| | |
|---|---|
| atgtccatgt cacttttagg tgtatatcct cctgttaaac gggacgaagc ctcagccatt | 60 |
| acctaccaaa gcaaacttca cggttctgtc attgtgcatg atccatacag cgcgcttgaa | 120 |
| ataccttcta atgatagttt ggagacaaag gcatttgtcc tctcacaagg taaattttca | 180 |
| cgggcttact tggatgaaat tccgacaagg aaaaattggt tgaaaatatt aaagagtaac | 240 |
| tggagttacc ggcggttttc tgccttgaag cgtgaaagtg acaaccattt ctatttcgaa | 300 |
| tataatgatg gccttcaacc ccagtcatcc atttatcggg tgaaggttgg tgaagaggat | 360 |
| tccatcctta ctgaatctgg acctgggggt gaattgtttt tgatcccaa tttgctttca | 420 |
| ttggatgggg ttgctgcact tactggtgct gcgatgagtc cttctgggaa gtactgggca | 480 |
| tatggtgtat ctgaacatgg aaacaattca atgacaattt atgttcgaaa aacttcatca | 540 |
| ccacatcaac catctcaaga aaagggaaca gatcccggac ggatgaatga tgttctccaa | 600 |
| cacattcgca tgctctttgt gtcctggaca agagatagca aaggtttctt ctaccaaaga | 660 |
| tatccaccag agaaaaatga aggaaatggg aatgcaccag gcagaattg caagatatat | 720 |
| tatcactaca ttgggacaga acaggatagt gacatcctta ttcatgagga ccctgatcat | 780 |
| ccggactggt tctcatatgt acagctctcc ccaagtggtc aatatgtcct gctactcata | 840 |
| aatcgtgatt caagttttwaa ttacctcgcc aagattgctg atttatctgt caatgatatt | 900 |
| gggacccata tccaatggaa gaatttgcat gattcttgga accatttcac aatgattggg | 960 |
| aatgactact ctgtcatcta tttcaaaaca aatctggatg cacagaacta caaagttgca | 1020 |
| acaatcgact tcttcaacc agagatgggc ttcacaactc tggtcaagga aaatcccaat | 1080 |

```
tcagtccttg tggaggccaa aatattcaga gaagacaagc ttgtgctttt gtaccagcag   1140
aatgctagcc atcaaataca catttatgat ctcaagagtg gcgmatggct tcaacaaatc   1200
ttcaagaatc taactggatt cataactaca gttccaaatg ggcgcgctga agatgagatg   1260 tttttctct acaatgactt tattacacct gggacaatat atcaatataa atttgatgat   1320
gaaagtgaca agggcttggt gttccgtgcc atccaaatcg atggactcaa cctagatgat   1380
ttcgtgacaa aatcaaagtt ttacccatcc aaggatggaa cttcggttca catgttcatc   1440
acccgcccga aggatgtact catcgacgga actgccgcag tctatatgta tggctatggt   1500
ggcttctcaa tctcagtgct tccgacgttc tccatctcaa ccctgctatt ttgcaaaatt   1560
taccgggcaa tgtatgtcgt gcctaacata cgcggaggtt cggagtttgg agaatcatgg   1620
caccgggagg gaatgttgga caaaaaacag aatggacatg atgacttcca tgcagctgct   1680
gaatggctca tcgcaaataa gtacgccaaa aaggattgtg ttgccattcg cgggggtcc    1740 agcggaggga ttttgactac cgcatgtgca aatcaagcac ccgaactcta ccgctgtgta   1800
attaccattg aaggcataat tgacatgctc aaatttccca agttcacgtt tggtgctttg   1860
ttgcgttcgg aatatggcga tcccgaggac ccagaagctt ttgactacat ctacaaatac   1920
tcgccttatc ataacattcc gttgggtgat gtagtcatgc accgatgct attcttcaat    1980 gcggatatg atgaccgcgt tcctcctcta cacaccttca agcatgttgc tgcactacaa    2040
catagatttc ctaaaggccc gaatccaatt ctcatgcgca tggacctaag ttcagggcat   2100
tatgctggca agagtgtaca aaagatgatt gaggaaactg cagatgaata cagcttcatt   2160
gggaagtcta tggggcttac tatgcaagtc agagcaaaac catctaataa ccgttggtcc   2220
tgtgtagtga cttga                                                    2235
```

<210> SEQ ID NO 61
<211> LENGTH: 861
<212> TYPE: PRT
<213> ORGANISM: Anomoporia bombycina

<400> SEQUENCE: 61

```
Met Ser Ser Pro Ala Val Glu Thr Lys Val Pro Ala Ser Pro Asp Val
1               5                   10                  15

Thr Ala Glu Val Ile Pro Ala Pro Pro Ser Ser His Arg Pro Leu Pro
            20                  25                  30

Phe Gly Leu Arg Pro Gly Lys Leu Val Ile Val Gly Ser Gly Ile Gly
        35                  40                  45

Ser Ile Gly Gln Phe Thr Leu Ser Ala Val Ala His Ile Glu Gln Ala
    50                  55                  60

Asp Arg Val Phe Phe Val Val Ala Asp Pro Ala Thr Glu Ala Phe Ile
65                  70                  75                  80

Tyr Ser Lys Asn Lys Asn Ser Val Asp Leu Tyr Lys Phe Tyr Asp Asp
                85                  90                  95

Lys Lys Pro Arg Met Asp Thr Tyr Ile Gln Met Ala Glu Val Met Leu
            100                 105                 110

Arg Glu Leu Arg Lys Gly Tyr Ser Val Gly Val Ile Tyr Gly His
        115                 120                 125

Pro Gly Val Phe Val Thr Pro Ser His Arg Ala Ile Ser Ile Ala Arg
    130                 135                 140

Asp Glu Gly Tyr Ser Ala Lys Met Leu Pro Gly Val Ser Ala Glu Asp
145                 150                 155                 160
```

```
Asn Leu Phe Ala Asp Ile Gly Ile Asp Pro Ser Arg Pro Gly Cys Leu
                165                 170                 175

Thr Tyr Glu Ala Thr Asp Leu Leu Arg Asn Arg Thr Leu Val Pro
        180                 185                 190

Ser Ser His Leu Val Leu Phe Gln Val Gly Cys Ile Gly Leu Ser Asp
            195                 200                 205

Phe Arg Phe Lys Gly Phe Asp Asn Ile Asn Phe Asp Val Leu Leu Asp
        210                 215                 220

Arg Leu Glu Gln Val Tyr Gly Pro Asp His Ala Val Ile His Tyr Met
225                 230                 235                 240

Ala Ala Val Leu Pro Gln Ser Thr Thr Thr Ile Asp Arg Tyr Thr Ile
                245                 250                 255

Lys Glu Leu Arg Asp Pro Val Ile Lys Lys Arg Ile Thr Ala Ile Ser
                260                 265                 270

Thr Phe Tyr Leu Pro Pro Lys Ala Leu Ser Pro Leu His Glu Glu Ser
            275                 280                 285

Ala Ala Lys Leu Gly Leu Met Lys Ala Gly Tyr Lys Ile Leu Asp Gly
        290                 295                 300

Ala Gln Ala Pro Tyr Pro Pro Phe Pro Trp Ala Gly Pro Asn Val Pro
305                 310                 315                 320

Ile Gly Ile Ala Tyr Gly Arg Arg Glu Leu Ala Ala Val Ala Lys Leu
                325                 330                 335

Asp Ser His Val Pro Pro Ala Asn Tyr Lys Pro Leu Arg Ala Ser Asn
            340                 345                 350

Ala Met Lys Ser Thr Met Ile Lys Leu Ala Thr Asp Pro Lys Ala Phe
        355                 360                 365

Ala Gln Tyr Ser Arg Asn Pro Ala Leu Leu Ala Asn Ser Thr Pro Gly
        370                 375                 380

Leu Thr Thr Pro Glu Arg Lys Ala Leu Gln Thr Gly Ser Gln Gly Leu
385                 390                 395                 400

Val Arg Ser Val Met Lys Thr Ser Pro Glu Asp Val Ala Lys Gln Phe
                405                 410                 415

Val Gln Ala Glu Leu Arg Asp Pro Thr Leu Ala Lys Gln Tyr Ser Gln
            420                 425                 430

Glu Cys Tyr Asp Gln Thr Gly Asn Thr Asp Gly Ile Ala Val Ile Ser
        435                 440                 445

Ala Trp Leu Lys Ser Lys Gly Tyr Asp Thr Thr Pro Thr Ala Ile Asn
        450                 455                 460

Asp Ala Trp Ala Asp Met Gln Ala Asn Ser Leu Asp Val Tyr Gln Ser
465                 470                 475                 480

Thr Tyr Asn Thr Met Val Asp Gly Lys Ser Gly Pro Ala Ile Thr Ile
                485                 490                 495

Lys Ser Gly Val Val Tyr Ile Gly Asn Thr Val Val Lys Lys Phe Ala
            500                 505                 510

Phe Ser Lys Ser Val Leu Thr Trp Ser Ser Thr Asp Gly Asn Pro Ser
        515                 520                 525

Ser Ala Thr Leu Ser Phe Val Val Leu Thr Asp Asp Gly Gln Pro
        530                 535                 540

Leu Pro Ala Asn Ser Tyr Ile Gly Pro Gln Phe Thr Gly Phe Tyr Trp
545                 550                 555                 560

Thr Ser Gly Ala Lys Pro Ala Ala Ala Asn Thr Leu Gly Arg Asn Gly
                565                 570                 575

Ala Phe Pro Ser Gly Gly Gly Gly Gly Ser Gly Gly Gly Gly Gly Ser
```

```
                580             585             590
    Ser Ser Gln Gly Ala Asp Ile Ser Thr Trp Val Asp Ser Tyr Gln Thr
                    595             600             605
    Tyr Val Val Thr Thr Ala Gly Ser Trp Lys Asp Glu Asp Ile Leu Lys
                610             615             620
    Ile Asp Asp Asp Thr Ala His Thr Ile Thr Tyr Gly Pro Leu Lys Ile
    625             630             635             640
    Val Lys Tyr Ser Leu Ser Asn Asp Thr Val Ser Trp Ser Ala Thr Asp
                    645             650             655
    Gly Asn Pro Phe Asn Ala Val Ile Phe Phe Lys Val Asn Lys Pro Thr
                660             665             670
    Lys Ala Asn Pro Thr Ala Gly Asn Gln Phe Val Gly Lys Lys Trp Leu
            675             680             685
    Pro Ser Asp Pro Ala Pro Ala Ala Val Asn Trp Thr Gly Leu Ile Gly
            690             695             700
    Ser Thr Ala Asp Pro Lys Gly Thr Ala Ala Asn Ala Thr Ala Ser
    705             710             715             720
    Met Trp Lys Ser Ile Gly Ile Asn Leu Gly Val Ala Val Ser Ala Met
                    725             730             735
    Val Leu Gly Thr Ala Val Ile Lys Ala Ile Gly Ala Ala Trp Asp Lys
                740             745             750
    Gly Ser Ala Ala Trp Lys Ala Ala Lys Ala Ala Asp Lys Ala Lys
                755             760             765
    Lys Asp Ala Glu Ala Ala Glu Lys Asp Ser Ala Val Asp Asp Glu Lys
        770             775             780
    Phe Ala Asp Glu Glu Pro Pro Asp Leu Glu Glu Leu Pro Ile Pro Asp
    785             790             795             800
    Ala Asp Pro Leu Val Asp Val Thr Asp Val Asp Val Thr Asp Val Asp
                    805             810             815
    Val Thr Asp Val Asp Val Thr Asp Val Asp Val Thr Asp Val Asp Val
                820             825             830
    Thr Asp Val Asp Val Thr Asp Val Asp Val Thr Asp Val Asp Val Thr
                835             840             845
    Asp Val Asp Val Asp Val Leu Asp Val Asp Val Ile
        850             855             860

<210> SEQ ID NO 62
<211> LENGTH: 402
<212> TYPE: PRT
<213> ORGANISM: Armillaria gallica

<400> SEQUENCE: 62

Met Pro Ala Asn Lys Gly Thr Leu Thr Ile Ala Gly Ser Gly Ile Ala
    1               5                   10                  15

Ser Ile Gly His Ile Thr Leu Glu Thr Leu Ser Tyr Ile Gln Gly Ala
                20                  25                  30

Asp Lys Val Tyr Tyr Val Ile Thr Asp Pro Ala Thr Glu Ala Phe Ile
                35                  40                  45

Gln Asp Lys Ser Glu Gly Asp Cys Phe Asp Leu Thr Val Tyr Tyr Asp
        50                  55                  60

Lys Asn Lys Ile Arg Tyr Glu Thr Tyr Val Gln Met Cys Glu Val Met
    65                  70                  75                  80

Leu Arg Asp Val Arg Ala Asp Tyr Asn Val Val Gly Val Phe Tyr Gly
                    85                  90                  95
```

His Pro Gly Val Phe Val Ser Pro Ser His Arg Ala Ile Ala Ile Ala
                100                 105                 110

Arg Asp Glu Gly Tyr Arg Ala Arg Met Leu Pro Gly Val Ser Ala Glu
            115                 120                 125

Asp Tyr Met Phe Ser Asp Leu Gly Phe Asp Pro Ala Val Pro Gly Cys
        130                 135                 140

Met Thr Gln Glu Ala Thr Ala Met Leu Asn His Asn Lys Lys Leu Asp
145                 150                 155                 160

Pro Ser Ile His Asn Ile Ile Trp Gln Val Gly Ala Val Gly Ile Asp
                165                 170                 175

Thr Met Val Phe Asp Asn Arg Lys Phe His Leu Leu Val Asp Arg Leu
            180                 185                 190

Glu Glu Asp Phe Gly Pro Asp His Arg Val Val Asn Tyr Ile Gly Ala
        195                 200                 205

Val Leu Pro Gln Ser Thr Thr Val Met Asp Glu Phe Thr Ile Gly Asp
210                 215                 220

Leu Arg Lys Glu Asp Val Val Lys Gln Phe Thr Thr Val Ser Thr Phe
225                 230                 235                 240

Tyr Val Pro Pro Arg Thr Arg Ala Pro Val Asp Gln Glu Ala Met Gln
            245                 250                 255

Lys Phe Gly Pro Ser Asp Ala Pro Leu Ala His Thr Val Arg His Leu
        260                 265                 270

Tyr Pro Pro Ser Lys Trp Ala Gly Thr Gln Thr Ser Val Val Pro Ala
        275                 280                 285

Tyr Gly Pro Cys Glu Arg Ala Ala Val Asp Arg Ile Ala Asp Tyr Thr
        290                 295                 300

Pro Pro Pro Asp His Met Ile Leu Arg Ala Ser Pro Ala Ile Arg Gln
305                 310                 315                 320

Phe Met Thr Asp Leu Ala Leu Asn Pro Gly Leu Arg Asp Arg Tyr Lys
                325                 330                 335

Ala Asp Pro Val Ala Val Leu Asp Ala Thr Pro Asp Leu Ser Thr Gln
            340                 345                 350

Glu Lys Phe Ala Leu Ser Phe Asp Lys Pro Gly Pro Val Tyr Thr Val
        355                 360                 365

Met Arg Ala Thr Pro Ala Ala Ile Ala Ser Gly Gln Glu Pro Thr Phe
370                 375                 380

Asp Asp Ile Ala Gly Ala Thr Glu Ser Ala Ser Pro Pro Leu Phe Val
385                 390                 395                 400

Ile Thr

<210> SEQ ID NO 63
<211> LENGTH: 401
<212> TYPE: PRT
<213> ORGANISM: Armillaria gallica

<400> SEQUENCE: 63

Met Pro Ala Asn Lys Lys Gly Thr Leu Thr Ile Ala Gly Ser Gly Ile
1               5                   10                  15

Ala Ser Ile Gly His Ile Thr Leu Glu Thr Leu Ser Tyr Ile Gln Glu
            20                  25                  30

Ala Asp Lys Val Tyr Tyr Ala Ile Thr Asp Pro Ala Thr Glu Ala Phe
        35                  40                  45

Ile Gln Asp Lys Ser Glu Gly Asp Cys Phe Asp Leu Thr Val Tyr Tyr
    50                  55                  60

```
Asp Lys Asn Lys Ile Arg Tyr Glu Thr Tyr Val Gln Met Cys Glu Val
 65                  70                  75                  80

Met Leu Arg Asp Val Arg Ala Asp Tyr Asn Val Gly Val Phe Tyr
             85                  90                  95

Gly His Pro Gly Val Phe Val Ser Pro Ser His Arg Ala Ile Ala Ile
            100                 105                 110

Ala Arg Asp Glu Gly Tyr Arg Ala Arg Met Leu Pro Gly Val Ser Ala
            115                 120                 125

Glu Asp Tyr Met Phe Ser Asp Leu Gly Phe Asp Pro Ala Val Pro Gly
            130                 135                 140

Cys Met Thr Gln Glu Ala Thr Ala Met Leu Asn His Asn Lys Lys Leu
145                 150                 155                 160

Asp Pro Ser Ile His Asn Ile Ile Trp Gln Val Gly Ala Val Gly Ile
                165                 170                 175

Asp Thr Met Val Phe Asp Asn Arg Lys Phe His Leu Leu Val Asp Arg
                180                 185                 190

Leu Glu Glu Asp Phe Gly Pro Asp His Arg Val Val Asn Tyr Ile Gly
            195                 200                 205

Ala Val Leu Pro Gln Ser Thr Thr Val Met Asp Glu Phe Thr Ile Gly
            210                 215                 220

Asp Leu Arg Lys Glu Asp Val Val Lys Gln Phe Thr Thr Val Ser Thr
225                 230                 235                 240

Phe Tyr Val Pro Pro Arg Thr Arg Ala Pro Val Asp Gln Glu Ala Met
                245                 250                 255

Gln Lys Phe Gly Pro Ser Asp Ala Pro Leu Val Tyr Pro Pro Ser Lys
                260                 265                 270

Trp Ala Gly Thr Gln Thr Phe Val Pro Ala Tyr Gly Pro Cys Glu
            275                 280                 285

Arg Ala Ala Val Asp Arg Ile Ala Asp Tyr Thr Pro Pro Asp His
            290                 295                 300

Met Ile Leu Arg Ala Ser Pro Ala Ile Arg Gln Phe Met Thr Asp Leu
305                 310                 315                 320

Ala Leu Asn Pro Gly Leu Arg Asp Arg Tyr Lys Ala Asp Pro Val Ala
                325                 330                 335

Val Leu Asp Ala Thr Pro Asp Leu Ser Thr Gln Glu Lys Phe Ala Leu
                340                 345                 350

Ser Phe Asp Lys Pro Gly Pro Val Tyr Ile Val Met Arg Ala Thr Pro
            355                 360                 365

Ala Ala Ile Ala Ser Gly Gln Glu Pro Thr Phe Asp Asp Ile Ala Gly
            370                 375                 380

Ala Thr Glu Ser Ala Ser Pro Pro Leu Phe Ile Ile Val Gln Val Pro
385                 390                 395                 400

Ala

<210> SEQ ID NO 64
<211> LENGTH: 421
<212> TYPE: PRT
<213> ORGANISM: Arthrobotrys oligospora

<400> SEQUENCE: 64

Met Ser Glu Gly Gly Lys Leu Ile Leu Val Gly Thr Gly Val Arg Ser
  1               5                  10                  15

Leu Cys Gln Leu Thr Leu Glu Ala Ile Asp Glu Ile Glu Arg Ala Asp
             20                  25                  30
```

Val Ile Tyr Tyr Ala Val Arg Asp Ala Thr Thr Glu Gly Phe Ile Lys
            35                  40                  45

Lys Arg Asn Lys Glu Ala Ile Asp Leu Tyr Gln Tyr Phe Ile Asn Asp
 50                  55                  60

Glu Glu Ile Pro Glu Ala Asp Ile Tyr Ile Gln Ile Ala Glu Val Met
 65                  70                  75                  80

Leu Ala Ala Thr Arg Lys Gly Arg Arg Val Val Gly Ala Phe Phe Gly
                85                  90                  95

His Pro Gly Leu Phe Met Ser Pro Asn Arg Arg Ala Leu Ala Ile Ala
                100                 105                 110

Gln Ala Glu Gly Tyr Thr Ala Lys Ile Leu Pro Gly Val Ser Val Asp
                115                 120                 125

Asp Cys Leu Leu Ala Asp Leu Gly Val Asp Pro Ser Phe Ile Gly Cys
    130                 135                 140

Leu Thr Cys Glu Ala Arg Asp Phe Met Ile His Asp His Leu Gly Leu
145                 150                 155                 160

Thr Ser Arg His Val Ile Met Tyr Glu Val Gly Tyr Leu Gly Phe Tyr
                165                 170                 175

Gly Asp Asp Ser Lys Thr Asp Tyr Phe Glu Tyr Phe Val Asn Arg Leu
                180                 185                 190

Glu Glu Ile Tyr Gly Asn Glu His Ser Leu Val Asn Tyr Thr Ala Ala
                195                 200                 205

Ile Ser Pro Leu Met Gln Pro Val Ile Asn Thr Leu Thr Ile Gly Asp
                210                 215                 220

Leu Arg Lys Pro Glu Val Arg Lys Gln Ile Thr Ser Ala Ser Thr Leu
225                 230                 235                 240

Tyr Phe Pro Pro Lys Glu Ile Leu Lys Leu Asn Lys Phe Gly Cys Asp
                245                 250                 255

Leu Leu Asp Gln Gly Ile Thr Asn Lys Glu Gln Phe Gln His Ala Ile
                260                 265                 270

Phe Pro Gly Gln Pro Leu Tyr Gln Leu Ile Gly Lys Ala Leu Pro His
                275                 280                 285

Glu Ala Tyr Ser Glu His Ala Gln Gln Val Ile Ala Gly Leu His Arg
                290                 295                 300

Arg Lys Ile Ser Pro Arg Tyr Pro Leu Tyr Arg Ala Ser Ala Ala Met
305                 310                 315                 320

Gln Ser Thr Met Glu Asp Ile Tyr Leu Lys Asn Glu Val Arg Lys Glu
                325                 330                 335

Tyr Leu Ile Ser Pro Thr Ser Phe Thr Leu Arg Val Val Pro Gly Leu
                340                 345                 350

Lys Glu Met Glu Lys Ile Ala Leu Ala Ser Gly Asn Tyr Ser Gln Ile
                355                 360                 365

Asp Gly Ala Met Lys Ser Gly Asp Leu Asp Gln Leu Thr Thr Gly Ala
                370                 375                 380

Ile Glu Ile Gly Asn Tyr Lys Val Ile Leu Tyr Ser Gly Tyr Ala Ile
385                 390                 395                 400

Gly Tyr Glu Arg Ala Thr Phe Ala Ile Ala Asp Phe Thr Asn Phe Ser
                405                 410                 415

Phe Phe Asn Ile Tyr
                420

<210> SEQ ID NO 65
<211> LENGTH: 407
<212> TYPE: PRT

<213> ORGANISM: Armillaria ostoyae

<400> SEQUENCE: 65

```
Met Pro Ala Asn Lys Gly Thr Leu Thr Ile Ala Gly Ser Gly Ile
1               5                   10                  15

Ala Ser Ile Gly His Ile Thr Leu Glu Thr Leu Ser Tyr Ile Gln Glu
            20                  25                  30

Ala Asp Lys Val Tyr Tyr Ala Ile Thr Asp Pro Ala Thr Glu Ala Phe
            35                  40                  45

Ile His Asp Lys Ser Lys Gly Asp Cys Phe Asp Leu Ser Val Tyr Tyr
        50                  55                  60

Asp Lys Asn Lys Asn Arg Tyr Glu Thr Tyr Val Gln Met Cys Glu Val
65                  70                  75                  80

Met Leu Arg Asp Val Arg Ala Asp Tyr Asn Val Leu Gly Val Phe Tyr
                85                  90                  95

Gly His Pro Gly Val Phe Val Ser Pro Ser His Arg Ala Ile Ala Ile
                100                 105                 110

Ala Arg Asp Glu Gly Tyr Arg Ala Arg Met Leu Pro Gly Val Ser Ala
            115                 120                 125

Glu Asp Tyr Met Phe Ser Asp Leu Gly Phe Asp Pro Ala Val Pro Gly
130                 135                 140

Cys Met Thr Gln Glu Ala Thr Ala Met Leu Ile His Asn Lys Lys Leu
145                 150                 155                 160

Asp Pro Leu Ile His Asn Ile Ile Trp Gln Val Gly Ser Val Gly Val
                165                 170                 175

Asp Thr Met Val Phe Asp Asn Arg Lys Phe His Leu Leu Val Asp Arg
                180                 185                 190

Leu Glu Glu Asp Phe Gly Leu Asp His Lys Val Val His Tyr Ile Gly
            195                 200                 205

Ala Val Leu Pro Gln Ser Thr Thr Val Met Asp Glu Phe Thr Ile Gly
210                 215                 220

Asp Leu Arg Lys Glu Asp Val Val Lys Gln Phe Thr Thr Met Ser Thr
225                 230                 235                 240

Phe Tyr Val Pro Pro Arg Thr Pro Ala Pro Val Asp Gln Glu Ala Met
                245                 250                 255

Gln Lys Phe Arg Ser Leu Asp Ala Pro Leu Ala Arg Thr Val His Leu
                260                 265                 270

Tyr Pro Pro Ser Lys Trp Ala Gly Thr Gln Thr Ser Val Val Pro Ala
            275                 280                 285

Tyr Gly Pro Tyr Glu Arg Ala Ala Val Asp Arg Ile Ala Asp Tyr Thr
290                 295                 300

Pro Pro Pro Asp His Met Ile Leu Arg Ala Ser Pro Ala Ile Arg Gln
305                 310                 315                 320

Phe Met Met Asp Leu Ala Leu Asn Pro Gly Leu Arg Asp Arg Tyr Lys
                325                 330                 335

Ala Asp Pro Val Ala Val Leu Asp Ala Thr Pro Asp Leu Ser Thr Gln
            340                 345                 350

Glu Lys Phe Ala Leu Ser Phe Asp Lys Pro Gly Pro Val Tyr Thr Val
            355                 360                 365

Met Arg Ala Thr Pro Ala Ala Ile Ala Ser Gly Gln Glu Pro Thr Phe
370                 375                 380

Asp Gly Ile Ala Gly Ala Ala Lys Pro Ala Ser Phe Pro Gly Val Ala
385                 390                 395                 400
```

```
Pro Leu Ile Ile Ile Ser Val
                405

<210> SEQ ID NO 66
<211> LENGTH: 857
<212> TYPE: PRT
<213> ORGANISM: Apodospora peruviana

<400> SEQUENCE: 66
```

Met Ala Ala Glu His Ala Thr Pro Ser Pro Val Glu Thr His Phe Gly
1               5                   10                  15

Arg Thr Val Pro Ala Met Gly Arg Pro Gly Lys Leu Val Met Val
            20                  25                  30

Gly Ser Gly Ile Lys Ser Ile Ser His Met Thr Leu Glu Thr Val Ser
        35                  40                  45

His Ile Glu Gln Ala Asp Lys Val Phe Tyr Cys Val Ala Asp Pro Gly
    50                  55                  60

Thr Glu Leu Phe Val Lys Ser Lys Ala Lys Trp Ser Phe Asp Leu Tyr
65                  70                  75                  80

Thr Leu Tyr Asp Asn Asp Lys Asn Arg Tyr Ile Thr Tyr Val Gln Met
                85                  90                  95

Ala Glu Leu Cys Leu Gln Ala Ala Arg Asp Gly Phe Phe Ser Val Gly
            100                 105                 110

Val Phe Tyr Gly His Pro Gly Val Phe Val Ser Pro Ser His Arg Ala
        115                 120                 125

Ile Gly Ile Ala Lys Arg Glu Gly Ile Glu Ala Tyr Met Leu Pro Gly
    130                 135                 140

Ile Ser Ala Glu Asp Cys Leu Phe Ala Asp Leu Gly Val Asp Pro Ser
145                 150                 155                 160

Phe Thr Gly Cys Gln Thr Tyr Glu Ala Thr Asp Leu Leu Leu Arg Asp
                165                 170                 175

Arg Pro Ile Ser Pro Tyr Ser His Leu Ile Val Trp Gln Val Gly Val
            180                 185                 190

Val Gly Asp Thr Gly Phe Asn Phe Gly Gly Phe Thr Gln Thr Lys Phe
        195                 200                 205

Gln Val Leu Val Asp Arg Leu Glu Glu Val Tyr Gly Ser Asp His Arg
    210                 215                 220

Leu Ile His Tyr Phe Ala Ser Thr Leu Ser His Gly Pro Ala His Ile
225                 230                 235                 240

Glu Pro Leu Arg Ile Ser Asp Leu Arg Lys Pro Glu Val Glu Lys Arg
                245                 250                 255

Met Asn Gly Ile Ser Thr Phe Tyr Val Pro Gln Ile Gly Lys Ser Ala
            260                 265                 270

His Asn Pro Lys Thr Ala Glu Arg Leu Gly Leu Arg Val Asp Ser Lys
        275                 280                 285

Thr Pro Asp Arg Ser Phe Gly His Leu Ile Gly Pro Ala Ile Ser Tyr
    290                 295                 300

Asn Thr Leu Glu Thr Arg Ala Val Gln Ala Leu Lys Thr His Lys Pro
305                 310                 315                 320

Ser Pro Ser Tyr Arg Lys Asn Arg Leu Pro Thr Ser Thr Leu Pro Val
                325                 330                 335

Leu Thr Ala Leu Ala Thr Ser Pro Lys Ala Val Ala His Phe Lys Arg
            340                 345                 350

Asn Thr Thr Gln Phe Leu Asp Ala Phe Pro Asp Met Ala Thr His Val
        355                 360                 365

```
Lys Lys Val Leu Gln Thr Gly Ser Pro Gly Leu Leu Arg Leu Leu Ser
        370                 375                 380

Leu Asn Ser Ser Ala Asp Val Ala Ala Lys Phe Val Gln Ala Glu Phe
385                 390                 395                 400

Arg Asp Ser Thr Leu Ala Ser Lys Tyr Ala Ala Val Leu Lys Glu Asn
                405                 410                 415

Asn Gly Asp Pro Asp Gly Glu Thr Asn Ile Ile Lys Phe Leu Gln Asp
                420                 425                 430

Gln Gly Tyr Asp Thr Thr Pro Glu Asp Val Ser Thr Ala Tyr Leu Ser
            435                 440                 445

Ala Ile Ser Val Asp Leu Asn Thr Tyr Ala Gly Tyr Tyr Ala Ser Thr
450                 455                 460

Phe Thr Asn Gly Gly Val Gly Pro Asn Ile Leu Ile Gln Asn Gly Ala
465                 470                 475                 480

Val Thr Val Asp Asp Thr Val Ile Lys Asn Pro Val Tyr Ala Gln Ser
                485                 490                 495

Leu Leu Gln Trp Ser Ile Lys Asp Gly Asn Ala Phe Asn Ala Lys Leu
            500                 505                 510

Thr Phe Arg Ile Leu Thr Asp Asp Gly Lys Pro Leu Ala Pro Gly
            515                 520                 525

Ala Tyr Ile Gly Pro Gln Phe Tyr Gly Thr Tyr Trp Lys Ser Glu Glu
530                 535                 540

Pro Ser Thr Pro Asn Ile Gln Gly Lys Thr Gly Thr Ala Pro Ile Lys
545                 550                 555                 560

Pro Val Asn Pro Val Thr Pro Val Thr Pro Thr Pro Leu Asp Thr Phe
                565                 570                 575

Thr Gly Asn Phe Val Ala Tyr Lys Ala Asp Ala Thr Thr Gly Lys Trp
            580                 585                 590

Ser Glu Asp Gly Thr Phe Val Val Ser Asp Pro Ala Gly Ser Thr Val
            595                 600                 605

Pro Thr Ala Val Tyr Lys Gly Lys Thr Leu Asn Asn Tyr Gln Tyr Ser
610                 615                 620

Gly Asn Glu Thr Leu Thr Trp Ser Ser Thr Asp Gly Asn Asp Ser Asn
625                 630                 635                 640

Gly Ser Ile Ser Phe Phe Ile Asn Lys Thr Ala Thr Ser Thr Asn Pro
                645                 650                 655

Thr Leu Gly Ala Gln Ala Thr Gly Arg Val Trp Ala Pro Ala Glu Ala
            660                 665                 670

Met Pro Ala Lys Val Asn Phe Phe Met Ser Leu Gly Gln Ser Ala Asn
            675                 680                 685

Pro Ser Thr Gln Ser Val Pro Ser Gln Ser Ala Ser Glu Trp Lys Ser
            690                 695                 700

Val Gly Ile Asn Val Gly Val Gly Leu Ala Thr Met Leu Leu Gly Thr
705                 710                 715                 720

Ala Ile Ile Glu Ala Ile Lys Trp Arg Ile Lys Leu Lys Ala Asn Pro
                725                 730                 735

Thr Asp Pro Glu Ile Asn Gln Gly Val Lys Asp Ser Glu Lys Val
            740                 745                 750

Ser Gln Ser Ser Glu Gln Glu Ala Val Gln Lys Ser Ser Val Glu
            755                 760                 765

Ser Asp Ala Ser Gly Ser Ala Asp Val Gln Pro Ser Asp Ile Pro Val
            770                 775                 780
```

-continued

```
Pro Asp Ala Pro Val Thr Thr Thr Asp Thr Thr Thr Asp Thr
785                 790                 795                 800

Thr Thr Thr Asp Thr Thr Thr Asp Thr Thr Thr Asp Thr Thr
            805                 810                 815

Thr Thr Asp Thr Thr Thr Thr Asp Thr Thr Thr Asp Thr Thr
        820                 825                 830

Thr Thr Thr Asp Val Thr Thr Asp Val Thr Asp Val Asp Val Val
            835                 840                 845

Val Asp Val Asp Val Ile Val Ile Leu
    850                 855
```

<210> SEQ ID NO 67
<211> LENGTH: 411
<212> TYPE: PRT
<213> ORGANISM: Bjerkandera adusta

<400> SEQUENCE: 67

```
Met Ser Thr Thr Thr Ser Asn Asn Ala Gly Ser Leu Thr Ile Ala Gly
1               5                   10                  15

Ser Gly Ile Ala Ser Val Ala His Ile Thr Leu Glu Thr Leu Ser His
            20                  25                  30

Ile Arg Glu Ala Asp Lys Val Phe Tyr Ile Val Cys Asp Pro Ala Thr
        35                  40                  45

Glu Ala Phe Ile His Asp Asn Ala Lys Ala Glu Ala Val Asp Leu Thr
    50                  55                  60

Val Tyr Tyr Asp Thr Asn Lys Ala Arg Tyr Asp Ser Tyr Val Gln Met
65                  70                  75                  80

Ala Glu Val Met Leu Gln Asp Val Arg Gly Gly Lys Asp Val Leu Gly
                85                  90                  95

Ile Phe Tyr Gly His Pro Gly Val Phe Val Ser Pro Ser His Arg Ala
            100                 105                 110

Leu Ala Ile Ala Arg Ser Glu Gly Tyr Lys Ala Lys Met Leu Pro Gly
        115                 120                 125

Val Ser Ala Glu Asp Tyr Leu Phe Ala Asp Leu Glu Phe Asp Pro Ser
    130                 135                 140

Val His Gly Cys Ala Thr Phe Glu Ala Thr Glu Leu Leu Leu Arg Glu
145                 150                 155                 160

Lys Pro Leu Asn Thr Thr Met His Asn Ile Ile Trp Gln Val Gly Ala
                165                 170                 175

Val Gly Val Asp Asp Met Val Phe Thr Asn Ser Lys Leu His Val Leu
            180                 185                 190

Val Asp Arg Leu Glu Lys Asp Phe Gly Pro Glu His Gln Val Val His
        195                 200                 205

Tyr Ile Gly Ala Val Leu Pro Gly Ser Arg Thr Val Met Asp Thr Phe
    210                 215                 220

Thr Val Ala Asp Leu Cys Lys Asp Asp Val Val Lys Gln Phe Asn Pro
225                 230                 235                 240

Ser Ser Thr Leu Tyr Ile Pro Pro Arg Ser Leu Ala Ala Asn Ser Ser
                245                 250                 255

Asp Ile Ala Ala Ser Leu Gly Ala Lys Pro Asp His Pro Leu Val Asp
            260                 265                 270

Pro Thr Leu Phe Pro Pro Leu Arg Trp Thr Lys Ser Thr Ser Pro Glu
        275                 280                 285

Ala Pro Ala Tyr Gly Pro Leu Glu Gln Ala Ala Val Ala Glu Leu Ala
    290                 295                 300
```

Asn His Lys Val Pro Ser Gln His Lys Val Leu Ala Ala Ser Pro Ala
305 310 315 320

Met Arg Thr Leu Val Ala Glu Leu Asn Val Ala Leu Arg Lys Lys Leu
325 330 335

Ala Ala Asp Pro Lys Ala Phe Ala Gly Gly Arg Glu Gly Leu Thr Glu
340 345 350

Val Glu Lys Leu Ala Val Gly Thr Gly Asn Val Gly Thr Met Gly Ala
355 360 365

Val Met Arg Ala Leu Pro Gly Gly Glu Gln Ser Thr Asp Met Val Thr
370 375 380

Ser Pro Ala Ser Ile Glu Gln Gln Ser Arg Arg Glu Ala Phe Phe Leu
385 390 395 400

Ile Val Leu Ile Val Ser Thr Arg Ile Leu His
405 410

<210> SEQ ID NO 68
<211> LENGTH: 434
<212> TYPE: PRT
<213> ORGANISM: Cercospora beticola

<400> SEQUENCE: 68

Met Pro Ser Gln Thr Ser Ile Trp Asn His Ile Asp Glu Leu Thr Arg
1 5 10 15

His Asp Val Phe Pro Ser Thr Glu Ala Gly Lys Gly Glu Leu Val Val
20 25 30

Val Gly Thr Gly Ile Ala Ser Ile Arg Gln Met Thr Val Glu Ala Leu
35 40 45

Asp Tyr Ile Gln Arg Ala Asp Lys Val Phe Tyr Ala Thr Leu Asp Ala
50 55 60

Val Thr Glu Thr Phe Ile Lys His His Ala Pro Ser Ala Glu Asp Leu
65 70 75 80

Tyr Gln Tyr Tyr Asp Thr Glu Lys Asn Arg Val Thr Thr Tyr Val Gln
85 90 95

Met Ala Glu Val Ile Leu Ser Ser Val Arg Lys Gly Lys Leu Thr Val
100 105 110

Ala Val Phe Tyr Gly His Pro Gly Val Phe Val Thr Pro Ser His Arg
115 120 125

Ala Ile Tyr Ile Ala Arg His Glu Gly Tyr Lys Ala Gln Met Leu Pro
130 135 140

Gly Val Ser Ala Glu Asp Cys Leu Tyr Ala Asp Leu Gly Ile Asp Pro
145 150 155 160

Ala Ser Ser Gly Cys Ser Met Tyr Glu Ala Ser Phe Leu Leu Asn Glu
165 170 175

Pro Asn Arg Leu Asp Ser Arg His His Leu Ile Ile Trp Gln Val Gly
180 185 190

Cys Val Gly Lys Glu Ala Met Ile Phe Asp Asn Lys Glu Ile Tyr Lys
195 200 205

Leu Ala Asp Tyr Leu Glu Ala Glu Tyr Gly Pro Asp His Pro Val Ile
210 215 220

Ala Tyr Leu Ala Ala Ile Gln Pro Phe His Asp Ser Lys Met Asp Lys
225 230 235 240

Met Thr Val Gln Asp Leu Arg Asp Gln Asp Lys Val Gln Asn Ile Pro
245 250 255

Ile Thr Ala Gly Thr Thr Leu Tyr Val Pro Pro Lys Lys Leu Pro Ala

```
            260                 265                 270
Asn Pro Pro Ala Tyr Lys Asp Met Ala Ile Gly Tyr Gln Leu Ala Leu
            275                 280                 285

Thr Ser Ala Phe Arg Ile Ser His Pro Asp Leu Asp Val Val Glu Thr
        290                 295                 300

Tyr Thr Gln Glu Glu Lys Ser Trp Cys Glu Leu Ala Ser Trp Ser
305                 310                 315                 320

Pro Pro Lys Ser Tyr Asn Ala Asn Ala Pro Pro Val Leu Arg Arg
                325                 330                 335

Ile Ala Val Lys Leu Ala Leu Leu His His Arg Leu His Gly Asn Val
            340                 345                 350

Ala Leu Ser Asp Val Ala Asn Ala Ile Thr Thr Ala Glu Pro Ser Leu
            355                 360                 365

Thr Asp Glu Glu Ala Asn Leu Leu Arg Gln Phe Val Gly His Leu Asp
        370                 375                 380

Phe Met Phe Lys Lys Glu Arg Pro Pro Gln Ser Val Thr Thr Ser Ile
385                 390                 395                 400

Ile Asn Asn Thr Ile Val Pro Pro Ile Val Thr Gln Leu Asn Ile Ile
                405                 410                 415

Arg Lys Asp Gly Ser Ile Met Lys Gly Val Lys Pro Ser Leu Tyr
            420                 425                 430

Val Tyr

<210> SEQ ID NO 69
<211> LENGTH: 409
<212> TYPE: PRT
<213> ORGANISM: Ceratobasidium sp.

<400> SEQUENCE: 69

Met Ala Ser Ile Thr Thr Gly Arg Asp Thr Thr Lys Ser Gly Ser Leu
1               5                   10                  15

Ile Ile Ala Gly Ser Gly Ile Ser Ser Val Ala His Leu Thr Leu Glu
            20                  25                  30

Thr Val Ser His Leu Lys Asn Ala Asp Asn Val Phe Tyr Leu Val Gly
        35                  40                  45

Asp Pro Val Thr Glu Ala Phe Ile Gln Glu Asn Asn Lys Ser Thr Thr
    50                  55                  60

Asn Leu Val Ala His Tyr Ala Thr Ser Lys His Arg Tyr Gln Thr Tyr
65                  70                  75                  80

Val Glu Met Ala Glu Val Met Leu Arg Glu Val Arg Ala Gly His Ser
                85                  90                  95

Val Phe Gly Ile Phe Tyr Gly His Pro Gly Val Leu Thr Thr Pro Ala
            100                 105                 110

His Arg Ala Leu Thr Leu Ala Arg Gln Glu Gly Tyr Glu Ala Arg Met
        115                 120                 125

Leu Pro Gly Val Ser Ser Val Asp Tyr Met Phe Ala Asp Leu Glu Leu
    130                 135                 140

Glu Pro Gly Gln His Gly Cys Met Ile His Glu Ala Thr Asp Leu Leu
145                 150                 155                 160

Ala Arg Asp Arg Arg Leu Asp Pro Ser Val His Asn Ile Ile Leu Gln
                165                 170                 175

Pro Ser Arg Val Gly Ser Ala Thr Leu Glu Lys Glu Ala Ser Lys Phe
            180                 185                 190

Gln Leu Leu Val Asp Arg Leu Val Arg Asp Phe Gly Pro Asp His Lys
```

```
                195                 200                 205
Ile Val His Tyr Ser Gly Ala Val Leu Pro Gln Ser Ser Ala Met
210                 215                 220

Val Val Phe Val Ile Glu Asn Leu Arg Asn Glu Gln Leu Ala Asn Gln
225                 230                 235                 240

Ile Arg Ser Thr Ser Ile Leu Tyr Ile Pro Arg Asp Ile Val Pro
                245                 250                 255

Val His Pro Asp Ala Ala Ala Leu Lys Leu Pro Asp Met Leu Gly
            260                 265                 270

Leu Leu Ser Thr Ser Val Gln Trp Val Gly Pro Arg Phe Ile Glu Thr
                275                 280                 285

Ala Asp Tyr Gly Pro Val Glu Arg Lys Phe Val Asp Gln Leu Glu Arg
            290                 295                 300

Gln Val Ile Pro Glu Gly Gln Gln Ser Leu Arg Ala Ser Thr Ala Met
305                 310                 315                 320

Arg Lys Phe Met Ile Asn Leu Ala Leu Asp Pro Asn Gly Leu Lys Glu
                325                 330                 335

Tyr Lys Glu Ser Pro Ser Ala Val Ala Ala Gly Val Pro Gly Leu Thr
                340                 345                 350

Asp Arg Glu Arg Ser Ala Leu Ala Ile Ala Ser Glu Gly Pro Ile Phe
                355                 360                 365

Val Val Met Ser Arg Thr Asp Asp Glu Glu Pro Thr Glu Glu Gln Leu
370                 375                 380

Met Glu Ala Asp Arg Asn Gly Ala Arg Ile Val Asp Ser Cys Thr Met
385                 390                 395                 400

Cys Thr Leu Gly Gly Gly Arg Asn Ser
                405

<210> SEQ ID NO 70
<211> LENGTH: 412
<212> TYPE: PRT
<213> ORGANISM: Ceratobasidium sp.

<400> SEQUENCE: 70

Met Thr Thr Pro Ser Asp Thr Asn Lys Lys Gly Thr Leu Thr Ile Ala
1               5                   10                  15

Gly Ser Gly Ile Ala Ser Ile Arg His Ile Thr Leu Glu Thr Leu Ser
                20                  25                  30

Tyr Ile Lys Glu Ser Asp Lys Ile Tyr Tyr Leu Val Ala Asp Pro Ala
                35                  40                  45

Thr Glu Ala Phe Ile Ile Glu Asn Ala Asn Gly Ser Cys Val Ser Leu
            50                  55                  60

Tyr Gly Leu Tyr Gly Ile Asp Lys Ile Arg Tyr Asp Thr Tyr Val Gln
65                  70                  75                  80

Met Ser Glu Val Leu Leu Arg Asp Val Arg Ala Gly Phe Asp Val Leu
                85                  90                  95

Gly Ile Phe Tyr Gly His Pro Gly Val Phe Val Ser Pro Thr Gln Arg
                100                 105                 110

Ala Met Ser Ile Ala Leu Glu Glu Gly Phe Gln Ala Arg Met Leu Pro
            115                 120                 125

Gly Val Ser Ala Glu Asp Tyr Leu Phe Ala Asp Leu Arg Val Asp Pro
        130                 135                 140

Cys Met Phe Gly Cys Ala Ala Tyr Glu Ala Thr Glu Leu Leu Tyr Arg
145                 150                 155                 160
```

```
Lys Arg Arg Leu Asn Pro Thr Met Gln Asn Ile Ile Trp Gln Val Gly
            165                 170                 175

Lys Arg Phe Thr Ile Ile Lys Leu Thr Ser Pro Asp Thr Gln Asn Ser
        180                 185                 190

Lys Phe Gly Leu Leu Val Asp His Leu Glu Glu Asp Tyr Gly Pro Asp
        195                 200                 205

His Lys Val Val His Tyr Ile Gly Ala Val Leu Pro Gln Ala Thr Thr
    210                 215                 220

Val Ile Gln Pro Tyr Thr Ile Ser Glu Leu Arg Lys Pro Glu Val Ala
225                 230                 235                 240

Ser Gln Ile Arg Ala Cys Ser Thr Phe Tyr Ile Pro Pro Arg Asp Glu
                245                 250                 255

Ile Leu Pro Asp Ala Ser Met Ser Glu Arg Leu Gly Leu Asp Ala Pro
            260                 265                 270

Ile Ser His Leu Leu Gly Gly Arg Tyr Pro Arg Pro Ala Trp Ser Val
        275                 280                 285

Ser Gly Phe Lys Thr Ala Pro Ala Tyr Gly Pro Arg Glu Lys His Leu
        290                 295                 300

Val Ala Glu Leu Asn Val Arg Gly Ile Pro Glu Pro Asp Met Val Leu
305                 310                 315                 320

Phe Ala Ser Gln Pro Met Arg Lys Phe Met Ala Asp Leu Ala Leu Lys
                325                 330                 335

Pro Arg Leu Arg Asp Ser Tyr Arg Ser Asn Pro Gln Val Ile Val Asp
            340                 345                 350

Ala Val Lys Gly Leu Thr Ser Leu Glu Asn Met Ala Leu Lys Leu Asn
        355                 360                 365

Arg Val Thr Ala Ile Thr Arg Val Met Ser Val Asn Pro Thr Ala Leu
        370                 375                 380

Ile Leu Gly Ile Glu Pro Thr Glu Thr Asp Leu Ala Ile Asp Pro Tyr
385                 390                 395                 400

Met Asp Asn Gly Asp Pro Lys Ile Val Val Ser Gly
                405                 410

<210> SEQ ID NO 71
<211> LENGTH: 406
<212> TYPE: PRT
<213> ORGANISM: Cerrena unicolor

<400> SEQUENCE: 71

Met Ala Thr Gln Lys Ser Gly Ser Leu Thr Ile Ala Gly Ser Gly Ile
1               5                   10                  15

Ala Ser Ile Gly His Ile Thr Leu Glu Thr Leu Ser Tyr Ile Glu Gln
            20                  25                  30

Ala Asp Lys Val Tyr Tyr Ala Val Ala Asp Pro Ala Thr Glu Ala Phe
        35                  40                  45

Ile Gln Asp Lys Ser Lys Val Glu Cys Phe Asp Leu Thr Val Tyr Tyr
    50                  55                  60

Asp Lys Asp Lys Ile Arg Phe Glu Thr Tyr Ile Gln Met Ser Glu Val
65                  70                  75                  80

Met Leu Arg Asp Val Arg Ala Gly His Ser Val Leu Gly Ile Phe Tyr
                85                  90                  95

Gly His Pro Gly Val Phe Val Cys Pro Ser His Arg Ala Ile Ala Ile
            100                 105                 110

Ala Leu Ser Glu Gly Tyr Lys Ala Arg Met Leu Pro Gly Ile Ser Ala
        115                 120                 125
```

Glu Asp Tyr Met Phe Ser Asp Ile Gly Phe Asp Pro Ala Leu Pro Gly
            130                 135                 140

Cys Thr Thr Gln Glu Ala Thr His Leu Leu His Asn Lys Lys Leu
145                 150                 155                 160

Asp Pro Ser Met His Asn Ile Ile Trp Gln Val Gly Val Gly Ala
                165                 170                 175

Asp Thr Met Asn Phe Asp Asn Arg Gln Phe His Gln Leu Val Asp Cys
            180                 185                 190

Leu Glu Arg Asp Phe Gly Ser Ser His Lys Val Val His Tyr Ile Gly
            195                 200                 205

Ala Val Met Pro Gln Ser Thr Thr Ile Met Asp Glu Phe Ser Ile Ala
            210                 215                 220

Asp Leu Arg Lys Glu Glu Val Val Lys Gln Phe Thr Thr Trp Ser Thr
225                 230                 235                 240

Phe Tyr Ile Pro Pro Arg Asp Ala Ala Pro Val Asp Glu Gly Ile Met
                245                 250                 255

Gln Ser Leu Gly Leu Ser Ser Asn Asp Met Gln Tyr Thr Met Tyr Pro
            260                 265                 270

Pro Ser Ser Thr Met Arg Leu Gly Ile Arg Ser Pro Asn Leu Asp Val
            275                 280                 285

Tyr Gly Arg Ala Gly Arg Ala Ala Ile Glu Lys Leu Asp His His Thr
290                 295                 300

Pro Ala Ala Arg His Gln Val Leu Arg Ala Ser Pro Ala Ile Arg Lys
305                 310                 315                 320

Phe Met Glu Asp Leu Ala Leu Lys Ser Asp Leu Arg Asp Arg Tyr Lys
                325                 330                 335

Ala Asp Pro His Thr Val Leu Asp Ala Ile Pro Gly Leu Thr Ser Gln
            340                 345                 350

Glu Lys Ile Ala Leu Gly Phe Gly Lys Pro Gly Pro Val Tyr Lys Val
            355                 360                 365

Met Arg Ala Thr Gly Arg Glu Thr Ala Asp Gly Gln Glu His Val Pro
            370                 375                 380

His Asp Leu Thr Thr Thr Asp Glu Pro Gly Ala Pro Val Leu Leu Leu
385                 390                 395                 400

Leu Leu Leu Gln Thr Thr
                405

<210> SEQ ID NO 72
<211> LENGTH: 407
<212> TYPE: PRT
<213> ORGANISM: Cerrena unicolor

<400> SEQUENCE: 72

Met Ala Thr Thr Lys Thr Gly Ser Leu Thr Ile Ala Gly Ser Gly Ile
1               5                   10                  15

Ala Ser Val Ala His Ile Thr Leu Glu Val Leu Ser Tyr Leu Gln Glu
            20                  25                  30

Ala Asp Lys Ile Tyr Tyr Ala Ile Val Asp Pro Val Thr Glu Ala Phe
            35                  40                  45

Ile Gln Asp Lys Ser Lys Gly Arg Cys Phe Asp Leu Arg Val Tyr Tyr
        50                  55                  60

Asp Lys Asp Lys Met Arg Ser Glu Thr Tyr Val Gln Met Ser Glu Val
65                  70                  75                  80

Met Leu Arg Asp Val Arg Ser Gly Tyr Asn Val Leu Ala Ile Phe Tyr

```
                85                  90                  95
Gly His Pro Gly Val Phe Val Cys Pro Thr His Arg Ala Ile Ser Ile
            100                 105                 110

Ala Arg Ser Glu Gly Tyr Thr Ala Lys Met Leu Pro Gly Val Ser Ala
        115                 120                 125

Glu Asp Tyr Met Phe Ser Asp Ile Gly Phe Asp Pro Ala Val Pro Gly
    130                 135                 140

Cys Met Thr Gln Glu Ala Thr Ser Leu Leu Ile Tyr Asn Lys Gln Leu
145                 150                 155                 160

Asp Pro Ser Val His Asn Ile Ile Trp Gln Val Gly Ser Val Gly Val
                165                 170                 175

Asp Asn Met Val Phe Asp Asn Lys Gln Phe His Leu Leu Val Asp His
            180                 185                 190

Leu Glu Arg Asp Phe Gly Ser Ile His Lys Val Ile His Tyr Val Gly
        195                 200                 205

Ala Ile Met Pro Gln Ser Ala Thr Val Met Asp Glu Tyr Thr Ile Ser
    210                 215                 220

Asp Leu Arg Lys Glu Asp Val Val Lys Lys Phe Thr Thr Thr Ser Thr
225                 230                 235                 240

Leu Tyr Ile Pro Pro Arg Glu Ile Ala Pro Val Asp Gln Arg Ile Met
                245                 250                 255

Gln Ala Leu Glu Phe Ser Gly Asn Gly Asp Arg Tyr Met Ala Leu Ser
            260                 265                 270

Gln Leu Arg Gly Val His Ala Arg Asn Ser Gly Leu Cys Ala Tyr Gly
        275                 280                 285

Pro Ala Glu Gln Ala Ala Val Asp Lys Leu Asp His His Thr Pro Pro
    290                 295                 300

Asp Asp Tyr Glu Val Leu Arg Ala Ser Pro Ala Ile Arg Arg Phe Thr
305                 310                 315                 320

Glu Asp Leu Ala Leu Lys Pro Asp Leu Arg Ser Arg Tyr Lys Glu Asp
                325                 330                 335

Pro Leu Ser Val Leu Asp Ala Ile Pro Gly Leu Thr Ser Gln Glu Lys
            340                 345                 350

Phe Ala Leu Ser Phe Asp Lys Pro Gly Pro Val Tyr Lys Val Met Arg
        355                 360                 365

Ala Thr Pro Ala Ala Ile Ala Ala Gly Gln Glu His Ser Leu Asp Glu
    370                 375                 380

Ile Ala Gly Ser Ala Asp Ser Glu Ser Pro Gly Ala Leu Ala Thr Thr
385                 390                 395                 400

Ile Val Val Ile Val His Ile
                405

<210> SEQ ID NO 73
<211> LENGTH: 432
<212> TYPE: PRT
<213> ORGANISM: Cladosporium fulvum

<400> SEQUENCE: 73

Met Pro Ser Gln Ser Ile Trp Ser His Ile Ala Glu Leu Thr Arg Gly
1               5                   10                  15

Gly Pro Val Pro Lys Asp Val Pro His Lys Gly Glu Leu Val Val Val
            20                  25                  30

Gly Thr Gly Ile Ala Ser Leu Arg Gln Leu Thr Val Glu Ala Leu Asp
        35                  40                  45
```

```
Tyr Ile Gln Arg Ala Asp Val Val Phe Tyr Ala Thr Leu Asp Ala Val
         50                  55                  60
Thr Glu Ala Phe Ile Lys Gln His Ala Lys Ala Ala Glu Asn Leu Tyr
 65                  70                  75                  80
Gln Tyr Tyr Asp Thr Glu Lys Asn Arg Asn Ala Thr Tyr Thr Gln Met
                 85                  90                  95
Ala Glu Thr Ile Leu Ala Ser Val Arg Lys Gly Asn Met Thr Val Ala
            100                 105                 110
Val Phe Tyr Gly His Pro Gly Val Phe Val Thr Pro Ser His Arg Ala
        115                 120                 125
Ile Tyr Ile Ala Arg Gln Glu Gly Tyr Lys Ala Lys Met Leu Pro Gly
    130                 135                 140
Val Ser Ala Glu Asp Cys Leu Tyr Ala Asp Leu Asp Ile Asp Pro Ala
145                 150                 155                 160
Ser Ser Gly Cys Ser Met Tyr Glu Ala Ser Phe Leu Leu Leu Glu Pro
                165                 170                 175
Asp Arg Leu Asp Ser Arg His His Leu Ile Ile Trp Gln Val Gly Cys
            180                 185                 190
Val Gly Lys Glu Ala Met Val Phe Asp Asn Lys Glu Leu Tyr Lys Leu
        195                 200                 205
Ala Asp Tyr Leu Glu Ala Glu Tyr Gly Pro Lys His Pro Ala Ile Ala
    210                 215                 220
Tyr Leu Ala Ala Ile Gln Pro Phe Asn Asp Ser Lys Met Asp His Met
225                 230                 235                 240
Thr Val Glu Asp Leu Arg Asp Pro Glu Lys Val Arg Ser Ile Pro Ile
                245                 250                 255
Asn Ala Gly Thr Thr Leu Tyr Val Pro Pro Lys Lys Leu Pro Ala Asn
            260                 265                 270
Pro Gln Ala Tyr Lys Asp Ile Glu Ile Gly Tyr Lys Leu Gly Leu Thr
        275                 280                 285
Ser Ala Phe Arg Ile Ser His Pro Glu Leu Asp Val Ala Glu Thr Tyr
    290                 295                 300
Ser Glu Ile Glu Lys Gly Trp Cys Glu Glu Leu Val Ser Trp Thr Pro
305                 310                 315                 320
Pro Lys Ser Tyr Ile Pro Asn Ala Ala Thr Pro Ala Leu Arg Arg Ile
                325                 330                 335
Ala Ile Lys Leu Ala Leu Leu His His Arg Leu His Gly Ser Met Ser
            340                 345                 350
Leu Glu Asp Ile Ala Asn Ala Ala Thr Ala Ala Glu Pro Ser Leu Thr
        355                 360                 365
Thr Asp Glu Ser Asp Leu Leu Lys Gln Ser Val Gly Phe Leu Asp Ser
    370                 375                 380
Met Phe Asn Lys Glu Arg Pro Pro Gln Ser Val Thr Thr Ser Ile Val
385                 390                 395                 400
Arg Ser Val Val Pro Pro Ile Val Thr Gln Leu Asn Ile Ile Arg Lys
                405                 410                 415
Asp Gly Thr Val Met Met Gly Asp Gly Lys Pro Ser Ile Tyr Val Phe
            420                 425                 430

<210> SEQ ID NO 74
<211> LENGTH: 402
<212> TYPE: PRT
<213> ORGANISM: Chalara longipes

<400> SEQUENCE: 74
```

-continued

```
Met Ala Thr Ser Ser Ser Phe Gln Gln Leu Pro Arg Gly Ser Leu Thr
1               5                   10                  15

Ile Val Gly Ser Gly Phe Arg Ser Ile Ile Gln Phe Thr Thr Glu Ala
            20                  25                  30

Leu Met His Ile Glu Ala Ala Glu Lys Leu Tyr Tyr Cys Val Leu Asp
        35                  40                  45

Ala Ala Thr Arg Gly Phe Ile Lys Ala Lys Asn Ser Asn Ser Val Asp
    50                  55                  60

Leu Tyr Glu Cys Tyr Ser Asn Thr Lys Pro Arg Tyr Glu Thr Tyr Ile
65                  70                  75                  80

Gln Met Thr Glu Ala Met Leu Arg Ser Val Arg Asp Gly Leu Lys Ala
                85                  90                  95

Thr Val Val Leu Tyr Gly His Pro Gly Val Phe Ile His Pro Ser His
            100                 105                 110

Arg Ala Ile Ala Ile Ala Arg Ser Glu Gly Tyr Asp Ala Trp Met Leu
        115                 120                 125

Leu Gly Ile Ser Val Glu Asp Tyr Leu Phe Ala Asp Leu Leu Ile Asp
    130                 135                 140

Pro Ser Asn Pro Gly Thr Gln Thr Val Glu Ala Thr Glu Ile Leu Leu
145                 150                 155                 160

Lys Glu Arg Pro Leu Leu Thr Ser Ser His Val Ile Ile Tyr Gln Val
                165                 170                 175

Gly Cys Ile Gly Asn Phe Thr Phe Asn Phe Ser Gly Ile Lys Asn Asp
            180                 185                 190

Lys Phe Asp Ala Leu Val Asp Arg Leu Ile Gln Glu Tyr Gly Pro Asp
        195                 200                 205

His Pro Leu Val Asn Tyr Gln Ala Ala Ile Ser Pro Leu Ser Glu Ala
    210                 215                 220

Ser Ile Gly Arg His Ile Val Ser Asp Leu Arg Lys Ala Glu Val Gln
225                 230                 235                 240

Glu Ser Val Thr Gly Ala Ser Thr Phe Tyr Ile Pro Pro Lys Thr Val
                245                 250                 255

Leu Gln Val Thr Pro Gln Gly Ala Lys Leu Val Ser Glu Ser Asp Glu
            260                 265                 270

Leu Pro Thr Tyr Leu Ser Lys Asp Val Pro Val Phe Pro Pro Phe Pro
        275                 280                 285

Phe Asn Gln Ser Leu Ala Pro Ile Ala Pro Ala Tyr Ser Ser Ala Glu
    290                 295                 300

Arg Lys Ala Ile Glu Glu Leu Asp Asn His Ile Thr Pro Leu Glu Tyr
305                 310                 315                 320

Arg Lys Tyr Asn Ala Ser Ser Ala Met Gln Lys Thr Val Glu Ser Ile
                325                 330                 335

Ser Phe Ser Leu Asp Thr Ile Lys Lys Phe Arg Glu Ser Pro Ser Ala
            340                 345                 350

Phe Ala Ser Ser Ile Glu Glu Leu Glu Pro His Glu Ile Asp Ala Leu
        355                 360                 365

Ser Thr Gly Ser Gly Glu Arg Ile Asp Ala Ala Met Gln Gly Asn Ala
    370                 375                 380

Ala Val Asn Pro Asn Ala Ala Trp Leu Ile Thr Phe Ala Ile Ile Phe
385                 390                 395                 400

Gly Lys
```

```
<210> SEQ ID NO 75
<211> LENGTH: 391
<212> TYPE: PRT
<213> ORGANISM: Coprinopsis marcescibilis

<400> SEQUENCE: 75
```

| | | | | | | | | | | | | | | |
|---|---|---|---|---|---|---|---|---|---|---|---|---|---|---|
|Met|Asp|Ala|Thr|Ala|Asn|Pro|Lys|Ala|Gly|Gln|Leu|Thr|Ile|Val|Gly
|1| | | |5| | | | |10| | | | |15|

Ser Gly Ile Ala Ser Ile Asn His Met Thr Leu Gln Ala Val Ala Cys
            20                  25                  30

Ile Glu Thr Ala Asp Val Val Cys Tyr Val Ala Asp Gly Ala Thr
                35                  40                  45

Glu Ala Phe Ile Arg Lys Lys Asn Glu Asn Cys Ile Asp Leu Tyr Pro
50                  55                  60

Leu Tyr Ser Glu Thr Lys Glu Arg Thr Asp Thr Tyr Ile Gln Met Ala
65                  70                  75                  80

Glu Phe Met Leu Asn His Val Arg Ala Gly Lys Asn Val Val Gly Val
                85                  90                  95

Phe Tyr Gly His Pro Gly Val Phe Val Cys Pro Thr His Arg Ala Ile
                100                 105                 110

Tyr Ile Ala Arg Asn Glu Gly Tyr Arg Ala Val Met Leu Pro Gly Leu
                115                 120                 125

Ser Ala Glu Asp Cys Leu Tyr Ala Asp Leu Gly Ile Asp Pro Ser Thr
130                 135                 140

Val Gly Cys Ile Thr Tyr Glu Ala Thr Asp Met Leu Val Tyr Asn Arg
145                 150                 155                 160

Pro Leu Asn Ser Ser His Leu Val Leu Tyr Gln Val Gly Ile Val
                165                 170                 175

Gly Lys Ala Asp Phe Lys Phe Ala Tyr Asp Pro Lys Glu Asn His His
                180                 185                 190

Phe Gly Lys Leu Ile Asp Arg Leu Glu Leu Glu Tyr Gly Pro Asp His
                195                 200                 205

Thr Val Val His Tyr Ile Ala Pro Ile Phe Pro Thr Glu Glu Pro Val
                210                 215                 220

Met Glu Arg Phe Thr Ile Gly Gln Leu Lys Leu Lys Glu Asn Ser Asp
225                 230                 235                 240

Lys Ile Ala Thr Ile Ser Thr Phe Tyr Leu Pro Pro Lys Ala Pro Ser
                245                 250                 255

Ala Lys Val Ser Leu Asn Arg Glu Phe Leu Arg Ser Leu Asn Ile Ala
                260                 265                 270

Asp Ser Arg Asp Pro Met Thr Pro Phe Pro Trp Asn Pro Thr Ala Ala
                275                 280                 285

Pro Tyr Gly Glu Arg Glu Lys Lys Val Ile Leu Glu Leu Glu Ser His
                290                 295                 300

Val Pro Pro Pro Gly Tyr Arg Pro Leu Lys Lys Asn Ser Gly Leu Ala
305                 310                 315                 320

Gln Ala Leu Glu Lys Leu Ser Leu Asp Thr Arg Ala Leu Ala Ala Trp
                325                 330                 335

Lys Thr Asp Arg Lys Ala Tyr Ala Asp Ser Val Ser Gly Leu Thr Asp
                340                 345                 350

Asp Glu Arg Asp Ala Leu Ala Ser Gly Lys His Ala Gln Leu Ser Gly
                355                 360                 365

Ala Leu Lys Glu Gly Gly Val Pro Met Asn His Ala Gln Leu Thr Phe
                370                 375                 380

```
Phe Phe Ile Ile Ser Asn Leu
385                 390

<210> SEQ ID NO 76
<211> LENGTH: 389
<212> TYPE: PRT
<213> ORGANISM: Coprinellus micaceus

<400> SEQUENCE: 76

Met Ile Gly Ala Ser Leu Ala Lys Lys Gly Gln Leu Thr Ile Val Gly
1               5                   10                  15

Ser Gly Ile Ala Ser Ile Ser His Leu Thr Leu Gln Ala Val Ser Ala
            20                  25                  30

Ile Glu Asn Ala Asp Ile Val Cys Tyr Val Val Ala Asp Gly Ala Thr
        35                  40                  45

Glu Ala Phe Ile Arg Lys Lys Asn Pro Asn Ser Leu Asp Leu Tyr His
    50                  55                  60

Leu Tyr Gly Glu Asp Lys Gln Arg Thr Asp Thr Tyr Ile Gln Met Ala
65                  70                  75                  80

Glu Phe Met Leu Ile Arg Val Arg Gln Gly Gln Asn Val Val Gly Val
                85                  90                  95

Phe Tyr Gly His Pro Gly Val Phe Val Cys Pro Thr His Arg Ala Leu
            100                 105                 110

Tyr Ile Ala Arg Ser Glu Gly Tyr Lys Ala Arg Met Leu Pro Gly Leu
        115                 120                 125

Ser Ala Glu Asp Cys Leu Phe Ala Asp Leu Gly Ile Asp Pro Ser Ser
    130                 135                 140

Val Gly Cys Val Thr Tyr Glu Ala Thr Asp Leu Leu Val Phe Lys Arg
145                 150                 155                 160

Pro Ile Asn Pro Ala Ser His Leu Val Leu Tyr Gln Val Gly Ile Val
                165                 170                 175

Gly Lys Ser Asn Phe Lys Phe Asp Tyr Thr Ser Asp Glu Asn Ile His
            180                 185                 190

Phe Thr Lys Leu Leu Asp Arg Leu Glu Glu Ala Tyr Gly Pro Glu His
        195                 200                 205

Ser Val Thr His Tyr Ile Ala Pro Leu Phe Pro Thr Glu Asp Pro Ile
    210                 215                 220

Ala Glu Glu Tyr Thr Ile Ala Gln Leu Arg Leu Pro Glu Ile Arg Asp
225                 230                 235                 240

Lys Ile His Thr Ile Ser Thr Phe Tyr Val Pro Pro Lys Thr Ser Glu
                245                 250                 255

Ser Leu Ile Tyr Asp Glu Val Leu Leu Ala Ser Leu Gly Val Thr His
            260                 265                 270

Lys Pro Ser Val Pro Tyr Pro Trp Asn Pro Glu Ala Thr Pro Tyr Gly
        275                 280                 285

Pro Arg Glu Lys Lys Ala Ile Glu Leu Leu Ala Glu His Glu Pro Pro
    290                 295                 300

Lys Gly Tyr Arg Pro Leu Lys Glu Arg Ser Gly Leu Leu Ala Val Leu
305                 310                 315                 320

Glu Lys Leu Cys Leu Glu Pro Leu Glu Met Lys Lys Tyr Asn Glu Asp
                325                 330                 335

Arg Gln Ala Tyr Ala Asp Gly Leu Lys Gly Leu Thr Glu Asn Glu Lys
            340                 345                 350

Glu Ala Leu Val Lys Gly Asp His Arg Thr Leu Ala Gly Ala Leu Lys
        355                 360                 365
```

```
Val Gly Asp Thr Pro Thr Asn Pro Ala Ala Leu Val Phe Thr Phe Ile
    370                 375                 380

Ile Thr Arg Leu Asp
385

<210> SEQ ID NO 77
<211> LENGTH: 413
<212> TYPE: PRT
<213> ORGANISM: Cystostereum murrayi

<400> SEQUENCE: 77

Met Pro Ala Pro Arg Lys Gly Thr Leu Thr Ile Ala Gly Ser Gly Ile
1               5                   10                  15

Ala Ser Ile Gly His Ile Thr Leu Glu Thr Leu Ser His Ile Gln Gly
                20                  25                  30

Ala Asp Lys Ile His Tyr Ala Val Thr Asp Pro Ala Thr Glu Ala Phe
            35                  40                  45

Ile Leu Glu Lys Ser Lys Asp Ser Ser Ser Cys Phe Asp Leu Gly Ile
        50                  55                  60

Tyr Tyr Asp Lys Asn Lys Met Arg Tyr Glu Thr Tyr Val Gln Met Cys
65                  70                  75                  80

Glu Val Met Leu Arg Asp Val Arg Gly Gly His Asn Val Leu Gly Ile
                85                  90                  95

Phe Tyr Gly His Pro Gly Val Phe Val Ser Pro Thr His Arg Ala Ile
                100                 105                 110

Ala Leu Ala Arg Asp Glu Gly Tyr Thr Ala Lys Met Leu Pro Gly Ile
            115                 120                 125

Ser Ala Glu Asp Tyr Met Phe Ser Asp Leu Gly Phe Asp Pro Ala Phe
        130                 135                 140

Pro Gly Cys Met Thr Gln Glu Ala Thr Ile Leu Leu Val Arg Gly Arg
145                 150                 155                 160

Lys Leu Asp Pro Ser Val His Asn Ile Ile Trp Gln Val Gly Gly Val
                165                 170                 175

Gly Val Asp Thr Met Val Phe Asp Asn Ala Asn Phe Tyr Ile Leu Val
                180                 185                 190

Asp Arg Leu Glu Glu Asp Leu Gly Pro Asp His Lys Val Val His Tyr
            195                 200                 205

Ile Gly Ala Val Leu Pro Gln Ser Thr Ala Val Ile Asp Glu Phe Thr
        210                 215                 220

Val Ala Gly Leu Arg Lys Glu Glu Val Val Lys Gln Ile Thr Thr Val
225                 230                 235                 240

Ser Thr Phe Tyr Leu Pro Pro Arg Thr Leu Leu His Ala Asp Gln Asp
                245                 250                 255

Met Val Gln Lys Leu Gly Leu Ser Asp Ser Leu Gly Lys Arg Ala Val
                260                 265                 270

His Val Tyr Pro Arg Thr Lys Trp Ile Asn Ala Glu Ser Pro Ser Pro
            275                 280                 285

Pro Ala Tyr Gly Pro Phe Glu Arg Ala Ala Val Asp Arg Leu Ala Asp
        290                 295                 300

His Thr Ile Pro Ser Asn His Leu Phe Leu Arg Gly Ser Gln Ala Leu
305                 310                 315                 320

Arg Gln Leu Met Thr Asp Leu Ala Leu Gln Pro Thr Leu Arg Ala Arg
                325                 330                 335

Tyr Val Ala Asp Pro Thr Ser Val Leu Asp Asp Val Thr Gly Met Ser
```

```
                 340                 345                 350

Ala Glu Glu Thr Phe Ala Leu Thr Leu Arg His Pro Ala Pro Val Phe
            355                 360                 365

Lys Val Met Arg Ala Thr Gly Glu Ala Ile Ala Asn Gly Val Pro Thr
        370                 375                 380

Leu Gly Glu Ile Ala Glu Ser Ala Asn Ser Ser Ile Ala Gly Ser Ser
385                 390                 395                 400

Cys Ala Leu Ile Gly Phe Phe Val Val Val Leu Glu Ile
                405                 410

<210> SEQ ID NO 78
<211> LENGTH: 355
<212> TYPE: PRT
<213> ORGANISM: Coprinellus pellucidus

<400> SEQUENCE: 78

Met Pro Ser Thr Thr Arg Gly Ser Leu Thr Leu Ala Gly Ala Gly Val
1               5                   10                  15

Thr Ser Ile Gly His Leu Thr Leu Gln Thr Val Ser Ala Ile Glu Asn
            20                  25                  30

Ala Asp Ile Val Cys Tyr Ile Leu Asn Asp Pro Val Thr Glu Ala Phe
        35                  40                  45

Ile Ile Lys Lys Asn Pro Asn Val Tyr Asp Leu Tyr Gln Leu Tyr Asp
    50                  55                  60

Asp Gly Lys Pro Arg Ile Glu Thr Tyr His Gln Met Val Glu Val Leu
65                  70                  75                  80

Met Ser Lys Val Arg Ser Gly Gln Asp Val Val Gly Leu Phe Thr Gly
            85                  90                  95

His Pro Gly Val Val Asn Thr Pro Ala Ala Gln Ala Phe Lys Ile Ala
        100                 105                 110

Arg Gln Glu Gly Tyr Thr Ala Arg Met Leu Pro Gly Ile Thr Thr Asn
    115                 120                 125

Asp Ala Leu Leu Ala Asp Val Val Asp Pro Ala Leu Gly Gly Ala
130                 135                 140

Met Ala Tyr Glu Ala Thr Asp Phe Leu Asn Asn Asn Arg Val Leu His
145                 150                 155                 160

Pro Glu Met Asn Val Phe Ile Gln Gln Val Gly Val Val Gly Asn Lys
            165                 170                 175

His Phe Asn Phe Met Glu Met Arg Ser Ser Leu Leu Asp Lys Leu Ile
        180                 185                 190

Asp Arg Leu Glu Glu Thr Tyr Gly Gly Glu Lys Glu Ile Ile His Tyr
    195                 200                 205

Ile Ala Pro Met Leu Pro Ile Asp Lys Pro Val Met Gln Lys Met Thr
210                 215                 220

Val Ser Asp Leu Lys Lys Pro Glu Tyr Lys Ala Lys Ile Val Pro Ser
225                 230                 235                 240

Ser Thr Phe Tyr Ile Thr Pro Asn Glu Gln Leu Ser Ser Val Leu Asp
            245                 250                 255

Ser Thr Glu Gly Lys Lys Leu His Arg Glu Ala Met Ser Ala Leu Ala
        260                 265                 270

Asn His Thr His Gly Lys Asn Tyr Ala Pro Met Lys Glu Asn Leu Ala
    275                 280                 285

Leu Thr Glu Ala Leu Glu Arg Leu Ala Leu Glu Pro Lys Ser Leu Glu
290                 295                 300
```

```
Ala Tyr Arg Ser Asp Pro Gln Ser Tyr Val Asn Glu Asn Gly Arg Gly
305                 310                 315                 320

Leu Thr Glu Glu Arg Lys Ala Leu Val Thr Gly Arg Gly Ile Arg
            325                 330                 335

Glu Leu Leu Ser Asp Gly Pro Val Ala Ala His Arg Ile Ala Pro Leu
            340                 345                 350

Ala Leu Val
        355

<210> SEQ ID NO 79
<211> LENGTH: 417
<212> TYPE: PRT
<213> ORGANISM: Dendrothele bispora

<400> SEQUENCE: 79

Met Pro Val Arg Ile Pro Ser Pro Gln Lys Glu Ala Gly Ser Leu Thr
1               5                   10                  15

Ile Val Gly Thr Gly Ile Glu Ser Ile Gly Gln Ile Thr Leu Gln Ala
                20                  25                  30

Ile Ser His Ile Glu Thr Ala Ser Lys Val Phe Tyr Cys Val Val Asp
            35                  40                  45

Pro Ala Thr Glu Ala Phe Ile Arg Thr Lys Asn Lys Asn Cys Phe Asp
50                  55                  60

Leu Tyr Pro Tyr Tyr Asp Asn Gly Lys His Arg Met Asp Thr Tyr Ile
65                  70                  75                  80

Gln Met Ala Glu Val Met Leu Lys Glu Val Arg Asn Gly Leu Asp Val
                85                  90                  95

Val Gly Val Phe Tyr Gly His Pro Gly Val Phe Val Ser Pro Ser His
                100                 105                 110

Arg Ala Leu Ala Ile Ala Glu Ser Glu Gly Tyr Lys Ala Arg Met Leu
            115                 120                 125

Pro Gly Val Ser Ala Glu Asp Cys Leu Phe Ala Asp Leu Arg Ile Asp
        130                 135                 140

Pro Ser His Pro Gly Cys Met Thr Tyr Glu Ala Ser Asp Phe Leu Ile
145                 150                 155                 160

Arg Glu Arg Pro Val Asn Ile His Ser His Leu Val Leu Trp Gln Val
                165                 170                 175

Gly Cys Val Gly Val Ala Asp Phe Asn Ser Gly Gly Phe Lys Asn Thr
            180                 185                 190

Lys Phe Asp Val Leu Val Asp Arg Leu Glu Gln Glu Tyr Gly Ala Asp
        195                 200                 205

His Pro Val Val His Tyr Met Ala Ser Ile Leu Pro Tyr Glu Asp Pro
210                 215                 220

Val Thr Asp Lys Phe Thr Val Ser Gln Phe Arg Asp Pro Gln Ile Ala
225                 230                 235                 240

Lys Arg Ile Cys Gly Ile Ser Thr Phe Tyr Ile Pro Pro Lys Glu Thr
                245                 250                 255

Lys Asp Ser Asn Val Glu Ala Met His Arg Leu Gln Leu Leu Pro Ser
            260                 265                 270

Gly Lys Gly Val Leu Lys Glu Thr Gly Arg Tyr Pro Ser Asn Lys Trp
        275                 280                 285

Ala Pro Ser Gly Ser Phe His Asp Val Asp Pro Tyr Gly Pro Arg Glu
    290                 295                 300

Leu Ala Ala Val Thr Lys Leu Lys Ser His Thr Ile Pro Glu His Tyr
305                 310                 315                 320
```

```
Gln Pro Leu Ala Thr Ser Lys Ala Met Thr Asp Val Met Thr Lys Leu
                325                 330                 335

Ala Leu Asp Pro Arg Val Leu Ser Glu Tyr Lys Ala Ser Arg Gln Asp
            340                 345                 350

Phe Val His Ser Val Pro Gly Leu Thr Pro Asn Glu Lys Asn Ala Leu
            355                 360                 365

Val Lys Gly Glu Ile Ala Ala Ile Arg Cys Gly Met Lys Asn Ile Pro
    370                 375                 380

Ile Ser Glu Lys Gln Trp Glu Leu Arg Asp Gly Leu Val Thr Lys Phe
385                 390                 395                 400

Ile Val Val Pro Ile Trp Val Ser Ile Asp Asp Thr Thr Gly Asn Leu
                405                 410                 415

Glu

<210> SEQ ID NO 80
<211> LENGTH: 417
<212> TYPE: PRT
<213> ORGANISM: Dendrothele bispora

<400> SEQUENCE: 80

Met Glu Ser Ser Thr Gln Thr Lys Pro Gly Ser Leu Ile Val Val Gly
1               5                   10                  15

Thr Gly Ile Glu Ser Ile Gly Gln Met Thr Leu Gln Ala Leu Ser Tyr
            20                  25                  30

Ile Glu Ala Ala Ser Lys Val Phe Tyr Cys Val Ile Asp Pro Ala Thr
        35                  40                  45

Glu Ala Phe Ile Leu Thr Lys Asn Lys Asn Cys Val Asp Leu Tyr Gln
    50                  55                  60

Tyr Tyr Asp Asn Gly Lys Ser Arg Met Asp Thr Tyr Thr Gln Met Ala
65                  70                  75                  80

Glu Leu Met Leu Lys Glu Val Arg Asn Gly Leu Asp Val Val Gly Val
                85                  90                  95

Phe Tyr Gly His Pro Gly Val Phe Val Asn Pro Ser His Arg Ala Leu
            100                 105                 110

Ala Ile Ala Arg Ser Glu Gly Tyr Gln Ala Arg Met Leu Pro Gly Val
        115                 120                 125

Ser Ala Glu Asp Cys Leu Phe Ala Asp Leu Cys Ile Asp Pro Ser Asn
    130                 135                 140

Pro Gly Cys Leu Thr Tyr Glu Ala Ser Asp Phe Leu Ile Arg Glu Arg
145                 150                 155                 160

Pro Val Asn Val His Ser His Leu Ile Leu Phe Gln Val Gly Cys Val
                165                 170                 175

Gly Ile Ala Asp Phe Asn Phe Ser Gly Phe Asp Asn Ser Lys Phe Thr
            180                 185                 190

Ile Leu Val Asp Arg Leu Glu Gln Glu Tyr Gly Pro Asp His Thr Val
        195                 200                 205

Val His Tyr Ile Ala Ala Met Met Pro His Gln Asp Pro Val Thr Asp
    210                 215                 220

Lys Phe Thr Ile Gly Gln Leu Arg Glu Pro Glu Ile Ala Lys Arg Val
225                 230                 235                 240

Gly Gly Val Ser Thr Phe Tyr Ile Pro Pro Lys Ala Arg Lys Asp Ile
                245                 250                 255

Asn Thr Asp Ile Ile Arg Leu Leu Glu Phe Leu Pro Ala Gly Lys Val
            260                 265                 270
```

```
Pro Asp Lys His Thr Gln Ile Tyr Pro Pro Asn Gln Trp Glu Pro Asp
        275                 280                 285

Val Pro Thr Leu Pro Pro Tyr Gly Gln Asn Glu Gln Ala Ala Ile Thr
    290                 295                 300

Arg Leu Glu Ala His Ala Pro Pro Glu Tyr Gln Pro Leu Ala Thr
305                 310                 315                 320

Ser Lys Ala Met Thr Asp Val Met Thr Lys Leu Ala Leu Asp Pro Lys
                325                 330                 335

Ala Leu Ala Glu Tyr Lys Ala Asp His Arg Ala Phe Ala Gln Ser Val
                340                 345                 350

Pro Asp Leu Thr Pro Gln Glu Arg Ala Leu Glu Leu Gly Asp Ser
                355                 360                 365

Trp Ala Ile Arg Cys Ala Met Lys Asn Met Pro Ser Ser Leu Leu Glu
        370                 375                 380

Ala Ala Ser Gln Ser Val Glu Ala Ser Met Asn Gly Phe Pro Trp
385                 390                 395                 400

Val Ile Val Thr Gly Ile Val Gly Val Ile Gly Ser Val Ser Ser
                405                 410                 415

Ala

<210> SEQ ID NO 81
<211> LENGTH: 411
<212> TYPE: PRT
<213> ORGANISM: Fomitiporia mediterranea

<400> SEQUENCE: 81

Met Ala Thr Ser Thr Glu Thr Thr Glu Lys Lys Gly Ser Leu Thr Ile
1               5                   10                  15

Ala Gly Thr Gly Ile Ala Ser Ile Lys His Ile Thr Leu Glu Thr Leu
                20                  25                  30

Ser Tyr Ile Lys Glu Ala Glu Lys Val Tyr Tyr Leu Val Ala Asp Pro
            35                  40                  45

Ala Thr Glu Ala Phe Ile Gln Asp Asn Ala Ser Gly Thr Cys Phe Asn
        50                  55                  60

Leu His Val Phe Tyr Asp Thr Asn Lys His Arg Tyr Asp Ser Tyr Val
65                  70                  75                  80

Gln Met Ala Glu Val Met Leu Leu Asp Val Arg Ala Gly His Ser Val
                85                  90                  95

Leu Gly Ile Phe Tyr Gly His Pro Gly Val Phe Val Ser Pro Ser His
            100                 105                 110

Arg Ala Ile Ala Ile Ala Arg Glu Glu Gly Phe Lys Ala His Met Leu
        115                 120                 125

Pro Gly Ile Ser Ala Glu Asp Tyr Met Phe Ala Asp Ile Gly Phe Asp
    130                 135                 140

Pro Ala Thr His Gly Cys Val Ser Tyr Glu Ala Thr Glu Leu Val
145                 150                 155                 160

Arg Asp Lys Pro Leu Leu Pro Ser Ser His Asn Ile Ile Trp Gln Val
                165                 170                 175

Gly Ala Ile Gly Ala Asn Ala Met Val Phe Asp Asn Gly Lys Phe Asn
            180                 185                 190

Ile Leu Val Asp Arg Leu Glu Gln Val Phe Gly Pro Asp His Lys Val
        195                 200                 205

Val His Tyr Ile Gly Ala Val Leu Pro Gln Ser Thr Ser Thr Ile Glu
    210                 215                 220
```

```
Ala Tyr Thr Ile Ser Asp Leu Arg Lys Gly Asp Val Glu Lys Phe
225                 230                 235                 240

Ser Thr Thr Ser Thr Leu Tyr Val Pro Pro Ser Val Glu Ala Arg Leu
                245                 250                 255

Ser Gly Ile Met Val Arg Glu Leu Gly Leu Glu Asp Ser Gly Phe His
            260                 265                 270

Thr Lys Ser Ser Gln Ser Arg Thr Leu Trp Ala Gly Pro Val Thr Ser
        275                 280                 285

Ser Ala Pro Ala Tyr Gly Pro Gln Glu Arg Ile Val Ile Ala Gln Ile
290                 295                 300

Asp Lys Asp Val Ile Pro Asp Ser His Gln Ile Leu Gln Ala Ser Asp
305                 310                 315                 320

Ala Met Lys Lys Thr Met Ala Asn Leu Ala Leu Asn Pro Lys Leu Ser
                325                 330                 335

Glu Glu Tyr Tyr Ala Ser Pro Ser Thr Val Val Glu Lys Val Thr Gly
            340                 345                 350

Leu Ser Glu Gln Glu Lys Lys Ala Leu Ile Leu Cys Ser Ala Gly Ala
        355                 360                 365

Ile His Met Val Met Ala Ala Thr Gln Thr Asn Ile Ala Gln Gly His
370                 375                 380

Gln Trp Ser Ala Glu Glu Leu Glu Ala Ala Gly Thr Pro His Pro Ala
385                 390                 395                 400

Leu Ala Leu Leu Val Val Ile Ile Cys Leu Ile
                405                 410

<210> SEQ ID NO 82
<211> LENGTH: 432
<212> TYPE: PRT
<213> ORGANISM: Fomitiporia mediterranea

<400> SEQUENCE: 82

Met Ala Ala Thr Thr Glu Thr Met Lys Lys Gly Ser Leu Thr Ile Ala
1               5                   10                  15

Gly Ser Gly Ile Ala Ser Ile Lys His Met Thr Leu Glu Thr Val Ser
            20                  25                  30

His Ile Lys Glu Ala Glu Lys Val Tyr Tyr Ile Val Thr Asp Pro Ala
        35                  40                  45

Thr Glu Ala Tyr Ile Lys Asp Asn Ala Val Gly Ala Cys Phe Asp Leu
    50                  55                  60

Arg Val Phe Tyr Asp Thr Asn Lys Pro Arg Tyr Glu Ser Tyr Val Gln
65                  70                  75                  80

Met Ser Glu Val Met Leu Arg Asp Val Arg Val Gly His Ser Val Leu
                85                  90                  95

Gly Ile Phe Tyr Gly His Pro Gly Val Phe Val Ser Pro Ser His Arg
            100                 105                 110

Ala Ile Ala Ile Ala Lys Glu Glu Gly Phe Gln Ala Arg Met Leu Pro
        115                 120                 125

Gly Ile Ser Ala Glu Asp Tyr Leu Phe Ala Asp Ile Gly Phe Asp Pro
    130                 135                 140

Ala Ala His Gly Cys Met Ser Tyr Glu Ala Thr Glu Leu Leu Val Arg
145                 150                 155                 160

Asn Lys Pro Leu Asn Thr Ser Thr His Asn Ile Ile Trp Gln Val Gly
                165                 170                 175

Ala Leu Gly Ala Glu Ala Met Val Phe Asp Asn Ala Lys Phe Ser Leu
```

```
                    180                 185                 190
Leu Val Asp Arg Leu Glu Gln Asp Tyr Gly Ser Asp His Lys Val Val
        195                 200                 205

His Tyr Ile Gly Ala Ile Leu Pro Gln Ala Asp Pro Thr Val Glu Ala
    210                 215                 220

Tyr Ile Val Ala Asp Leu Arg Lys Glu Asp Val Val Lys Gln Phe Asn
225                 230                 235                 240

Ala Ile Ser Thr Leu Tyr Ile Pro Pro Arg Val Ala Gly Lys Phe Leu
                245                 250                 255

Asp Asp Met Ala Lys Lys Leu Gly Ile Ala Asp Ser Ala Ala Tyr Leu
            260                 265                 270

Lys Asn His Tyr Pro Gln Ala Pro Tyr Thr Gly Pro Glu Phe Ala Thr
        275                 280                 285

Asp Pro Ala Tyr Gly Pro Arg Glu Lys Ala Val Ile Asp Gln Ile Asp
    290                 295                 300

Asn His Ala Ala Pro Glu Gly His Thr Val Leu His Ala Ser Asp Ala
305                 310                 315                 320

Leu Lys Lys Leu Asn Thr Asp Leu Ala Leu Ser Pro Lys Phe Leu Glu
                325                 330                 335

Glu Tyr Lys Glu Asn Pro Met Pro Ile Leu Glu Ala Met Asp Gly Leu
            340                 345                 350

Thr Asn Glu Glu Lys Ala Ala Leu Met Gln Asn Pro Leu Gly Ala Thr
        355                 360                 365

His Glu Leu Met Trp Ala Thr Pro Asp Glu Ile Ala Asn Gly Arg Ala
    370                 375                 380

Leu Pro Val Val Asn Phe Met Ala Tyr Gly Gly Tyr Gly Gly Tyr Tyr
385                 390                 395                 400

Gly Gly Gly Cys Arg Pro Cys Pro Cys Val Val Thr Asp Arg Trp
                405                 410                 415

Ser Ser Gly Gly Ser Asn Lys Cys Asn Met Val Asn Asn Leu Asn Val
                420                 425                 430

<210> SEQ ID NO 83
<211> LENGTH: 421
<212> TYPE: PRT
<213> ORGANISM: Fomitiporia mediterranea

<400> SEQUENCE: 83

Met Ala Ala Thr Thr Glu Thr Thr Lys Lys Gly Ser Leu Thr Ile Ala
1               5                   10                  15

Gly Ser Gly Ile Ala Ser Ile Lys His Met Thr Leu Glu Thr Val Ser
                20                  25                  30

His Ile Lys Glu Val Glu Lys Val Tyr Tyr Ile Val Ser Asp Pro Ala
            35                  40                  45

Thr Glu Ala Tyr Ile Lys Asp Asn Ala Val Gly Thr Cys Phe Asp Leu
        50                  55                  60

Arg Val Phe Tyr Asp Thr Asn Lys Pro Arg Tyr Glu Ser Asp Val Gln
65                  70                  75                  80

Met Ser Glu Val Met Leu Arg Asp Val Arg Ala Gly His Ser Val Leu
                85                  90                  95

Gly Ile Phe Tyr Gly His Pro Gly Val Phe Val Ser Pro Ser His Arg
            100                 105                 110

Ala Ile Ala Ile Ala Lys Glu Glu Gly Phe Gln Ala Arg Met Leu Pro
        115                 120                 125
```

```
Gly Ile Ser Ala Glu Asp Tyr Leu Phe Ala Asp Ile Gly Phe Asp Pro
            130                 135                 140

Ala Val His Gly Cys Met Ser Tyr Glu Ala Thr Glu Leu Leu Val Arg
145                 150                 155                 160

Asn Lys Pro Leu Asn Thr Ser Thr Tyr Asn Ile Ile Trp Gln Val Gly
                165                 170                 175

Ala Leu Gly Ala Glu Ala Met Val Phe Asp Asn Ala Lys Phe Ser Leu
            180                 185                 190

Leu Val Asp Arg Leu Glu Arg Asp Tyr Gly Ser Asp His Lys Val Val
                195                 200                 205

His Tyr Ile Gly Ala Ile Leu Pro Gln Ala Asp Ser Thr Ile Glu Ala
            210                 215                 220

His Thr Val Ser Asp Leu Arg Lys Glu Asp Ile Val Lys Gln Phe Asn
225                 230                 235                 240

Ala Ile Ser Thr Leu Tyr Ile Pro Pro Arg Val Ala Gly Lys Phe Leu
                245                 250                 255

Asp Asp Met Val Glu Lys Leu Gly Ile Ala Asp Pro Ala Thr Phe Leu
            260                 265                 270

Lys Asn His Tyr Thr Gln Pro Pro Tyr Ser Gly Pro Glu Phe Ala Thr
                275                 280                 285

Asp Pro Ala Tyr Gly Pro Arg Glu Lys Ala Val Ile Asp Gln Ile Asp
            290                 295                 300

Asn His Ala Ala Pro Glu Gly His Thr Val Leu His Ala Thr Asp Ala
305                 310                 315                 320

Leu Lys Lys Leu Asn Thr Asp Leu Ala Leu Ser Pro Lys Phe Leu Lys
                325                 330                 335

Glu Tyr Lys Glu Asn Pro Met Pro Ile Leu Glu Ala Met Asp Gly Leu
            340                 345                 350

Thr Asp Glu Glu Gln Ala Ala Leu Met Gln Asn Pro Leu Gly Ala Thr
                355                 360                 365

His Glu Leu Met Trp Ala Thr Pro Asp Glu Ile Ala Asn Gly Arg Val
            370                 375                 380

Leu Pro Val Val Asn Phe Cys Phe Leu Gly Gly Asn Arg Arg Gly Tyr
385                 390                 395                 400

Arg Arg Gly Tyr Gln Ala Val Asn Tyr Gly Gly Ser Tyr Asn Thr Tyr
                405                 410                 415

Ile Ile Asn Asn Phe
            420

<210> SEQ ID NO 84
<211> LENGTH: 413
<212> TYPE: PRT
<213> ORGANISM: Fomitiporia mediterranea

<400> SEQUENCE: 84

Met Ala Thr Ser Thr Glu Thr Ala Gln Lys Lys Gly Ser Leu Thr Ile
1               5                   10                  15

Ala Gly Thr Gly Ile Ala Ser Ile Lys His Ile Thr Leu Glu Thr Leu
            20                  25                  30

Ser Tyr Ile Lys Glu Ala Glu Lys Val Tyr Tyr Leu Val Ala Asp Pro
        35                  40                  45

Ala Thr Glu Ala Phe Ile His Asp Asn Ala Ser Gly Thr Cys Phe Asn
    50                  55                  60

Leu His Val Phe Tyr Asp Thr Asn Lys Leu Arg Tyr Asp Ser Tyr Val
65              70                  75                  80
```

Gln Met Ala Glu Val Met Leu Arg Asp Val Arg Ala Gly Asn Ser Val
                    85                  90                  95

Leu Gly Leu Phe Tyr Gly His Pro Gly Val Phe Val Ser Pro Ser His
                100                 105                 110

Arg Ala Ile Ala Val Ala Arg Glu Glu Gly Phe Lys Ala Gln Thr Leu
            115                 120                 125

Pro Gly Ile Ser Ala Glu Asp Tyr Met Phe Ala Asp Ile Gly Phe Asp
        130                 135                 140

Pro Ala Ser His Gly Cys Val Ser Tyr Glu Ala Thr Asp Leu Leu Ala
145                 150                 155                 160

Arg Asp Lys Pro Leu Leu Pro Ser Ser His Asn Ile Ile Trp Gln Val
                165                 170                 175

Gly Ala Ile Gly Ala Asn Ala Met Val Phe Asp Asn Gly Lys Phe Asn
                180                 185                 190

Val Leu Val Asp Arg Leu Glu Arg Asp Phe Gly Pro Asn His Lys Val
                195                 200                 205

Val His Tyr Ile Gly Ala Val Leu Pro Gln Ser Thr Ser Lys Val Glu
        210                 215                 220

Gln Tyr Thr Val Ala Asp Leu Arg Lys Asp Tyr Val Lys Thr Phe
225                 230                 235                 240

Thr Thr Thr Ser Thr Leu Tyr Val Pro Pro Cys Val Asp Ala Gly Ile
                245                 250                 255

Ser Asn Ile Met Ala Arg Glu Leu Gly Leu Glu Asp Ser Thr Gly Leu
                260                 265                 270

Arg Thr Arg Gly Asn Gln Pro Leu Pro Leu Lys Thr Gly Pro Ala Ile
            275                 280                 285

Ser Leu Ala Ser Val Tyr Gly Ser His Glu Arg Thr Thr Ile Ala Gln
        290                 295                 300

Ile Asp Lys Gly Val Thr Pro Asp Thr Leu Gln Ile Leu Gln Ala Ser
305                 310                 315                 320

Asp Ala Met Lys Lys Leu Met Ala Asp Leu Ala Leu Lys Pro Lys Leu
                325                 330                 335

Leu Glu Lys Tyr Arg Gly Asn Pro Ser Val Val Ile Asp Glu Val Thr
                340                 345                 350

Gly Leu Ala Pro Gln Glu Lys Ala Ala Leu Thr Leu Cys Ser Ala Gly
            355                 360                 365

Ala Ile Tyr Met Val Met Ala Ala Ser Gln Ile Asp Ile Ala Lys Gly
        370                 375                 380

Arg Gln Trp Ser Thr Glu Glu Leu Lys Thr Ala Ala Asp Val Ser Ala
385                 390                 395                 400

Pro Val Ile Leu Val Leu Ser Gln Tyr Asn Thr Val His
                405                 410

<210> SEQ ID NO 85
<211> LENGTH: 385
<212> TYPE: PRT
<213> ORGANISM: Gyromitra esculenta

<400> SEQUENCE: 85

Met Ser Val Gln Pro Gln Ser Ser Ala Lys Lys Gly Gly Leu Val Val
1               5                   10                  15

Val Gly Ser Gly Ile Arg Ser Val Ser Gln Leu Thr Leu Glu Ala Val
            20                  25                  30

Met His Ile Glu Lys Ala Asp Thr Val Leu Tyr Cys Val Cys Asp Pro

```
                35                  40                  45
Ser Thr Glu Gly Phe Ile Lys Arg Lys Asn Lys Asn Ala Ile Asp Ile
 50                  55                  60

Tyr Gly Tyr Tyr Ser Asp Leu Lys Glu Arg Pro Asp Ala Phe Val Gln
 65                  70                  75                  80

Met Ala Glu Val Ile Leu Arg Glu Val Arg Lys Gly Ile Asn Val Val
                 85                  90                  95

Ala Val Phe Tyr Gly His Pro Gly Ile Phe Val His Pro Ser Arg Arg
                100                 105                 110

Ala Leu Ala Ile Ala Lys Lys Glu Gly Tyr Ala Ala Arg Met Leu Pro
                115                 120                 125

Gly Ile Ser Ala Glu Asp Cys Leu Phe Ala Asp Leu Leu Val Asn Pro
            130                 135                 140

Ser Phe Pro Gly Ala Gln Leu Val Glu Ala Ser Asp Ile Val Tyr Arg
145                 150                 155                 160

Ala Arg Pro Leu Ala Thr Ser Cys His Val Val Ile Phe Gln Ala Ala
                165                 170                 175

Cys Phe Gly His Trp Lys Tyr Asn Phe Thr Ala Phe Glu Asn Gly Lys
                180                 185                 190

Phe Asp His Leu Val Asn Arg Leu Gln Lys Asp Tyr Gly Pro Asp His
                195                 200                 205

Pro Ile Val Ser Tyr Met Ala Ala Val Ser Pro Leu Glu Asp Pro Val
            210                 215                 220

Ile Asn Arg His Thr Ile Ser Asp Leu Tyr Lys Ala Asp Val Lys Lys
225                 230                 235                 240

Glu Ile Thr Pro Asn Cys Thr Leu Tyr Ile Pro Pro Lys Asp Leu Leu
                245                 250                 255

Pro Ile Ser Pro Ala Gly Glu Leu Ile Ile Leu Gly His Gln Ala Gly
                260                 265                 270

Pro Asp Glu Thr Pro Lys Phe Pro Pro Leu Pro Ile His His Tyr Leu
            275                 280                 285

Ala Pro Glu Glu Glu Thr Tyr Gly Pro Gln Glu Thr Ser Ala Val Ala
290                 295                 300

Ala Leu Glu Lys Gly Ala Ile Ser Ala Asp Tyr Arg Pro Tyr Cys Ala
305                 310                 315                 320

Ser Pro Ala Met Gln Lys Val Thr Glu Ser Leu Ser Leu Asp Pro Glu
                325                 330                 335

Val Leu Lys Thr Tyr Arg Glu Ser Pro Gln Ala Phe Ala Glu Ser Ile
                340                 345                 350

Pro Gly Leu Glu Ala Arg Glu Val Lys Ala Leu Ala Ser Gly Ser Pro
            355                 360                 365

Val Lys Ile His Asp Ser Met Trp Val Glu Gly Lys Ser Glu Val Arg
    370                 375                 380

Trp
385

<210> SEQ ID NO 86
<211> LENGTH: 419
<212> TYPE: PRT
<213> ORGANISM: Gymnopilus junonius

<400> SEQUENCE: 86

Met Ala Thr Pro Ile Ala Thr Thr Asn Thr Pro Thr Lys Ala Gly
 1               5                  10                  15
```

-continued

Ser Leu Thr Ile Ala Gly Ser Gly Ile Ala Ser Val Gly His Ile Thr
            20                  25                  30

Leu Glu Thr Leu Ala Tyr Ile Lys Glu Ser His Lys Val Phe Tyr Leu
        35                  40                  45

Val Cys Asp Pro Val Thr Glu Ala Phe Ile Gln Glu Asn Gly Lys Gly
 50                  55                  60

Pro Cys Ile Asn Leu Ser Ile Tyr Tyr Asp Ser Gln Lys Ser Arg Tyr
 65                  70                  75                  80

Asp Ser Tyr Leu Gln Met Cys Glu Val Met Leu Arg Asp Val Arg Asn
                85                  90                  95

Gly Leu Asp Val Leu Gly Val Phe Tyr Gly His Pro Gly Val Phe Val
                100                 105                 110

Ser Pro Ser His Arg Ala Ile Ala Leu Ala Arg Glu Glu Gly Phe Asn
            115                 120                 125

Ala Lys Met Leu Ala Gly Val Ser Ala Glu Asp Cys Leu Phe Ala Asp
        130                 135                 140

Leu Glu Phe Asp Pro Ala Ser Phe Gly Cys Met Thr Cys Glu Ala Ser
145                 150                 155                 160

Glu Leu Leu Ile Arg Asn Arg Pro Leu Asn Pro Tyr Ile His Asn Val
                165                 170                 175

Ile Trp Gln Val Gly Ser Val Gly Val Thr Asp Met Thr Phe Asn Asn
            180                 185                 190

Asn Lys Phe Pro Ile Leu Ile Asp Arg Leu Glu Lys Asp Phe Gly Pro
        195                 200                 205

Asn His Thr Val Ile His Tyr Val Gly Arg Val Ile Pro Gln Ser Val
210                 215                 220

Ser Lys Ile Glu Thr Phe Thr Ile Ala Asp Leu Arg Lys Glu Glu Val
225                 230                 235                 240

Met Asn His Phe Asp Ala Ile Ser Thr Leu Tyr Val Pro Pro Arg Asp
                245                 250                 255

Ile Ser Pro Val Asp Pro Thr Met Ala Glu Lys Leu Gly Pro Ser Gly
            260                 265                 270

Thr Arg Val Glu Pro Ile Glu Ala Phe Arg Pro Ser Leu Lys Trp Ser
        275                 280                 285

Ala Gln Asn Asp Lys Arg Ser Tyr Ala Tyr Asn Pro Tyr Glu Ser Asp
290                 295                 300

Val Val Ala Gln Leu Asp Asn Tyr Val Thr Pro Glu Gly His Arg Ile
305                 310                 315                 320

Leu Gln Gly Ser Pro Ala Met Lys Lys Phe Leu Ile Thr Leu Ala Thr
                325                 330                 335

Ser Pro Gln Leu Leu Gln Ala Tyr Arg Glu Asn Pro Ser Ala Ile Val
            340                 345                 350

Asp Thr Val Glu Gly Leu Asn Glu Gln Glu Lys Tyr Gly Leu Lys Leu
        355                 360                 365

Gly Ser Glu Gly Ala Val Tyr Ala Leu Met Ser Arg Pro Thr Gly Asp
370                 375                 380

Ile Ala Arg Glu Lys Glu Leu Thr Asn Asp Glu Ile Ala Asn Asn His
385                 390                 395                 400

Gly Ala Pro Tyr Ala Phe Val Ser Ala Val Ile Ile Ala Ala Ile Ile
                405                 410                 415

Cys Ala Leu

<210> SEQ ID NO 87

```
<211> LENGTH: 420
<212> TYPE: PRT
<213> ORGANISM: Gymnopus fusipes

<400> SEQUENCE: 87
```

| | | | | | | | | | | | | | | |
|---|---|---|---|---|---|---|---|---|---|---|---|---|---|---|
|Met|Gln|Ser|Ser|Thr|Gln|Lys|Gln|Ala|Gly|Ser|Leu|Thr|Ile|Val|Gly
|1| | | |5| | | | |10| | | | |15|

Ser Gly Ile Glu Ser Ile Ser Gln Ile Thr Leu Gln Ser Leu Ser His
                20                  25                  30

Ile Glu Ala Ala Ser Lys Val Phe Tyr Cys Val Val Asp Pro Ala Thr
            35                  40                  45

Glu Ala Tyr Leu Leu Ala Lys Asn Lys Asn Cys Val Asp Leu Tyr Gln
        50                  55                  60

Tyr Tyr Asp Asn Gly Lys Pro Arg Met Asp Thr Tyr Ile Gln Met Ala
65                  70                  75                  80

Glu Val Met Leu Arg Glu Val Arg Asn Gly Leu Asp Ile Val Gly Val
                85                  90                  95

Phe Tyr Gly His Pro Gly Val Phe Val Asn Pro Ser Gln Arg Ala Ile
            100                 105                 110

Ala Ile Ala Lys Ser Glu Gly Tyr Gln Ala Arg Met Leu Pro Gly Ile
        115                 120                 125

Ser Ala Glu Asp Cys Leu Phe Ala Asp Leu Gly Ile Asp Pro Cys Asn
130                 135                 140

Pro Gly Cys Val Ser Tyr Glu Ala Ser Asp Phe Leu Ile Arg Glu Arg
145                 150                 155                 160

Pro Val Asn Val Ser Ser His Phe Ile Leu Trp Gln Val Gly Cys Ile
                165                 170                 175

Gly Val Ala Asp Phe Thr Phe Val Lys Phe Asn Asn Ser Lys Phe Gly
            180                 185                 190

Val Leu Leu Asp Arg Leu Glu His Glu Tyr Gly Ala Asp His Thr Val
        195                 200                 205

Val His Tyr Ile Ala Ala Val Leu Pro Tyr Glu Asn Pro Val Ile Asp
        210                 215                 220

Lys Leu Thr Ile Ser Gln Leu Arg Asp Thr Glu Val Ala Lys Arg Val
225                 230                 235                 240

Ser Gly Ile Ser Thr Phe Tyr Ile Pro Pro Lys Glu Leu Lys Asp Pro
                245                 250                 255

Ser Met Asp Ile Met Arg Arg Leu Glu Leu Leu Ala Ala Asp Gln Val
            260                 265                 270

Pro Asp Lys Gln Trp His Phe Tyr Pro Thr Asn Gln Trp Ala Pro Ser
        275                 280                 285

Ala Pro Asn Val Val Pro Tyr Gly Pro Ile Glu Gln Ala Ala Ile Val
        290                 295                 300

Gln Leu Gly Ser His Thr Ile Pro Glu Gln Phe Gln Pro Ile Ala Thr
305                 310                 315                 320

Ser Lys Ala Met Thr Asp Ile Leu Thr Lys Leu Ala Leu Asp Pro Lys
                325                 330                 335

Met Leu Thr Glu Tyr Lys Ala Asp Arg Arg Ala Phe Ala Gln Ser Ala
            340                 345                 350

Leu Glu Leu Thr Val Asn Glu Arg Asp Ala Leu Glu Met Gly Thr Phe
        355                 360                 365

Trp Ala Leu Arg Cys Ala Met Lys Lys Met Pro Ser Ser Phe Met Asp
370                 375                 380

Glu Val Asp Ala Asn Asn Leu Pro Val Val Ala Val Val Gly Val Ala

-continued

```
            385                 390                 395                 400
Val Gly Ala Val Ala Val Thr Val Val Ser Leu Asn Asp Leu Thr
                405                 410                 415

Asp Ser Val Asn
            420

<210> SEQ ID NO 88
<211> LENGTH: 408
<212> TYPE: PRT
<213> ORGANISM: Hydnomerulius pinastri

<400> SEQUENCE: 88

Met Pro Val Pro Thr Thr Thr Asn Lys Asn Gly Ser Leu Thr Ile Ala
1               5                   10                  15

Gly Ser Gly Ile Ala Ser Ile Arg His Met Thr Leu Glu Thr Leu Ser
            20                  25                  30

Ala Ile Lys Ser Ala Asp Lys Val Tyr Tyr Thr Val Cys Asp Pro Ala
        35                  40                  45

Thr Glu Ala Phe Ile Gln Asp Asn Ala Thr Gly Ser Cys Ser Asp Leu
    50                  55                  60

Thr Val Tyr Tyr Asp Lys Glu Lys Ser Arg Tyr Asp Thr Tyr Val Gln
65                  70                  75                  80

Met Cys Glu Val Met Leu Arg Glu Val Arg Ala Gly His Asn Val Leu
                85                  90                  95

Gly Val Phe Tyr Gly His Pro Gly Val Phe Val Ser Pro Ser His Arg
            100                 105                 110

Ala Ile Ala Ile Ala Arg Ala Glu Gly Tyr Lys Ala Glu Met Leu Ala
        115                 120                 125

Gly Val Ser Ala Glu Asp Tyr Met Phe Ala Asp Leu Gly Phe Asp Pro
    130                 135                 140

Ala Ala His Gly Cys Val Thr Tyr Glu Ala Thr Glu Met Leu Leu Arg
145                 150                 155                 160

Lys Lys Gln Leu Asn Pro Ala Thr His Asn Ile Ile Trp Gln Val Gly
                165                 170                 175

Gly Val Gly Val Ser Asn Met Ile Phe Asp Asn Ala Arg Phe His Leu
            180                 185                 190

Leu Val Asp Arg Leu Glu Asp Thr Phe Gly Pro Asp His Gln Val Val
        195                 200                 205

His Tyr Ile Gly Ala Val Leu Pro Leu Ser Val Lys Thr Met Glu Thr
    210                 215                 220

Tyr Thr Ile Ala Asp Leu Arg Lys Glu Asp Val Val Ala Gln Phe Asn
225                 230                 235                 240

Pro Thr Ser Thr Leu Tyr Ile Pro Pro Arg Asp Val Ser Pro Asn Asp
                245                 250                 255

Pro Glu Val Ala Gln Gln Leu Ser Ser Phe Glu Ala Val Val Arg Ser
            260                 265                 270

Lys Tyr Pro Pro Pro Gly Trp Thr Thr Ser Glu Pro Ser Ser Ala Leu
        275                 280                 285

Ala Tyr Gly Pro Arg Glu Arg Asp Ala Ile Ala Gln Leu Asp Ser His
    290                 295                 300

Val Ala Pro Asp Ser His Lys Val Leu Arg Ala Ser Ser Ala Ile Arg
305                 310                 315                 320

Arg Leu Met Ala Asp Leu Ala Leu Ser Pro Glu Leu Leu Ala Thr Tyr
                325                 330                 335
```

```
Arg Lys Asp Pro Gln Ala Val Val Ala Ala Thr Glu Gly Leu Thr Val
                340                 345                 350

Gln Glu Lys Ala Ala Leu Ser Leu Asn Lys Ala Gly Ala Ile Tyr Gly
            355                 360                 365

Val Met Lys Ala Thr Pro Tyr Asp Ile Ala Asn Asn Arg Ser Leu Ser
370                 375                 380

Val Ala Asp Met Gly Ala Ile Asn Glu Pro Ala Ala Leu Thr Thr Met
385                 390                 395                 400

Ile Asn Ile His Val Thr His Val
                405

<210> SEQ ID NO 89
<211> LENGTH: 417
<212> TYPE: PRT
<213> ORGANISM: Lentinula edodes

<400> SEQUENCE: 89

Met Glu Thr Pro Thr Leu Asn Lys Ser Gly Ser Leu Thr Ile Val Gly
1               5                   10                  15

Thr Gly Ile Glu Ser Ile Gly Gln Met Thr Leu Gln Thr Leu Ser Tyr
            20                  25                  30

Ile Glu Ala Ala Asp Lys Val Phe Tyr Cys Val Ile Asp Pro Ala Thr
        35                  40                  45

Glu Ala Phe Ile Leu Thr Lys Asn Lys Asp Cys Val Asp Leu Tyr Gln
50                  55                  60

Tyr Tyr Asp Asn Gly Lys Ser Arg Met Asp Thr Tyr Thr Gln Met Ser
65                  70                  75                  80

Glu Val Met Leu Arg Glu Val Arg Lys Gly Leu Asp Val Val Gly Val
                85                  90                  95

Phe Tyr Gly His Pro Gly Val Phe Val Asn Pro Ser Leu Arg Ala Leu
            100                 105                 110

Ala Ile Ala Lys Ser Glu Gly Phe Lys Ala Arg Met Leu Pro Gly Val
        115                 120                 125

Ser Ala Glu Asp Cys Leu Tyr Ala Asp Leu Cys Ile Asp Pro Ser Asn
130                 135                 140

Pro Gly Cys Leu Thr Tyr Glu Ala Ser Asp Phe Leu Ile Arg Glu Arg
145                 150                 155                 160

Pro Thr Asn Ile Tyr Ser His Phe Ile Leu Phe Gln Val Gly Cys Val
                165                 170                 175

Gly Ile Ala Asp Phe Asn Phe Thr Gly Phe Glu Asn Ser Lys Phe Gly
            180                 185                 190

Ile Leu Val Asp Arg Leu Glu Lys Glu Tyr Gly Ala Glu His Pro Val
        195                 200                 205

Val His Tyr Ile Ala Ala Met Leu Pro His Glu Asp Pro Val Thr Asp
210                 215                 220

Gln Trp Thr Ile Gly Gln Leu Arg Glu Pro Glu Phe Tyr Lys Arg Val
225                 230                 235                 240

Gly Gly Val Ser Thr Phe Tyr Ile Pro Pro Lys Glu Arg Lys Glu Ile
                245                 250                 255

Asn Val Asp Ile Ile Arg Glu Leu Lys Phe Leu Pro Glu Gly Lys Val
            260                 265                 270

Pro Asp Thr Arg Thr Gln Ile Tyr Pro Pro Asn Gln Trp Glu Pro Glu
        275                 280                 285

Val Pro Thr Val Pro Ala Tyr Gly Ser Asn Glu His Ala Ala Ile Ala
290                 295                 300
```

```
Gln Leu Asp Thr His Thr Pro Pro Glu Gln Tyr Gln Pro Leu Ala Thr
305                 310                 315                 320

Ser Lys Ala Met Thr Asp Val Met Thr Lys Leu Ala Leu Asp Pro Lys
            325                 330                 335

Ala Leu Ala Glu Tyr Lys Ala Asp His Arg Ala Phe Ala Gln Ser Val
        340                 345                 350

Pro Asp Leu Thr Ala Asn Glu Arg Thr Ala Leu Glu Ile Gly Asp Ser
    355                 360                 365

Trp Ala Phe Arg Cys Ala Met Lys Glu Met Pro Ile Ser Leu Leu Asp
370                 375                 380

Asn Ala Lys Gln Ser Met Glu Glu Ala Ser Gln Gly Phe Pro Trp
385                 390                 395                 400

Ile Ile Val Val Gly Val Val Gly Ser Val Val Ser Ser
                405                 410                 415

Ala
```

<210> SEQ ID NO 90
<211> LENGTH: 417
<212> TYPE: PRT
<213> ORGANISM: Lentinula lateritia

<400> SEQUENCE: 90

```
Met Glu Thr Pro Thr Leu Asn Lys Ser Gly Ser Leu Thr Ile Val Gly
1               5                   10                  15

Thr Gly Ile Glu Ser Ile Gly Gln Met Thr Leu Gln Thr Leu Ser Tyr
            20                  25                  30

Ile Glu Ala Ala Asp Lys Val Phe Tyr Cys Val Ile Asp Pro Ala Thr
        35                  40                  45

Glu Ala Phe Ile Leu Thr Lys Asn Lys Asp Cys Val Asp Leu Tyr Gln
    50                  55                  60

Tyr Tyr Asp Asn Gly Lys Ser Arg Met Asp Thr Tyr Thr Gln Met Ser
65                  70                  75                  80

Glu Val Met Leu Arg Glu Val Arg Lys Gly Leu Glu Val Val Gly Val
                85                  90                  95

Phe Tyr Gly His Pro Gly Val Phe Val Asn Pro Ser Leu Arg Ala Leu
            100                 105                 110

Ala Ile Ala Lys Ser Glu Gly Tyr Lys Ala Arg Met Leu Pro Gly Val
        115                 120                 125

Ser Ala Glu Asp Cys Leu Tyr Ala Asp Leu Cys Ile Asp Pro Ser Asn
    130                 135                 140

Pro Gly Cys Leu Thr Tyr Glu Ala Ser Asp Phe Leu Ile Arg Glu Arg
145                 150                 155                 160

Pro Thr Asn Ile Tyr Ser His Phe Ile Leu Phe Gln Val Gly Cys Val
                165                 170                 175

Gly Ile Ala Asp Phe Asn Phe Thr Gly Phe Glu Asn Ser Lys Phe Gly
            180                 185                 190

Ile Leu Val Asp Arg Leu Glu Lys Glu Tyr Gly Ala Asp His Pro Val
        195                 200                 205

Val His Tyr Ile Ala Ala Met Leu Pro His Glu Asp Pro Val Thr Asp
    210                 215                 220

Gln Trp Thr Ile Gly Gln Leu Arg Glu Pro Glu Phe Tyr Lys Arg Val
225                 230                 235                 240

Gly Gly Val Ser Thr Phe Tyr Ile Pro Pro Lys Glu Arg Lys Glu Ile
                245                 250                 255
```

```
Asn Val Asp Ile Ile Arg Glu Leu Lys Phe Leu Pro Glu Gly Lys Val
            260                 265                 270

Pro Asp Thr Arg Thr Gln Ile Tyr Pro Pro Asn Gln Trp Glu Pro Glu
        275                 280                 285

Val Pro Thr Val Pro Ala Tyr Gly Ser Asn Glu His Ala Ala Ile Ala
290                 295                 300

Gln Leu Asp Ala His Ser Ala Pro Glu Gln Tyr Gln Pro Leu Ala Thr
305                 310                 315                 320

Ser Lys Ala Met Thr Asp Val Met Thr Lys Leu Ala Leu Asp Pro Lys
                325                 330                 335

Ala Leu Ala Glu Tyr Lys Ala Asp His Arg Ala Phe Ala Gln Ser Val
            340                 345                 350

Pro Asp Leu Thr Ala Asn Glu Arg Thr Ala Leu Glu Ile Gly Asp Ser
        355                 360                 365

Trp Ala Phe Arg Cys Ala Met Lys Glu Met Pro Val Ser Leu Leu Asp
370                 375                 380

Asn Ala Lys Gln Ser Met Glu Glu Ala Ser Glu Gln Gly Phe Pro Trp
385                 390                 395                 400

Ile Ile Val Val Gly Val Val Gly Val Gly Ser Val Ser Ser
                405                 410                 415

Ala

<210> SEQ ID NO 91
<211> LENGTH: 417
<212> TYPE: PRT
<213> ORGANISM: Lentinula raphanica

<400> SEQUENCE: 91

Met Glu Ser Ser Thr Gln Thr Lys Thr Gly Ser Leu Ile Ile Val Gly
1               5                   10                  15

Thr Gly Ile Glu Ser Ile Gly Gln Met Thr Leu Gln Thr Leu Ser Tyr
            20                  25                  30

Ile Glu Ala Ala Asp Arg Val Phe Tyr Cys Val Ile Asp Pro Ala Thr
        35                  40                  45

Glu Ala Phe Ile Leu Thr Lys Asn Lys Asn Cys Val Asp Leu Tyr Gln
50                  55                  60

Tyr Tyr Asp Asn Gly Lys Thr Arg Met Asp Thr Tyr Thr Gln Met Ser
65                  70                  75                  80

Glu Val Met Leu Arg Glu Val Arg Lys Gly Leu Lys Val Val Gly Val
                85                  90                  95

Phe Tyr Gly His Pro Gly Val Phe Val Asn Pro Ser Leu Arg Ala Leu
            100                 105                 110

Ala Ile Ala Lys Ser Glu Gly Phe Lys Ala Arg Met Leu Pro Gly Val
        115                 120                 125

Ser Ala Glu Asp Cys Leu Tyr Ala Asp Leu Cys Ile Asp Pro Ser Asn
130                 135                 140

Pro Gly Cys Leu Thr Tyr Glu Ala Ser Asp Phe Leu Ile Arg Glu Arg
145                 150                 155                 160

Pro Ala Asn Ile Tyr Ser His Phe Ile Leu Phe Gln Val Gly Cys Val
                165                 170                 175

Gly Ile Ala Asp Phe Ser Phe Thr Gly Phe Asp Asn Ser Lys Phe Gly
            180                 185                 190

Val Leu Val Asp Arg Leu Glu Lys Glu Tyr Gly Gly Asp His Pro Val
        195                 200                 205
```

```
Val His Tyr Ile Ala Met Leu Pro His Glu Glu Pro Val Thr Asp
    210                 215                 220

Lys Phe Thr Ile Ala Gln Leu Arg Glu Pro Glu Val Tyr Lys Arg Val
225                 230                 235                 240

Gly Gly Val Ser Thr Phe Tyr Ile Pro Pro Lys Glu Arg Lys Glu Ile
                245                 250                 255

Asn Ala Asp Ile Ile His Gln Leu Lys Phe Leu Pro Glu Gly Lys Val
                260                 265                 270

Pro Asp Lys Arg Thr Gln Ile Phe Pro Pro Asn Gln Trp Glu Pro Glu
            275                 280                 285

Val Pro Thr Leu Pro Ala Tyr Gly Pro Asn Asp Tyr Ala Thr Ile Ala
    290                 295                 300

Leu Ile Asp Ser His Thr Pro Pro Glu Gln Tyr Gln Pro Leu Ala Thr
305                 310                 315                 320

Ser Lys Ala Met Thr Asp Val Met Ile Lys Leu Ala Leu Asp Pro Gln
                325                 330                 335

Ala Leu Glu Glu Tyr Lys Ala Asp His Arg Ala Phe Ala Gln Ser Ile
            340                 345                 350

Pro Asp Leu Thr Thr His Glu Arg Ile Ala Leu Glu Met Gly Asp Ser
        355                 360                 365

Trp Ala Phe Arg Cys Ala Met Lys Asp Met Pro Gln Ser Leu Leu Glu
370                 375                 380

Arg Ala Gln Gln Asn Met Glu Glu Ser Ala Gln His Gly Phe Pro Trp
385                 390                 395                 400

Ile Ile Val Val Gly Val Gly Val Val Gly Ser Val Val Ser Ser
                405                 410                 415

Ala

<210> SEQ ID NO 92
<211> LENGTH: 434
<212> TYPE: PRT
<213> ORGANISM: Mycosphaerella eumusae

<400> SEQUENCE: 92

Met Ala Ser Ser Ser Val Trp Ser Tyr Ile Asp His Leu Thr Gln Glu
1               5                   10                  15

Asp Asp Ile Ser Ser Ser Cys Gly Asp Ala Gly Asp Lys Lys Gly Glu
            20                  25                  30

Leu Val Val Val Gly Thr Gly Ile Ala Ser Leu Arg Gln Met Thr Val
        35                  40                  45

Glu Ala Leu Asp Tyr Ile Gln Arg Ala Asp Met Val Phe Tyr Val Val
    50                  55                  60

Leu Asp Ala Met Thr Glu Cys Phe Ile Gln Thr His Ala Lys Lys His
65                  70                  75                  80

His Asp Leu Tyr Gln Tyr Tyr Asp Lys Asn Lys Pro Arg Asn Ala Ser
                85                  90                  95

Tyr Val Gln Met Ala Glu Leu Met Val Gln Ser Val Arg Asp Gly Asn
            100                 105                 110

Leu Thr Val Ala Val Tyr Tyr Gly His Pro Gly Val Phe Val Phe Pro
        115                 120                 125

Thr His Arg Ala Ile His Ile Ala Arg Glu Glu Gly Tyr Lys Ala Lys
    130                 135                 140

Met Leu Pro Gly Val Ser Ala Glu Asp Cys Leu Tyr Ala Asp Leu Gly
145                 150                 155                 160
```

```
Ile Asp Pro Gly Thr Thr Gly Cys Ser Met Phe Glu Ala Thr Tyr Leu
                165                 170                 175

Leu Asn Glu Pro Asp Arg Leu Asp Pro Arg Asn His Val Ile Ile Trp
            180                 185                 190

Gln Pro Gly Cys Val Gly Lys Ser Thr Met Val Phe Asp Asn Ser Glu
            195                 200                 205

Ile His Glu Leu Ala Asp Tyr Leu Glu Lys Thr Tyr Gly Pro Glu Tyr
        210                 215                 220

Pro Ile Ile Ala Tyr Leu Ala Ala Val Arg Pro Phe Asn Asp Pro Gln
225                 230                 235                 240

Ile Asp Lys Leu Met Val Lys Asp Leu Arg Asp Leu Glu Lys Leu Lys
            245                 250                 255

Ala Ile Pro Phe Asn Ala Ala Thr Thr Leu Tyr Ile Pro Pro Lys Thr
            260                 265                 270

Leu Pro Val Val Pro Gln Asp Met Glu Asp Pro Ile Glu Leu Gln Leu
            275                 280                 285

Ala Arg Asn Ser Ala Phe Arg Met Ser His Pro Glu Met Asn Leu Val
        290                 295                 300

Asp Asn Tyr Thr Lys Gln Asp Lys Gln Trp Val Glu Asp Leu Lys His
305                 310                 315                 320

Phe Val Pro Pro Asn Asp Tyr Lys Arg Met Thr Ala Ser Thr Ala Met
                325                 330                 335

Arg Arg Ala Ala Ile Lys Leu Ala Leu Leu His His Arg Leu His Gly
            340                 345                 350

Val Leu Pro Arg Glu Leu Ile Ala Asp Arg Ala Leu Ser Lys Ser Gly
            355                 360                 365

Leu Thr Pro Asn Glu Ala Glu Ser Leu Arg Val Met Ile Asp Asn Leu
        370                 375                 380

Asp Leu Phe Leu Arg Glu Gly Val Glu Arg Pro Pro Ala Val Asn Gly
385                 390                 395                 400

Val Ser Val Ile Val Phe Ala Leu Leu Ile Ile Arg Asn Glu Asp Gln
                405                 410                 415

Arg Val Asn Leu His Gly Gly Lys Met Gly Trp Lys Arg Ser Val Val
            420                 425                 430

Val Asn

<210> SEQ ID NO 93
<211> LENGTH: 390
<212> TYPE: PRT
<213> ORGANISM: Marasmius fiardii

<400> SEQUENCE: 93

Met Thr Phe Asn Asp Lys Lys Gly Ser Leu Thr Ile Ala Gly Ser Gly
1               5                   10                  15

Ile Ala Ser Ile Arg His Ile Thr Leu Glu Thr Leu Ser His Ile Glu
            20                  25                  30

Arg Ala Asp Lys Val Tyr Tyr Leu Val Ala Asp Pro Ala Thr Glu Ala
        35                  40                  45

Phe Ile Gln Asp Lys Ser Lys Gly Asp Tyr Val Asp Leu Ala Ile Tyr
    50                  55                  60

Tyr Asp Lys Asp Lys Asn Arg Tyr Glu Ser Tyr Val Gln Met Ser Glu
65                  70                  75                  80

Val Ile Leu Asn Asp Val Arg Ala Gly Tyr Asn Val Leu Gly Val Phe
                85                  90                  95
```

Tyr Gly His Pro Gly Val Phe Val Ser Pro Ser His Arg Thr Val Ala
            100                 105                 110

Ile Ala Arg Asp Glu Gly Tyr Arg Val Asn Met Leu Pro Gly Val Ser
            115                 120                 125

Ala Gln Asp Tyr Met Phe Ser Asp Ile Gly Phe Asp Pro Ala Ile Pro
        130                 135                 140

Gly Cys Thr Ile Gln Glu Ala Ser Thr Ile Leu Phe Leu Asp Lys Arg
145                 150                 155                 160

Leu Asp Pro Thr Val His Asn Ile Ile Gly Gln Val Gly Cys Val Gly
                165                 170                 175

Val Gly Thr Met Ala Phe Asp Asn Arg Gln Phe His Leu Leu Val Asp
            180                 185                 190

His Leu Glu Lys Asp Phe Gly Pro Glu His Lys Val Val His Tyr Ile
        195                 200                 205

Gly Ala Val Leu Pro Gln Ser Ala Thr Val Lys Asp Glu Phe Lys Ile
    210                 215                 220

Ala Asp Leu Arg Lys Asp Val Val Lys Gln Ile Ser Thr Ile Ser
225                 230                 235                 240

Thr Phe Tyr Ile Pro Pro Arg Gln Val Thr Pro Val Pro Lys Glu Val
                245                 250                 255

Ala Glu Lys Leu Gly Phe His Pro Leu Pro Thr Leu Pro Ile Ser Thr
            260                 265                 270

Arg Ile Tyr Pro Phe Leu Gly Ser Lys Ala Ser Ser Ser Thr Ser
        275                 280                 285

Phe Tyr Glu Pro Phe Glu Arg Asn Ala Val Asp Arg Leu Gln Asn His
    290                 295                 300

Leu Pro Pro Leu Asp Tyr Asn Thr Leu Arg Ala Ser Pro Ala Val Arg
305                 310                 315                 320

Gln Phe Met Thr Asp Leu Ala Leu Arg Pro Asp Val Leu Asn Leu Tyr
                325                 330                 335

Gln Ala Asp Pro Met Val Leu Val Asp Glu Ile Pro Gly Leu Thr Pro
            340                 345                 350

Ser Glu Lys Ser Ala Leu Arg Ser Gly Asp Pro Gly Pro Val Tyr Glu
        355                 360                 365

Leu Met Arg Ser Asn Phe Thr Arg Glu Lys Ser Thr Gln Met Gly Ala
    370                 375                 380

Ile Val Phe Val Ser Ile
385                 390

<210> SEQ ID NO 94
<211> LENGTH: 397
<212> TYPE: PRT
<213> ORGANISM: Mycena rosella

<400> SEQUENCE: 94

Met Ala Leu Lys Lys Pro Gly Ser Leu Thr Ile Ala Gly Ser Gly Ile
1               5                   10                  15

Ala Ser Ile Gly His Ile Thr Leu Glu Thr Leu Ala Leu Ile Lys Glu
            20                  25                  30

Ala Asp Lys Ile Phe Tyr Ala Val Thr Asp Pro Ala Thr Glu Cys Tyr
        35                  40                  45

Ile Gln Glu Asn Ser Arg Gly Asp His Phe Asp Leu Thr Thr Phe Tyr
    50                  55                  60

Asp Thr Asn Lys Lys Arg Tyr Glu Ser Tyr Val Gln Met Ser Glu Val

```
                65                  70                  75                  80
        Met Leu Arg Asp Val Arg Ala Gly Arg Asn Val Leu Gly Ile Phe Tyr
                        85                  90                  95

Gly His Pro Gly Val Phe Val Ala Pro Ser His Arg Ala Ile Ala Ile
                        100                 105                 110

Ala Arg Glu Glu Gly Phe Gln Ala Lys Met Leu Pro Gly Ile Ser Ala
                        115                 120                 125

Glu Asp Tyr Met Phe Ala Asp Leu Gly Phe Asp Pro Ser Thr Tyr Gly
                        130                 135                 140

Cys Met Thr Gln Glu Ala Thr Glu Leu Leu Val Arg Asn Lys Lys Leu
        145                 150                 155                 160

Asp Pro Ser Ile His Asn Ile Ile Trp Gln Val Gly Ser Val Gly Val
                        165                 170                 175

Asp Thr Met Val Phe Asp Asn Gly Lys Phe His Leu Leu Val Glu Arg
                        180                 185                 190

Leu Glu Lys Asp Phe Gly Leu Asp His Lys Ile Gln His Tyr Ile Gly
                        195                 200                 205

Ala Ile Leu Pro Gln Ser Val Thr Val Lys Asp Thr Phe Ala Ile Arg
                        210                 215                 220

Asp Leu Arg Lys Glu Glu Val Leu Lys Gln Phe Thr Thr Ser Thr
        225                 230                 235                 240

Phe Tyr Val Pro Pro Arg Thr Pro Ala Pro Ile Asp Pro Lys Ala Val
                        245                 250                 255

Gln Ala Leu Gly Leu Pro Ala Thr Val Thr Lys Gly Ala Gln Asp Trp
                        260                 265                 270

Thr Gly Phe Gln Ser Val Ser Pro Ala Tyr Gly Pro Asp Glu Met Arg
                        275                 280                 285

Ala Val Ala Ala Leu Asp Ser Phe Val Pro Ser Gln Glu Lys Ala Val
                        290                 295                 300

Val His Ala Ser Arg Ala Met Gln Ser Leu Met Val Asp Leu Ala Leu
        305                 310                 315                 320

Arg Pro Ala Leu Leu Glu Gln Tyr Lys Ala Asp Pro Val Ala Phe Ala
                        325                 330                 335

Asn Thr Arg Asn Gly Leu Thr Ala Gln Glu Lys Phe Ala Leu Gly Leu
                        340                 345                 350

Lys Lys Pro Gly Pro Ile Phe Val Met Arg Gln Leu Pro Ser Ala
                        355                 360                 365

Ile Ala Ser Gly Gln Glu Pro Ser Gln Glu Ile Ala Arg Ala Asp
                        370                 375                 380

Asp Ala Thr Ala Phe Ile Ile Ile Tyr Ile Val Gln Gly
        385                 390                 395

<210> SEQ ID NO 95
<211> LENGTH: 392
<212> TYPE: PRT
<213> ORGANISM: Mycena rosella

<400> SEQUENCE: 95

Met Ala Leu Asn Lys Pro Gly Ser Leu Thr Ile Ala Gly Ser Gly Ile
1               5                   10                  15

Ala Ser Ile Gly His Ile Thr Leu Glu Thr Leu Ala Leu Ile Lys Glu
                20                  25                  30

Ala Asp Lys Ile Phe Tyr Ala Val Thr Asp Pro Ala Thr Glu Cys Tyr
                35                  40                  45
```

```
Ile Gln Glu Asn Ser Arg Gly Asp His Phe Asp Leu Thr Thr Phe Tyr
 50                  55                  60

Asp Thr Asn Lys Lys Arg Tyr Glu Ser Tyr Val Gln Met Ser Glu Val
 65                  70                  75                  80

Met Leu Arg Glu Val Arg Ala Gly Arg Asn Val Leu Gly Ile Phe Tyr
                 85                  90                  95

Gly His Pro Gly Val Phe Val Ala Pro Ser His Arg Ala Ile Ala Ile
                100                 105                 110

Ala Arg Glu Glu Gly Phe Gln Ala Lys Met Leu Pro Gly Ile Ser Ala
            115                 120                 125

Glu Asp Tyr Met Phe Ala Asp Leu Gly Phe Asp Pro Ser Thr Gln Gly
            130                 135                 140

Cys Met Thr Gln Glu Ala Thr Glu Leu Leu Val Arg Asn Lys Lys Leu
145                 150                 155                 160

Asp Pro Ser Val His Asn Ile Ile Trp Gln Val Gly Ser Val Gly Val
                165                 170                 175

Asp Thr Met Val Phe Asp Asn Gly Lys Phe His Leu Leu Val Glu Arg
                180                 185                 190

Leu Glu Lys Asp Phe Gly Leu Asp His Lys Ile Gln His Tyr Ile Gly
            195                 200                 205

Ala Ile Leu Pro Gln Ser Val Thr Val Lys Asp Ala Phe Ala Ile Arg
            210                 215                 220

Asp Leu Arg Lys Glu Glu Val Leu Lys Gln Phe Thr Thr Thr Ser Thr
225                 230                 235                 240

Phe Tyr Ile Pro Pro Arg Ala Pro Ala Pro Ile Asp Ala Lys Val Leu
                245                 250                 255

Gln Ala Leu Gly Leu Pro Pro Ala Gln Ala Thr Lys Asp Arg Thr
                260                 265                 270

Gly Tyr Gly Pro Leu Glu Lys Gln Ala Val Ala Ala Leu Asp Ser Phe
            275                 280                 285

Ile Pro Ser Gln Glu Lys Gln Val Val His Ala Ser Pro Ala Met Gln
            290                 295                 300

Ser Leu Met Ala Asp Leu Ala Leu Arg Pro Ala Leu Phe Glu Gln Tyr
305                 310                 315                 320

Lys Ala Asp Pro Val Gly Phe Ala Asn Thr Arg Asn Leu Asn Gly Leu
                325                 330                 335

Thr Ala Gln Glu Lys Phe Ala Leu Gly Phe Asn Lys Ser Gly Pro Ile
            340                 345                 350

Phe Ala Val Met Arg His Leu Pro Ser Ala Ile Ala Ser Gly Gln Glu
            355                 360                 365

Arg Ser Gln Glu Glu Ile Ala His Ala Ala Asp Asp Lys Glu Leu Leu
370                 375                 380

Ala Leu Val Val Val Ile Val Gln
385                 390

<210> SEQ ID NO 96
<211> LENGTH: 417
<212> TYPE: PRT
<213> ORGANISM: Omphalotus olearius

<400> SEQUENCE: 96

Met Glu Thr Ser Thr Gln Thr Lys Ala Gly Ser Leu Thr Ile Val Gly
1               5                  10                  15

Thr Gly Ile Glu Ser Ile Gly Gln Met Thr Leu Gln Ala Leu Ser Tyr
            20                  25                  30
```

Ile Glu Ala Ala Ala Lys Val Phe Tyr Cys Val Ile Asp Pro Ala Thr
35                  40                  45

Glu Ala Phe Ile Leu Thr Lys Asn Lys Asn Cys Val Asp Leu Tyr Gln
50                  55                  60

Tyr Tyr Asp Asn Gly Lys Ser Arg Leu Asn Thr Tyr Thr Gln Met Ser
65                  70                  75                  80

Glu Leu Met Val Arg Glu Val Arg Lys Gly Leu Asp Val Val Gly Val
                85                  90                  95

Phe Tyr Gly His Pro Gly Val Phe Val Asn Pro Ser His Arg Ala Leu
            100                 105                 110

Ala Ile Ala Lys Ser Glu Gly Tyr Arg Ala Arg Met Leu Pro Gly Val
        115                 120                 125

Ser Ala Glu Asp Cys Leu Phe Ala Asp Leu Cys Ile Asp Pro Ser Asn
130                 135                 140

Pro Gly Cys Leu Thr Tyr Glu Ala Ser Asp Phe Leu Ile Arg Asp Arg
145                 150                 155                 160

Pro Val Ser Ile His Ser His Leu Val Leu Phe Gln Val Gly Cys Val
                165                 170                 175

Gly Ile Ala Asp Phe Asn Phe Thr Gly Phe Asp Asn Asn Lys Phe Gly
            180                 185                 190

Val Leu Val Asp Arg Leu Glu Gln Glu Tyr Gly Ala Glu His Pro Val
        195                 200                 205

Val His Tyr Ile Ala Ala Met Met Pro His Gln Asp Pro Val Thr Asp
210                 215                 220

Lys Tyr Thr Val Ala Gln Leu Arg Glu Pro Glu Ile Ala Lys Arg Val
225                 230                 235                 240

Gly Gly Val Ser Thr Phe Tyr Ile Pro Pro Lys Ala Arg Lys Ala Ser
                245                 250                 255

Asn Leu Asp Ile Ile Arg Arg Leu Glu Leu Leu Pro Ala Gly Gln Val
            260                 265                 270

Pro Asp Lys Lys Ala Arg Ile Tyr Pro Ala Asn Gln Trp Glu Pro Asp
        275                 280                 285

Val Pro Glu Val Glu Pro Tyr Arg Pro Ser Asp Gln Ala Ala Ile Ala
290                 295                 300

Gln Leu Ala Asp His Ala Pro Pro Glu Gln Tyr Gln Pro Leu Ala Thr
305                 310                 315                 320

Ser Lys Ala Met Ser Asp Val Met Thr Lys Leu Ala Leu Asp Pro Lys
                325                 330                 335

Ala Leu Ala Asp Tyr Lys Ala Asp His Arg Ala Phe Ala Gln Ser Val
            340                 345                 350

Pro Asp Leu Thr Pro Gln Glu Arg Ala Ala Leu Glu Leu Gly Asp Ser
        355                 360                 365

Trp Ala Ile Arg Cys Ala Met Lys Asn Met Pro Ser Ser Leu Leu Asp
370                 375                 380

Ala Ala Arg Glu Ser Gly Glu Glu Ala Ser Gln Asn Gly Phe Pro Trp
385                 390                 395                 400

Val Ile Val Val Gly Val Ile Gly Val Ile Gly Ser Val Met Ser Thr
                405                 410                 415

Glu

<210> SEQ ID NO 97
<211> LENGTH: 556
<212> TYPE: PRT

-continued

<213> ORGANISM: Phlebiopsis gigantea

<400> SEQUENCE: 97

```
Met Ser Ser Ala Ser Ser Asp Ser Asn Thr Gly Ser Leu Thr Ile Ala
1               5                   10                  15

Gly Ser Gly Ile Ala Ser Val Arg His Met Thr Leu Glu Thr Leu Ala
            20                  25                  30

His Val Gln Glu Ala Asp Ile Val Phe Tyr Val Val Ala Asp Pro Val
        35                  40                  45

Thr Glu Ala Tyr Ile Lys Lys Asn Ala Arg Gly Pro Cys Lys Asp Leu
    50                  55                  60

Glu Val Leu Phe Asp Lys Asp Lys Val Arg Tyr Asp Thr Tyr Val Gln
65                  70                  75                  80

Met Ala Glu Thr Met Leu Asn Ala Val Arg Glu Gly Gln Lys Val Leu
                85                  90                  95

Gly Ile Phe Tyr Gly His Pro Gly Val Phe Val Ser Pro Ser Arg Arg
            100                 105                 110

Ala Leu Ser Ile Ala Arg Lys Glu Gly Tyr Gln Ala Lys Met Leu Pro
        115                 120                 125

Gly Ile Ser Ser Glu Asp Tyr Met Phe Ala Asp Leu Glu Phe Asp Pro
    130                 135                 140

Ala Val His Gly Cys Cys Ala Tyr Glu Ala Thr Gln Leu Leu Leu Arg
145                 150                 155                 160

Glu Val Ser Leu Asp Thr Ala Met Ser Asn Ile Ile Trp Gln Val Gly
                165                 170                 175

Gly Val Gly Val Ser Lys Ile Asp Phe Glu Asn Ser Lys Val Lys Leu
            180                 185                 190

Leu Val Asp Arg Leu Glu Lys Asp Phe Gly Pro Asp His His Val Val
        195                 200                 205

His Tyr Ile Gly Ala Val Leu Pro Gln Ser Ala Thr Val Gln Asp Val
    210                 215                 220

Leu Lys Ile Ser Asp Leu Arg Lys Glu Glu Ile Val Ala Gln Phe Asn
225                 230                 235                 240

Ser Cys Ser Thr Leu Tyr Val Pro Pro Leu Thr His Ala Asn Lys Phe
                245                 250                 255

Ser Gly Asn Met Val Lys Gln Leu Phe Gly Gln Asp Val Thr Glu Val
            260                 265                 270

Ser Ser Ala Leu Cys Pro Thr Pro Lys Trp Ala Ala Gly Ser His Leu
        275                 280                 285

Gly Asp Val Val Glu Tyr Gly Pro Arg Glu Lys Ala Ala Val Asp Ala
    290                 295                 300

Leu Val Glu His Thr Val Pro Ala Asp Tyr Arg Val Leu Gly Gly Ser
305                 310                 315                 320

Leu Ala Phe Gln Gln Phe Met Ile Asp Leu Ala Leu Arg Pro Ala Ile
                325                 330                 335

Gln Ala Asn Tyr Lys Glu Asn Pro Arg Ala Leu Val Asp Ala Thr Lys
            340                 345                 350

Gly Leu Thr Thr Val Glu Gln Ala Ala Leu Leu Leu Arg Gln Pro Gly
        355                 360                 365

Ala Val Phe Gly Val Met Lys Leu Arg Ala Ser Glu Val Ala Asn Glu
    370                 375                 380

Gln Gly His Pro Val Ala Pro Ser Leu Asp His Val Ala Phe Thr
385                 390                 395                 400
```

```
Ala Pro Ser Pro Ala Ser Leu Asp His Val Ala Phe Ser Ala Pro Asn
                405                 410                 415
Pro Ala Ser Leu Asp His Val Ala Phe Ile Ala Pro Thr Pro Ala Ser
            420                 425                 430
Leu Asp His Val Ala Phe Ser Ala Pro Thr Pro Ala Ser Leu Asp His
        435                 440                 445
Val Ser Phe Gly Thr Pro Thr Ser Ala Ser Leu Asp His Val Ala Phe
    450                 455                 460
Glu Ala Pro Val Pro Ala Ser Leu Asp His Val Ala Phe Ala Ala Pro
465                 470                 475                 480
Val Pro Ala Ser Leu Asp His Val Ala Phe Ala Ala Pro Thr Pro Ala
                485                 490                 495
Ser Leu Asp His Val Ala Phe Ala Ala Pro Thr Pro Ala Ser Leu Asp
            500                 505                 510
His Val Ala Phe Ala Val Pro Val Pro Ala Ser Leu Asp His Ile Ala
        515                 520                 525
Phe Ser Val Pro Thr Pro Ala Ser Leu Asp His Val Ala Phe Ala Val
    530                 535                 540
Pro Val Pro Asp His Val Ala Gly Ile Pro Cys Met
545                 550                 555

<210> SEQ ID NO 98
<211> LENGTH: 413
<212> TYPE: PRT
<213> ORGANISM: Phlebiopsis gigantea

<400> SEQUENCE: 98

Met Ser His Asp Ala Thr Thr Thr Lys Arg Gly Ser Leu Thr Ile Ala
1               5                   10                  15
Gly Ser Gly Ile Ala Ser Val Ala His Ile Thr Leu Glu Thr Val Ala
                20                  25                  30
Tyr Leu Ala Glu Ala Asp Ser Val Phe Tyr Ile Val Ala Asp Pro Val
            35                  40                  45
Thr Glu Ala Phe Ile His Lys Asn Ala Lys Val Pro Cys Gln Asp Leu
        50                  55                  60
His Val Phe Tyr Asp Lys Asp Lys Ser Arg Tyr Asp Thr Tyr Val Gln
65                  70                  75                  80
Met Ala Glu Thr Met Leu Asn Ser Val Arg Ala Gly Glu Lys Val Leu
                85                  90                  95
Gly Ile Phe Tyr Gly His Pro Gly Val Phe Val Ser Pro Ser Arg Arg
                100                 105                 110
Ala Leu Ala Ile Ala Arg Glu Glu Gly Tyr Glu Ala Lys Met Leu Pro
            115                 120                 125
Gly Val Ser Ala Glu Asp Tyr Met Phe Ala Asp Leu Glu Phe Asp Pro
        130                 135                 140
Ala Thr His Gly Cys Cys Ala Tyr Glu Ala Thr His Ile Leu Leu Lys
145                 150                 155                 160
Asn Ile Pro Leu Asp Thr Ser Ile Asn Asn Ile Ile Trp Gln Val Gly
                165                 170                 175
Gly Val Gly Val Thr Lys Ile Asp Phe Glu Asn Ser Lys Phe Lys Phe
                180                 185                 190
Leu Val Asp Arg Leu Glu Lys Asp Phe Gly Leu Asp His Lys Val Val
            195                 200                 205
His Tyr Ile Gly Ala Val Leu Pro Gln Ser Ala Thr Val Lys Glu Val
        210                 215                 220
```

```
Tyr Thr Ile Ser Asp Leu Arg Lys Pro Glu Val Ala Thr Gln Phe Asn
225                 230                 235                 240

Ala Cys Ser Thr Leu Tyr Val Pro Pro Arg Lys Gly Ala Ala Asp Pro
                245                 250                 255

Phe Pro Ala His Val Val Glu Gln Leu Leu Gly Thr Thr Thr Ser Lys
            260                 265                 270

Val Val Asp Ala Leu Tyr Pro Val Ala Gln Trp Asp Leu Gly Asn Asn
        275                 280                 285

Leu Pro Ala Val Pro Ala Tyr Gly Pro Tyr Glu Gln Lys Val Val Ala
    290                 295                 300

Ala Met Gly Asp His Thr Thr Pro Asp Asp Tyr Arg Ala Leu Ala Gly
305                 310                 315                 320

Ser Pro Ala Met Gln Gln Phe Met Ala Glu Leu Ala Leu Arg Pro Thr
                325                 330                 335

Leu Gln Ala Lys Tyr Arg Ala Ser Pro Gln Ala Val Val Asp Ala Thr
            340                 345                 350

Pro Gly Leu Thr Asp Leu Glu Arg Ala Ala Leu Leu Leu Asn Ala Ala
        355                 360                 365

Gly Pro Val Leu Ala Val Met Lys Pro Arg Ala Gly Glu Val Met Thr
370                 375                 380

Val Asp Lys Leu Lys Glu Ser Val Thr Pro Ser Ala Ala Tyr Leu Phe
385                 390                 395                 400

Ile Phe Ile Val Ile Ala Ala Ala Ala His Ile Leu Val
                405                 410

<210> SEQ ID NO 99
<211> LENGTH: 431
<212> TYPE: PRT
<213> ORGANISM: Pseudocercospora musae

<400> SEQUENCE: 99

Met Ala Ser Thr Val Trp Ser Tyr Phe Asp Gln Leu Thr Arg Asp Asp
1               5                   10                  15

Asp Phe Gly Ser Cys Glu Asp Ala Cys Ser Lys Gln Gly Glu Leu Val
            20                  25                  30

Val Val Gly Thr Gly Ile Ala Ser Leu Arg Gln Met Thr Val Glu Ala
        35                  40                  45

Leu Asp Tyr Ile Gln Arg Ala Asp Met Val Phe Tyr Val Val Leu Asp
    50                  55                  60

Ala Met Thr Glu Ala Phe Ile Gln Thr His Ala Lys Lys His His Asp
65                  70                  75                  80

Leu Tyr Gln Tyr Tyr Asp Lys Asn Lys Pro Arg Ser Ala Ser Tyr Ile
                85                  90                  95

Gln Met Ala Glu Leu Met Val Gln Ser Val Arg Asp Gly Asn Leu Thr
            100                 105                 110

Val Ala Val Tyr Tyr Gly His Pro Gly Val Phe Val Phe Pro Thr His
        115                 120                 125

Arg Ala Ile His Ile Ala Arg Glu Glu Gly Phe Lys Ala Lys Met Leu
    130                 135                 140

Pro Gly Val Ser Ala Glu Asp Cys Leu Tyr Ala Asp Leu Gly Ile Asp
145                 150                 155                 160

Pro Gly Ser Thr Gly Cys Ser Met Phe Glu Ala Thr Tyr Leu Leu Asn
                165                 170                 175

Glu Pro Asp Arg Leu Asp Pro Arg Asn His Val Ile Ile Trp Gln Pro
```

```
              180                 185                 190
Gly Cys Val Gly Lys Ser Ala Met Val Phe Asp Asn Ser Glu Ile His
            195                 200                 205
Glu Leu Ala Asp Tyr Leu Glu Lys Thr Tyr Gly Ala Glu Tyr Pro Val
        210                 215                 220
Ile Ala Tyr Leu Ala Ala Val Arg Pro Phe Asn Asp Pro Gln Ile Asp
225                 230                 235                 240
Lys Leu Met Val Lys Asp Leu Arg Asp Leu Glu Lys Leu Arg Ala Ile
                245                 250                 255
Pro Phe Asn Ala Ala Thr Thr Leu Tyr Ile Pro Pro Lys Thr Leu Pro
            260                 265                 270
Ala Val Pro Gln Asp Ile Ala Asn Pro Ile Glu Val Gln Leu Ala Arg
        275                 280                 285
Asn Ser Ala Phe Arg Leu Ser His Pro Glu Met Asn Leu Val Asp Met
    290                 295                 300
Tyr Thr Lys Gln Asp Lys Gln Trp Cys Asp Asp Leu Lys His Phe Val
305                 310                 315                 320
Pro Pro Asn Asp Tyr Lys Pro Met Thr Ala Thr Pro Ala Met Arg Arg
                325                 330                 335
Leu Ala Ile Lys Leu Ala Leu Leu His His Arg Leu His Gly Ala Leu
            340                 345                 350
Pro Thr Glu Leu Ile Ala Ser Lys Ala Leu Ser Lys Ser Glu Leu Ser
        355                 360                 365
Ser Ser Glu Ala Glu Ser Leu Arg Leu Met Ile Lys Asn Leu Asp Leu
    370                 375                 380
Phe Leu Arg Glu Gly Val Glu Arg Pro Pro Ala Val Asn Gly Val Ser
385                 390                 395                 400
Val Ile Val Phe Ala Leu Leu Ile Ile Arg Ser Glu Asp Gln Arg Val
                405                 410                 415
Gly Phe Asp Gly Lys Met Glu Trp Lys Arg Ser Val Val Val Asn
            420                 425                 430

<210> SEQ ID NO 100
<211> LENGTH: 405
<212> TYPE: PRT
<213> ORGANISM: Porodaedalea chrysoloma

<400> SEQUENCE: 100

Met Pro Val Ser Thr Thr Thr Lys Asn Gly Thr Leu Val Ile Ala
1               5                   10                  15
Gly Ser Gly Ile Ala Ser Ile Ala His Ile Thr Leu Glu Thr Leu Ser
                20                  25                  30
His Ile Lys Glu Ser Asp Arg Val Tyr Tyr Ile Val Gly Asp Pro Ala
            35                  40                  45
Thr Glu Ala Phe Ile Gln Asp Asn Ala Ser Gly Thr Cys Phe Asp Leu
        50                  55                  60
Thr Ile Phe Tyr Asp Thr Asn Lys Val Arg Tyr Asp Ser Tyr Val Gln
65                  70                  75                  80
Met Cys Glu Val Met Leu Arg Asp Val Arg Ala Gly His Thr Val Leu
                85                  90                  95
Gly Val Phe Tyr Gly His Pro Gly Val Phe Val Ser Pro Ser His Arg
                100                 105                 110
Ala Ile Ala Ile Ala Arg Asp Glu Gly Tyr Lys Ala Arg Met Leu Pro
            115                 120                 125
```

```
Gly Val Ser Ala Glu Asp Tyr Leu Phe Ala Asp Leu Gly Phe Asp Pro
    130                 135                 140

Ala Thr His Gly Cys Thr Ser Tyr Glu Ala Thr Asp Leu Leu Val Arg
145                 150                 155                 160

Asn Lys Pro Leu Asn Ala Ser Thr His Asn Ile Ile Trp Gln Val Gly
                165                 170                 175

Gly Val Gly Val Gly Thr Met Val Phe Asp Asn Ala Lys Phe His Leu
                180                 185                 190

Leu Val Asp Arg Leu Glu Lys Asp Phe Gly Pro Ser His Thr Val Val
        195                 200                 205

His Tyr Ile Gly Ala Val Leu Pro Gln Ser Ile Thr Thr Met Asp Lys
    210                 215                 220

Leu Thr Ile Ala Asp Leu Arg Lys Asp Ala Val Val Lys Gln Phe Asn
225                 230                 235                 240

Pro Thr Ser Thr Phe Tyr Ile Pro Pro Arg Asp Ile Ser Leu Pro Leu
                245                 250                 255

Asp Thr Met Ala Lys Lys Leu Gly Met Asp Asp Ala Ser Ala Arg Pro
                260                 265                 270

Val Ser Leu Tyr Pro Pro Ser Arg Trp Thr Gly Thr Lys Phe Thr Thr
        275                 280                 285

Ala Pro Ala Tyr Gly Pro Arg Glu Lys Asp Val Ile Ala Lys Ile Asp
290                 295                 300

Thr Tyr Ala Ala Pro Lys Asp His Lys Ile Leu His Ala Ser Arg Ser
305                 310                 315                 320

Met Lys Lys Leu Met Thr Asp Leu Ala Leu Asn Pro Lys Leu Leu Glu
                325                 330                 335

Lys Tyr Arg Ala Asn Thr Lys Ala Val Val Glu Ala Thr Glu Gly Leu
                340                 345                 350

Ser Ala Gln Glu Lys Ala Ala Leu Asn Met Asp Leu Ala Gly Pro Val
        355                 360                 365

His Ala Val Met Lys Ala Thr Pro Ser Asp Ile Thr Asp Gly Arg Glu
    370                 375                 380

Met Ser Val Asp Ala Val Ala Ser Ala Thr Glu Pro Ser Ala Ala Leu
385                 390                 395                 400

Ile Leu Leu Leu Val
                405

<210> SEQ ID NO 101
<211> LENGTH: 420
<212> TYPE: PRT
<213> ORGANISM: Rhizopogon vinicolor

<400> SEQUENCE: 101

Met Ile Thr Ser Asn Ser Ser Asn Gly Ser Asn Ser Thr Lys Cys Gly
1               5                   10                  15

Thr Leu Thr Ile Ala Gly Ser Gly Ile Ala Ser Val Ala His Ile Thr
                20                  25                  30

Leu Glu Thr Leu Ser Tyr Ile Lys Glu Ser Glu Lys Ile Phe Tyr Leu
            35                  40                  45

Val Cys Asp Pro Val Thr Glu Ala Tyr Ile Gln Asp Asn Thr Thr Ala
        50                  55                  60

Asp Cys Phe Asp Leu Ser Val Phe Tyr Gly Lys Asn Lys Gly Arg His
65                  70                  75                  80

Asp Ser Tyr Ile Gln Met Cys Glu Val Met Leu Lys Ala Val Arg Ala
                85                  90                  95
```

```
Gly His Asp Val Leu Gly Val Phe Tyr Gly His Pro Gly Val Phe Val
            100                 105                 110

Ser Pro Ser His Arg Ala Ile Ala Val Ala Arg Gln Glu Gly Tyr Lys
            115                 120                 125

Ala Lys Met Leu Pro Gly Ile Ser Ala Glu Asp Tyr Met Phe Ala Asp
            130                 135                 140

Leu Glu Phe Asp Pro Ser Leu Ser Gly Cys Lys Thr Cys Glu Ala Thr
145                 150                 155                 160

Glu Ile Leu Leu Arg Asp Lys Pro Leu Asp Pro Ser Ile Gln Asn Ile
                165                 170                 175

Ile Trp Gln Val Gly Ser Val Gly Val Val Asp Met Glu Phe Glu Lys
            180                 185                 190

Ser Lys Phe Gln Leu Leu Val Asp Arg Leu Glu Lys Asp Phe Gly Pro
            195                 200                 205

Gly His Lys Val Val His Tyr Ile Gly Ala Val Leu Pro Gln Ser Thr
            210                 215                 220

Thr Thr Met Asp Thr Phe Thr Ile Ala Asp Leu Arg Lys Glu Asp Val
225                 230                 235                 240

Ala Lys Gln Phe Gly Thr Ile Ser Thr Leu Tyr Val Pro Pro Arg Asp
                245                 250                 255

Glu Gly His Val Asn Pro Ser Met Ala Glu Ala Phe Gly Thr Pro Ala
            260                 265                 270

Gly Pro Ala Arg Leu Asn Asp Ser Val Lys Trp Val Gly Pro Lys Leu
            275                 280                 285

Ser Ile Val Ser Ala Asn Gly Pro His Gln Arg Asp Val Ile Ala Gln
            290                 295                 300

Ile Asp Thr His Ile Ala Pro Glu Gly His Lys Lys Leu His Ala Ser
305                 310                 315                 320

Ala Ala Met Lys Lys Phe Met Thr Asp Leu Ala Leu Arg Pro Lys Phe
                325                 330                 335

Leu Asp Glu Tyr Lys Leu Asn Pro Val Ala Val Glu Ser Ala Gln
            340                 345                 350

Gly Leu Ser Asn Leu Glu Gln Phe Gly Leu Lys Phe Ala Arg Gly Gly
            355                 360                 365

Pro Val Asp Ala Leu Met Lys Ala Thr Glu Ser Asp Ile Ala Ser Gly
            370                 375                 380

Arg Gln Leu Thr Glu Glu Ile Ala Lys Gly Asn Gly Pro Pro Gly
385                 390                 395                 400

Ala Ala Ala Thr Val Leu Leu Leu Gly Ala Leu Ile Ile Thr Leu Ser
                405                 410                 415

Leu Asn Phe Ser
            420

<210> SEQ ID NO 102
<211> LENGTH: 413
<212> TYPE: PRT
<213> ORGANISM: Rhizopogon vinicolor

<400> SEQUENCE: 102

Met Ser Thr Lys Arg Gly Thr Leu Thr Ile Ala Gly Ser Gly Ile Ala
1               5                   10                  15

Ser Val Gly His Ile Thr Leu Gly Thr Leu Ser Tyr Ile Lys Glu Ser
            20                  25                  30

Asp Lys Ile Phe Tyr Leu Val Cys Asp Pro Val Thr Glu Ala Phe Ile
```

```
            35                  40                  45
Tyr Asp Asn Ser Thr Ala Asp Cys Phe Asp Leu Ser Val Phe Tyr Asp
 50                  55                  60

Lys Thr Lys Gly Arg Tyr Asp Ser Tyr Ile Gln Met Cys Glu Val Met
 65                  70                  75                  80

Leu Lys Ala Val Arg Ala Gly His Asp Val Leu Gly Val Phe Tyr Gly
                 85                  90                  95

His Pro Gly Val Phe Val Ser Pro Ser His Arg Ala Ile Ala Val Ala
            100                 105                 110

Arg Gln Glu Gly Tyr Lys Ala Lys Met Leu Pro Gly Ile Ser Ala Glu
        115                 120                 125

Asp Tyr Met Phe Ala Asp Leu Glu Phe Asp Pro Ser Val Ser Gly Cys
    130                 135                 140

Lys Thr Cys Glu Ala Thr Glu Ile Leu Leu Arg Asp Lys Pro Leu Asp
145                 150                 155                 160

Pro Thr Ile Gln Asn Ile Ile Trp Gln Val Gly Ser Val Gly Val Val
                165                 170                 175

Asp Met Glu Phe Ser Lys Ser Lys Phe Gln Leu Leu Val Asp Arg Leu
            180                 185                 190

Glu Lys Asp Phe Gly Pro Asp His Lys Val Val His Tyr Ile Gly Ala
        195                 200                 205

Val Leu Pro Gln Ser Thr Thr Thr Met Asp Thr Phe Thr Ile Ala Asp
    210                 215                 220

Leu Arg Lys Glu Asp Val Ala Lys Gln Phe Gly Thr Ile Ser Thr Leu
225                 230                 235                 240

Tyr Ile Pro Pro Arg Asp Glu Gly His Val Asn Leu Ser Met Ala Lys
                245                 250                 255

Val Phe Gly Gly Pro Gly Ala Ser Val Lys Leu Asn Asp Ser Ile Lys
            260                 265                 270

Trp Ala Gly Pro Lys Leu Asn Ile Val Ser Ala Asn Asp Pro His Glu
        275                 280                 285

Arg Asp Val Ile Ala Gln Val Asp Thr His Val Ala Pro Glu Gly His
    290                 295                 300

Lys Lys Leu Arg Val Ser Ala Ala Met Lys Lys Phe Met Thr Asp Leu
305                 310                 315                 320

Ala Leu Lys Pro Lys Phe Leu Glu Glu Tyr Lys Leu Asp Pro Val Ala
                325                 330                 335

Val Val Glu Ser Ala Glu Gly Leu Ser Asn Leu Glu Arg Phe Gly Leu
            340                 345                 350

Lys Phe Ala Arg Ser Gly Pro Ala Asp Ala Leu Met Lys Ala Thr Glu
        355                 360                 365

Ser Asp Ile Ala Ser Gly Arg Gln Leu Thr Glu Glu Ile Ala Gln
    370                 375                 380

Gly Thr Gly Pro Val Gly Leu Gln Thr Ala Leu Ala Leu Leu Val Leu
385                 390                 395                 400

Leu Gly Leu Gly Val Ala Ile Val Thr Arg Pro Asp Asp
                405                 410
```

<210> SEQ ID NO 103
<211> LENGTH: 412
<212> TYPE: PRT
<213> ORGANISM: Rhizopogon vinicolor

<400> SEQUENCE: 103

```
Met Thr Thr Ser Asn Ser Ser Asn Gly Thr Lys Arg Gly Thr Leu Thr
1               5                   10                  15

Ile Ala Gly Ser Gly Ile Ala Ser Val Gly His Ile Thr Leu Gly Thr
                20                  25                  30

Leu Ser Tyr Ile Lys Glu Ser Asp Lys Ile Phe Tyr Leu Val Cys Asp
            35                  40                  45

Pro Val Thr Glu Ala Phe Ile His Asp Asn Ser Thr Ala Asp Cys Phe
50                      55                  60

Asp Leu Ser Val Phe Tyr Asp Lys Asn Lys Gly Arg Tyr Asp Ser Tyr
65                  70                  75                  80

Ile Gln Met Cys Glu Val Met Leu Lys Asp Val Arg Ala Gly His His
                85                  90                  95

Val Leu Gly Val Phe Tyr Gly His Pro Gly Val Phe Val Ser Pro Ser
                100                 105                 110

His Arg Ala Ile Ala Val Ala Arg Gln Glu Gly Tyr Asn Ala Lys Met
            115                 120                 125

Leu Pro Gly Ile Ser Ala Glu Asp Tyr Met Phe Ala Asp Leu Glu Phe
    130                 135                 140

Asp Pro Ser Leu Tyr Gly Cys Lys Thr Cys Glu Ala Thr Glu Ile Leu
145                 150                 155                 160

Leu Arg Asp Lys Pro Leu Asp Pro Ser Ile His Asn Ile Ile Trp Gln
                165                 170                 175

Val Gly Ser Val Gly Val Val Asp Met Glu Phe Ser Lys Ser Lys Phe
                180                 185                 190

His Leu Leu Val Asp Arg Leu Glu Lys Asp Phe Gly Leu Glu His Lys
            195                 200                 205

Val Val His Tyr Ile Gly Ala Val Leu Pro Gln Ser Ala Thr Thr Met
    210                 215                 220

Asp Thr Phe Thr Ile Ala Asp Leu Arg Lys Glu Asp Val Ala Lys Gln
225                 230                 235                 240

Phe Gly Thr Ile Ser Thr Leu Tyr Ile Pro Pro Arg Asp Glu Arg Pro
                245                 250                 255

Phe Asn Pro Arg Met Ala Glu Ala Phe Gly Ser Pro Ala Ala Pro Ala
            260                 265                 270

Met Pro Ile Ser Ser Val Lys Trp Ala Gly Pro Lys Leu Asn Ile Pro
    275                 280                 285

Pro Val Tyr Gly Pro His Glu Arg Asp Val Ile Ala Gln Ile Asp Thr
    290                 295                 300

His Val Ala Pro Glu Gly His Lys Lys Leu His Thr Ser Ala Ala Met
305                 310                 315                 320

Lys Lys Phe Met Thr Asp Leu Ala Met Lys Pro Lys Leu Leu Glu Glu
            325                 330                 335

Tyr Lys Arg Asp Pro Val Ala Val Val Glu Ala Ala Glu Ala Leu Ser
            340                 345                 350

Asp Leu Glu Lys Phe Gly Leu Lys Phe Ala Arg Val Gly Pro Ala Asp
    355                 360                 365

Val Leu Met Lys Ala Thr Glu Ser Asp Ile Ala Ser Gly Arg Gln Leu
    370                 375                 380

Thr Glu Glu Glu Ile Ala Lys Ala Asn Gly Pro Gln Gly Leu Gly Thr
385                 390                 395                 400

Ile Ile Leu Val Trp His Thr Val His Gly Ile Ala
                405                 410
```

```
<210> SEQ ID NO 104
<211> LENGTH: 411
<212> TYPE: PRT
<213> ORGANISM: Rhizopogon vinicolor

<400> SEQUENCE: 104

Met Thr Thr Asp Ile Lys Arg Gly Thr Leu Thr Ile Ala Gly Ser Gly
1               5                   10                  15

Ile Ala Cys Ile Ala His Ile Thr Leu Glu Thr Leu Ser Tyr Ile Lys
                20                  25                  30

Glu Ser Asp Lys Leu Phe Tyr Leu Val Cys Asp Pro Val Thr Glu Ala
            35                  40                  45

Phe Ile Gln Asp Asn Ala Thr Gly Gly Cys Phe Asp Leu Ser Val Phe
    50                  55                  60

Tyr Asp Lys Asn Lys Ser Arg Tyr Asp Ser Tyr Ile Gln Met Cys Glu
65                  70                  75                  80

Val Met Leu Lys Ala Val Arg Val Gly Tyr Asp Val Leu Gly Val Phe
                85                  90                  95

Tyr Gly His Pro Gly Val Phe Val Ser Pro Ser His Arg Ala Ile Ala
                100                 105                 110

Val Ala Arg Glu Glu Gly Tyr Lys Ala Arg Met Leu Pro Gly Ile Ser
            115                 120                 125

Ala Glu Asp Tyr Leu Phe Ala Asp Leu Glu Phe Asp Pro Ser Leu His
    130                 135                 140

Gly Cys Asn Thr Tyr Glu Ala Thr Glu Leu Leu Leu Arg Gly Lys Pro
145                 150                 155                 160

Leu Asp Pro Leu Ile His Asn Ile Ile Trp Gln Val Gly Ser Val Gly
                165                 170                 175

Val Ile Asp Met Glu Phe Glu Lys Ser Lys Phe His Leu Leu Val Asp
                180                 185                 190

Arg Leu Glu Asn Asp Phe Gly Pro Asp His Lys Val Val His Tyr Ile
            195                 200                 205

Gly Ala Val Leu Pro Gln Ser Thr Thr Thr Met Asp Thr Phe Thr Ile
    210                 215                 220

Ser Asp Leu Arg Lys Glu Asp Val Ala Lys Gln Phe Gly Thr Ile Ser
225                 230                 235                 240

Thr Leu Tyr Val Pro Leu Arg Asp Glu Ala Leu Val Asn Pro Ile Met
                245                 250                 255

Ala Glu Ala Phe Gly Arg Thr Ala Ala Pro Val Thr Met Asn Ser Ser
                260                 265                 270

Val Lys Trp Ala Gly Pro Lys Leu Asn Ile Val Ser Ala Tyr Gly Pro
            275                 280                 285

His Glu Arg Ser Val Ile Ala Gln Ile Asp Thr His Val Ala Pro Glu
    290                 295                 300

Gly His Lys Lys Leu His Thr Ser Thr Ala Met Asn Lys Phe Met Thr
305                 310                 315                 320

Asp Leu Ala Leu Lys Pro Lys Phe Leu Glu Glu Tyr Lys Leu Asp Pro
                325                 330                 335

Ala Ala Val Val Glu Ser Ala Glu Gly Leu Ser Asn Met Glu Lys Phe
                340                 345                 350

Gly Leu Lys Val Ala Lys Ala Gly Ala Ala His Ile Leu Met Lys Ala
            355                 360                 365

Thr Glu Ser Asp Ile Ala Ser Gly Arg Gln Leu Thr Glu Asp Glu Ile
    370                 375                 380
```

```
Ala Arg Ala Asp Gly Pro Glu Gly Leu Ala Val Val Ile Val Leu
385                 390                 395                 400

Val Ala Thr Val Ala Leu Leu Ala Leu Leu Val
            405                 410

<210> SEQ ID NO 105
<211> LENGTH: 415
<212> TYPE: PRT
<213> ORGANISM: Rhizopogon vinicolor

<400> SEQUENCE: 105

Met Thr Thr Gly Thr Glu Arg Gly Thr Leu Thr Ile Ala Gly Ser Gly
1               5                   10                  15

Ile Ala Cys Val Ala His Ile Thr Leu Glu Thr Leu Ser Tyr Ile Lys
            20                  25                  30

Glu Ser Asp Lys Leu Phe Tyr Leu Val Cys Asp Pro Val Thr Glu Ala
        35                  40                  45

Phe Ile Gln Asp Asn Ala Thr Gly Asp Cys Phe Asp Leu Ser Val Phe
    50                  55                  60

Tyr Asp Lys Asn Lys Ser Arg Tyr Asp Ser Tyr Ile Gln Met Cys Glu
65                  70                  75                  80

Val Met Leu Lys Ala Val Arg Ala Gly His Val Leu Gly Val Phe
                85                  90                  95

Tyr Gly His Pro Gly Val Leu Val Ser Pro Ser Tyr Arg Ala Ile Ala
            100                 105                 110

Val Ala Arg Glu Glu Gly Tyr Lys Ala Arg Met Leu Pro Gly Ile Ser
        115                 120                 125

Ala Glu Asp Tyr Leu Phe Ala Asp Leu Glu Phe Asp Pro Cys Phe Pro
    130                 135                 140

Ser Gly Cys Asn Thr Tyr Glu Ala Thr Glu Leu Leu Leu Arg Asp Arg
145                 150                 155                 160

Ser Leu Asp Pro Ser Ile His Asn Ile Ile Trp Gln Val Gly Ser Val
                165                 170                 175

Gly Val Thr Asp Met Glu Phe Glu Lys Ser Lys Leu Asn Leu Leu Val
            180                 185                 190

Asp Arg Leu Glu Asn Asp Phe Gly Pro Asp His Lys Val Val His Tyr
        195                 200                 205

Ile Gly Ala Val Leu Pro Gln Ser Thr Thr Thr Met Asp Thr Phe Ala
    210                 215                 220

Val Ser Asp Leu His Lys Glu Asp Val Ala Lys Gln Phe Gly Thr Ile
225                 230                 235                 240

Ser Thr Leu Tyr Ile Pro Pro Arg Asp Glu Ala Pro Val Ser Ser Asn
                245                 250                 255

Met Met Glu Val Leu Asn Arg Pro Val Pro Asn Met Pro Pro
            260                 265                 270

Ser Val Met Trp Val Ala Pro Lys Leu Asn Ile Ser Ser Ala Tyr Thr
        275                 280                 285

Pro His Glu Arg Asp Val Ile Ala Gln Ile Asp Thr His Val Ala Pro
    290                 295                 300

Glu Gly Tyr Lys Lys Leu His Thr Ser Ala Ala Met Lys Lys Phe Met
305                 310                 315                 320

Thr Asp Leu Ala Leu Lys Pro Lys Phe Val Glu Glu Tyr Met Leu Asp
                325                 330                 335

Pro Val Ala Val Ile Glu Ser Ala Glu Gly Leu Ser Asp Val Glu Lys
            340                 345                 350
```

-continued

```
Phe Ala Leu Lys Val Ala Lys Gly Gly Ala Ala Asn Ile Leu Met Lys
            355                 360                 365

Ala Thr Glu Ser Glu Ile Ala Ser Gly Arg His Leu Thr Glu Asp Glu
370                 375                 380

Ile Ser Asn Ala Val Gly Pro Leu Gly Leu Ser Ala Thr Val Val Leu
385                 390                 395                 400

Val Val Ala Glu Ala Val Val Ile Met Ala Met Ala Val Leu Val
                405                 410                 415

<210> SEQ ID NO 106
<211> LENGTH: 411
<212> TYPE: PRT
<213> ORGANISM: Rhizopogon vinicolor

<400> SEQUENCE: 106

Met Thr Thr Gly Thr Glu Arg Gly Thr Leu Thr Ile Ala Gly Ser Gly
1               5                   10                  15

Ile Ala Cys Val Ala His Ile Thr Leu Gln Met Leu Ser Tyr Ile Lys
            20                  25                  30

Glu Ser Asp Lys Leu Phe Tyr Leu Val Cys Asp Pro Val Thr Glu Ala
        35                  40                  45

Phe Ile Gln Asp Asn Ala Thr Gly Asp Cys Phe Asp Leu Ser Val Phe
    50                  55                  60

Tyr Asp Lys Asn Lys Ser Arg His Asp Ser Tyr Ile Gln Met Cys Glu
65                  70                  75                  80

Ile Met Leu Arg Ala Val Arg Ala Asp His His Val Leu Gly Val Phe
                85                  90                  95

Tyr Gly His Pro Gly Ile Phe Val Ser Pro Ser Tyr Arg Ala Met Ala
            100                 105                 110

Val Ala Arg Glu Glu Gly Tyr Lys Ala Lys Met Leu Pro Gly Ile Ser
        115                 120                 125

Thr Glu Asp Tyr Leu Phe Ala Asp Leu Glu Phe Asp Pro Cys Leu Pro
    130                 135                 140

Gly Cys Asn Thr Tyr Glu Ala Thr Glu Leu Leu Leu Arg Asp Arg Ser
145                 150                 155                 160

Leu Asp Pro Ser Ile His Asn Ile Ile Trp Gln Val Gly Ser Val Gly
                165                 170                 175

Val Ile Asp Ile Gln Phe Glu Lys Ser Lys Phe His Leu Leu Val Asp
            180                 185                 190

Arg Leu Glu Lys Asp Phe Gly Pro Asp His Lys Val Val His Tyr Ile
        195                 200                 205

Gly Ala Val Leu Pro Gln Ser Thr Thr Thr Met Asp Thr Phe Thr Ile
    210                 215                 220

Ser Asp Leu Arg Lys Glu Asp Val Ala Lys Gln Phe Gly Thr Ile Ser
225                 230                 235                 240

Thr Leu Tyr Ile Pro Pro Arg Asp Lys Pro Leu Ala His Pro Gly Met
                245                 250                 255

Ala Glu Ala Ile Gly Ser Leu Thr Ala Pro Ala Lys Leu Tyr Ser Pro
            260                 265                 270

Val Lys Trp Ala Gly Pro Lys Leu Asn Ile Val Ser Pro Tyr Ser Pro
        275                 280                 285

Tyr Glu Arg Asp Val Ile Ala Arg Ile Asp Thr His Val Ala Pro Glu
    290                 295                 300

Gly His Lys Lys Leu Tyr Thr Ser Ala Ala Met Lys Lys Phe Met Thr
```

```
            305                 310                 315                 320
Asp Leu Ala Leu Lys Pro Lys Leu Leu Glu Glu Tyr Met Leu Asp Pro
                325                 330                 335

Val Ala Val Val Glu Ser Ala Asp Gly Leu Ser Asp Val Glu Lys Phe
                340                 345                 350

Gly Leu Lys Leu Ala Lys Asp Gly Val Ala Asn Ile Leu Met Met Ala
                355                 360                 365

Thr Glu Ser Asp Ile Ala Ser Gly Arg His Leu Ala Glu Asp Glu Ile
                370                 375                 380

Ala Lys Ala Lys Gly Pro Leu Gly Leu Leu Thr Val Val Leu Val Ile
385                 390                 395                 400

Val Gly Ser Ser Leu Val Val His Arg Leu Thr
                405                 410

<210> SEQ ID NO 107
<211> LENGTH: 415
<212> TYPE: PRT
<213> ORGANISM: Rhizopogon vinicolor

<400> SEQUENCE: 107

Met Thr Thr Ser Asn Ser Ser Asp Gly Thr Lys Arg Gly Thr Leu Thr
1               5                   10                  15

Ile Ala Gly Ser Gly Ile Ala Ser Val Gly His Ile Thr Leu Gly Thr
                20                  25                  30

Leu Ser Tyr Ile Lys Glu Ser Asp Lys Ile Phe Tyr Leu Val Cys Asp
                35                  40                  45

Pro Val Thr Glu Ala Phe Ile His Asp Asn Ser Thr Ala Asp Cys Phe
                50                  55                  60

Asp Leu Ser Val Phe Tyr Asp Lys Asn Lys Gly Arg Tyr Asp Ser Tyr
65              70                  75                  80

Ile Gln Met Cys Glu Val Met Leu Lys Ala Val Arg Ala Gly His Asp
                85                  90                  95

Val Leu Gly Val Phe Tyr Gly His Pro Gly Val Phe Val Ser Pro Ser
                100                 105                 110

His Arg Ala Ile Ala Val Ala Arg Gln Glu Gly Tyr Lys Ala Lys Met
                115                 120                 125

Leu Pro Gly Ile Ser Ala Glu Asp Tyr Met Phe Ala Asp Leu Glu Phe
                130                 135                 140

Asp Pro Ser Leu Tyr Gly Cys Lys Thr Cys Glu Ala Thr Glu Ile Leu
145                 150                 155                 160

Leu Arg Asp Lys Pro Leu Asp Pro Thr Ile Gln Asn Ile Ile Trp Gln
                165                 170                 175

Val Gly Ser Val Gly Val Val Asp Met Glu Phe Ser Lys Ser Lys Phe
                180                 185                 190

His Leu Leu Val Asp Arg Leu Glu Lys Asp Phe Gly Pro Asp His Lys
                195                 200                 205

Val Val His Tyr Ile Gly Ala Val Leu Pro Gln Ser Ala Thr Ile Met
                210                 215                 220

Asp Thr Phe Thr Ile Ala Asp Leu Arg Lys Glu Asp Val Ala Lys Gln
225                 230                 235                 240

Phe Gly Thr Ile Ser Thr Leu Tyr Ile Pro Pro Arg Asp Glu Arg Pro
                245                 250                 255

Val His Ser Gly Met Ala Glu Ala Phe Gly Ser Pro Gly Ala Ala Val
                260                 265                 270
```

Lys Pro Asn Thr Ser Ile Lys Trp Ala Gly Pro Lys Leu Asn Ile Val
            275                 280                 285

Ser Ala Cys Gly Pro His Glu Pro Asp Val Ile Ala Gln Ile Asp Thr
        290                 295                 300

His Val Thr Pro Glu Gly Tyr Lys Lys Leu His Ala Ser Val Ser Met
305                 310                 315                 320

Lys Lys Phe Met Thr Asp Leu Ala Leu Lys Pro Lys Phe Leu Glu Glu
                325                 330                 335

Tyr Lys Leu Asp Pro Val Ala Val Glu Ala Ala Glu Gly Leu Ser
            340                 345                 350

Asp Leu Glu Lys Phe Gly Leu Lys Phe Ala Arg Asp Gly Pro Ala Asp
        355                 360                 365

Thr Leu Met Lys Ala Thr Glu Ser Asp Ile Ala Ser Gly Arg Gln Leu
            370                 375                 380

Thr Glu Glu Glu Val Ala Asn Gly Asn Gly Pro Leu Gly Leu Gln Thr
385                 390                 395                 400

Val Val Val Val Trp Leu Thr Thr Lys Ile Val Ser Pro Glu Leu
            405                 410                 415

<210> SEQ ID NO 108
<211> LENGTH: 410
<212> TYPE: PRT
<213> ORGANISM: Rhizopogon vinicolor

<400> SEQUENCE: 108

Met Thr Thr Asp Thr Lys Arg Gly Thr Leu Thr Ile Ala Gly Ser Gly
1               5                   10                  15

Ile Ala Ser Ile Ala His Ile Thr Leu Glu Thr Leu Ser Tyr Ile Lys
            20                  25                  30

Glu Ser Asp Lys Leu Phe Tyr Leu Val Cys Asp Pro Val Thr Glu Ala
        35                  40                  45

Phe Ile Gln Asp Asn Ala Thr Gly Asp Phe Phe Asp Leu Ser Val Phe
    50                  55                  60

Tyr Asp Lys Asn Lys Ser Arg Tyr Asp Ser Tyr Ile Gln Met Cys Glu
65                  70                  75                  80

Ile Met Leu Arg Ala Val Arg Ala Gly His Ser Val Leu Gly Ile Phe
                85                  90                  95

Tyr Gly His Pro Gly Val Phe Val Ser Pro Ser His Arg Ala Ile Ala
            100                 105                 110

Val Ala Arg Glu Glu Gly Tyr Lys Ala Arg Met Leu Pro Gly Val Ser
        115                 120                 125

Ala Glu Asp Tyr Met Phe Ala Asp Leu Glu Phe Asp Pro Ser Gln Ser
    130                 135                 140

Thr Cys Asn Thr Tyr Glu Ala Thr Glu Leu Leu Arg Asp Arg Pro
145                 150                 155                 160

Leu Asp Pro Ala Ile Gln Asn Ile Ile Trp Gln Val Gly Ser Val Gly
            165                 170                 175

Val Val Asp Met Glu Phe Glu Lys Ser Lys Phe His Leu Leu Val Asp
        180                 185                 190

Arg Leu Glu Gln Asp Phe Gly Pro Asp His Lys Val Val His Tyr Ile
    195                 200                 205

Gly Ala Val Leu Pro Gln Ser Thr Thr Thr Met Asp Ile Phe Thr Ile
210                 215                 220

Ser Asp Leu Arg Lys Glu Asn Val Ala Lys Gln Phe Gly Thr Ile Ser
225                 230                 235                 240

```
Thr Leu Tyr Ile Pro Pro Arg Asp Glu Gly Pro Val Ser Ser Ser Met
                245                 250                 255

Thr Gln Ala Phe Asp Phe Lys Ala Gly Ala Met Val Tyr Ser Pro Val
            260                 265                 270

Lys Trp Ala Gly Pro Lys Leu Asn Ile Val Ser Ala Leu Ser Pro Tyr
        275                 280                 285

Glu Arg Asp Val Ile Ser Gln Ile Asp Thr His Val Ala Pro Glu Gly
    290                 295                 300

Tyr Lys Ile Leu His Thr Ser Ala Ala Met Asn Lys Phe Met Thr Asp
305                 310                 315                 320

Leu Ser Leu Lys Pro Lys Phe Leu Glu Glu Tyr Lys Leu Tyr Pro Glu
                325                 330                 335

Ala Val Val Glu Ser Ala Glu Gly Leu Ser Asn Leu Glu Lys Phe Gly
            340                 345                 350

Leu Lys Phe Gly Ser Asp Gly Ala Val Tyr Ile Leu Met Lys Ala Thr
        355                 360                 365

Glu Ser Asp Ile Ala Ser Gly Arg Gln Leu Thr Glu Asp Glu Ile Ala
    370                 375                 380

Lys Ala His Lys Ser Val Gly Phe Pro Thr Val Leu Val Ile Leu Pro
385                 390                 395                 400

Thr Val Ile Val Val Leu Ile Gly Arg Glu
                405                 410

<210> SEQ ID NO 109
<211> LENGTH: 410
<212> TYPE: PRT
<213> ORGANISM: Sanghuangporus baumii

<400> SEQUENCE: 109

Met Ala Gly Ser Gln Lys Gly Thr Leu Thr Ile Ala Gly Ser Gly Ile
1               5                   10                  15

Ala Ser Ile Gly His Ile Thr Leu Glu Thr Leu Ser Tyr Ile Gln Glu
            20                  25                  30

Ala Asp Lys Ile His Tyr Ala Val Ala Asp Pro Ala Thr Glu Ala Phe
        35                  40                  45

Ile Leu Asp Lys Ser Lys Asp Ser Ser His Cys Phe Asp Leu Thr Val
    50                  55                  60

Tyr Tyr Asp Thr Asn Lys Met Arg Tyr Glu Thr Tyr Val Gln Met Cys
65                  70                  75                  80

Glu Val Met Leu Arg Asp Val Arg Gly Gly Tyr Asn Val Leu Gly Ile
                85                  90                  95

Phe Tyr Gly His Pro Gly Val Phe Val Ser Pro Ser His Arg Ala Ile
            100                 105                 110

Ala Ile Ala Arg Asp Glu Gly Tyr Ile Ala Lys Met Leu Pro Gly Val
        115                 120                 125

Ser Ala Glu Asp Tyr Met Phe Ser Asp Ile Gly Phe Asp Pro Ala Val
    130                 135                 140

Pro Gly Cys Met Ser Gln Glu Ala Thr Gly Leu Leu Val Cys Lys Lys
145                 150                 155                 160

Lys Leu Asp Pro Ser Ile His Asn Ile Ile Trp Gln Val Gly Ser Val
                165                 170                 175

Gly Val Asp Thr Met Asn Arg Glu Phe His Ile Leu Val Asp Arg Leu
            180                 185                 190

Glu Glu Asp Phe Gly Leu Asp His Lys Val Val His Tyr Ile Gly Ala
```

```
                195                 200                 205
Val Leu Pro Gln Ser Thr Thr Val Met Asp Glu Phe Thr Ile Ala Asp
210                 215                 220

Leu Arg Lys Glu Glu Val Val Lys Gln Ile Thr Thr Thr Ser Thr Phe
225                 230                 235                 240

Tyr Leu Pro Pro Arg Ser Met Ala His Ile Asp Gln Asp Met Leu Gln
                245                 250                 255

Lys Leu Arg Leu Ser Leu Ser Pro Val Glu His Val Met His Val Tyr
                260                 265                 270

Pro Arg Ser Lys Trp Ala Ser Ala Glu Ser Pro Asn Pro Pro Ala Tyr
                275                 280                 285

Gly Pro Ile Glu Arg Glu Ala Val Ser His Leu Thr Asn His Thr Ile
                290                 295                 300

Pro Asn Asp His Gln Phe Leu Arg Gly Ser Arg Pro Leu Arg Gln Leu
305                 310                 315                 320

Met Val Asp Leu Ala Leu Gln Pro Gly Leu Arg Asn Arg Tyr Lys Ala
                325                 330                 335

Asp Pro Ala Ser Val Leu Asp Ala Ile Pro Gly Met Ser Ala Glu Glu
                340                 345                 350

Lys Phe Ala Leu Thr Leu Asn His Ala Ala Pro Ile Phe Lys Val Met
                355                 360                 365

Arg Ala Ser Arg Ala Asp Gly Glu Ala Pro Thr Leu Asp Glu Ile Ala
370                 375                 380

Gly Thr Val Asn Pro Ser Leu Ala Cys Pro Ala Ile Val Val Cys Phe
385                 390                 395                 400

Val Gly Ile Met Val Ile Val Ile Ala Leu
                405                 410

<210> SEQ ID NO 110
<211> LENGTH: 408
<212> TYPE: PRT
<213> ORGANISM: Serendipita vermifera ssp. bescii

<400> SEQUENCE: 110

Met Ala Ser Ser Thr His Pro Lys Arg Gly Ser Leu Thr Ile Ala Gly
1               5                   10                  15

Thr Gly Ile Ala Thr Leu Ala His Met Thr Leu Glu Thr Val Ser His
                20                  25                  30

Ile Lys Glu Ala Asp Lys Val Tyr Tyr Ile Val Thr Asp Pro Val Thr
                35                  40                  45

Gln Ala Phe Ile Glu Glu Asn Ala Lys Gly Pro Thr Phe Asp Leu Ser
                50                  55                  60

Val Tyr Tyr Asp Ala Asp Lys Tyr Arg Tyr Thr Ser Tyr Val Gln Met
65                  70                  75                  80

Ala Glu Val Met Leu Asn Ala Val Arg Glu Gly Cys Asn Val Leu Gly
                85                  90                  95

Leu Phe Tyr Gly His Pro Gly Ile Phe Val Ser Pro Ser His Arg Ala
                100                 105                 110

Leu Ala Ile Ala Arg Glu Glu Gly Tyr Glu Ala Arg Met Leu Pro Gly
                115                 120                 125

Val Ser Ala Glu Asp Tyr Met Phe Ala Asp Leu Gly Leu Asp Pro Ala
                130                 135                 140

Leu Pro Gly Cys Val Cys Tyr Glu Ala Thr Asn Phe Leu Ile Arg Asn
145                 150                 155                 160
```

```
Lys Pro Leu Asn Pro Ala Thr His Asn Ile Leu Trp Gln Val Gly Ala
            165                 170                 175

Val Gly Ile Thr Ala Met Asp Phe Glu Asn Ser Lys Phe Ser Leu Leu
        180                 185                 190

Val Asp Arg Leu Glu Arg Asp Leu Gly Pro Asn His Lys Val Val His
        195                 200                 205

Tyr Val Gly Ala Val Leu Pro Gln Ser Ala Thr Ile Met Glu Thr Tyr
        210                 215                 220

Thr Ile Ala Glu Leu Arg Lys Pro Glu Val Ile Lys Arg Ile Ser Thr
225                 230                 235                 240

Thr Ser Ser Thr Phe Tyr Ile Pro Pro Arg Asp Ser Glu Ala Ile Asp
                245                 250                 255

Tyr Asp Met Val Ala Arg Leu Gly Ile Pro Pro Glu Lys Tyr Arg Lys
            260                 265                 270

Ile Pro Ser Tyr Pro Pro Asn Gln Trp Ala Gly Pro Asn Tyr Thr Ser
        275                 280                 285

Thr Pro Ala Tyr Gly Pro Glu Glu Lys Ala Ala Val Ser Gln Leu Ala
        290                 295                 300

Asn His Val Val Pro Asn Ser Tyr Lys Thr Leu His Ala Ser Pro Ala
305                 310                 315                 320

Met Lys Lys Val Met Ile Asp Leu Ala Thr Asp Arg Ser Leu Tyr Lys
                325                 330                 335

Lys Tyr Glu Ala Asn Arg Asp Ala Phe Val Asp Ala Val Lys Gly Leu
            340                 345                 350

Thr Glu Leu Glu Lys Val Ala Leu Lys Met Gly Thr Asp Gly Ser Val
        355                 360                 365

Tyr Lys Val Met Ser Ala Thr Gln Ala Asp Ile Glu Leu Gly Lys Glu
        370                 375                 380

Pro Ser Ile Glu Glu Leu Glu Glu Gly Arg Gly Arg Leu Leu Leu Val
385                 390                 395                 400

Val Ile Thr Ala Ala Val Val Val
                405

<210> SEQ ID NO 111
<211> LENGTH: 407
<212> TYPE: PRT
<213> ORGANISM: Thanatephorus cucumeris

<400> SEQUENCE: 111

Met Ala Thr Phe Thr Glu Asp Asn His Pro Lys Arg Gly Ser Leu Ile
1               5                   10                  15

Ile Ala Gly Ser Gly Ile Ala Ser Val Ala His Phe Thr Leu Glu Thr
            20                  25                  30

Val Ser His Leu Lys Asn Ala Asp Lys Val Phe Tyr Leu Val Asn Asp
        35                  40                  45

Pro Val Thr Glu Ala Phe Ile Gln Glu Asn Asn Pro Asp Thr Phe Asp
    50                  55                  60

Leu Val Thr Phe Tyr Ser Glu Thr Lys Pro Arg Tyr His Ser Tyr Val
65                  70                  75                  80

Glu Met Ala Glu Ile Met Leu Lys Glu Val Arg Ala Gly His Lys Val
                85                  90                  95

Leu Gly Ile Phe Tyr Gly His Pro Gly Val Phe Val His Pro Ser Arg
            100                 105                 110

Arg Ala Leu Phe Ile Ala Arg Gln Glu Asn Tyr Glu Ala Arg Met Leu
        115                 120                 125
```

```
Pro Gly Ile Ser Ser Glu Asp Tyr Met Phe Ala Asp Leu Glu Leu Asp
    130                 135                 140

Pro Ala Glu Phe Gly Cys Met Thr Cys Glu Ala Thr Glu Leu Ile Ala
145                 150                 155                 160

Arg Asn Arg Pro Leu Asn Thr Ser Val His Asn Ile Ile Trp Gln Ala
                165                 170                 175

Gly Ile Val Gly Val Ser Thr Leu Glu Tyr Gln Glu Ser Lys Phe Gln
                180                 185                 190

Leu Leu Val Asp Arg Leu Glu Arg Asp Phe Gly Pro Glu His Lys Val
            195                 200                 205

Val His Tyr Val Gly Ala Ile Arg Met Thr Pro Gln Ala Gln Ser Ala
    210                 215                 220

Met Val Val Tyr Ser Ile Gln Glu Leu Arg Asn Pro Ala Val Ala Asn
225                 230                 235                 240

Phe Ile Asn Ser Gly Ser Thr Leu Tyr Val Pro Pro Arg Leu Arg Asp
                245                 250                 255

Val Pro Arg Val Asp Pro Asp Ser Ala Thr Ala Leu Gly Leu Pro Pro
                260                 265                 270

Val Thr Thr Gly Phe Leu Ser Ala Ser Pro Thr Trp Val Gly Ser Arg
            275                 280                 285

Phe Val Thr Pro Ser Ser Tyr Gly Asp Leu Glu Asn Asn Ile Val Ala
    290                 295                 300

Gln Met Asn Glu Asn Arg Ser Arg Ser Arg Ile Thr Glu Pro Ser Pro
305                 310                 315                 320

Ala Met Lys Gly Leu Met Ile Lys Leu Ala Gln Glu Leu Lys Leu Gln
                325                 330                 335

Glu Glu Tyr Lys Lys Asp Pro Ala Lys Val Ala Ala Asp Thr Pro Asp
                340                 345                 350

Leu Lys Glu Ile Glu Arg Arg Ala Leu Ser Tyr Gly Leu Asp Asn Thr
            355                 360                 365

Ile Arg Ala Val Met Ser His Arg Gly Ser Ser Gly Pro Thr Glu
    370                 375                 380

Glu Gln Leu Lys Glu Ile Ser Trp Glu Gly Ser Thr Ile Lys His Val
385                 390                 395                 400

Thr Ala Ser Ser Ile Ala Gln
                405

<210> SEQ ID NO 112
<211> LENGTH: 855
<212> TYPE: PRT
<213> ORGANISM: Trypethelium eluteriae

<400> SEQUENCE: 112

Met Ala Pro Ser Thr Ser Asp Arg Ser Lys Leu Pro Val Ala Gly Tyr
1               5                   10                  15

Arg Pro Gly Arg Leu Val Met Val Gly Ser Gly Ile Lys Ser Ile Ala
                20                  25                  30

His Leu Thr Leu Glu Ala Ile Gly His Ile Glu Gln Ala Asp Lys Val
            35                  40                  45

Phe Phe Val Val Ala Asp Met Thr Thr Ala Ala Phe Ile His Ser Arg
    50                  55                  60

Asn Ala Asn Ala Val Asp Met Tyr Asn Leu Tyr Asp Ile Gly Lys Pro
65                  70                  75                  80

Arg Tyr His Thr Tyr Val Gln Met Ala Glu Arg Met Leu Arg Glu Val
```

-continued

```
                85                  90                  95
Arg Asn Gly Phe Tyr Val Val Gly Val Phe Tyr Gly His Pro Gly Ile
                100                 105                 110

Phe Val Asn Pro Ser His Arg Ala Ile Ala Ile Ala Arg Gln Glu Gly
                115                 120                 125

His Gln Ala Phe Met Leu Pro Gly Ile Ser Ala Glu Ala Cys Leu Phe
                130                 135                 140

Ala Asp Val Gly Ile Asp Pro Ser Thr Ser Gly Cys Gln Thr Ile Glu
145                 150                 155                 160

Ala Thr Asp Leu Leu Leu Arg Asn Arg Pro Ile Asn Thr Gly Ser His
                165                 170                 175

Leu Ile Ile Phe Gln Val Gly Ile Val Gly Asp Ser Gly Phe His Pro
                180                 185                 190

Gln Gly Phe Lys Asn Thr Lys Leu His Val Leu Leu Glu Lys Leu Thr
                195                 200                 205

Glu Val Tyr Gly Ser Gly His Arg Leu Val His Tyr Ile Ala Pro Ser
                210                 215                 220

Met Ala Thr Val Glu Pro Thr Ile Asp Phe Leu Thr Leu Gly Ala Leu
225                 230                 235                 240

Lys Lys Ser Arg Asn Ala Arg Arg Val Thr Gly Ile Ser Thr Phe Tyr
                245                 250                 255

Ile Pro Pro Lys His Asp Val Gln Pro Ser Pro Ser Ala Ala Lys Lys
                260                 265                 270

Leu Gly Leu Lys Val Gln Gln Gly Ala Lys Ser Arg Asn Phe Gly Arg
                275                 280                 285

Leu Thr Met Pro Glu Asp Pro Tyr Gly Pro Arg Glu Arg Val Ala Ile
                290                 295                 300

Asp Glu Leu Asp Lys His Lys Asp Pro Ala Trp Tyr Lys Arg Val Arg
305                 310                 315                 320

Ala Ser Gln Pro Met Phe Asp Leu Leu Tyr Arg Leu Gly Ser Asp Pro
                325                 330                 335

Arg Ala Ala Ala Lys Phe Lys Ala Asn Pro Asp Lys Phe Leu Ile Pro
                340                 345                 350

Tyr Asp Ser Asp Leu Thr Gln Thr Glu Arg Ala Ala Leu Leu Thr Arg
                355                 360                 365

Arg Ser Phe Pro Val Arg Gln Ala Leu Gln Pro Ser Ala Asp Asp Val
                370                 375                 380

Ala Asn Gln Val Val Gln Arg Leu Phe Arg Asp Pro Ser Phe Ala Thr
385                 390                 395                 400

Gln Trp Ala Ser Thr Leu Lys Lys Asn Lys Ser Asp Pro Asn Gly Glu
                405                 410                 415

Gln Asn Ile Ile Ala Trp Leu Lys Gln Gln Gly Tyr Asp Thr Thr Pro
                420                 425                 430

Glu Ala Val Asp Ser Ala Tyr Leu Gln Ala Leu Asn Val Asp Leu Asp
                435                 440                 445

Ile Tyr Asp Ser Ala Tyr Ala Thr Ser Phe Ser Gly Ser Thr Gly
                450                 455                 460

Pro Leu Ile Val Ile Leu Asn Gly Lys Val Thr Val Ala Gly Val Glu
465                 470                 475                 480

Ile Lys Asn Pro Ile Tyr Ser Gln Ser Ile Leu Ser Trp Gly Thr Thr
                485                 490                 495

Asp Gly Asn Glu Tyr Asn Ala Gln Leu Phe Leu Arg Val Leu Thr Asn
                500                 505                 510
```

Asp Asp Gly Lys Pro Leu Pro Gln Asn Ala Tyr Val Gly Pro Gln Leu
            515                 520                 525

Tyr Gly Tyr Tyr Trp Ser Pro Asn Ser Val Lys Pro Thr Lys Pro Asn
        530                 535                 540

Ile Asn Gly Lys Val Gly Gln Pro Ser Pro Ser Asn Gly Ser Asp Pro
545                 550                 555                 560

Val Gln Pro Thr Pro Leu Ser Lys Phe Ala Ala Thr Tyr Asn Thr Tyr
                565                 570                 575

Ile Ala Gly Ala Thr Gly Lys Tyr Ala Ala Asp Ser Gln Leu Val Val
            580                 585                 590

Ala Asn Pro Glu Pro Asn Thr Thr Val Thr Tyr Lys Gly Ile Val Ile
        595                 600                 605

Lys Lys Trp Thr Tyr Ala Asn Glu Ser Leu Ser Trp Leu Ala Thr Asp
    610                 615                 620

Gly Asn Ala Gln Asn Val Ala Ile Arg Phe Phe Ile Asn Thr Ser Ser
625                 630                 635                 640

Thr Ser Ser Asp Pro Thr Leu Gly Pro Gln Phe Leu Gly Thr Thr Trp
                645                 650                 655

Ala Gln Gly Gln Asn Pro Pro Ser Lys Ser Asn Phe Phe Gly Gln Ile
            660                 665                 670

Gly Gln Ser Ala Asp Pro Asp Thr Thr Ala Asn Ile Leu Thr Lys Ala
        675                 680                 685

Asn Thr Trp Ile Gln Phe Gly Leu Asn Leu Val Asn Gly Ile Ala Ala
    690                 695                 700

Met Leu Ile Cys His Ala Ile Met Ser Leu Phe Lys Ala Arg Asn Ala
705                 710                 715                 720

Glu Ala Ala Asn Pro Ser Pro Glu Asn Gln Gln Ala Glu Gln Gln Ala
                725                 730                 735

Glu Gln Asp Ala Asn Asp Ala Ile Asn Glu Gln Glu Ala Ile Gln Asp
            740                 745                 750

Asn Ala Ala Asp Gln Gly Gly Asn Glu Glu Val Asp Pro Asn Asp Leu
        755                 760                 765

Asp Pro Asp Glu Ala Gly Glu Pro Asn Ala Asn Ala Asp Ala Asp Ala
    770                 775                 780

Asp Ala Asp Ala Asp Ala Asp Ala Asp Ala Asp Ala Asp Ala Asp Ala
785                 790                 795                 800

Asp Ala Asp Ala Glu Ala Asp Ala Asp Ala Glu Ala Asp Ala Asp Ala
                805                 810                 815

Glu Ala Asp Ala Asp Ala Glu Ala Asp Ala Asp Ala Glu Ala Asp Ala
            820                 825                 830

Asp Ala Glu Ala Asp Ala Asp Ala Asp Ile Asp Ile Asp Ile Asp Ala
        835                 840                 845

Asp Val Val Asp Ile Ile Leu
    850                 855

<210> SEQ ID NO 113
<211> LENGTH: 381
<212> TYPE: PRT
<213> ORGANISM: Trichophaea hybrida

<400> SEQUENCE: 113

Met Thr Gln Gly Ser Leu Phe Ile Val Gly Ser Gly Ile Arg Ser Ile
1               5                   10                  15

Ala Gln Leu Thr Leu Glu Ala Ile Met His Ile Glu Asn Ala Asp Lys

```
                    20                  25                  30
Val Phe Tyr Val Val Cys Asp Pro Val Thr Glu Gly Phe Ile Lys Glu
            35                  40                  45

Lys Asn Pro Asn Ala Val Asp Leu Tyr Glu Tyr Tyr Ser Asn Thr Lys
        50                  55                  60

Leu Arg Asn Glu Thr Tyr Ile Gln Met Ala Glu Ile Met Leu Arg Glu
65                  70                  75                  80

Val Arg Ser Gly Leu Arg Val Val Gly Val Phe Tyr Gly His Pro Gly
                    85                  90                  95

Asn Phe Val Ser Pro Thr Arg Arg Ala Leu Ala Ile Ala Arg Asp Glu
            100                 105                 110

Gly Tyr Val Ala Lys Met Leu Pro Gly Ile Ser Ala Asp Asp Cys Leu
        115                 120                 125

Phe Ala Asp Leu Leu Ile Asp Pro Cys Tyr Pro Gly Leu Gln Thr Val
        130                 135                 140

Glu Ala Thr Asp Val Leu Val Arg Asn Arg Pro Leu Gln Thr Thr Ser
145                 150                 155                 160

His Val Val Ile Tyr Gln Val Gly Val Ile Cys Lys Ser Gly Phe Asp
                    165                 170                 175

Phe Tyr Ser Ile Glu Asn Asp Lys Phe Asp His Phe Val Thr Arg Leu
            180                 185                 190

Gln Glu Asp Tyr Gly Pro Asn His Pro Val Val Asn Tyr Val Ala Ala
        195                 200                 205

Val Ser Pro Leu Ala Glu Pro Thr Ile Gln Arg His Thr Ile Ser Glu
        210                 215                 220

Leu Phe Lys Asp Ser Val Lys Ala Ser Ile Ser Gly Val Ser Thr Phe
225                 230                 235                 240

Tyr Ile Pro Pro Lys Glu Leu Leu Pro Leu Thr Ala Ala Gly Glu Lys
                    245                 250                 255

Leu Ile Leu Asp Leu Asn Thr Asp Lys Ala Ala Val Gln Val Lys Thr
            260                 265                 270

Tyr Pro Pro Leu Pro Tyr Cys Pro Leu Ser Thr Gly Gln Gln Ala Tyr
        275                 280                 285

Gly Ala Tyr Glu Lys Ser Val Ile Glu Lys Ile Lys Asn His Thr Thr
        290                 295                 300

Pro Ala Gly Tyr Lys Pro Tyr Gln Thr Ser Arg Ala Met His Lys Ala
305                 310                 315                 320

Leu Glu Arg Leu Tyr Leu Asp Pro Glu Thr Val Lys Lys Tyr Arg Arg
                    325                 330                 335

Asp Pro Glu Gly Phe Ala Ala Glu Phe Glu Gly Leu Lys Glu Asn Glu
            340                 345                 350

Ala Glu Ala Leu Arg Ser Gly Asn Pro Asp Ser Cys Ala Ser Leu Gly
        355                 360                 365

Ala Ala Val Leu His Ala Val Ala Val Trp Ile Ala Cys
        370                 375                 380

<210> SEQ ID NO 114
<211> LENGTH: 828
<212> TYPE: PRT
<213> ORGANISM: Talaromyces islandicus

<400> SEQUENCE: 114

Met Ser Thr Ser Glu His His Arg Pro Ala Ser His Gly Phe Arg Pro
1               5                   10                  15
```

```
Gly Lys Leu Val Ile Val Gly Ser Gly Ile Arg Ser Ile Gln Phe
             20                  25                  30

Thr Leu Glu Ala Val Ala His Ile Glu His Ala Asp Lys Val Phe Tyr
             35                  40                  45

Cys Val Ala Asp Pro Gly Thr Asp Ala Phe Ile Glu Arg His Asn Lys
 50                  55                  60

Asn Ala Val Asp Leu Tyr Asn Leu Tyr Gly Asp Gly Lys Pro Arg His
 65                  70                  75                  80

Gln Thr Tyr Thr Gln Met Ala Glu Val Ile Leu Gln Glu Val Arg Lys
                 85                  90                  95

Gly Phe Ser Val Val Gly Val Phe Tyr Gly His Pro Gly Val Phe Val
                100                 105                 110

Asn Pro Ala His Arg Ala Val Ser Ile Ala Ala Ser Glu Gly Tyr Glu
            115                 120                 125

Ala Thr Met Leu Pro Gly Val Ser Ala Glu Asp Cys Leu Tyr Ala Asp
            130                 135                 140

Leu Leu Ile Asp Pro Ser Arg Pro Gly Cys Gln Thr Leu Glu Ala Thr
145                 150                 155                 160

Asp Val Leu Leu Arg Lys Arg Pro Ile Ala Lys Asp Cys His Val Ile
                165                 170                 175

Ile Phe Gln Val Gly Ala Val Gly Asp Leu Gly Phe Asn Phe Lys Gly
            180                 185                 190

Phe Lys Asn Thr Lys Phe Glu Ile Leu Val Gln His Leu Leu Glu Val
            195                 200                 205

Tyr Gly Pro Asp His Ser Val Val His Tyr Ile Ala Ser Gln Leu Thr
210                 215                 220

Phe Ala Ala Pro Ile Arg Asp Arg Tyr Ala Ile Gln Asp Leu Val Lys
225                 230                 235                 240

Pro Glu Val Ala Lys Arg Ile Thr Gly Ile Ser Thr Phe Tyr Leu Pro
                245                 250                 255

Pro Lys Asp Leu Leu Gln Pro Asp Glu Val Ala Ala Lys Ser Leu Gly
            260                 265                 270

Leu Val Ser Arg Pro Thr Thr Thr Ala Ser Phe Gly Pro Tyr Ala Pro
            275                 280                 285

Asp Gln Pro Tyr Gly Pro Arg Glu Leu Ala Ala Ile Lys Ala Leu Lys
290                 295                 300

Ala His Lys Asp Pro Ala Asn Tyr Asn Lys Thr Arg Ala Ser Pro Ala
305                 310                 315                 320

Leu Tyr Gln Ala Leu Glu Ser Leu Ala Leu Asn Pro Lys Asp Val Leu
                325                 330                 335

Lys Phe Arg Ser Ser Arg Glu Lys Phe Ile Ala Arg Ile Asp Gly Leu
            340                 345                 350

Thr Lys Pro Glu Gln Lys Ala Leu Arg Phe Ala Ser Thr Gly Leu Ile
            355                 360                 365

Arg Gln Val Leu Lys Ser Ala Lys Asp Ile Ala Thr Lys Phe Val
370                 375                 380

Gln Asp Glu Phe Arg Asn Pro Thr Leu Ala Thr Gln Tyr Ala Gln Ile
385                 390                 395                 400

Leu Lys Glu Asn Arg Asn Lys Thr Asp Gly Ile Asp Lys Ile Thr Glu
                405                 410                 415

Trp Leu Lys Ala Gln Gly Tyr Asp Thr Thr Pro Glu Ala Ile Gly Glu
            420                 425                 430

Ala Tyr Lys Gln Glu Leu Ser Arg Asn Leu Asp Ser Tyr Asp Gly Lys
```

```
                435                 440                 445
Tyr Thr Thr Asn Val Asp Gly Lys Pro Gly Pro Gln Leu Leu Leu Gln
450                 455                 460

Lys Gly Thr Val Leu Val Asp Gly Val Lys Ile Pro Asn Trp Ser Tyr
465                 470                 475                 480

Ser Ser Ser Gln Leu Ser Trp Thr Val Glu Asp Gly Asn Pro Ser Ser
                485                 490                 495

Ala Met Leu His Phe Gln Leu Leu Thr Asn Asp Thr Gly Lys Pro Leu
            500                 505                 510

Pro Pro Gly Ser Tyr Ile Gly Pro Gln Phe Tyr Gly Leu Tyr Trp Arg
        515                 520                 525

Lys Gly Ser Ser Lys Pro Thr Gly Asn Asn Thr Val Gly Lys Val Gly
    530                 535                 540

Glu Val Pro Pro Pro Asp Pro Ile Thr Pro Val Lys Pro Thr Pro Ile
545                 550                 555                 560

Ser Ala Trp Leu Asp Thr Tyr Gln Thr Tyr Leu Lys Ser Ser Ser Gly
                565                 570                 575

Thr Trp Asp Lys Ala Gly Glu Leu Ala Ile Thr Gly Asp Glu Thr Asn
            580                 585                 590

Pro Thr Val Thr Tyr Lys Gly Lys Gln Ile Gln Lys Tyr Ser Tyr Gln
        595                 600                 605

Asn Glu Thr Ile Ser Trp Ser Ser Ala Asp Gly Asn Pro Asn Asn Ala
    610                 615                 620

Leu Ser Phe Tyr Phe Asn Lys Asn Pro Thr Gln Lys Asn Pro Ala Pro
625                 630                 635                 640

Gly Asn Gln Phe Ser Gly Lys Tyr Trp Glu Ser Gly Gln Ala Pro Pro
                645                 650                 655

Thr Ala Ala Asn Leu Phe Gly Gln Ile Gly Ser Ser Ser Pro Gly
            660                 665                 670

Thr Ala Ala Asn Asp Ala Met Thr Ala Ala Gln Trp Lys Thr Ile Gly
        675                 680                 685

Ile Asn Leu Gly Val Gly Ile Leu Thr Phe Val Leu Gly Asp Phe Thr
    690                 695                 700

Leu Lys Ala Ile Asn Ala Leu Ile Lys Trp Val Arg Asn Pro Thr Lys
705                 710                 715                 720

Glu Asn Arg Asp Ala Leu Asp Gln Ala Asn Asp Asp Ala Gly Glu Ala
                725                 730                 735

Glu Ala Gln Gln Glu Ala Val Glu Ala Glu Gly Ala Asp Leu Asn Pro
            740                 745                 750

Gly Gly Asp Ile Val Asp Ala Gly Asp Val Pro Ala Gln Ala Ala Glu
        755                 760                 765

Ala Ala Glu Ala Ala Glu Ala Ala Glu Val Ala Glu Val Ala Glu Val
    770                 775                 780

Ala Glu Ala Ala Glu Ala Ala Glu Ala Ala Glu Ala Ala Glu Ala Ala
785                 790                 795                 800

Glu Val Ala Glu Val Ala Glu Val Ala Glu Val Ala Glu Val Ala Glu
                805                 810                 815

Val Ala Glu Val Val Asp Val Val Glu Val Ile Ile
            820                 825

<210> SEQ ID NO 115
<211> LENGTH: 374
<212> TYPE: PRT
<213> ORGANISM: Wilcoxina mikolae
```

<400> SEQUENCE: 115

| | | | | | | | | | | | | | | |
|---|---|---|---|---|---|---|---|---|---|---|---|---|---|---|
|Met|Pro|Gln|Gly|Ser|Leu|Thr|Ile|Val|Gly|Ser|Gly|Ile|Arg|Ser|Ile|
|1| | | |5| | | |10| | | |15| | |
|Ala|Gln|Leu|Thr|Leu|Glu|Ala|Ile|Met|His|Ile|Glu|Asn|Ala|Asp|Lys|
| | | |20| | | | |25| | | |30| | | |
|Val|Phe|Tyr|Val|Val|Cys|Asp|Pro|Ala|Thr|Glu|Gly|Phe|Ile|Lys|Gln|
| | | |35| | | | |40| | | |45| | | |
|Lys|Asn|Pro|Asn|Ala|Val|Asp|Leu|Tyr|Glu|Tyr|Tyr|Ser|Asn|Thr|Lys|
| |50| | | | |55| | | | |60| | | | |
|Leu|Arg|Asn|Glu|Thr|Tyr|Ile|Gln|Met|Ala|Glu|Ile|Met|Leu|Arg|Glu|
|65| | | | |70| | | | |75| | | | |80|
|Val|Arg|Ser|Gly|Leu|Arg|Val|Val|Gly|Val|Phe|Tyr|Gly|His|Pro|Gly|
| | | | |85| | | | |90| | | | |95| |
|Asn|Phe|Val|Ser|Pro|Thr|Arg|Arg|Ala|Leu|Ala|Ile|Ala|Gln|Asp|Glu|
| | | |100| | | | |105| | | | |110| | |
|Gly|Tyr|Val|Ala|Lys|Met|Leu|Pro|Gly|Ile|Ser|Ala|Asp|Asp|Cys|Leu|
| | | |115| | | | |120| | | | |125| | |
|Phe|Ala|Asp|Leu|Leu|Ile|Asp|Pro|Cys|Tyr|Pro|Gly|Leu|Gln|Thr|Val|
| |130| | | | |135| | | | |140| | | | |
|Glu|Ala|Thr|Asp|Val|Leu|Val|Arg|Asp|Arg|Pro|Leu|Gln|Ile|Thr|Ser|
|145| | | | |150| | | | |155| | | | |160|
|His|Val|Val|Ile|Tyr|Gln|Val|Gly|Val|Ile|Cys|Lys|Ser|Gly|Phe|Asp|
| | | | |165| | | | |170| | | | |175| |
|Phe|Thr|Ser|Ile|Glu|Asn|Asp|Lys|Phe|Asp|His|Phe|Val|Asn|Arg|Leu|
| | | |180| | | | |185| | | | |190| | |
|Gln|Gln|Asp|Tyr|Gly|Pro|Ser|His|Pro|Val|Ile|Asn|Tyr|Val|Ala|Ala|
| | | |195| | | | |200| | | | |205| | |
|Val|Ser|Pro|Leu|Ala|Glu|Pro|Thr|Ile|Gln|Arg|Tyr|Thr|Ile|Ser|Asp|
| |210| | | | |215| | | | |220| | | | |
|Leu|Phe|Lys|Asp|Ser|Val|Lys|Ala|Cys|Ile|Ser|Gly|Val|Ser|Thr|Phe|
|225| | | | |230| | | | |235| | | | |240|
|Tyr|Leu|Pro|Pro|Lys|Glu|Leu|Leu|Pro|Ile|Thr|Asp|Val|Gly|Glu|Lys|
| | | | |245| | | | |250| | | | |255| |
|Leu|Ile|Leu|Asp|Leu|Gly|Thr|Asp|Lys|Ala|Ala|Leu|Gln|Val|Lys|Thr|
| | | |260| | | | |265| | | | |270| | |
|Tyr|Pro|Pro|Leu|Pro|Tyr|Cys|Pro|Leu|Ser|Thr|Gly|Gln|Gln|Pro|Tyr|
| | | |275| | | | |280| | | | |285| | |
|Gly|Pro|Tyr|Glu|Lys|Ala|Val|Ile|Glu|Arg|Ile|Lys|Asp|His|Thr|Thr|
| | |290| | | | |295| | | | |300| | | |
|Pro|Ala|Asp|Tyr|Arg|Pro|Tyr|Asn|Thr|Ser|Gln|Ala|Met|Tyr|Lys|Ala|
|305| | | | |310| | | | |315| | | | |320|
|Leu|Glu|Arg|Leu|Tyr|Leu|Asp|Pro|Glu|Ala|Val|Lys|Lys|Tyr|Arg|Arg|
| | | | |325| | | | |330| | | | |335| |
|Asp|Pro|Glu|Gly|Phe|Ala|Ala|Phe|Glu|Gly|Leu|Lys|Glu|Asn|Glu|
| | | |340| | | | |345| | | | |350| | |
|Ala|Gln|Ala|Leu|Lys|Ser|Gly|Asn|Pro|Asp|Ser|Ser|Ala|Ser|Leu|Gly|
| | | |355| | | | |360| | | | |365| | |
|His|Val|Arg|His|Pro|Val|
| | | |370| | |

<210> SEQ ID NO 116
<211> LENGTH: 417
<212> TYPE: PRT

<213> ORGANISM: Lentinula novae-zelandiae

<400> SEQUENCE: 116

Met Glu Thr Pro Thr Leu Asn Asn Ser Gly Ser Leu Thr Ile Val Gly
1               5                   10                  15

Thr Gly Ile Glu Ser Ile Gly Gln Met Thr Leu Gln Thr Leu Ser Tyr
            20                  25                  30

Ile Glu Ala Ala Asp Lys Val Phe Tyr Cys Val Ile Asp Pro Ala Thr
        35                  40                  45

Glu Ala Phe Ile Leu Thr Lys Asn Lys Asp Cys Val Asp Leu Tyr Gln
    50                  55                  60

Tyr Tyr Asp Asn Gly Lys Ser Arg Met Asp Thr Tyr Thr Gln Met Ser
65                  70                  75                  80

Glu Val Met Leu Arg Glu Val Arg Lys Gly Leu Asp Val Val Gly Val
                85                  90                  95

Phe Tyr Gly His Pro Gly Val Phe Val Asn Pro Ser Leu Arg Ala Leu
            100                 105                 110

Ala Ile Ala Lys Ser Glu Gly Tyr Lys Ala Arg Met Leu Pro Gly Val
        115                 120                 125

Ser Ala Glu Asp Cys Leu Tyr Ala Asp Leu Cys Ile Asp Pro Ser Asn
    130                 135                 140

Pro Gly Cys Leu Thr Tyr Glu Ala Ser Asp Phe Leu Ile Arg Glu Arg
145                 150                 155                 160

Pro Thr Asn Ile Tyr Ser His Phe Ile Leu Phe Gln Val Gly Cys Val
                165                 170                 175

Gly Ile Ala Asp Phe Asn Phe Thr Gly Phe Glu Asn Ser Lys Phe Gly
            180                 185                 190

Ile Leu Val Asp Arg Leu Glu Lys Glu Tyr Gly Ala Asp His Pro Val
        195                 200                 205

Val His Tyr Ile Ala Ala Met Leu Pro His Glu Glu Pro Val Thr Asp
    210                 215                 220

Gln Trp Thr Ile Gly Gln Leu Arg Glu Pro Glu Phe Tyr Lys Arg Val
225                 230                 235                 240

Gly Gly Val Ser Thr Phe Tyr Ile Pro Lys Glu Arg Lys Glu Ile
                245                 250                 255

Asn Val Asp Ile Ile Arg Glu Leu Lys Phe Leu Pro Glu Gly Lys Val
                260                 265                 270

Pro Asp Thr Arg Thr Gln Ile Tyr Pro Pro Asn Gln Trp Glu Pro Glu
            275                 280                 285

Val Pro Thr Val Pro Ala Tyr Gly Ser Asn Glu His Ala Ala Ile Ala
        290                 295                 300

Gln Leu Asp Ala His Ser Ala Pro Glu Gln Tyr Gln Pro Leu Ala Thr
305                 310                 315                 320

Ser Lys Ala Met Thr Asp Val Met Thr Lys Leu Ala Leu Asp Pro Lys
                325                 330                 335

Ala Leu Ala Glu Tyr Lys Ala Asp His Arg Ala Phe Ala Gln Ser Val
            340                 345                 350

Pro Asp Leu Thr Ala Asn Glu Arg Thr Ala Leu Glu Ile Gly Asp Ser
        355                 360                 365

Trp Ala Phe Arg Cys Ala Met Lys Glu Met Pro Val Ser Leu Leu Asp
    370                 375                 380

Asn Ala Lys Gln Ser Met Glu Glu Ala Ser Glu Gln Gly Phe Pro Trp
385                 390                 395                 400

```
Ile Ile Val Val Gly Val Val Gly Val Val Gly Ser Val Val Ser Ser
            405                 410                 415
Ala
```

<210> SEQ ID NO 117
<211> LENGTH: 1019
<212> TYPE: DNA
<213> ORGANISM: Gymnopus fusipes

<400> SEQUENCE: 117

| | | | | | |
|---|---|---|---|---|---|
| gactgcgtcg | acttgtatca | gtattacgac | aatggcaaat | ccagaatggc | tacttacacc | 60 |
| caaatgtcag | aggtaagctc | cgtacacttc | aacagttgcc | aggacccgat | gctgacatat | 120 |
| gcgtagctca | tggtcaggga | agtccgcaag | ggcctcgatg | tcgtgggcgt | cttctatgga | 180 |
| cacccgggag | tgttcgtgaa | cccttctcac | cgagctctgg | ctatcgccag | gagtgagggc | 240 |
| taccgagcga | ggatgctccc | aggcgtgtct | gcggaagatt | gcctcttcgc | cgacttgtgc | 300 |
| attgatcctt | cgaacccggg | ttgcttgacc | tacgaagcat | cggatttcct | gatcagggat | 360 |
| cgtccggtca | gcatccacag | tcacttggtc | ctgttccaag | tcggttgtgt | tggtattgca | 420 |
| gacttcacat | ttgtaagatt | caatgtaagc | attcagtatt | gcccaagatt | ttgtgtctaa | 480 |
| aatgttacct | ggttcagaat | tcaaaatttg | gggtacttct | cgaccggctc | gagcacgaat | 540 |
| atggcgctga | tcatacagtt | gtgcactata | tcgcagccat | gctgccttac | gagaatccag | 600 |
| tgattgacaa | actcaccatc | agccagctcc | gtgacaccga | gatcgcgaag | cgcgtgagtg | 660 |
| gtatatcgac | cttctatatc | cctccaaagg | agctaaagga | cccgagcatg | gatatcatgc | 720 |
| gccgcctaga | acttttggct | gttgaccaag | ttccagataa | gcaatggcac | ttctacccaa | 780 |
| caaaccagtg | ggcaccatct | gcacccaacg | tagttcctta | tggaccaaga | gaacaagccg | 840 |
| ccattgtcca | gttgggcagt | cacaccattc | cagagcaatt | tcagcctatt | gctacttcca | 900 |
| aagctatgac | tgacatcttg | acaaagctgg | ctttggaccc | caagatgctc | actgagtaca | 960 |
| aggctgaccg | tcgtgccttt | gctcaatctg | cgctggagtt | gacagtcaat | gagagagat | 1019 |

<210> SEQ ID NO 118
<211> LENGTH: 912
<212> TYPE: DNA
<213> ORGANISM: Gymnopus fusipes

<400> SEQUENCE: 118

| | | | | | |
|---|---|---|---|---|---|
| gactgcgtcg | acttgtatca | gtattacgac | aatggcaaat | ccagaatggc | tacttacacc | 60 |
| caaatgtcag | agctcatggt | cagggaagtc | cgcaagggcc | tcgatgtcgt | gggcgtcttc | 120 |
| tatggacacc | cgggagtgtt | cgtgaaccct | tctcaccgag | ctctggctat | cgccaggagt | 180 |
| gagggctacc | gagcgaggat | gctcccaggc | gtgtctgcgg | aagattgcct | cttcgccgac | 240 |
| ttgtgcattg | atccttcgaa | cccgggttgc | ttgacctacg | aagcatcgga | tttcctgatc | 300 |
| agggatcgtc | cggtcagcat | ccacagtcac | ttggtcctgt | tccaagtcgg | ttgtgttggt | 360 |
| attgcagact | tcacatttgt | aagattcaat | aattcaaaat | ttggggtact | tctcgaccgg | 420 |
| ctcgagcacg | aatatggcgc | tgatcataca | gttgtgcact | atatcgcagc | catgctgcct | 480 |
| tacgagaatc | cagtgattga | caaactcacc | atcagccagc | tccgtgacac | cgagatcgcg | 540 |
| aagcgcgtga | gtggtatatc | gaccttctat | atccctccaa | aggagctaaa | ggacccgagc | 600 |
| atggatatca | tgcgccgcct | agaacttttg | gctgttgacc | aagttccaga | taagcaatgg | 660 |
| cacttctacc | caacaaacca | gtgggcacca | tctgcaccca | acgtagttcc | ttatggacca | 720 |

-continued

```
agagaacaag ccgccattgt ccagttgggc agtcacacca ttccagagca atttcagcct    780
attgctactt ccaaagctat gactgacatc ttgacaaagc tggctttgga ccccaagatg    840
ctcactgagt acaaggctga ccgtcgtgcc tttgctcaat ctgcgctgga gttgacagtc    900
aatgagagag at                                                        912
```

<210> SEQ ID NO 119
<211> LENGTH: 569
<212> TYPE: PRT
<213> ORGANISM: Rhizophogun vinicolor

<400> SEQUENCE: 119

```
Met Ala Lys Val Phe Gly Leu Val Leu Gly Phe Leu Ser Gln Thr Phe
1               5                  10                  15

Thr Tyr Pro Ser Gln Val Trp Phe Ser Pro Val Gly Ala Asn Asn Gly
            20                  25                  30

Gln Val Ile Thr Pro Glu Leu Ser Asn Ser Ile Gln Glu Thr Leu Asp
        35                  40                  45

Val Trp Asn Ile Thr Gly Leu Ser Val Ala Ile Ile Pro Lys Ser Gly
    50                  55                  60

Glu Pro Glu Tyr His Ser Trp Gly Asp Arg Thr Glu Asp Gly Glu Ser
65                  70                  75                  80

Val Thr Gln Asp Thr Leu Phe His Met Ala Ser Val Ser Lys Ala Phe
                85                  90                  95

Cys Val Ser Ala Leu Gly Ile Leu Met Asp Asp Phe Glu His Gly Arg
            100                 105                 110

Asn Val Thr Pro Leu Pro Pro Ala Leu Thr Glu Phe Asn Trp His Thr
        115                 120                 125

Ser Ile Gln Asp Leu Leu Pro Gly Glu Trp Gln Leu Met Asp Glu Trp
    130                 135                 140

Ala Ser Arg Lys Ala Asn Met Lys Asp Ile Leu Ser His Val Ser Gly
145                 150                 155                 160

Leu Pro Arg His Asp Phe Ala Phe Gly Pro Tyr Glu Ser Pro Lys Glu
                165                 170                 175

Ala Val Ser Arg Leu Arg Tyr Leu Arg Pro Ala Phe Glu Leu Arg Glu
            180                 185                 190

Gln Trp Ser Tyr Asn Asn Gln Met Phe Met Val Ala Gly His Ile Val
        195                 200                 205

Glu Thr Tyr Ser Gly Lys Thr Tyr Thr Ser Phe Val Glu Asp Arg Ile
    210                 215                 220

Phe Thr Pro Leu Gly Met Ser Ser Ser Thr Phe Ser Pro Ala Lys Ala
225                 230                 235                 240

Ala Lys Thr Gly Lys Phe Thr Gln Gly Trp Thr Ser Ser Gly Arg Leu
                245                 250                 255

Leu Pro Glu Leu Phe Pro Glu Asp Met Val Met Leu Met Ala Gly Ala
            260                 265                 270

Gly Gly Val Ile Ser Ser Ala Val Asp Met Ser Lys Trp Val Ala Leu
        275                 280                 285

Trp Leu Asn Lys Gly Val Tyr Asp Asn Val Thr Val Ile Pro Ser Ser
    290                 295                 300

Val Tyr Gly Asn Ala Ser Gln Ser Tyr Ala Val Ser Ile Ser Thr Pro
305                 310                 315                 320

Val Asp Ser Glu His Ser Ile Gln Gly Tyr Gly Leu Gly Trp Phe Gln
                325                 330                 335
```

-continued

```
Asn Ser Tyr Leu Gly His Asn Val Val Tyr His Ser Gly Ser Ile Pro
                340                 345                 350

Gly Leu Ser Met Leu Val Ser Phe Leu Pro Asp Asp Val Gly Phe
            355                 360                 365

Val Val Phe Ala Asn Gly Gly Asp Lys Ala Ala Pro Val Met Asn Ile
            370                 375                 380

Ser Asn Ser Ile Ile Asp Ala Ala Leu His Leu Arg Ser Gly Pro Ala
385                 390                 395                 400

Pro Pro Ile Met Pro Glu Lys Lys Ala Val Thr Ser Pro Ser Glu Asp
                405                 410                 415

Ile Val Asn Leu Glu Leu Pro Leu Glu Glu Phe Ser Gly Thr Tyr Thr
            420                 425                 430

Asp Pro Gly Tyr Gly Thr Phe Thr Phe Cys Ser Pro Ser Ser Ser
            435                 440                 445

Ser Tyr Cys Gln Gln Val Met Thr Asp Phe Thr Ala Val Asp Ser Val
    450                 455                 460

His Pro Ser Ala Pro Ser Pro Leu Gln Leu Leu Ala Ala Trp Pro Arg
465                 470                 475                 480

Met Gly Ser Ser His Ile Arg Ala Val His Gln Ser Gly Asn Lys Phe
                485                 490                 495

Leu Leu Leu Cys Thr Ala Leu Phe Pro Glu Gly Tyr Gly Arg Asp Ser
            500                 505                 510

Thr Pro Phe Glu Thr Ala Glu Ile Gly Thr Pro Gly Ala Thr Ala Glu
            515                 520                 525

Phe Val Val Glu Asp Gly Lys Val Val Gly Phe Gly Leu Phe Gly Leu
            530                 535                 540

Val Asp Gln Val Thr Glu Arg Glu Arg Thr Gln Thr Thr Val Lys Asp
545                 550                 555                 560

Arg Ala Glu Val Trp Phe Asp Lys Val
                565

<210> SEQ ID NO 120
<211> LENGTH: 571
<212> TYPE: PRT
<213> ORGANISM: Rhizophogun vinicolor

<400> SEQUENCE: 120

Met Ile Met Ala Lys Val Phe Gly Leu Val Leu Gly Phe Leu Ser Gln
1               5                   10                  15

Thr Phe Thr Tyr Pro Ser Gln Ile Arg Leu Ser Pro Val Gly Val Asn
            20                  25                  30

Asn Gly Gln Val Ile Thr Pro Glu Leu Ser Asn Ser Ile Gln Glu Thr
        35                  40                  45

Leu Asp Val Trp Asn Ile Thr Gly Leu Ser Val Ala Ile Ile Pro Lys
    50                  55                  60

Ser Gly Glu Pro Glu Tyr His Ser Trp Gly Asp Arg Thr Glu Asp Gly
65                  70                  75                  80

Glu Ser Val Thr Gln Asp Thr Leu Phe His Met Ala Ser Val Ser Lys
                85                  90                  95

Ala Phe Cys Val Ser Ala Leu Gly Ile Leu Met Asp Asp Phe Glu His
            100                 105                 110

Gly Arg Asn Val Thr Pro Leu Pro Pro Ala Leu Thr Glu Phe Asn Trp
        115                 120                 125

His Thr Ser Ile Gln Asp Leu Leu Pro Gly Glu Trp Gln Leu Met Asp
    130                 135                 140
```

```
Glu Trp Ala Ser Arg Lys Ala Asn Val Lys Asp Ile Leu Ser His Val
145                 150                 155                 160

Ser Gly Leu Pro Ser His His Phe Ala Phe Gly Pro Tyr Glu Ser Pro
                165                 170                 175

Lys Glu Val Val Ser Arg Leu Arg Tyr Leu Arg Pro Ala Phe Glu Leu
            180                 185                 190

Arg Glu Gln Trp Ser Tyr Asn Asn Gln Met Phe Thr Val Ala Gly His
        195                 200                 205

Ile Val Glu Thr Tyr Ser Gly Lys Thr Tyr Thr Ser Phe Val Glu Asp
210                 215                 220

Arg Ile Phe Thr Pro Leu Gly Met Phe Ser Ser Thr Phe Ser Pro Ala
225                 230                 235                 240

Lys Ala Val Lys Thr Gly Lys Phe Thr Gln Gly Trp Thr Ser Ser Gly
                245                 250                 255

Arg Leu Leu Pro Glu Phe Phe Gln Glu Asp Met Ile Met Pro Met Ala
            260                 265                 270

Gly Pro Gly Gly Val Ile Ser Ser Ala Val Asp Met Ser Lys Trp Val
        275                 280                 285

Ala Leu Trp Leu Asn Lys Gly Val His Asp Asn Val Thr Ile Ile Pro
290                 295                 300

Ser Ser Val Tyr Gly Asn Ala Ser Gln Ser Tyr Ala Val Ser Ile Ser
305                 310                 315                 320

Thr Pro Val Asp Ser Glu His Ser Ile Leu Gly Tyr Gly Leu Gly Trp
                325                 330                 335

Phe Arg Asn Ser Tyr Leu Gly His Asp Val Val Tyr His Ser Gly Ser
            340                 345                 350

Ile Pro Gly Leu Ser Thr Leu Val Ser Phe Leu Pro Asp Asp Asp Val
        355                 360                 365

Gly Phe Val Val Phe Ala Asn Gly Asp Asn Lys Ala Ala Pro Val Met
370                 375                 380

Asn Ile Ser Asn Arg Ile Ile Asp Ala Ala Leu His Leu Arg Ser Gly
385                 390                 395                 400

Pro Ala Pro Pro Ile Met Pro Glu Lys Lys Ala Val Thr Ser Pro Ser
                405                 410                 415

Glu Asp Ile Val Asn Leu Glu Leu Pro Leu Glu Glu Phe Ser Gly Thr
            420                 425                 430

Tyr Thr Asp Pro Gly Tyr Gly Thr Phe Thr Phe Cys Ser Pro Ser Ser
        435                 440                 445

Ser Ser Pro Tyr Cys Gln Gln Val Ile Ala Asn Phe Thr Thr Val Asp
450                 455                 460

Ser Val Arg Pro Ser Ala Pro Ser Ser Leu Gln Leu Leu Ala Ala Trp
465                 470                 475                 480

Pro Arg Val Gly Ser Ser His Ile Arg Thr Val His Gln Ser Gly Asn
                485                 490                 495

Lys Phe Met Leu Leu Pro Thr Ala Leu Phe Pro Glu Gly Tyr Gly Arg
            500                 505                 510

Asp Ser Thr Pro Phe Glu Thr Ala Glu Ile Gly Thr Arg Gly Ala Pro
        515                 520                 525

Val Glu Phe Val Val Glu Asp Gly Arg Val Gly Phe Gly Leu Phe
530                 535                 540

Gly Leu Val Gly Gln Val Thr Glu Arg Glu Arg Thr Gln Thr Thr Val
545                 550                 555                 560
```

Lys Asp Arg Ala Gly Val Trp Phe Asp Lys Val
                565                 570

<210> SEQ ID NO 121
<211> LENGTH: 413
<212> TYPE: PRT
<213> ORGANISM: Rhizophogun vinicolor

<400> SEQUENCE: 121

Met Ser Thr Lys Arg Gly Thr Leu Thr Ile Ala Gly Ser Gly Ile Ala
1               5                   10                  15

Ser Val Gly His Ile Thr Leu Gly Thr Leu Ser Tyr Ile Lys Glu Ser
                20                  25                  30

Asp Lys Ile Phe Tyr Leu Val Cys Asp Pro Val Thr Glu Ala Phe Ile
            35                  40                  45

Tyr Asp Asn Ser Thr Ala Asp Cys Phe Asp Leu Ser Val Phe Tyr Asp
        50                  55                  60

Lys Thr Lys Gly Arg Tyr Asp Ser Tyr Ile Gln Met Cys Glu Val Met
65                  70                  75                  80

Leu Lys Ala Val Arg Ala Gly His Asp Val Leu Gly Val Phe Tyr Gly
                85                  90                  95

His Pro Gly Val Phe Val Ser Pro Ser His Arg Ala Ile Ala Val Ala
            100                 105                 110

Arg Gln Glu Gly Tyr Lys Ala Lys Met Leu Pro Gly Ile Ser Ala Glu
        115                 120                 125

Asp Tyr Met Phe Ala Asp Leu Glu Phe Asp Pro Ser Val Ser Gly Cys
    130                 135                 140

Lys Thr Cys Glu Ala Thr Glu Ile Leu Leu Arg Asp Lys Pro Leu Asp
145                 150                 155                 160

Pro Thr Ile Gln Asn Ile Ile Trp Gln Val Gly Ser Val Gly Val Val
                165                 170                 175

Asp Met Glu Phe Ser Lys Ser Lys Phe Gln Leu Leu Val Asp Arg Leu
            180                 185                 190

Glu Lys Asp Phe Gly Pro Asp His Lys Val Val His Tyr Ile Gly Ala
        195                 200                 205

Val Leu Pro Gln Ser Thr Thr Thr Met Asp Thr Phe Thr Ile Ala Asp
    210                 215                 220

Leu Arg Lys Glu Asp Val Ala Lys Gln Phe Gly Thr Ile Ser Thr Leu
225                 230                 235                 240

Tyr Ile Pro Pro Arg Asp Glu Gly His Val Asn Leu Ser Met Ala Lys
                245                 250                 255

Val Phe Gly Gly Pro Gly Ala Ser Val Lys Leu Asn Asp Ser Ile Lys
            260                 265                 270

Trp Ala Gly Pro Lys Leu Asn Ile Val Ser Ala Asn Asp Pro His Glu
        275                 280                 285

Arg Asp Val Ile Ala Gln Val Asp Thr His Val Ala Pro Glu Gly His
    290                 295                 300

Lys Lys Leu Arg Val Ser Ala Ala Met Lys Lys Phe Met Thr Asp Leu
305                 310                 315                 320

Ala Leu Lys Pro Lys Phe Leu Glu Glu Tyr Lys Leu Asp Pro Val Ala
                325                 330                 335

Val Val Glu Ser Ala Glu Gly Leu Ser Asn Leu Glu Arg Phe Gly Leu
            340                 345                 350

Lys Phe Ala Arg Ser Gly Pro Ala Asp Ala Leu Met Lys Ala Thr Glu
        355                 360                 365

Ser Asp Ile Ala Ser Gly Arg Gln Leu Thr Glu Glu Ile Ala Gln
    370                 375                 380

Gly Thr Gly Pro Val Gly Leu Gln Thr Ala Leu Ala Leu Val Leu
385                 390                 395                 400

Leu Gly Leu Gly Val Ala Ile Val Thr Arg Pro Asp Asp
                405                 410

<210> SEQ ID NO 122
<211> LENGTH: 598
<212> TYPE: PRT
<213> ORGANISM: Rhizophogun vinicolor

<400> SEQUENCE: 122

Met Thr Ser Asp Asn Leu Gln Pro Glu Val Ile Ser Ala Asn Trp Leu
1               5                   10                  15

Lys Ser Leu Glu Ala Ala Ser Ser Thr Gly Asp Thr Ala Ser Phe Val
            20                  25                  30

Ser His Phe Leu Pro Asp Gly Trp Phe Arg Asp Met Leu Cys Phe Thr
        35                  40                  45

Trp Asn Phe Arg Thr Leu Ser Gly Gln Glu Lys Ile His Gly Phe Ile
    50                  55                  60

Ser Glu Val Val Asp Gly Gln Ser Arg Leu Ser Tyr Ser His Leu His
65                  70                  75                  80

Asp Phe Lys Leu Asp Asp His Ser Val Asn Ala Pro Ser Pro Phe Lys
                85                  90                  95

Leu Pro Gly Pro Pro Asp Ile Glu Gly Val Gln Gly Ala Phe Thr Phe
            100                 105                 110

Ser Ile Thr Lys Pro Ala Ala Tyr Gly Arg Gly Phe Phe Arg Leu Thr
        115                 120                 125

Gln Asp Val His Gly Asn Trp Lys Ala Leu Thr Leu Phe Thr Asn Met
    130                 135                 140

Gln Asp Leu Val Gly His Glu Glu Ser Ser Ala Asp Glu Tyr Asp Pro
145                 150                 155                 160

His Glu Lys Ala Asn Pro Thr Val Val Ile Val Lys Val Gly Gly
                165                 170                 175

Gly Gln Ser Gly Leu Ile Cys Ala Ala Arg Leu Gly Lys Leu Gly Ile
            180                 185                 190

Arg Ala Leu Val Ile Asp Lys Asn Ala Arg Val Gly Asp Ile Trp Arg
        195                 200                 205

Gln Arg Tyr Ala Glu Ala Leu Pro Ser Phe Ala Val Leu Ser Arg Gln
    210                 215                 220

Glu Thr Gln Val Pro Glu Pro Tyr Ala Ala Tyr Ser Gln Ile Ser Lys
225                 230                 235                 240

Leu Leu Pro Tyr Pro Ser Asn Phe Pro Lys Tyr Leu Pro Lys Gly Lys
                245                 250                 255

Leu Ala Asn Phe Leu Glu Ser Tyr Ala Ile Asn Gln Glu Leu Cys Ile
            260                 265                 270

Trp Leu Ser Ser Thr Val Ser Pro Ser Pro Val Tyr Asp Ser Phe Ser
        275                 280                 285

Ala Arg Trp Thr Val Glu Val Glu His Glu Asn Arg Lys Val Ile Leu
    290                 295                 300

His Pro Lys His Leu Val Leu Ala Thr Gly His Gly Arg Pro Arg Ile
305                 310                 315                 320

Pro Thr Trp Asn Gly Met Asp Asp Phe Gln Gly Thr Leu Tyr His Ser

```
              325                 330                 335
Asp Phe His Arg Asp Ala Glu Lys Phe Arg Gly Lys Cys Val Val Val
                340                 345                 350

Ile Gly Ala Gly Asn Ala Ser Gly Asp Ile Cys Glu Asp Phe Val Ala
                355                 360                 365

Gln Gly Ala Ala Glu Val Thr Ile Val Gln Arg Ser Ala Thr Cys Val
            370                 375                 380

Val Ser Ser Ala Thr Ala Asp Ala Phe Val Phe Lys Leu Pro Phe Ser
385                 390                 395                 400

Asp Lys Thr Pro Ile Glu Glu Leu Asp Phe Arg His Asn Ser Met Pro
                405                 410                 415

Leu Ala Phe Val Leu Gln Leu Met Lys Ser Gly Gly Thr Gln His Met
                420                 425                 430

Lys Ala His Asp Lys Glu His His Glu Gly Leu Arg Lys Ala Gly Phe
                435                 440                 445

Asn Leu Thr Trp Glu Pro Ser Pro Gly Ser Gly Glu Val Gly Leu Leu
            450                 455                 460

Gly Phe Val Phe Glu Arg Ala Gly Ser Gly Thr Met Ile Asp Thr Gly
465                 470                 475                 480

Phe Gly Lys Leu Ile Val Glu Gly Thr Val Lys Val Lys Gln Gly Gln
                485                 490                 495

Asn Ile Ser His Phe Asp Lys Glu Gly Ile Thr Phe Lys Asp Gly Ser
                500                 505                 510

Lys Leu Pro Ala Asp Val Ile Val Ala Ala Thr Gly Asn Glu Leu Thr
            515                 520                 525

Met Asp Ala Ile Arg Ala Val Leu Gly Asp Thr Ile Ala Glu Gln Leu
            530                 535                 540

Pro Pro Lys Val Trp Gly Leu Asp Ala Glu Gly Glu Leu Asn Gln Met
545                 550                 555                 560

Tyr Arg Pro Ser Gly His Pro Gly Leu Trp Phe Ala Val Gly Ser Leu
                565                 570                 575

Gly Met Thr Arg Phe Cys Ser Lys His Leu Gly Leu Gln Ile Leu Ala
            580                 585                 590

Gln Glu Val Gly Ile Ala
            595

<210> SEQ ID NO 123
<211> LENGTH: 515
<212> TYPE: PRT
<213> ORGANISM: Galerina marginata

<400> SEQUENCE: 123

Met Gly Lys Met Ala Tyr His Thr Val Leu Asp Asp Ile Ala Leu Tyr
1               5                   10                  15

Leu Leu Gly Ser Ala Ala Leu Val Ile Phe Tyr Arg Ser Phe Phe Tyr
            20                  25                  30

Pro Tyr Phe Leu Ser Gly Arg Arg Leu Ala Pro Gly Pro Thr Lys Gly
            35                  40                  45

Glu Leu Ser Lys Glu Leu Lys Gln Phe Asn Asn Glu Ile Asn Val His
        50                  55                  60

Phe Leu Arg His Met Val Lys Glu Tyr Gly Pro Ile Phe Arg Leu Val
65              70                  75                  80

Gly Ala Pro Met Ile Pro Gly Pro Gly Leu Val Val Cys Thr Pro Thr
                85                  90                  95
```

```
Ala Gln Gln Arg Ile Leu Val Ser Asn Ser Ile Asn Tyr Gly Gln Pro
            100                 105                 110

Arg Leu Ala Phe Phe Arg Trp Val Thr Gly Gly Leu Phe Thr Leu Pro
            115                 120                 125

Glu Arg Glu His Arg Gly Met Arg Lys Ile Leu Asp Pro Val Phe Ser
            130                 135                 140

Phe Arg Asn Leu Ile Ser Thr Thr Gly Val Tyr Tyr Asn Thr Val Gln
145                 150                 155                 160

Ser Leu Ile Thr Ile Phe Arg Ser Lys Ile Asp Gly Glu Asn Gly Ala
            165                 170                 175

Lys Asp Gly Asp Val Ile Leu Val Tyr Glu Trp Leu Ala Arg Leu Ala
            180                 185                 190

Ile Asp Asn Val Ser Glu Ala Ile Leu Gly Phe Lys Leu Asp Thr Leu
            195                 200                 205

His Asp Pro Asn Asn Glu Leu Ile Thr Thr Leu Asp Glu Leu Ser Arg
            210                 215                 220

Ile Pro Thr Ala Ala Phe Glu Leu Leu Val Arg Val Pro Gly Phe Leu
225                 230                 235                 240

Arg Leu Val Thr Phe Asp Ser Val Arg His Ser Thr Leu Trp Gln Arg
            245                 250                 255

Arg Val Pro Gly Arg Leu Gly Val Phe Phe Thr Phe Met Arg Cys Leu
            260                 265                 270

Ser Thr Ile Arg Lys Asn Ala Leu Ala Ile Lys Ala Thr Ile Leu Gln
            275                 280                 285

Glu Asp Ser Ala Asn Arg Asp Leu Asn Val Ile Ser Val Leu Gln His
            290                 295                 300

Met Gln Ser Ser Asp Glu Thr Ala Asn Ala Asp Ile Ala Gly Asn Ile
305                 310                 315                 320

Ile Met Leu Trp Met Ser Gly Arg Ala Thr Ile Ala Thr Arg Ile Ser
            325                 330                 335

Trp Leu Leu Trp Leu Leu Ala Lys Asp Gln Gln Cys Gln Gln Gln Leu
            340                 345                 350

Arg Asp Glu Ile Ala Pro Leu Phe Ser Arg Asp Pro Arg Pro Asp Tyr
            355                 360                 365

Arg Ser Leu Asp Lys Leu Gln Trp Leu Asp Ser Val Ile Met Glu Ser
            370                 375                 380

Ile Arg Leu Phe Leu Phe Gly Pro Asn Ile Arg Val Ala Leu Asn Asp
385                 390                 395                 400

Asp Tyr Ile Asp Gly Val Phe Val Pro Lys Gly Thr Val Val Ile
            405                 410                 415

Pro Leu Asp Leu Phe Thr Arg Gly Asp Ile Trp Gly Glu Asp Pro Asp
            420                 425                 430

Gln Phe Lys Pro Ala Arg Trp Leu Asp Ser Thr Lys Arg Tyr Lys Ile
            435                 440                 445

Ser Pro Pro Phe Leu Ser Phe Leu Thr Gly Pro His Arg Cys Ile Ala
            450                 455                 460

Lys Gly Met Ala Ile Met Gln Thr Lys Ile Val Ile Ala Ser Leu Ile
465                 470                 475                 480

Ala Asn Phe Glu Phe Lys Pro Ala Tyr Glu Gly Gln His Val Glu Gly
            485                 490                 495

Asn Pro Ser Ile Ile Gly His Gly Met Pro Leu His Val Lys Pro Ile
            500                 505                 510

Arg Pro Ser
```

-continued

515

<210> SEQ ID NO 124
<211> LENGTH: 1318
<212> TYPE: PRT
<213> ORGANISM: Galerina marginata

<400> SEQUENCE: 124

```
Met Pro Tyr Val Pro Asp Pro Lys Tyr Phe Glu His Arg Glu Gln Ser
1               5                   10                  15

Ser Gly Ala Thr Leu Tyr Tyr Cys Leu Val Cys Arg Asp Gly Arg Glu
            20                  25                  30

Arg Gln Pro His His Ile Lys Thr His Glu Ala Ser Gln Ala His Arg
        35                  40                  45

Thr Ala Leu Ser Val Phe Asp Ser Gln Ala Glu Ser Ser Ser Gln Gln
    50                  55                  60

Thr His Gly Asn Pro Thr Gln Pro Gly Tyr Phe Asp Pro Val Ile Asp
65                  70                  75                  80

Asp Ala Val Arg Ala Leu Leu Val Ser Gly Ser Gly Asp Pro His Gln
                85                  90                  95

Pro Leu Tyr Pro Ala Gly His Pro Asn Val Tyr Gly Glu Pro Asn Phe
            100                 105                 110

Thr Asp Ser Arg Arg Thr Ser Pro Val Thr Gly Ile Asp Trp Asp
        115                 120                 125

Gln Phe Glu Ala Gln Glu Asp Thr His Ala Val Pro Ser Ala Gln Asp
    130                 135                 140

Gln Leu Arg Ala Asp Ile Cys Gln Ala Thr Leu Asp Trp Leu Asn Asp
145                 150                 155                 160

Asp Ile Ser Asp Asp Glu Arg Glu Pro Ser Glu Val Asp Ser Val
                165                 170                 175

Asp Ser Asp Ala Glu Ser Asp Arg Glu Pro Ile Pro Asp Asp Gln Pro
            180                 185                 190

Arg Lys Arg Ala Arg Thr Asn Arg Asp Asn Pro Ile Ser Glu Asp Trp
        195                 200                 205

Tyr Pro Trp Gln Asp Lys Ile Thr Cys Thr Leu Asp Ile Leu Met His
    210                 215                 220

Leu Pro Arg Ser Val Phe Ser Arg Lys Gln Leu Asp Leu Phe Leu Trp
225                 230                 235                 240

Leu Leu Arg Val Asn Asn Val Asp Asp Val Pro Thr Gly Lys Ser Met
                245                 250                 255

Lys Met Leu Asn Lys Ile Leu Gln Gly Met Cys Gly Ile Glu Thr Ile
            260                 265                 270

Ala Tyr Glu Gly Lys Leu Gly His Asn Tyr His Val Asn Asn Ile Ala
        275                 280                 285

Gln Ile Leu Ala Gln Glu Leu Cys Asn Pro Lys Val Gly Pro His Ile
    290                 295                 300

Tyr Phe Tyr Pro Glu Asp Ser Gly Asp Asn Leu Ala Glu Ala Arg Gln
305                 310                 315                 320

Ala Ala Arg Trp Leu His Glu Leu Arg Pro Glu Glu Thr Thr Pro Met
                325                 330                 335

Ile His Leu Pro Ser Gly Asp Tyr Tyr Ile Tyr Glu Pro Ala Met Leu
            340                 345                 350

Ser Asn Arg Ser Phe Cys Ile Pro Phe Arg Trp Phe Thr Arg Asn Gly
        355                 360                 365
```

```
Lys Phe His Ala Arg Ala Trp Ser Leu Glu Thr Gly Val Val Asp Asn
    370                 375                 380

Thr Leu Gly Trp Ile Val His Lys Glu Asn Glu Val Glu Ile Ser Glu
385                 390                 395                 400

Asp Asp Leu Leu Lys Asp Phe Thr Arg Phe Ser Ser Asp Cys Glu Ala
                405                 410                 415

Tyr Asn Val Pro His Pro Ser Arg Ile Leu Gly Val Ser Cys Ala Asp
                420                 425                 430

Ser Gly Asn Leu Leu Pro Trp Asn His Thr Asn Pro Val Leu Gly Asn
            435                 440                 445

Arg Trp Arg Gln Leu Ala Lys Gly His Arg Thr Leu Cys Leu Pro Leu
450                 455                 460

Trp Met Tyr Cys Asp Asp Thr Ser Gly Asn Thr Ser Lys Lys Trp Asn
465                 470                 475                 480

Glu His Asn Ser Phe Leu Phe Thr Leu Ala Gly Leu Pro Arg Glu His
                485                 490                 495

Thr Ala Lys Glu Tyr Asn Ile His Phe Leu Cys Thr Ser Asn Leu Ala
                500                 505                 510

Pro Pro Leu Glu Met Met Asp Gly Val Val Ser Gln Ile Glu Ala Ala
            515                 520                 525

Gln Gln Asn Gly Ile Trp Ala Trp Asp Cys Val Arg Lys Glu Pro Val
    530                 535                 540

Leu Ile Phe Pro Thr Ile Leu Ala Leu Leu Gly Asp Asn Pro Met His
545                 550                 555                 560

Ser Glu Phe Ala Cys His Ile Gly Leu Arg Gly Lys Phe Phe Cys Arg
                565                 570                 575

Thr Cys Trp Val Lys Gly Ser Asp Ala Gln Asp Asp Ala Asn Ile Val
                580                 585                 590

Thr Pro Gly Leu His Glu Thr Pro Glu Asn Ser Pro Ala Pro Ser Pro
            595                 600                 605

Ala Pro Ser Pro Ala Pro Ser Pro Ala Pro Ser Pro Ala Pro Ser Pro
610                 615                 620

Ala Leu Ser Met Ala Pro Gln Ser Gln Pro Pro Thr Pro Ser Glu Pro
625                 630                 635                 640

Ser Met Gln Val Pro Ala Pro Pro Ser Thr Ala Ala Pro Thr Lys Ala
                645                 650                 655

Arg Gly Lys Lys Lys Glu Thr Met Ser Ala Met Leu Asn Arg Ile Thr
                660                 665                 670

Ala Phe Ile Lys Pro Gly Arg Leu Arg Asn Lys Ser Glu Thr Gln Lys
                675                 680                 685

Thr Leu Gln Asn Phe Lys Glu Gln Ala Gln Thr Ile Gly Ala Lys Thr
    690                 695                 700

Lys Leu Lys Thr Ala Arg Thr Glu Thr Gly Ile Lys Asp Thr Val Gln
705                 710                 715                 720

Glu Phe Phe Phe Glu Lys Leu Phe Ser Ser Tyr Lys Asn Lys Arg Gly
                725                 730                 735

Pro Gln Ala Lys Gln Glu Ala Leu Asp Gln Ala Val Asn Gln Leu Pro
                740                 745                 750

Ser Asp Ile Thr Ser Pro Val Trp Arg Leu Lys Gly Leu Asp Pro His
                755                 760                 765

Gln Asp Thr Pro Val Glu Ile Leu His Val Val Leu Leu Gly Phe Ile
            770                 775                 780

Lys Tyr Phe Trp Arg Asp Leu Val Gln Asn Gln Ile Asn Asp Asp Gln
```

```
785             790             795             800
Lys Gln Thr Leu Ile Gln Arg Leu Asn Ser Phe Asp Val Thr Gly Leu
                805             810             815
Gly Ile Thr Gln Leu Gly Gly Glu Thr Leu Val Asn Tyr Ala Gly Ser
                820             825             830
Leu Thr Gly Arg Asp Phe Arg Ala Val Ala Gln Val Ala Pro Phe Val
                835             840             845
Ile Tyr Asp Met Val Pro Ala Asp Val Phe Asp Ala Trp Leu Ala Leu
                850             855             860
Ser Lys Leu Val Pro Leu Val Trp Gln Pro Tyr Ile Glu Asn Val Ala
865             870             875             880
Gln Tyr Leu Thr Thr Leu Glu His Glu Ile His Val Phe Leu Leu Arg
                885             890             895
Thr Ala Arg Trp Thr Thr Gly Trp Phe Asn Lys Ser Lys Phe His Ile
                900             905             910
Ile Leu His Leu Pro Ser His Ile Arg Arg Phe Gly Pro Ala Ile Leu
                915             920             925
Phe Ala Thr Glu Ala Phe Glu Ser Phe Asn Ala Val Ile Arg Ala Lys
                930             935             940
Ser Val His Ser Asn Arg Gln Ala Pro Ser Arg Asp Ile Ala Leu Ala
945             950             955             960
Phe Ala Gln Gly Asn Arg Ile Arg His Leu Leu Ser Gly Gly His Phe
                965             970             975
Leu Ser Ala Asp Thr His Met Val Val Asp Pro Asp Gln Pro Gln Leu
                980             985             990
Gly Gln Tyr Glu Arg Leu Ala Arg Gly Arg Trp Arg Ser Val Gly Pro
        995             1000            1005
Gly Pro Gly His Leu Val Ser Ala Glu Pro Ile Leu Pro Ser Tyr
        1010            1015            1020
Leu Gly Ile Pro Pro Gln Ser Thr Thr Ser Ser Ala Gly Leu Cys
        1025            1030            1035
Lys Arg Thr Lys Thr Pro Pro Gln Thr Phe Leu Gln Thr Leu Thr
        1040            1045            1050
Gly Leu Lys Leu Pro Asn Val Ser Arg Pro Gly Ala Arg Glu Leu
        1055            1060            1065
Trp Gln Thr Cys Ser Glu Val Tyr Leu Leu Asn Asp Asp Lys Cys
        1070            1075            1080
Leu Ile Gly His His Val Ile Val Gln Arg Gln Ser Glu Gln Ala
        1085            1090            1095
Ser Phe Val Ser Pro Pro Phe Ile Ala Arg Ile Gly Glu Ile Leu
        1100            1105            1110
Gln Lys Val Gly Ser Ala Asn His Ala His Asp Lys Pro Asp Gly
        1115            1120            1125
Ile Leu Val Gln Thr Leu Lys Ser Ser Glu Val Ala Asp Lys Phe
        1130            1135            1140
Gln Met Pro Arg Leu Val Pro Gln Asn Glu Trp Ser Phe Val Pro
        1145            1150            1155
Leu Ala Asp Ile Leu Cys Thr Val Asn Ala Gln His Asp Cys Asp
        1160            1165            1170
Arg Asn Gly Cys Thr Ala Ser Gly Phe Arg Tyr Val Tyr Gln Glu
        1175            1180            1185
Arg Ile Gln Thr Asn Asp Gln Arg Pro Val Val Glu His Val Asn
        1190            1195            1200
```

Gln Pro Glu Asp Phe Ile Leu Asn Thr Ala Gln Met Arg Asp Ala
    1205                1210                1215

Leu His Leu Gln Lys Phe Arg Ile Arg Ser Arg Ser Leu Asp Glu
    1220                1225                1230

Gln Thr Ile Ile His Glu Ser Val Ala Arg Thr Ile Asn Gln Arg
    1235                1240                1245

Lys Ala Gln Asp Asn Ser Ser Gly Thr Gly Gly Ala Gly Val
    1250                1255                1260

Ser Gly Arg Gly Arg Gly Arg Gly Arg Gly Gly Gly Val
    1265                1270                1275

Glu Gly Pro Ser Thr Ser Arg Gly Arg Gly Gly Ile Glu Gly
    1280                1285                1290

Arg Gly Ala Ser Ser Ser Gly Asn Gly Arg Gly Arg Gly Arg
    1295                1300                1305

Gly Ala Arg Ser Ala Gln Ser Val Pro Phe
    1310                1315

<210> SEQ ID NO 125
<211> LENGTH: 1262
<212> TYPE: PRT
<213> ORGANISM: Galerina marginata

<400> SEQUENCE: 125

Met Pro Arg Lys Lys Pro Ala Pro Glu Cys Phe Glu Thr Asp Glu Ala
1               5                   10                  15

Ser Lys Met Ile Arg Cys Leu Ile Cys Lys Glu Asn Asp Thr Val Gln
            20                  25                  30

Gln Gly Thr Trp Ile Lys His Gly Ser Ala Ser Gln His Ile Glu Thr
        35                  40                  45

Asn Ala His Lys Leu Ala Val Ala Arg Arg Glu Gln Leu Leu Gln Val
    50                  55                  60

Gln Gln Glu Glu Glu Arg Arg Leu Gln Glu Ile Tyr Gly Gly Asn Thr
65                  70                  75                  80

Ile Pro Leu Ser Gly Asn Ala Gln Leu Tyr Pro Thr Tyr Pro Arg Ala
                85                  90                  95

Asn Met Tyr Gly Asn Gln Asp Ala Val Asp Thr Asp Met Asp Asn Gln
            100                 105                 110

Asn Ser Pro Pro Gln Ala Tyr Met Leu Cys Asp Ala Asp Ile Pro Asp
        115                 120                 125

Leu Gly Ile Lys Pro Ile Glu Arg Pro Asp Pro Ser Gln Glu Arg Glu
    130                 135                 140

Arg Leu Arg Gln Gln Val Glu Gln Leu Leu Gln Ala Glu His Glu
145                 150                 155                 160

Asp Glu Phe Gly Ser Pro Asp Pro Asp Asp Leu Thr Ser Thr Asn
                165                 170                 175

Ile Ala Gln Ala Phe Ala Asp Leu Asp Leu Glu Met Leu Asp Glu
            180                 185                 190

Glu Glu Val Phe Asp Tyr Phe Asn Gln Val Ser Pro Glu His Asp Tyr
        195                 200                 205

Tyr Pro Tyr Pro Asn Lys Thr Thr Met Leu Leu Asp Ile Leu Asp Asn
    210                 215                 220

Leu Pro Arg Leu Arg Met Ser Ser Asn Gln Leu Arg Leu Ile Leu Trp
225                 230                 235                 240

Leu Leu Lys Gln Thr Gly Val Ser Asn Val Pro Ser Phe Ser Gly Phe

-continued

```
                245                 250                 255
Arg Asn Met Gln Thr His Leu Arg Asn Met Cys Gly Thr Thr Pro Lys
            260                 265                 270
Gln His Val Ser Ser Leu Gly Asn Ile Phe Tyr Ser Asn Asn Ile Gly
        275                 280                 285
Glu Ser Val Met Arg Asp Phe Ala Asn Pro Glu Val Ala Lys His Leu
    290                 295                 300
His Leu Tyr Pro Glu Glu Thr Glu Gly Pro Ile Ser Glu Val Trp Gln
305                 310                 315                 320
Ala Glu Arg Trp Lys Glu Phe Ala Pro Ser Glu Leu Thr Pro Met Phe
                325                 330                 335
Ser Gln Gly His Arg Gln Phe Phe Ile Asp Glu Val Ala Gln Leu Gln
            340                 345                 350
Asp Gly Gln Tyr Val Ile Pro Arg Asn Trp Val Met Arg Lys Gly Lys
        355                 360                 365
Leu Thr Ser Asp Cys His Ile Val Thr Val Asn Pro Val Arg Phe Ser
    370                 375                 380
Lys Leu His Gly Ser Leu Val Leu Val Leu Lys Gln Cys Phe Gln Ser
385                 390                 395                 400
Gly Trp Thr Leu Leu Ser Glu Thr Gln Ile Phe His Ala Asp Asp Phe
                405                 410                 415
Gln Phe Asn Tyr Phe Asp Val Val Ser Arg Ile Arg Gly Pro Ile Ser
            420                 425                 430
Trp Ser Glu Gly Thr Glu Val Pro Ala Met Pro Asn Asn Leu Arg Glu
        435                 440                 445
Leu Ala Gly Asp Asp Leu Val Val Ile Met Val Pro Leu Trp Cys
    450                 455                 460
Asp Asp Val Ser Gly Asn Lys Ser Lys Gln Tyr Asn Lys His Ile Asn
465                 470                 475                 480
Val Tyr Met Ala Asn Ser Asn Ile Pro Gly Arg Leu Leu Gln Gln Glu
                485                 490                 495
Tyr Phe Val Arg Phe Val Ser Thr Ser Pro Asn Ala Thr Ser Pro Glu
            500                 505                 510
Gln Phe Ser Ala Leu Lys Asp Gln Ile Asn Glu Thr Gln Lys Lys Pro
        515                 520                 525
Ile Gln Cys Tyr Asn Ala His Thr Asn Lys Lys Thr Arg Ala Ile Leu
    530                 535                 540
Arg Val Pro Gly Leu Pro Ala Asp Asn Pro Gln Gln Ser Glu Glu Ser
545                 550                 555                 560
Cys His Met Gly Gly Asn Ala Asn Cys Lys Cys Arg Lys Cys His Val
                565                 570                 575
Gly Gly Pro His Glu Lys Lys Glu Ser Asn Glu Gly Tyr His Glu His
            580                 585                 590
Tyr Leu Thr Gly Ile Lys Arg Ser Ala Glu Glu Thr Arg Leu Glu Leu
        595                 600                 605
Glu Lys Gln Ile Lys Leu Ala Met Tyr Gly Val Glu Lys Pro Ile Asn
    610                 615                 620
Glu Thr Gln Thr Asn Thr Gly Thr Lys Asp Lys Val Ala Gln His Trp
625                 630                 635                 640
Ile Asp Ile Leu Leu Ala Lys Ser Arg Glu Leu Lys Ser Ala Asn Pro
                645                 650                 655
Ser Arg Ser Val Glu Glu Ile Ala Gln Glu Leu Gln Thr Trp Phe Asp
            660                 665                 670
```

-continued

```
Glu Gln Pro Gly Asp Lys Ile Asn Pro Leu Leu Ser Ile Ala Gly Leu
            675                 680                 685

Asp Pro Thr Gln Asp Thr Pro Val Glu Ile Leu His Thr Ile Leu Leu
        690                 695                 700

Gly Ile Val Lys Tyr Ala Trp His His Leu His Ser Asn Trp Thr Glu
705                 710                 715                 720

Ala Glu Gln Asn Leu Phe Thr Val Arg Leu Gln Ser Thr Asp Ile Asp
                725                 730                 735

Gly Leu Ser Val Pro Pro Ile Arg Val Ala Tyr Met Met Gln Tyr Arg
            740                 745                 750

Asn Gly Leu Ile Gly Lys His Phe Lys Thr Leu Met Gln Thr Leu Pro
        755                 760                 765

Phe His Val His Gly Thr Val Ser Asp Ala Gln Phe Lys Leu Val Lys
770                 775                 780

Ala Ile Gly Glu Leu Gly Ser Val Leu Trp Val His Glu Ile Gly Asp
785                 790                 795                 800

Met Glu Lys Tyr Leu Ser Asp Leu Glu Ile Leu Ile Gly Asn Val Leu
                805                 810                 815

Asp Ala Phe Ala Glu Ile Asp Pro Ser Thr Ala Met Tyr Ala Arg Phe
            820                 825                 830

Ile Tyr Glu Pro Met Pro Val Pro Ser Lys Ile Ile Val Lys Leu Lys
        835                 840                 845

Leu His Met Leu Pro His Leu Ile Glu Asp Ile Lys Arg Phe Gly Pro
850                 855                 860

Ala Ile Arg Asn Ser Thr Glu Val Phe Glu Cys Phe Asn Ala Ile Phe
865                 870                 875                 880

Arg Leu Cys Ser Ile Leu Ser Asn His Gln Ala Ala Ser Arg Asp Ile
                885                 890                 895

Ala Leu Lys Phe Ala Ser Met Asp Arg Leu Lys His Met Leu Ser Gly
            900                 905                 910

Gly Tyr Trp Leu Ser Glu Val Glu Glu Gly Lys Phe Glu Trp Ile Arg
        915                 920                 925

Ala Gly Glu Asn Val Arg Asn Ile Leu Gln Ser Glu Pro Thr Ile Gln
930                 935                 940

Arg His Leu Gly Trp Ala Pro Ser Ala Lys Phe Gln Ser Gly Arg Lys
945                 950                 955                 960

Arg Thr Pro Pro Thr Ser Trp Glu Asn Thr Lys Ala Ser Gln Phe Met
                965                 970                 975

Asp Ser Glu Glu Thr Ala Ala Ile Gly Phe Pro Asn Pro Arg Leu Leu
            980                 985                 990

Ser Trp Arg Lys Gly Val Thr Thr Thr Ala Gln Ser Gly Asp Arg Cys
        995                 1000                1005

Ser Thr  Gly Ser Trp Val Val  Ala Arg Asn His Lys  Val Cys Tyr
    1010                1015                1020

Ile Leu Ala Ser His Tyr Cys  Ser Ile Ala Lys Asn  Asp Gln Gly
    1025                1030                1035

Glu Ser  Cys Ile Gly Arg Ile  His Glu Ile Ile Gly  Pro Asp Glu
    1040                1045                1050

Lys Ser  Ala Ser Ser Thr Gly  Ile Ile Thr Leu Glu  Cys Phe Gln
    1055                1060                1065

Leu Gly  Lys Glu His His Pro  Asp Phe Gly Leu Pro  Thr Leu Gln
    1070                1075                1080
```

```
Arg Pro Gln Ala Asp Leu Pro Lys Tyr Ile Leu Lys Ala Trp Gln
    1085                1090                1095

Asp Pro Leu Phe Ile Phe Ser Ala His His Asp Cys His Thr Ala
    1100                1105                1110

Ser Cys Gln Ala Thr Ala Leu Gln Pro Gln Leu Gln Glu Arg Gln
    1115                1120                1125

Leu Thr Ser Arg Met Asn Lys Leu Ile Ala His Asn Asp Ser Asp
    1130                1135                1140

His Phe Ile Ile Asn Leu Tyr Gly Leu His Asn Ala Ile Leu Leu
    1145                1150                1155

Arg Glu Phe Leu Pro Arg Glu Leu Thr Ala Pro Gln Pro Leu His
    1160                1165                1170

Gln Asp Arg Lys Ala Phe His Tyr Glu Val Ala Ala Lys Leu Arg
    1175                1180                1185

Val Gln Gln Ala Glu Lys Arg Ala Lys Thr Asn Ala Arg Arg Lys
    1190                1195                1200

Ala Thr Arg Ala Ala Asn Lys Ala Lys Gln Val Glu Arg Gln Lys
    1205                1210                1215

Gln Asn Pro Asp His Glu Gln Glu Ser Glu Gln Glu Met Asp Glu
    1220                1225                1230

Arg Pro Asn Ser Glu Asn Gly Ser Asp Ile Glu Leu Gly Gly Asp
    1235                1240                1245

Asp Asp Ile Glu Val Glu Thr Arg Arg Lys Arg Arg Arg Asn
    1250                1255                1260

<210> SEQ ID NO 126
<211> LENGTH: 1206
<212> TYPE: PRT
<213> ORGANISM: Hypsizygus marmoreus

<400> SEQUENCE: 126

Met Gly Arg Arg Ala Glu Glu Leu Pro Ala Tyr Val Glu Leu Ser Glu
1               5                   10                  15

Asp Gly Thr Leu Val Arg Cys Asn Leu Cys Leu Met His Asn Arg Leu
            20                  25                  30

Asp Tyr Ser Lys Glu Trp Ile Gln Arg Lys Gly Trp Arg Ser His Lys
        35                  40                  45

Gly Ser Gly Ile His Asp Arg Ser Glu Ala Lys Gln Arg Val Leu Asp
    50                  55                  60

Asp Ala Ala Met Asp Leu Gln Glu Pro Ala Ser Ala Glu Val Glu Val
65                  70                  75                  80

Val Thr Phe Asn Asp Ile Leu Ile Asn Ala Pro Lys Thr Pro Thr
                85                  90                  95

Gly Asn Met Gln Ser Glu Glu Gln Ala Met Trp Asp His Phe Asp Ala
            100                 105                 110

Gly Ser Phe Thr Leu Glu Ala Gly Glu Asp Pro Asn His Ser Ser Gln
        115                 120                 125

Arg Leu Tyr Gln Asp Leu Ala Arg Lys Ala Asp Ala Tyr Gly Ala Trp
    130                 135                 140

Asp Gly Thr Glu Ala Leu Pro Gly Tyr Arg Asp Leu Asp Asp Val Ser
145                 150                 155                 160

Gln Phe Leu Asp Glu Asp Glu Glu Asp Leu Leu Ser Glu Ile Leu
                165                 170                 175

Arg Gly Leu Gly Leu Glu Glu Glu His Glu Asp Ser Ser Asp Arg Asn
            180                 185                 190
```

```
Pro Ala Glu Glu Leu Asn Ser Pro Trp Tyr Pro Tyr Gly Ser Lys Leu
        195                 200                 205

Met Phe Leu Leu Asp Thr Ile Asp Asn Leu Pro Arg Leu Arg Ile Ser
210                 215                 220

Gly Ala Met Met Arg Val Phe Leu Trp Leu Leu Arg Glu Val Gly Val
225                 230                 235                 240

Arg Gln Val Pro Ser Phe Asp Lys Leu Arg Lys Ile Gln Arg Lys Leu
                245                 250                 255

Arg Glu Gly Ser Gly Val Pro Thr Val His Trp Met Ser Pro Lys Gly
                260                 265                 270

Asn Ala Tyr Ser Phe Asn Asp Pro Ala Val Ile Val Ala Asn Asp Trp
        275                 280                 285

Ala Ser Pro Ile Thr Arg Pro His Leu Arg Arg Tyr Pro Val Ile Pro
        290                 295                 300

Lys Asp Gly Val Ile Thr Glu Val Tyr His Ala Glu Lys Trp His Arg
305                 310                 315                 320

Glu Ile Asn Arg His Phe Leu Thr Pro Met Tyr Asp Asp Gly Phe Arg
                325                 330                 335

His Tyr Phe Ile Asp Glu Leu Ala Gln Leu Lys Asp Gly Arg Tyr Ala
        340                 345                 350

Val Pro Val Arg Trp Leu Glu Asp Val Asp Gly Arg Ile Val Ala Asp
        355                 360                 365

Ala Trp Arg Val Glu Leu Glu Asp Asp Asn Arg Ala Thr Ile Ile Asp
370                 375                 380

Thr Ala Thr Val Arg Ile His Ser Gln Glu Leu Ala Leu Asn Phe Glu
385                 390                 395                 400

Glu Ile Ile Glu Ser Asn Leu Met Pro Glu Trp Ser Asp Thr Thr Thr
                405                 410                 415

Glu Ala Gly His Pro Ser Arg Met Pro Asn Pro Asp Arg Ala Leu Ala
        420                 425                 430

Glu Gly Asp Pro Ile Tyr Thr Ser Phe Ile Asp Ile Phe Gly Asp Asp
        435                 440                 445

Val Ser Gly Asn Arg Ser Lys Ser Trp Asn Lys His Trp Asn Met Tyr
450                 455                 460

Ile Ser His Arg Asn Leu Pro Arg Lys Leu Leu His Gln Gln Tyr His
465                 470                 475                 480

Thr His Phe Val Ser Thr Ser Thr Phe Ala Ser Ile Pro Glu Gln Phe
                485                 490                 495

Val Gly Val Lys Glu Ala Ile Glu Ser Thr His Ser Lys Pro Val Lys
        500                 505                 510

Val Arg Asp Ala Asp Thr Gly Lys Gln Ile Arg Leu Lys Ile Tyr Cys
        515                 520                 525

Asn Cys Gly Pro Gly Asp Asn Pro Ser Gln Ser Glu Thr Ser Gly His
530                 535                 540

Ile Gly Gly Asn Gly Asn Tyr Pro Cys Arg Lys Cys His Thr Gly Gly
545                 550                 555                 560

Thr Gln Lys Ser Lys Glu Thr Asp Glu Gly Phe Tyr Lys Met Phe Thr
                565                 570                 575

Ala Gly Glu Ala Arg Ser Ser Lys Glu Thr Leu Ala Glu Val Lys Ser
        580                 585                 590

Gln Val Glu Ala Ala Cys Thr Gly Val Ala Lys Thr Val Ala Asp Ala
        595                 600                 605
```

-continued

```
Gln Ser Asp Thr Gly Val Lys Asp Ala Tyr Thr Gln Tyr Trp Ile Asp
610             615                 620

Ala Ile Ile Glu Lys Ala Arg Ala Met Gln Lys Glu Asn Pro Gly Met
625             630                 635                 640

Pro Thr Thr Thr Ile Gln Ala Thr Leu Ile Lys Trp Val Tyr Asp His
                645                 650                 655

Glu Glu Ala Ile Tyr Asn Ser Phe Leu Thr Leu Asp Gly Phe Asp Ala
                660                 665                 670

Ser Arg Asp Thr Pro Val Glu Ile Leu His Thr Ile Leu Leu Gly Ile
                675                 680                 685

Val Lys Tyr Leu Trp His Arg Ser His Thr Ser Trp Asn Ala Ala Gln
690             695                 700

Lys Lys Ile Tyr Ser Thr Arg Leu Gln Gly Thr Asn Thr Gln Gly Leu
705             710                 715                 720

Ser Ile His His Ile Arg Ala Asn Tyr Ile Met Gln Tyr Ala Asn Ser
                725                 730                 735

Leu Ile Gly Arg Gln Leu Lys Thr Leu Ala Gln Val Asn Val Phe His
                740                 745                 750

Val Tyr Asp Leu Val Asp Pro Leu Arg Phe Leu Phe Thr Lys Ala Thr
                755                 760                 765

Gly Glu Leu Cys Ala Leu Leu Trp Phe Thr Glu Ile Arg Asp Leu Glu
                770                 775             780

Glu Tyr Leu Ser Asp Val Asp Ile Ala Ala Ala Asn Val Leu Asp Ile
785                 790                 795                 800

Ala Ala Val Ile Asp Pro Ser Lys Ile Val Ser Lys Ile Lys Tyr His
                805                 810                 815

Leu Leu Ser His Leu Arg Glu Asp Ile Ile Arg Phe Gly Pro Leu Val
                820                 825                 830

Gly Val Ala Thr Glu Val Phe Glu Cys Phe Asn Ala Val Phe Arg Tyr
                835                 840                 845

Cys Ser Ile Leu Ser Asn His Leu Ala Pro Ser Arg Asp Ile Ala Tyr
850                 855                 860

Lys Leu Ala Ala Gln Glu Thr Met Lys His Phe Leu Ser Gly Gly Trp
865                 870                 875                 880

Trp His Val Lys Asp Ser Val Asp Leu Gln Gly Asn Pro Lys Trp Val
                885                 890                 895

Gln Pro Gly Pro Ser Val Arg Thr Phe Met Ala Ser Asn Pro Val Leu
                900                 905                 910

His Thr Leu Cys Gly Trp Thr Arg Asn Asn Asp Ser Thr Pro Gly Thr
                915                 920                 925

Val Lys Ser Glu Pro Arg Lys Arg Gly Pro Asp Lys Gln Thr Leu Leu
930                 935                 940

Pro Leu Val Arg Leu Ala Trp Leu Glu Thr Gln Gly Ser Arg Ala Leu
945                 950                 955                 960

Asn Asn Thr Ser Pro Asn Asn Glu Thr Gln Trp Gln Arg Cys Lys Tyr
                965                 970                 975

Val Ile Ala Glu Thr Gln Asp Gln Cys Asn Val Gly Ser Trp Val Phe
                980                 985                 990

Ala Arg Ser Pro Leu Leu Glu Asn Ile Pro Ile Pro Gly Arg Ile Val
                995                 1000                1005

Glu Ile Leu Gln Asp Thr Ser Ala Ser Pro Ser Ala Phe Val Val
        1010            1015            1020

Ile Asp Val Phe Gln Val Ser Ala Thr Arg Asp Glu Val Phe Gly
```

```
                1025                1030                1035
Met Pro Val Leu Leu Arg Arg Phe Asn Glu Cys Cys Leu His Val
    1040                1045                1050

Ile Pro Ala Ser Ser Val Ile Phe Asp Phe Asn Ala Gln His Asp
    1055                1060                1065

Cys Arg Tyr Ala Lys Cys Glu Ala Thr Gly Glu Gln Pro Leu Ile
    1070                1075                1080

Gln Glu Arg Val Pro Ser Gly Val Thr Glu Asn Phe Val Val His
    1085                1090                1095

Lys Ala Ile Asp Arg Tyr Leu Ile Asn Ile His Ala Leu His Asn
    1100                1105                1110

Ala His Leu Ile Arg Ala Thr Leu Pro Arg Asp Leu Thr Ala Pro
    1115                1120                1125

Ile Pro Tyr Ala Pro Asn Arg Glu Ala His His Ser Ala Ile Ala
    1130                1135                1140

Ala Glu Leu Arg Ser Ala Gln Asp Thr Lys Arg Ala Lys Thr Ala
    1145                1150                1155

Ala Lys Thr Ala Ala Asn Ala Ala Ala Lys Lys Ala Glu Ala Ala
    1160                1165                1170

Leu Lys Asp Thr Thr Ser Gly Pro Ala Ala Lys Arg Arg Arg Val
    1175                1180                1185

Asp Asp Glu Gly Ser Gly Glu Glu Asp Asn Arg Asp Val Asp Met
    1190                1195                1200

Val Ser Val
    1205

<210> SEQ ID NO 127
<211> LENGTH: 1213
<212> TYPE: PRT
<213> ORGANISM: Galerina marginata

<400> SEQUENCE: 127

Met Ala Lys Gly Arg Lys Leu Asn Asn Pro Leu Pro Asp Phe Ile Glu
1               5                   10                  15

Ile Ser Asn Asp Gly Leu Gln Val Arg Cys Thr Leu Cys Leu Ala Ala
                20                  25                  30

Arg Gln His Asn Gly Ser Gly Trp Ile Lys Arg Gly Ser Val Ser Asn
            35                  40                  45

His Leu Lys Ser Asp Asn His Thr Asn Ser Leu Glu Ala His Glu Met
        50                  55                  60

Lys Lys Ser Ala Glu Lys Ala Glu Gly Arg Ser Val Gln Glu Glu Ile
65                  70                  75                  80

Ala Met Glu Glu Gly Met Asp Phe Val Ile Leu Ser Ser Lys Ile Gln
                85                  90                  95

Pro Glu Ile Thr Ala Pro Ala Arg Ala Pro Arg Arg Ser Asn Glu Glu
                100                 105                 110

Gln Glu Met Trp Asp Arg Tyr Thr Leu Gly Gly Glu Val Phe Asp Ala
            115                 120                 125

Gly Val Asp His Thr Leu Val Glu Ala Glu Arg Lys Arg Leu Glu
        130                 135                 140

Arg Glu Ala Thr Asp Phe Asp Leu Trp His Gly Ala Asp Phe Leu Pro
145                 150                 155                 160

Glu Glu Asp Pro Asn Asp Gly Glu Leu Leu Asp Glu Leu Glu Gln
                165                 170                 175
```

```
Asp Asp Ile Leu Ser Glu Leu Leu Arg Asn Ala His Leu Asn Ala Pro
            180                 185                 190

Asp Ala Ala Asp Val Leu Thr Glu Glu Pro Arg Ala Ala Ala Asp Pro
        195                 200                 205

Arg Ile Cys Asp Ala Trp Ser Pro Tyr Glu Ser Lys Met Met Phe Leu
        210                 215                 220

Leu Asp Thr Leu Asp Asn Leu Pro Arg Leu Arg Ile Ser Asn Ser Leu
225                 230                 235                 240

Met Asn Val Phe Leu Trp Ile Leu Arg Glu Gly Gly Ala Arg Asp Val
            245                 250                 255

Pro Ser Leu Tyr His Leu Arg Gln Val Gln Thr Thr Leu Arg Lys Ser
            260                 265                 270

Thr Gly Val Pro Thr Thr Gln His Lys Ser Pro Lys Gly Asn Val Tyr
            275                 280                 285

Ser Met Asn Asp Pro Arg Thr Leu Val Ala Met Asp Trp Ala Asn Pro
            290                 295                 300

Val Ile Cys Asp His Ile Arg Arg Tyr Pro Val Ile Pro Arg Asn Gly
305                 310                 315                 320

Val Ile Ser Glu Val Tyr His Ala Gln Lys Trp Arg Lys Asp Val Asp
                325                 330                 335

Pro His Thr Leu Ser Pro Met Tyr Asp Ala Gly Asn Cys His Tyr Tyr
            340                 345                 350

Ile Asp Glu Val Ala Arg Leu Lys Asn Gly Thr Phe Ile Ile Pro Val
            355                 360                 365

Arg Trp Leu Glu Asp Glu Asp Arg Asn Val Cys Ala Asp Ala Tyr Val
        370                 375                 380

Val Gln Phe Asp Asp Gln Phe Ile Ala Ser Val Val Asp Gly Glu Thr
385                 390                 395                 400

Ile Ile Val Gln Ala Ser Asp Leu Gln Asn Asn Phe Leu Asp Leu Lys
                405                 410                 415

Asp Met Gly Leu Leu Pro Thr Trp Gly Asn Gln Thr Ile Glu Ser Gly
            420                 425                 430

His Pro Ala Arg Met Pro Asn Pro Asp Arg Ala Leu Ala Glu Gly Asp
            435                 440                 445

Pro Leu Tyr Thr Ser Trp Ile Asp Val Phe Gly Asp Asp Val Ser Gly
450                 455                 460

Asn Arg Ser Lys Asn Trp Asn Lys His Trp Asn Ile Tyr Ile Ser His
465                 470                 475                 480

Arg Asn Leu Pro Arg Lys Leu Leu Gln Gln Glu Phe His Thr His Phe
                485                 490                 495

Val Ser Thr Ser Pro Val Ala Ser Val Thr Glu Gln Phe His Gly Ile
            500                 505                 510

Lys Gln Val Ile Glu Leu Thr His Lys Ser Pro Val Lys Val Arg His
            515                 520                 525

Gly Thr Ser Gly Ala Gln Ile Arg Phe Lys Ile Asn Val Asn Cys Gly
            530                 535                 540

Pro Gly Asp Asn Pro Ala Gln Ser Glu Val Cys Gly His Ile Gly Val
545                 550                 555                 560

Asn Gly Asn Lys Leu Cys Arg Lys Cys His Thr Gly Thr His Thr His Glu
                565                 570                 575

Val Lys Glu Ser Asp Glu Gly Phe Asn Ser Leu Phe Glu Pro Gly Asp
            580                 585                 590

Ala Arg Ser Ala Gln Glu Ile Val Ala Asp Val Glu Ser Gln Val Gln
```

```
                        595                     600                     605
Leu Ala Cys Leu Gly Ile Ala Gln His Val Gln Asn Gln Gln Thr Lys
610                     615                     620

Asn Gly Ile Lys Asp Ala Tyr Thr Gln Tyr Trp Ile Asp Tyr Leu Ile
625                     630                     635                     640

Asn Arg Ala Arg Thr Leu Arg Lys Glu Gln Pro Arg Thr Thr Ala
                        645                     650                     655

Asp Ile Gln Ser Glu Leu Leu Val Trp Val Gln Glu His Lys Asp Glu
                        660                     665                     670

Ile Tyr Asn Pro Phe Leu Lys Leu Asp Gly Phe Asp Ala Ala Val Asp
                        675                     680                     685

Thr Pro Val Glu Ile Leu His Thr Ile Leu Leu Gly Ile Val Lys Tyr
                        690                     695                     700

Leu Trp His Gly Ser His Thr Ser Trp Thr Ala Ile Gln Lys Gln Thr
705                     710                     715                     720

Tyr Ser Val Arg Leu Gln Ser Thr Asp Thr Ser Gly Leu Ser Ile His
                        725                     730                     735

Ala Ile Arg Ala Asn Tyr Ile Met Gln Tyr Ala Asn Ser Leu Ile Gly
                        740                     745                     750

Arg Gln Phe Lys Thr Ile Ala Gln Val Asn Val Phe His Val Tyr Asp
                        755                     760                     765

Leu Val Asp Thr Thr Gln Phe Leu Leu Thr Lys Ala Val Gly Glu Leu
                        770                     775                     780

Thr Ala Leu Leu Trp Ile Pro Glu Ile Ala Asn Met Glu Glu Tyr Leu
785                     790                     795                     800

Leu Asp Val Glu Ala Ala Ala Asn Val Leu Asp Leu Phe Ala Leu
                        805                     810                     815

Ile Asp Pro Ser Lys Met Thr Asn Lys Leu Lys Leu His Leu Leu Val
                        820                     825                     830

His Leu Lys Ala Asp Ile Leu Arg Phe Gly Pro Leu Val Gly Val Ala
                        835                     840                     845

Thr Glu Thr Phe Glu Cys Phe Asn Ala Ile Phe Arg Phe Cys Ser Ile
850                     855                     860

Tyr Ser Asn His Leu Ala Pro Ser Arg Asp Ile Ala Phe Gln Leu Ala
865                     870                     875                     880

Ser Gln Glu Val Leu Lys Tyr Arg Leu Thr Gly Gly Trp Pro Ala
                        885                     890                     895

Ser Asp Gly Glu Trp Lys Arg Pro Gly Pro Ser Val Arg Asn Phe Ile
                        900                     905                     910

His Asp His Pro Thr Leu Gln Ala Leu Leu Gly Trp Thr Lys Glu Glu
                        915                     920                     925

Lys Leu Val Asn Gly Ser Phe Arg Leu Glu Pro Leu Lys Arg Asp Ala
                        930                     935                     940

Ser Gln Lys Ile Glu Ser Arg Lys His Leu Pro Trp Leu Gln Thr Gln
945                     950                     955                     960

Gly Ala Lys Ala Val Asn Ser Ser Glu Asp Asn Asp Ser Lys Trp Thr
                        965                     970                     975

Ala Cys Arg Phe Ala Val Ala Asn Ser Gly Asp Lys Cys Ser Val Gly
                        980                     985                     990

Ser Trp Val Phe Ala Thr Ser Pro  Phe Asn Ser Asn Gln  Ser Val Thr
                        995                    1000                    1005

Gly Arg  Ile Val Glu Val Leu  Ala Glu Ser Glu  Gly  Lys Arg Ala
        1010                   1015                    1020
```

```
Val Val Val Leu Asp Ile Phe Glu Val Cys Ser Thr Arg His Lys
    1025                1030                1035

Ile Phe Gly Met Pro Met Leu Ala Arg Arg His Glu Glu Pro Val
    1040                1045                1050

Tyr Ala Val Ile Ala Ser Thr Asn Ile Glu Phe Leu Tyr Asn Val
    1055                1060                1065

Gln His Asp Cys Pro Leu Ala Lys Cys Thr Ala Ser Gly Lys Gln
    1070                1075                1080

Pro Leu Ile Gln Glu Arg Val Glu Ser Gly Leu Phe Lys Thr Tyr
    1085                1090                1095

Ile Glu His Lys Pro Ile Glu Arg Phe Val Ile Asn Thr His Ala
    1100                1105                1110

Phe His Asn Ala His Arg Leu Arg Ala Val Leu Gln Arg Ser Leu
    1115                1120                1125

Val Val Pro Ile Pro Leu Tyr Pro Pro Glu Ile Arg Lys Thr Lys
    1130                1135                1140

His Ala Glu Phe Ala His Asn Leu Gln Ala Thr Gln Lys Val Lys
    1145                1150                1155

Leu Glu Ala Arg Ala Ala Gln Lys Ala Lys Glu Ile Ile Thr Pro
    1160                1165                1170

Ala Asp Lys Thr Asp Ser Thr Ile Pro Lys Lys Arg Thr Arg Ser
    1175                1180                1185

Glu Met Glu Thr Glu Thr Asp Asp Thr Ala Ile Ala Thr Gln Ala
    1190                1195                1200

Asp Val Phe Phe Asn Ala Gln Gly Cys Pro
    1205                1210

<210> SEQ ID NO 128
<211> LENGTH: 517
<212> TYPE: PRT
<213> ORGANISM: Galerina marginata

<400> SEQUENCE: 128

Met Val Gln Ile Lys Arg Leu Leu Gly Phe Leu Ser Ser Pro Ser
1               5                   10                  15

Gln Thr Pro Leu Glu Ser Asn His Gly Pro Val Pro Ser Lys Ser Ile
                20                  25                  30

Ala Val Val Gly Ala Gly Ser Ala Gly Leu Ala Met Leu Arg Thr Leu
                35                  40                  45

Val Glu Leu Glu Ala Phe Ser Arg Asn Asn Trp Glu Val Val Leu Tyr
    50                  55                  60

Glu Glu Arg Glu Ser Val Gly Gly Ile Trp Leu Pro Asp Asn Asn Asp
65                  70                  75                  80

Val Phe Pro Pro Glu Ile Pro Lys Thr Pro Leu Tyr Pro Leu Leu Arg
                85                  90                  95

Thr Asn Thr Pro Val Pro Ser Met Thr Tyr Pro Gly Phe Pro Phe Pro
                100                 105                 110

Pro Ser Thr Pro Leu Tyr Pro Arg His Asp His Val Glu Ala Tyr His
            115                 120                 125

Leu Arg Tyr Ala Arg Arg His Asn Leu Leu Asp Phe Ile Lys Phe Asp
        130                 135                 140

Thr Met Val Glu Lys Ala Phe Trp Asn Gly Thr Pro Glu Glu Gly Tyr
145                 150                 155                 160

Trp Asn Leu Thr Leu Ser Ser Lys Glu Gly Arg Met Arg Tyr Lys Thr
```

```
                    165                 170                 175
Phe Asp His Leu Val Ala Thr Gly Asn Asn His Ile Pro His Ile
            180                 185                 190
Pro Val Trp Lys Gly Gln Glu Asp Trp Leu Ala Ser Pro Asn His
            195                 200                 205
Ser Arg Lys Ile Ile His Ser Val Tyr Tyr Arg Gly Pro Glu Ala Phe
210                 215                 220
Ser Asn Gln Thr Val Leu Ile Val Gly Asn Gly Ser Gly Arg Asp
225                 230                 235                 240
Ala Ala Thr Gln Ile Leu Gly Tyr Ala Ser Gln Thr Phe Met Ser Ile
            245                 250                 255
Arg Arg Ser Tyr Gly Pro Val Asp Asp Gly Val Ile Val Lys Pro Asp
            260                 265                 270
Ile Ser His Phe Thr Glu Ala Gly Val Val Phe Val Asp Gly Thr Ile
            275                 280                 285
Leu Asp Pro Asp Val Ile Leu Leu Gly Thr Gly Tyr Glu Met Gln Lys
            290                 295                 300
Pro Leu Leu Ser Glu Gly Gly Glu Leu Ser Phe Asp Pro Thr Ala Lys
305                 310                 315                 320
Asp Asn Ser Ser Val Arg Gly Thr Leu Val Thr Asn Gly His Tyr Ile
                325                 330                 335
Phe Pro Leu His Arg His Ile Phe Ser Leu Ser Pro Arg Tyr Pro Pro
            340                 345                 350
Asn Ala Leu Ala Phe Ile Gly Leu Leu Ser Phe Ile Ala Ser Cys Pro
            355                 360                 365
Ser Asp Ile Ala Gln Ser Leu Phe Ala Ala His Ala Ile Leu Asp Pro
370                 375                 380
Ser Ile Leu Pro Pro Arg His Leu Leu Leu Glu Glu Leu Ala Ser Tyr
385                 390                 395                 400
Glu Asp Lys Ala Arg Arg Gln Gly Leu Asp Pro Tyr Leu Lys Gly Pro
                405                 410                 415
Ile Met Leu Asn Asn Thr Ser Asn Asp Tyr Gln Asp Glu Leu Val Glu
                420                 425                 430
Tyr Leu Lys Gln Lys Asn Ala Ile Pro Asp Asp Gly Lys Lys Phe Val
            435                 440                 445
Glu Glu Trp Arg Arg Glu Ile Leu Ala Tyr His Tyr Leu Gln Arg Gly
            450                 455                 460
Trp Ser Arg Ile Glu Lys Leu Gly Met Gly Pro Ala Trp Thr Glu Gly
465                 470                 475                 480
Val Lys Thr Glu Ala Gln Trp Phe Asp Leu Met Thr Arg Val Asn Glu
                485                 490                 495
Trp Gln Lys Asn Trp Glu Thr Glu Asn Gly Ile Ala Phe Arg Val Asp
            500                 505                 510
Leu Asp Leu Thr Gly
            515

<210> SEQ ID NO 129
<211> LENGTH: 28
<212> TYPE: PRT
<213> ORGANISM: Gypsophila vaccaria

<400> SEQUENCE: 129

Asp Met Leu Arg Phe His Lys Phe Thr Leu Gly Tyr Leu Trp Thr Gly
1               5                   10                  15
```

-continued

Asp Tyr Gly Cys Ser Asp Lys Glu Glu Glu Phe Lys
            20                  25

<210> SEQ ID NO 130
<211> LENGTH: 28
<212> TYPE: PRT
<213> ORGANISM: Gymnopus fusipes

<400> SEQUENCE: 130

Asp Met Leu Lys Phe Pro Lys Phe Thr Phe Gly Ala Leu Leu Arg Ser
1               5                   10                  15

Glu Tyr Gly Asp Pro Glu Asp Pro Glu Ala Phe Asp
            20                  25

<210> SEQ ID NO 131
<211> LENGTH: 28
<212> TYPE: PRT
<213> ORGANISM: Lentinula raphanica

<400> SEQUENCE: 131

Asp Met Leu Arg Phe Pro Lys Phe Thr Phe Gly Ala Leu Trp Cys Ser
1               5                   10                  15

Glu Tyr Gly Asp Pro Asp Asp Pro Glu Ala Phe Asp
            20                  25

<210> SEQ ID NO 132
<211> LENGTH: 28
<212> TYPE: PRT
<213> ORGANISM: Lentinula novae-zelandiae

<400> SEQUENCE: 132

Asp Met Leu Arg Phe Pro Lys Phe Thr Phe Gly Ala Leu Trp Arg Ser
1               5                   10                  15

Glu Tyr Gly Asp Pro Glu Asp Pro Glu Asp Phe Asp
            20                  25

<210> SEQ ID NO 133
<211> LENGTH: 28
<212> TYPE: PRT
<213> ORGANISM: Lentinula lateritia

<400> SEQUENCE: 133

Asp Met Leu Arg Phe Pro Lys Phe Thr Phe Gly Ala Leu Trp Arg Ser
1               5                   10                  15

Glu Tyr Gly Asp Pro Glu Asp Pro Glu Asp Phe Asp
            20                  25

<210> SEQ ID NO 134
<211> LENGTH: 28
<212> TYPE: PRT
<213> ORGANISM: Lentinula edodes

<400> SEQUENCE: 134

Asp Met Leu Arg Phe Pro Lys Phe Thr Phe Gly Ala Leu Trp Arg Ser
1               5                   10                  15

Glu Tyr Gly Asp Pro Glu Asp Pro Glu Asp Phe Asp
            20                  25

<210> SEQ ID NO 135
<211> LENGTH: 28
<212> TYPE: PRT
<213> ORGANISM: Dendrothele bispora -continued

<400> SEQUENCE: 135

Asp Met Leu Arg Phe Pro Lys Phe Thr Phe Gly Ala Leu Trp Cys Ser
1               5                   10                  15

Glu Tyr Gly Asp Pro Glu Asp Pro Glu Ala Phe Asp
            20                  25

<210> SEQ ID NO 136
<211> LENGTH: 28
<212> TYPE: PRT
<213> ORGANISM: Omphalotus olearius

<400> SEQUENCE: 136

Asp Met Leu Arg Phe Pro Lys Phe Thr Phe Gly Ala Ser Trp Arg Ser
1               5                   10                  15

Glu Tyr Gly Asp Pro Glu Asp Pro Glu Asp Phe Asp
            20                  25

<210> SEQ ID NO 137
<211> LENGTH: 28
<212> TYPE: PRT
<213> ORGANISM: Galerina marginata

<400> SEQUENCE: 137

Asp Leu Leu Lys Phe His Lys Phe Thr Gly Gly Gln Ala Trp Ile Ser
1               5                   10                  15

Glu Tyr Gly Asn Pro Ser Ile Pro Glu Glu Phe Asp
            20                  25

<210> SEQ ID NO 138
<211> LENGTH: 28
<212> TYPE: PRT
<213> ORGANISM: Amanita bisporigera

<400> SEQUENCE: 138

Asp Leu Leu Lys Phe Asn Lys Phe Thr Gly Gly Met Ala Trp Thr Ser
1               5                   10                  15

Glu Tyr Gly Asn Pro Phe Ile Lys Glu Asp Phe Asp
            20                  25

<210> SEQ ID NO 139
<211> LENGTH: 28
<212> TYPE: PRT
<213> ORGANISM: Galerina marginata

<400> SEQUENCE: 139

Asp Leu Leu Lys Phe His Lys Phe Thr Ile Gly Lys Ala Trp Thr Ser
1               5                   10                  15

Asp Tyr Gly Asn Pro Asp Asp Pro Asn Asp Phe Asp
            20                  25

<210> SEQ ID NO 140
<211> LENGTH: 28
<212> TYPE: PRT
<213> ORGANISM: Amanita bisporigera

<400> SEQUENCE: 140

Asp Leu Leu Lys Phe Pro Lys Phe Thr Ile Gly Lys Ala Trp Ile Ser
1               5                   10                  15

Asp Tyr Gly Asp Pro Glu Asp Pro Arg Asp Phe Asp
            20                  25

```
<210> SEQ ID NO 141
<211> LENGTH: 58
<212> TYPE: DNA
<213> ORGANISM: Gymnopus fusipes

<400> SEQUENCE: 141
cctcagtttc ccaagttcac gtttggtgct tgttgcgtt cggaatatgg cgatgtat      58

<210> SEQ ID NO 142
<211> LENGTH: 16
<212> TYPE: PRT
<213> ORGANISM: Gymnopus fusipes

<400> SEQUENCE: 142

Phe Pro Lys Phe Thr Phe Gly Ala Leu Leu Arg Ser Glu Tyr Gly Asp
1               5                   10                  15

<210> SEQ ID NO 143
<211> LENGTH: 35
<212> TYPE: PRT
<213> ORGANISM: Gypsophila vaccaria

<400> SEQUENCE: 143

Ser Ala Ala Glu Tyr Leu Ile Ser Ser Gly Tyr Thr Lys Ala Arg Arg
1               5                   10                  15

Val Ala Ile Glu Gly Gly Ser Asn Gly Gly Leu Leu Val Ala Ala Cys
            20                  25                  30

Ile Asn Gln
        35

<210> SEQ ID NO 144
<211> LENGTH: 35
<212> TYPE: PRT
<213> ORGANISM: Gymnopus fusipes

<400> SEQUENCE: 144

Ala Ala Ala Glu Trp Leu Ile Ala Asn Lys Tyr Ala Lys Lys Asp Cys
1               5                   10                  15

Val Ala Ile Arg Gly Gly Ser Ser Gly Gly Ile Leu Thr Thr Ala Cys
            20                  25                  30

Ala Asn Gln
        35

<210> SEQ ID NO 145
<211> LENGTH: 35
<212> TYPE: PRT
<213> ORGANISM: Lentinula raphanica

<400> SEQUENCE: 145

Ala Ala Ala Glu Trp Leu Ile Ala Asn Lys Tyr Ala Lys Ser Asn Cys
1               5                   10                  15

Val Ala Ile Arg Gly Gly Ser Asn Gly Gly Val Leu Thr Thr Ala Cys
            20                  25                  30

Thr Asn Gln
        35

<210> SEQ ID NO 146
<211> LENGTH: 35
<212> TYPE: PRT
<213> ORGANISM: Lentinula novae-zelandiae

<400> SEQUENCE: 146
```

-continued

Ala Ala Thr Lys Trp Leu Val Ala Asn Lys Tyr Ala Asn Lys Tyr Asn
1               5                   10                  15

Val Ala Ile Arg Gly Gly Ser Asn Gly Gly Val Leu Thr Thr Ala Cys
            20                  25                  30

Ala Asn Gln
        35

<210> SEQ ID NO 147
<211> LENGTH: 35
<212> TYPE: PRT
<213> ORGANISM: Lentinula lateritia

<400> SEQUENCE: 147

Ala Ala Thr Lys Trp Leu Val Ala Asn Lys Tyr Ala Asn Lys Tyr Asn
1               5                   10                  15

Val Ala Ile Arg Gly Gly Ser Asn Gly Gly Val Leu Thr Thr Ala Cys
            20                  25                  30

Ala Asn Gln
        35

<210> SEQ ID NO 148
<211> LENGTH: 35
<212> TYPE: PRT
<213> ORGANISM: Lentinula edodes

<400> SEQUENCE: 148

Ala Ala Thr Lys Trp Leu Val Ala Asn Lys Tyr Ala Asn Lys Tyr Asn
1               5                   10                  15

Val Ala Ile Arg Gly Gly Ser Asn Gly Gly Val Leu Thr Thr Ala Cys
            20                  25                  30

Ala Asn Gln
        35

<210> SEQ ID NO 149
<211> LENGTH: 35
<212> TYPE: PRT
<213> ORGANISM: Dendrothele bispora

<400> SEQUENCE: 149

Ala Ala Thr Glu Trp Leu Val Ala Asn Lys Tyr Ala Asn Lys Asp Arg
1               5                   10                  15

Val Ala Ile Arg Gly Gly Ser Asn Gly Gly Val Leu Thr Thr Ala Cys
            20                  25                  30

Ala Asn Gln
        35

<210> SEQ ID NO 150
<211> LENGTH: 35
<212> TYPE: PRT
<213> ORGANISM: Omphalotus olearius

<400> SEQUENCE: 150

Ala Ala Thr Glu Trp Leu Ile Ala Asn Lys Tyr Ala Ser Lys Asp Arg
1               5                   10                  15

Ile Ala Ile Arg Gly Gly Ser Asn Gly Gly Val Leu Thr Thr Ala Cys
            20                  25                  30

Ala Asn Gln
        35

<210> SEQ ID NO 151

<211> LENGTH: 35
<212> TYPE: PRT
<213> ORGANISM: Galerina marginata

<400> SEQUENCE: 151

Ala Ala Ala Gln Phe Leu Val Lys Asn Lys Tyr Ala Ala Pro Gly Lys
1               5                   10                  15

Val Ala Ile Asn Gly Ala Ser Asn Gly Gly Leu Leu Val Met Gly Ser
            20                  25                  30

Ile Val Arg
        35

<210> SEQ ID NO 152
<211> LENGTH: 35
<212> TYPE: PRT
<213> ORGANISM: Amanita bisporigera

<400> SEQUENCE: 152

Ala Ala Ala Gln Phe Leu Val Lys Asn Lys Tyr Ala Ala Pro Gly Lys
1               5                   10                  15

Val Ala Ile Thr Gly Ala Ser Asn Gly Gly Phe Leu Val Cys Gly Ser
            20                  25                  30

Val Val Arg
        35

<210> SEQ ID NO 153
<211> LENGTH: 35
<212> TYPE: PRT
<213> ORGANISM: Galerina marginata

<400> SEQUENCE: 153

Ala Ala Thr Gln Tyr Leu Val Lys Asn Lys Tyr Ala Ala Pro Asp Lys
1               5                   10                  15

Val Thr Ile Asn Gly Gly Ser Asn Gly Gly Leu Leu Val Ser Ala Cys
            20                  25                  30

Val Asn Arg
        35

<210> SEQ ID NO 154
<211> LENGTH: 35
<212> TYPE: PRT
<213> ORGANISM: Amanita bisporigera

<400> SEQUENCE: 154

Ala Ala Thr Gln Phe Leu Val Lys Asn Lys Tyr Ala Ala Gly Gly Lys
1               5                   10                  15

Val Ala Ile Asn Gly Gly Ser Asn Gly Gly Leu Leu Val Ala Ala Cys
            20                  25                  30

Val Asn Arg
        35

<210> SEQ ID NO 155
<211> LENGTH: 19
<212> TYPE: DNA
<213> ORGANISM: Gymnopus fusipes

<400> SEQUENCE: 155 cgcgggggt ccagcggaa                                              19

<210> SEQ ID NO 156
<211> LENGTH: 6

```
<212> TYPE: PRT
<213> ORGANISM: Gymnopus fusipes

<400> SEQUENCE: 156

Arg Gly Gly Ser Ser Gly
1               5
```

What is claimed is:

1. A method for identifying a molecule that elicits degradation of a first test protein in a host cell, the method comprising:
   (a) expressing in the host cell:
      (i) an E3 ubiquitin ligase; and
      (ii) a first fusion protein comprising a first DNA-binding moiety, the first test protein, and a first gene-activating moiety;
      wherein (i) the host cell comprises a promoter sequence for controlling expression of a death agent and (ii) the first DNA-binding moiety specifically binds to the promoter sequence; and
   (b) delivering the molecule to the host cell;
   wherein, in the absence of the molecule, expression of the death agent is activated; and
   wherein, in the presence of the molecule, the E3 ubiquitin ligase ubiquitinates the first fusion protein thereby eliciting degradation of the first fusion protein in the host cell.

2. The method of claim 1, further comprising expressing a second fusion protein comprising a second DNA-binding moiety, a second test protein, and a second gene-activating moiety in the host cell, wherein the host cell further comprises one or more positive selection reporters driven by one or more promoters with a sequence specific for the second DNA-binding moiety.

3. The method of claim 2, wherein a plurality of positive selection reporters are disposed within the host cell, wherein each positive selection reporter of the plurality of positive selection reporters is operably linked to a promoter sequence specific for the second DNA-binding moiety.

4. The method of claim 2, wherein the first test protein is a KRAS variant selected from the group consisting of KRAS G12, KRAS G12V, KRAS G12C, KRAS G12S, KRAS G13D, RKAS Q61K, and KRAS Q61L .

5. The method of claim 4, wherein the second test protein is KRAS.

6. The method of claim 1, wherein the molecule is from a library of molecules.

7. The method claim 1, wherein the molecule is delivered exogenously.

8. The method of claim 1, wherein the host cell comprises more than one sequence of a gene for expressing a death agent that is activated by a promoter DNA sequence specific for the first DNA-binding moiety.

9. The method of claim 1, wherein the host cell comprises a DNA sequence encoding the fusion protein, a DNA sequence encoding the E3 ubiquitin ligase, and a DNA sequence encoding the death agent.

10. The method of claim 1, wherein the death agent is an overexpressed product of a genetic element selected from DNA or RNA.

11. The method of claim 1, wherein the death agent is a ribosomally encoded xenobiotic agent, a ribosomally encoded poison, a ribosomally encoded endogenous or exogenous gene that results in severe growth defects upon mild overexpression, a ribosomally encoded recombinase that excises an essential gene for viability, a limiting factor involved in the synthesis of a toxic secondary metabolite, a growth inhibitory sequence, or any combination thereof.

12. The method of claim 11, wherein the death agent is Cholera toxin, SpvB toxin, CARDS toxin, SpyA Toxin, HopUl, Chelt toxin, Certhrax toxin, EFV toxin, ExoT, CdtB, Diphtheria toxin, ExoU/VipB, HopPtoE, HopPtoF, HopPtoG, VopF, YopJ, AvrPtoB, SdbA, SidG, VpdA, Lpg0969, Lpg1978, YopE, SptP, SopE2, SopB/SigD, SipA, YpkA, YopM, Amatoxin, Phallacidin, Killer toxin KP1, Killer toxin KP6, Killer Toxin K1, Killer Toxin K28 (KHR), Killer Toxin K28 (KHS), Anthrax lethal factor endopeptidase, Shiga Toxin, Saporin Toxin, Ricin Toxin, or any combination thereof.

13. The method of claim 1, wherein the host cell is a eukaryote.

14. The method of claim 1, wherein the host cell is from an animal, plant, or fungus.

15. The method of claim 14, wherein the host cell is a fungal cell.

16. The method of claim 1, wherein the molecule is a small molecule.

17. The method of claim 1, wherein the molecule is a peptide or a protein.

18. The method of claim 17 wherein the peptide or protein is product of an endogenously expressed recombinant gene.

19. The method of claim 1, wherein the molecule is a polypeptide expressed from a test DNA molecule introduced into the host cell, wherein the test DNA molecule encodes the polypeptide.

20. The method of claim 19, wherein the test DNA molecule is from a library of DNA sequences that encode different polypeptides.

21. The method of claim 20, wherein each DNA sequence of the library of DNA sequences is disposed within a separate vector.

22. The method of claim 20, wherein the library encodes polypeptides of 60 or fewer amino acids in length.

23. The method of claim 19, wherein the polypeptide is processed into a cyclic or bicyclic peptide in the host cell.

24. A host cell configured to express:
   an E3 ubiquitin ligase;
   a first fusion protein comprising a first test protein, a first DNA-binding moiety, and a first gene-activating moiety;
   a death agent, wherein the expression of the death agent is under control of a promoter DNA sequence specific for the first DNA-binding moiety; and
   a polypeptide of 60 or fewer amino acids, wherein the polypeptide modulates an interaction between the first fusion protein and the E3 ubiquitin ligase in a manner that leads to accelerated degradation of the first fusion protein.

* * * * *